US007101988B2

(12) United States Patent
Harris, Jr. et al.

(10) Patent No.: US 7,101,988 B2
(45) Date of Patent: Sep. 5, 2006

(54) POLYVALENT CATION-SENSING RECEPTOR IN ATLANTIC SALMON

(75) Inventors: H. William Harris, Jr., Portland, ME (US); Jacqueline Nearing, N. Yarmouth, ME (US); Marlies Betka, Portland, ME (US)

(73) Assignee: MariCal, Inc., Portland, ME (US)

(*) Notice: Subject to any disclaimer, the term of this patent is extended or adjusted under 35 U.S.C. 154(b) by 194 days.

(21) Appl. No.: 10/410,885

(22) Filed: Apr. 9, 2003

(65) Prior Publication Data
US 2003/0232366 A1    Dec. 18, 2003

Related U.S. Application Data

(63) Continuation-in-part of application No. 10/125,792, filed on Apr. 18, 2002, now Pat. No. 6,979,559, and a continuation-in-part of application No. 10/125,778, filed on Apr. 18, 2002, now Pat. No. 6,979,558, and a continuation-in-part of application No. 10/125,772, filed on Apr. 18, 2002, now Pat. No. 6,951,739, which is a continuation-in-part of application No. 10/121,441, filed on Apr. 11, 2002, now abandoned, which is a continuation-in-part of application No. PCT/US01/31704, filed on Oct. 11, 2001.

(60) Provisional application No. 60/240,392, filed on Oct. 12, 2000, provisional application No. 60/240,003, filed on Oct. 12, 2000.

(51) Int. Cl.
C07H 21/04   (2006.01)
C12P 21/02   (2006.01)
C07K 1/00    (2006.01)
C07K 14/00   (2006.01)

(52) U.S. Cl. ............... 536/23.5; 536/23.1; 530/300; 530/350; 435/69.1; 435/253.3; 435/254.11; 435/320.1; 435/325

(58) Field of Classification Search .............. 536/24.31; 530/300, 350; 435/325
See application file for complete search history.

(56) References Cited

U.S. PATENT DOCUMENTS

| 4,683,202 | A  | 7/1987  | Mullis          |
| 5,545,808 | A  | 8/1996  | Hew et al.      |
| 5,763,569 | A  | 6/1998  | Brown et al.    |
| 5,858,684 | A  | 1/1999  | Nemeth et al.   |
| 5,962,314 | A  | 10/1999 | Brown et al.    |
| 5,981,599 | A  | 11/1999 | Moe et al.      |
| 6,001,884 | A  | 12/1999 | Nemeth et al.   |
| 6,337,391 | B1 | 1/2002  | Harris et al.   |
| 6,463,882 | B1 | 10/2002 | Harris, Jr. et al. |
| 6,463,883 | B1 | 10/2002 | Harris, Jr. et al. |
| 6,475,792 | B1 | 11/2002 | Harris, Jr. et al. |
| 6,481,379 | B1 | 11/2002 | Harris, Jr. et al. |
| 6,564,747 | B1 | 5/2003  | Harris, Jr. et al. |
| 2003/0051269 | A1 | 3/2003 | Harris et al. |
| 2003/0082574 | A1 | 5/2003 | Harris et al. |
| 2003/0124657 | A1 | 7/2003 | Harris et al. |

FOREIGN PATENT DOCUMENTS

| SU | (11) 1784152 A1 | 12/1992 |
| WO | WO 97/35977     | 10/1997 |
| WO | WO 02/30182 A3  | 4/2002  |
| WO | WO 02/031149 A3 | 4/2002  |
| WO | WO 03/030639 A2 | 4/2003  |

OTHER PUBLICATIONS

Voet et al. Biochemistry. 1990. John Wiley & Sons, Inc. 126-128 and 228-234.*

Mickle JE et al. Genotype-phenotype relationships in cystic fibrosis. Med Clin North Am. May 2000;84(3):597-607.*

Yan et al., Two-amino acid molecular switch in an epithelial morphogen that regulates binding to two distinct receptors. Science 290: 523-527, 2000.*

Wells, J.A., "Additivity of Mutational Effects in Proteins," *Biochemistry* 29(37): 8509-8517 (Sep. 1990).

Ngo et al., "Chapter 14: Computational Complexity Protein Structure Prediction, and the Levinthal Paradox." In *The Protein Folding Problem and Tertiary Structure Prediction*, K. M. Merz, Jr. et al., eds. (Boston: Birkhauser), pp. 433-506 (Mar. 1995).

Skolnick, J. and J.S. Fetrow, "From genes to protein structure and function: novel applications of computational approaches in the genomic era." Trends in Biotech. 18(1):34-39, (2000).

Doerks, T. et al., "Protein annotation: detective work for function prediction," *Trends in Genetics* 14(6): 248-250 (Jun. 1998).

Smith T. and X. Zhang, "The challenges of genome sequence annotation or 'The devil is in the details'," *Nature Biotechnology* 15:1222-1223 (Nov. 1997).

Brenner, S.E., "Errors in genome annotation," *Trends in Genetics* 15(4): 132-133 (Apr. 1999).

Bork, P. and A. Bailroc, "Go hunting in sequence databases but watch out for the traps." *Trends in Genetics* 12(10): 425-427 (Oct. 1996).

(Continued)

Primary Examiner—Janet L. Andres
Assistant Examiner—Gregory S Emch
(74) Attorney, Agent, or Firm—Hamilton, Brook, Smith & Reynolds, P.C.

(57) ABSTRACT

The present invention encompasses four full length nucleic acid and amino acid sequences for PolyValent Cation-Sensing Receptors (PVCR) in Atlantic Salmon. These PVCR have been named SalmoKCaR#1, SalmoKCaR#2, SalmoKCaR#3, and SalmoKCaR#4. The present invention includes homologs thereof, antibodies thereto, and methods for assessing SalmoKCaR nucleic acid molecules and polypeptides. The present invention further includes plasmids, vectors, host cells containing the nucleic acid sequences of SalmoKCaR #1,2 3 and/or 4.

15 Claims, 129 Drawing Sheets

OTHER PUBLICATIONS

Naito, T., et al., "Putative pheromone receptors related to the $Ca^{2+}$-sensing receptor in *Fugu*," *Proc. Natl Acad. Science.* 95: 5178-5181 (Apr. 1998).

Clark, M.S., et al., "*Sparus aurata* mRNA for extracellular calcium sensing receptor (casr gene)," *EMBL Database Accession No. AJ289717* (Jun. 9, 2001).

Nearing, J., "Polyvalent canon receptor proteins (CaRs) are salinity sensors in fish," *PNAS.* 99(14): 9231-9236 (2002).

Nearing, J, et al., "Cloning and expression of a homologue of the calcium (Ca2+)/polyvalent cation receptor (CaR) protein that acts as a magnesium (Mg2+) sensor in dogfish shark (*Squalus acanthias*) kidney," *Journal of The American Society of Nephrology,* 8: 40A. (From ASN Program and Abstracts, 1997, Abstract No. A0194)(1997).

Baum, M.A., et al. "An Apical Extracellular Calcium/Polyvalent Cation Sensing Receptor (CaR) Present in the Osmoregulatory Organs of Salt Water (SW) and Fresh Water (FW) Fish Likely Plays a Role in Salinity Adaptation," *Journal of Am. Society of Nephrology* 7(9): 1276 (1996).

Riccardi, D., et al., "Cloning and functional expression of a rat kidney extracellular calcium/polyvalent canon-sensing receptor," *Proc. Nat. Acad. Sci.USA.* 92 131-135 (1995).

Brown, E.M., et al., "Calcium-Ion-Sensing Cell-Surface Receptors," *The New England Journal of Medicine,* 333(4): 234-240 (Jul. 1995).

Brown, E.M., et al., "Cloning and Characterization of an Extracellular $Ca^{2+}$-Sensing Receptor from Bovine Parathyroid," *Nature* 366:575-580 (Dec. 1993).

Brown, E.M., et al., "Neomycin mimics the Effects of High Extracellular Calcium Concentrations on Parathyroid Function in Dispersed Bovine Parathyroid Cells," *Endocrinology* 128(6): 3047-3054 (1991).

Sands, J.M., et al., "Apical Extracellular Calcium/Polyvalent Cation-sensing Receptor Regulates Vasopressin-elicited Water Permeability in Rat Kidney Inner Medullary Collecting Duct," *J. Clinical Investigation* 99(6): 1399-1405 (Mar. 1997).

Garrett, J.E., et al., "Molecular Cloning and Functional Expression of Human Parathyroid Calcium Receptor cDNAs," *Journal of Biological Chemistry,* 270(21): 12919-12925 (1995).

Sands, A.T., et al., "High susceptibility to ultraviolet-induced carcinogenesis in mice lacking XPC," *Nature,* 377: 162-165 (Sep. 1995).

Aida, K., et al., "Molecular Cloning of a Putative $Ca^{2+}$Sensing Receptor cDNA from Human Kidney," *Biochemical & Biophysical Research Communications,* 214(2): 524-529(Sep. 1995).

Ward, D.T., et al., "Disulfide Bonds in the Extracellular Calcium-Polyvalent Cation-sensing Receptor Correlate with Dimer Formation and Its Response to Divalent Cations *in vitro,*" *J. Bio. Chemistry,* 273: 14476-14483 (1998).

Radman, D.P., et al., "Evidence for calcium-sensing receptor mediated stanniocalcin secretion in fish," *Molecular and Cellular Endocrinology,* 186: 111-119 (2002).

Abnet, C.C., et al., "Two Forms of Aryl Hydrocarbon Receptor Type 2 in Rainbow Trout (*Oncorhynchus mykiss*)," *J. of Biological Chemistry,* 274: 15159-15166 (1999).

Usher, M. L., et al., Effects of transfer to seawater on growth and feeding in Atlantic salmon smolts (*Salmo salar L.*), *Aquaculture,* 94: 309-326 (1991).

Morkore, T. and K. Rorvik, "Seasonal variations in growth, feed utilisation and product quality of farmed Atlantic salmon (*Sakni sakar*) transferred to seawater as 0+ smolts or 1 + smolts," *Aquaculture,* 199: 145-157 (2001).

Johnston, I. A., et al . "Muscle fibre density in relation to the colour and texture of smoked Atlantic salmon (*Salmo salar L.* )," *Aquaculture,* 189: 335-349 (2000).

Pace, A.J., et al., "Dimerization of the calcium-sensing receptor occurs within the extracellular domain and is eliminated by Cys to Ser mutations at $Cys^{101}$ and $Cys^{236}$," *J. Biol Chemistry,* 274: 11629-11634 (1999).

Bai, M., et al., "Expression and Characterization of Inactivating and Activating Mutations in the Human $Ca^{2+}$-sensing Receptor," *J Biol. Chemistry,* 271(32): 19537-19545 (1996).

Pearce, S.H.S., et al., "Functional Characterization of Calcium-sensing Receptor Mutations Expressed in Human Embryonic Kidney Cells," *J. Clin. Invest.,* 98(8): 1860-1866 (1996).

Ray, K., et al., "The Carboxyl Terminus of the Human Calcium Receptor. Requirements for Cell Surface Expression and Signal Transduction," *J. Biol. Chem.,* 272(50): 31355-31361 (1997).

Gama, L., and G.E. Breitwieser, "A Carboxyl-terminal Domain Controls the Cooperativity for Extracellular $Ca^{2+}$ Activation of the Human Calcium Sensing Receptor. A study with receptor-green fluorescent protein fusions," *J. Biol. Chemistry,* 273:29712-29718 (1998).

Ho, C., et al., "A mouse model of human familial hypocalciuric hypercalcemia and neonatal severe hyperparathyroidism," *Nature (Genetics),* 11: 389-394 (1995).

Pollak, M.R., et al., "Mutations in the Human $Ca^{2+}$-Sensing Receptor Gene Cause Familial Hypocalciuric Hypercalcemia and Neonatal Severe Hyperparathyroidism," *Cell.* 75: 1297-1303 (Dec. 1993).

Malaga-Trillo, E. and A. Meyer, "Genome Duplications and Accelerated evolution of *Hox* Genes and Cluster Architecture in Teleost Fishes," *Amer. Zool.,* 41: 676-686 (2001).

Lopreato, G.F., et al., "Evolution and divergence of sodium channel genes in verterbrates," *Proc. Nat. Acad. Sci.,* 98(13): 7588-7592 (2001).

Chen, T.T., et al., "Transgenic Fish," *Trends in Biotechnology,* 8: 209-215 (Aug. 1990).

Takeo, J. and S. Yamashita, "Two Distinct Isoforms of cDNA Encoding Rainbow Trout Androgen Receptors," *J. Biol. Chem,* 274(9): 5674-5680 (1999).

Robinson-Rechavi, M., et al., "An ancestral whole-genome duplication may not have been responsible for the abundance of duplicated fish genes," *Current Biology,* 11(12): R458-R459 (2001).

Mattila, P., et al., "Fidelity of DNA synthesis by the *Thermococcus iitoralis* DNA polymerase—an extremely heat stable enzyme with proofreading activity," *Nucleic Acid Research,* 19(18): 4967-4973 (Aug. 1991).

Nowak, M.A., et al., "Evolution of genetic redundancy," *Nature,* 388: 167-171 (Jul. 1997).

Force. A., et al., Preservation of Duplicate Genes by Complementary, Degenerative Mutations, *Genetics,* 151.1531-1545 (Apr. 1999).

Lynch, M. and Force, A , "Probability of Duplicate Gene Preservation by Subfunctionalization," *Genetics,* 154: 459-473 (2000).

Nemeth, E.F., et al., "Calcimimetics with potent and selective activity on the parathyroid calcium receptor," *Proc Natl. Acad. Sci.,* 95: 4040-4045 (1998).

Quinn, S.J., et al., "The $Ca^{2+}$-sensing receptor: a target for polyamines," *American Journal of Physiology,* 273(4): C1315-C1323 (Oct. 1997).

Conigrave, A.D., et al., "L-Amino acid sensing by the extracellular $Ca^{2+}$-sensing receptor," *Proc. Natl. Acad. Sci.,* 97(9): 4414-4819 (2000).

Siner, J., et al., "Cloning of an aquaporin homologue present in water channel containing endosomes of toad urinary bladder," *Am. J. Physiol.,* 270:C372-C381 (1996).

Bodznick, D., "Calcium Ion: An Odorant for Natural Water Discriminations and the Migratory Behavior of Sockeye Salmon," *J. Comp. Physiol—A.* 127: 157-166 (1978).

Hubbard, P.C., et al., "Olfactory Sensitivity to Changes in Environmental [$Ca^{2+}$] in the Marine Teleost *Sparus aurata,*" *J. Exp. Biol:* 203: 3821-3829 (2000).

Royce-Malmgren, C.H. and W.H. Watson, "Modification of Olfactory-related Behavior in Juvenile Atlantic Salmon by Changes in pH," *J. of Chemical Ecology,* 13(3): 533-546 (1987).

Bork, Peer, "Powers and Pitfalls in Sequence Analysis: The 70% Hurdle," Genome Research 10.398-400 (2000).

Clark, M.S. et al , "Calcitonin: characterisation and expression in a teleost fish, *Fugu rubripes,*" *J. Mol. Endocrin* 28(2):111-123 (Apr. 2002).

Lo, Y.H. et al., "High-affinity $Ca^{2+}$, $Mg^{2+}$-ATPase in plasma membrane-rich preparations from olfactory epithelium of Atlantic salmon," Biochimica et Biophysica Acta 1192(2):153-158 (1994).

\* cited by examiner

```
aattccgttg ctgtcggttc agtccaagtc tcctccagtg caaaatgaga aatggtggtc  60
gccattacag gaacatgcac tacatctgtg ttaatgaaat attgtcagtt atctgaaggt 120
tattaaaatg tttctgcaag gatggcttca cgagaaatca attctgcacg ttttcccatt 180
gtcattgtat gaataactga ccaaagggat gtaacaaaat ggaacaaagc tgaggaccac 240
gttcacccrt tcttggagca tacgatcaac ctgaaggag atggaagact tgaggaggaa 300
atggggattg atcttccagg agttctgctg taaagcgatc cctcaccatt acaaagataa 360
gcagaaatcc tccaggcatc ctctgtaaac gggctggcgt agtgtggctt ggtcaaggaa 420
cagagacagg gctgcaca atg gct cag ctt cac tgc caa ctc tta ttc ttg    471
                    Met Ala Gln Leu His Cys Gln Leu Leu Phe Leu
                     1               5                  10 gga ttt aca ctc cta cag tcg tac aat gtc tca ggg tat ggt cca aac    519
Gly Phe Thr Leu Leu Gln Ser Tyr Asn Val Ser Gly Tyr Gly Pro Asn
            15                  20                  25 caa agg gcc cag aag aaa gga gac atc ata ctg gga ggt ctc ttc cca    567
Gln Arg Ala Gln Lys Lys Gly Asp Ile Ile Leu Gly Gly Leu Phe Pro
        30                  35                  40 ata cac ttt gga gta gcc gcc aag gat cag gac tta aaa tcg aga ccg    615
Ile His Phe Gly Val Ala Ala Lys Asp Gln Asp Leu Lys Ser Arg Pro
 45                  50                  55 gag gcg aca aaa tgt att cgg tac aat ttt cga ggc ttc cga tgg ctc    663
Glu Ala Thr Lys Cys Ile Arg Tyr Asn Phe Arg Gly Phe Arg Trp Leu
 60                  65                  70                  75 cag gcg atg ata ttc gca att gaa gag att aac aac agt atg act ttc    711
Gln Ala Met Ile Phe Ala Ile Glu Glu Ile Asn Asn Ser Met Thr Phe
                80                  85                  90 ctg ccc aat atc acc ctg gga tat cgc ata ttt gac acg tgt aac acc    759
Leu Pro Asn Ile Thr Leu Gly Tyr Arg Ile Phe Asp Thr Cys Asn Thr
            95                  100                 105 gtg tcc aag gcg cta gag gca aca ctc agc ttt gtg gcc cag aac aaa    807
Val Ser Lys Ala Leu Glu Ala Thr Leu Ser Phe Val Ala Gln Asn Lys
        110                 115                 120 atc gac tcg ctg aac tta gat gag ttc tgt aac tgc tct gac cat atc    855
Ile Asp Ser Leu Asn Leu Asp Glu Phe Cys Asn Cys Ser Asp His Ile
125                 130                 135 cca tcc aca ata gca gtg gtc ggg gca acc ggg tca gga atc tcc acg    903
Pro Ser Thr Ile Ala Val Val Gly Ala Thr Gly Ser Gly Ile Ser Thr
140                 145                 150                 155 gct gtg gcc aat cta ttg gga tta ttt tac att cca cag gtc agc tat    951
Ala Val Ala Asn Leu Leu Gly Leu Phe Tyr Ile Pro Gln Val Ser Tyr
                160                 165                 170 gcc tcc tcg agc agg ctg ctc agc aac aag aat gag tac aag gcc ttc    999
Ala Ser Ser Ser Arg Leu Leu Ser Asn Lys Asn Glu Tyr Lys Ala Phe
            175                 180                 185 ctg agg acc atc ccc aat gat gag caa cag gcc acg gcc atg gcc gag   1047
Leu Arg Thr Ile Pro Asn Asp Glu Gln Gln Ala Thr Ala Met Ala Glu
        190                 195                 200
```

FIG. 1A

```
atc atc gag cac ttc cag tgg aac tgg gtg gga acc ctg gca gcc gac    1095
Ile Ile Glu His Phe Gln Trp Asn Trp Val Gly Thr Leu Ala Ala Asp
        205                 210                 215 gat gac tat ggc cgc cca ggc att gac aag ttc cgg gag gag gcc gtt    1143
Asp Asp Tyr Gly Arg Pro Gly Ile Asp Lys Phe Arg Glu Glu Ala Val
220                 225                 230                 235 aag agg gac atc tgt att gac ttc agt gag atg atc tct cag tac tac    1191
Lys Arg Asp Ile Cys Ile Asp Phe Ser Glu Met Ile Ser Gln Tyr Tyr
                240                 245                 250 acc cag aag cag ttg gag ttc atc gcc gac gtc atc cag aac tcc tcg    1239
Thr Gln Lys Gln Leu Glu Phe Ile Ala Asp Val Ile Gln Asn Ser Ser
            255                 260                 265 gcc aag gtc atc gtg gtc ttc tcc aat ggc ccc gac ctg gag ccg ctc    1287
Ala Lys Val Ile Val Val Phe Ser Asn Gly Pro Asp Leu Glu Pro Leu
        270                 275                 280 atc cag gag ata gtt cgg aga aac atc acc gat cgg atc tgg ctg gcc    1335
Ile Gln Glu Ile Val Arg Arg Asn Ile Thr Asp Arg Ile Trp Leu Ala
        285                 290                 295 agc gag gct tgg gcc agc tct tcg ctc att gcc aag cca gag tac ttc    1383
Ser Glu Ala Trp Ala Ser Ser Ser Leu Ile Ala Lys Pro Glu Tyr Phe
300                 305                 310                 315 cac gtg gtc ggc ggc acc atc ggc ttc gct ctc agg gcg ggg cgt atc    1431
His Val Val Gly Gly Thr Ile Gly Phe Ala Leu Arg Ala Gly Arg Ile
                320                 325                 330 cca ggg ttc aac aag ttc ctg aag gag gtc cac ccc agc agg tcc tcg    1479
Pro Gly Phe Asn Lys Phe Leu Lys Glu Val His Pro Ser Arg Ser Ser
            335                 340                 345 gac aat ggg ttt gtc aag gag ttc tgg gag gag acc ttc aac tgc tac    1527
Asp Asn Gly Phe Val Lys Glu Phe Trp Glu Glu Thr Phe Asn Cys Tyr
        350                 355                 360 ttc acc gag aag acc ctg acg cag ctg aag aat tcc aag gtg ccc tcg    1575
Phe Thr Glu Lys Thr Leu Thr Gln Leu Lys Asn Ser Lys Val Pro Ser
365                 370                 375 cac gga ccg gcg gct caa ggg gac ggc tcc aag gcg ggg aac tcc aga    1623
His Gly Pro Ala Ala Gln Gly Asp Gly Ser Lys Ala Gly Asn Ser Arg
380                 385                 390                 395 cgg aca gcc cta cgc cac ccc tgc act ggg gag gag aac atc acc agc    1671
Arg Thr Ala Leu Arg His Pro Cys Thr Gly Glu Glu Asn Ile Thr Ser
                400                 405                 410 gtg gag acc ccc tac ctg gat tat aca cac ctg agg atc tcc tac aat    1719
Val Glu Thr Pro Tyr Leu Asp Tyr Thr His Leu Arg Ile Ser Tyr Asn
            415                 420                 425 gta tac gtg gcc gtc tac tcc att gct cac gcc ctg caa gac atc cac    1767
Val Tyr Val Ala Val Tyr Ser Ile Ala His Ala Leu Gln Asp Ile His
        430                 435                 440
```

FIG. 1B

```
tct tgc aaa ccc ggc acg ggc atc ttt gca aac gga tct tgt gca gat     1815
Ser Cys Lys Pro Gly Thr Gly Ile Phe Ala Asn Gly Ser Cys Ala Asp
    445             450                 455 att aaa aaa gtt gag gcc tgg cag gtc ctc aac cat ctg ctg cat ctg     1863
Ile Lys Lys Val Glu Ala Trp Gln Val Leu Asn His Leu Leu His Leu
460             465                 470                 475 aag ttt acc aac agc atg ggt gag cag gtt gac ttt gac gat caa ggt     1911
Lys Phe Thr Asn Ser Met Gly Glu Gln Val Asp Phe Asp Asp Gln Gly
                480                 485                 490 gac ctc aag ggg aac tac acc att atc aac tgg cag ctc tcc gca gag     1959
Asp Leu Lys Gly Asn Tyr Thr Ile Ile Asn Trp Gln Leu Ser Ala Glu
            495                 500                 505 gat gaa tcg gtg ttg ttc cat gag gtg ggc aac tac aac gcc tac gct     2007
Asp Glu Ser Val Leu Phe His Glu Val Gly Asn Tyr Asn Ala Tyr Ala
        510                 515                 520 aag ccc agt gac cga ctc aac atc aac gaa aag aaa atc ctc tgg agt     2055
Lys Pro Ser Asp Arg Leu Asn Ile Asn Glu Lys Lys Ile Leu Trp Ser
    525                 530                 535 ggc ttc tcc aaa gtg gtt cct ttc tcc aac tgc agt cga gac tgt gtg     2103
Gly Phe Ser Lys Val Val Pro Phe Ser Asn Cys Ser Arg Asp Cys Val
540                 545                 550                 555 ccg ggc acc agg aag ggg atc atc gag ggg gag ccc acc tgc tgc ttt     2151
Pro Gly Thr Arg Lys Gly Ile Ile Glu Gly Glu Pro Thr Cys Cys Phe
                560                 565                 570 gaa tgc atg gca tgt gca gag gga gag ttc agt gat gaa aac gat gca     2199
Glu Cys Met Ala Cys Ala Glu Gly Glu Phe Ser Asp Glu Asn Asp Ala
            575                 580                 585 agt gcg tgt aca aag tgc ccg aat gat ttc tgg tcg aat gag aac cac     2247
Ser Ala Cys Thr Lys Cys Pro Asn Asp Phe Trp Ser Asn Glu Asn His
        590                 595                 600 acg tcg tgc atc gcc aag gag atc gag tac ctg tcg tgg acg gag ccc     2295
Thr Ser Cys Ile Ala Lys Glu Ile Glu Tyr Leu Ser Trp Thr Glu Pro
    605                 610                 615 ttc ggg atc gct ctg acc atc ttc gcc gta ctg ggc atc ctg atc acc     2343
Phe Gly Ile Ala Leu Thr Ile Phe Ala Val Leu Gly Ile Leu Ile Thr
620                 625                 630                 635 tcc ttc gtg ctg ggg gtc ttc atc aag ttc agg aac act ccc atc gtg     2391
Ser Phe Val Leu Gly Val Phe Ile Lys Phe Arg Asn Thr Pro Ile Val
                640                 645                 650 aag gcc acc aac cgg gag ttg tcc tac ctg ctg ctc ttc tcc ctc atc     2439
Lys Ala Thr Asn Arg Glu Leu Ser Tyr Leu Leu Leu Phe Ser Leu Ile
            655                 660                 665 tgc tgc ttc tcc agc tcg ctc atc ttc atc ggc gag ccc agg gac tgg     2487
Cys Cys Phe Ser Ser Ser Leu Ile Phe Ile Gly Glu Pro Arg Asp Trp
        670                 675                 680
```

FIG. 1C

```
acc tgt cgg ctc cgc caa ccg gcc ttt ggc atc agc ttc gtc ctg tgc    2535
Thr Cys Arg Leu Arg Gln Pro Ala Phe Gly Ile Ser Phe Val Leu Cys
    685                 690                 695 atc tcc tgc atc ctg gtg aag acc aac cgg gtg ctg ctg gtc ttc gag    2583
Ile Ser Cys Ile Leu Val Lys Thr Asn Arg Val Leu Leu Val Phe Glu
700                 705                 710                 715 gcc aag atc ccc acc agc ctc cac cgc aag tgg gtg ggc ctc aac ctg    2631
Ala Lys Ile Pro Thr Ser Leu His Arg Lys Trp Val Gly Leu Asn Leu
                720                 725                 730 cag ttc ctc ctg gtc ttc ctc tgc atc ctg gtg caa atc gtc acc tgc    2679
Gln Phe Leu Leu Val Phe Leu Cys Ile Leu Val Gln Ile Val Thr Cys
            735                 740                 745 atc atc tgg ctc tac acc gcg cct ccc tcc agc tac agg aac cat gag    2727
Ile Ile Trp Leu Tyr Thr Ala Pro Pro Ser Ser Tyr Arg Asn His Glu
        750                 755                 760 ctg gag gac gag gtc atc ttc atc acc tgc gac gag ggc tcg ctc atg    2775
Leu Glu Asp Glu Val Ile Phe Ile Thr Cys Asp Glu Gly Ser Leu Met
    765                 770                 775 gcg ctg ggc ttc ctc atc ggc tac acc tgc ctc ctc gcc gcc atc tgc    2823
Ala Leu Gly Phe Leu Ile Gly Tyr Thr Cys Leu Leu Ala Ala Ile Cys
780                 785                 790                 795 ttc ttc ttc gcc ttc aag tcc cgt aag ctg ccg gag aac ttc aac gag    2871
Phe Phe Phe Ala Phe Lys Ser Arg Lys Leu Pro Glu Asn Phe Asn Glu
                800                 805                 810 gct aag ttc atc acc ttc agc atg ttg atc ttc ttc atc gtc tgg atc    2919
Ala Lys Phe Ile Thr Phe Ser Met Leu Ile Phe Phe Ile Val Trp Ile
            815                 820                 825 tcc atc atc ccc gcc tat gtc agc acc tac ggc aag ttt gtg tcg gcc    2967
Ser Ile Ile Pro Ala Tyr Val Ser Thr Tyr Gly Lys Phe Val Ser Ala
        830                 835                 840 gtg gag gtg att gcc atc ctg gcc tcc agc ttc ggg ctg ctg ggc tgc    3015
Val Glu Val Ile Ala Ile Leu Ala Ser Ser Phe Gly Leu Leu Gly Cys
    845                 850                 855 att tac ttc aac aag tgt tac atc atc ctg ttc aag ccg tgc cgt aac    3063
Ile Tyr Phe Asn Lys Cys Tyr Ile Ile Leu Phe Lys Pro Cys Arg Asn
860                 865                 870                 875 acc atc gag gag gtg cgc tgc agc acg gcg gcc cac gcc ttc aag gtg    3111
Thr Ile Glu Glu Val Arg Cys Ser Thr Ala Ala His Ala Phe Lys Val
                880                 885                 890 gcg gcc cgg gcc acc ctc cgg cgc agc gcc gcg tct cgc aag cgc tcc    3159
Ala Ala Arg Ala Thr Leu Arg Arg Ser Ala Ala Ser Arg Lys Arg Ser
            895                 900                 905 agc agc ctg tgc ggc tcc acc atc tcc tcg ccc gcc tcg tcc acc tgc    3207
Ser Ser Leu Cys Gly Ser Thr Ile Ser Ser Pro Ala Ser Ser Thr Cys
        910                 915                 920
```

FIG. 1D

```
ggg ccg ggc ctc acc atg gag atg cag cgc tgc agc acg cag aag gtc    3255
Gly Pro Gly Leu Thr Met Glu Met Gln Arg Cys Ser Thr Gln Lys Val
    925             930             935 agc ttc ggc agc ggc acc gtc acc ctg tcg ctc agc ttc gag gag aca    3303
Ser Phe Gly Ser Gly Thr Val Thr Leu Ser Leu Ser Phe Glu Glu Thr
940             945             950             955 ggc cga tac gcc acc ctc agc cgc acg gcc cgc agc agg aac tcg gcg    3351
Gly Arg Tyr Ala Thr Leu Ser Arg Thr Ala Arg Ser Arg Asn Ser Ala
                960             965             970 gat ggc cgc agc ggc gac gac ctg cca tct aga cac cac gac cag ggc    3399
Asp Gly Arg Ser Gly Asp Asp Leu Pro Ser Arg His His Asp Gln Gly
        975             980             985 ccg cct cag aaa tgc gag ccc cag ccc gcc aac gat gcc cga tac aag    3447
Pro Pro Gln Lys Cys Glu Pro Gln Pro Ala Asn Asp Ala Arg Tyr Lys
            990             995             1000 gcg gcg ccg acc aag ggc acc cta gag tcg ccg ggc ggc agc aag gag    3495
Ala Ala Pro Thr Lys Gly Thr Leu Glu Ser Pro Gly Gly Ser Lys Glu
    1005            1010            1015 cgc ccc aca act atg gag gaa acc taa tccaactcct ccatcaaccc          3542
Arg Pro Thr Thr Met Glu Glu Thr  *  (SEQ ID NO: 2)
1020            1025 caagaacatc ctccacggca gcaccgtcga caactgacat caactcctaa ccggtggctg  3602
cccaacctct ccctctccg gcactttgcg ttttgctgaa gattgcagca tctgcagttc   3662
cttttatccc tgatttctg acttggatat ttactagtgt gcgatggaat atcacaacat  3722
aatgagttgc acaattaggt gagcagagtt gtgtcaaagt atctgaacta tctgaagtat  3782
ctgaactact ttattctctc gaattgtatt acaaacattt gaagtatttt tagtgacatt  3842
atgttctaac attgtcaaga taatttgtta caacatataa ggtaccacct gaagcagtga  3902
ctgagattgc cactgtgatg acagaactgt tttataacat ttatcattga aacctggatt  3962
gcaacaggaa tataatgact gtaacaaaaa aattgttgat tatcttaaaa atgcaaattg  4022
taatcagatg tgtaaaattg gtaattactt ctgtacatta aatgcatatt tcttgataaa  4082
aaaaaaaaa aaaaaaaaaa aaaaaaaaaa aaagcggcc gacagcaac gg             4134
                                                 (SEQ ID NO: 1)
```

FIG. 1E

Sequence Range: 1 to 594

```
            10          20          30          40          50
             *           *           *           *           *
C TTG GCA TTA TGC TCT GTG CTG GGG GTA TTC TTG ACA GCA TTC GTG ATG GGA
  Leu Ala Leu Cys Ser Val Leu Gly Val Phe Leu Thr Ala Phe Val Met Gly>
  ___a___a___a___TRANSLATION OF ATLANTIC SALMON NA.MV____a___a___a___>

60          70          80          90         100
        *           *           *           *           *
GTG TTT ATC AAA TTT CGC AAC ACC CCA ATT GTT AAG GCC ACA AAC AGA GAG CTA
Val Phe Ile Lys Phe Arg Asn Thr Pro Ile Val Lys Ala Thr Asn Arg Glu Leu>
___a___a___a___a_TRANSLATION OF ATLANTIC SALMON NA.MV__a___a___a___a___>

110         120         130         140         150         160
    *           *           *           *           *           *
TCC TAC CTC CTC CTG TTC TCA CTC ATC TGC TGT TTC TCC AGT TCC CTC ATC TTC
Ser Tyr Leu Leu Leu Phe Ser Leu Ile Cys Cys Phe Ser Ser Ser Leu Ile Phe>
___a___a___a___a_TRANSLATION OF ATLANTIC SALMON NA.MV__a___a___a___a___>

170         180         190         200         210
            *           *           *           *           *
ATT GGT GAA CCC CAG GAC TGG ACA TGC CGT CTA CGC CAG CCT GCA TTC GGG ATA
Ile Gly Glu Pro Gln Asp Trp Thr Cys Arg Leu Arg Gln Pro Ala Phe Gly Ile>
___a___a___a___a_TRANSLATION OF ATLANTIC SALMON NA.MV__a___a___a___a___>

220         230         240         250         260
        *           *           *           *           *
AGT TTT GTT CTC TGC ATC TCC TGC ATC CTG GTA AAA ACT AAC CGA GTA CTT CTA
Ser Phe Val Leu Cys Ile Ser Cys Ile Leu Val Lys Thr Asn Arg Val Leu Leu>
___a___a___a___a_TRANSLATION OF ATLANTIC SALMON NA.MV__a___a___a___a___>

270         280         290         300         310         320
 *           *           *           *           *           *
GTG TTC GAA GCC AAG ATC CCC ACC AGT CTC CAT CGT AAG TGG TGG GGG CTA AAC
Val Phe Glu Ala Lys Ile Pro Thr Ser Leu His Arg Lys Trp Trp Gly Leu Asn>
___a___a___a___a_TRANSLATION OF ATLANTIC SALMON NA.MV_a___a___a___a___>

330         340         350         360         370
           *           *           *           *           *
TTG CAG TTC CTG TTA GTG TTC CTG TTC ACA TTT GTG CAA GTG ATG ATA TGT GTG
Leu Gln Phe Leu Leu Val Phe Leu Phe Thr Phe Val Gln Val Met Ile Cys Val>
___a___a___a___a_TRANSLATION OF ATLANTIC SALMON NA.MV__a___a___a___a___>

380         390         400         410         420         430
    *           *           *           *           *           *
GTC TGG CTT TAC AAT GCT CCT CCG GCG AGC TAC AGG AAC CAT GAC ATT GAT GAG
Val Trp Leu Tyr Asn Ala Pro Pro Ala Ser Tyr Arg Asn His Asp Ile Asp Glu>
___a___a___a___a_TRANSLATION OF ATLANTIC SALMON NA.MV__a___a___a___a___>

440         450         460         470         480
        *           *           *           *           *
ATA ATT TTC ATT ACA TGC AAT GAG GGC TCT ATG ATG GCG CTT GGC TTC CTA ATT
Ile Ile Phe Ile Thr Cys Asn Glu Gly Ser Met Met Ala Leu Gly Phe Leu Ile>
___a___a___a___a_TRANSLATION OF ATLANTIC SALMON NA.MV__a___a___a___a___>

490         500         510         520         530
        *           *           *           *           *
GGG TAC ACA TGC CTG CTG GCA GCC ATA TRC TTC TTC TTT GCA TTT AAA TCA CGA
Gly Tyr Thr Cys Leu Leu Ala Ala Ile Xxx Phe Phe Phe Ala Phe Lys Ser Arg>
___a___a___a___a_TRANSLATION OF ATLANTIC SALMON NA.MV__a___a___a___a___>

```
AAA CTG CCA GAG AAC TTT ACT GAG GCT AAG TTC ATC ACC TTC AGC ATG CTC ATC
Lys Leu Pro Glu Asn Phe Thr Glu Ala Lys Phe Ile Thr Phe Ser Met Leu Ile>
___a___a___a____a_TRANSLATION OF ATLANTIC SALMON NA.MV__a___a___a___a___>

TT   (SEQ ID NO: 3)
Xxx> (SEQ ID NO: 4)
__>
```

FIG. 7B

```
         10        20        30        40        50        60        70
....|....|....|....|....|....|....|....|....|....|....|....|....|....|
GTGATCACAAAGGTAAGAAAGACAGTGAAAAATCTGAACTACCCATTATATAATCTGTTGCTATTTCAT   70
ATGTTTCTATCAATAATACAAACACTACTTCTCTATTCCTGCAGATGCCAGTGTTTGTACCAAGTGTCCC 140
AATGACTCATGGTCTAATGAGAACCACACATCTTGTTTCCTGAAGGAGATACAGTTTCTGTCTTGGACAG 210
AGCCCTTTGGGATCGCCTTGGCATTATGCTCTGTGCTGGGGTATTCTTGACAGCATTCGTGATGGGAGT 280
GTTTATCAAATTTCGCAACACCCCAATTGTTAAGGCCACAAACAGAGAGCTATCCTACCTCCTCCTGTTC 350
         360       370       380       390       400       410       420
....|....|....|....|....|....|....|....|....|....|....|....|....|....|
TCACTCATCTGCTGTTTCTCCAGTTCCCTCATCTTCATTGGTGAACCCCAGGACTGGACATGCCGTCTAC 420
GCCAGCCTGCATTCGGGATAAGTTTTGTTCTCTGCATCTCCTGCATCCTGGTAAAAACTAACCGAGTACT 490
TCTAGTGTTCGAAGCCAAGATCCCCACCAGTCTCCATCGTAAGTGGTGGGGGCTAAACTTGCAGTTCCTG 560
TTAGTGTTCCTGTTCACATTTGTGCAAGTGATCATATGTGTGGTCTGGCTTTACAATGCTCCTCCGGCGA 630
GCTACAGGAACCATGACATTGATGAGATAATTTTCATTACATGCAATGAGGGCTCTATGATGGCGCTTGG 700
         710       720       730       740       750       760       770
....|....|....|....|....|....|....|....|....|....|....|....|....|....|
CTTCCTAATTGGGTACACATGCCTGCTGGCAGCCATATGCTTCTTCTTTGCATTTAAATCACGAAAACTG 770
CCAGAGAACTTTACTGAGGCTAAGTTCATCAGCCTTCAGCATGCTCATCTTCTTCATCGTCTGGATCTCTT 840
TCATCCCTGCCTACTTCAGCACTTACGGAAAGTTTGTGTCGGCTGTGGAGGTCATCGCCATACTAGCCTC 910
CAGCTTTGGCCTGCTGGCCTGTATTTTCTTCAATAAAGTCTACATCATCCTCTTCAAACCGTCCAGGAAC 980
ACTATAGAGGAGGTTCGCTGTAGCACTGCGGCCCATTCTTTCAAAGTGGCAGCCAAGGCCACTCTGAGAC 1050
         1060      1070      1080      1090      1100      1110      1120
....|....|....|....|....|....|....|....|....|....|....|....|....|....|
ACAGCTCAGCCTCCAGGAAGAGGTCCAGCAGTGTGGGGGGATCCTGTGCCTCAACTCCCTCCTCATCCAT 1120
CAGCCTCAAGACCAATGACAATGACTCCCCATCAGGTCAGCAGAGAATCCATAAGCCAAGAGTAAGCTTT 1190
GGAAGTGGAACAGTTACTCTGTCCTTCAGCTTTGAGGAGTCCAGAAAGAATTCTATGAAGTAGGGAAGTG 1260
TCTTTTGGTGGGCCGAGAGCCTTGTCAAAACCTGAGTTGGTGTTGCATTCTTTGTTGGCTGGGTAGTTGG 1330
AGCAGAAATTATGATATTAAAAGCTTTGATGTATTCAGAATGGTGACACAGCATAGCTGGCCAAGATTCC 1400
```

FIG. 8A

```
        1410      1420      1430      1440      1450      1460      1470
....|....|....|....|....|....|....|....|....|....|....|....|....|....|
ATTATATTACAATAATCTGTGTTGTTCATTATGAGGACATTTCAAAATGCTGAAAATCATCAAATACATA 1470
ATTTACTGAGTTTTCTTGATAATCTTGAGAATAGAATAGCCTATTCAAGTCATCGTTGAGCAGACATTAA 1540
TTAACAATGATGTAATACTTTCCATACCTATTTTCTTAACAATAGATTCACATTGTTAAAGTTCAACTA 1610
TGACCTGTAAAATACATGAGGTATAACAGGAGACAATAAAACTATGCATATCCTAGCTTCTGGCCTGAG 1680
TAGCAGGCAGTTTACTCTGGGCACGCTTTTCATCCAAACTTCCGAATGCTGCCCCAATCCTAGTGAGGT 1750
        1760      1770      1780      1790      1800      1810      1820
....|....|....|....|....|....|....|....|....|....|....|....|....|....|
TAAAGGCCCAGTGCAGTCATATCTTTTCTCTAGGCACGCTTTTCATCCAAACTTCCGAATGCGGCTATAT 1820
CAGTCTCTTTCCTACTGTCTTTTTCATTAGGCCAGTGTTTAACAACCCTGGTCCTTAAGTACACACAACA 1890
GAACACATTTTTGTTGTAGCCCTGGACAATCACTCCTCACTCAGCTCATTGAGGGCCTGATCATTAGTTG 1960
ACAAGTTGAATCAGGTGTGCTTGTCCAGGGTTACAATACAAATGTGTACTGTTGGGGGTAC 2021
```

FIG. 8B

```
         10        20        30        40
    |....|....|....|....|....|....|....|....|
    YKHYFSIPADASVCTKCPNDSWSNEHHTSCFLKEIEFLSW  40
    TEPFGIALALCSVLGVFLTAFVMGVFIKFRNTPIVKATNR  80
    ELSYLLLFSLICCFSSSLIFIGEPQDWTCRLRQPAFGISF 120
    VLCISCILVKTNRVLLVFEAKIPTSLHRKWWGLNLQFLLV 160
    FLPTFVQVMICVVWLYNAPPASYRNHDIDEIIFITCNEGS 200
        210       220       230       240
    |....|....|....|....|....|....|....|....|
    MMALGFLIGYTCLLAAICFFFAFKSRKLPENFTEAKFITF 240
    SMLIFFIVWISFIPAYFSTYGKFVSAVEVIAILASSFGLL 280
    ACIFFNKVYIILFKPSRNTIEEVRCSTAAHSFKVAAKATL 320
    RHSSASRKRSSSVGGSCASTPSSSISLKTNDNDSPSGQQR 360
    IHKPRVSFGSGTVTLSLSFEESRKNSMK 388
```

FIG. 8C

Sequence Range: 1 to 3941

```
         10        20        30        40        50        60        70        80
TTCCAACAGCATATTTTTGTTGTATTTGCTTTGGTTTGTCTGAAATCAAGCATTATCAAGATCAAGAACAGCATGAGTCA 90       100       110       120       130       140       150       160
GAAACAAGGCGACAGCCAGAGTCACTGGAGGGGACAAGACTGAGGTTAACTCTGAAGTCTAATGTGCTGAGAGGACAAGG 170       180       190       200       210       220
CCCTCCTGAGAGCTGAACG ATG AGA TTT TAC CTG TAT TAC CTG GTG CTT TTG GGC TTC AGT TCT
                    Met Arg Phe Tyr Leu Tyr Tyr Leu Val Leu Leu Gly Phe Ser Ser>

230       240       250       260       270       280
GTC ATC TCC ACC TAT GGG CCT CAT CAG AGA GCA CAG AAG ACT GGG GAT ATT CTG CTG GGC
Val Ile Ser Thr Tyr Gly Pro His Gln Arg Ala Gln Lys Thr Gly Asp Ile Leu Leu Gly>

290       300       310       320       330       340
GGG CTG TTT CCA ATG CAC TTT GGT GTT ACC TCC AAA GAC CAA GAC CTG GCA GCG CGG CCA
Gly Leu Phe Pro Met His Phe Gly Val Thr Ser Lys Asp Gln Asp Leu Ala Ala Arg Pro>

350       360       370       380       390       400
GAA TCC ACA GAG TGT GTT AGG TAC AAT TTC CGG GGA TTC CGT TGG CTT CAG GCC ATG ATT
Glu Ser Thr Glu Cys Val Arg Tyr Asn Phe Arg Gly Phe Arg Trp Leu Gln Ala Met Ile>

410       420       430       440       450       460
TTT GCA ATA GAG GAG ATC AAC AAC AGC AGT ACT CTC CTG CCC AAC ATC ACA CTG GGC TAC
Phe Ala Ile Glu Glu Ile Asn Asn Ser Ser Thr Leu Leu Pro Asn Ile Thr Leu Gly Tyr>

470       480       490       500       510       520
AGG ATC TTT GAC ACC TGC AAC ACC GTG TCC AAG GCC CTG GAG GCT ACC CTC AGT TTC GTA
Arg Ile Phe Asp Thr Cys Asn Thr Val Ser Lys Ala Leu Glu Ala Thr Leu Ser Phe Val>

530       540       550       560       570       580
GCA CAG AAT AAG ATT GAC TCT CTG AAC TTG GAT GAA TTC TGT AAC TGC ACT GAT CAC ATC
Ala Gln Asn Lys Ile Asp Ser Leu Asn Leu Asp Glu Phe Cys Asn Cys Thr Asp His Ile>

590       600       610       620       630       640
CCA TCG ACT ATA GCA GTG GTG GGG GCT TCT GGG TCA GCG GTC TCC ACT GCT GTT GCC AAT
Pro Ser Thr Ile Ala Val Val Gly Ala Ser Gly Ser Ala Val Ser Thr Ala Val Ala Asn>

650       660       670       680       690       700
CTG TTG GGC CTT TTC TAC ATC CCA CAG ATC AGC TAT GCC TCT TCC AGT CGC CTA CTA AGC
Leu Leu Gly Leu Phe Tyr Ile Pro Gln Ile Ser Tyr Ala Ser Ser Ser Arg Leu Leu Ser>

710       720       730       740       750       760
AAC AAG AAC CAG TTC AAA TCC TTC ATG AGG ACC ATT CCC ACA GAT GAG CAC CAG GCC ACT
Asn Lys Asn Gln Phe Lys Ser Phe Met Arg Thr Ile Pro Thr Asp Glu His Gln Ala Thr>

770       780       790       800       810       820
GCC ATG GCA GAT ATC ATC GAC TAC TTC CAA TGG AAT TGG GTC ATT GCA GTT GCG TCT GAT
Ala Met Ala Asp Ile Ile Asp Tyr Phe Gln Trp Asn Trp Val Ile Ala Val Ala Ser Asp>

830       840       850       860       870       880
GAT GAG TAT GGA CGT CCG GGG ATT GAA AAA TTT GAG AAA GAG ATG GAA GAA CGA GAC ATT
Asp Glu Tyr Gly Arg Pro Gly Ile Glu Lys Phe Glu Lys Glu Met Glu Glu Arg Asp Ile>
```

FIG. 9A

```
     890          900          910          920          930          940
TGT ATC CAT CTG AGT GAG CTG ATC TCT CAG TAC TTT GAG GAG TGG CAG ATC CAA GGA TTG
Cys Ile His Leu Ser Glu Leu Ile Ser Gln Tyr Phe Glu Glu Trp Gln Ile Gln Gly Leu>

950          960          970          980          990         1000
GTT GAC CGT ATT GAG AAC TCC TCA GCT AAA GTT ATA GTC GTT TTC GCC AGT GGG CCT GAC
Val Asp Arg Ile Glu Asn Ser Ser Ala Lys Val Ile Val Val Phe Ala Ser Gly Pro Asp>

1010         1020         1030         1040         1050         1060
ATT GAG CCT CTT ATT AAA GAG ATG GTC AGA CGG AAC ATC ACC GAC CGC ATC TGG TTG GCC
Ile Glu Pro Leu Ile Lys Glu Met Val Arg Arg Asn Ile Thr Asp Arg Ile Trp Leu Ala>

1070         1080         1090         1100         1110         1120
AGC GAG GCT TGG GCA ACC ACC TCC CTC ATC GCC AAA CCA GAG TAC CTT GAT GTT GTA GTT
Ser Glu Ala Trp Ala Thr Thr Ser Leu Ile Ala Lys Pro Glu Tyr Leu Asp Val Val Val>

1130         1140         1150         1160         1170         1180
GGG ACC ATT GGC TTT GCT CTC AGA GCA GGC GAA ATA CCT GGC TTC AAG GAC TTC TTA CAA
Gly Thr Ile Gly Phe Ala Leu Arg Ala Gly Glu Ile Pro Gly Phe Lys Asp Phe Leu Gln>

1190         1200         1210         1220         1230         1240
GAG GTC ACA CCA AAG AAA TCC AGC CAC AAT GAA TTT GTC AGG GAG TTT TGG GAG GAG ACT
Glu Val Thr Pro Lys Lys Ser Ser His Asn Glu Phe Val Arg Glu Phe Trp Glu Glu Thr>

1250         1260         1270         1280         1290         1300
TTT AAC TGC TAT CTG GAA GAC AGC CAG AGA CTG AGA GAC AGT GAG AAT GGG AGC ACC AGT
Phe Asn Cys Tyr Leu Glu Asp Ser Gln Arg Leu Arg Asp Ser Glu Asn Gly Ser Thr Ser>

1310         1320         1330         1340         1350         1360
TTC AGA CCA TTG TGT ACT GGC GAG GAG GAC ATT ATG GGT GCA GAG ACC CCA TAT CTG GAT
Phe Arg Pro Leu Cys Thr Gly Glu Glu Asp Ile Met Gly Ala Glu Thr Pro Tyr Leu Asp>

1370         1380         1390         1400         1410         1420
TAC ACT CAT CTT CGT ATT TCC TAT AAT GTG TAT GTT GCA GTT CAC TCC ATT GCA CAG GCC
Tyr Thr His Leu Arg Ile Ser Tyr Asn Val Tyr Val Ala Val His Ser Ile Ala Gln Ala>

1430         1440         1450         1460         1470         1480
CTA CAG GAC ATT CTC ACC TGC ATT CCT GGA CGG GGT CTT TTT TCC AAC AAC TCA TGT GCA
Leu Gln Asp Ile Leu Thr Cys Ile Pro Gly Arg Gly Leu Phe Ser Asn Asn Ser Cys Ala>

1490         1500         1510         1520         1530         1540
GAT ATA AAG AAA ATA GAA GCA TGG CAG GTT CTC AAG CAG CTC AGA CAT TTA AAC TTC TCA
Asp Ile Lys Lys Ile Glu Ala Trp Gln Val Leu Lys Gln Leu Arg His Leu Asn Phe Ser>

1550         1560         1570         1580         1590         1600
AAC AGT ATG GGA GAA AAG GTA CAT TTT GAT GAG AAT GCT GAT CCG TCA GGA AAC TAC ACC
Asn Ser Met Gly Glu Lys Val His Phe Asp Glu Asn Ala Asp Pro Ser Gly Asn Tyr Thr>

1610         1620         1630         1640         1650         1660
ATT ATC AAT TGG CAC CGG TCT CCT GAG GAT GGT TCT GTT GTG TTT GAA GAG GTC GGT TTC
Ile Ile Asn Trp His Arg Ser Pro Glu Asp Gly Ser Val Val Phe Glu Glu Val Gly Phe>

1670         1680         1690         1700         1710         1720
TAC AAC ATG CGA GCT AAG AGA GGA GTA CAA CTT TTC ATT GAT AAC ACA AAG ATT CTA TGG
Tyr Asn Met Arg Ala Lys Arg Gly Val Gln Leu Phe Ile Asp Asn Thr Lys Ile Leu Trp>
```

FIG. 9B

```
     1730           1740           1750           1760           1770           1780
AAT GGA TAT AAT ACT GAG GTT CCA TTC TCT AAC TGT AGT GAA GAT TGT GAA CCA GGC ACC
Asn Gly Tyr Asn Thr Glu Val Pro Phe Ser Asn Cys Ser Glu Asp Cys Glu Pro Gly Thr>

1790           1800           1810           1820           1830           1840
AGA AAG GGG ATC ATA GAA AGC ATG CCA ACG TGT TGC TTT GAA TGT ACA GAA TGC TCA GAA
Arg Lys Gly Ile Ile Glu Ser Met Pro Thr Cys Cys Phe Glu Cys Thr Glu Cys Ser Glu>

1850           1860           1870           1880           1890           1900
GGA GAG TAT AGT GAT CAC AAA GAT GCC AGT GTT TGT ACC AAG TGT CCC AAT GAC TCA TGG
Gly Glu Tyr Ser Asp His Lys Asp Ala Ser Val Cys Thr Lys Cys Pro Asn Asp Ser Trp>

1910           1920           1930           1940           1950           1960
TCT AAT GAG AAC CAC ACA TCT TGT TTC CTG AAG GAG ATA GAG TTT CTG TCT TGG ACA GAG
Ser Asn Glu Asn His Thr Ser Cys Phe Leu Lys Glu Ile Glu Phe Leu Ser Trp Thr Glu>

1970           1980           1990           2000           2010           2020
CCC TTT GGG ATC GCC TTG GCA TTA TGC TCT GTG CTG GGG GTA TTC TTG ACA GCA TTC GTG
Pro Phe Gly Ile Ala Leu Ala Leu Cys Ser Val Leu Gly Val Phe Leu Thr Ala Phe Val>

2030           2040           2050           2060           2070           2080
ATG GGA GTG TTT ATC AAA TTT CGC AAC ACC CCA ATT GTT AAG GCC ACA AAC AGA GAG CTA
Met Gly Val Phe Ile Lys Phe Arg Asn Thr Pro Ile Val Lys Ala Thr Asn Arg Glu Leu>

2090           2100           2110           2120           2130           2140
TCC TAC CTC CTC CTG TTC TCA CTC ATC TGC TGT TTC TCC AGT TCC CTC ATC TTC ATT GGT
Ser Tyr Leu Leu Leu Phe Ser Leu Ile Cys Cys Phe Ser Ser Ser Leu Ile Phe Ile Gly>

2150           2160           2170           2180           2190           2200
GAA CCC CAG GAC TGG ACA TGC CGT CTA CGC CAG CCT GCA TTC GGG ATA AGT TTT GTT CTC
Glu Pro Gln Asp Trp Thr Cys Arg Leu Arg Gln Pro Ala Phe Gly Ile Ser Phe Val Leu>

2210           2220           2230           2240           2250           2260
TGC ATC TCC TGC ATC CTG GTA AAA ACT AAC CGA GTA CTT CTA GTG TTC GAA GCC AAG ATC
Cys Ile Ser Cys Ile Leu Val Lys Thr Asn Arg Val Leu Leu Val Phe Glu Ala Lys Ile>

2270           2280           2290           2300           2310           2320
CCC ACC AGT CTC CAT CGT AAG TGG TGG GGG CTA AAC TTG CAG TTC CTG TTA GTG TTC CTG
Pro Thr Ser Leu His Arg Lys Trp Trp Gly Leu Asn Leu Gln Phe Leu Leu Val Phe Leu>

2330           2340           2350           2360           2370           2380
TTC ACA TTT GTG CAA GTG ATG ATA TGT GTG GTC TGG CTT TAC AAT GCT CCT CCG GCG AGC
Phe Thr Phe Val Gln Val Met Ile Cys Val Val Trp Leu Tyr Asn Ala Pro Pro Ala Ser>

2390           2400           2410           2420           2430           2440
TAC AGG AAC CAT GAC ATT GAT GAG ATA ATT TTC ATT ACA TGC AAT GAG GGC TCT ATG ATG
Tyr Arg Asn His Asp Ile Asp Glu Ile Ile Phe Ile Thr Cys Asn Glu Gly Ser Met Met>

2450           2460           2470           2480           2490           2500
GCG CTT GGC TTC CTA ATT GGG TAC ACA TGC CTG CTG GCA GCC ATA TGC TTC TTC TTT GCA
Ala Leu Gly Phe Leu Ile Gly Tyr Thr Cys Leu Leu Ala Ala Ile Cys Phe Phe Phe Ala>

2510           2520           2530           2540           2550           2560
TTT AAA TCA CGA AAA CTG CCA GAG AAC TTT ACT GAG GCT AAG TTC ATC ACC TTC AGC ATG
Phe Lys Ser Arg Lys Leu Pro Glu Asn Phe Thr Glu Ala Lys Phe Ile Thr Phe Ser Met>
```

FIG. 9C

```
      2570          2580          2590          2600          2610          2620
CTC ATC TTC TTC ATC GTC TGG ATC TCT TTC ATC CCT GCC TAC TTC AGC ACT TAC GGA AAG
Leu Ile Phe Phe Ile Val Trp Ile Ser Phe Ile Pro Ala Tyr Phe Ser Thr Tyr Gly Lys>

2630          2640          2650          2660          2670          2680
TTT GTG TCG GCT GTG GAG GTC ATC GCC ATA CTA GCC TCC AGC TTT GGC CTG CTG GCC TGT
Phe Val Ser Ala Val Glu Val Ile Ala Ile Leu Ala Ser Ser Phe Gly Leu Leu Ala Cys>

2690          2700          2710          2720          2730          2740
ATT TTC TTC AAT AAA GTC TAC ATC ATC CTC TTC AAA CCG TCA GGA ACT ATA GAG GAG
Ile Phe Phe Asn Lys Val Tyr Ile Ile Leu Phe Lys Pro Ser Arg Asn Thr Ile Glu Glu>

2750          2760          2770          2780          2790          2800
GTT CGC TGT AGC ACT GCG GCC CAT TCT TTC AAA GTG GCA GCC AAG GCC ACT CTG AGA CAC
Val Arg Cys Ser Thr Ala Ala His Ser Phe Lys Val Ala Ala Lys Ala Thr Leu Arg His>

2810          2820          2830          2840          2850          2860
AGC TCA GCC TCC AGG AAG AGG TCC AGC AGT GTG GGG GGA TCC TGT GCC TCA ACT CCC TCC
Ser Ser Ala Ser Arg Lys Arg Ser Ser Ser Val Gly Gly Ser Cys Ala Ser Thr Pro Ser>

2870          2880          2890          2900          2910          2920
TCA TCC ATC AGC CTC AAG ACC AAT GAC AAT GAC TCC CCA TCA GGT CAG CAG AGA ATC CAT
Ser Ser Ile Ser Leu Lys Thr Asn Asp Asn Asp Ser Pro Ser Gly Gln Gln Arg Ile His>

2930          2940          2950          2960          2970          2980
AAG CCA AGA GTA AGC TTT GGA AGT GGA ACA GTT ACT CTG TCC TTG AGC TTT GAG GAG TCC
Lys Pro Arg Val Ser Phe Gly Ser Gly Thr Val Thr Leu Ser Leu Ser Phe Glu Glu Ser>

2990          3000          3010    3020          3030          3040
AGA AAG AAT TCT ATG AAG TAG GGAAGTGTCTTTTGGTGGGCCGAGAGCCTTGTCAA
Arg Lys Asn Ser Met Lys ***>  (SEQ ID NO: 8)

3050      3060      3070      3080      3090      3100      3110      3120
AACCTGAGTTGGTGTTGCATTCTTTGTTGGCTGGGTAGTTGGAGCAGAAATTATGATATTAAAAGCTTTGATGTATTCAG 3130      3140      3150      3160      3170      3180      3190      3200
AATGGTGACACAGCATAGGTGGCCAAGATTCCATTATATTACAATAATCTGTGTTGTTCATTATGAGGACATTTCAAAAT 3210      3220      3230      3240      3250      3260      3270      3280
GCTGAAAATCATCAAATACATAATTTACTGAGTTTTCTTGATAATCTTGAGAATAGAATAGCCTATTCAAGTCATCGTTG 3290      3300      3310      3320      3330      3340      3350      3360
AGCAGACATTAATTAACAATGATGTAATACTTTCCATACCTATTTTCTTTAACAATAGATTCACATTGTTAAAGTTCAAC 3370      3380      3390      3400      3410      3420      3430      3440
TATGACCTGTAAAATACATGAGGTATAACAGGAGACAATAAAACTATGCATATCCTAGCTTCTGGGCCTGAGTAGCAGGC 3450      3460      3470      3480      3490      3500      3510      3520
AGTTTACTCTGGGCACGCTTTTCATCCAAACTTCCGAATGCTGCCCCCAATCCTAGTGAGGTTAAAGGCCCAGTGCAGTC 3530      3540      3550      3560      3570      3580      3590      3600
ATATCTTTTCTCTAGGCACGCTTTTCATCCAAACTTCCGAATGCGGCTATATCAGTCTCTTTCCTACTGTCTTTTTCATT 3610      3620      3630      3640      3650      3660      3670      3680
AGGCCAGTGTTTAACAACCCTGGTCCTTAAGTACACACAACAGAGCACATTTTTGTTGTGGCCCTGGACAATCACTCCTC
```

FIG. 9D

```
      3690      3700      3710      3720      3730      3740      3750      3760
ACTCAGCTCATTGAGGGCCTGATGATTAGTTGACAAGTTGAGTCGGGTGTGCTTGTCCGGGGTTGCAATACAGATGTGTA 3770      3780      3790      3800      3810      3820      3830      3840
CTGTTGGGGGTACTCGAGGACCAGGATTGGGAAACATTACATTAGGACTACTGTAGGTTCTTCAATATGGTGTCATACGG 3850      3860      3870      3880      3890      3900      3910      3920
TCATATGGTGTCATATGGTGTCTGGTTGTTTTCTGCATATGTGTATTTCACCAAGTTACTGCACATGTTAGACCTATACA 3930      3940
CTGGAATAAACATTTTTTTTC (SEQ ID NO: 7)
```

FIG. 9E

```
Sequence Range: 1 to 4031
         10        20        30        40        50        60        70        80
GTTCCAACAGCATATTTTTGTTGTATTTGCTTTGGTTTGTCTGAAATCAAGCATTATCAAGGATTGAGCAAGACAACTGA 90       100       110       120       130       140       150       160
GTTGTCAGACTAAGAATATACACATTTCCAGTTCTCTCTTTAATGGACTTCTCACACTGATGTTCTTCAGATCAAGAACA 170       180       190       200       210       220       230       240
GCATGAGTCAGAAACAAGGCGACAGCCAGAGTCACTGGAGGGGACAAGACTGAGGTTAACTCTGAAGTCTAATGTGCTGA 250       260       270          280         290         300
GAGGACAAGGCCCTCCTGAGAGCTGAACG ATG AGA TTT TAC CTG TAT TAC CTG GTG CTT TTG GGC TTC
                              Met Arg Phe Tyr Leu Tyr Tyr Leu Val Leu Leu Gly Phe>

310         320         330         340         350         360
AGT TCT GTC ATC TCC ACC TAT GGG CCT CAT CAG AGA GCA CAG AAG ACT GGG GAT ATT CTG
Ser Ser Val Ile Ser Thr Tyr Gly Pro His Gln Arg Ala Gln Lys Thr Gly Asp Ile Leu>

370         380         390         400         410         420
CTG GGC GGG CTG TTT CCA ATG CAC TTT GGT GTT ACC TCC AAA GAC CAA GAC CTG GCA GCG
Leu Gly Gly Leu Phe Pro Met His Phe Gly Val Thr Ser Lys Asp Gln Asp Leu Ala Ala>

430         440         450         460         470         480
CGG CCA GAA TCC ACA GAG TGT GTT AGG TAC AAT TTC CGG GGA TTC CGT TGG CTT CAG GCC
Arg Pro Glu Ser Thr Glu Cys Val Arg Tyr Asn Phe Arg Gly Phe Arg Trp Leu Gln Ala>

490         500         510         520         530         540
ATG ATT TTT GCA ATA GAG GAG ATC AAC AAC AGC AGT ACT CTC CTG CCC AAC ATC ACA CTG
Met Ile Phe Ala Ile Glu Glu Ile Asn Asn Ser Ser Thr Leu Leu Pro Asn Ile Thr Leu>

550         560         570         580         590         600
GGC TAC AGG ATC TTT GAC ACC TGC AAC ACC GTG TCC AAG GCC CTG GAG GCT ACC CTC AGT
Gly Tyr Arg Ile Phe Asp Thr Cys Asn Thr Val Ser Lys Ala Leu Glu Ala Thr Leu Ser>

610         620         630         640         650         660
TTC GTA GCA CAG AAT AAG ATT GAC TCT CTG AAC TTG GAT GAA TTC TGT AAC TGC ACT GAT
Phe Val Ala Gln Asn Lys Ile Asp Ser Leu Asn Leu Asp Glu Phe Cys Asn Cys Thr Asp>

670         680         690         700         710         720
CAC ATC CCA TCG ACT ATA GCA GTG GTG GGG GCT TCT GGG TCA GCG GTC TCC ACT GCT GTT
His Ile Pro Ser Thr Ile Ala Val Val Gly Ala Ser Gly Ser Ala Val Ser Thr Ala Val>

730         740         750         760         770         780
GCC AAT CTG TTG GGC CTT TTC TAC ATC CCA CAG ATC AGC TAT GCC TCT TCC AGT CGC CTA
Ala Asn Leu Leu Gly Leu Phe Tyr Ile Pro Gln Ile Ser Tyr Ala Ser Ser Ser Arg Leu>

790         800         810         820         830         840
CTA AGC AAC AAG AAC CAG TTC AAA TCC TTC ATG AGG ACC ATT CCC ACA GAT GAG CAC CAG
Leu Ser Asn Lys Asn Gln Phe Lys Ser Phe Met Arg Thr Ile Pro Thr Asp Glu His Gln>

850         860         870         880         890         900
GCC ACT GCC ATG GCA GAT ATC ATC GAC TAC TTC CAA TGG AAT TGG GTC ATT GCA GTT GCG
Ala Thr Ala Met Ala Asp Ile Ile Asp Tyr Phe Gln Trp Asn Trp Val Ile Ala Val Ala>

910         920         930         940         950         960
TCT GAT GAT GAG TAT GGA CGT CCG GGG ATT GAA AAA TTT GAG AAA GAG ATG GAA GAA CGA
Ser Asp Asp Glu Tyr Gly Arg Pro Gly Ile Glu Lys Phe Glu Lys Glu Met Glu Glu Arg>
```

FIG. 10A

```
970         980           990          1000         1010         1020
GAC ATT TGT ATC CAT CTG AGT GAG CTG ATC TCT CAG TAC TTT GAG GAG TGG CAG ATC CAA
Asp Ile Cys Ile His Leu Ser Glu Leu Ile Ser Gln Tyr Phe Glu Glu Trp Gln Ile Gln>

1030         1040          1050         1060         1070         1080
GGA TTG GTT GGC CGT ATT GAG AAC TCC TCA GCT AAA GTT ATA GTC GTT TTC GCC AGT GGG
Gly Leu Val Gly Arg Ile Glu Asn Ser Ser Ala Lys Val Ile Val Val Phe Ala Ser Gly>

1090         1100          1110         1120         1130         1140
CCT GAC ATT GAG CCT CTT ATT AAA GAG ATG GTC AGA CGG AAC ATC ACC GAC CGC ATC TGG
Pro Asp Ile Glu Pro Leu Ile Lys Glu Met Val Arg Arg Asn Ile Thr Asp Arg Ile Trp>

1150         1160          1170         1180         1190         1200
TTG GCC AGC GAG GCT TGG GCA ACC ACC TCC CTC ATC GCC AAA CCA GAG TAC CTT GAT GTT
Leu Ala Ser Glu Ala Trp Ala Thr Thr Ser Leu Ile Ala Lys Pro Glu Tyr Leu Asp Val>

1210         1220          1230         1240         1250         1260
GTA GTT GGG ACC ATT GGC TTT GCT CTC AGA GCA GGC GAA ATA CCT GGC TTC AAG GAC TTC
Val Val Gly Thr Ile Gly Phe Ala Leu Arg Ala Gly Glu Ile Pro Gly Phe Lys Asp Phe>

1270         1280          1290         1300         1310         1320
TTA CAA GAG GTC ACA CCA AAG AAA TCC AGC CAC AAT GAA TTT GTC AGG GAG TTT TGG GAG
Leu Gln Glu Val Thr Pro Lys Lys Ser Ser His Asn Glu Phe Val Arg Glu Phe Trp Glu>

1330         1340          1350         1360         1370         1380
GAG ACT TTT AAC TGC TAT CTG GAA GAC AGC CAG AGA CTG AGA GAC AGT GAG AAT GGG AGC
Glu Thr Phe Asn Cys Tyr Leu Glu Asp Ser Gln Arg Leu Arg Asp Ser Glu Asn Gly Ser>

1390         1400          1410         1420         1430         1440
ACC AGT TTC AGA CCA TTG TGT ACT GGC GAG GAG GAC ATT ATG GGT GCA GAG ACC CCA TAT
Thr Ser Phe Arg Pro Leu Cys Thr Gly Glu Glu Asp Ile Met Gly Ala Glu Thr Pro Tyr>

1450         1460          1470         1480         1490         1500
CTG GAT TAC ACT CAT CTT CGT ATT TCC TAT AAT GTG TAT GTT GCA GTT CAC TCC ATT GCA
Leu Asp Tyr Thr His Leu Arg Ile Ser Tyr Asn Val Tyr Val Ala Val His Ser Ile Ala>

1510         1520          1530         1540         1550         1560
CAG GCC CTA CAG GAC ATT CTC ACC TGC ATT CCT GGA CGG GGT CTT TTT TCC AAC AAC TCA
Gln Ala Leu Gln Asp Ile Leu Thr Cys Ile Pro Gly Arg Gly Leu Phe Ser Asn Asn Ser>

1570         1580          1590         1600         1610         1620
TGT GCA GAT ATA AAG AAA ATA GAA GCA TGG CAG GTT CTC AAG CAG CTC AGA CAT TTA AAC
Cys Ala Asp Ile Lys Lys Ile Glu Ala Trp Gln Val Leu Lys Gln Leu Arg His Leu Asn>

1630         1640          1650         1660         1670         1680
TTC TCA AAC AGT ATG GGA GAA AAG GTA CAT TTT GAT GAG AAT GCT GAT CCG TCA GGA AAC
Phe Ser Asn Ser Met Gly Glu Lys Val His Phe Asp Glu Asn Ala Asp Pro Ser Gly Asn>

1690         1700          1710         1720         1730         1740
TAC ACC ATT ATC AAT TGG CAC CGG TCT CCT GAG GAT GGT TCT GTT GTG TTT GAA GAG GTC
Tyr Thr Ile Ile Asn Trp His Arg Ser Pro Glu Asp Gly Ser Val Val Phe Glu Glu Val>

1750         1760          1770         1780         1790         1800
GGT TTC TAC AAC ATG CGA GCT AAG AGA GGA GTA CAA CTT TTC ATT GAT AAC ACA AAG ATT
Gly Phe Tyr Asn Met Arg Ala Lys Arg Gly Val Gln Leu Phe Ile Asp Asn Thr Lys Ile>

```
       CTA TGG AAT GGA TAT AAT ACT GAG GTT CCA TTC TCT AAC TGT AGT GAA GAT TGT GAA CCA
       Leu Trp Asn Gly Tyr Asn Thr Glu Val Pro Phe Ser Asn Cys Ser Glu Asp Cys Glu Pro>

1870         1880         1890         1900         1910         1920
       GGC ACC AGA AAG GGG ATC ATA GAA AGC ATG CCA ACG TGT TGC TTT GAA TGT ACA GAA TGC
       Gly Thr Arg Lys Gly Ile Ile Glu Ser Met Pro Thr Cys Cys Phe Glu Cys Thr Glu Cys>

1930         1940         1950         1960         1970         1980
       TCA GAA GGA GAG TAT AGT GAT CAC AAA GAT GCC AGT GTT TGT ACC AAG TGT CCC AAT GAC
       Ser Glu Gly Glu Tyr Ser Asp His Lys Asp Ala Ser Val Cys Thr Lys Cys Pro Asn Asp>

1990         2000         2010         2020         2030         2040
       TCA TGG TCT AAT GAG AAC CAC ACA TCT TGT TTC CTG AAG GAG ATA GAG TTT CTG TCT TGG
       Ser Trp Ser Asn Glu Asn His Thr Ser Cys Phe Leu Lys Glu Ile Glu Phe Leu Ser Trp>

2050         2060         2070         2080         2090         2100
       ACA GAG CCC TTT GGG ATC GCC TTG GCA TTA TGC TCT GTG CTG GGG GTA TTC TTG ACA GCA
       Thr Glu Pro Phe Gly Ile Ala Leu Ala Leu Cys Ser Val Leu Gly Val Phe Leu Thr Ala>

2110         2120         2130         2140         2150         2160
       TTC GTG ATG GGA GTG TTT ATC AAA TTT CGC AAC ACC CCA ATT GTT AAG GCC ACA AAC AGA
       Phe Val Met Gly Val Phe Ile Lys Phe Arg Asn Thr Pro Ile Val Lys Ala Thr Asn Arg>

2170         2180         2190         2200         2210         2220
       GAG CTA TCC TAC CTC CTC CTG TTC TCA CTC ATC TGC TGT TTC TCC AGT CCC CTC ATC TTC
       Glu Leu Ser Tyr Leu Leu Leu Phe Ser Leu Ile Cys Cys Phe Ser Ser Ser Leu Ile Phe>

2230         2240         2250         2260         2270         2280
       ATT GGT GAA CCC CAG GAC TGG ACA TGC CGT CTA CGC CAG CCT GCA TTC GGG ATA AGT TTT
       Ile Gly Glu Pro Gln Asp Trp Thr Cys Arg Leu Arg Gln Pro Ala Phe Gly Ile Ser Phe>

2290         2300         2310         2320         2330         2340
       GTT CTC TGC ATC TCC TGC ATC CTG GTA AAA ACT AAC CGA GTA CTT CTA GTG TTC GAA GCC
       Val Leu Cys Ile Ser Cys Ile Leu Val Lys Thr Asn Arg Val Leu Leu Val Phe Glu Ala>

2350         2360         2370         2380         2390         2400
       AAG ATC CCC ACC AGT CTC CAT CGT AAG TGG TGG GGG CTA AAC TTG CAG TTC CTG TTA GTG
       Lys Ile Pro Thr Ser Leu His Arg Lys Trp Trp Gly Leu Asn Leu Gln Phe Leu Leu Val>

2410         2420         2430         2440         2450         2460
       TTC CTG TTC ACA TTT GTG CAA GTG ATG ATA TGT GTG GTC TGG CTT TAC AAT GCT CCT CCG
       Phe Leu Phe Thr Phe Val Gln Val Met Ile Cys Val Val Trp Leu Tyr Asn Ala Pro Pro>

2470         2480         2490         2500         2510         2520
       GCG AGC TAC AGG AAC CAT GAC ATT GAT GAG ATA ATT TTC ATT ACA TGC AAT GAG GGC TCT
       Ala Ser Tyr Arg Asn His Asp Ile Asp Glu Ile Ile Phe Ile Thr Cys Asn Glu Gly Ser>

2530         2540         2550         2560         2570         2580
       ATG ATG GCG CTT GGC TTC CTA ATT GGG TAC ACA TGC CTG CTG GCA GCC ATA TGC TTC TTC
       Met Met Ala Leu Gly Phe Leu Ile Gly Tyr Thr Cys Leu Leu Ala Ala Ile Cys Phe Phe>

2590         2600         2610         2620         2630         2640
       TTT GCA TTT AAA TCA CGA AAA CTG CCA GAG AAC TTT ACT GAG GCT AAG TTC ATC ACC TTC
       Phe Ala Phe Lys Ser Arg Lys Leu Pro Glu Asn Phe Thr Glu Ala Lys Phe Ile Thr Phe>

2650         2660         2670         2680         2690         2700
       AGC ATG CTC ATC TTC TTC ATC GTC TGG ATC TCT TTC ATC CCT GCC TAC TTC AGC ACT TAC
       Ser Met Leu Ile Phe Phe Ile Val Trp Ile Ser Phe Ile Pro Ala Tyr Phe Ser Thr Tyr>
```

FIG. 10C

```
2710            2720            2730            2740            2750            2760
GGA AAG TTT GTG TCG GCT GTG GAG GTC ATC GCC ATA CTA GCC TCC AGC TTT GGC CTG CTG
Gly Lys Phe Val Ser Ala Val Glu Val Ile Ala Ile Leu Ala Ser Ser Phe Gly Leu Leu>

2770            2780            2790            2800            2810            2820
GCC TGT ATT TTC TTC AAT AAA GTC TAC ATC ATC CTC TTC AAA CCG TCA GGA ACT ATA
Ala Cys Ile Phe Phe Asn Lys Val Tyr Ile Ile Leu Phe Lys Pro Ser Arg Asn Thr Ile>

2830            2840            2850            2860            2870            2880
GAG GAG GTT CGC TGT AGC ACT GCG GCC CAT TCT TTC AAA GTG GCA GCC AAG GCC ACT CTG
Glu Glu Val Arg Cys Ser Thr Ala Ala His Ser Phe Lys Val Ala Ala Lys Ala Thr Leu>

2890            2900            2910            2920            2930            2940
AGA CAC AGC TCA GCC TCC AGG AAG AGG TCC AGC AGT GTG GGG GGA TCC TGT GCC TCA ACT
Arg His Ser Ser Ala Ser Arg Lys Arg Ser Ser Ser Val Gly Gly Ser Cys Ala Ser Thr>

2950            2960            2970            2980            2990            3000
CCC TCC TCA TCC ATC AGC CTC AAG ACC AAT GAC AAT GAC TCC CCA TCA GGT CAG CAG AGA
Pro Ser Ser Ser Ile Ser Leu Lys Thr Asn Asp Asn Asp Ser Pro Ser Gly Gln Gln Arg>

3010            3020            3030            3040            3050            3060
ATC CAT AAG CCA AGA GTA AGC TTT GGA AGT GGA ACA GTT ACT CTG TCC TTG AGC TTT GAG
Ile His Lys Pro Arg Val Ser Phe Gly Ser Gly Thr Val Thr Leu Ser Leu Ser Phe Glu>

3070            3080            3090            3100            3110            3120
GAG TCC AGA AAG AAT TCT ATG AAG TAG GGAAGTGTCTTTTGGTGGGCCGAGA
Glu Ser Arg Lys Asn Ser Met Lys ***> (SEQ ID NO: 10)

3130      3140      3150      3160      3170      3180      3190      3200
GCCTTGTCAAAACCTGAGTTGGTGTTGCATTCTTTGTTGGCTGGGTAGTTGGAGCAGAAATTATGATATTAAAAGCTTTG 3210      3220      3230      3240      3250      3260      3270      3280
ATGTATTCAGAATGGTGACACAGCATAGGTGGCCAAGATTCCATTATATTACAATAATCTGTGTTGTTCATTATGAGGAC 3290      3300      3310      3320      3330      3340      3350      3360
ATTTCAAAATGCTGAAAATCATCAAATACATAATTTACTGAGTTTTCTTGATAATCTTGAGAATAGAATAGCCTATTCAA 3370      3380      3390      3400      3410      3420      3430      3440
GTCATCGTTGAGCAGACATTAATTAACAATGATGTAATACTTTCCATACCTATTTTCTTTAACAATAGATTCACATTGTT 3450      3460      3470      3480      3490      3500      3510      3520
AAAGTTCAACTATGACCTGTAAAATACATGAGGTATAACAGGAGACAATAAAAACTATGCATATCCTAGCTTCTGGGCCTG 3530      3540      3550      3560      3570      3580      3590      3600
AGTAGCAGGCAGTTTACTCTGGGCACGCTTTTCATCCAAACTTCCGAATGCTGCCCCCAATCCTAGTGAGGTTAAAGGCC 3610      3620      3630      3640      3650      3660      3670      3680
CAGTGCAGTCATATCTTTTCTCTAGGCACGCTTTTCATCCAAACTTCCGAATGCGGCTATATCAGTCTCTTTCCTACTGT 3690      3700      3710      3720      3730      3740      3750      3760
CTTTTTCATTAGGCCAGTGTTTAACAACCCTGGTCCTTAAGTACACACAACAGAGCACATTTTTGTTGTAGCCCTGGACA 3770      3780      3790      3800      3810      3820      3830      3840
ATCACTCCTCACTCAGCTCATTGAGGGCCTGATGATTAGTTGACAAGTTGAGTCGGGTGTGCTTGTCCAGGGTTACGATA 3850      3860      3870      3880      3890      3900      3910      3920
CAGATGTGTACTGTTGGGGGTGCTCGAGGACCAGGATTGGGAAACATTACATTAGGACTACTGTAGGTTCTTCAATATGG
```

FIG. 10D

```
      3930      3940      3950      3960      3970      3980      3990      4000
TGTCATACGGTCATATGGTGTCATATGGTGTCTGGTTGTTTTCTGCATATGTGTATTTCACCAAGTTACTGCACATGTTA 4010      4020      4030
GACCTATACACTGGAATAAACATTTTTTTTC  (SEQ ID NO: 9)
```

FIG. 10E

Sequence Range: 1 to 3824

```
          10        20        30        40        50        60        70        80
GTTCCAACAGCATATTTTTGTTGTATTTGCTTTGGTTTGTCTGAAATCAAGCATTATCAAGATCAAGAACAGCATGAGTC 90       100       110       120       130       140       150       160
AGAAACAAGGCGACAGCCAGAGTCACTGGAGGGGACAAGACTGAGGTTAACTCTGAAGTCTAATGTGCTGAGAGGACAAG 170       180       190       200       210       220
GCCCTCCTGAGAGCTGAACG ATG AGA TTT TAC CTG TAT TAC CTG GTG CTT TTG GGC TTC AGT TCT
                     Met Arg Phe Tyr Leu Tyr Tyr Leu Val Leu Leu Gly Phe Ser Ser>

230       240       250       260       270       280
GTC ATC TCC ACC TAT GGG CCT CAT CAG AGA GCA CAG AAG ACT GGG GAT ATT CTG CTG GGC
Val Ile Ser Thr Tyr Gly Pro His Gln Arg Ala Gln Lys Thr Gly Asp Ile Leu Leu Gly>

290       300       310       320       330       340
GGG CTG TTT CCA ATG CAC TTT GGT GTT ACC TCC AAA GAC CAA GAC CTG GCA GCG CGG CCA
Gly Leu Phe Pro Met His Phe Gly Val Thr Ser Lys Asp Gln Asp Leu Ala Ala Arg Pro>

350       360       370       380       390       400
GAA TCC ACA GAG TGT GTT AGG TAC AAT TTC CGG GGA TTC CGT TGG CTT CAG GCC ATG ATT
Glu Ser Thr Glu Cys Val Arg Tyr Asn Phe Arg Gly Phe Arg Trp Leu Gln Ala Met Ile>

410       420       430       440       450       460
TTT GCA ATA GAG GAG ATC AAC AAC AGC AGT ACT CTC CTG CCC AAC ATC ACA CTG GGC TAC
Phe Ala Ile Glu Glu Ile Asn Asn Ser Ser Thr Leu Leu Pro Asn Ile Thr Leu Gly Tyr>

470       480       490       500       510       520
AGG ATC TTT GAC ACC TGC AAC ACC GTG TCC AAG GCC CTG GAG GCT ACC CTC AGT TTC GTA
Arg Ile Phe Asp Thr Cys Asn Thr Val Ser Lys Ala Leu Glu Ala Thr Leu Ser Phe Val>

530       540       550       560       570       580
GCA CAG AAT AAG ATT GAC TCT CTG AAC TTG GAT GAA TTC TGT AAC TGC ACT GAT CAC ATC
Ala Gln Asn Lys Ile Asp Ser Leu Asn Leu Asp Glu Phe Cys Asn Cys Thr Asp His Ile>

590       600       610       620       630       640
CCA TCG ACT ATA GCA GTG GTG GGG GCT TCT GGG TCA GCG GTC TCC ACT GCT GTT GCC AAT
Pro Ser Thr Ile Ala Val Val Gly Ala Ser Gly Ser Ala Val Ser Thr Ala Val Ala Asn>

650       660       670       680       690       700
CTG TTG GGC CTT TTC TAC ATC CCA CAG ATC AGC TAT GCC TCT TCC AGT CGC CTA CTA AGC
Leu Leu Gly Leu Phe Tyr Ile Pro Gln Ile Ser Tyr Ala Ser Ser Ser Arg Leu Leu Ser>

710       720       730       740       750       760
AAC AAG AAC CAG TTC AAA TCC TTC ATG AGG ACC ATT CCC ACA GAT GAG CAC CAG GCC ACT
Asn Lys Asn Gln Phe Lys Ser Phe Met Arg Thr Ile Pro Thr Asp Glu His Gln Ala Thr>

770       780       790       800       810       820
GCC ATG GCA GAT ATC ATC GAC TAC TTC CAA TGG AAT TGG GTC ATT GCA GTT GCG TCT GAT
Ala Met Ala Asp Ile Ile Asp Tyr Phe Gln Trp Asn Trp Val Ile Ala Val Ala Ser Asp>

830       840       850       860       870       880
GAT GAG TAT GGA CGT CCG GGG ATT GAA AAA TTT GAG AAA GAG ATG GAA GAA CGA GAC ATT
Asp Glu Tyr Gly Arg Pro Gly Ile Glu Lys Phe Glu Lys Glu Met Glu Glu Arg Asp Ile>
```

FIG. 11A

```
      890         900         910         920         930         940
TGT ATC CAT CTG AGT GAG CTG ATC TCT CAG TAC TTT GAG GAG TGG CAG ATC CAA GGA TTG
Cys Ile His Leu Ser Glu Leu Ile Ser Gln Tyr Phe Glu Glu Trp Gln Ile Gln Gly Leu>

950         960         970         980         990        1000
GTT GAC CGT ATT GAG AAC TCC TCA GCT AAA GTT ATA GTC GTT TTC GCC AGT GGG CCT GAC
Val Asp Arg Ile Glu Asn Ser Ser Ala Lys Val Ile Val Val Phe Ala Ser Gly Pro Asp>

1010        1020        1030        1040        1050        1060
ATT GAG CCT CTT ATT AAA GAG ATG GTC AGA CGG AAC ATC ACC GAC CGC ATC TGG TTG GCC
Ile Glu Pro Leu Ile Lys Glu Met Val Arg Arg Asn Ile Thr Asp Arg Ile Trp Leu Ala>

1070        1080        1090        1100        1110        1120
AGC GAG GCT TGG GCA ACC ACC TCC CTC ATC GCC AAA CCA GAG TAC CTT GAT GTT GTA GTT
Ser Glu Ala Trp Ala Thr Thr Ser Leu Ile Ala Lys Pro Glu Tyr Leu Asp Val Val Val>

1130        1140        1150        1160        1170        1180
GGG ACC ATT GGC TTT GCT CTC AGA GCA GGC GAA ATA CCT GGC TTC AAG GAC TTC TTA CAA
Gly Thr Ile Gly Phe Ala Leu Arg Ala Gly Glu Ile Pro Gly Phe Lys Asp Phe Leu Gln>

1190        1200        1210        1220        1230        1240
GAG GTC ACA CCA AAG AAA TCC AGC CAC AAT GAA TTT GTC AGG GAG TTT TGG GAG GAG ACT
Glu Val Thr Pro Lys Lys Ser Ser His Asn Glu Phe Val Arg Glu Phe Trp Glu Glu Thr>

1250        1260        1270        1280        1290        1300
TTT AAC TGC TAT CTG GAA GAC AGC CAG AGA CTG AGA GAC AGT GAG AAT GGG AGC ACC AGT
Phe Asn Cys Tyr Leu Glu Asp Ser Gln Arg Leu Arg Asp Ser Glu Asn Gly Ser Thr Ser>

1310        1320        1330        1340        1350        1360
TTC AGA CCA TTG TGT ACT GGC GAG GAG GAC ATT ATG GGT GCA GAG ACC CCA TAT CTG GAT
Phe Arg Pro Leu Cys Thr Gly Glu Glu Asp Ile Met Gly Ala Glu Thr Pro Tyr Leu Asp>

1370        1380        1390        1400        1410        1420
TAC ACT CAT CTT CGT ATT TCC TAT AAT GTG TAT GTT GCA GTT CAC TCC ATT GCA CAG GCC
Tyr Thr His Leu Arg Ile Ser Tyr Asn Val Tyr Val Ala Val His Ser Ile Ala Gln Ala>

1430        1440        1450        1460        1470        1480
CTA CAG GAC ATT CTC ACC TGC ATT CCT GGA CGG GGT TTT TTT TCC AAC AAC TCA TGT GCA
Leu Gln Asp Ile Leu Thr Cys Ile Pro Gly Arg Gly Phe Phe Ser Asn Asn Ser Cys Ala>

1490        1500        1510        1520        1530        1540
GAT ATA AAG AAA ATA GAA GCA TGG CAG GTT CTC AAG CAG CTC AGA CAT TTA AAC TTC TCA
Asp Ile Lys Lys Ile Glu Ala Trp Gln Val Leu Lys Gln Leu Arg His Leu Asn Phe Ser>

1550        1560        1570        1580        1590        1600
AAC AGT ATG GGA GAA AAG GTA CAT TTT GAT GAG AAT GCT GAT CCG TCA GGA AAC TAC ACC
Asn Ser Met Gly Glu Lys Val His Phe Asp Glu Asn Ala Asp Pro Ser Gly Asn Tyr Thr>

1610        1620        1630        1640        1650        1660
ATT ATC AAT TGG CAC CGG TCT CCT GAG GAT GGT TCT GTT GTG TTT GAA GAG GTC GGT TTC
Ile Ile Asn Trp His Arg Ser Pro Glu Asp Gly Ser Val Val Phe Glu Glu Val Gly Phe>

1670        1680        1690        1700        1710        1720
TAC AAC ATG CGA GCT AAG AGA GGA GTA CAA CTT TTC ATT GAT AAC ACA AAG ATT CTA TGG
Tyr Asn Met Arg Ala Lys Arg Gly Val Gln Leu Phe Ile Asp Asn Thr Lys Ile Leu Trp>
```

FIG. 11B

```
     1730          1740          1750          1760          1770          1780
AAT GGA TAT AAT ACT GAG GTT CCA TTC TCT AAC TGT AGT GAA GAT TGT GAA CCA GGC ACC
Asn Gly Tyr Asn Thr Glu Val Pro Phe Ser Asn Cys Ser Glu Asp Cys Glu Pro Gly Thr>

1790          1800          1810          1820          1830          1840
AGA AAG GGG ATC ATA GAA AGC ATG CCA ACG TGT TGC TTT GAA TGT ACA GAA TGC TCA GAA
Arg Lys Gly Ile Ile Glu Ser Met Pro Thr Cys Cys Phe Glu Cys Thr Glu Cys Ser Glu>

1850          1860          1870          1880          1890          1900
GGA GAG TAT AGT GAT CAC AAA GAT GCC AGT GTT TGT ACC AAG TGT CCC AAT GAC TCA TGG
Gly Glu Tyr Ser Asp His Lys Asp Ala Ser Val Cys Thr Lys Cys Pro Asn Asp Ser Trp>

1910          1920          1930          1940          1950          1960
TCT AAT GAG AAC CAC ACA TCT TGT TTC CTG AAG GAG ATA GAG TTT CTG TCT TGG ACA GAG
Ser Asn Glu Asn His Thr Ser Cys Phe Leu Lys Glu Ile Glu Phe Leu Ser Trp Thr Glu>

1970          1980          1990          2000          2010          2020
CCC TTT GGG ATC GCC TTG GCA TTA TGC TCT GTG CTG GGG GTA TTC TTG ACA GCA TTC GTG
Pro Phe Gly Ile Ala Leu Ala Leu Cys Ser Val Leu Gly Val Phe Leu Thr Ala Phe Val>

2030          2040          2050          2060          2070          2080
ATG GGA GTG TTT ATC AAA TTT CGC AAC ACC CCA ATT GTT AAG GCC ACA AAC AGA GAG CTA
Met Gly Val Phe Ile Lys Phe Arg Asn Thr Pro Ile Val Lys Ala Thr Asn Arg Glu Leu>

2090          2100          2110          2120          2130          2140
TCC TAC CTC CTC CTG TTC TCA CTC ATC TGC TGT TTC TCC AGT TCC CTC ATC TTC ATT GGT
Ser Tyr Leu Leu Leu Phe Ser Leu Ile Cys Cys Phe Ser Ser Ser Leu Ile Phe Ile Gly>

2150          2160          2170          2180          2190          2200
GAA CCC CAG GAC TGG ACA TGC CGT CTA CGC CAG CCT GCA TTC GGG ATA AGT TTT GTT CTC
Glu Pro Gln Asp Trp Thr Cys Arg Leu Arg Gln Pro Ala Phe Gly Ile Ser Phe Val Leu>

2210          2220          2230          2240          2250          2260
TGC ATC TCC TGC ATC CTG GTA AAA ACT AAC CGA GTA CTT CTA GTG TTC GAA GCC AAG ATC
Cys Ile Ser Cys Ile Leu Val Lys Thr Asn Arg Val Leu Leu Val Phe Glu Ala Lys Ile>

2270          2280          2290          2300          2310          2320
CCC ACC AGT CTC CAT CGT AAG TGG TGG GGG CTA AAC TTG CAG TTC CTG TTA GTG TTC CTG
Pro Thr Ser Leu His Arg Lys Trp Trp Gly Leu Asn Leu Gln Phe Leu Leu Val Phe Leu>

2330          2340          2350          2360          2370          2380
TTC ACA TTT GTG CAA GTG ATG ATA TGT GTG GTC TGG CTT TAC AAT GCT CCT CCG GCG AGC
Phe Thr Phe Val Gln Val Met Ile Cys Val Val Trp Leu Tyr Asn Ala Pro Pro Ala Ser>

2390          2400          2410          2420          2430          2440
TAC AGG AAC CAT GAC ATT GAT GAG ATA ATT TTC ATT ACA TGC AAT GAG GGC TCT ATG ATG
Tyr Arg Asn His Asp Ile Asp Glu Ile Ile Phe Ile Thr Cys Asn Glu Gly Ser Met Met>

2450          2460          2470          2480          2490          2500
GCG CTT GGC TTC CTA ATT GGG TAC ACA TGC CTG CTG GCA GCC ATA TGC TTC TTC TTT GCA
Ala Leu Gly Phe Leu Ile Gly Tyr Thr Cys Leu Leu Ala Ala Ile Cys Phe Phe Phe Ala>

2510          2520          2530          2540          2550          2560
TTT AAA TCA CGA AAA CTG CCA GAG AAC TTT ACT GAG GCT AAG TTC ATC ACC TTC AGC ATG
Phe Lys Ser Arg Lys Leu Pro Glu Asn Phe Thr Glu Ala Lys Phe Ile Thr Phe Ser Met>
```

FIG. 11C

```
     2570         2580          2590         2600          2610          2620
CTC ATC TTC TTC ATC GTC TGG ATC TCT TTC ATC CCT GCC TAC TTC AGC ACT TAC GGA AAG
Leu Ile Phe Phe Ile Val Trp Ile Ser Phe Ile Pro Ala Tyr Phe Ser Thr Tyr Gly Lys>

2630         2640          2650         2660          2670          2680
TTT GTG TCG GCT GTG GAG GTC ATC GCC ATA CTA GCC TCC AGC TTT GGC CTG CTG GCC TGT
Phe Val Ser Ala Val Glu Val Ile Ala Ile Leu Ala Ser Ser Phe Gly Leu Leu Ala Cys>

2690         2700          2710         2720          2730
ATT TTC TTC AAT AAA GTC TAC ATC ATC CAT CAG CCT CAA GAC CAA TGA
Ile Phe Phe Asn Lys Val Tyr Ile Ile His Gln Pro Gln Asp Gln ***>(SEQ ID NO: 12)

2740      2750      2760      2770      2780      2790      2800
CAATGACTCCCCATCAGGTCAGCAGAGAATCCATAAGCCAAGAGTAAGCTTTGGAAGTGGAACAGTT 2810      2820      2830      2840      2850      2860      2870      2880
ACTCTGTCCTTGAGCTTTGAGGAGTCCAGAAAGAATTCTATGAAGTAGGGAAGTGTCTTTTGGTGGGCCGAGAGCCTTGT 2890      2900      2910      2920      2930      2940      2950      2960
CAAAACCTGAGTTGGTGTTGCATTCTTTGTTGGCTGGGTAGTTGGAGCAGAAATTATGATATTAAAAGCTTTGATGTATT 2970      2980      2990      3000      3010      3020      3030      3040
CAGAATGGTGACACAGCATAGGTGGCCAAGATTCCATTATATTACAATAATCTGTGTTGTTCATTATGAGGACATTTCAA 3050      3060      3070      3080      3090      3100      3110      3120
AATGCTGAAAATCATCAAATACATAATTTACTGAGTTTTCTTGATAATCTTGAGAATAGAATAGCCTATTCAAGTCATCG 3130      3140      3150      3160      3170      3180      3190      3200
TTGAGCAGACATTAATTAACAATGATGTAATACTTTCCATACCTATTTTCTTTAACAATAGATTCACATTGTTAAAGTTC 3210      3220      3230      3240      3250      3260      3270      3280
AACTATGACCTGTAAAATACATGAGGTATAACAGGAGACAATAAAACTATGCATATCCTAGCTTCTGGGCCTGAGTAGCA 3290      3300      3310      3320      3330      3340      3350      3360
GGCAGTTTACTCTGGGCACGCTTTTCATCCAAACTTCCGAATGCTGCCCCCAATCCTAGTGAGGTTAAAGGCCCAGTGCA 3370      3380      3390      3400      3410      3420      3430      3440
GTCATATCTTTTCTCTAGGCACGCTTTTCATCCAAACTTCCGAATGCGGCTATATCAGTCTCTTTCCTACTGTCTTTTTC 3450      3460      3470      3480      3490      3500      3510      3520
ATTAGGCCAGTGTTTAACAACCCTGGTCCTTGAGTACACACAACAGGGCACATTTTTGTTGTAGCCCTGGACAATCACTC 3530      3540      3550      3560      3570      3580      3590      3600
CTCACTCAGCTCATTGAGGGCCTGATGATTAGTTGACAAGTTGGGTCAGGTGTGCTTGTCCAGGGTTACAATACAGATGT 3610      3620      3630      3640      3650      3660      3670      3680
GTGCTGTTGGGGGTACTCGAGGACCAGGATTGGGAAACATTACATTAGGACTACTGTAGGTTCTTCAATATGGTGTCATA 3690      3700      3710      3720      3730      3740      3750      3760
CGGTCATATGGTGTCATATGGTGTCTGGTTGTTTTCTGCATATGTGTATTTCACCAAGTTACTGCACATGTTAGACCTAT 3770      3780      3790      3800      3810      3820
ACACTGGAATAAACATTTTTTTTCACAATGCATCCAATGACAATAAAATCACCATATGCCAATG(SEQ ID NO: 11)
```

FIG. 11D

Range: 1 to 3988

```
         10        20        30        40        50        60        70        80
GTTCCAACAGCATATTTTTGTTGTATTTGCTTTGGTTTGTCTGAAATCAAGCATTATCAAGATCAAGAACAGCATGAGTC 90       100       110       120       130       140       150       160
AGAAACAAGGCGACAGCCAGAGTCACTGGAGGGGACAAGACTGAGGTTAACTCTGAAGTCTAATGTGCTGAGAGGACAAG 170        180          190         200         210         220
GCCCTCCTGAGAGCTGAACG ATG AGA TTT TAC CTG TAT TAC CTG GTG CTT TTG GGC TTC AGT TCT
                     Met Arg Phe Tyr Leu Tyr Tyr Leu Val Leu Leu Gly Phe Ser Ser>

230         240         250         260         270         280
GTC ATC TCC ACC TAT GGG CCT CAT CAG AGA GCA CAG AAG ACT GGG GAT ATT CTG CTG GGC
Val Ile Ser Thr Tyr Gly Pro His Gln Arg Ala Gln Lys Thr Gly Asp Ile Leu Leu Gly>

290         300         310         320         330         340
GGG CTG TTT CCA ATG CAC TTT GGT GTT ACC TCC AAA GAC CAA GAC CTG GCA GCG CGG CCA
Gly Leu Phe Pro Met His Phe Gly Val Thr Ser Lys Asp Gln Asp Leu Ala Ala Arg Pro>

350         360         370         380         390         400
GAA TCC ACA GAG TGT GTT AGG TAC AAT TTC CGG GGA TTC CGT TGG CTT CAG GCC ATG ATT
Glu Ser Thr Glu Cys Val Arg Tyr Asn Phe Arg Gly Phe Arg Trp Leu Gln Ala Met Ile>

410         420         430         440         450         460
TTT GCA ATA GAG GAG ATC AAC AAC AGC AGT ACT CTC CTG CCC AAC ATC ACA CTG GGC TAC
Phe Ala Ile Glu Glu Ile Asn Asn Ser Ser Thr Leu Leu Pro Asn Ile Thr Leu Gly Tyr>

470         480         490         500         510         520
AGG ATC TTT GAC ACC TGC AAC ACC GTG TCC AAG GCC CTG GAG GCT ACC CTC AGT TTC GTA
Arg Ile Phe Asp Thr Cys Asn Thr Val Ser Lys Ala Leu Glu Ala Thr Leu Ser Phe Val>

530         540         550         560         570         580
GCA CAG AAT AAG ATT GAC TCT CTG AAC TTG GAT GAA TTC TGT AAC TGC ACT GAT CAC ATC
Ala Gln Asn Lys Ile Asp Ser Leu Asn Leu Asp Glu Phe Cys Asn Cys Thr Asp His Ile>

590         600         610         620         630         640
CCA TCG ACT ATA GCA GTG GTG GGG GCT TCT GGG TCA GCG GTC TCC ACT GCT GTT GCC AAT
Pro Ser Thr Ile Ala Val Val Gly Ala Ser Gly Ser Ala Val Ser Thr Ala Val Ala Asn>

650         660         670         680         690         700
CTG TTG GGC CTT TTC TAC ATC CCA CAG ATC AGC TAT GCC TCT TCC AGT CGC CTA CTA AGC
Leu Leu Gly Leu Phe Tyr Ile Pro Gln Ile Ser Tyr Ala Ser Ser Ser Arg Leu Leu Ser>

710         720         730         740         750         760
AAC AAG AAC CAG TTC AAA TCC TTC ATG AGG ACC ATT CCC ACA GAT GAG CAC CAG GCC ACT
Asn Lys Asn Gln Phe Lys Ser Phe Met Arg Thr Ile Pro Thr Asp Glu His Gln Ala Thr>

770         780         790         800         810         820
GCC ATG GCA GAT ATC ATC GAC TAC TTC CAA TGG AAT TGG GTC ATT GCA GTT GCG TCT GAT
Ala Met Ala Asp Ile Ile Asp Tyr Phe Gln Trp Asn Trp Val Ile Ala Val Ala Ser Asp>

830         840         850         860         870         880
GAT GAG TAT GGA CGT CCG GGG ATT GAA AAA TTT GAG AAA GAG ATG GAA GAA CGA GAC ATT
Asp Glu Tyr Gly Arg Pro Gly Ile Glu Lys Phe Glu Lys Glu Met Glu Glu Arg Asp Ile>

890         900         910         920         930         940
TGT ATC CAT CTG AGT GAG CTG ATC TCT CAG TAC TTT GAG GAG TGG CAG ATC CAA GGA TTG
```

FIG. 12A

```
Cys Ile His Leu Ser Glu Leu Ile Ser Gln Tyr Phe Glu Glu Trp Gln Ile Gln Gly Leu>

950         960         970         980         990        1000
GTT GAC CGT ATT GAG AAC TCC TCA GCT AAA GTT ATA GTC GTT TTC GCC AGT GGG CCT GAC
Val Asp Arg Ile Glu Asn Ser Ser Ala Lys Val Ile Val Val Phe Ala Ser Gly Pro Asp>

1010        1020        1030        1040        1050        1060
ATT GAG CCT CTT ATT AAA GAG ATG GTC AGA CGG AAC ATC ACC GAC CGC ATC TGG TTG GCC
Ile Glu Pro Leu Ile Lys Glu Met Val Arg Arg Asn Ile Thr Asp Arg Ile Trp Leu Ala>

1070        1080        1090        1100        1110        1120
AGC GAG GCT TGG GCA ACC ACC TCC CTC ATC GCC AAA CCA GAG TAC CTT GAT GTT GTA GTT
Ser Glu Ala Trp Ala Thr Thr Ser Leu Ile Ala Lys Pro Glu Tyr Leu Asp Val Val Val>

1130        1140        1150        1160        1170        1180
GGG ACC ATT GGC TTT GCT CTC AGA GCA GGA GAA ATA CCT GGC TTC AAG GAC TTC TTA CAA
Gly Thr Ile Gly Phe Ala Leu Arg Ala Gly Glu Ile Pro Gly Phe Lys Asp Phe Leu Gln>

1190        1200        1210        1220        1230        1240
GAG GTC ACA CCA AAG AAA TCC AGC CAC AAT GAA TTT GTC AGG GAG TTT TGG GAG GAG ACT
Glu Val Thr Pro Lys Lys Ser Ser His Asn Glu Phe Val Arg Glu Phe Trp Glu Glu Thr>

1250        1260        1270        1280        1290        1300
TTT AAC TGC TAT CTG GAA GAC AGC CAG AGA CTG AGA GAC AGT GAG AAT GGG AGC ACC AGT
Phe Asn Cys Tyr Leu Glu Asp Ser Gln Arg Leu Arg Asp Ser Glu Asn Gly Ser Thr Ser>

1310        1320        1330        1340        1350        1360
TTC AGA CCA TTG TGT ACT GGC GAG GAG GAC ATT ATG GGT GCA GAG ACC CCA TAT CTG GAT
Phe Arg Pro Leu Cys Thr Gly Glu Glu Asp Ile Met Gly Ala Glu Thr Pro Tyr Leu Asp>

1370        1380        1390        1400        1410        1420
TAC ACT CAT CTT CGT ATT TCC TAT AAT GTG TAT GTT GCA GTT CAC TCC ATT GCA CAG GCC
Tyr Thr His Leu Arg Ile Ser Tyr Asn Val Tyr Val Ala Val His Ser Ile Ala Gln Ala>

1430        1440        1450        1460        1470        1480
CTA CAG GAC ATT CTC ACC TGC ATT CCT GGA CGG GGT CTT TTT TCC AAC AAC TCA TGT GCA
Leu Gln Asp Ile Leu Thr Cys Ile Pro Gly Arg Gly Leu Phe Ser Asn Asn Ser Cys Ala>

1490        1500        1510        1520        1530        1540
GAT ATA AAG AAA ATA GAA GCA TGG CAG GTT CTC AAG CAG CTC AGA CAT TTA AAC TTC TCA
Asp Ile Lys Lys Ile Glu Ala Trp Gln Val Leu Lys Gln Leu Arg His Leu Asn Phe Ser>

1550        1560        1570        1580        1590        1600
AAC AGT ATG GGA GAA AAG GTA CAT TTT GAT GAG AAT GCT GAT CCG TCA GGA AAC TAC ACC
Asn Ser Met Gly Glu Lys Val His Phe Asp Glu Asn Ala Asp Pro Ser Gly Asn Tyr Thr>

1610        1620        1630        1640        1650        1660
ATT ATC AAT TGG CAC CGG TCT CCT GAG GAT GGT TCT GTT GTG TTT GAA GAG GTC GGT TTC
Ile Ile Asn Trp His Arg Ser Pro Glu Asp Gly Ser Val Val Phe Glu Glu Val Gly Phe>

1670        1680        1690        1700        1710        1720
TAC AAC ATG CGA GCT AAG AGA GGA GTA CAA CTT TTC ATT GAT AAC ACA AAG ATT CTA TGG
Tyr Asn Met Arg Ala Lys Arg Gly Val Gln Leu Phe Ile Asp Asn Thr Lys Ile Leu Trp>

1730        1740        1750        1760        1770        1780
AAT GGA TAT AAT ACT GAG GTT CCA TTC TCT AAC TGT AGT GAA GAT TGT GAA CCA GGC ACC
Asn Gly Tyr Asn Thr Glu Val Pro Phe Ser Asn Cys Ser Glu Asp Cys Glu Pro Gly Thr>
```

FIG. 12B

```
1790            1800            1810            1820            1830            1840
AGA AAG GGG ATC ATA GAA AGC ATG CCA ACG TGT TGC TTT GAA TGT ACA GAA TGC TCA GAA
Arg Lys Gly Ile Ile Glu Ser Met Pro Thr Cys Cys Phe Glu Cys Thr Glu Cys Ser Glu>

1850            1860            1870            1880            1890            1900
GGA GAG TAT AGT GAT CAC AAA GAT GCC AGT GTT TGT ACC AAG TGT CCC AAT GAC TCA TGG
Gly Glu Tyr Ser Asp His Lys Asp Ala Ser Val Cys Thr Lys Cys Pro Asn Asp Ser Trp>

1910            1920            1930            1940            1950            1960
TCT AAT GAG AAC CAC ACA TCT TGT TTC CTG AAG GAG ATA GAG TTT CTG TCT TGG ACA GAG
Ser Asn Glu Asn His Thr Ser Cys Phe Leu Lys Glu Ile Glu Phe Leu Ser Trp Thr Glu>

1970            1980            1990            2000            2010            2020
CCC TTT GGG ATC GCC TTG GCA TTA TGC TCT GTG CTG GGG GTA TTC TTG ACA GCA TTC GTG
Pro Phe Gly Ile Ala Leu Ala Leu Cys Ser Val Leu Gly Val Phe Leu Thr Ala Phe Val>

2030            2040            2050            2060            2070            2080
ATG GGA GTG TTT ATC AAA TTT CGC AAC ACC CCA ATT GTT AAG GCC ACA AAC AGA GAG CTA
Met Gly Val Phe Ile Lys Phe Arg Asn Thr Pro Ile Val Lys Ala Thr Asn Arg Glu Leu>

2090            2100            2110            2120            2130            2140
TCC TAC CTC CTC CTG TTC TCA CTC ATC TGC TGT TTC TCC AGT TCC CTC ATC TTC ATT GGT
Ser Tyr Leu Leu Leu Phe Ser Leu Ile Cys Cys Phe Ser Ser Ser Leu Ile Phe Ile Gly>

2150            2160            2170            2180            2190            2200
GAA CCC CAG GAC TGG ACA TGC CGT CTA CGC CAG CCT GCA TTC GGG ATA AGT TTT GTT CTC
Glu Pro Gln Asp Trp Thr Cys Arg Leu Arg Gln Pro Ala Phe Gly Ile Ser Phe Val Leu>

2210            2220            2230            2240            2250            2260
TGC ATC TCC TGC ATC CTG GTA AAA ACT AAC CGA GTA CTT CTA GTG TTC GAA GCC AAG ATC
Cys Ile Ser Cys Ile Leu Val Lys Thr Asn Arg Val Leu Leu Val Phe Glu Ala Lys Ile>

2270            2280            2290            2300            2310            2320
CCC ACC AGT CTC CAT CGT AAG TGG TGG GGG CTA AAC TTG CAG TTC CTG TTA GTG TTC CTG
Pro Thr Ser Leu His Arg Lys Trp Trp Gly Leu Asn Leu Gln Phe Leu Leu Val Phe Leu>

2330            2340            2350            2360            2370            2380
TTC ACA TTT GTG CAA GTG ATG ATA TGT GTG GTC TGG CTT TAC AAT GCT CCT CCG GCG AGC
Phe Thr Phe Val Gln Val Met Ile Cys Val Val Trp Leu Tyr Asn Ala Pro Pro Ala Ser>

2390            2400            2410            2420            2430            2440
TAC AGG AAC CAT GAC ATT GAT GAG ATA ATT TTC ATT ACA TGC AAT GAG GGC TCT ATG ATG
Tyr Arg Asn His Asp Ile Asp Glu Ile Ile Phe Ile Thr Cys Asn Glu Gly Ser Met Met>

2450            2460            2470            2480            2490            2500
GCG CTT GGC TTC CTA ATT GGG TAC ACA TGC CTG CTG GCA GCC ATA TGC TTC TTC TTT GCA
Ala Leu Gly Phe Leu Ile Gly Tyr Thr Cys Leu Leu Ala Ala Ile Cys Phe Phe Phe Ala>

2510            2520            2530            2540            2550            2560
TTT AAA TCA CGA AAA CTG CCA GAG AAC TTT ACT GAG GCT AAG TTC ATC ACC TTC AGC ATG
Phe Lys Ser Arg Lys Leu Pro Glu Asn Phe Thr Glu Ala Lys Phe Ile Thr Phe Ser Met>

2570            2580            2590            2600            2610            2620
CTC ATC TTC TTC ATC GTC TGG ATC TCT TTC ATC CCT GCC TAC TTC AGC ACT TAC GGA AAG
Leu Ile Phe Phe Ile Val Trp Ile Ser Phe Ile Pro Ala Tyr Phe Ser Thr Tyr Gly Lys>

2630            2640            2650            2660            2670            2680
TTT GTG TCG GCT GTG GAG GTC ATC GCC ATA CTA GCC TCC AGC TTT GGC CTG CTG GCC TGT
```

FIG. 12C

```
Phe Val Ser Ala Val Glu Val Ile Ala Ile Leu Ala Ser Ser Phe Gly Leu Leu Ala Cys>

2690          2700          2710          2720          2730          2740
         ATT TTC TTC AAT AAA GTC TAC ATC ATC CTC TTC AAA CCG TCC AGG AAC ACT ATA GAG GAG
         Ile Phe Phe Asn Lys Val Tyr Ile Ile Leu Phe Lys Pro Ser Arg Asn Thr Ile Glu Glu>

2750          2760          2770          2780          2790          2800
         GTT CGC TGT AGC ACT GCG GCC CAT TCT TTC AAA GTG GCA GCC AAG GCC ACT CTG AGA CAC
         Val Arg Cys Ser Thr Ala Ala His Ser Phe Lys Val Ala Ala Lys Ala Thr Leu Arg His>

2810          2820          2830          2840          2850          2860
         AGC TCA GCC TCC AGG AAG AGG TCC AGC AGT GTG GGG GGA TCC TGT GCC TCA ACT CCC TCC
         Ser Ser Ala Ser Arg Lys Arg Ser Ser Ser Val Gly Gly Ser Cys Ala Ser Thr Pro Ser>

2870          2880          2890          2900          2910          2920
         TCA TCC ATC AGC CTC AAG ACC AAT GAC AAT GAC TCC CCA TCA GGT CAG CAG AGA ATC CAT
         Ser Ser Ile Ser Leu Lys Thr Asn Asp Asn Asp Ser Pro Ser Gly Gln Gln Arg Ile His>

2930          2940          2950          2960          2970          2980
         AAG CCA AGA GTA AGC TTT GGA AGT GGA ACA GTT ACT CTG TCC TTG AGC TTT GAG GAG TCC
         Lys Pro Arg Val Ser Phe Gly Ser Gly Thr Val Thr Leu Ser Leu Ser Phe Glu Glu Ser>

2990          3000          3010     3020        3030          3040
         AGA AAG AAT TCT ATG AAG TAG GGAAGTGTCTTTTGGTGGGCCGAGAGCCTTGTCA
         Arg Lys Asn Ser Met Lys ***> (SEQ ID NO: 14)
         3050       3060       3070       3080       3090       3100       3110       3120
AAACCTGAGTTGGTGTTGCATTCTTTGTTGGCTGGGTAGTTGGAGCAGAAATTATGATATTAAAAGCTTTGATGTATTCA 3130       3140       3150       3160       3170       3180       3190       3200
GAATGGTGACACAGCATAGGTGGCCAAGATTCCATTATATTACAATAATCTGTGTTGTTCATTATGAGGACATTTCAAAA 3210       3220       3230       3240       3250       3260       3270       3280
TGCTGAAAATCATCAAATACATAATTTACTGAGTTTTCTTGATAATCTTGAGAATAGAATAGCCTATTCAAGTCATCGTT 3290       3300       3310       3320       3330       3340       3350       3360
GAGCAGACATTAATTAACAATGATGTAATACTTTCCATACCTATTTTCTTTAACAATAGATTCACATTGTTAAAGTTCAA 3370       3380       3390       3400       3410       3420       3430       3440
CTATGACCTGTAAAATACATGAGGTATAACAGGAGACAATAAAACTATGCATATCCTAGCTTCTGGGCCTGAGTAGCAGG 3450       3460       3470       3480       3490       3500       3510       3520
CAGTTTACTCTGGGCACGCTTTTCATCCAAACTTCCGAATGCTGCCCCCAATCCTAGTGAGGTTAAAGGCCCAGTGCAGT 3530       3540       3550       3560       3570       3580       3590       3600
CATATCTTTTCTCTAGGCACGCTTTTCATCCAAACTTCCGAATGCGGCTATATCAGTCTCTTTCCTACTGTCTTTTTCAT 3610       3620       3630       3640       3650       3660       3670       3680
TAGGCCAGTGTTTAACAACCCTGGTCCTTAAGTGCACACAACAGGGCACATTTTTGTTGTGGCCCTGGACAATCACTCCT 3690       3700       3710       3720       3730       3740       3750       3760
CACTCAGCTCATTGAGGGCCTGATGATTAGTTGACAAGTTGAGTCAGGTGTGCTTGTCCGGGGTTGCAATACAGATGTGT 3770       3780       3790       3800       3810       3820       3830       3840
ACTGTTGGGGGTGCTCGAGGACCAGGATTGGGAAACATTACATTAGGACTACTGTAGGTTCTTCAATATGGTGTCATACG 3850       3860       3870       3880       3890       3900       3910       3920
GTCATATGGTGTCATATGGTGTCTGGTTGTTTTCTGCATATGTGTATTTCACCAAGTTACTGCACATGTTAGACCTATAC
```

FIG. 12D

```
      3930      3940      3950      3960      3970      3980
ACTGGAATAAACATTTTTTTTCACAATGCATCCAATGACAATAAAATCACCATATGCCAATGAAAAAA
                                                          (SEQ ID NO: 13)
```

FIG. 12E

```
SalmoKCaR 1  - T T C C A A C A G C A T A T T T T T G T T G T A T T T G C T T T G G T T T G T  39
SalmoKCaR 2  G T T C C A A C A G C A T A T T T T T G T T G T A T T T G C T T T G G T T T G T  40
SalmoKCaR 3  G T T C C A A C A G C A T A T T T T T G T T G T A T T T G C T T T G G T T T G T  40
Salmon A26   - - - - - - - - - - - - - - - - - - - - - - - - - - - - - - - - - - - - - - -   0
Salmon PCR   - - - - - - - - - - - - - - - - - - - - - - - - - - - - - - - - - - - - - - -   0

SalmoKCaR 1  C T G A A A T C A A G C A T T A T C A A G - - - - - - - - - - - - - - - - - -  60
SalmoKCaR 2  C T G A A A T C A A G C A T T A T C A A G G A T T G A G C A A G A C A A C T G A  80
SalmoKCaR 3  C T G A A A T C A A G C A T T A T C A A G - - - - - - - - - - - - - - - - - -  61
Salmon A26   - - - - - - - - - - - - - - - - - - - - - - - - - - - - - - - - - - - - - - -   0
Salmon PCR   - - - - - - - - - - - - - - - - - - - - - - - - - - - - - - - - - - - - - - -   0

SalmoKCaR 1  - - - - - - - - - - - - - - - - - - - - - - - - - - - - - - - - - - - - - - -  60
SalmoKCaR 2  G T T G T C A G A C T A A G A A T A T A C A C A T T T C C A G T T C T C T C T T  120
SalmoKCaR 3  - - - - - - - - - - - - - - - - - - - - - - - - - - - - - - - - - - - - - - -  61
Salmon A26   - - - - - - - - - - - - - - - - - - - - - - - - - - - - - - - - - - - - - - -   0
Salmon PCR   - - - - - - - - - - - - - - - - - - - - - - - - - - - - - - - - - - - - - - -   0

SalmoKCaR 1  - - - - - - - - - - - - - - - - - - - - - - - - - - - - - A T C A A G A A C A  70
SalmoKCaR 2  T A A T G G A C T T C T C A C A C T G A T G T T C T T C A G A T C A A G A A C A  160
SalmoKCaR 3  - - - - - - - - - - - - - - - - - - - - - - - - - - - - - A T C A A G A A C A  71
Salmon A26   - - - - - - - - - - - - - - - - - - - - - - - - - - - - - - - - - - - - - - -   0
Salmon PCR   - - - - - - - - - - - - - - - - - - - - - - - - - - - - - - - - - - - - - - -   0

SalmoKCaR 1  G C A T G A G T C A G A A A C A A G G C G A C A G C C A G A G T C A C T G G A G  110
SalmoKCaR 2  G C A T G A G T C A G A A A C A A G G C G A C A G C C A G A G T C A C T G G A G  200
SalmoKCaR 3  G C A T G A G T C A G A A A C A A G G C G A C A G C C A G A G T C A C T G G A G  111
Salmon A26   - - - - - - - - - - - - - - - - - - - - - - - - - - - - - - - - - - - - - - -   0
Salmon PCR   - - - - - - - - - - - - - - - - - - - - - - - - - - - - - - - - - - - - - - -   0

SalmoKCaR 1  G G G A C A A G A C T G A G G T T A A C T C T G A A G T C T A A T G T G C T G A  150
SalmoKCaR 2  G G G A C A A G A C T G A G G T T A A C T C T G A A G T C T A A T G T G C T G A  240
SalmoKCaR 3  G G G A C A A G A C T G A G G T T A A C T C T G A A G T C T A A T G T G C T G A  151
Salmon A26   - - - - - - - - - - - - - - - - - - - - - - - - - - - - - - - - - - - - - - -   0
Salmon PCR   - - - - - - - - - - - - - - - - - - - - - - - - - - - - - - - - - - - - - - -   0

SalmoKCaR 1  G A G G A C A A G G C C C T C C T G A G A G C T G A A C G A T G A G A T T T T A  190
SalmoKCaR 2  G A G G A C A A G G C C C T C C T G A G A G C T G A A C G A T G A G A T T T T A  280
SalmoKCaR 3  G A G G A C A A G G C C C T C C T G A G A G C T G A A C G A T G A G A T T T T A  191
Salmon A26   - - - - - - - - - - - - - - - - - - - - - - - - - - - - - - - - - - - - - - -   0
Salmon PCR   - - - - - - - - - - - - - - - - - - - - - - - - - - - - - - - - - - - - - - -   0

SalmoKCaR 1  C C T G T A T T A C C T G G T G C T T T T G G G C T T C A G T T C T G T C A T C  230
SalmoKCaR 2  C C T G T A T T A C C T G G T G C T T T T G G G C T T C A G T T C T G T C A T C  320
SalmoKCaR 3  C C T G T A T T A C C T G G T G C T T T T G G G C T T C A G T T C T G T C A T C  231
Salmon A26   - - - - - - - - - - - - - - - - - - - - - - - - - - - - - - - - - - - - - - -   0
Salmon PCR   - - - - - - - - - - - - - - - - - - - - - - - - - - - - - - - - - - - - - - -   0

SalmoKCaR 1  T C C A C C T A T G G G C C T C A T C A G A G A G C A C A G A A G A C T G G G G  270
SalmoKCaR 2  T C C A C C T A T G G G C C T C A T C A G A G A G C A C A G A A G A C T G G G G  360
SalmoKCaR 3  T C C A C C T A T G G G C C T C A T C A G A G A G C A C A G A A G A C T G G G G  271
Salmon A26   - - - - - - - - - - - - - - - - - - - - - - - - - - - - - - - - - - - - - - -   0
Salmon PCR   - - - - - - - - - - - - - - - - - - - - - - - - - - - - - - - - - - - - - - -   0
```

FIG. 13A

```
SalmoKCaR 1  A T A T T C T G C T G G G C G G G C T G T T T C C A A T G C A C T T T G G T G T  310
SalmoKCaR 2  A T A T T C T G C T G G G C G G G C T G T T T C C A A T G C A C T T T G G T G T  400
SalmoKCaR 3  A T A T T C T G C T G G G C G G G C T G T T T C C A A T G C A C T T T G G T G T  311
Salmon A26   - - - - - - - - - - - - - - - - - - - - - - - - - - - - - - - - - - - - - - - -  0
Salmon PCR   - - - - - - - - - - - - - - - - - - - - - - - - - - - - - - - - - - - - - - - -  0

SalmoKCaR 1  T A C C T C C A A A G A C C A A G A C C T G G C A G C G C G G C C A G A A T C C  350
SalmoKCaR 2  T A C C T C C A A A G A C C A A G A C C T G G C A G C G C G G C C A G A A T C C  440
SalmoKCaR 3  T A C C T C C A A A G A C C A A G A C C T G G C A G C G C G G C C A G A A T C C  351
Salmon A26   - - - - - - - - - - - - - - - - - - - - - - - - - - - - - - - - - - - - - - - -  0
Salmon PCR   - - - - - - - - - - - - - - - - - - - - - - - - - - - - - - - - - - - - - - - -  0

SalmoKCaR 1  A C A G A G T G T G T T A G G T A C A A T T T C C G G G G A T T C C G T T G G C  390
SalmoKCaR 2  A C A G A G T G T G T T A G G T A C A A T T T C C G G G G A T T C C G T T G G C  480
SalmoKCaR 3  A C A G A G T G T G T T A G G T A C A A T T T C C G G G G A T T C C G T T G G C  391
Salmon A26   - - - - - - - - - - - - - - - - - - - - - - - - - - - - - - - - - - - - - - - -  0
Salmon PCR   - - - - - - - - - - - - - - - - - - - - - - - - - - - - - - - - - - - - - - - -  0

SalmoKCaR 1  T T C A G G C C A T G A T T T T T G C A A T A G A G G A G A T C A A C A A C A G  430
SalmoKCaR 2  T T C A G G C C A T G A T T T T T G C A A T A G A G G A G A T C A A C A A C A G  520
SalmoKCaR 3  T T C A G G C C A T G A T T T T T G C A A T A G A G G A G A T C A A C A A C A G  431
Salmon A26   - - - - - - - - - - - - - - - - - - - - - - - - - - - - - - - - - - - - - - - -  0
Salmon PCR   - - - - - - - - - - - - - - - - - - - - - - - - - - - - - - - - - - - - - - - -  0

SalmoKCaR 1  C A G T A C T C T C C T G C C C A A C A T C A C A C T G G G C T A C A G G A T C  470
SalmoKCaR 2  C A G T A C T C T C C T G C C C A A C A T C A C A C T G G G C T A C A G G A T C  560
SalmoKCaR 3  C A G T A C T C T C C T G C C C A A C A T C A C A C T G G G C T A C A G G A T C  471
Salmon A26   - - - - - - - - - - - - - - - - - - - - - - - - - - - - - - - - - - - - - - - -  0
Salmon PCR   - - - - - - - - - - - - - - - - - - - - - - - - - - - - - - - - - - - - - - - -  0

SalmoKCaR 1  T T T G A C A C C T G C A A C A C C G T G T C C A A G G C C C T G G A G G C T A  510
SalmoKCaR 2  T T T G A C A C C T G C A A C A C C G T G T C C A A G G C C C T G G A G G C T A  600
SalmoKCaR 3  T T T G A C A C C T G C A A C A C C G T G T C C A A G G C C C T G G A G G C T A  511
Salmon A26   - - - - - - - - - - - - - - - - - - - - - - - - - - - - - - - - - - - - - - - -  0
Salmon PCR   - - - - - - - - - - - - - - - - - - - - - - - - - - - - - - - - - - - - - - - -  0

SalmoKCaR 1  C C C T C A G T T T C G T A G C A C A G A A T A A G A T T G A C T C T C T G A A  550
SalmoKCaR 2  C C C T C A G T T T C G T A G C A C A G A A T A A G A T T G A C T C T C T G A A  640
SalmoKCaR 3  C C C T C A G T T T C G T A G C A C A G A A T A A G A T T G A C T C T C T G A A  551
Salmon A26   - - - - - - - - - - - - - - - - - - - - - - - - - - - - - - - - - - - - - - - -  0
Salmon PCR   - - - - - - - - - - - - - - - - - - - - - - - - - - - - - - - - - - - - - - - -  0

SalmoKCaR 1  C T T G G A T G A A T T C T G T A A C T G C A C T G A T C A C A T C C C A T C G  590
SalmoKCaR 2  C T T G G A T G A A T T C T G T A A C T G C A C T G A T C A C A T C C C A T C G  680
SalmoKCaR 3  C T T G G A T G A A T T C T G T A A C T G C A C T G A T C A C A T C C C A T C G  591
Salmon A26   - - - - - - - - - - - - - - - - - - - - - - - - - - - - - - - - - - - - - - - -  0
Salmon PCR   - - - - - - - - - - - - - - - - - - - - - - - - - - - - - - - - - - - - - - - -  0

SalmoKCaR 1  A C T A T A G C A G T G G T G G G G G C T T C T G G G T C A G C G G T C T C C A  630
SalmoKCaR 2  A C T A T A G C A G T G G T G G G G G C T T C T G G G T C A G C G G T C T C C A  720
SalmoKCaR 3  A C T A T A G C A G T G G T G G G G G C T T C T G G G T C A G C G G T C T C C A  631
Salmon A26   - - - - - - - - - - - - - - - - - - - - - - - - - - - - - - - - - - - - - - - -  0
Salmon PCR   - - - - - - - - - - - - - - - - - - - - - - - - - - - - - - - - - - - - - - - -  0
```

FIG. 13B

```
SalmoKCaR 1  C T G C T G T T G C C A A T C T G T T G G G C C T T T T C T A C A T C C C A C A 670
SalmoKCaR 2  C T G C T G T T G C C A A T C T G T T G G G C C T T T T C T A C A T C C C A C A 760
SalmoKCaR 3  C T G C T G T T G C C A A T C T G T T G G G C C T T T T C T A C A T C C C A C A 671
Salmon A26   - - - - - - - - - - - - - - - - - - - - - - - - - - - - - - - - - - - - - - - 0
Salmon PCR   - - - - - - - - - - - - - - - - - - - - - - - - - - - - - - - - - - - - - - - 0

SalmoKCaR 1  G A T C A G C T A T G C C T C T T C C A G T C G C C T A C T A A G C A A C A A G 710
SalmoKCaR 2  G A T C A G C T A T G C C T C T T C C A G T C G C C T A C T A A G C A A C A A G 800
SalmoKCaR 3  G A T C A G C T A T G C C T C T T C C A G T C G C C T A C T A A G C A A C A A G 711
Salmon A26   - - - - - - - - - - - - - - - - - - - - - - - - - - - - - - - - - - - - - - - 0
Salmon PCR   - - - - - - - - - - - - - - - - - - - - - - - - - - - - - - - - - - - - - - - 0

SalmoKCaR 1  A A C C A G T T C A A A T C C T T C A T G A G G A C C A T T C C C A C A G A T G 750
SalmoKCaR 2  A A C C A G T T C A A A T C C T T C A T G A G G A C C A T T C C C A C A G A T G 840
SalmoKCaR 3  A A C C A G T T C A A A T C C T T C A T G A G G A C C A T T C C C A C A G A T G 751
Salmon A26   - - - - - - - - - - - - - - - - - - - - - - - - - - - - - - - - - - - - - - - 0
Salmon PCR   - - - - - - - - - - - - - - - - - - - - - - - - - - - - - - - - - - - - - - - 0

SalmoKCaR 1  A G C A C C A G G C C A C T G C C A T G G C A G A T A T C A T C G A C T A C T T 790
SalmoKCaR 2  A G C A C C A G G C C A C T G C C A T G G C A G A T A T C A T C G A C T A C T T 880
SalmoKCaR 3  A G C A C C A G G C C A C T G C C A T G G C A G A T A T C A T C G A C T A C T T 791
Salmon A26   - - - - - - - - - - - - - - - - - - - - - - - - - - - - - - - - - - - - - - - 0
Salmon PCR   - - - - - - - - - - - - - - - - - - - - - - - - - - - - - - - - - - - - - - - 0

SalmoKCaR 1  C C A A T G G A A T T G G G T C A T T G C A G T T G C G T C T G A T G A T G A G 830
SalmoKCaR 2  C C A A T G G A A T T G G G T C A T T G C A G T T G C G T C T G A T G A T G A G 920
SalmoKCaR 3  C C A A T G G A A T T G G G T C A T T G C A G T T G C G T C T G A T G A T G A G 831
Salmon A26   - - - - - - - - - - - - - - - - - - - - - - - - - - - - - - - - - - - - - - - 0
Salmon PCR   - - - - - - - - - - - - - - - - - - - - - - - - - - - - - - - - - - - - - - - 0

SalmoKCaR 1  T A T G G A C G T C C G G G G A T T G A A A A A T T T G A G A A A G A G A T G G 870
SalmoKCaR 2  T A T G G A C G T C C G G G G A T T G A A A A A T T T G A G A A A G A G A T G G 960
SalmoKCaR 3  T A T G G A C G T C C G G G G A T T G A A A A A T T T G A G A A A G A G A T G G 871
Salmon A26   - - - - - - - - - - - - - - - - - - - - - - - - - - - - - - - - - - - - - - - 0
Salmon PCR   - - - - - - - - - - - - - - - - - - - - - - - - - - - - - - - - - - - - - - - 0

SalmoKCaR 1  A A G A A C G A G A C A T T T G T A T C C A T C T G A G T G A G C T G A T C T C 910
SalmoKCaR 2  A A G A A C G A G A C A T T T G T A T C C A T C T G A G T G A G C T G A T C T C 1000
SalmoKCaR 3  A A G A A C G A G A C A T T T G T A T C C A T C T G A G T G A G C T G A T C T C 911
Salmon A26   - - - - - - - - - - - - - - - - - - - - - - - - - - - - - - - - - - - - - - - 0
Salmon PCR   - - - - - - - - - - - - - - - - - - - - - - - - - - - - - - - - - - - - - - - 0

SalmoKCaR 1  T C A G T A C T T T G A G G A G T G G C A G A T C C A A G G A T T G G T T G A C 950
SalmoKCaR 2  T C A G T A C T T T G A G G A G T G G C A G A T C C A A G G A T T G G T T G G C 1040
SalmoKCaR 3  T C A G T A C T T T G A G G A G T G G C A G A T C C A A G G A T T G G T T G A C 951
Salmon A26   - - - - - - - - - - - - - - - - - - - - - - - - - - - - - - - - - - - - - - - 0
Salmon PCR   - - - - - - - - - - - - - - - - - - - - - - - - - - - - - - - - - - - - - - - 0

SalmoKCaR 1  C G T A T T G A G A A C T C C T C A G C T A A A G T T A T A G T C G T T T T C G 990
SalmoKCaR 2  C G T A T T G A G A A C T C C T C A G C T A A A G T T A T A G T C G T T T T C G 1080
SalmoKCaR 3  C G T A T T G A G A A C T C C T C A G C T A A A G T T A T A G T C G T T T T C G 991
Salmon A26   - - - - - - - - - - - - - - - - - - - - - - - - - - - - - - - - - - - - - - - 0
Salmon PCR   - - - - - - - - - - - - - - - - - - - - - - - - - - - - - - - - - - - - - - - 0
```

FIG. 13C

```
SalmoKCaR 1  C C A G T G G G C C T G A C A T T G A G C C T C T T A T T A A A G A G A T G G T  1030
SalmoKCaR 2  C C A G T G G G C C T G A C A T T G A G C C T C T T A T T A A A G A G A T G G T  1120
SalmoKCaR 3  C C A G T G G G C C T G A C A T T G A G C C T C T T A T T A A A G A G A T G G T  1031
Salmon A26   - - - - - - - - - - - - - - - - - - - - - - - - - - - - - - - - - - - - - - -  0
Salmon PCR   - - - - - - - - - - - - - - - - - - - - - - - - - - - - - - - - - - - - - - -  0

SalmoKCaR 1  C A G A C G G A A C A T C A C C G A C C G C A T C T G G T T G G C C A G C G A G  1070
SalmoKCaR 2  C A G A C G G A A C A T C A C C G A C C G C A T C T G G T T G G C C A G C G A G  1160
SalmoKCaR 3  C A G A C G G A A C A T C A C C G A C C G C A T C T G G T T G G C C A G C G A G  1071
Salmon A26   - - - - - - - - - - - - - - - - - - - - - - - - - - - - - - - - - - - - - - -  0
Salmon PCR   - - - - - - - - - - - - - - - - - - - - - - - - - - - - - - - - - - - - - - -  0

SalmoKCaR 1  G C T T G G G C A A C C A C C T C C C T C A T C G C C A A A C C A G A G T A C C  1110
SalmoKCaR 2  G C T T G G G C A A C C A C C T C C C T C A T C G C C A A A C C A G A G T A C C  1200
SalmoKCaR 3  G C T T G G G C A A C C A C C T C C C T C A T C G C C A A A C C A G A G T A C C  1111
Salmon A26   - - - - - - - - - - - - - - - - - - - - - - - - - - - - - - - - - - - - - - -  0
Salmon PCR   - - - - - - - - - - - - - - - - - - - - - - - - - - - - - - - - - - - - - - -  0

SalmoKCaR 1  T T G A T G T T G T A G T T G G G A C C A T T G G C T T T G C T C T C A G A G C  1150
SalmoKCaR 2  T T G A T G T T G T A G T T G G G A C C A T T G G C T T T G C T C T C A G A G C  1240
SalmoKCaR 3  T T G A T G T T G T A G T T G G G A C C A T T G G C T T T G C T C T C A G A G C  1151
Salmon A26   - - - - - - - - - - - - - - - - - - - - - - - - - - - - - - - - - - - - - - -  0
Salmon PCR   - - - - - - - - - - - - - - - - - - - - - - - - - - - - - - - - - - - - - - -  0

SalmoKCaR 1  A G G C G A A A T A C C T G G C T T C A A G G A C T T C T T A C A A G A G G T C  1190
SalmoKCaR 2  A G G C G A A A T A C C T G G C T T C A A G G A C T T C T T A C A A G A G G T C  1280
SalmoKCaR 3  A G G C G A A A T A C C T G G C T T C A A G G A C T T C T T A C A A G A G G T C  1191
Salmon A26   - - - - - - - - - - - - - - - - - - - - - - - - - - - - - - - - - - - - - - -  0
Salmon PCR   - - - - - - - - - - - - - - - - - - - - - - - - - - - - - - - - - - - - - - -  0

SalmoKCaR 1  A C A C C A A A G A A A T C C A G C C A C A A T G A A T T T G T C A G G G A G T  1230
SalmoKCaR 2  A C A C C A A A G A A A T C C A G C C A C A A T G A A T T T G T C A G G G A G T  1320
SalmoKCaR 3  A C A C C A A A G A A A T C C A G C C A C A A T G A A T T T G T C A G G G A G T  1231
Salmon A26   - - - - - - - - - - - - - - - - - - - - - - - - - - - - - - - - - - - - - - -  0
Salmon PCR   - - - - - - - - - - - - - - - - - - - - - - - - - - - - - - - - - - - - - - -  0

SalmoKCaR 1  T T T G G G A G G A G A C T T T T A A C T G C T A T C T G G A A G A C A G C C A  1270
SalmoKCaR 2  T T T G G G A G G A G A C T T T T A A C T G C T A T C T G G A A G A C A G C C A  1360
SalmoKCaR 3  T T T G G G A G G A G A C T T T T A A C T G C T A T C T G G A A G A C A G C C A  1271
Salmon A26   - - - - - - - - - - - - - - - - - - - - - - - - - - - - - - - - - - - - - - -  0
Salmon PCR   - - - - - - - - - - - - - - - - - - - - - - - - - - - - - - - - - - - - - - -  0

SalmoKCaR 1  G A G A C T G A G A G A C A G T G A G A A T G G G A G C A C C A G T T T C A G A  1310
SalmoKCaR 2  G A G A C T G A G A G A C A G T G A G A A T G G G A G C A C C A G T T T C A G A  1400
SalmoKCaR 3  G A G A C T G A G A G A C A G T G A G A A T G G G A G C A C C A G T T T C A G A  1311
Salmon A26   - - - - - - - - - - - - - - - - - - - - - - - - - - - - - - - - - - - - - - -  0
Salmon PCR   - - - - - - - - - - - - - - - - - - - - - - - - - - - - - - - - - - - - - - -  0

SalmoKCaR 1  C C A T T G T G T A C T G G C G A G G A G G A C A T T A T G G G T G C A G A G A  1350
SalmoKCaR 2  C C A T T G T G T A C T G G C G A G G A G G A C A T T A T G G G T G C A G A G A  1440
SalmoKCaR 3  C C A T T G T G T A C T G G C G A G G A G G A C A T T A T G G G T G C A G A G A  1351
Salmon A26   - - - - - - - - - - - - - - - - - - - - - - - - - - - - - - - - - - - - - - -  0
Salmon PCR   - - - - - - - - - - - - - - - - - - - - - - - - - - - - - - - - - - - - - - -  0
```

FIG. 13D

```
SalmoKCaR 1  C C C C A T A T C T G G A T T A C A C T C A T C T T C G T A T T T C C T A T A A  1390
SalmoKCaR 2  C C C C A T A T C T G G A T T A C A C T C A T C T T C G T A T T T C C T A T A A  1480
SalmoKCaR 3  C C C C A T A T C T G G A T T A C A C T C A T C T T C G T A T T T C C T A T A A  1391
Salmon A26   - - - - - - - - - - - - - - - - - - - - - - - - - - - - - - - - - - - - - - -   0
Salmon PCR   - - - - - - - - - - - - - - - - - - - - - - - - - - - - - - - - - - - - - - -   0

SalmoKCaR 1  T G T G T A T G T T G C A G T T C A C T C C A T T G C A C A G G C C C T A C A G  1430
SalmoKCaR 2  T G T G T A T G T T G C A G T T C A C T C C A T T G C A C A G G C C C T A C A G  1520
SalmoKCaR 3  T G T G T A T G T T G C A G T T C A C T C C A T T G C A C A G G C C C T A C A G  1431
Salmon A26   - - - - - - - - - - - - - - - - - - - - - - - - - - - - - - - - - - - - - - -   0
Salmon PCR   - - - - - - - - - - - - - - - - - - - - - - - - - - - - - - - - - - - - - - -   0

SalmoKCaR 1  G A C A T T C T C A C C T G C A T T C C T G G A C G G G G T C T T T T T T C C A  1470
SalmoKCaR 2  G A C A T T C T C A C C T G C A T T C C T G G A C G G G G T C T T T T T T C C A  1560
SalmoKCaR 3  G A C A T T C T C A C C T G C A T T C C T G G A C G G G G T T T T T T T T C C A  1471
Salmon A26   - - - - - - - - - - - - - - - - - - - - - - - - - - - - - - - - - - - - - - -   0
Salmon PCR   - - - - - - - - - - - - - - - - - - - - - - - - - - - - - - - - - - - - - - -   0

SalmoKCaR 1  A C A A C T C A T G T G C A G A T A T A A A G A A A A T A G A A G C A T G G C A  1510
SalmoKCaR 2  A C A A C T C A T G T G C A G A T A T A A A G A A A A T A G A A G C A T G G C A  1600
SalmoKCaR 3  A C A A C T C A T G T G C A G A T A T A A A G A A A A T A G A A G C A T G G C A  1511
Salmon A26   - - - - - - - - - - - - - - - - - - - - - - - - - - - - - - - - - - - - - - -   0
Salmon PCR   - - - - - - - - - - - - - - - - - - - - - - - - - - - - - - - - - - - - - - -   0

SalmoKCaR 1  G G T T C T C A A G C A G C T C A G A C A T T T A A A C T T C T C A A A C A G T  1550
SalmoKCaR 2  G G T T C T C A A G C A G C T C A G A C A T T T A A A C T T C T C A A A C A G T  1640
SalmoKCaR 3  G G T T C T C A A G C A G C T C A G A C A T T T A A A C T T C T C A A A C A G T  1551
Salmon A26   - - - - - - - - - - - - - - - - - - - - - - - - - - - - - - - - - - - - - - -   0
Salmon PCR   - - - - - - - - - - - - - - - - - - - - - - - - - - - - - - - - - - - - - - -   0

SalmoKCaR 1  A T G G G A G A A A A G G T A C A T T T T G A T G A G A A T G C T G A T C C G T  1590
SalmoKCaR 2  A T G G G A G A A A A G G T A C A T T T T G A T G A G A A T G C T G A T C C G T  1680
SalmoKCaR 3  A T G G G A G A A A A G G T A C A T T T T G A T G A G A A T G C T G A T C C G T  1591
Salmon A26   - - - - - - - - - - - - - - - - - - - - - - - - - - - - - - - - - - - - - - -   0
Salmon PCR   - - - - - - - - - - - - - - - - - - - - - - - - - - - - - - - - - - - - - - -   0

SalmoKCaR 1  C A G G A A A C T A C A C C A T T A T C A A T T G G C A C C G G T C T C C T G A  1630
SalmoKCaR 2  C A G G A A A C T A C A C C A T T A T C A A T T G G C A C C G G T C T C C T G A  1720
SalmoKCaR 3  C A G G A A A C T A C A C C A T T A T C A A T T G G C A C C G G T C T C C T G A  1631
Salmon A26   - - - - - - - - - - - - - - - - - - - - - - - - - - - - - - - - - - - - - - -   0
Salmon PCR   - - - - - - - - - - - - - - - - - - - - - - - - - - - - - - - - - - - - - - -   0

SalmoKCaR 1  G G A T G G T T C T G T T G T G T T T G A A G A G G T C G G T T T C T A C A A C  1670
SalmoKCaR 2  G G A T G G T T C T G T T G T G T T T G A A G A G G T C G G T T T C T A C A A C  1760
SalmoKCaR 3  G G A T G G T T C T G T T G T G T T T G A A G A G G T C G G T T T C T A C A A C  1671
Salmon A26   - - - - - - - - - - - - - - - - - - - - - - - - - - - - - - - - - - - - - - -   0
Salmon PCR   - - - - - - - - - - - - - - - - - - - - - - - - - - - - - - - - - - - - - - -   0

SalmoKCaR 1  A T G C G A G C T A A G A G A G G A G T A C A A C T T T T C A T T G A T A A C A  1710
SalmoKCaR 2  A T G C G A G C T A A G A G A G G A G T A C A A C T T T T C A T T G A T A A C A  1800
SalmoKCaR 3  A T G C G A G C T A A G A G A G G A G T A C A A C T T T T C A T T G A T A A C A  1711
Salmon A26   - - - - - - - - - - - - - - - - - - - - - - - - - - - - - - - - - - - - - - -   0
Salmon PCR   - - - - - - - - - - - - - - - - - - - - - - - - - - - - - - - - - - - - - - -   0
```

FIG. 13E

```
SalmoKCaR 1  C A A A G A T T C T A T G G A A T G G A T A T A A T A C T G A G G T T C C A T T  1750
SalmoKCaR 2  C A A A G A T T C T A T G G A A T G G A T A T A A T A C T G A G G T T C C A T T  1840
SalmoKCaR 3  C A A A G A T T C T A T G G A A T G G A T A T A A T A C T G A G G T T C C A T T  1751
Salmon A26   - - - - - - - - - - - - - - - - - - - - - - - - - - - - - - - - - - - - - -  0
Salmon PCR   - - - - - - - - - - - - - - - - - - - - - - - - - - - - - - - - - - - - - -  0

SalmoKCaR 1  C T C T A A C T G T A G T G A A G A T T G T G A A C C A G G C A C C A G A A A G  1790
SalmoKCaR 2  C T C T A A C T G T A G T G A A G A T T G T G A A C C A G G C A C C A G A A A G  1880
SalmoKCaR 3  C T C T A A C T G T A G T G A A G A T T G T G A A C C A G G C A C C A G A A A G  1791
Salmon A26   - - G T G A T C A C A A A G G T A A G A A A G A C A G T G A A A A A T C T G A A  38
Salmon PCR   - - - - - - - - - - - - - - - - - - - - - - - - - - - - - - - - - - - - - -  0

SalmoKCaR 1  G G G A T C A T A G A A A G C A T G C C A A C G T G T T G C T T T G A A T G T A  1830
SalmoKCaR 2  G G G A T C A T A G A A A G C A T G C C A A C G T G T T G C T T T G A A T G T A  1920
SalmoKCaR 3  G G G A T C A T A G A A A G C A T G C C A A C G T G T T G C T T T G A A T G T A  1831
Salmon A26   C T A C C C C A T T A T A T A A T C T G T T G C T A T T T C A T A T G T T T C T  78
Salmon PCR   - - - - - - - - - - - - - - - - - - - - - - - - - - - - - - - - - - - - - -  0

SalmoKCaR 1  C A G A A T G C T C A G A A G G A G A G T A T A G T G A T C A C A A A G A T G C  1870
SalmoKCaR 2  C A G A A T G C T C A G A A G G A G A G T A T A G T G A T C A C A A A G A T G C  1960
SalmoKCaR 3  C A G A A T G C T C A G A A G G A G A G T A T A G T G A T C A C A A A G A T G C  1871
Salmon A26   A T C A A T A A T A C A A A C A C T A C T T C T C T A T T C C T G C A G A T G C  118
Salmon PCR   - - - - - - - - - - - - - - - - - - - - - - - - - - - - - - - - - - - - - -  0

SalmoKCaR 1  C A G T G T T T G T A C C A A G T G T C C C A A T G A C T C A T G G T C T A A T  1910
SalmoKCaR 2  C A G T G T T T G T A C C A A G T G T C C C A A T G A C T C A T G G T C T A A T  2000
SalmoKCaR 3  C A G T G T T T G T A C C A A G T G T C C C A A T G A C T C A T G G T C T A A T  1911
Salmon A26   C A G T G T T T G T A C C A A G T G T C C C A A T G A C T C A T G G T C T A A T  158
Salmon PCR   - - - - - - - - - - - - - - - - - - - - - - - - - - - - - - - - - - - - - -  0

SalmoKCaR 1  G A G A A C C A C A C A T C T T G T T T C C T G A A G G A G A T A G A G T T T C  1950
SalmoKCaR 2  G A G A A C C A C A C A T C T T G T T T C C T G A A G G A G A T A G A G T T T C  2040
SalmoKCaR 3  G A G A A C C A C A C A T C T T G T T T C C T G A A G G A G A T A G A G T T T C  1951
Salmon A26   G A G A A C C A C A C A T C T T G T T T C C T G A A G G A G A T A G A G T T T C  198
Salmon PCR   - - - - - - - - - - - - - - - - - - - - - - - - - - - - - - - - - - - - - -  0

SalmoKCaR 1  T G T C T T G G A C A G A G C C C T T T G G G A T C G C C T T G G C A T T A T G  1990
SalmoKCaR 2  T G T C T T G G A C A G A G C C C T T T G G G A T C G C C T T G G C A T T A T G  2080
SalmoKCaR 3  T G T C T T G G A C A G A G C C C T T T G G G A T C G C C T T G G C A T T A T G  1991
Salmon A26   T G T C T T G G A C A G A G C C C T T T G G G A T C G C C T T G G C A T T A T G  238
Salmon PCR   - - - - - - - - - - - - - - - - - - - - - C T T G G C A T T A T G  12

SalmoKCaR 1  C T C T G T G C T G G G G G T A T T C T T G A C A G C A T T C G T G A T G G G A  2030
SalmoKCaR 2  C T C T G T G C T G G G G G T A T T C T T G A C A G C A T T C G T G A T G G G A  2120
SalmoKCaR 3  C T C T G T G C T G G G G G T A T T C T T G A C A G C A T T C G T G A T G G G A  2031
Salmon A26   C T C T G T G C T G G G G G T A T T C T T G A C A G C A T T C G T G A T G G G A  278
Salmon PCR   C T C T G T G C T G G G G G T A T T C T T G A C A G C A T T C G T G A T G G G A  52

SalmoKCaR 1  G T G T T T A T C A A A T T T C G C A A C A C C C C A A T T G T T A A G G C C A  2070
SalmoKCaR 2  G T G T T T A T C A A A T T T C G C A A C A C C C C A A T T G T T A A G G C C A  2160
SalmoKCaR 3  G T G T T T A T C A A A T T T C G C A A C A C C C C A A T T G T T A A G G C C A  2071
Salmon A26   G T G T T T A T C A A A T T T C G C A A C A C C C C A A T T G T T A A G G C C A  318
Salmon PCR   G T G T T T A T C A A A T T T C G C A A C A C C C C A A T T G T T A A G G C C A  92
```

FIG. 13F

```
SalmoKCaR 1   C A A A C A G A G A G C T A T C C T A C C T C C T C C T G T T C T C A C T C A T   2110
SalmoKCaR 2   C A A A C A G A G A G C T A T C C T A C C T C C T C C T G T T C T C A C T C A T   2200
SalmoKCaR 3   C A A A C A G A G A G C T A T C C T A C C T C C T C C T G T T C T C A C T C A T   2111
Salmon A26    C A A A C A G A G A G C T A T C C T A C C T C C T C C T G T T C T C A C T C A T   358
Salmon PCR    C A A A C A G A G A G C T A T C C T A C C T C C T C C T G T T C T C A C T C A T   132

SalmoKCaR 1   C T G C T G T T T C T C C A G T T C C C T C A T C T T C A T T G G T G A A C C C   2150
SalmoKCaR 2   C T G C T G T T T C T C C A G T T C C C T C A T C T T C A T T G G T G A A C C C   2240
SalmoKCaR 3   C T G C T G T T T C T C C A G T T C C C T C A T C T T C A T T G G T G A A C C C   2151
Salmon A26    C T G C T G T T T C T C C A G T T C C C T C A T C T T C A T T G G T G A A C C C   398
Salmon PCR    C T G C T G T T T C T C C A G T T C C C T C A T C T T C A T T G G T G A A C C C   172

SalmoKCaR 1   C A G G A C T G G A C A T G C C G T C T A C G C C A G C C T G C A T T C G G G A   2190
SalmoKCaR 2   C A G G A C T G G A C A T G C C G T C T A C G C C A G C C T G C A T T C G G G A   2280
SalmoKCaR 3   C A G G A C T G G A C A T G C C G T C T A C G C C A G C C T G C A T T C G G G A   2191
Salmon A26    C A G G A C T G G A C A T G C C G T C T A C G C C A G C C T G C A T T C G G G A   438
Salmon PCR    C A G G A C T G G A C A T G C C G T C T A C G C C A G C C T G C A T T C G G G A   212

SalmoKCaR 1   T A A G T T T T G T T C T C T G C A T C T C C T G C A T C C T G G T A A A A A C   2230
SalmoKCaR 2   T A A G T T T T G T T C T C T G C A T C T C C T G C A T C C T G G T A A A A A C   2320
SalmoKCaR 3   T A A G T T T T G T T C T C T G C A T C T C C T G C A T C C T G G T A A A A A C   2231
Salmon A26    T A A G T T T T G T T C T C T G C A T C T C C T G C A T C C T G G T A A A A A C   478
Salmon PCR    T A A G T T T T G T T C T C T G C A T C T C C T G C A T C C T G G T A A A A A C   252

SalmoKCaR 1   T A A C C G A G T A C T T C T A G T G T T C G A A G C C A A G A T C C C C A C C   2270
SalmoKCaR 2   T A A C C G A G T A C T T C T A G T G T T C G A A G C C A A G A T C C C C A C C   2360
SalmoKCaR 3   T A A C C G A G T A C T T C T A G T G T T C G A A G C C A A G A T C C C C A C C   2271
Salmon A26    T A A C C G A G T A C T T C T A G T G T T C G A A G C C A A G A T C C C C A C C   518
Salmon PCR    T A A C C G A G T A C T T C T A G T G T T C G A A G C C A A G A T C C C C A C C   292

SalmoKCaR 1   A G T C T C C A T C G T A A G T G G T G G G G G C T A A A C T T G C A G T T C C   2310
SalmoKCaR 2   A G T C T C C A T C G T A A G T G G T G G G G G C T A A A C T T G C A G T T C C   2400
SalmoKCaR 3   A G T C T C C A T C G T A A G T G G T G G G G G C T A A A C T T G C A G T T C C   2311
Salmon A26    A G T C T C C A T C G T A A G T G G T G G G G G C T A A A C T T G C A G T T C C   558
Salmon PCR    A G T C T C C A T C G T A A G T G G T G G G G G C T A A A C T T G C A G T T C C   332

SalmoKCaR 1   T G T T A G T G T T C C T G T T C A C A T T T G T G C A A G T G A T G A T A T G   2350
SalmoKCaR 2   T G T T A G T G T T C C T G T T C A C A T T T G T G C A A G T G A T G A T A T G   2440
SalmoKCaR 3   T G T T A G T G T T C C T G T T C A C A T T T G T G C A A G T G A T G A T A T G   2351
Salmon A26    T G T T A G T G T T C C T G T T C A C A T T T G T G C A A G T G A T G A T A T G   598
Salmon PCR    T G T T A G T G T T C C T G T T C A C A T T T G T G C A A G T G A T G A T A T G   372

SalmoKCaR 1   T G T G G T C T G G C T T T A C A A T G C T C C T C C G G C G A G C T A C A G G   2390
SalmoKCaR 2   T G T G G T C T G G C T T T A C A A T G C T C C T C C G G C G A G C T A C A G G   2480
SalmoKCaR 3   T G T G G T C T G G C T T T A C A A T G C T C C T C C G G C G A G C T A C A G G   2391
Salmon A26    T G T G G T C T G G C T T T A C A A T G C T C C T C C G G C G A G C T A C A G G   638
Salmon PCR    T G T G G T C T G G C T T T A C A A T G C T C C T C C G G C G A G C T A C A G G   412

SalmoKCaR 1   A A C C A T G A C A T T G A T G A G A T A A T T T T C A T T A C A T G C A A T G   2430
SalmoKCaR 2   A A C C A T G A C A T T G A T G A G A T A A T T T T C A T T A C A T G C A A T G   2520
SalmoKCaR 3   A A C C A T G A C A T T G A T G A G A T A A T T T T C A T T A C A T G C A A T G   2431
Salmon A26    A A C C A T G A C A T T G A T G A G A T A A T T T T C A T T A C A T G C A A T G   678
Salmon PCR    A A C C A T G A C A T T G A T G A G A T A A T T T T C A T T A C A T G C A A T G   452
```

FIG. 13G

```
SalmoKCaR 1  A G G G C T C T A T G A T G G C G C T T G G C T T C C T A A T T G G G T A C A C  2470
SalmoKCaR 2  A G G G C T C T A T G A T G G C G C T T G G C T T C C T A A T T G G G T A C A C  2560
SalmoKCaR 3  A G G G C T C T A T G A T G G C G C T T G G C T T C C T A A T T G G G T A C A C  2471
Salmon A26   A G G G C T C T A T G A T G G C G C T T G G C T T C C T A A T T G G G T A C A C  718
Salmon PCR   A G G G C T C T A T G A T G G C G C T T G G C T T C C T A A T T G G G T A C A C  492

SalmoKCaR 1  A T G C C T G C T G G C A G C C A T A T G C T T C T T C T T T G C A T T T A A A  2510
SalmoKCaR 2  A T G C C T G C T G G C A G C C A T A T G C T T C T T C T T T G C A T T T A A A  2600
SalmoKCaR 3  A T G C C T G C T G G C A G C C A T A T G C T T C T T C T T T G C A T T T A A A  2511
Salmon A26   A T G C C T G C T G G C A G C C A T A T G C T T C T T C T T T G C A T T T A A A  758
Salmon PCR   A T G C C T G C T G G C A G C C A T A T R C T T C T T C T T T G C A T T T A A A  532

SalmoKCaR 1  T C A C G A A A A C T G C C A G A G A A C T T T A C T G A G G C T A A G T T C A  2550
SalmoKCaR 2  T C A C G A A A A C T G C C A G A G A A C T T T A C T G A G G C T A A G T T C A  2640
SalmoKCaR 3  T C A C G A A A A C T G C C A G A G A A C T T T A C T G A G G C T A A G T T C A  2551
Salmon A26   T C A C G A A A A C T G C C A G A G A A C T T T A C T G A G G C T A A G T T C A  798
Salmon PCR   T C A C G A A A A C T G C C A G A G A A C T T T A C T G A G G C T A A G T T C A  572

SalmoKCaR 1  T C A C C T T C A G C A T G C T C A T C T T C T T C A T C G T C T G G A T C T C  2590
SalmoKCaR 2  T C A C C T T C A G C A T G C T C A T C T T C T T C A T C G T C T G G A T C T C  2680
SalmoKCaR 3  T C A C C T T C A G C A T G C T C A T C T T C T T C A T C G T C T G G A T C T C  2591
Salmon A26   T C A C C T T C A G C A T G C T C A T C T T C T T C A T C G T C T G G A T C T C  838
Salmon PCR   T C A C C T T C A G C A T G C T C A T C T T  (SEQ ID NO: 3)                    594

SalmoKCaR 1  T T T C A T C C C T G C C T A C T T C A G C A C T T A C G G A A A G T T T G T G  2630
SalmoKCaR 2  T T T C A T C C C T G C C T A C T T C A G C A C T T A C G G A A A G T T T G T G  2720
SalmoKCaR 3  T T T C A T C C C T G C C T A C T T C A G C A C T T A C G G A A A G T T T G T G  2631
Salmon A26   T T T C A T C C C T G C C T A C T T C A G C A C T T A C G G A A A G T T T G T G  878
Salmon PCR                                                                              594

SalmoKCaR 1  T C G G C T G T G G A G G T C A T C G C C A T A C T A G C C T C C A G C T T T G  2670
SalmoKCaR 2  T C G G C T G T G G A G G T C A T C G C C A T A C T A G C C T C C A G C T T T G  2760
SalmoKCaR 3  T C G G C T G T G G A G G T C A T C G C C A T A C T A G C C T C C A G C T T T G  2671
Salmon A26   T C G G C T G T G G A G G T C A T C G C C A T A C T A G C C T C C A G C T T T G  918
Salmon PCR                                                                              594

SalmoKCaR 1  G C C T G C T G G C C T G T A T T T T C T T C A A T A A A G T C T A C A T C A T  2710
SalmoKCaR 2  G C C T G C T G G C C T G T A T T T T C T T C A A T A A A G T C T A C A T C A T  2800
SalmoKCaR 3  G C C T G C T G G C C T G T A T T T T C T T C A A T A A A G T C T A C A T C A T  2711
Salmon A26   G C C T G C T G G C C T G T A T T T T C T T C A A T A A A G T C T A C A T C A T  958
Salmon PCR                                                                              594

SalmoKCaR 1  C C T C T T C A A A C C G T C C A G G A A C A C T A T A G A G G A G G T T C G C  2750
SalmoKCaR 2  C C T C T T C A A A C C G T C C A G G A A C A C T A T A G A G G A G G T T C G C  2840
SalmoKCaR 3  C C - - - - - - - - - - - - - - - - - - - - - - - - - - - - - - - - - - - - - -  2713
Salmon A26   C C T C T T C A A A C C G T C C A G G A A C A C T A T A G A G G A G G T T C G C  998
Salmon PCR                                                                              594

SalmoKCaR 1  T G T A G C A C T G C G G C C C A T T C T T T C A A A G T G G C A G C C A A G G  2790
SalmoKCaR 2  T G T A G C A C T G C G G C C C A T T C T T T C A A A G T G G C A G C C A A G G  2880
SalmoKCaR 3  - - - - - - - - - - - - - - - - - - - - - - - - - - - - - - - - - - - - - - - -  2713
Salmon A26   T G T A G C A C T G C G G C C C A T T C T T T C A A A G T G G C A G C C A A G G  1038
Salmon PCR                                                                              594
```

FIG. 13H

```
SalmoKCaR 1  C C A C T C T G A G A C A C A G C T C A G C C T C C A G G A A G A G G T C C A G  2830
SalmoKCaR 2  C C A C T C T G A G A C A C A G C T C A G C C T C C A G G A A G A G G T C C A G  2920
SalmoKCaR 3  - - - - - - - - - - - - - - - - - - - - - - - - - - - - - - - - - - - - - - -  2713
Salmon A26   C C A C T C T G A G A C A C A G C T C A G C C T C C A G G A A G A G G T C C A G  1078
Salmon PCR                                                                                  594

SalmoKCaR 1  C A G T G T G G G G G G A T C C T G T G C C T C A A C T C C C T C C T C A T C C  2870
SalmoKCaR 2  C A G T G T G G G G G G A T C C T G T G C C T C A A C T C C C T C C T C A T C C  2960
SalmoKCaR 3  - - - - - - - - - - - - - - - - - - - - - - - - - - - - - - - - - - - - - - -  2713
Salmon A26   C A G T G T G G G G G G A T C C T G T G C C T C A A C T C C C T C C T C A T C C  1118
Salmon PCR                                                                                  594

SalmoKCaR 1  A T C A G C C T C A A G A C C A A T G A C A A T G A C T C C C C A T C A G G T C  2910
SalmoKCaR 2  A T C A G C C T C A A G A C C A A T G A C A A T G A C T C C C C A T C A G G T C  3000
SalmoKCaR 3  A T C A G C C T C A A G A C C A A T G A C A A T G A C T C C C C A T C A G G T C  2753
Salmon A26   A T C A G C C T C A A G A C C A A T G A C A A T G A C T C C C C A T C A G G T C  1158
Salmon PCR                                                                                  594

SalmoKCaR 1  A G C A G A G A A T C C A T A A G C C A A G A G T A A G C T T T G G A A G T G G  2950
SalmoKCaR 2  A G C A G A G A A T C C A T A A G C C A A G A G T A A G C T T T G G A A G T G G  3040
SalmoKCaR 3  A G C A G A G A A T C C A T A A G C C A A G A G T A A G C T T T G G A A G T G G  2793
Salmon A26   A G C A G A G A A T C C A T A A G C C A A G A G T A A G C T T T G G A A G T G G  1198
Salmon PCR                                                                                  594

SalmoKCaR 1  A A C A G T T A C T C T G T C C T T G A G C T T T G A G G A G T C C A G A A A G  2990
SalmoKCaR 2  A A C A G T T A C T C T G T C C T T G A G C T T T G A G G A G T C C A G A A A G  3080
SalmoKCaR 3  A A C A G T T A C T C T G T C C T T G A G C T T T G A G G A G T C C A G A A A G  2833
Salmon A26   A A C A G T T A C T C T G T C C T T G A G C T T T G A G G A G T C C A G A A A G  1238
Salmon PCR                                                                                  594

SalmoKCaR 1  A A T T C T A T G A A G T A G G G A A G T G T C T T T T G G T G G G C C G A G A  3030
SalmoKCaR 2  A A T T C T A T G A A G T A G G G A A G T G T C T T T T G G T G G G C C G A G A  3120
SalmoKCaR 3  A A T T C T A T G A A G T A G G G A A G T G T C T T T T G G T G G G C C G A G A  2873
Salmon A26   A A T T C T A T G A A G T A G G G A A G T G T C T T T T G G T G G G C C G A G A  1278
Salmon PCR                                                                                  594

SalmoKCaR 1  G C C T T G T C A A A A C C T G A G T T G G T G T T G C A T T C T T T G T T G G  3070
SalmoKCaR 2  G C C T T G T C A A A A C C T G A G T T G G T G T T G C A T T C T T T G T T G G  3160
SalmoKCaR 3  G C C T T G T C A A A A C C T G A G T T G G T G T T G C A T T C T T T G T T G G  2913
Salmon A26   G C C T T G T C A A A A C C T G A G T T G G T G T T G C A T T C T T T G T T G G  1318
Salmon PCR                                                                                  594

SalmoKCaR 1  C T G G G T A G T T G G A G C A G A A A T T A T G A T A T T A A A A G C T T T G  3110
SalmoKCaR 2  C T G G G T A G T T G G A G C A G A A A T T A T G A T A T T A A A A G C T T T G  3200
SalmoKCaR 3  C T G G G T A G T T G G A G C A G A A A T T A T G A T A T T A A A A G C T T T G  2953
Salmon A26   C T G G G T A G T T G G A G C A G A A A T T A T G A T A T T A A A A G C T T T G  1358
Salmon PCR                                                                                  594

SalmoKCaR 1  A T G T A T T C A G A A T G G T G A C A C A G C A T A G G T G G C C A A G A T T  3150
SalmoKCaR 2  A T G T A T T C A G A A T G G T G A C A C A G C A T A G G T G G C C A A G A T T  3240
SalmoKCaR 3  A T G T A T T C A G A A T G G T G A C A C A G C A T A G G T G G C C A A G A T T  2993
Salmon A26   A T G T A T T C A G A A T G G T G A C A C A G C A T A G G T G G C C A A G A T T  1398
Salmon PCR                                                                                  594
```

FIG. 13I

```
SalmoKCaR 1  C C A T T A T A T T A C A A T A A T C T G T G T T G T T C A T T A T G A G G A C  3190
SalmoKCaR 2  C C A T T A T A T T A C A A T A A T C T G T G T T G T T C A T T A T G A G G A C  3280
SalmoKCaR 3  C C A T T A T A T T A C A A T A A T C T G T G T T G T T C A T T A T G A G G A C  3033
Salmon A26   C C A T T A T A T T A C A A T A A T C T G T G T T G T T C A T T A T G A G G A C  1438
Salmon PCR                                                                                594

SalmoKCaR 1  A T T T C A A A A T G C T G A A A A T C A T C A A A T A C A T A A T T T A C T G  3230
SalmoKCaR 2  A T T T C A A A A T G C T G A A A A T C A T C A A A T A C A T A A T T T A C T G  3320
SalmoKCaR 3  A T T T C A A A A T G C T G A A A A T C A T C A A A T A C A T A A T T T A C T G  3073
Salmon A26   A T T T C A A A A T G C T G A A A A T C A T C A A A T A C A T A A T T T A C T G  1478
Salmon PCR                                                                                594

SalmoKCaR 1  A G T T T T C T T G A T A A T C T T G A G A A T A G A A T A G C C T A T T C A A  3270
SalmoKCaR 2  A G T T T T C T T G A T A A T C T T G A G A A T A G A A T A G C C T A T T C A A  3360
SalmoKCaR 3  A G T T T T C T T G A T A A T C T T G A G A A T A G A A T A G C C T A T T C A A  3113
Salmon A26   A G T T T T C T T G A T A A T C T T G A G A A T A G A A T A G C C T A T T C A A  1518
Salmon PCR                                                                                594

SalmoKCaR 1  G T C A T C G T T G A G C A G A C A T T A A T T A A C A A T G A T G T A A T A C  3310
SalmoKCaR 2  G T C A T C G T T G A G C A G A C A T T A A T T A A C A A T G A T G T A A T A C  3400
SalmoKCaR 3  G T C A T C G T T G A G C A G A C A T T A A T T A A C A A T G A T G T A A T A C  3153
Salmon A26   G T C A T C G T T G A G C A G A C A T T A A T T A A C A A T G A T G T A A T A C  1558
Salmon PCR                                                                                594

SalmoKCaR 1  T T T C C A T A C C T A T T T T C T T T A A C A A T A G A T T C A C A T T G T T  3350
SalmoKCaR 2  T T T C C A T A C C T A T T T T C T T T A A C A A T A G A T T C A C A T T G T T  3440
SalmoKCaR 3  T T T C C A T A C C T A T T T T C T T T A A C A A T A G A T T C A C A T T G T T  3193
Salmon A26   T T T C C A T A C C T A T T T T C T T T A A C A A T A G A T T C A C A T T G T T  1598
Salmon PCR                                                                                594

SalmoKCaR 1  A A A G T T C A A C T A T G A C C T G T A A A A T A C A T G A G G T A T A A C A  3390
SalmoKCaR 2  A A A G T T C A A C T A T G A C C T G T A A A A T A C A T G A G G T A T A A C A  3480
SalmoKCaR 3  A A A G T T C A A C T A T G A C C T G T A A A A T A C A T G A G G T A T A A C A  3233
Salmon A26   A A A G T T C A A C T A T G A C C T G T A A A A T A C A T G A G G T A T A A C A  1638
Salmon PCR                                                                                594

SalmoKCaR 1  G G A G A C A A T A A A A C T A T G C A T A T C C T A G C T T C T G G G C C T G  3430
SalmoKCaR 2  G G A G A C A A T A A A A C T A T G C A T A T C C T A G C T T C T G G G C C T G  3520
SalmoKCaR 3  G G A G A C A A T A A A A C T A T G C A T A T C C T A G C T T C T G G G C C T G  3273
Salmon A26   G G A G A C A A T A A A A C T A T G C A T A T C C T A G C T T C T G G G C C T G  1678
Salmon PCR                                                                                594

SalmoKCaR 1  A G T A G C A G G C A G T T T A C T C T G G G C A C G C T T T T C A T C C A A A  3470
SalmoKCaR 2  A G T A G C A G G C A G T T T A C T C T G G G C A C G C T T T T C A T C C A A A  3560
SalmoKCaR 3  A G T A G C A G G C A G T T T A C T C T G G G C A C G C T T T T C A T C C A A A  3313
Salmon A26   A G T A G C A G G C A G T T T A C T C T G G G C A C G C T T T T C A T C C A A A  1718
Salmon PCR                                                                                594

SalmoKCaR 1  C T T C C G A A T G C T G C C C C A A T C C T A G T G A G G T T A A A G G C C  3510
SalmoKCaR 2  C T T C C G A A T G C T G C C C C A A T C C T A G T G A G G T T A A A G G C C  3600
SalmoKCaR 3  C T T C C G A A T G C T G C C C C A A T C C T A G T G A G G T T A A A G G C C  3353
Salmon A26   C T T C C G A A T G C T G C C C C A A T C C T A G T G A G G T T A A A G G C C  1758
Salmon PCR                                                                                594
```

FIG. 13J

```
SalmoKCaR 1  C A G T G C A G T C A T A T C T T T T C T C T A G G C A C G C T T T T C A T C C  3550
SalmoKCaR 2  C A G T G C A G T C A T A T C T T T T C T C T A G G C A C G C T T T T C A T C C  3640
SalmoKCaR 3  C A G T G C A G T C A T A T C T T T T C T C T A G G C A C G C T T T T C A T C C  3393
Salmon A26   C A G T G C A G T C A T A T C T T T T C T C T A G G C A C G C T T T T C A T C C  1798
Salmon PCR                                                                                594

SalmoKCaR 1  A A A C T T C C G A A T G C G G C T A T A T C A G T C T C T T T C C T A C T G T  3590
SalmoKCaR 2  A A A C T T C C G A A T G C G G C T A T A T C A G T C T C T T T C C T A C T G T  3680
SalmoKCaR 3  A A A C T T C C G A A T G C G G C T A T A T C A G T C T C T T T C C T A C T G T  3433
Salmon A26   A A A C T T C C G A A T G C G G C T A T A T C A G T C T C T T T C C T A C T G T  1838
Salmon PCR                                                                                594

SalmoKCaR 1  C T T T T T C A T T A G G C C A G T G T T T A A C A A C C C T G G T C C T T A A  3630
SalmoKCaR 2  C T T T T T C A T T A G G C C A G T G T T T A A C A A C C C T G G T C C T T A A  3720
SalmoKCaR 3  C T T T T T C A T T A G G C C A G T G T T T A A C A A C C C T G G T C C T T G A  3473
Salmon A26   C T T T T T C A T T A G G C C A G T G T T T A A C A A C C C T G G T C C T T A A  1878
Salmon PCR                                                                                594

SalmoKCaR 1  G T A C A C A C A A C A G A G C A C A T T T T T G T T G T G G C C C T G G A C A  3670
SalmoKCaR 2  G T A C A C A C A A C A G A G C A C A T T T T T G T T G T A G C C C T G G A C A  3760
SalmoKCaR 3  G T A C A C A C A A C A G G G C A C A T T T T T G T T G T A G C C C T G G A C A  3513
Salmon A26   G T A C A C A C A A C A G A A C A C A T T T T T G T T G T A G C C C T G G A C A  1918
Salmon PCR                                                                                594

SalmoKCaR 1  A T C A C T C C T C A C T C A G C T C A T T G A G G G C C T G A T G A T T A G T  3710
SalmoKCaR 2  A T C A C T C C T C A C T C A G C T C A T T G A G G G C C T G A T G A T T A G T  3800
SalmoKCaR 3  A T C A C T C C T C A C T C A G C T C A T T G A G G G C C T G A T G A T T A G T  3553
Salmon A26   A T C A C T C C T C A C T C A G C T C A T T G A G G G C C T G A T G A T T A G T  1958
Salmon PCR                                                                                594

SalmoKCaR 1  T G A C A A G T T G A G T C G G G T G T G C T T G T C C G G G G T T G C A A T A  3750
SalmoKCaR 2  T G A C A A G T T G A G T C G G G T G T G C T T G T C C A G G G T T A C G A T A  3840
SalmoKCaR 3  T G A C A A G T T G G G T C A G G T G T G C T T G T C C A G G G T T A C A A T A  3593
Salmon A26   T G A C A A G T T G A A T C A G G T G T G C T T G T C C A G G G T T A C A A T A  1998
Salmon PCR                                                                                594

SalmoKCaR 1  C A G A T G T G T A C T G T T G G G G G T A C T C G A G G A C C A G G A T T G G  3790
SalmoKCaR 2  C A G A T G T G T A C T G T T G G G G G T G C T C G A G G A C C A G G A T T G G  3880
SalmoKCaR 3  C A G A T G T G T G C T G T T G G G G G T A C T C G A G G A C C A G G A T T G G  3633
Salmon A26   C A A A T G T G T A C T G T T G G G G G T A C (SEQ ID NO: 5)                   2021
Salmon PCR                                                                                594

SalmoKCaR 1  G A A A C A T T A C A T T A G G A C T A C T G T A G G T T C T T C A A T A T G G  3830
SalmoKCaR 2  G A A A C A T T A C A T T A G G A C T A C T G T A G G T T C T T C A A T A T G G  3920
SalmoKCaR 3  G A A A C A T T A C A T T A G G A C T A C T G T A G G T T C T T C A A T A T G G  3673
Salmon A26                                                                                2021
Salmon PCR                                                                                594

SalmoKCaR 1  T G T C A T A C G G T C A T A T G G T G T C A T A T G G T G T C T G G T T G T T  3870
SalmoKCaR 2  T G T C A T A C G G T C A T A T G G T G T C A T A T G G T G T C T G G T T G T T  3960
SalmoKCaR 3  T G T C A T A C G G T C A T A T G G T G T C A T A T G G T G T C T G G T T G T T  3713
Salmon A26                                                                                2021
Salmon PCR                                                                                594
```

FIG. 13K

```
SalmoKCaR 1  T T C T G C A T A T G T G T A T T T C A C C A A G T T A C T G C A C A T G T T A  3910
SalmoKCaR 2  T T C T G C A T A T G T G T A T T T C A C C A A G T T A C T G C A C A T G T T A  4000
SalmoKCaR 3  T T C T G C A T A T G T G T A T T T C A C C A A G T T A C T G C A C A T G T T A  3753
Salmon A26                                                                                  2021
Salmon PCR                                                                                   594

SalmoKCaR 1  G A C C T A T A C A C T G G A A T A A A C A T T T T T T T T C (SEQ ID NO: 7)  3941
SalmoKCaR 2  G A C C T A T A C A C T G G A A T A A A C A T T T T T T T T C (SEQ ID NO: 9)  4031
SalmoKCaR 3  G A C C T A T A C A C T G G A A T A A A C A T T T T T T T T C A C A A T G C A T  3793
Salmon A26                                                                                  2021
Salmon PCR                                                                                   594

SalmoKCaR 1                                                                                 3941
SalmoKCaR 2                                                                                 4031
SalmoKCaR 3  C C A A T G A C A A T A A A A T C A C C A T A T G C C A A T G (SEQ ID NO: 11) 3824
Salmon A26                                                                                  2021
Salmon PCR                                                                                   594
```

FIG. 13L

```
SalmoKCaR 1   M R F Y L Y Y L V L L G F S S V I S T Y G P H Q R A Q K T G D I L L G G L F P M   40
SalmoKCaR 2   M R F Y L Y Y L V L L G F S S V I S T Y G P H Q R A Q K T G D I L L G G L F P M   40
SalmoKCaR 3   M R F Y L Y Y L V L L G F S S V I S T Y G P H Q R A Q K T G D I L L G G L F P M   40
Salmon A26    - - - - - - - - - - - - - - - - - - - - - - - - - - - - - - - - - - - - - - - -    0
Salmon PCR    - - - - - - - - - - - - - - - - - - - - - - - - - - - - - - - - - - - - - - - -    0

SalmoKCaR 1   H F G V T S K D Q D L A A R P E S T E C V R Y N F R G F R W L Q A M I F A I E E   80
SalmoKCaR 2   H F G V T S K D Q D L A A R P E S T E C V R Y N F R G F R W L Q A M I F A I E E   80
SalmoKCaR 3   H F G V T S K D Q D L A A R P E S T E C V R Y N F R G F R W L Q A M I F A I E E   80
Salmon A26    - - - - - - - - - - - - - - - - - - - - - - - - - - - - - - - - - - - - - - - -    0
Salmon PCR    - - - - - - - - - - - - - - - - - - - - - - - - - - - - - - - - - - - - - - - -    0

SalmoKCaR 1   I N N S S T L L P N I T L G Y R I F D T C N T V S K A L E A T L S F V A Q N K I   120
SalmoKCaR 2   I N N S S T L L P N I T L G Y R I F D T C N T V S K A L E A T L S F V A Q N K I   120
SalmoKCaR 3   I N N S S T L L P N I T L G Y R I F D T C N T V S K A L E A T L S F V A Q N K I   120
Salmon A26    - - - - - - - - - - - - - - - - - - - - - - - - - - - - - - - - - - - - - - - -    0
Salmon PCR    - - - - - - - - - - - - - - - - - - - - - - - - - - - - - - - - - - - - - - - -    0

SalmoKCaR 1   D S L N L D E F C N C T D H I P S T I A V V G A S G S A V S T A V A N L L G L F   160
SalmoKCaR 2   D S L N L D E F C N C T D H I P S T I A V V G A S G S A V S T A V A N L L G L F   160
SalmoKCaR 3   D S L N L D E F C N C T D H I P S T I A V V G A S G S A V S T A V A N L L G L F   160
Salmon A26    - - - - - - - - - - - - - - - - - - - - - - - - - - - - - - - - - - - - - - - -    0
Salmon PCR    - - - - - - - - - - - - - - - - - - - - - - - - - - - - - - - - - - - - - - - -    0

SalmoKCaR 1   Y I P Q I S Y A S S S R L L S N K N Q F K S F M R T I P T D E H Q A T A M A D I   200
SalmoKCaR 2   Y I P Q I S Y A S S S R L L S N K N Q F K S F M R T I P T D E H Q A T A M A D I   200
SalmoKCaR 3   Y I P Q I S Y A S S S R L L S N K N Q F K S F M R T I P T D E H Q A T A M A D I   200
Salmon A26    - - - - - - - - - - - - - - - - - - - - - - - - - - - - - - - - - - - - - - - -    0
Salmon PCR    - - - - - - - - - - - - - - - - - - - - - - - - - - - - - - - - - - - - - - - -    0

SalmoKCaR 1   I D Y F Q W N W V I A V A S D D E Y G R P G I E K F E K E M E E R D I C I H L S   240
SalmoKCaR 2   I D Y F Q W N W V I A V A S D D E Y G R P G I E K F E K E M E E R D I C I H L S   240
SalmoKCaR 3   I D Y F Q W N W V I A V A S D D E Y G R P G I E K F E K E M E E R D I C I H L S   240
Salmon A26    - - - - - - - - - - - - - - - - - - - - - - - - - - - - - - - - - - - - - - - -    0
Salmon PCR    - - - - - - - - - - - - - - - - - - - - - - - - - - - - - - - - - - - - - - - -    0

SalmoKCaR 1   E L I S Q Y F E E W Q I Q G L V D R I E N S S A K V I V V F A S G P D I E P L I   280
SalmoKCaR 2   E L I S Q Y F E E W Q I Q G L V G R I E N S S A K V I V V F A S G P D I E P L I   280
SalmoKCaR 3   E L I S Q Y F E E W Q I Q G L V D R I E N S S A K V I V V F A S G P D I E P L I   280
Salmon A26    - - - - - - - - - - - - - - - - - - - - - - - - - - - - - - - - - - - - - - - -    0
Salmon PCR    - - - - - - - - - - - - - - - - - - - - - - - - - - - - - - - - - - - - - - - -    0

SalmoKCaR 1   K E M V R R N I T D R I W L A S E A W A T T S L I A K P E Y L D V V V G T I G F   320
SalmoKCaR 2   K E M V R R N I T D R I W L A S E A W A T T S L I A K P E Y L D V V V G T I G F   320
SalmoKCaR 3   K E M V R R N I T D R I W L A S E A W A T T S L I A K P E Y L D V V V G T I G F   320
Salmon A26    - - - - - - - - - - - - - - - - - - - - - - - - - - - - - - - - - - - - - - - -    0
Salmon PCR    - - - - - - - - - - - - - - - - - - - - - - - - - - - - - - - - - - - - - - - -    0

SalmoKCaR 1   A L R A G E I P G F K D F L Q E V T P K K S S H N E F V R E F W E E T F N C Y L   360
SalmoKCaR 2   A L R A G E I P G F K D F L Q E V T P K K S S H N E F V R E F W E E T F N C Y L   360
SalmoKCaR 3   A L R A G E I P G F K D F L Q E V T P K K S S H N E F V R E F W E E T F N C Y L   360
Salmon A26    - - - - - - - - - - - - - - - - - - - - - - - - - - - - - - - - - - - - - - - -    0
Salmon PCR    - - - - - - - - - - - - - - - - - - - - - - - - - - - - - - - - - - - - - - - -    0
```

FIG. 14A

```
SalmoKCaR 1  E D S Q R L R D S E N G S T S F R P L C T G E E D I M G A E T P Y L D Y T H L R  400
SalmoKCaR 2  E D S Q R L R D S E N G S T S F R P L C T G E E D I M G A E T P Y L D Y T H L R  400
SalmoKCaR 3  E D S Q R L R D S E N G S T S F R P L C T G E E D I M G A E T P Y L D Y T H L R  400
Salmon A26   - - - - - - - - - - - - - - - - - - - - - - - - - - - - - - - - - - - - - - - -  0
Salmon PCR   - - - - - - - - - - - - - - - - - - - - - - - - - - - - - - - - - - - - - - - -  0

SalmoKCaR 1  I S Y N V Y V A V H S I A Q A L Q D I L T C I P G R G L F S N N S C A D I K K I  440
SalmoKCaR 2  I S Y N V Y V A V H S I A Q A L Q D I L T C I P G R G L F S N N S C A D I K K I  440
SalmoKCaR 3  I S Y N V Y V A V H S I A Q A L Q D I L T C I P G R G F F S N N S C A D I K K I  440
Salmon A26   - - - - - - - - - - - - - - - - - - - - - - - - - - - - - - - - - - - - - - - -  0
Salmon PCR   - - - - - - - - - - - - - - - - - - - - - - - - - - - - - - - - - - - - - - - -  0

SalmoKCaR 1  E A W Q V L K Q L R H L N F S N S M G E K V H F D E N A D P S G N Y T I I N W H  480
SalmoKCaR 2  E A W Q V L K Q L R H L N F S N S M G E K V H F D E N A D P S G N Y T I I N W H  480
SalmoKCaR 3  E A W Q V L K Q L R H L N F S N S M G E K V H F D E N A D P S G N Y T I I N W H  480
Salmon A26   - - - - - - - - - - - - - - - - - - - - - - - - - - - - - - - - - - - - - - - -  0
Salmon PCR   - - - - - - - - - - - - - - - - - - - - - - - - - - - - - - - - - - - - - - - -  0

SalmoKCaR 1  R S P E D G S V V F E E V G F Y N M R A K R G V Q L F I D N T K I L W N G Y N T  520
SalmoKCaR 2  R S P E D G S V V F E E V G F Y N M R A K R G V Q L F I D N T K I L W N G Y N T  520
SalmoKCaR 3  R S P E D G S V V F E E V G F Y N M R A K R G V Q L F I D N T K I L W N G Y N T  520
Salmon A26   - - - - - - - - - - - - - - - - - - - - - - - - - - - - - - - - - - - - - - - -  0
Salmon PCR   - - - - - - - - - - - - - - - - - - - - - - - - - - - - - - - - - - - - - - - -  0

SalmoKCaR 1  E V P F S N C S E D C E P G T R K G I I E S M P T C C F E C T E C S E G E Y S D  560
SalmoKCaR 2  E V P F S N C S E D C E P G T R K G I I E S M P T C C F E C T E C S E G E Y S D  560
SalmoKCaR 3  E V P F S N C S E D C E P G T R K G I I E S M P T C C F E C T E C S E G E Y S D  560
Salmon A26   - - - - - - - - - - - - - - - - - - - - - - - - - - - - - - - Y K H Y F S I  7
Salmon PCR   - - - - - - - - - - - - - - - - - - - - - - - - - - - - - - - - - - - - - - - -  0

SalmoKCaR 1  H K D A S V C T K C P N D S W S N E N H T S C F L K E I E F L S W T E P F G I A  600
SalmoKCaR 2  H K D A S V C T K C P N D S W S N E N H T S C F L K E I E F L S W T E P F G I A  600
SalmoKCaR 3  H K D A S V C T K C P N D S W S N E N H T S C F L K E I E F L S W T E P F G I A  600
Salmon A26   P A D A S V C T K C P N D S W S N E N H T S C F L K E I E F L S W T E P F G I A  47
Salmon PCR   - - - - - - - - - - - - - - - - - - - - - - - - - - - - - - - - - - - - - - - -  0

SalmoKCaR 1  L A L C S V L G V F L T A F V M G V F I K F R N T P I V K A T N R E L S Y L L L  640
SalmoKCaR 2  L A L C S V L G V F L T A F V M G V F I K F R N T P I V K A T N R E L S Y L L L  640
SalmoKCaR 3  L A L C S V L G V F L T A F V M G V F I K F R N T P I V K A T N R E L S Y L L L  640
Salmon A26   L A L C S V L G V F L T A F V M G V F I K F R N T P I V K A T N R E L S Y L L L  87
Salmon PCR   L A L C S V L G V F L T A F V M G V F I K F R N T P I V K A T N R E L S Y L L L  40

SalmoKCaR 1  F S L I C C F S S S L I F I G E P Q D W T C R L R Q P A F G I S F V L C I S C I  680
SalmoKCaR 2  F S L I C C F S S S L I F I G E P Q D W T C R L R Q P A F G I S F V L C I S C I  680
SalmoKCaR 3  F S L I C C F S S S L I F I G E P Q D W T C R L R Q P A F G I S F V L C I S C I  680
Salmon A26   F S L I C C F S S S L I F I G E P Q D W T C R L R Q P A F G I S F V L C I S C I  127
Salmon PCR   F S L I C C F S S S L I F I G E P Q D W T C R L R Q P A F G I S F V L C I S C I  80

SalmoKCaR 1  L V K T N R V L L V F E A K I P T S L H R K W W G L N L Q F L L V F L F T F V Q  720
SalmoKCaR 2  L V K T N R V L L V F E A K I P T S L H R K W W G L N L Q F L L V F L F T F V Q  720
SalmoKCaR 3  L V K T N R V L L V F E A K I P T S L H R K W W G L N L Q F L L V F L F T F V Q  720
Salmon A26   L V K T N R V L L V F E A K I P T S L H R K W W G L N L Q F L L V F L F T F V Q  167
Salmon PCR   L V K T N R V L L V F E A K I P T S L H R K W W G L N L Q F L L V F L F T F V Q  120
```

FIG. 14B

```
SalmoKCaR 1  V M I C V V W L Y N A P P A S Y R N H D I D E I I F I T C N E G S M M A L G F L  760
SalmoKCaR 2  V M I C V V W L Y N A P P A S Y R N H D I D E I I F I T C N E G S M M A L G F L  760
SalmoKCaR 3  V M I C V V W L Y N A P P A S Y R N H D I D E I I F I T C N E G S M M A L G F L  760
Salmon A26   V M I C V V W L Y N A P P A S Y R N H D I D E I I F I T C N E G S M M A L G F L  207
Salmon PCR   V M I C V V W L Y N A P P A S Y R N H D I D E I I F I T C N E G S M M A L G F L  160

SalmoKCaR 1  I G Y T C L L A A I C F F F A F K S R K L P E N F T E A K F I T F S M L I F F I  800
SalmoKCaR 2  I G Y T C L L A A I C F F F A F K S R K L P E N F T E A K F I T F S M L I F F I  800
SalmoKCaR 3  I G Y T C L L A A I C F F F A F K S R K L P E N F T E A K F I T F S M L I F F I  800
Salmon A26   I G Y T C L L A A I C F F F A F K S R K L P E N F T E A K F I T F S M L I F F I  247
Salmon PCR   I G Y T C L L A A I C F F F A F K S R K L P E N F T E A K F I T F S M L I             197

SalmoKCaR 1  V W I S F I P A Y F S T Y G K F V S A V E V I A I L A S S F G L L A C I F F N K  840
SalmoKCaR 2  V W I S F I P A Y F S T Y G K F V S A V E V I A I L A S S F G L L A C I F F N K  840
SalmoKCaR 3  V W I S F I P A Y F S T Y G K F V S A V E V I A I L A S S F G L L A C I F F N K  840
Salmon A26   V W I S F I P A Y F S T Y G K F V S A V E V I A I L A S S F G L L A C I F F N K  287
Salmon PCR                                                                                   197

SalmoKCaR 1  V Y I I L F K P S R N T I E E V R C S T A A H S F K V A A K A T L R H S S A S R  880
SalmoKCaR 2  V Y I I L F K P S R N T I E E V R C S T A A H S F K V A A K A T L R H S S A S R  880
SalmoKCaR 3  V Y I I H Q P Q D Q                                                              850
Salmon A26   V Y I I L F K P S R N T I E E V R C S T A A H S F K V A A K A T L R H S S A S R  327
Salmon PCR                                                                                   197

SalmoKCaR 1  K R S S S V G G S C A S T P S S S I S L K T N D N D S P S G Q Q R I H K P R V S  920
SalmoKCaR 2  K R S S S V G G S C A S T P S S S I S L K T N D N D S P S G Q Q R I H K P R V S  920
SalmoKCaR 3                                                                                   850
Salmon A26   K R S S S V G G S C A S T P S S S I S L K T N D N D S P S G Q Q R I H K P R V S  367
Salmon PCR                                                                                   197

SalmoKCaR 1  F G S G T V T L S L S F E E S R K N S M K  (SEQ ID NO: 8)                        941
SalmoKCaR 2  F G S G T V T L S L S F E E S R K N S M K  (SEQ ID NO: 10)                       941
SalmoKCaR 3                                                                                   850
Salmon A26   F G S G T V T L S L S F E E S R K N S M K  (SEQ ID NO: 12)                      388
Salmon PCR                                                                                   197
```

FIG. 14C

```
SalmoKCaR 1 - T T C C A A C A G C A T A T T T T T G T T G T A T T T G C T T T G G T T T G T 39
SalmoKCaR 2 G T T C C A A C A G C A T A T T T T T G T T G T A T T T G C T T T G G T T T G T 40
SalmoKCaR 3 G T T C C A A C A G C A T A T T T T T G T T G T A T T T G C T T T G G T T T G T 40

SalmoKCaR 1 C T G A A A T C A A G C A T T A T C A A G - - - - - - - - - - - - - - - - - - - 60
SalmoKCaR 2 C T G A A A T C A A G C A T T A T C A A G G A T T G A G C A A G A C A A C T G A 80
SalmoKCaR 3 C T G A A A T C A A G C A T T A T C A A G - - - - - - - - - - - - - - - - - - - 61

SalmoKCaR 1 - - - - - - - - - - - - - - - - - - - - - - - - - - - - - - - - - - - - - - - - 60
SalmoKCaR 2 G T T G T C A G A C T A A G A A T A T A C A C A T T T C C A G T T C T C T C T T 120
SalmoKCaR 3 - - - - - - - - - - - - - - - - - - - - - - - - - - - - - - - - - - - - - - - - 61

SalmoKCaR 1 - - - - - - - - - - - - - - - - - - - - - - - - - - - - - A T C A A G A A C A 70
SalmoKCaR 2 T A A T G G A C T T C T C A C A C T G A T G T T C T T C A G A T C A A G A A C A 160
SalmoKCaR 3 - - - - - - - - - - - - - - - - - - - - - - - - - - - - - A T C A A G A A C A 71

SalmoKCaR 1 G C A T G A G T C A G A A A C A A G G C G A C A G C C A G A G T C A C T G G A G 110
SalmoKCaR 2 G C A T G A G T C A G A A A C A A G G C G A C A G C C A G A G T C A C T G G A G 200
SalmoKCaR 3 G C A T G A G T C A G A A A C A A G G C G A C A G C C A G A G T C A C T G G A G 111

SalmoKCaR 1 G G A C A A G A C T G A G G T T A A C T C T G A A G T C T A A T G T G C T G A 150
SalmoKCaR 2 G G A C A A G A C T G A G G T T A A C T C T G A A G T C T A A T G T G C T G A 240
SalmoKCaR 3 G G A C A A G A C T G A G G T T A A C T C T G A A G T C T A A T G T G C T G A 151

SalmoKCaR 1 G A G G A C A A G G C C C T C C T G A G A G C T G A A C G A T G A G A T T T T A 190
SalmoKCaR 2 G A G G A C A A G G C C C T C C T G A G A G C T G A A C G A T G A G A T T T T A 280
SalmoKCaR 3 G A G G A C A A G G C C C T C C T G A G A G C T G A A C G A T G A G A T T T T A 191

SalmoKCaR 1 C C T G T A T T A C C T G G T G C T T T T G G G C T T C A G T T C T G T C A T C 230
SalmoKCaR 2 C C T G T A T T A C C T G G T G C T T T T G G G C T T C A G T T C T G T C A T C 320
SalmoKCaR 3 C C T G T A T T A C C T G G T G C T T T T G G G C T T C A G T T C T G T C A T C 231

SalmoKCaR 1 T C C A C C T A T G G G C C T C A T C A G A G A G C A C A G A A G A C T G G G G 270
SalmoKCaR 2 T C C A C C T A T G G G C C T C A T C A G A G A G C A C A G A A G A C T G G G G 360
SalmoKCaR 3 T C C A C C T A T G G G C C T C A T C A G A G A G C A C A G A A G A C T G G G G 271

SalmoKCaR 1 A T A T T C T G C T G G G C G G G C T G T T T C C A A T G C A C T T T G G T G T 310
SalmoKCaR 2 A T A T T C T G C T G G G C G G G C T G T T T C C A A T G C A C T T T G G T G T 400
SalmoKCaR 3 A T A T T C T G C T G G G C G G G C T G T T T C C A A T G C A C T T T G G T G T 311

SalmoKCaR 1 T A C C T C C A A A G A C C A A G A C C T G G C A G C G C G G C C A G A A T C C 350
SalmoKCaR 2 T A C C T C C A A A G A C C A A G A C C T G G C A G C G C G G C C A G A A T C C 440
SalmoKCaR 3 T A C C T C C A A A G A C C A A G A C C T G G C A G C G C G G C C A G A A T C C 351

SalmoKCaR 1 A C A G A G T G T G T T A G G T A C A A T T T C C G G G G A T T C C G T T G G C 390
SalmoKCaR 2 A C A G A G T G T G T T A G G T A C A A T T T C C G G G G A T T C C G T T G G C 480
SalmoKCaR 3 A C A G A G T G T G T T A G G T A C A A T T T C C G G G G A T T C C G T T G G C 391

SalmoKCaR 1 T T C A G G C C A T G A T T T T T G C A A T A G A G G A G A T C A A C A A C A G 430
SalmoKCaR 2 T T C A G G C C A T G A T T T T T G C A A T A G A G G A G A T C A A C A A C A G 520
SalmoKCaR 3 T T C A G G C C A T G A T T T T T G C A A T A G A G G A G A T C A A C A A C A G 431

SalmoKCaR 1 C A G T A C T C T C C T G C C C A A C A T C A C A C T G G G C T A C A G G A T C 470
SalmoKCaR 2 C A G T A C T C T C C T G C C C A A C A T C A C A C T G G G C T A C A G G A T C 560
SalmoKCaR 3 C A G T A C T C T C C T G C C C A A C A T C A C A C T G G G C T A C A G G A T C 471
```

FIG. 16A

```
SalmoKCaR 1  T T T G A C A C C T G C A A C A C C G T G T C C A A G G C C C T G G A G G C T A  510
SalmoKCaR 2  T T T G A C A C C T G C A A C A C C G T G T C C A A G G C C C T G G A G G C T A  500
SalmoKCaR 3  T T T G A C A C C T G C A A C A C C G T G T C C A A G G C C C T G G A G G C T A  511

SalmoKCaR 1  C C C T C A G T T T C G T A G C A C A G A A T A A G A T T G A C T C T C T G A A  550
SalmoKCaR 2  C C C T C A G T T T C G T A G C A C A G A A T A A G A T T G A C T C T C T G A A  540
SalmoKCaR 3  C C C T C A G T T T C G T A G C A C A G A A T A A G A T T G A C T C T C T G A A  551

SalmoKCaR 1  C T T G G A T G A A T T C T G T A A C T G C A C T G A T C A C A T C C C A T C G  590
SalmoKCaR 2  C T T G G A T G A A T T C T G T A A C T G C A C T G A T C A C A T C C C A T C G  580
SalmoKCaR 3  C T T G G A T G A A T T C T G T A A C T G C A C T G A T C A C A T C C C A T C G  591

SalmoKCaR 1  A C T A T A G C A C T G G T G G G G C T T C T G G G T C A G C G G T C T C C A  630
SalmoKCaR 2  A C T A T A G C A G T G G T G G G G C T T C T G G G T C A G C G G T C T C C A  720
SalmoKCaR 3  A C T A T A G C A G T G G T G G G G C T T C T G G G T C A G C G G T C T C C A  631

SalmoKCaR 1  C T G C T G T T G C C A A T C T G T T G G G C C T T T T C T A C A T C C C A C A  670
SalmoKCaR 2  C T G C T G T T G C C A A T C T G T T G G G C C T T T T C T A C A T C C C A C A  760
SalmoKCaR 3  C T G C T G T T G C C A A T C T G T T G G G C C T T T T C T A C A T C C C A C A  671

SalmoKCaR 1  G A T C A C C T A T G C C T C T T C C A G T C G C C T A C T A A G C A A C A A G  710
SalmoKCaR 2  G A T C A G C T A T G C C T C T T C C A G T C G C C T A C T A A G C A A C A A G  800
SalmoKCaR 3  G A T C A G C T A T G C C T C T T C C A G T C G C C T A C T A A G C A A C A A G  711

SalmoKCaR 1  A A C C A G T T C A A A T C C T T C A T G A G G A C C A T T C C C A C A G A T G  750
SalmoKCaR 2  A A C C A G T T C A A A T C C T T C A T G A G G A C C A T T C C C A C A G A T G  840
SalmoKCaR 3  A A C C A G T T C A A A T C C T T C A T G A G G A C C A T T C C C A C A G A T G  751

SalmoKCaR 1  A G C A C C A G G C C A C T G C C A T G G C A G A T A T C A T C G A C T A C T T  790
SalmoKCaR 2  A G C A C C A G G C C A C T G C C A T G G C A G A T A T C A T C G A C T A C T T  880
SalmoKCaR 3  A G C A C C A G G C C A C T G C C A T G G C A G A T A T C A T C G A C T A C T T  791

SalmoKCaR 1  C C A A T G G A A T T G G G T C A T T G C A G T T G C G T C T G A T G A T G A G  830
SalmoKCaR 2  C C A A T G G A A T T G G G T C A T T G C A G T T G C G T C T G A T G A T G A G  920
SalmoKCaR 3  C C A A T G G A A T T G G G T C A T T G C A G T T G C G T C T G A T G A T G A G  831

SalmoKCaR 1  T A T G G A C G T C C G G G G A T T G A A A A A T T T G A G A A A G A G A T G G  870
SalmoKCaR 2  T A T G G A C G T C C G G G G A T T G A A A A A T T T G A G A A A G A G A T G G  960
SalmoKCaR 3  T A T G G A C G T C C G G G G A T T G A A A A A T T T G A G A A A G A G A T G G  871

SalmoKCaR 1  A A G A A C G A G A C A T T T G T A T C C A T C T G A G T G A G C T G A T C T C  910
SalmoKCaR 2  A A G A A C G A G A C A T T T G T A T C C A T C T G A G T G A G C T G A T C T C  1000
SalmoKCaR 3  A A G A A C G A G A C A T T T G T A T C C A T C T G A G T G A G C T G A T C T C  911

SalmoKCaR 1  T C A G T A C T T T G A G G A G T G G C A G A T C C A A G G A T T G G T T G A C  950
SalmoKCaR 2  T C A G T A C T T T G A G G A G T G G C A G A T C C A A G G A T T G G T T G G C  1040
SalmoKCaR 3  T C A G T A C T T T G A G G A G T G G C A G A T C C A A G G A T T G G T T G A C  951

SalmoKCaR 1  C G T A T T G A G A A C T C C T C A G C T A A A G T T A T A G T C G T T T C G  990
SalmoKCaR 2  C G T A T T G A G A A C T C C T C A G C T A A A G T T A T A G T C G T T T C G  1080
SalmoKCaR 3  C G T A T T G A G A A C T C C T C A G C T A A A G T T A T A G T C G T T T C G  991

SalmoKCaR 1  C C A G T G G G C C T G A C A T T G A G C C T C T T A T T A A A G A G A T G G T  1030
SalmoKCaR 2  C C A G T G G G C C T G A C A T T G A G C C T C T T A T T A A A G A G A T G G T  1120
SalmoKCaR 3  C C A G T G G G C C T G A C A T T G A G C C T C T T A T T A A A G A G A T G G T  1031
```

FIG. 16B

```
SalmoKCaR 1  C A G A C G G A A C A T C A C C G A C C G C A T C T G G T T G G C C A G C G A G  1070
SalmoKCaR 2  C A G A C G G A A C A T C A C C G A C C G C A T C T G G T T G G C C A G C G A G  1160
SalmoKCaR 3  C A G A C G G A A C A T C A C C G A C C G C A T C T G G T T G G C C A G C G A G  1071

SalmoKCaR 1  G C T T G G G C A A C C A C C T C C C T C A T C G C C A A A C C A G A G T A C C  1110
SalmoKCaR 2  G C T T G G G C A A C C A C C T C C C T C A T C G C C A A A C C A G A G T A C C  1200
SalmoKCaR 3  G C T T G G G C A A C C A C C T C C C T C A T C G C C A A A C C A G A G T A C C  1111

SalmoKCaR 1  T T G A T G T T G T A G T T G G G A C C A T T G G C T T T G C T C T C A G A G C  1150
SalmoKCaR 2  T T G A T G T T G T A G T T G G G A C C A T T G G C T T T G C T C T C A G A G C  1240
SalmoKCaR 3  T T G A T G T T G T A G T T G G G A C C A T T G G C T T T G C T C T C A G A G C  1151

SalmoKCaR 1  A G G C G A A A T A C C T G G C T T C A A G G A C T T C T T A C A A G A G G T C  1190
SalmoKCaR 2  A G G C G A A A T A C C T G G C T T C A A G G A C T T C T T A C A A G A G G T C  1280
SalmoKCaR 3  A G G C G A A A T A C C T G G C T T C A A G G A C T T C T T A C A A G A G G T C  1191

SalmoKCaR 1  A C A C C A A A G A A A T C C A G C C A C A A T G A A T T T G T C A G G G A G T  1230
SalmoKCaR 2  A C A C C A A A G A A A T C C A G C C A C A A T G A A T T T G T C A G G G A G T  1320
SalmoKCaR 3  A C A C C A A A G A A A T C C A G C C A C A A T G A A T T T G T C A G G G A G T  1231

SalmoKCaR 1  T T T G G G A G G A G A C T T T T A A C T G C T A T C T G G A A G A C A G C C A  1270
SalmoKCaR 2  T T T G G G A G G A G A C T T T T A A C T G C T A T C T G G A A G A C A G C C A  1360
SalmoKCaR 3  T T T G G G A G G A G A C T T T T A A C T G C T A T C T G G A A G A C A G C C A  1271

SalmoKCaR 1  G A G A C T G A G A G A C A G T G A G A A T G G G A G C A C C A G T T T C A G A  1310
SalmoKCaR 2  G A G A C T G A G A G A C A G T G A G A A T G G G A G C A C C A G T T T C A G A  1400
SalmoKCaR 3  G A G A C T G A G A G A C A G T G A G A A T G G G A G C A C C A G T T T C A G A  1311

SalmoKCaR 1  C C A T T G T G T A C T G G C G A G G A G G A C A T T A T G G G T G C A G A G A  1350
SalmoKCaR 2  C C A T T G T G T A C T G G C G A G G A G G A C A T T A T G G G T G C A G A G A  1440
SalmoKCaR 3  C C A T T G T G T A C T G G C G A G G A G G A C A T T A T G G G T G C A G A G A  1351

SalmoKCaR 1  C C C C A T A T C T G G A T T A C A C T C A T C T T C G T A T T T C C T A T A A  1390
SalmoKCaR 2  C C C C A T A T C T G G A T T A C A C T C A T C T T C G T A T T T C C T A T A A  1480
SalmoKCaR 3  C C C C A T A T C T G G A T T A C A C T C A T C T T C G T A T T T C C T A T A A  1391

SalmoKCaR 1  T G T G T A T G T T G C A G T T C A C T C C A T T G C A C A G G C C C T A C A G  1430
SalmoKCaR 2  T G T G T A T G T T G C A G T T C A C T C C A T T G C A C A G G C C C T A C A G  1520
SalmoKCaR 3  T G T G T A T G T T G C A G T T C A C T C C A T T G C A C A G G C C C T A C A G  1431

SalmoKCaR 1  G A C A T T C T C A C C T G C A T T C C T G G A C G G G T C T T T T T T C C A  1470
SalmoKCaR 2  G A C A T T C T C A C C T G C A T T C C T G G A C G G G T C T T T T T T C C A  1560
SalmoKCaR 3  G A C A T T C T C A C C T G C A T T C C T G G A C G G G T T T T T T T T C C A  1471

SalmoKCaR 1  A C A A C T C A T G T G C A G A T A T A A A G A A A A T A G A A G C A T G G C A  1510
SalmoKCaR 2  A C A A C T C A T G T G C A G A T A T A A A G A A A A T A G A A G C A T G G C A  1600
SalmoKCaR 3  A C A A C T C A T G T G C A G A T A T A A A G A A A A T A G A A G C A T G G C A  1511

SalmoKCaR 1  G G T T C T C A A G C A G C T C A G A C A T T T A A A C T T C T C A A A C A G T  1550
SalmoKCaR 2  G G T T C T C A A G C A G C T C A G A C A T T T A A A C T T C T C A A A C A G T  1640
SalmoKCaR 3  G G T T C T C A A G C A G C T C A G A C A T T T A A A C T T C T C A A A C A G T  1551

SalmoKCaR 1  A T G G G A G A A A A G G T A C A T T T T G A T G A G A A T G C T G A T C C G T  1590
SalmoKCaR 2  A T G G G A G A A A A G G T A C A T T T T G A T G A G A A T G C T G A T C C G T  1680
SalmoKCaR 3  A T G G G A G A A A A G G T A C A T T T T G A T G A G A A T G C T G A T C C G T  1591
```

FIG. 16C

```
SalmoKCaR 1  C A G G A A A C T A C A C C A T T A T C A A T T G G C A C C G G T C T C C T G A  1630
SalmoKCaR 2  C A G G A A A C T A C A C C A T T A T C A A T T G G C A C C G G T C T C C T G A  1720
SalmoKCaR 3  C A G G A A A C T A C A C C A T T A T C A A T T G G C A C C G G T C T C C T G A  1631

SalmoKCaR 1  G G A T G G T T C T G T T G T G T T T G A A G A G G T C G G T T T C T A C A A C  1670
SalmoKCaR 2  G G A T G G T T C T G T T G T G T T T G A A G A G G T C G G T T T C T A C A A C  1760
SalmoKCaR 3  G G A T G G T T C T G T T G T G T T T G A A G A G G T C G G T T T C T A C A A C  1671

SalmoKCaR 1  A T G C G A G C T A A G A G A G G A G T A C A A C T T T T C A T T G A T A A C A  1710
SalmoKCaR 2  A T G C G A G C T A A G A G A G G A G T A C A A C T T T T C A T T G A T A A C A  1800
SalmoKCaR 3  A T G C G A G C T A A G A G A G G A G T A C A A C T T T T C A T T G A T A A C A  1711

SalmoKCaR 1  C A A A G A T T C T A T G G A A T G G A T A T A A T A C T G A G G T T C C A T T  1750
SalmoKCaR 2  C A A A G A T T C T A T G G A A T G G A T A T A A T A C T G A G G T T C C A T T  1840
SalmoKCaR 3  C A A A G A T T C T A T G G A A T G G A T A T A A T A C T G A G G T T C C A T T  1751

SalmoKCaR 1  C T C T A A C T G T A G T G A A G A T T G T G A A C C A G G C A C C A G A A A G  1790
SalmoKCaR 2  C T C T A A C T G T A G T G A A G A T T G T G A A C C A G G C A C C A G A A A G  1880
SalmoKCaR 3  C T C T A A C T G T A G T G A A G A T T G T G A A C C A G G C A C C A G A A A G  1791

SalmoKCaR 1  G G G A T C A T A G A A A G C A T G C C A A C G T G T T G C T T T G A A T G T A  1830
SalmoKCaR 2  G G G A T C A T A G A A A G C A T G C C A A C G T G T T G C T T T G A A T G T A  1920
SalmoKCaR 3  G G G A T C A T A G A A A G C A T G C C A A C G T G T T G C T T T G A A T G T A  1831

SalmoKCaR 1  C A G A A T G C T C A G A A G G A G A G T A T A G T G A T C A C A A A G A T G C  1870
SalmoKCaR 2  C A G A A T G C T C A G A A G G A G A G T A T A G T G A T C A C A A A G A T G C  1960
SalmoKCaR 3  C A G A A T G C T C A G A A G G A G A G T A T A G T G A T C A C A A A G A T G C  1871

SalmoKCaR 1  C A G T G T T T G T A C C A A G T G T C C C A A T G A C T C A T G G T C T A A T  1910
SalmoKCaR 2  C A G T G T T T G T A C C A A G T G T C C C A A T G A C T C A T G G T C T A A T  2000
SalmoKCaR 3  C A G T G T T T G T A C C A A G T G T C C C A A T G A C T C A T G G T C T A A T  1911

SalmoKCaR 1  G A G A A C C A C A C A T C T T G T T T C C T G A A G G A G A T A G A G T T T C  1950
SalmoKCaR 2  G A G A A C C A C A C A T C T T G T T T C C T G A A G G A G A T A G A G T T T C  2040
SalmoKCaR 3  G A G A A C C A C A C A T C T T G T T T C C T G A A G G A G A T A G A G T T T C  1951

SalmoKCaR 1  T G T C T T G G A C A G A G C C C T T T G G G A T C G C C T T G G C A T T A T G  1990
SalmoKCaR 2  T G T C T T G G A C A G A G C C C T T T G G G A T C G C C T T G G C A T T A T G  2080
SalmoKCaR 3  T G T C T T G G A C A G A G C C C T T T G G G A T C G C C T T G G C A T T A T G  1991

SalmoKCaR 1  C T C T G T G C T G G G G G T A T T C T T G A C A G C A T T C G T G A T G G G A  2030
SalmoKCaR 2  C T C T G T G C T G G G G G T A T T C T T G A C A G C A T T C G T G A T G G G A  2120
SalmoKCaR 3  C T C T G T G C T G G G G G T A T T C T T G A C A G C A T T C G T G A T G G G A  2031

SalmoKCaR 1  G T G T T T A T C A A A T T T C G C A A C A C C C A A T T G T T A A G G C C A  2070
SalmoKCaR 2  G T G T T T A T C A A A T T T C G C A A C A C C C A A T T G T T A A G G C C A  2160
SalmoKCaR 3  G T G T T T A T C A A A T T T C G C A A C A C C C A A T T G T T A A G G C C A  2071

SalmoKCaR 1  C A A A C A G A G A G C T A T C C T A C C T C C T C C T G T T C T C A C T C A T  2110
SalmoKCaR 2  C A A A C A G A G A G C T A T C C T A C C T C C T C C T G T T C T C A C T C A T  2200
SalmoKCaR 3  C A A A C A G A G A G C T A T C C T A C C T C C T C C T G T T C T C A C T C A T  2111

SalmoKCaR 1  C T G C T G T T T C T C C A G T T C C C T C A T C T T C A T T G G T G A A C C C  2150
SalmoKCaR 2  C T G C T G T T T C T C C A G T T C C C T C A T C T T C A T T G G T G A A C C C  2240
SalmoKCaR 3  C T G C T G T T T C T C C A G T T C C C T C A T C T T C A T T G G T G A A C C C  2151
```

FIG. 16D

```
SalmoKCaR 1  C A G G A C T G G A C A T G C C G T C T A C G C C A G C C T G C A T T C G G G A  2190
SalmoKCaR 2  C A G G A C T G G A C A T G C C G T C T A C G C C A G C C T G C A T T C G G G A  2280
SalmoKCaR 3  C A G G A C T G G A C A T G C C G T C T A C G C C A G C C T G C A T T C G G G A  2191

SalmoKCaR 1  T A A G T T T T G T T C T C T G C A T C T C C T G C A T C C T G G T A A A A A C  2230
SalmoKCaR 2  T A A G T T T T G T T C T C T G C A T C T C C T G C A T C C T G G T A A A A A C  2320
SalmoKCaR 3  T A A G T T T T G T T C T C T G C A T C T C C T G C A T C C T G G T A A A A A C  2231

SalmoKCaR 1  T A A C C G A G T A C T T C T A G T G T T C G A A G C C A A G A T C C C A C C  2270
SalmoKCaR 2  T A A C C G A G T A C T T C T A G T G T T C G A A G C C A A G A T C C C A C C  2360
SalmoKCaR 3  T A A C C G A G T A C T T C T A G T G T T C G A A G C C A A G A T C C C A C C  2271

SalmoKCaR 1  A G T C T C C A T C G T A A G T G G T G G G G C T A A A C T T G C A G T T C C  2310
SalmoKCaR 2  A G T C T C C A T C G T A A G T G G T G G G G C T A A A C T T G C A G T T C C  2400
SalmoKCaR 3  A G T C T C C A T C G T A A G T G G T G G G G C T A A A C T T G C A G T T C C  2311

SalmoKCaR 1  T G T T A G T G T T C C T G T T C A C A T T T G T G C A A G T G A T G A T A T G  2350
SalmoKCaR 2  T G T T A G T G T T C C T G T T C A C A T T T G T G C A A G T G A T G A T A T G  2440
SalmoKCaR 3  T G T T A G T G T T C C T G T T C A C A T T T G T G C A A G T G A T G A T A T G  2351

SalmoKCaR 1  T G T G G T C T G G C T T T A C A A T G C T C C T C C G G C G A G C T A C A G G  2390
SalmoKCaR 2  T G T G G T C T G G C T T T A C A A T G C T C C T C C G G C G A G C T A C A G G  2480
SalmoKCaR 3  T G T G G T C T G G C T T T A C A A T G C T C C T C C G G C G A G C T A C A G G  2391

SalmoKCaR 1  A A C C A T G A C A T T G A T G A G A T A A T T T T C A T T A C A T G C A A T G  2430
SalmoKCaR 2  A A C C A T G A C A T T G A T G A G A T A A T T T T C A T T A C A T G C A A T G  2520
SalmoKCaR 3  A A C C A T G A C A T T G A T G A G A T A A T T T T C A T T A C A T G C A A T G  2431

SalmoKCaR 1  A G G G C T C T A T G A T G G C G C T T G G C T T C C T A A T T G G T A C A C  2470
SalmoKCaR 2  A G G G C T C T A T G A T G G C G C T T G G C T T C C T A A T T G G T A C A C  2560
SalmoKCaR 3  A G G G C T C T A T G A T G G C G C T T G G C T T C C T A A T T G G T A C A C  2471

SalmoKCaR 1  A T G C C T G C T G G C A G C C A T A T G C T T C T T C T T T G C A T T T A A A  2510
SalmoKCaR 2  A T G C C T G C T G G C A G C C A T A T G C T T C T T C T T T G C A T T T A A A  2600
SalmoKCaR 3  A T G C C T G C T G G C A G C C A T A T G C T T C T T C T T T G C A T T T A A A  2511

SalmoKCaR 1  T C A C G A A A A C T G C C A G A G A A C T T T A C T G A G G C T A A G T T C A  2550
SalmoKCaR 2  T C A C G A A A A C T G C C A G A G A A C T T T A C T G A G G C T A A G T T C A  2640
SalmoKCaR 3  T C A C G A A A A C T G C C A G A G A A C T T T A C T G A G G C T A A G T T C A  2551

SalmoKCaR 1  T C A C C T T C A G C A T G C T C A T C T T C T T C A T C G T C T G G A T C T C  2590
SalmoKCaR 2  T C A C C T T C A G C A T G C T C A T C T T C T T C A T C G T C T G G A T C T C  2680
SalmoKCaR 3  T C A C C T T C A G C A T G C T C A T C T T C T T C A T C G T C T G G A T C T C  2591

SalmoKCaR 1  T T T C A T C C C T G C C T A C T T C A G C A C T T A C G G A A A G T T T G T G  2630
SalmoKCaR 2  T T T C A T C C C T G C C T A C T T C A G C A C T T A C G G A A A G T T T G T G  2720
SalmoKCaR 3  T T T C A T C C C T G C C T A C T T C A G C A C T T A C G G A A A G T T T G T G  2631

SalmoKCaR 1  T C G G C T G T G G A G G T C A T C G C C A T A C T A G C C T C C A G C T T T G  2670
SalmoKCaR 2  T C G G C T G T G G A G G T C A T C G C C A T A C T A G C C T C C A G C T T T G  2760
SalmoKCaR 3  T C G G C T G T G G A G G T C A T C G C C A T A C T A G C C T C C A G C T T T G  2671

SalmoKCaR 1  G C C T G C T G G C C T G T A T T T T C T T C A A T A A A G T C T A C A T C A T  2710
SalmoKCaR 2  G C C T G C T G G C C T G T A T T T T C T T C A A T A A A G T C T A C A T C A T  2800
SalmoKCaR 3  G C C T G C T G G C C T G T A T T T T C T T C A A T A A A G T C T A C A T C A T  2711
```

FIG. 16E

```
SalmoKCaR 1 C C T C T T C A A A C C G T C C A G G A A C A C T A T A G A G G A G G T T C G C 2750
SalmoKCaR 2 C C T C T T C A A A C C G T C C A G G A A C A C T A T A G A G G A G G T T C G C 2840
SalmoKCaR 3 C C - - - - - - - - - - - - - - - - - - - - - - - - - - - - - - - - - - - - - 2713

SalmoKCaR 1 T G T A G C A C T G C G G C C C A T T C T T T C A A A G T G G C A G C C A A G G 2790
SalmoKCaR 2 T G T A G C A C T G C G G C C C A T T C T T T C A A A G T G G C A G C C A A G G 2880
SalmoKCaR 3 - - - - - - - - - - - - - - - - - - - - - - - - - - - - - - - - - - - - - - - 2713

SalmoKCaR 1 C C A C T C T G A G A C A C A G C T C A G C C T C C A G G A A G A G G T C C A G 2830
SalmoKCaR 2 C C A C T C T G A G A C A C A G C T C A G C C T C C A G G A A G A G G T C C A G 2920
SalmoKCaR 3 - - - - - - - - - - - - - - - - - - - - - - - - - - - - - - - - - - - - - - - 2713

SalmoKCaR 1 C A G T G T G G G G G A T C C T G T G C C T C A A C T C C C T C C T C A T C C 2870
SalmoKCaR 2 C A G T G T G G G G G A T C C T G T G C C T C A A C T C C C T C C T C A T C C 2960
SalmoKCaR 3 - - - - - - - - - - - - - - - - - - - - - - - - - - - - - - - - - - - - - - - 2713

SalmoKCaR 1 A T C A G C C T C A A G A C C A A T G A C A A T G A C T C C C C A T C A G G T C 2910
SalmoKCaR 2 A T C A G C C T C A A G A C C A A T G A C A A T G A C T C C C C A T C A G G T C 3000
SalmoKCaR 3 A T C A G C C T C A A G A C C A A T G A C A A T G A C T C C C C A T C A G G T C 2753

SalmoKCaR 1 A G C A G A G A A T C C A T A A G C C A A G A G T A A G C T T T G G A A G T G G 2950
SalmoKCaR 2 A G C A G A G A A T C C A T A A G C C A A G A G T A A G C T T T G G A A G T G G 3040
SalmoKCaR 3 A G C A G A G A A T C C A T A A G C C A A G A G T A A G C T T T G G A A G T G G 2793

SalmoKCaR 1 A A C A G T T A C T C T G T C C T T G A G C T T T G A G G A G T C C A G A A A G 2990
SalmoKCaR 2 A A C A G T T A C T C T G T C C T T G A G C T T T G A G G A G T C C A G A A A G 3080
SalmoKCaR 3 A A C A G T T A C T C T G T C C T T G A G C T T T G A G G A G T C C A G A A A G 2833

SalmoKCaR 1 A A T T C T A T G A A G T A G G G A A G T G T C T T T T G G T G G C C G A G A 3030
SalmoKCaR 2 A A T T C T A T G A A G T A G G G A A G T G T C T T T T G G T G G C C G A G A 3120
SalmoKCaR 3 A A T T C T A T G A A G T A G G G A A G T G T C T T T T G G T G G C C G A G A 2873

SalmoKCaR 1 G C C T T G T C A A A A C C T G A G T T G G T G T T G C A T T C T T T G T T G G 3070
SalmoKCaR 2 G C C T T G T C A A A A C C T G A G T T G G T G T T G C A T T C T T T G T T G G 3160
SalmoKCaR 3 G C C T T G T C A A A A C C T G A G T T G G T G T T G C A T T C T T T G T T G G 2913

SalmoKCaR 1 C T G G G T A G T T G G A G C A G A A A T T A T G A T A T T A A A A G C T T T G 3110
SalmoKCaR 2 C T G G G T A G T T G G A G C A G A A A T T A T G A T A T T A A A A G C T T T G 3200
SalmoKCaR 3 C T G G G T A G T T G G A G C A G A A A T T A T G A T A T T A A A A G C T T T G 2953

SalmoKCaR 1 A T G T A T T C A G A A T G G T G A C A C A G C A T A G G T G G C C A A G A T T 3150
SalmoKCaR 2 A T G T A T T C A G A A T G G T G A C A C A G C A T A G G T G G C C A A G A T T 3240
SalmoKCaR 3 A T G T A T T C A G A A T G G T G A C A C A G C A T A G G T G G C C A A G A T T 2993

SalmoKCaR 1 C C A T T A T A T T A C A A T A A T C T G T G T T G T T C A T T A T G A G G A C 3190
SalmoKCaR 2 C C A T T A T A T T A C A A T A A T C T G T G T T G T T C A T T A T G A G G A C 3280
SalmoKCaR 3 C C A T T A T A T T A C A A T A A T C T G T G T T G T T C A T T A T G A G G A C 3033

SalmoKCaR 1 A T T T C A A A A T G C T G A A A A T C A T C A A A T A C A T A A T T T A C T G 3230
SalmoKCaR 2 A T T T C A A A A T G C T G A A A A T C A T C A A A T A C A T A A T T T A C T G 3320
SalmoKCaR 3 A T T T C A A A A T G C T G A A A A T C A T C A A A T A C A T A A T T T A C T G 3073

SalmoKCaR 1 A G T T T T C T T G A T A A T C T T G A G A A T A G A A T A G C C T A T T C A A 3270
SalmoKCaR 2 A G T T T T C T T G A T A A T C T T G A G A A T A G A A T A G C C T A T T C A A 3360
SalmoKCaR 3 A G T T T T C T T G A T A A T C T T G A G A A T A G A A T A G C C T A T T C A A 3113
```

```
SalmoKCaR 1  T G T C A T A C G G T C A T A T G G T G T C A T A T G G T G T C T G T T G T T  3870
SalmoKCaR 2  T G T C A T A C G G T C A T A T G G T G T C A T A T G G T G T C T G G T T G T T  3960
SalmoKCaR 3  T G T C A T A C G G T C A T A T G G T G T C A T A T G G T G T C T G G T T G T T  3713

SalmoKCaR 1  T T C T G C A T A T G T G T A T T T C A C C A A G T T A C T G C A C A T G T T A  3910
SalmoKCaR 2  T T C T G C A T A T G T G T A T T T C A C C A A G T T A C T G C A C A T G T T A  4000
SalmoKCaR 3  T T C T G C A T A T G T G T A T T T C A C C A A G T T A C T G C A C A T G T T A  3753

SalmoKCaR 1  G A C C T A T A C A C T G G A A T A A A C A T T T T T T T T C                    3941
SalmoKCaR 2  G A C C T A T A C A C T G G A A T A A A C A T T T T T T T T C                    4031
SalmoKCaR 3  G A C C T A T A C A C T G G A A T A A A C A T T T T T T T T C A C A A T G C A T  3793

SalmoKCaR 1                                                                               3941
SalmoKCaR 2                                                                               4031
SalmoKCaR 3  C C A A T G A C A A T A A A A T C A C C A T A T G C C A A T G                 3824
```

FIG. 16H

```
SalmoKCaR 1  - T T C C A A C A G C A T A T T T T T G T T G T A T T T G C T T T G G T T T G T  39
SalmoKCaR 2  G T T C C A A C A G C A T A T T T T T G T T G T A T T T G C T T T G G T T T G T  40
SalmoKCaR 3  G T T C C A A C A G C A T A T T T T T G T T G T A T T T G C T T T G G T T T G T  40
SalmoKCaR 4  G T T C C A A C A G C A T A T T T T T G T T G T A T T T G C T T T G G T T T G T  40
At. sal. PCR - - - - - - - - - - - - - - - - - - - - - - - - - - - - - - - - - - - - - - -  0
At. sal. A26 - - - - - - - - - - - - - - - - - - - - - - - - - - - - - - - - - - - - - - -  0

SalmoKCaR 1  C T G A A A T C A A G C A T T A T C A A G - - - - - - - - - - - - - - - - - - -  60
SalmoKCaR 2  C T G A A A T C A A G C A T T A T C A A G G A T T G A G C A A G A C A A C T G A  80
SalmoKCaR 3  C T G A A A T C A A G C A T T A T C A A G - - - - - - - - - - - - - - - - - - -  61
SalmoKCaR 4  C T G A A A T C A A G C A T T A T C A A G - - - - - - - - - - - - - - - - - - -  61
At. sal. PCR - - - - - - - - - - - - - - - - - - - - - - - - - - - - - - - - - - - - - - -  0
At. sal. A26 - - - - - - - - - - - - - - - - - - - - - - - - - - - - - - - - - - - - - - -  0

SalmoKCaR 1  - - - - - - - - - - - - - - - - - - - - - - - - - - - - - - - - - - - - - - -  60
SalmoKCaR 2  G T T G T C A G A C T A A G A A T A T A C A C A T T T C C A G T T C T C T C T T  120
SalmoKCaR 3  - - - - - - - - - - - - - - - - - - - - - - - - - - - - - - - - - - - - - - -  61
SalmoKCaR 4  - - - - - - - - - - - - - - - - - - - - - - - - - - - - - - - - - - - - - - -  61
At. sal. PCR - - - - - - - - - - - - - - - - - - - - - - - - - - - - - - - - - - - - - - -  0
At. sal. A26 - - - - - - - - - - - - - - - - - - - - - - - - - - - - - - - - - - - - - - -  0

SalmoKCaR 1  - - - - - - - - - - - - - - - - - - - - - - - - - - - - - A T C A A G A A C A  70
SalmoKCaR 2  T A A T G G A C T T C T C A C A C T G A T G T T C T T C A G A T C A A G A A C A  160
SalmoKCaR 3  - - - - - - - - - - - - - - - - - - - - - - - - - - - - - A T C A A G A A C A  71
SalmoKCaR 4  - - - - - - - - - - - - - - - - - - - - - - - - - - - - - A T C A A G A A C A  71
At. sal. PCR - - - - - - - - - - - - - - - - - - - - - - - - - - - - - - - - - - - - - - -  0
At. sal. A26 - - - - - - - - - - - - - - - - - - - - - - - - - - - - - - - - - - - - - - -  0

SalmoKCaR 1  G C A T G A G T C A G A A A C A A G G C G A C A G C C A G A G T C A C T G G A G  110
SalmoKCaR 2  G C A T G A G T C A G A A A C A A G G C G A C A G C C A G A G T C A C T G G A G  200
SalmoKCaR 3  G C A T G A G T C A G A A A C A A G G C G A C A G C C A G A G T C A C T G G A G  111
SalmoKCaR 4  G C A T G A G T C A G A A A C A A G G C G A C A G C C A G A G T C A C T G G A G  111
At. sal. PCR - - - - - - - - - - - - - - - - - - - - - - - - - - - - - - - - - - - - - - -  0
At. sal. A26 - - - - - - - - - - - - - - - - - - - - - - - - - - - - - - - - - - - - - - -  0

SalmoKCaR 1  G G G A C A A G A C T G A G G T T A A C T C T G A A G T C T A A T G T G C T G A  150
SalmoKCaR 2  G G G A C A A G A C T G A G G T T A A C T C T G A A G T C T A A T G T G C T G A  240
SalmoKCaR 3  G G G A C A A G A C T G A G G T T A A C T C T G A A G T C T A A T G T G C T G A  151
SalmoKCaR 4  G G G A C A A G A C T G A G G T T A A C T C T G A A G T C T A A T G T G C T G A  151
At. sal. PCR - - - - - - - - - - - - - - - - - - - - - - - - - - - - - - - - - - - - - - -  0
At. sal. A26 - - - - - - - - - - - - - - - - - - - - - - - - - - - - - - - - - - - - - - -  0

SalmoKCaR 1  G A G G A C A A G G C C C T C C T G A G A G C T G A A C G A T G A G A T T T T A  190
SalmoKCaR 2  G A G G A C A A G G C C C T C C T G A G A G C T G A A C G A T G A G A T T T T A  280
SalmoKCaR 3  G A G G A C A A G G C C C T C C T G A G A G C T G A A C G A T G A G A T T T T A  191
SalmoKCaR 4  G A G G A C A A G G C C C T C C T G A G A G C T G A A C G A T G A G A T T T T A  191
At. sal. PCR - - - - - - - - - - - - - - - - - - - - - - - - - - - - - - - - - - - - - - -  0
At. sal. A26 - - - - - - - - - - - - - - - - - - - - - - - - - - - - - - - - - - - - - - -  0

SalmoKCaR 1  C C T G T A T T A C C T G G T G C T T T T G G G C T T C A G T T C T G T C A T C  230
SalmoKCaR 2  C C T G T A T T A C C T G G T G C T T T T G G G C T T C A G T T C T G T C A T C  320
SalmoKCaR 3  C C T G T A T T A C C T G G T G C T T T T G G G C T T C A G T T C T G T C A T C  231
SalmoKCaR 4  C C T G T A T T A C C T G G T G C T T T T G G G C T T C A G T T C T G T C A T C  231
At. sal. PCR - - - - - - - - - - - - - - - - - - - - - - - - - - - - - - - - - - - - - - -  0
At. sal. A26 - - - - - - - - - - - - - - - - - - - - - - - - - - - - - - - - - - - - - - -  0

SalmoKCaR 1  T C C A C C T A T G G G C C T C A T C A G A G A G C A C A G A A G A C T G G G G  270
SalmoKCaR 2  T C C A C C T A T G G G C C T C A T C A G A G A G C A C A G A A G A C T G G G G  360
SalmoKCaR 3  T C C A C C T A T G G G C C T C A T C A G A G A G C A C A G A A G A C T G G G G  271
SalmoKCaR 4  T C C A C C T A T G G G C C T C A T C A G A G A G C A C A G A A G A C T G G G G  271
At. sal. PCR - - - - - - - - - - - - - - - - - - - - - - - - - - - - - - - - - - - - - - -  0
At. sal. A26 - - - - - - - - - - - - - - - - - - - - - - - - - - - - - - - - - - - - - - -  0
```

FIG. 17A

```
SalmoKCaR 1   A T A T T C T G C T G G G C G G G C T G T T T C C A A T G C A C T T T G G T G T  310
SalmoKCaR 2   A T A T T C T G C T G G G C G G G C T G T T T C C A A T G C A C T T T G G T G T  400
SalmoKCaR 3   A T A T T C T G C T G G G C G G G C T G T T T C C A A T G C A C T T T G G T G T  311
SalmoKCaR 4   A T A T T C T G C T G G G C G G G C T G T T T C C A A T G C A C T T T G G T G T  311
At. sal. PCR  - - - - - - - - - - - - - - - - - - - - - - - - - - - - - - - - - - - - - - -  0
At. sal. A26  - - - - - - - - - - - - - - - - - - - - - - - - - - - - - - - - - - - - - - -  0

SalmoKCaR 1   T A C C T C C A A A G A C C A A G A C C T G G C A G C G C G G C C A G A A T C C  350
SalmoKCaR 2   T A C C T C C A A A G A C C A A G A C C T G G C A G C G C G G C C A G A A T C C  440
SalmoKCaR 3   T A C C T C C A A A G A C C A A G A C C T G G C A G C G C G G C C A G A A T C C  351
SalmoKCaR 4   T A C C T C C A A A G A C C A A G A C C T G G C A G C G C G G C C A G A A T C C  351
At. sal. PCR  - - - - - - - - - - - - - - - - - - - - - - - - - - - - - - - - - - - - - - -  0
At. sal. A26  - - - - - - - - - - - - - - - - - - - - - - - - - - - - - - - - - - - - - - -  0

SalmoKCaR 1   A C A G A G T G T G T T A G G T A C A A T T T C C G G G G A T T C C G T T G G C  390
SalmoKCaR 2   A C A G A G T G T G T T A G G T A C A A T T T C C G G G G A T T C C G T T G G C  480
SalmoKCaR 3   A C A G A G T G T G T T A G G T A C A A T T T C C G G G G A T T C C G T T G G C  391
SalmoKCaR 4   A C A G A G T G T G T T A G G T A C A A T T T C C G G G G A T T C C G T T G G C  391
At. sal. PCR  - - - - - - - - - - - - - - - - - - - - - - - - - - - - - - - - - - - - - - -  0
At. sal. A26  - - - - - - - - - - - - - - - - - - - - - - - - - - - - - - - - - - - - - - -  0

SalmoKCaR 1   T T C A G G C C A T G A T T T T T G C A A T A G A G G A G A T C A A C A A C A G  430
SalmoKCaR 2   T T C A G G C C A T G A T T T T T G C A A T A G A G G A G A T C A A C A A C A G  520
SalmoKCaR 3   T T C A G G C C A T G A T T T T T G C A A T A G A G G A G A T C A A C A A C A G  431
SalmoKCaR 4   T T C A G G C C A T G A T T T T T G C A A T A G A G G A G A T C A A C A A C A G  431
At. sal. PCR  - - - - - - - - - - - - - - - - - - - - - - - - - - - - - - - - - - - - - - -  0
At. sal. A26  - - - - - - - - - - - - - - - - - - - - - - - - - - - - - - - - - - - - - - -  0

SalmoKCaR 1   C A G T A C T C T C C T G C C C A A C A T C A C A C T G G G C T A C A G G A T C  470
SalmoKCaR 2   C A G T A C T C T C C T G C C C A A C A T C A C A C T G G G C T A C A G G A T C  560
SalmoKCaR 3   C A G T A C T C T C C T G C C C A A C A T C A C A C T G G G C T A C A G G A T C  471
SalmoKCaR 4   C A G T A C T C T C C T G C C C A A C A T C A C A C T G G G C T A C A G G A T C  471
At. sal. PCR  - - - - - - - - - - - - - - - - - - - - - - - - - - - - - - - - - - - - - - -  0
At. sal. A26  - - - - - - - - - - - - - - - - - - - - - - - - - - - - - - - - - - - - - - -  0

SalmoKCaR 1   T T T G A C A C C T G C A A C A C C G T G T C C A A G G C C C T G G A G G C T A  510
SalmoKCaR 2   T T T G A C A C C T G C A A C A C C G T G T C C A A G G C C C T G G A G G C T A  600
SalmoKCaR 3   T T T G A C A C C T G C A A C A C C G T G T C C A A G G C C C T G G A G G C T A  511
SalmoKCaR 4   T T T G A C A C C T G C A A C A C C G T G T C C A A G G C C C T G G A G G C T A  511
At. sal. PCR  - - - - - - - - - - - - - - - - - - - - - - - - - - - - - - - - - - - - - - -  0
At. sal. A26  - - - - - - - - - - - - - - - - - - - - - - - - - - - - - - - - - - - - - - -  0

SalmoKCaR 1   C C C T C A G T T T C G T A G C A C A G A A T A A G A T T G A C T C T C T G A A  550
SalmoKCaR 2   C C C T C A G T T T C G T A G C A C A G A A T A A G A T T G A C T C T C T G A A  640
SalmoKCaR 3   C C C T C A G T T T C G T A G C A C A G A A T A A G A T T G A C T C T C T G A A  551
SalmoKCaR 4   C C C T C A G T T T C G T A G C A C A G A A T A A G A T T G A C T C T C T G A A  551
At. sal. PCR  - - - - - - - - - - - - - - - - - - - - - - - - - - - - - - - - - - - - - - -  0
At. sal. A26  - - - - - - - - - - - - - - - - - - - - - - - - - - - - - - - - - - - - - - -  0

SalmoKCaR 1   C T T G G A T G A A T T C T G T A A C T G C A C T G A T C A C A T C C C A T C G  590
SalmoKCaR 2   C T T G G A T G A A T T C T G T A A C T G C A C T G A T C A C A T C C C A T C G  680
SalmoKCaR 3   C T T G G A T G A A T T C T G T A A C T G C A C T G A T C A C A T C C C A T C G  591
SalmoKCaR 4   C T T G G A T G A A T T C T G T A A C T G C A C T G A T C A C A T C C C A T C G  591
At. sal. PCR  - - - - - - - - - - - - - - - - - - - - - - - - - - - - - - - - - - - - - - -  0
At. sal. A26  - - - - - - - - - - - - - - - - - - - - - - - - - - - - - - - - - - - - - - -  0

SalmoKCaR 1   A C T A T A G C A G T G G T G G G G G C T T C T G G G T C A G C G G T C T C C A  630
SalmoKCaR 2   A C T A T A G C A G T G G T G G G G G C T T C T G G G T C A G C G G T C T C C A  720
SalmoKCaR 3   A C T A T A G C A G T G G T G G G G G C T T C T G G G T C A G C G G T C T C C A  631
SalmoKCaR 4   A C T A T A G C A G T G G T G G G G G C T T C T G G G T C A G C G G T C T C C A  631
At. sal. PCR  - - - - - - - - - - - - - - - - - - - - - - - - - - - - - - - - - - - - - - -  0
At. sal. A26  - - - - - - - - - - - - - - - - - - - - - - - - - - - - - - - - - - - - - - -  0
```

FIG. 17B

```
SalmoKCaR 1  C T G C T G T T G C C A A T C T G T T G G G C C T T T T C T A C A T C C C A C A  670
SalmoKCaR 2  C T G C T G T T G C C A A T C T G T T G G G C C T T T T C T A C A T C C C A C A  760
SalmoKCaR 3  C T G C T G T T G C C A A T C T G T T G G G C C T T T T C T A C A T C C C A C A  671
SalmoKCaR 4  C T G C T G T T G C C A A T C T G T T G G G C C T T T T C T A C A T C C C A C A  671
At. sal. PCR  - - - - - - - - - - - - - - - - - - - - - - - - - - - - - - - - - - - - - - - -  0
At. sal. A26  - - - - - - - - - - - - - - - - - - - - - - - - - - - - - - - - - - - - - - - -  0

SalmoKCaR 1  G A T C A G C T A T G C C T C T T C C A G T C G C C T A C T A A G C A A C A A G  710
SalmoKCaR 2  G A T C A G C T A T G C C T C T T C C A G T C G C C T A C T A A G C A A C A A G  800
SalmoKCaR 3  G A T C A G C T A T G C C T C T T C C A G T C G C C T A C T A A G C A A C A A G  711
SalmoKCaR 4  G A T C A G C T A T G C C T C T T C C A G T C G C C T A C T A A G C A A C A A G  711
At. sal. PCR  - - - - - - - - - - - - - - - - - - - - - - - - - - - - - - - - - - - - - - - -  0
At. sal. A26  - - - - - - - - - - - - - - - - - - - - - - - - - - - - - - - - - - - - - - - -  0

SalmoKCaR 1  A A C C A G T T C A A A T C C T T C A T G A G G A C C A T T C C C A C A G A T G  750
SalmoKCaR 2  A A C C A G T T C A A A T C C T T C A T G A G G A C C A T T C C C A C A G A T G  840
SalmoKCaR 3  A A C C A G T T C A A A T C C T T C A T G A G G A C C A T T C C C A C A G A T G  751
SalmoKCaR 4  A A C C A G T T C A A A T C C T T C A T G A G G A C C A T T C C C A C A G A T G  751
At. sal. PCR  - - - - - - - - - - - - - - - - - - - - - - - - - - - - - - - - - - - - - - - -  0
At. sal. A26  - - - - - - - - - - - - - - - - - - - - - - - - - - - - - - - - - - - - - - - -  0

SalmoKCaR 1  A G C A C C A G G C C A C T G C C A T G G C A G A T A T C A T C G A C T A C T T  790
SalmoKCaR 2  A G C A C C A G G C C A C T G C C A T G G C A G A T A T C A T C G A C T A C T T  880
SalmoKCaR 3  A G C A C C A G G C C A C T G C C A T G G C A G A T A T C A T C G A C T A C T T  791
SalmoKCaR 4  A G C A C C A G G C C A C T G C C A T G G C A G A T A T C A T C G A C T A C T T  791
At. sal. PCR  - - - - - - - - - - - - - - - - - - - - - - - - - - - - - - - - - - - - - - - -  0
At. sal. A26  - - - - - - - - - - - - - - - - - - - - - - - - - - - - - - - - - - - - - - - -  0

SalmoKCaR 1  C C A A T G G A A T T G G G T C A T T G C A G T T G C G T C T G A T G A T G A G  830
SalmoKCaR 2  C C A A T G G A A T T G G G T C A T T G C A G T T G C G T C T G A T G A T G A G  920
SalmoKCaR 3  C C A A T G G A A T T G G G T C A T T G C A G T T G C G T C T G A T G A T G A G  831
SalmoKCaR 4  C C A A T G G A A T T G G G T C A T T G C A G T T G C G T C T G A T G A T G A G  831
At. sal. PCR  - - - - - - - - - - - - - - - - - - - - - - - - - - - - - - - - - - - - - - - -  0
At. sal. A26  - - - - - - - - - - - - - - - - - - - - - - - - - - - - - - - - - - - - - - - -  0

SalmoKCaR 1  T A T G G A C G T C C G G G G A T T G A A A A A T T T G A G A A A G A G A T G G  870
SalmoKCaR 2  T A T G G A C G T C C G G G G A T T G A A A A A T T T G A G A A A G A G A T G G  960
SalmoKCaR 3  T A T G G A C G T C C G G G G A T T G A A A A A T T T G A G A A A G A G A T G G  871
SalmoKCaR 4  T A T G G A C G T C C G G G G A T T G A A A A A T T T G A G A A A G A G A T G G  871
At. sal. PCR  - - - - - - - - - - - - - - - - - - - - - - - - - - - - - - - - - - - - - - - -  0
At. sal. A26  - - - - - - - - - - - - - - - - - - - - - - - - - - - - - - - - - - - - - - - -  0

SalmoKCaR 1  A A G A A C G A G A C A T T T G T A T C C A T C T G A G T G A G C T G A T C T C  910
SalmoKCaR 2  A A G A A C G A G A C A T T T G T A T C C A T C T G A G T G A G C T G A T C T C  1000
SalmoKCaR 3  A A G A A C G A G A C A T T T G T A T C C A T C T G A G T G A G C T G A T C T C  911
SalmoKCaR 4  A A G A A C G A G A C A T T T G T A T C C A T C T G A G T G A G C T G A T C T C  911
At. sal. PCR  - - - - - - - - - - - - - - - - - - - - - - - - - - - - - - - - - - - - - - - -  0
At. sal. A26  - - - - - - - - - - - - - - - - - - - - - - - - - - - - - - - - - - - - - - - -  0

SalmoKCaR 1  T C A G T A C T T T G A G G A G T G G C A G A T C C A A G G A T T G G T T G A C  950
SalmoKCaR 2  T C A G T A C T T T G A G G A G T G G C A G A T C C A A G G A T T G G T T G G C  1040
SalmoKCaR 3  T C A G T A C T T T G A G G A G T G G C A G A T C C A A G G A T T G G T T G A C  951
SalmoKCaR 4  T C A G T A C T T T G A G G A G T G G C A G A T C C A A G G A T T G G T T G A C  951
At. sal. PCR  - - - - - - - - - - - - - - - - - - - - - - - - - - - - - - - - - - - - - - - -  0
At. sal. A26  - - - - - - - - - - - - - - - - - - - - - - - - - - - - - - - - - - - - - - - -  0

SalmoKCaR 1  C G T A T T G A G A A C T C C T C A G C T A A A G T T A T A G T C G T T T T C G  990
SalmoKCaR 2  C G T A T T G A G A A C T C C T C A G C T A A A G T T A T A G T C G T T T T C G  1080
SalmoKCaR 3  C G T A T T G A G A A C T C C T C A G C T A A A G T T A T A G T C G T T T T C G  991
SalmoKCaR 4  C G T A T T G A G A A C T C C T C A G C T A A A G T T A T A G T C G T T T T C G  991
At. sal. PCR  - - - - - - - - - - - - - - - - - - - - - - - - - - - - - - - - - - - - - - - -  0
At. sal. A26  - - - - - - - - - - - - - - - - - - - - - - - - - - - - - - - - - - - - - - - -  0
```

FIG. 17C

```
SalmoKCaR 1  C C A G T G G G C C T G A C A T T G A G C C T C T T A T T A A A G A G A T G G T  1030
SalmoKCaR 2  C C A G T G G G C C T G A C A T T G A G C C T C T T A T T A A A G A G A T G G T  1120
SalmoKCaR 3  C C A G T G G G C C T G A C A T T G A G C C T C T T A T T A A A G A G A T G G T  1031
SalmoKCaR 4  C C A G T G G G C C T G A C A T T G A G C C T C T T A T T A A A G A G A T G G T  1031
At. sal. PCR - - - - - - - - - - - - - - - - - - - - - - - - - - - - - - - - - - - - - - - - -  0
At. sal. A26 - - - - - - - - - - - - - - - - - - - - - - - - - - - - - - - - - - - - - - - - -  0

SalmoKCaR 1  C A G A C G G A A C A T C A C C G A C C G C A T C T G G T T G G C C A G C G A G  1070
SalmoKCaR 2  C A G A C G G A A C A T C A C C G A C C G C A T C T G G T T G G C C A G C G A G  1160
SalmoKCaR 3  C A G A C G G A A C A T C A C C G A C C G C A T C T G G T T G G C C A G C G A G  1071
SalmoKCaR 4  C A G A C G G A A C A T C A C C G A C C G C A T C T G G T T G G C C A G C G A G  1071
At. sal. PCR - - - - - - - - - - - - - - - - - - - - - - - - - - - - - - - - - - - - - - - - -  0
At. sal. A26 - - - - - - - - - - - - - - - - - - - - - - - - - - - - - - - - - - - - - - - - -  0

SalmoKCaR 1  G C T T G G G C A A C C A C C T C C C T C A T C G C C A A A C C A G A G T A C C  1110
SalmoKCaR 2  G C T T G G G C A A C C A C C T C C C T C A T C G C C A A A C C A G A G T A C C  1200
SalmoKCaR 3  G C T T G G G C A A C C A C C T C C C T C A T C G C C A A A C C A G A G T A C C  1111
SalmoKCaR 4  G C T T G G G C A A C C A C C T C C C T C A T C G C C A A A C C A G A G T A C C  1111
At. sal. PCR - - - - - - - - - - - - - - - - - - - - - - - - - - - - - - - - - - - - - - - - -  0
At. sal. A26 - - - - - - - - - - - - - - - - - - - - - - - - - - - - - - - - - - - - - - - - -  0

SalmoKCaR 1  T T G A T G T T G T A G T T G G G A C C A T T G G C T T T G C T C T C A G A G C  1150
SalmoKCaR 2  T T G A T G T T G T A G T T G G G A C C A T T G G C T T T G C T C T C A G A G C  1240
SalmoKCaR 3  T T G A T G T T G T A G T T G G G A C C A T T G G C T T T G C T C T C A G A G C  1151
SalmoKCaR 4  T T G A T G T T G T A G T T G G G A C C A T T G G C T T T G C T C T C A G A G C  1151
At. sal. PCR - - - - - - - - - - - - - - - - - - - - - - - - - - - - - - - - - - - - - - - - -  0
At. sal. A26 - - - - - - - - - - - - - - - - - - - - - - - - - - - - - - - - - - - - - - - - -  0

SalmoKCaR 1  A G G C G A A A T A C C T G G C T T C A A G G A C T T C T T A C A A G A G G T C  1190
SalmoKCaR 2  A G G C G A A A T A C C T G G C T T C A A G G A C T T C T T A C A A G A G G T C  1280
SalmoKCaR 3  A G G C G A A A T A C C T G G C T T C A A G G A C T T C T T A C A A G A G G T C  1191
SalmoKCaR 4  A G G C G A A A T A C C T G G C T T C A A G G A C T T C T T A C A A G A G G T C  1191
At. sal. PCR - - - - - - - - - - - - - - - - - - - - - - - - - - - - - - - - - - - - - - - - -  0
At. sal. A26 - - - - - - - - - - - - - - - - - - - - - - - - - - - - - - - - - - - - - - - - -  0

SalmoKCaR 1  A C A C C A A A G A A A T C C A G C C A C A A T G A A T T T G T C A G G G A G T  1230
SalmoKCaR 2  A C A C C A A A G A A A T C C A G C C A C A A T G A A T T T G T C A G G G A G T  1320
SalmoKCaR 3  A C A C C A A A G A A A T C C A G C C A C A A T G A A T T T G T C A G G G A G T  1231
SalmoKCaR 4  A C A C C A A A G A A A T C C A G C C A C A A T G A A T T T G T C A G G G A G T  1231
At. sal. PCR - - - - - - - - - - - - - - - - - - - - - - - - - - - - - - - - - - - - - - - - -  0
At. sal. A26 - - - - - - - - - - - - - - - - - - - - - - - - - - - - - - - - - - - - - - - - -  0

SalmoKCaR 1  T T T G G G A G G A G A C T T T T A A C T G C T A T C T G G A A G A C A G C C A  1270
SalmoKCaR 2  T T T G G G A G G A G A C T T T T A A C T G C T A T C T G G A A G A C A G C C A  1360
SalmoKCaR 3  T T T G G G A G G A G A C T T T T A A C T G C T A T C T G G A A G A C A G C C A  1271
SalmoKCaR 4  T T T G G G A G G A G A C T T T T A A C T G C T A T C T G G A A G A C A G C C A  1271
At. sal. PCR - - - - - - - - - - - - - - - - - - - - - - - - - - - - - - - - - - - - - - - - -  0
At. sal. A26 - - - - - - - - - - - - - - - - - - - - - - - - - - - - - - - - - - - - - - - - -  0

SalmoKCaR 1  G A G A C T G A G A G A C A G T G A G A A T G G G A G C A C C A G T T T C A G A  1310
SalmoKCaR 2  G A G A C T G A G A G A C A G T G A G A A T G G G A G C A C C A G T T T C A G A  1400
SalmoKCaR 3  G A G A C T G A G A G A C A G T G A G A A T G G G A G C A C C A G T T T C A G A  1311
SalmoKCaR 4  G A G A C T G A G A G A C A G T G A G A A T G G G A G C A C C A G T T T C A G A  1311
At. sal. PCR - - - - - - - - - - - - - - - - - - - - - - - - - - - - - - - - - - - - - - - - -  0
At. sal. A26 - - - - - - - - - - - - - - - - - - - - - - - - - - - - - - - - - - - - - - - - -  0

SalmoKCaR 1  C C A T T G T G T A C T G G C G A G G A G G A C A T T A T G G G T G C A G A G A  1350
SalmoKCaR 2  C C A T T G T G T A C T G G C G A G G A G G A C A T T A T G G G T G C A G A G A  1440
SalmoKCaR 3  C C A T T G T G T A C T G G C G A G G A G G A C A T T A T G G G T G C A G A G A  1351
SalmoKCaR 4  C C A T T G T G T A C T G G C G A G G A G G A C A T T A T G G G T G C A G A G A  1351
At. sal. PCR - - - - - - - - - - - - - - - - - - - - - - - - - - - - - - - - - - - - - - - - -  0
At. sal. A26 - - - - - - - - - - - - - - - - - - - - - - - - - - - - - - - - - - - - - - - - -  0
```

FIG. 17D

```
SalmoKCaR 1  C C C C A T A T C T G G A T T A C A C T C A T C T T C G T A T T T C C T A T A A  1390
SalmoKCaR 2  C C C C A T A T C T G G A T T A C A C T C A T C T T C G T A T T T C C T A T A A  1480
SalmoKCaR 3  C C C C A T A T C T G G A T T A C A C T C A T C T T C G T A T T T C C T A T A A  1391
SalmoKCaR 4  C C C C A T A T C T G G A T T A C A C T C A T C T T C G T A T T T C C T A T A A  1391
At. sal. PCR - - - - - - - - - - - - - - - - - - - - - - - - - - - - - - - - - - - - - - - -  0
At. sal. A26 - - - - - - - - - - - - - - - - - - - - - - - - - - - - - - - - - - - - - - - -  0

SalmoKCaR 1  T G T G T A T G T T G C A G T T C A C T C C A T T G C A C A G G C C C T A C A G  1430
SalmoKCaR 2  T G T G T A T G T T G C A G T T C A C T C C A T T G C A C A G G C C C T A C A G  1520
SalmoKCaR 3  T G T G T A T G T T G C A G T T C A C T C C A T T G C A C A G G C C C T A C A G  1431
SalmoKCaR 4  T G T G T A T G T T G C A G T T C A C T C C A T T G C A C A G G C C C T A C A G  1431
At. sal. PCR - - - - - - - - - - - - - - - - - - - - - - - - - - - - - - - - - - - - - - - -  0
At. sal. A26 - - - - - - - - - - - - - - - - - - - - - - - - - - - - - - - - - - - - - - - -  0

SalmoKCaR 1  G A C A T T C T C A C C T G C A T T C C T G G A C G G G G T C T T T T T T C C A  1470
SalmoKCaR 2  G A C A T T C T C A C C T G C A T T C C T G G A C G G G G T C T T T T T T C C A  1560
SalmoKCaR 3  G A C A T T C T C A C C T G C A T T C C T G G A C G G G G T T T T T T T T C C A  1471
SalmoKCaR 4  G A C A T T C T C A C C T G C A T T C C T G G A C G G G G T C T T T T T T C C A  1471
At. sal. PCR - - - - - - - - - - - - - - - - - - - - - - - - - - - - - - - - - - - - - - - -  0
At. sal. A26 - - - - - - - - - - - - - - - - - - - - - - - - - - - - - - - - - - - - - - - -  0

SalmoKCaR 1  A C A A C T C A T G T G C A G A T A T A A A G A A A A T A G A A G C A T G G C A  1510
SalmoKCaR 2  A C A A C T C A T G T G C A G A T A T A A A G A A A A T A G A A G C A T G G C A  1600
SalmoKCaR 3  A C A A C T C A T G T G C A G A T A T A A A G A A A A T A G A A G C A T G G C A  1511
SalmoKCaR 4  A C A A C T C A T G T G C A G A T A T A A A G A A A A T A G A A G C A T G G C A  1511
At. sal. PCR - - - - - - - - - - - - - - - - - - - - - - - - - - - - - - - - - - - - - - - -  0
At. sal. A26 - - - - - - - - - - - - - - - - - - - - - - - - - - - - - - - - - - - - - - - -  0

SalmoKCaR 1  G G T T C T C A A G C A G C T C A G A C A T T T A A A C T T C T C A A A C A G T  1550
SalmoKCaR 2  G G T T C T C A A G C A G C T C A G A C A T T T A A A C T T C T C A A A C A G T  1640
SalmoKCaR 3  G G T T C T C A A G C A G C T C A G A C A T T T A A A C T T C T C A A A C A G T  1551
SalmoKCaR 4  G G T T C T C A A G C A G C T C A G A C A T T T A A A C T T C T C A A A C A G T  1551
At. sal. PCR - - - - - - - - - - - - - - - - - - - - - - - - - - - - - - - - - - - - - - - -  0
At. sal. A26 - - - - - - - - - - - - - - - - - - - - - - - - - - - - - - - - - - - - - - - -  0

SalmoKCaR 1  A T G G G A G A A A A G G T A C A T T T T G A T G A G A A T G C T G A T C C G T  1590
SalmoKCaR 2  A T G G G A G A A A A G G T A C A T T T T G A T G A G A A T G C T G A T C C G T  1680
SalmoKCaR 3  A T G G G A G A A A A G G T A C A T T T T G A T G A G A A T G C T G A T C C G T  1591
SalmoKCaR 4  A T G G G A G A A A A G G T A C A T T T T G A T G A G A A T G C T G A T C C G T  1591
At. sal. PCR - - - - - - - - - - - - - - - - - - - - - - - - - - - - - - - - - - - - - - - -  0
At. sal. A26 - - - - - - - - - - - - - - - - - - - - - - - - - - - - - - - - - - - - - - - -  0

SalmoKCaR 1  C A G G A A A C T A C A C C A T T A T C A A T T G G C A C C G G T C T C C T G A  1630
SalmoKCaR 2  C A G G A A A C T A C A C C A T T A T C A A T T G G C A C C G G T C T C C T G A  1720
SalmoKCaR 3  C A G G A A A C T A C A C C A T T A T C A A T T G G C A C C G G T C T C C T G A  1631
SalmoKCaR 4  C A G G A A A C T A C A C C A T T A T C A A T T G G C A C C G G T C T C C T G A  1631
At. sal. PCR - - - - - - - - - - - - - - - - - - - - - - - - - - - - - - - - - - - - - - - -  0
At. sal. A26 - - - - - - - - - - - - - - - - - - - - - - - - - - - - - - - - - - - - - - - -  0

SalmoKCaR 1  G G A T G G T T C T G T T G T G T T T G A A G A G G T C G G T T T C T A C A A C  1670
SalmoKCaR 2  G G A T G G T T C T G T T G T G T T T G A A G A G G T C G G T T T C T A C A A C  1760
SalmoKCaR 3  G G A T G G T T C T G T T G T G T T T G A A G A G G T C G G T T T C T A C A A C  1671
SalmoKCaR 4  G G A T G G T T C T G T T G T G T T T G A A G A G G T C G G T T T C T A C A A C  1671
At. sal. PCR - - - - - - - - - - - - - - - - - - - - - - - - - - - - - - - - - - - - - - - -  0
At. sal. A26 - - - - - - - - - - - - - - - - - - - - - - - - - - - - - - - - - - - - - - - -  0

SalmoKCaR 1  A T G C G A G C T A A G A G A G G A G T A C A A C T T T T C A T T G A T A A C A  1710
SalmoKCaR 2  A T G C G A G C T A A G A G A G G A G T A C A A C T T T T C A T T G A T A A C A  1800
SalmoKCaR 3  A T G C G A G C T A A G A G A G G A G T A C A A C T T T T C A T T G A T A A C A  1711
SalmoKCaR 4  A T G C G A G C T A A G A G A G G A G T A C A A C T T T T C A T T G A T A A C A  1711
At. sal. PCR - - - - - - - - - - - - - - - - - - - - - - - - - - - - - - - - - - - - - - - -  0
At. sal. A26 - - - - - - - - - - - - - - - - - - - - - - - - - - - - - - - - - - - - - - - -  0
```

FIG. 17E

```
SalmoKCaR 1  C A A A G A T T C T A T G G A A T G G A T A T A A T A C T G A G G T T C C A T T  1750
SalmoKCaR 2  C A A A G A T T C T A T G G A A T G G A T A T A A T A C T G A G G T T C C A T T  1840
SalmoKCaR 3  C A A A G A T T C T A T G G A A T G G A T A T A A T A C T G A G G T T C C A T T  1751
SalmoKCaR 4  C A A A G A T T C T A T G G A A T G G A T A T A A T A C T G A G G T T C C A T T  1751
At. sal. PCR  - - - - - - - - - - - - - - - - - - - - - - - - - - - - - - - - - - - - - - - -  0
At. sal. A26  - - - - - - - - - - - - - - - - - - - - - - - - - - - - - - - - - - - - - - - -  0

SalmoKCaR 1  C T C T A A C T G T A G T G A A G A T T G T G A A C C A G G C A C C A G A A A G  1790
SalmoKCaR 2  C T C T A A C T G T A G T G A A G A T T G T G A A C C A G G C A C C A G A A A G  1880
SalmoKCaR 3  C T C T A A C T G T A G T G A A G A T T G T G A A C C A G G C A C C A G A A A G  1791
SalmoKCaR 4  C T C T A A C T G T A G T G A A G A T T G T G A A C C A G G C A C C A G A A A G  1791
At. sal. PCR  - - - - - - - - - - - - - - - - - - - - - - - - - - - - - - - - - - - - - - - -  0
At. sal. A26  - - G T G A T C A C A A A G G T A A G A A A G A C A G T G A A A A A T C T G A A  38

SalmoKCaR 1  G G G A T C A T A G A A A G C A T G C C A A C G T G T T G C T T T G A A T G T A  1830
SalmoKCaR 2  G G G A T C A T A G A A A G C A T G C C A A C G T G T T G C T T T G A A T G T A  1920
SalmoKCaR 3  G G G A T C A T A G A A A G C A T G C C A A C G T G T T G C T T T G A A T G T A  1831
SalmoKCaR 4  G G G A T C A T A G A A A G C A T G C C A A C G T G T T G C T T T G A A T G T A  1831
At. sal. PCR  - - - - - - - - - - - - - - - - - - - - - - - - - - - - - - - - - - - - - - - -  0
At. sal. A26  C T A C C C C A T T A T A T A A T C T G T T G C T A T T T C A T A T G T T T C T  78

SalmoKCaR 1  C A G A A T G C T C A G A A G G A G A G T A T A G T G A T C A C A A A G A T G C  1870
SalmoKCaR 2  C A G A A T G C T C A G A A G G A G A G T A T A G T G A T C A C A A A G A T G C  1960
SalmoKCaR 3  C A G A A T G C T C A G A A G G A G A G T A T A G T G A T C A C A A A G A T G C  1871
SalmoKCaR 4  C A G A A T G C T C A G A A G G A G A G T A T A G T G A T C A C A A A G A T G C  1871
At. sal. PCR  - - - - - - - - - - - - - - - - - - - - - - - - - - - - - - - - - - - - - - - -  0
At. sal. A26  A T C A A T A A T A C A A A C A C T A C T T C T C T A T T C C T G C A G A T G C  118

SalmoKCaR 1  C A G T G T T T G T A C C A A G T G T C C C A A T G A C T C A T G G T C T A A T  1910
SalmoKCaR 2  C A G T G T T T G T A C C A A G T G T C C C A A T G A C T C A T G G T C T A A T  2000
SalmoKCaR 3  C A G T G T T T G T A C C A A G T G T C C C A A T G A C T C A T G G T C T A A T  1911
SalmoKCaR 4  C A G T G T T T G T A C C A A G T G T C C C A A T G A C T C A T G G T C T A A T  1911
At. sal. PCR  - - - - - - - - - - - - - - - - - - - - - - - - - - - - - - - - - - - - - - - -  0
At. sal. A26  C A G T G T T T G T A C C A A G T G T C C C A A T G A C T C A T G G T C T A A T  158

SalmoKCaR 1  G A G A A C C A C A C A T C T T G T T T C C T G A A G G A G A T A G A G T T T C  1950
SalmoKCaR 2  G A G A A C C A C A C A T C T T G T T T C C T G A A G G A G A T A G A G T T T C  2040
SalmoKCaR 3  G A G A A C C A C A C A T C T T G T T T C C T G A A G G A G A T A G A G T T T C  1951
SalmoKCaR 4  G A G A A C C A C A C A T C T T G T T T C C T G A A G G A G A T A G A G T T T C  1951
At. sal. PCR  - - - - - - - - - - - - - - - - - - - - - - - - - - - - - - - - - - - - - - - -  0
At. sal. A26  G A G A A C C A C A C A T C T T G T T T C C T G A A G G A G A T A G A G T T T C  198

SalmoKCaR 1  T G T C T T G G A C A G A G C C C T T T G G G A T C G C C T T G G C A T T A T G  1990
SalmoKCaR 2  T G T C T T G G A C A G A G C C C T T T G G G A T C G C C T T G G C A T T A T G  2080
SalmoKCaR 3  T G T C T T G G A C A G A G C C C T T T G G G A T C G C C T T G G C A T T A T G  1991
SalmoKCaR 4  T G T C T T G G A C A G A G C C C T T T G G G A T C G C C T T G G C A T T A T G  1991
At. sal. PCR  - - - - - - - - - - - - - - - - - - - - - - - - - - C T T G G C A T T A T G  12
At. sal. A26  T G T C T T G G A C A G A G C C C T T T G G G A T C G C C T T G G C A T T A T G  238

SalmoKCaR 1  C T C T G T G C T G G G G G T A T T C T T G A C A G C A T T C G T G A T G G G A  2030
SalmoKCaR 2  C T C T G T G C T G G G G G T A T T C T T G A C A G C A T T C G T G A T G G G A  2120
SalmoKCaR 3  C T C T G T G C T G G G G G T A T T C T T G A C A G C A T T C G T G A T G G G A  2031
SalmoKCaR 4  C T C T G T G C T G G G G G T A T T C T T G A C A G C A T T C G T G A T G G G A  2031
At. sal. PCR  C T C T G T G C T G G G G G T A T T C T T G A C A G C A T T C G T G A T G G G A  52
At. sal. A26  C T C T G T G C T G G G G G T A T T C T T G A C A G C A T T C G T G A T G G G A  278

SalmoKCaR 1  G T G T T T A T C A A A T T T C G C A A C A C C C C A A T T G T T A A G G C C A  2070
SalmoKCaR 2  G T G T T T A T C A A A T T T C G C A A C A C C C C A A T T G T T A A G G C C A  2160
SalmoKCaR 3  G T G T T T A T C A A A T T T C G C A A C A C C C C A A T T G T T A A G G C C A  2071
SalmoKCaR 4  G T G T T T A T C A A A T T T C G C A A C A C C C C A A T T G T T A A G G C C A  2071
At. sal. PCR  G T G T T T A T C A A A T T T C G C A A C A C C C C A A T T G T T A A G G C C A  92
At. sal. A26  G T G T T T A T C A A A T T T C G C A A C A C C C C A A T T G T T A A G G C C A  318
```

FIG. 17F

```
SalmoKCaR 1   C A A A C A G A G A G C T A T C C T A C C T C C T C C T G T T C T C A C T C A T 2110
SalmoKCaR 2   C A A A C A G A G A G C T A T C C T A C C T C C T C C T G T T C T C A C T C A T 2200
SalmoKCaR 3   C A A A C A G A G A G C T A T C C T A C C T C C T C C T G T T C T C A C T C A T 2111
SalmoKCaR 4   C A A A C A G A G A G C T A T C C T A C C T C C T C C T G T T C T C A C T C A T 2111
At. sal. PCR  C A A A C A G A G A G C T A T C C T A C C T C C T C C T G T T C T C A C T C A T 132
At. sal. A26  C A A A C A G A G A G C T A T C C T A C C T C C T C C T G T T C T C A C T C A T 358

SalmoKCaR 1   C T G C T G T T T C T C C A G T T C C C T C A T C T T C A T T G G T G A A C C C 2150
SalmoKCaR 2   C T G C T G T T T C T C C A G T T C C C T C A T C T T C A T T G G T G A A C C C 2240
SalmoKCaR 3   C T G C T G T T T C T C C A G T T C C C T C A T C T T C A T T G G T G A A C C C 2151
SalmoKCaR 4   C T G C T G T T T C T C C A G T T C C C T C A T C T T C A T T G G T G A A C C C 2151
At. sal. PCR  C T G C T G T T T C T C C A G T T C C C T C A T C T T C A T T G G T G A A C C C 172
At. sal. A26  C T G C T G T T T C T C C A G T T C C C T C A T C T T C A T T G G T G A A C C C 398

SalmoKCaR 1   C A G G A C T G G A C A T G C C G T C T A C G C C A G C C T G C A T T C G G G A 2190
SalmoKCaR 2   C A G G A C T G G A C A T G C C G T C T A C G C C A G C C T G C A T T C G G G A 2280
SalmoKCaR 3   C A G G A C T G G A C A T G C C G T C T A C G C C A G C C T G C A T T C G G G A 2191
SalmoKCaR 4   C A G G A C T G G A C A T G C C G T C T A C G C C A G C C T G C A T T C G G G A 2191
At. sal. PCR  C A G G A C T G G A C A T G C C G T C T A C G C C A G C C T G C A T T C G G G A 212
At. sal. A26  C A G G A C T G G A C A T G C C G T C T A C G C C A G C C T G C A T T C G G G A 438

SalmoKCaR 1   T A A G T T T T G T T C T C T G C A T C T C C T G C A T C C T G G T A A A A A C 2230
SalmoKCaR 2   T A A G T T T T G T T C T C T G C A T C T C C T G C A T C C T G G T A A A A A C 2320
SalmoKCaR 3   T A A G T T T T G T T C T C T G C A T C T C C T G C A T C C T G G T A A A A A C 2231
SalmoKCaR 4   T A A G T T T T G T T C T C T G C A T C T C C T G C A T C C T G G T A A A A A C 2231
At. sal. PCR  T A A G T T T T G T T C T C T G C A T C T C C T G C A T C C T G G T A A A A A C 252
At. sal. A26  T A A G T T T T G T T C T C T G C A T C T C C T G C A T C C T G G T A A A A A C 478

SalmoKCaR 1   T A A C C G A G T A C T T C T A G T G T T C G A A G C C A A G A T C C C C A C C 2270
SalmoKCaR 2   T A A C C G A G T A C T T C T A G T G T T C G A A G C C A A G A T C C C C A C C 2360
SalmoKCaR 3   T A A C C G A G T A C T T C T A G T G T T C G A A G C C A A G A T C C C C A C C 2271
SalmoKCaR 4   T A A C C G A G T A C T T C T A G T G T T C G A A G C C A A G A T C C C C A C C 2271
At. sal. PCR  T A A C C G A G T A C T T C T A G T G T T C G A A G C C A A G A T C C C C A C C 292
At. sal. A26  T A A C C G A G T A C T T C T A G T G T T C G A A G C C A A G A T C C C C A C C 518

SalmoKCaR 1   A G T C T C C A T C G T A A G T G G T G G G G G C T A A A C T T G C A G T T C C 2310
SalmoKCaR 2   A G T C T C C A T C G T A A G T G G T G G G G G C T A A A C T T G C A G T T C C 2400
SalmoKCaR 3   A G T C T C C A T C G T A A G T G G T G G G G G C T A A A C T T G C A G T T C C 2311
SalmoKCaR 4   A G T C T C C A T C G T A A G T G G T G G G G G C T A A A C T T G C A G T T C C 2311
At. sal. PCR  A G T C T C C A T C G T A A G T G G T G G G G G C T A A A C T T G C A G T T C C 332
At. sal. A26  A G T C T C C A T C G T A A G T G G T G G G G G C T A A A C T T G C A G T T C C 558

SalmoKCaR 1   T G T T A G T G T T C C T G T T C A C A T T T G T G C A A G T G A T G A T A T G 2350
SalmoKCaR 2   T G T T A G T G T T C C T G T T C A C A T T T G T G C A A G T G A T G A T A T G 2440
SalmoKCaR 3   T G T T A G T G T T C C T G T T C A C A T T T G T G C A A G T G A T G A T A T G 2351
SalmoKCaR 4   T G T T A G T G T T C C T G T T C A C A T T T G T G C A A G T G A T G A T A T G 2351
At. sal. PCR  T G T T A G T G T T C C T G T T C A C A T T T G T G C A A G T G A T G A T A T G 372
At. sal. A26  T G T T A G T G T T C C T G T T C A C A T T T G T G C A A G T G A T G A T A T G 598

SalmoKCaR 1   T G T G G T C T G G C T T T A C A A T G C T C C T C C G G C G A G C T A C A G G 2390
SalmoKCaR 2   T G T G G T C T G G C T T T A C A A T G C T C C T C C G G C G A G C T A C A G G 2480
SalmoKCaR 3   T G T G G T C T G G C T T T A C A A T G C T C C T C C G G C G A G C T A C A G G 2391
SalmoKCaR 4   T G T G G T C T G G C T T T A C A A T G C T C C T C C G G C G A G C T A C A G G 2391
At. sal. PCR  T G T G G T C T G G C T T T A C A A T G C T C C T C C G G C G A G C T A C A G G 412
At. sal. A26  T G T G G T C T G G C T T T A C A A T G C T C C T C C G G C G A G C T A C A G G 638

SalmoKCaR 1   A A C C A T G A C A T T G A T G A G A T A A T T T T C A T T A C A T G C A A T G 2430
SalmoKCaR 2   A A C C A T G A C A T T G A T G A G A T A A T T T T C A T T A C A T G C A A T G 2520
SalmoKCaR 3   A A C C A T G A C A T T G A T G A G A T A A T T T T C A T T A C A T G C A A T G 2431
SalmoKCaR 4   A A C C A T G A C A T T G A T G A G A T A A T T T T C A T T A C A T G C A A T G 2431
At. sal. PCR  A A C C A T G A C A T T G A T G A G A T A A T T T T C A T T A C A T G C A A T G 452
At. sal. A26  A A C C A T G A C A T T G A T G A G A T A A T T T T C A T T A C A T G C A A T G 678
```

FIG. 17G

```
SalmoKCaR 1    A G G G C T C T A T G A T G G C G C T T G G C T T C C T A A T T G G G T A C A C  2470
SalmoKCaR 2    A G G G C T C T A T G A T G G C G C T T G G C T T C C T A A T T G G G T A C A C  2560
SalmoKCaR 3    A G G G C T C T A T G A T G G C G C T T G G C T T C C T A A T T G G G T A C A C  2471
SalmoKCaR 4    A G G G C T C T A T G A T G G C G C T T G G C T T C C T A A T T G G G T A C A C  2471
At. sal. PCR   A G G G C T C T A T G A T G G C G C T T G G C T T C C T A A T T G G G T A C A C  492
At. sal. A26   A G G G C T C T A T G A T G G C G C T T G G C T T C C T A A T T G G G T A C A C  718

SalmoKCaR 1    A T G C C T G C T G G C A G C C A T A T G C T T C T T C T T T G C A T T T A A A  2510
SalmoKCaR 2    A T G C C T G C T G G C A G C C A T A T G C T T C T T C T T T G C A T T T A A A  2600
SalmoKCaR 3    A T G C C T G C T G G C A G C C A T A T G C T T C T T C T T T G C A T T T A A A  2511
SalmoKCaR 4    A T G C C T G C T G G C A G C C A T A T G C T T C T T C T T T G C A T T T A A A  2511
At. sal. PCR   A T G C C T G C T G G C A G C C A T A T R C T T C T T C T T T G C A T T T A A A  532
At. sal. A26   A T G C C T G C T G G C A G C C A T A T G C T T C T T C T T T G C A T T T A A A  758

SalmoKCaR 1    T C A C G A A A A C T G C C A G A G A A C T T T A C T G A G G C T A A G T T C A  2550
SalmoKCaR 2    T C A C G A A A A C T G C C A G A G A A C T T T A C T G A G G C T A A G T T C A  2640
SalmoKCaR 3    T C A C G A A A A C T G C C A G A G A A C T T T A C T G A G G C T A A G T T C A  2551
SalmoKCaR 4    T C A C G A A A A C T G C C A G A G A A C T T T A C T G A G G C T A A G T T C A  2551
At. sal. PCR   T C A C G A A A A C T G C C A G A G A A C T T T A C T G A G G C T A A G T T C A  572
At. sal. A26   T C A C G A A A A C T G C C A G A G A A C T T T A C T G A G G C T A A G T T C A  798

SalmoKCaR 1    T C A C C T T C A G C A T G C T C A T C T T C T T C A T C G T C T G G A T C T C  2590
SalmoKCaR 2    T C A C C T T C A G C A T G C T C A T C T T C T T C A T C G T C T G G A T C T C  2680
SalmoKCaR 3    T C A C C T T C A G C A T G C T C A T C T T C T T C A T C G T C T G G A T C T C  2591
SalmoKCaR 4    T C A C C T T C A G C A T G C T C A T C T T C T T C A T C G T C T G G A T C T C  2591
At. sal. PCR   T C A C C T T C A G C A T G C T C A T C T T                                    594
At. sal. A26   T C A C C T T C A G C A T G C T C A T C T T C T T C A T C G T C T G G A T C T C  838

SalmoKCaR 1    T T T C A T C C C T G C C T A C T T C A G C A C T T A C G G A A A G T T T G T G  2630
SalmoKCaR 2    T T T C A T C C C T G C C T A C T T C A G C A C T T A C G G A A A G T T T G T G  2720
SalmoKCaR 3    T T T C A T C C C T G C C T A C T T C A G C A C T T A C G G A A A G T T T G T G  2631
SalmoKCaR 4    T T T C A T C C C T G C C T A C T T C A G C A C T T A C G G A A A G T T T G T G  2631
At. sal. PCR                                                                                 594
At. sal. A26   T T T C A T C C C T G C C T A C T T C A G C A C T T A C G G A A A G T T T G T G  878

SalmoKCaR 1    T C G G C T G T G G A G G T C A T C G C C A T A C T A G C C T C C A G C T T T G  2670
SalmoKCaR 2    T C G G C T G T G G A G G T C A T C G C C A T A C T A G C C T C C A G C T T T G  2760
SalmoKCaR 3    T C G G C T G T G G A G G T C A T C G C C A T A C T A G C C T C C A G C T T T G  2671
SalmoKCaR 4    T C G G C T G T G G A G G T C A T C G C C A T A C T A G C C T C C A G C T T T G  2671
At. sal. PCR                                                                                 594
At. sal. A26   T C G G C T G T G G A G G T C A T C G C C A T A C T A G C C T C C A G C T T T G  918

SalmoKCaR 1    G C C T G C T G G C C T G T A T T T T C T T C A A T A A A G T C T A C A T C A T  2710
SalmoKCaR 2    G C C T G C T G G C C T G T A T T T T C T T C A A T A A A G T C T A C A T C A T  2800
SalmoKCaR 3    G C C T G C T G G C C T G T A T T T T C T T C A A T A A A G T C T A C A T C A T  2711
SalmoKCaR 4    G C C T G C T G G C C T G T A T T T T C T T C A A T A A A G T C T A C A T C A T  2711
At. sal. PCR                                                                                 594
At. sal. A26   G C C T G C T G G C C T G T A T T T T C T T C A A T A A A G T C T A C A T C A T  958

SalmoKCaR 1    C C T C T T C A A A C C G T C C A G G A A C A C T A T A G A G G A G G T T C G C  2750
SalmoKCaR 2    C C T C T T C A A A C C G T C C A G G A A C A C T A T A G A G G A G G T T C G C  2840
SalmoKCaR 3    C C - - - - - - - - - - - - - - - - - - - - - - - - - - - - - - - - - - - - -  2713
SalmoKCaR 4    C C T C T T C A A A C C G T C C A G G A A C A C T A T A G A G G A G G T T C G C  2751
At. sal. PCR                                                                                 594
At. sal. A26   C C T C T T C A A A C C G T C C A G G A A C A C T A T A G A G G A G G T T C G C  998

SalmoKCaR 1    T G T A G C A C T G C G G C C C A T T C T T T C A A A G T G G C A G C C A A G G  2790
SalmoKCaR 2    T G T A G C A C T G C G G C C C A T T C T T T C A A A G T G G C A G C C A A G G  2880
SalmoKCaR 3    - - - - - - - - - - - - - - - - - - - - - - - - - - - - - - - - - - - - - - -  2713
SalmoKCaR 4    T G T A G C A C T G C G G C C C A T T C T T T C A A A G T G G C A G C C A A G G  2791
At. sal. PCR                                                                                 594
At. sal. A26   T G T A G C A C T G C G G C C C A T T C T T T C A A A G T G G C A G C C A A G G  1038
```

FIG. 17H

```
SalmoKCaR 1  CCACTCTGAGACACAGCTCAGCCTCCAGGAAGAGGTCCAG 2830
SalmoKCaR 2  CCACTCTGAGACACAGCTCAGCCTCCAGGAAGAGGTCCAG 2920
SalmoKCaR 3  ---------------------------------------- 2713
SalmoKCaR 4  CCACTCTGAGACACAGCTCAGCCTCCAGGAAGAGGTCCAG 2831
At. sal. PCR                                          594
At. sal. A26 CCACTCTGAGACACAGCTCAGCCTCCAGGAAGAGGTCCAG 1078

SalmoKCaR 1  CAGTGTGGGGGGATCCTGTGCCTCAACTCCCTCCTCATCC 2870
SalmoKCaR 2  CAGTGTGGGGGGATCCTGTGCCTCAACTCCCTCCTCATCC 2960
SalmoKCaR 3  ---------------------------------------- 2713
SalmoKCaR 4  CAGTGTGGGGGGATCCTGTGCCTCAACTCCCTCCTCATCC 2871
At. sal. PCR                                          594
At. sal. A26 CAGTGTGGGGGGATCCTGTGCCTCAACTCCCTCCTCATCC 1118

SalmoKCaR 1  ATCAGCCTCAAGACCAATGACAATGACTCCCCATCAGGTC 2910
SalmoKCaR 2  ATCAGCCTCAAGACCAATGACAATGACTCCCCATCAGGTC 3000
SalmoKCaR 3  ATCAGCCTCAAGACCAATGACAATGACTCCCCATCAGGTC 2753
SalmoKCaR 4  ATCAGCCTCAAGACCAATGACAATGACTCCCCATCAGGTC 2911
At. sal. PCR                                          594
At. sal. A26 ATCAGCCTCAAGACCAATGACAATGACTCCCCATCAGGTC 1158

SalmoKCaR 1  AGCAGAGAATCCATAAGCCAAGAGTAAGCTTTGGAAGTGG 2950
SalmoKCaR 2  AGCAGAGAATCCATAAGCCAAGAGTAAGCTTTGGAAGTGG 3040
SalmoKCaR 3  AGCAGAGAATCCATAAGCCAAGAGTAAGCTTTGGAAGTGG 2793
SalmoKCaR 4  AGCAGAGAATCCATAAGCCAAGAGTAAGCTTTGGAAGTGG 2951
At. sal. PCR                                          594
At. sal. A26 AGCAGAGAATCCATAAGCCAAGAGTAAGCTTTGGAAGTGG 1198

SalmoKCaR 1  AACAGTTACTCTGTCCTTGAGCTTTGAGGAGTCCAGAAAG 2990
SalmoKCaR 2  AACAGTTACTCTGTCCTTGAGCTTTGAGGAGTCCAGAAAG 3080
SalmoKCaR 3  AACAGTTACTCTGTCCTTGAGCTTTGAGGAGTCCAGAAAG 2833
SalmoKCaR 4  AACAGTTACTCTGTCCTTGAGCTTTGAGGAGTCCAGAAAG 2991
At. sal. PCR                                          594
At. sal. A26 AACAGTTACTCTGTCCTTGAGCTTTGAGGAGTCCAGAAAG 1238

SalmoKCaR 1  AATTCTATGAAGTAGGGAAGTGTCTTTTGGTGGGCCGAGA 3030
SalmoKCaR 2  AATTCTATGAAGTAGGGAAGTGTCTTTTGGTGGGCCGAGA 3120
SalmoKCaR 3  AATTCTATGAAGTAGGGAAGTGTCTTTTGGTGGGCCGAGA 2873
SalmoKCaR 4  AATTCTATGAAGTAGGGAAGTGTCTTTTGGTGGGCCGAGA 3031
At. sal. PCR                                          594
At. sal. A26 AATTCTATGAAGTAGGGAAGTGTCTTTTGGTGGGCCGAGA 1278

SalmoKCaR 1  GCCTTGTCAAAACCTGAGTTGGTGTTGCATTCTTTGTTGG 3070
SalmoKCaR 2  GCCTTGTCAAAACCTGAGTTGGTGTTGCATTCTTTGTTGG 3160
SalmoKCaR 3  GCCTTGTCAAAACCTGAGTTGGTGTTGCATTCTTTGTTGG 2913
SalmoKCaR 4  GCCTTGTCAAAACCTGAGTTGGTGTTGCATTCTTTGTTGG 3071
At. sal. PCR                                          594
At. sal. A26 GCCTTGTCAAAACCTGAGTTGGTGTTGCATTCTTTGTTGG 1318

SalmoKCaR 1  CTGGGTAGTTGGAGCAGAAATTATGATATTAAAAGCTTTG 3110
SalmoKCaR 2  CTGGGTAGTTGGAGCAGAAATTATGATATTAAAAGCTTTG 3200
SalmoKCaR 3  CTGGGTAGTTGGAGCAGAAATTATGATATTAAAAGCTTTG 2953
SalmoKCaR 4  CTGGGTAGTTGGAGCAGAAATTATGATATTAAAAGCTTTG 3111
At. sal. PCR                                          594
At. sal. A26 CTGGGTAGTTGGAGCAGAAATTATGATATTAAAAGCTTTG 1358

SalmoKCaR 1  ATGTATTCAGAATGGTGACACAGCATAGGTGGCCAAGATT 3150
SalmoKCaR 2  ATGTATTCAGAATGGTGACACAGCATAGGTGGCCAAGATT 3240
SalmoKCaR 3  ATGTATTCAGAATGGTGACACAGCATAGGTGGCCAAGATT 2993
SalmoKCaR 4  ATGTATTCAGAATGGTGACACAGCATAGGTGGCCAAGATT 3151
At. sal. PCR                                          594
At. sal. A26 ATGTATTCAGAATGGTGACACAGCATAGGTGGCCAAGATT 1398
```

FIG. 17I

```
SalmoKCaR 1   C C A T T A T A T T A C A A T A A T C T G T G T T G T T C A T T A T G A G G A C  3190
SalmoKCaR 2   C C A T T A T A T T A C A A T A A T C T G T G T T G T T C A T T A T G A G G A C  3280
SalmoKCaR 3   C C A T T A T A T T A C A A T A A T C T G T G T T G T T C A T T A T G A G G A C  3033
SalmoKCaR 4   C C A T T A T A T T A C A A T A A T C T G T G T T G T T C A T T A T G A G G A C  3191
At. sal. PCR                                                                                   594
At. sal. A26  C C A T T A T A T T A C A A T A A T C T G T G T T G T T C A T T A T G A G G A C  1438

SalmoKCaR 1   A T T T C A A A A T G C T G A A A A T C A T C A A A T A C A T A A T T T A C T G  3230
SalmoKCaR 2   A T T T C A A A A T G C T G A A A A T C A T C A A A T A C A T A A T T T A C T G  3320
SalmoKCaR 3   A T T T C A A A A T G C T G A A A A T C A T C A A A T A C A T A A T T T A C T G  3073
SalmoKCaR 4   A T T T C A A A A T G C T G A A A A T C A T C A A A T A C A T A A T T T A C T G  3231
At. sal. PCR                                                                                   594
At. sal. A26  A T T T C A A A A T G C T G A A A A T C A T C A A A T A C A T A A T T T A C T G  1478

SalmoKCaR 1   A G T T T T C T T G A T A A T C T T G A G A A T A G A A T A G C C T A T T C A A  3270
SalmoKCaR 2   A G T T T T C T T G A T A A T C T T G A G A A T A G A A T A G C C T A T T C A A  3360
SalmoKCaR 3   A G T T T T C T T G A T A A T C T T G A G A A T A G A A T A G C C T A T T C A A  3113
SalmoKCaR 4   A G T T T T C T T G A T A A T C T T G A G A A T A G A A T A G C C T A T T C A A  3271
At. sal. PCR                                                                                   594
At. sal. A26  A G T T T T C T T G A T A A T C T T G A G A A T A G A A T A G C C T A T T C A A  1518

SalmoKCaR 1   G T C A T C G T T G A G C A G A C A T T A A T T A A C A A T G A T G T A A T A C  3310
SalmoKCaR 2   G T C A T C G T T G A G C A G A C A T T A A T T A A C A A T G A T G T A A T A C  3400
SalmoKCaR 3   G T C A T C G T T G A G C A G A C A T T A A T T A A C A A T G A T G T A A T A C  3153
SalmoKCaR 4   G T C A T C G T T G A G C A G A C A T T A A T T A A C A A T G A T G T A A T A C  3311
At. sal. PCR                                                                                   594
At. sal. A26  G T C A T C G T T G A G C A G A C A T T A A T T A A C A A T G A T G T A A T A C  1558

SalmoKCaR 1   T T T C C A T A C C T A T T T T C T T T A A C A A T A G A T T C A C A T T G T T  3350
SalmoKCaR 2   T T T C C A T A C C T A T T T T C T T T A A C A A T A G A T T C A C A T T G T T  3440
SalmoKCaR 3   T T T C C A T A C C T A T T T T C T T T A A C A A T A G A T T C A C A T T G T T  3193
SalmoKCaR 4   T T T C C A T A C C T A T T T T C T T T A A C A A T A G A T T C A C A T T G T T  3351
At. sal. PCR                                                                                   594
At. sal. A26  T T T C C A T A C C T A T T T T C T T T A A C A A T A G A T T C A C A T T G T T  1598

SalmoKCaR 1   A A A G T T C A A C T A T G A C C T G T A A A A T A C A T G A G G T A T A A C A  3390
SalmoKCaR 2   A A A G T T C A A C T A T G A C C T G T A A A A T A C A T G A G G T A T A A C A  3480
SalmoKCaR 3   A A A G T T C A A C T A T G A C C T G T A A A A T A C A T G A G G T A T A A C A  3233
SalmoKCaR 4   A A A G T T C A A C T A T G A C C T G T A A A A T A C A T G A G G T A T A A C A  3391
At. sal. PCR                                                                                   594
At. sal. A26  A A A G T T C A A C T A T G A C C T G T A A A A T A C A T G A G G T A T A A C A  1638

SalmoKCaR 1   G G A G A C A A T A A A A C T A T G C A T A T C C T A G C T T C T G G G C C T G  3430
SalmoKCaR 2   G G A G A C A A T A A A A C T A T G C A T A T C C T A G C T T C T G G G C C T G  3520
SalmoKCaR 3   G G A G A C A A T A A A A C T A T G C A T A T C C T A G C T T C T G G G C C T G  3273
SalmoKCaR 4   G G A G A C A A T A A A A C T A T G C A T A T C C T A G C T T C T G G G C C T G  3431
At. sal. PCR                                                                                   594
At. sal. A26  G G A G A C A A T A A A A C T A T G C A T A T C C T A G C T T C T G G G C C T G  1678

SalmoKCaR 1   A G T A G C A G G C A G T T T A C T C T G G G C A C G C T T T T C A T C C A A A  3470
SalmoKCaR 2   A G T A G C A G G C A G T T T A C T C T G G G C A C G C T T T T C A T C C A A A  3560
SalmoKCaR 3   A G T A G C A G G C A G T T T A C T C T G G G C A C G C T T T T C A T C C A A A  3313
SalmoKCaR 4   A G T A G C A G G C A G T T T A C T C T G G G C A C G C T T T T C A T C C A A A  3471
At. sal. PCR                                                                                   594
At. sal. A26  A G T A G C A G G C A G T T T A C T C T G G G C A C G C T T T T C A T C C A A A  1718

SalmoKCaR 1   C T T C C G A A T G C T G C C C C A A T C C T A G T G A G G T T A A A G G C C  3510
SalmoKCaR 2   C T T C C G A A T G C T G C C C C A A T C C T A G T G A G G T T A A A G G C C  3600
SalmoKCaR 3   C T T C C G A A T G C T G C C C C A A T C C T A G T G A G G T T A A A G G C C  3353
SalmoKCaR 4   C T T C C G A A T G C T G C C C C A A T C C T A G T G A G G T T A A A G G C C  3511
At. sal. PCR                                                                                   594
At. sal. A26  C T T C C G A A T G C T G C C C C A A T C C T A G T G A G G T T A A A G G C C  1758
```

FIG. 17J

```
SalmoKCaR 1   C A G T G C A G T C A T A T C T T T T C T C T A G G C A C G C T T T T C A T C C  3550
SalmoKCaR 2   C A G T G C A G T C A T A T C T T T T C T C T A G G C A C G C T T T T C A T C C  3640
SalmoKCaR 3   C A G T G C A G T C A T A T C T T T T C T C T A G G C A C G C T T T T C A T C C  3393
SalmoKCaR 4   C A G T G C A G T C A T A T C T T T T C T C T A G G C A C G C T T T T C A T C C  3551
At. sal. PCR                                                                              594
At. sal. A26  C A G T G C A G T C A T A T C T T T T C T C T A G G C A C G C T T T T C A T C C  1798

SalmoKCaR 1   A A A C T T C C G A A T G C G G C T A T A T C A G T C T C T T T C C T A C T G T  3590
SalmoKCaR 2   A A A C T T C C G A A T G C G G C T A T A T C A G T C T C T T T C C T A C T G T  3680
SalmoKCaR 3   A A A C T T C C G A A T G C G G C T A T A T C A G T C T C T T T C C T A C T G T  3433
SalmoKCaR 4   A A A C T T C C G A A T G C G G C T A T A T C A G T C T C T T T C C T A C T G T  3591
At. sal. PCR                                                                              594
At. sal. A26  A A A C T T C C G A A T G C G G C T A T A T C A G T C T C T T T C C T A C T G T  1838

SalmoKCaR 1   C T T T T T C A T T A G G C C A G T G T T T A A C A A C C C T G G T C C T T A A  3630
SalmoKCaR 2   C T T T T T C A T T A G G C C A G T G T T T A A C A A C C C T G G T C C T T A A  3720
SalmoKCaR 3   C T T T T T C A T T A G G C C A G T G T T T A A C A A C C C T G G T C C T T G A  3473
SalmoKCaR 4   C T T T T T C A T T A G G C C A G T G T T T A A C A A C C C T G G T C C T T A A  3631
At. sal. PCR                                                                              594
At. sal. A26  C T T T T T C A T T A G G C C A G T G T T T A A C A A C C C T G G T C C T T A A  1878

SalmoKCaR 1   G T A C A C A C A A C A G A G C A C A T T T T T G T T G T G G C C C T G G A C A  3670
SalmoKCaR 2   G T A C A C A C A A C A G A G C A C A T T T T T G T T G T A G C C C T G G A C A  3760
SalmoKCaR 3   G T A C A C A C A A C A G G G C A C A T T T T T G T T G T A G C C C T G G A C A  3513
SalmoKCaR 4   G T G C A C A C A A C A G G G C A C A T T T T T G T T G T G G C C C T G G A C A  3671
At. sal. PCR                                                                              594
At. sal. A26  G T A C A C A C A A C A G A A C A C A T T T T T G T T G T A G C C C T G G A C A  1918

SalmoKCaR 1   A T C A C T C C T C A C T C A G C T C A T T G A G G G C C T G A T G A T T A G T  3710
SalmoKCaR 2   A T C A C T C C T C A C T C A G C T C A T T G A G G G C C T G A T G A T T A G T  3800
SalmoKCaR 3   A T C A C T C C T C A C T C A G C T C A T T G A G G G C C T G A T G A T T A G T  3553
SalmoKCaR 4   A T C A C T C C T C A C T C A G C T C A T T G A G G G C C T G A T G A T T A G T  3711
At. sal. PCR                                                                              594
At. sal. A26  A T C A C T C C T C A C T C A G C T C A T T G A G G G C C T G A T G A T T A G T  1958

SalmoKCaR 1   T G A C A A G T T G A G T C G G G T G T G C T T G T C C G G G G T T G C A A T A  3750
SalmoKCaR 2   T G A C A A G T T G A G T C G G G T G T G C T T G T C C A G G G T T A C G A T A  3840
SalmoKCaR 3   T G A C A A G T T G G G T C A G G T G T G C T T G T C C A G G G T T A C A A T A  3593
SalmoKCaR 4   T G A C A A G T T G A G T C A G G T G T G C T T G T C C G G G G T T G C A A T A  3751
At. sal. PCR                                                                              594
At. sal. A26  T G A C A A G T T G A A T C A G G T G T G C T T G T C C A G G G T T A C A A T A  1998

SalmoKCaR 1   C A G A T G T G T A C T G T T G G G G G T A C T C G A G G A C C A G G A T T G G  3790
SalmoKCaR 2   C A G A T G T G T A C T G T T G G G G G T G C T C G A G G A C C A G G A T T G G  3880
SalmoKCaR 3   C A G A T G T G T G C T G T T G G G G G T A C T C G A G G A C C A G G A T T G G  3633
SalmoKCaR 4   C A G A T G T G T A C T G T T G G G G G T G C T C G A G G A C C A G G A T T G G  3791
At. sal. PCR                                                                              594
At. sal. A26  C A A A T G T G T A C T G T T G G G G G T A C                                  2021

SalmoKCaR 1   G A A A C A T T A C A T T A G G A C T A C T G T A G G T T C T T C A A T A T G G  3830
SalmoKCaR 2   G A A A C A T T A C A T T A G G A C T A C T G T A G G T T C T T C A A T A T G G  3920
SalmoKCaR 3   G A A A C A T T A C A T T A G G A C T A C T G T A G G T T C T T C A A T A T G G  3673
SalmoKCaR 4   G A A A C A T T A C A T T A G G A C T A C T G T A G G T T C T T C A A T A T G G  3831
At. sal. PCR                                                                              594
At. sal. A26                                                                              2021

SalmoKCaR 1   T G T C A T A C G G T C A T A T G G T G T C A T A T G G T G T C T G G T T G T T  3870
SalmoKCaR 2   T G T C A T A C G G T C A T A T G G T G T C A T A T G G T G T C T G G T T G T T  3960
SalmoKCaR 3   T G T C A T A C G G T C A T A T G G T G T C A T A T G G T G T C T G G T T G T T  3713
SalmoKCaR 4   T G T C A T A C G G T C A T A T G G T G T C A T A T G G T G T C T G G T T G T T  3871
At. sal. PCR                                                                              594
At. sal. A26                                                                              2021
```

FIG. 17K

```
SalmoKCaR 1   T T C T G C A T A T G T G T A T T T C A C C A A G T T A C T G C A C A T G T T A   3910
SalmoKCaR 2   T T C T G C A T A T G T G T A T T T C A C C A A G T T A C T G C A C A T G T T A   4000
SalmoKCaR 3   T T C T G C A T A T G T G T A T T T C A C C A A G T T A C T G C A C A T G T T A   3753
SalmoKCaR 4   T T C T G C A T A T G T G T A T T T C A C C A A G T T A C T G C A C A T G T T A   3911
At. sal. PCR                                                                                  594
At. sal. A26                                                                                  2021

SalmoKCaR 1   G A C C T A T A C A C T G G A A T A A A C A T T T T T T T T C A A A A A A A A -   3949
SalmoKCaR 2   G A C C T A T A C A C T G G A A T A A A C A T T T T T T T T C A A A A A A A A A   4040
SalmoKCaR 3   G A C C T A T A C A C T G G A A T A A A C A T T T T T T T T C A C A A T G C A T   3793
SalmoKCaR 4   G A C C T A T A C A C T G G A A T A A A C A T T T T T T T T C A C A A T G C A T   3951
At. sal. PCR                                                                                  594
At. sal. A26                                                                                  2021

SalmoKCaR 1   - - - - - - - - - - - - - - - - - - - - - - - - - - - - A A - - - - - - - - - - -   3951
SalmoKCaR 2   A - - - - - - - - - - - - - - - - - - - - - - - - - - - - A A - - - - - - - - - -   4043
SalmoKCaR 3   C C A A T G A C A A T A A A A T C A C C A T A T G C C A A T G A A A A A A A A A   3833
SalmoKCaR 4   C C A A T G A C A A T A A A A T C A C C A T A T G C C A A - - - - - - - - - - -   3980
At. sal. PCR                                                                                  594
At. sal. A26                                                                                  2021

SalmoKCaR 1   - A A A A A A A A                                                                 3959
SalmoKCaR 2   - A A A A A A A A                                                                 4051
SalmoKCaR 3   A A A A A A A A A                                                                 3842
SalmoKCaR 4   - T G A A A A A A                                                                 3988
At. sal. PCR                                                                                  594
At. sal. A26                                                                                  2021
```

FIG. 17L

```
SalmoKCaR 1   M R F Y L Y Y L V L L G F S S V I S T Y G P H Q R A Q K T G D I L L G G L F P M  40
SalmoKCaR 2   M R F Y L Y Y L V L L G F S S V I S T Y G P H Q R A Q K T G D I L L G G L F P M  40
SalmoKCaR 3   M R F Y L Y Y L V L L G F S S V I S T Y G P H Q R A Q K T G D I L L G G L F P M  40
SalmoKCaR 4   M R F Y L Y Y L V L L G F S S V I S T Y G P H Q R A Q K T G D I L L G G L F P M  40
At. sal. PCR  - - - - - - - - - - - - - - - - - - - - - - - - - - - - - - - - - - - - - - - -   0
At. sal. A26  - - - - - - - - - - - - - - - - - - - - - - - - - - - - - - - - - - - - - - - -   0

SalmoKCaR 1   H F G V T S K D Q D L A A R P E S T E C V R Y N F R G F R W L Q A M I F A I E E  80
SalmoKCaR 2   H F G V T S K D Q D L A A R P E S T E C V R Y N F R G F R W L Q A M I F A I E E  80
SalmoKCaR 3   H F G V T S K D Q D L A A R P E S T E C V R Y N F R G F R W L Q A M I F A I E E  80
SalmoKCaR 4   H F G V T S K D Q D L A A R P E S T E C V R Y N F R G F R W L Q A M I F A I E E  80
At. sal. PCR  - - - - - - - - - - - - - - - - - - - - - - - - - - - - - - - - - - - - - - - -   0
At. sal. A26  - - - - - - - - - - - - - - - - - - - - - - - - - - - - - - - - - - - - - - - -   0

SalmoKCaR 1   I N N S S T L L P N I T L G Y R I F D T C N T V S K A L E A T L S F V A Q N K I  120
SalmoKCaR 2   I N N S S T L L P N I T L G Y R I F D T C N T V S K A L E A T L S F V A Q N K I  120
SalmoKCaR 3   I N N S S T L L P N I T L G Y R I F D T C N T V S K A L E A T L S F V A Q N K I  120
SalmoKCaR 4   I N N S S T L L P N I T L G Y R I F D T C N T V S K A L E A T L S F V A Q N K I  120
At. sal. PCR  - - - - - - - - - - - - - - - - - - - - - - - - - - - - - - - - - - - - - - - -   0
At. sal. A26  - - - - - - - - - - - - - - - - - - - - - - - - - - - - - - - - - - - - - - - -   0

SalmoKCaR 1   D S L N L D E F C N C T D H I P S T I A V V G A S G S A V S T A V A N L L G L F  160
SalmoKCaR 2   D S L N L D E F C N C T D H I P S T I A V V G A S G S A V S T A V A N L L G L F  160
SalmoKCaR 3   D S L N L D E F C N C T D H I P S T I A V V G A S G S A V S T A V A N L L G L F  160
SalmoKCaR 4   D S L N L D E F C N C T D H I P S T I A V V G A S G S A V S T A V A N L L G L F  160
At. sal. PCR  - - - - - - - - - - - - - - - - - - - - - - - - - - - - - - - - - - - - - - - -   0
At. sal. A26  - - - - - - - - - - - - - - - - - - - - - - - - - - - - - - - - - - - - - - - -   0

SalmoKCaR 1   Y I P Q I S Y A S S S R L L S N K N Q F K S F M R T I P T D E H Q A T A M A D I  200
SalmoKCaR 2   Y I P Q I S Y A S S S R L L S N K N Q F K S F M R T I P T D E H Q A T A M A D I  200
SalmoKCaR 3   Y I P Q I S Y A S S S R L L S N K N Q F K S F M R T I P T D E H Q A T A M A D I  200
SalmoKCaR 4   Y I P Q I S Y A S S S R L L S N K N Q F K S F M R T I P T D E H Q A T A M A D I  200
At. sal. PCR  - - - - - - - - - - - - - - - - - - - - - - - - - - - - - - - - - - - - - - - -   0
At. sal. A26  - - - - - - - - - - - - - - - - - - - - - - - - - - - - - - - - - - - - - - - -   0

SalmoKCaR 1   I D Y F Q W N W V I A V A S D D E Y G R P G I E K F E K E M E E R D I C I H L S  240
SalmoKCaR 2   I D Y F Q W N W V I A V A S D D E Y G R P G I E K F E K E M E E R D I C I H L S  240
SalmoKCaR 3   I D Y F Q W N W V I A V A S D D E Y G R P G I E K F E K E M E E R D I C I H L S  240
SalmoKCaR 4   I D Y F Q W N W V I A V A S D D E Y G R P G I E K F E K E M E E R D I C I H L S  240
At. sal. PCR  - - - - - - - - - - - - - - - - - - - - - - - - - - - - - - - - - - - - - - - -   0
At. sal. A26  - - - - - - - - - - - - - - - - - - - - - - - - - - - - - - - - - - - - - - - -   0

SalmoKCaR 1   E L I S Q Y F E E W Q I Q G L V D R I E N S S A K V I V V F A S G P D I E P L I  280
SalmoKCaR 2   E L I S Q Y F E E W Q I Q G L V D R I E N S S A K V I V V F A S G P D I E P L I  280
SalmoKCaR 3   E L I S Q Y F E E W Q I Q G L V D R I E N S S A K V I V V F A S G P D I E P L I  280
SalmoKCaR 4   E L I S Q Y F E E W Q I Q G L V D R I E N S S A K V I V V F A S G P D I E P L I  280
At. sal. PCR  - - - - - - - - - - - - - - - - - - - - - - - - - - - - - - - - - - - - - - - -   0
At. sal. A26  - - - - - - - - - - - - - - - - - - - - - - - - - - - - - - - - - - - - - - - -   0

SalmoKCaR 1   K E M V R R N I T D R I W L A S E A W A T T S L I A K P E Y L D V V V G T I G F  320
SalmoKCaR 2   K E M V R R N I T D R I W L A S E A W A T T S L I A K P E Y L D V V V G T I G F  320
SalmoKCaR 3   K E M V R R N I T D R I W L A S E A W A T T S L I A K P E Y L D V V V G T I G F  320
SalmoKCaR 4   K E M V R R N I T D R I W L A S E A W A T T S L I A K P E Y L D V V V G T I G F  320
At. sal. PCR  - - - - - - - - - - - - - - - - - - - - - - - - - - - - - - - - - - - - - - - -   0
At. sal. A26  - - - - - - - - - - - - - - - - - - - - - - - - - - - - - - - - - - - - - - - -   0

SalmoKCaR 1   A L R A G E I P G F K D F L Q E V T P K K S S H N E F V R E F W E E T F N C Y L  360
SalmoKCaR 2   A L R A G E I P G F K D F L Q E V T P K K S S H N E F V R E F W E E T F N C Y L  360
SalmoKCaR 3   A L R A G E I P G F K D F L Q E V T P K K S S H N E F V R E F W E E T F N C Y L  360
SalmoKCaR 4   A L R A G E I P G F K D F L Q E V T P K K S S H N E F V R E F W E E T F N C Y L  360
At. sal. PCR  - - - - - - - - - - - - - - - - - - - - - - - - - - - - - - - - - - - - - - - -   0
At. sal. A26  - - - - - - - - - - - - - - - - - - - - - - - - - - - - - - - - - - - - - - - -   0
```

FIG. 18A

```
SalmoKCaR 1  E D S Q R L R D S E N G S T S F R P L C T G E E D I M G A E T P Y L D Y T H L R  400
SalmoKCaR 2  E D S Q R L R D S E N G S T S F R P L C T G E E D I M G A E T P Y L D Y T H L R  400
SalmoKCaR 3  E D S Q R L R D S E N G S T S F R P L C T G E E D I M G A E T P Y L D Y T H L R  400
SalmoKCaR 4  E D S Q R L R D S E N G S T S F R P L C T G E E D I M G A E T P Y L D Y T H L R  400
At. sal. PCR - - - - - - - - - - - - - - - - - - - - - - - - - - - - - - - - - - - - - - - -  0
At. sal. A26 - - - - - - - - - - - - - - - - - - - - - - - - - - - - - - - - - - - - - - - -  0

SalmoKCaR 1  I S Y N V Y V A V H S I A Q A L Q D I L T C I P G R G L F S N N S C A D I K K I  440
SalmoKCaR 2  I S Y N V Y V A V H S I A Q A L Q D I L T C I P G R G L F S N N S C A D I K K I  440
SalmoKCaR 3  I S Y N V Y V A V H S I A Q A L Q D I L T C I P G R G F F S N N S C A D I K K I  440
SalmoKCaR 4  I S Y N V Y V A V H S I A Q A L Q D I L T C I P G R G L F S N N S C A D I K K I  440
At. sal. PCR - - - - - - - - - - - - - - - - - - - - - - - - - - - - - - - - - - - - - - - -  0
At. sal. A26 - - - - - - - - - - - - - - - - - - - - - - - - - - - - - - - - - - - - - - - -  0

SalmoKCaR 1  E A W Q V L K Q L R H L N F S N S M G E K V H F D E N A D P S G N Y T I I N W H  480
SalmoKCaR 2  E A W Q V L K Q L R H L N F S N S M G E K V H F D E N A D P S G N Y T I I N W H  480
SalmoKCaR 3  E A W Q V L K Q L R H L N F S N S M G E K V H F D E N A D P S G N Y T I I N W H  480
SalmoKCaR 4  E A W Q V L K Q L R H L N F S N S M G E K V H F D E N A D P S G N Y T I I N W H  480
At. sal. PCR - - - - - - - - - - - - - - - - - - - - - - - - - - - - - - - - - - - - - - - -  0
At. sal. A26 - - - - - - - - - - - - - - - - - - - - - - - - - - - - - - - - - - - - - - - -  0

SalmoKCaR 1  R S P E D G S V V F E E V G F Y N M R A K R G V Q L F I D N T K I L W N G Y N T  520
SalmoKCaR 2  R S P E D G S V V F E E V G F Y N M R A K R G V Q L F I D N T K I L W N G Y N T  520
SalmoKCaR 3  R S P E D G S V V F E E V G F Y N M R A K R G V Q L F I D N T K I L W N G Y N T  520
SalmoKCaR 4  R S P E D G S V V F E E V G F Y N M R A K R G V Q L F I D N T K I L W N G Y N T  520
At. sal. PCR - - - - - - - - - - - - - - - - - - - - - - - - - - - - - - - - - - - - - - - -  0
At. sal. A26 - - - - - - - - - - - - - - - - - - - - - - - - - - - - - - - - - - - - - - - -  0

SalmoKCaR 1  E V P F S N C S E D C E P G T R K G I I E S M P T C C F E C T E C S E G E Y S D  560
SalmoKCaR 2  E V P F S N C S E D C E P G T R K G I I E S M P T C C F E C T E C S E G E Y S D  560
SalmoKCaR 3  E V P F S N C S E D C E P G T R K G I I E S M P T C C F E C T E C S E G E Y S D  560
SalmoKCaR 4  E V P F S N C S E D C E P G T R K G I I E S M P T C C F E C T E C S E G E Y S D  560
At. sal. PCR - - - - - - - - - - - - - - - - - - - - - - - - - - - - - - - - - - - - - - - -  0
At. sal. A26 - - - - - - - - - - - - - - - - - - - - - - - - - - - - - - - Y K H Y F S I     7

SalmoKCaR 1  H K D A S V C T K C P N D S W S N E N H T S C F L K E I E F L S W T E P F G I A  600
SalmoKCaR 2  H K D A S V C T K C P N D S W S N E N H T S C F L K E I E F L S W T E P F G I A  600
SalmoKCaR 3  H K D A S V C T K C P N D S W S N E N H T S C F L K E I E F L S W T E P F G I A  600
SalmoKCaR 4  H K D A S V C T K C P N D S W S N E N H T S C F L K E I E F L S W T E P F G I A  600
At. sal. PCR - - - - - - - - - - - - - - - - - - - - - - - - - - - - - - - - - - - - - - - -  0
At. sal. A26 P A D A S V C T K C P N D S W S N E N H T S C F L K E I E F L S W T E P F G I A  47

SalmoKCaR 1  L A L C S V L G V F L T A F V M G V F I K F R N T P I V K A T N R E L S Y L L L  640
SalmoKCaR 2  L A L C S V L G V F L T A F V M G V F I K F R N T P I V K A T N R E L S Y L L L  640
SalmoKCaR 3  L A L C S V L G V F L T A F V M G V F I K F R N T P I V K A T N R E L S Y L L L  640
SalmoKCaR 4  L A L C S V L G V F L T A F V M G V F I K F R N T P I V K A T N R E L S Y L L L  640
At. sal. PCR L A L C S V L G V F L T A F V M G V F I K F R N T P I V K A T N R E L S Y L L L  40
At. sal. A26 L A L C S V L G V F L T A F V M G V F I K F R N T P I V K A T N R E L S Y L L L  87

SalmoKCaR 1  F S L I C C F S S S L I F I G E P Q D W T C R L R Q P A F G I S F V L C I S C I  680
SalmoKCaR 2  F S L I C C F S S S L I F I G E P Q D W T C R L R Q P A F G I S F V L C I S C I  680
SalmoKCaR 3  F S L I C C F S S S L I F I G E P Q D W T C R L R Q P A F G I S F V L C I S C I  680
SalmoKCaR 4  F S L I C C F S S S L I F I G E P Q D W T C R L R Q P A F G I S F V L C I S C I  680
At. sal. PCR F S L I C C F S S S L I F I G E P Q D W T C R L R Q P A F G I S F V L C I S C I  80
At. sal. A26 F S L I C C F S S S L I F I G E P Q D W T C R L R Q P A F G I S F V L C I S C I  127

SalmoKCaR 1  L V K T N R V L L V F E A K I P T S L H R K W W G L N L Q F L L V F L F T F V Q  720
SalmoKCaR 2  L V K T N R V L L V F E A K I P T S L H R K W W G L N L Q F L L V F L F T F V Q  720
SalmoKCaR 3  L V K T N R V L L V F E A K I P T S L H R K W W G L N L Q F L L V F L F T F V Q  720
SalmoKCaR 4  L V K T N R V L L V F E A K I P T S L H R K W W G L N L Q F L L V F L F T F V Q  720
At. sal. PCR L V K T N R V L L V F E A K I P T S L H R K W W G L N L Q F L L V F L F T F V Q  120
At. sal. A26 L V K T N R V L L V F E A K I P T S L H R K W W G L N L Q F L L V F L F T F V Q  167
```

FIG. 18B

```
SalmoKCaR 1   V M I C V V W L Y N A P P A S Y R N H D I D E I I F I T C N E G S M M A L G F L  760
SalmoKCaR 2   V M I C V V W L Y N A P P A S Y R N H D I D E I I F I T C N E G S M M A L G F L  760
SalmoKCaR 3   V M I C V V W L Y N A P P A S Y R N H D I D E I I F I T C N E G S M M A L G F L  760
SalmoKCaR 4   V M I C V V W L Y N A P P A S Y R N H D I D E I I F I T C N E G S M M A L G F L  760
At. sal. PCR  V M I C V V W L Y N A P P A S Y R N H D I D E I I F I T C N E G S M M A L G F L  160
At. sal. A26  V M I C V V W L Y N A P P A S Y R N H D I D E I I F I T C N E G S M M A L G F L  207

SalmoKCaR 1   I G Y T C L L A A I C F F F A F K S R K L P E N F T E A K F I T F S M L I F F I  800
SalmoKCaR 2   I G Y T C L L A A I C F F F A F K S R K L P E N F T E A K F I T F S M L I F F I  800
SalmoKCaR 3   I G Y T C L L A A I C F F F A F K S R K L P E N F T E A K F I T F S M L I F F I  800
SalmoKCaR 4   I G Y T C L L A A I C F F F A F K S R K L P E N F T E A K F I T F S M L I F F I  800
At. sal. PCR  I G Y T C L L A A I X F F F A F K S R K L P E N F T E A K F I T F S M L I          197
At. sal. A26  I G Y T C L L A A I C F F F A F K S R K L P E N F T E A K F I T F S M L I F F I  247

SalmoKCaR 1   V W I S F I P A Y F S T Y G K F V S A V E V I A I L A S S F G L L A C I F F N K  840
SalmoKCaR 2   V W I S F I P A Y F S T Y G K F V S A V E V I A I L A S S F G L L A C I F F N K  840
SalmoKCaR 3   V W I S F I P A Y F S T Y G K F V S A V E V I A I L A S S F G L L A C I F F N K  840
SalmoKCaR 4   V W I S F I P A Y F S T Y G K F V S A V E V I A I L A S S F G L L A C I F F N K  840
At. sal. PCR                                                                                  197
At. sal. A26  V W I S F I P A Y F S T Y G K F V S A V E V I A I L A S S F G L L A C I F F N K  287

SalmoKCaR 1   V Y I I L F K P S R N T I E E V R C S T A A H S F K V A A K A T L R H S S A S R  880
SalmoKCaR 2   V Y I I L F K P S R N T I E E V R C S T A A H S F K V A A K A T L R H S S A S R  880
SalmoKCaR 3   V Y I I - - - - - - - - - - - - - - - - - - - - - - - - - - - - - - - - - - - -  844
SalmoKCaR 4   V Y I I L F K P S R N T I E E V R C S T A A H S F K V A A K A T L R H S S A S R  880
At. sal. PCR                                                                                  197
At. sal. A26  V Y I I L F K P S R N T I E E V R C S T A A H S F K V A A K A T L R H S S A S R  327

SalmoKCaR 1   K R S S S V G G S C A S T P S S S I S L K T N D N D S P S G Q Q R I H K P R V S  920
SalmoKCaR 2   K R S S S V G G S C A S T P S S S I S L K T N D N D S P S G Q Q R I H K P R V S  920
SalmoKCaR 3   - - - - - - - - - - - - - - - - - - - - - - - - - - - - - - - - - - - - - - - -  844
SalmoKCaR 4   K R S S S V G G S C A S T P S S S I S L K T N D N D S P S G Q Q R I H K P R V S  920
At. sal. PCR                                                                                  197
At. sal. A26  K R S S S V G G S C A S T P S S S I S L K T N D N D S P S G Q Q R I H K P R V S  367

SalmoKCaR 1   F G S G T V T L S L S F E E S R K N S M K                                        941
SalmoKCaR 2   F G S G T V T L S L S F E E S R K N S M K                                        941
SalmoKCaR 3   - - - - - - - - - - - - - - H Q P Q D Q                                         850
SalmoKCaR 4   F G S G T V T L S L S F E E S R K N S M K                                        941
At. sal. PCR                                                                                  197
At. sal. A26  F G S G T V T L S L S F E E S R K N S M K                                        388
```

FIG. 18C

```
HuPCaR       M A F Y S C C W V L L A L T W H - - - - T S A Y S P S Q P A Q K K G D I I L G G  36
SKCaR        M A Q L H C Q L L F L G F T L L Q S Y N V S G Y G P N Q R A Q K K G D I I L G G  40
SalmoKCaR 1  M R F Y L Y Y L V L L G F S S V - - - - I S T Y G P H Q R A Q K T G D I L L G G  36
SalmoKCaR 2  M R F Y L Y Y L V L L G F S S V - - - - I S T Y G P H Q R A Q K T G D I L L G G  36
SalmoKCaR 3  M R F Y L Y Y L V L L G F S S V - - - - I S T Y G P H Q R A Q K T G D I L L G G  36
SalmoKCaR 4  M R F Y L Y Y L V L L G F S S V - - - - I S T Y G P H Q R A Q K T G D I L L G G  36

HuPCaR       L F P I H F G V A A K D Q D L K S R P E S V E C I R Y N F R G F R W L Q A M I F  76
SKCaR        L F P I H F G V A A K D Q D L K S R P E A T K C I R Y N F R G F R W L Q A M I F  80
SalmoKCaR 1  L F P M H F G V T S K D Q D L A A R P E S T E C V R Y N F R G F R W L Q A M I F  76
SalmoKCaR 2  L F P M H F G V T S K D Q D L A A R P E S T E C V R Y N F R G F R W L Q A M I F  76
SalmoKCaR 3  L F P M H F G V T S K D Q D L A A R P E S T E C V R Y N F R G F R W L Q A M I F  76
SalmoKCaR 4  L F P M H F G V T S K D Q D L A A R P E S T E C V R Y N F R G F R W L Q A M I F  76

HuPCaR       A I E E I N S S P A L L P N L T L G Y R I F D T C N T V S K A L E A T L S F V A  116
SKCaR        A I E E I N N S M T F L P N I T L G Y R I F D T C N T V S K A L E A T L S F V A  120
SalmoKCaR 1  A I E E I N N S S T L L P N I T L G Y R I F D T C N T V S K A L E A T L S F V A  116
SalmoKCaR 2  A I E E I N N S S T L L P N I T L G Y R I F D T C N T V S K A L E A T L S F V A  116
SalmoKCaR 3  A I E E I N N S S T L L P N I T L G Y R I F D T C N T V S K A L E A T L S F V A  116
SalmoKCaR 4  A I E E I N N S S T L L P N I T L G Y R I F D T C N T V S K A L E A T L S F V A  116

HuPCaR       Q N K I D S L N L D E F C N C S E H I P S T I A V V G A T G S G V S T A V A N L  156
SKCaR        Q N K I D S L N L D E F C N C S D H I P S T I A V V G A T G S G I S T A V A N L  160
SalmoKCaR 1  Q N K I D S L N L D E F C N C T D H I P S T I A V V G A S G S A V S T A V A N L  156
SalmoKCaR 2  Q N K I D S L N L D E F C N C T D H I P S T I A V V G A S G S A V S T A V A N L  156
SalmoKCaR 3  Q N K I D S L N L D E F C N C T D H I P S T I A V V G A S G S A V S T A V A N L  156
SalmoKCaR 4  Q N K I D S L N L D E F C N C T D H I P S T I A V V G A S G S A V S T A V A N L  156

HuPCaR       L G L F Y I P Q V S Y A S S S R L L S N K N Q F K S F L R T I P N D E H C A T A  196
SKCaR        L G L F Y I P Q V S Y A S S S R L L S N K N E Y K A F L R T I P N D E Q Q A T A  200
SalmoKCaR 1  L G L F Y I P Q I S Y A S S S R L L S N K N Q F K S F M R T I P T D E H Q A T A  196
SalmoKCaR 2  L G L F Y I P Q I S Y A S S S R L L S N K N Q F K S F M R T I P T D E H Q A T A  196
SalmoKCaR 3  L G L F Y I P Q I S Y A S S S R L L S N K N Q F K S F M R T I P T D E H Q A T A  196
SalmoKCaR 4  L G L F Y I P Q I S Y A S S S R L L S N K N Q F K S F M R T I P T D E H Q A T A  196

HuPCaR       M A D I I E Y F R W N W V G T I A A D D D Y G R P G I E K F R E E A E E R D I C  236
SKCaR        M A E I I E H F Q W N W V G T L A A D D D Y G R P G I D K F R E E A V K R D I C  240
SalmoKCaR 1  M A D I I D Y F Q W N W V I A V A S D D E Y G R P G I E K F E K E M E E R D I C  236
SalmoKCaR 2  M A D I I D Y F Q W N W V I A V A S D D E Y G R P G I E K F E K E M E E R D I C  236
SalmoKCaR 3  M A D I I D Y F Q W N W V I A V A S D D E Y G R P G I E K F E K E M E E R D I C  236
SalmoKCaR 4  M A D I I D Y F Q W N W V I A V A S D D E Y G R P G I E K F E K E M E E R D I C  236

HuPCaR       I D F S E L I S Q Y S D E E E I Q M V V E V I Q N S T A K V I V V F S S G P D L  276
SKCaR        I D F S E M I S Q Y Y T Q K L E F I A D V I Q N S S A K V I V V F S N G P D L  280
SalmoKCaR 1  I H L S E L I S Q Y F E E W Q I Q G L V D R I E N S S A K V I V V F A S G P D I  276
SalmoKCaR 2  I H L S E L I S Q Y F E E W Q I Q G L V D R I E N S S A K V I V V F A S G P D I  276
SalmoKCaR 3  I H L S E L I S Q Y F E E W Q I Q G L V D R I E N S S A K V I V V F A S G P D I  276
SalmoKCaR 4  I H L S E L I S Q Y F E E W Q I Q G L V D R I E N S S A K V I V V F A S G P D I  276

HuPCaR       E P L I K E I V P R N I T G K I W L A S E A W A S S S L I A M P Q Y F H V V G G  316
SKCaR        E P L I Q E I V R R N I T D R I W L A S E A W A S S S L I A K P E Y F H V V G G  320
SalmoKCaR 1  E P L I K E M V R R N I T D R I W L A S E A W A T T S L I A K P E Y L D V V V G  316
SalmoKCaR 2  E P L I K E M V R R N I T D R I W L A S E A W A T T S L I A K P E Y L D V V V G  316
SalmoKCaR 3  E P L I K E M V R R N I T D R I W L A S E A W A T T S L I A K P E Y L D V V V G  316
SalmoKCaR 4  E P L I K E M V R R N I T D R I W L A S E A W A T T S L I A K P E Y L D V V V G  316
```

FIG. 19A

```
HuPCaR      T I G F A L K A G Q I P G F R E F L K K V H P P K S V N N G F A K E F W E E T F  356
SKCaR       T I G F A L R A G R I P G F N K F L K E V H P S R S S D N G F V K E F W E E T F  360
SalmoKCaR 1 T I G F A L R A G E I P G F K D F L Q E V T P K K S S H N E F V R E F W E E T F  356
SalmoKCaR 2 T I G F A L R A G E I P G F K D F L Q E V T P K K S S H N E F V R E F W E E T F  356
SalmoKCaR 3 T I G F A L R A G E I P G F K D F L Q E V T P K K S S H N E F V R E F W E E T F  356
SalmoKCaR 4 T I G F A L R A G E I P G F K D F L Q E V T P K K S S H N E F V R E F W E E T F  356

HuPCaR      M C H L Q E G A - - - - K G P L P V D T F L A G H E E S G D R F S N S S T A F P  392
SKCaR       N C Y F T E K T L T Q L K N S K V P S H G P A A Q G D G S K A G N S R R T A L R  400
SalmoKCaR 1 N C Y L E D S Q - - - - R L R D S - - - - - - - - - - - - - - - E N G S T S F R  377
SalmoKCaR 2 N C Y L E D S Q - - - - R L R D S - - - - - - - - - - - - - - - E N G S T S F R  377
SalmoKCaR 3 N C Y L E D S Q - - - - R L R D S - - - - - - - - - - - - - - - E N G S T S F R  377
SalmoKCaR 4 N C Y L E D S Q - - - - R L R D S - - - - - - - - - - - - - - - E N G S T S F R  377

HuPCaR      P L C T G D E N I S S V E T P Y I D Y T N L R I S Y N V Y L A V Y S I A N A L Q  432
SKCaR       H P C T G E E N I T S V E T P Y L D Y T H L R I S Y N V Y V A V Y S I A H A L Q  440
SalmoKCaR 1 P L C T G E E D I M G A E T P Y L D Y T H L R I S Y N V Y V A V H S I A Q A L Q  417
SalmoKCaR 2 P L C T G E E D I M G A E T P Y L D Y T H L R I S Y N V Y V A V H S I A Q A L Q  417
SalmoKCaR 3 P L C T G E E D I M G A E T P Y L D Y T H L R I S Y N V Y V A V H S I A Q A L Q  417
SalmoKCaR 4 P L C T G E E D I M G A E T P Y L D Y T H L R I S Y N V Y V A V H S I A Q A L Q  417

HuPCaR      D I Y T C L P G R G L F T N G S C A D I K K V E A W Q V L K H L R N L N F T N N  472
SKCaR       D I H S C K P G T G I F A N G S C A D I K K V E A W Q V L N H L L H L K F T N S  480
SalmoKCaR 1 D I L T C I P G R G L F S N N S C A D I K K I E A W Q V L K Q L R H L N F S N S  457
SalmoKCaR 2 D I L T C I P G R G L F S N N S C A D I K K I E A W Q V L K Q L R H L N F S N S  457
SalmoKCaR 3 D I L T C I P G R G F F S N N S C A D I K K I E A W Q V L K Q L R H L N F S N S  457
SalmoKCaR 4 D I L T C I P G R G L F S N N S C A D I K K I E A W Q V L K Q L R H L N F S N S  457

HuPCaR      M G E Q V T F D E C G D L V G N Y S I I N W H L S P E D G S I V F K E V G Y Y N  512
SKCaR       M G E Q V D F D D Q G D L K G N Y T I I N W Q L S A E D E S V L F H E V G N Y N  520
SalmoKCaR 1 M G E K V H F D E N A D P S G N Y T I I N W H R S P E D G S V V F E E V G F Y N  497
SalmoKCaR 2 M G E K V H F D E N A D P S G N Y T I I N W H R S P E D G S V V F E E V G F Y N  497
SalmoKCaR 3 M G E K V H F D E N A D P S G N Y T I I N W H R S P E D G S V V F E E V G F Y N  497
SalmoKCaR 4 M G E K V H F D E N A D P S G N Y T I I N W H R S P E D G S V V F E E V G F Y N  497

HuPCaR      V Y A K K G E R L F I N E E K I L W S G F S R E V P F S N C S R D C L A G T R K  552
SKCaR       A Y A K P S D R L N I N E K K I L W S G F S K V V P F S N C S R D C V P G T R K  560
SalmoKCaR 1 M R A K R G V Q L F I D N T K I L W N G Y N T E V P F S N C S E D C E P G T R K  537
SalmoKCaR 2 M R A K R G V Q L F I D N T K I L W N G Y N T E V P F S N C S E D C E P G T R K  537
SalmoKCaR 3 M R A K R G V Q L F I D N T K I L W N G Y N T E V P F S N C S E D C E P G T R K  537
SalmoKCaR 4 M R A K R G V Q L F I D N T K I L W N G Y N T E V P F S N C S E D C E P G T R K  537

HuPCaR      G I I E G E P T C C F E C V E C P D G E Y S D E T D A S A C N K C P D D F W S N  592
SKCaR       G I I E G E P T C C F E C M A C A E G E F S D E N D A S A C T K C P N D F W S N  600
SalmoKCaR 1 G I I E S M P T C C F E C T E C S E G E Y S D H K D A S V C T K C P N D S W S N  577
SalmoKCaR 2 G I I E S M P T C C F E C T E C S E G E Y S D H K D A S V C T K C P N D S W S N  577
SalmoKCaR 3 G I I E S M P T C C F E C T E C S E G E Y S D H K D A S V C T K C P N D S W S N  577
SalmoKCaR 4 G I I E S M P T C C F E C T E C S E G E Y S D H K D A S V C T K C P N D S W S N  577

HuPCaR      E N H T S C I A K E I E F L S W T E P F G I A L T L F A V L G I S L T A F V L G  632
SKCaR       E N H T S C I A K E I E Y L S W T E P F G I A L T I F A V L G I L I T S F V L G  640
SalmoKCaR 1 E N H T S C F L K E I E F L S W T E P F G I A L A L C S V L G V F L T A F V M G  617
SalmoKCaR 2 E N H T S C F L K E I E F L S W T E P F G I A L A L C S V L G V F L T A F V M G  617
SalmoKCaR 3 E N H T S C F L K E I E F L S W T E P F G I A L A L C S V L G V F L T A F V M G  617
SalmoKCaR 4 E N H T S C F L K E I E F L S W T E P F G I A L A L C S V L G V F L T A F V M G  617
```

FIG. 19B

```
HuPCaR       V F I K F R N T P I V K A T N R E L S Y L L L F S L L C C F S S S L F F I G E P  672
SKCaR        V F I K F R N T P I V K A T N R E L S Y L L L F S L I C C F S S S L I F I G E P  680
SalmoKCaR 1  V F I K F R N T P I V K A T N R E L S Y L L L F S L I C C F S S S L I F I G E P  657
SalmoKCaR 2  V F I K F R N T P I V K A T N R E L S Y L L L F S L I C C F S S S L I F I G E P  657
SalmoKCaR 3  V F I K F R N T P I V K A T N R E L S Y L L L F S L I C C F S S S L I F I G E P  657
SalmoKCaR 4  V F I K F R N T P I V K A T N R E L S Y L L L F S L I C C F S S S L I F I G E P  657

HuPCaR       Q D W T C R L R Q P A F G I S F V L C I S C I L V K T N R V L L V F E A K I P T  712
SKCaR        R D W T C R L R Q P A F G I S F V L C I S C I L V K T N R V L L V F E A K I P T  720
SalmoKCaR 1  Q D W T C R L R Q P A F G I S F V L C I S C I L V K T N R V L L V F E A K I P T  697
SalmoKCaR 2  Q D W T C R L R Q P A F G I S F V L C I S C I L V K T N R V L L V F E A K I P T  697
SalmoKCaR 3  Q D W T C R L R Q P A F G I S F V L C I S C I L V K T N R V L L V F E A K I P T  697
SalmoKCaR 4  Q D W T C R L R Q P A F G I S F V L C I S C I L V K T N R V L L V F E A K I P T  697

HuPCaR       S F M F K W W G L N L Q F L L V F L C T F N Q I V I C V I W L Y T A P P S S Y R  752
SKCaR        S L H R K W V G L N L Q F L L V F L C I L V Q I V T C I I W L Y T A P P S S Y R  760
SalmoKCaR 1  S L H R K W W G L N L Q F L L V F L F T F V Q V M I C V V W L Y N A P P A S Y R  737
SalmoKCaR 2  S L H R K W W G L N L Q F L L V F L F T F V Q V M I C V V W L Y N A P P A S Y R  737
SalmoKCaR 3  S L H R K W W G L N L Q F L L V F L F T F V Q V M I C V V W L Y N A P P A S Y R  737
SalmoKCaR 4  S L H R K W W G L N L Q F L L V F L F T F V Q V M I C V V W L Y N A P P A S Y R  737

HuPCaR       N Q E L E D E I I F I T C N E G S L M A L G F L I G Y T C L L A A I C F F F A F  792
SKCaR        N H E L E D E V I F I T C D E G S L M A L G F L I G Y T C L L A A I C F F F A F  800
SalmoKCaR 1  N H D I - D E I I F I T C N E G S M M A L G F L I G Y T C L L A A I C F F F A F  776
SalmoKCaR 2  N H D I - D E I I F I T C N E G S M M A L G F L I G Y T C L L A A I C F F F A F  776
SalmoKCaR 3  N H D I - D E I I F I T C N E G S M M A L G F L I G Y T C L L A A I C F F F A F  776
SalmoKCaR 4  N H D I - D E I I F I T C N E G S M M A L G F L I G Y T C L L A A I C F F F A F  776

HuPCaR       K S R K L P E N F N E A K F I T F S M L I F F I V W I S F I P A Y A S T Y G K F  832
SKCaR        K S R K L P E N F N E A K F I T F S M L I F F I V W I S F I P A Y V S T Y G K F  840
SalmoKCaR 1  K S R K L P E N F T E A K F I T F S M L I F F I V W I S F I P A Y F S T Y G K F  816
SalmoKCaR 2  K S R K L P E N F T E A K F I T F S M L I F F I V W I S F I P A Y F S T Y G K F  816
SalmoKCaR 3  K S R K L P E N F T E A K F I T F S M L I F F I V W I S F I P A Y F S T Y G K F  816
SalmoKCaR 4  K S R K L P E N F T E A K F I T F S M L I F F I V W I S F I P A Y F S T Y G K F  816

HuPCaR       V S A V E V I A I L A A S F G L L A C I F F N K I Y I I L F K P S R N T I E E V  872
SKCaR        V S A V E V I A I L A S S F G L L G C I Y F N K C Y I I L F K P C R N T I E E V  880
SalmoKCaR 1  V S A V E V I A I L A S S F G L L A C I F F N K V Y I I L F K P S R N T I E E V  856
SalmoKCaR 2  V S A V E V I A I L A S S F G L L A C I F F N K V Y I I L F K P S R N T I E E V  856
SalmoKCaR 3  V S A V E V I A I L A S S F G L L A C I F F N K V Y I I - - - - - - - - - - - -  844
SalmoKCaR 4  V S A V E V I A I L A S S F G L L A C I F F N K V Y I I L F K P S R N T I E E V  856

HuPCaR       R C S T A A N A F K V A A R A T L R R S N V S R K R S S S L G G S T G S T P S S  912
SKCaR        R C S T A A H A F K V A A R A T L R R S A A S R K R S S S L C G S T I S S P A S  920
SalmoKCaR 1  R C S T A A H S F K V A A K A T L R H S S A S R K R S S S V G G S C A S T P S S  896
SalmoKCaR 2  R C S T A A H S F K V A A K A T L R H S S A S R K R S S S V G G S C A S T P S S  896
SalmoKCaR 3  - - - - - - - - - - - - - - - - - - - - - - - - - - - - - - - - - - - - - - - -  844
SalmoKCaR 4  R C S T A A H S F K V A A K A T L R H S S A S R K R S S S V G G S C A S T P S S  896

HuPCaR       S I S S K S N S E D P F P R P E R Q K Q Q Q P L A L T Q Q E Q Q Q Q P L T L P Q  952
SKCaR        S T C G P G L T M E - - - - - - - - - - - - - - - - - - - - - - - - - - - - - -  930
SalmoKCaR 1  S I S L K T N D N D S P S G Q Q R I H K P R - - - - - - - - - - - - - - - - - -  918
SalmoKCaR 2  S I S L K T N D N D S P S G Q Q R I H K P R - - - - - - - - - - - - - - - - - -  918
SalmoKCaR 3  - - - - - - - - - - - - - - - - - - - - - - - - - - - - - - - - - - - - - - - -  844
SalmoKCaR 4  S I S L K T N D N D S P S G Q Q R I H K P R - - - - - - - - - - - - - - - - - -  918
```

FIG. 19C

```
HuPCaR      Q Q R S Q Q Q P R C K Q K V I F G S G T V T F S L S F D E P Q K N A M A N R N S  992
SKCaR       - - - - - M Q R C S T Q K V S F G S G T V T L S L S F E E T G R Y A T L S R T A  965
SalmoKCaR 1 - - - - - - - - - - - - - - - - - - - - - - - - - - - - - - - - - - - - - - -  918
SalmoKCaR 2 - - - - - - - - - - - - - - - - - - - - - - - - - - - - - - - - - - - - - - -  918
SalmoKCaR 3 - - - - - - - - - - - - - - - - - - - - - - - - - - - - - - - - - - - - - - -  844
SalmoKCaR 4 - - - - - - - - - - - - - - - - - - - - - - - - - - - - - - - - - - - - - - -  918

HuPCaR      T N Q N S L E A Q K S S D T L T A N Q P L L P L Q C G E T D L D L T V Q E T G L  1032
SKCaR       R S R N S A D G R S G D D L P S R H H D Q G P P Q K C E P Q - - - - - - - - - -  995
SalmoKCaR 1 - - - - - - - - - - - - - - - - - - - - - - - - - - - - - - - - - - - - - - -  918
SalmoKCaR 2 - - - - - - - - - - - - - - - - - - - - - - - - - - - - - - - - - - - - - - -  918
SalmoKCaR 3 - - - - - - - - - - - - - - - - - - - - - - - - - - - - - - - - - - - - - - -  844
SalmoKCaR 4 - - - - - - - - - - - - - - - - - - - - - - - - - - - - - - - - - - - - - - -  918

HuPCaR      Q G P V G G D Q R P E V E D P E E L S P A L V V S S S Q S F V I S G G G S T V T  1072
SKCaR       - - - - - - - - - - - - - P A N D A R Y K A A P T K G T L E S P G G S K E R P  1021
SalmoKCaR 1 - - - - - - - - - - - - - - - - - - - - - - V S F G S G T V T L S L S F E E S  935
SalmoKCaR 2 - - - - - - - - - - - - - - - - - - - - - - V S F G S G T V T L S L S F E E S  935
SalmoKCaR 3 - - - - - - - - - - - - - - - - - - - - - - - - - - - - - - - - - - - - - - -  844
SalmoKCaR 4 - - - - - - - - - - - - - - - - - - - - - - V S F G S G T V T L S L S F E E S  935

HuPCaR      E N V V N S                                                                     1078
SKCaR       T T M E E T                                                                     1027
SalmoKCaR 1 R K N S M K                                                                     941
SalmoKCaR 2 R K N S M K                                                                     941
SalmoKCaR 3 H Q P Q D Q                                                                     850
SalmoKCaR 4 R K N S M K                                                                     941
```

FIG. 19D

Saltwater

Deg. Primers – Ethidium Bromide

Freshwater

Deg. Primers – Ethidium Bromide

Saltwater

Deg. Primers – Southern

Freshwater

Deg. Primers – Southern

 
FIG. 20E
Saltwater
1 2 3 4 5 6 7 8 9 10 11 12 13 14
Actin Primers – Ethidium Bromide
FIG. 20F
Freshwater
1 2 3 4 5 6 7 8 9 10 11 12 13 14
Actin Primers – Ethidium Bromide

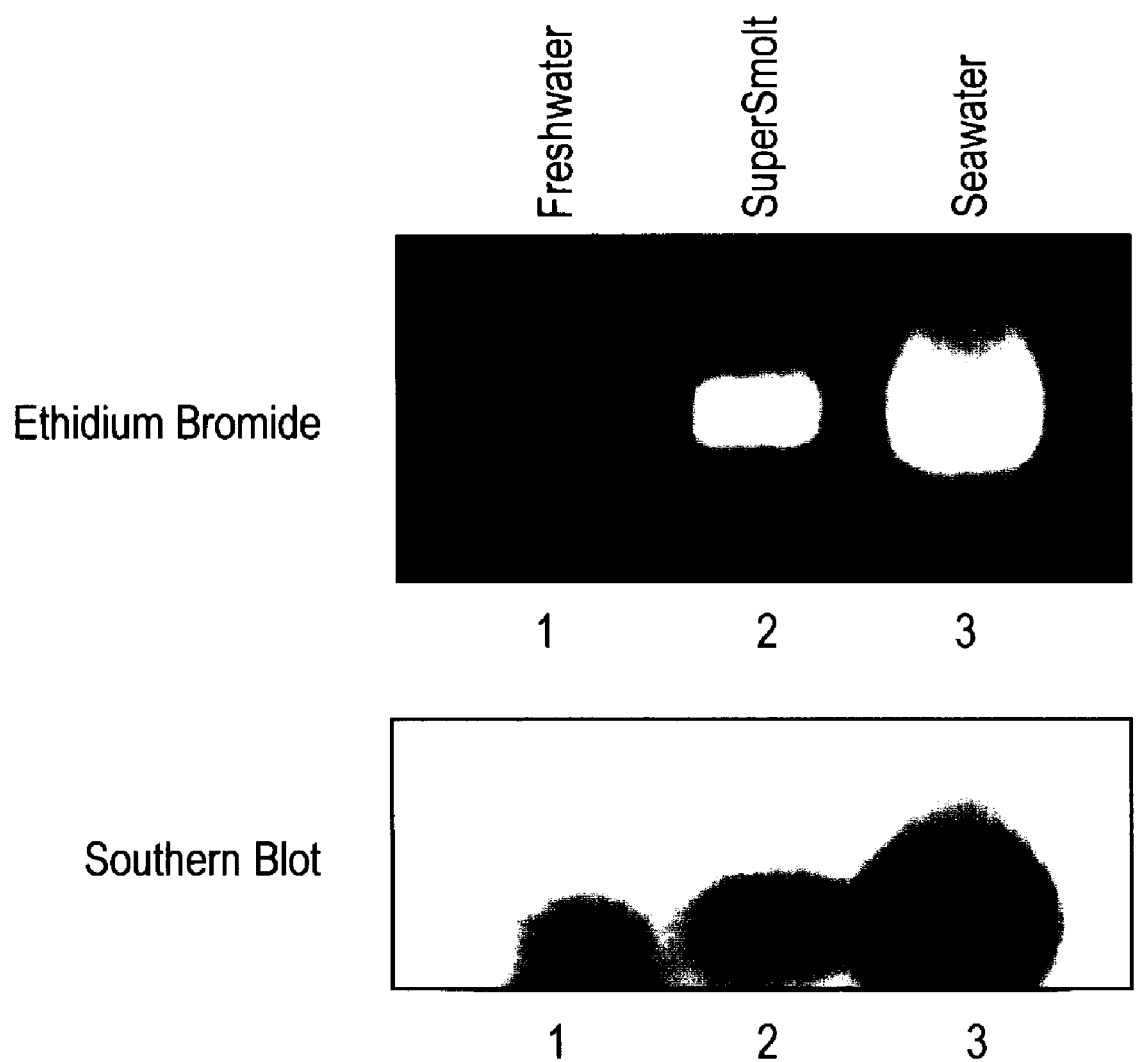

FIG. 21B
Panel A
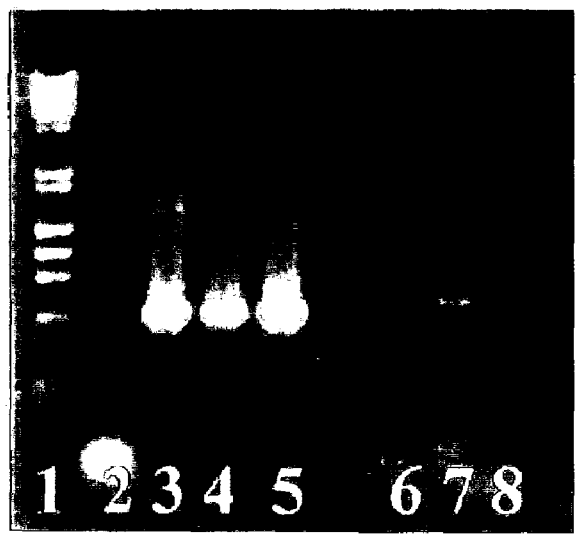
Panel B
Panel C
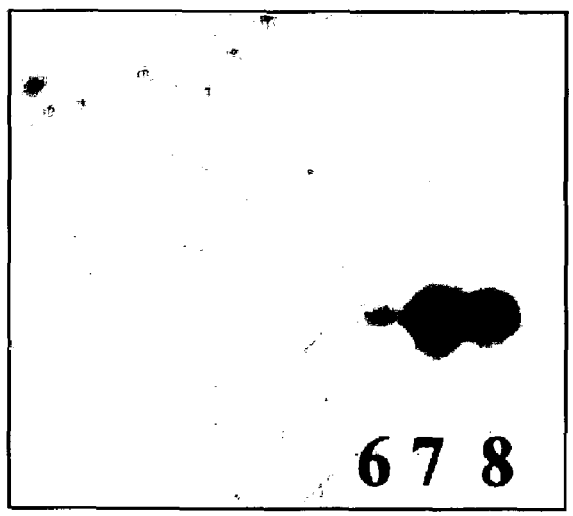

FIG. 21C
Panel A
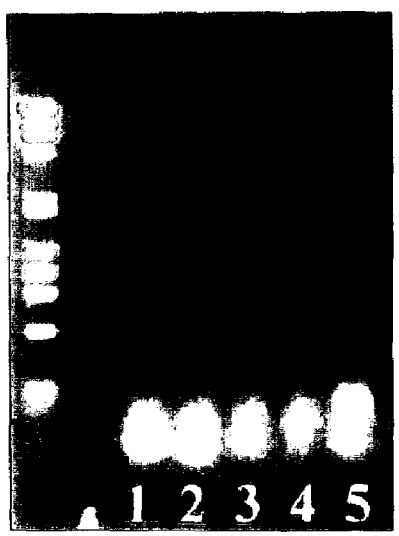
1 2 3 4 5
Panel C
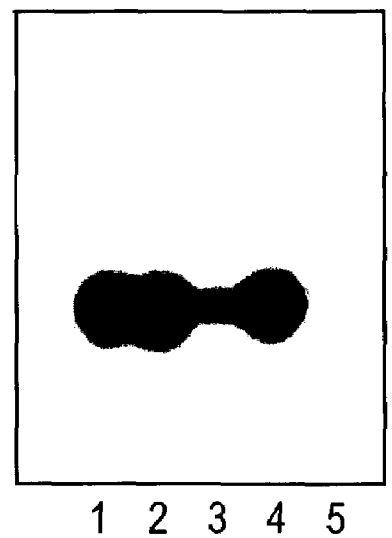
1 2 3 4 5
Panel B
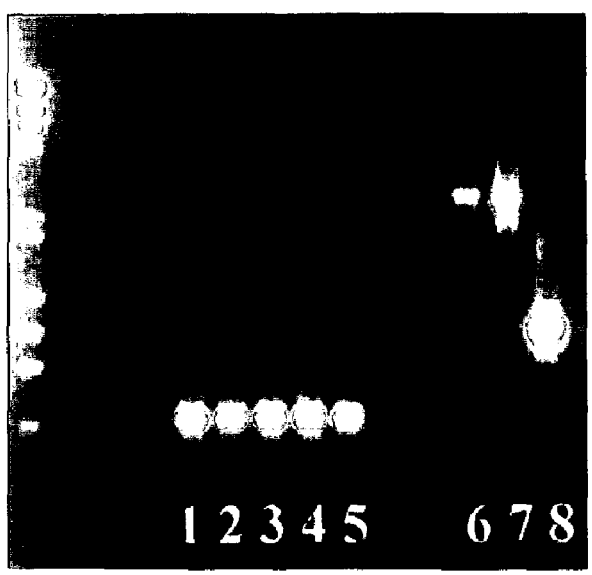
1 2 3 4 5   6 7 8

Kidney Poly A+ RNA Probed with full length SalmoKCaR #1.

← 4.2 kb

FW    SW

Saltwater 1 2 3 4 5 6 7 8 9 10 11 12 13 14

SalmoKCaR #3 Primers - Ethidium Bromide

Freshwater 1 2 3 4 5 6 7 8 9 10 11 12 13 14

SalmoKCaR #3 Primers - Ethidium Bromide

Saltwater 1 2 3 4 5 6 7 8 9 10 11 12 13 14

SalmoKCaR #3 Primers - Southern

Freshwater 1 2 3 4 5 6 7 8 9 10 11 12 13 14

SalmoKCaR #3 Primers - Southern

Saltwater

Actin Primers – Ethidium Bromide

Freshwater

Actin Primers – Ethidium Bromide

Saltwater

SalmoKCaR #1 Primers - Ethidium Bromide

Freshwater

SalmoKCaR #1 Primers - Ethidium Bromide

Saltwater

SalmoKCaR #1 Primers - Southern

Freshwater

SalmoKCaR #1 Primers - Southern

Saltwater 1 2 3 4 5 6 7 8 9 10 11 12 13 14

Actin Primers – Ethidium Bromide

Freshwater 1 2 3 4 5 6 7 8 9 10 11 12 13 14

Actin Primers – Ethidium Bromide

Saltwater

SalmoKCaR #2 Primers - Ethidium Bromide

Freshwater

SalmoKCaR #2 Primers - Ethidium Bromide

Saltwater

SalmoKCaR #1 Primers - Southern

Freshwater

SalmoKCaR #1 Primers - Southern

Saltwater

Actin Primers – Ethidium Bromide

Freshwater

Actin Primers – Ethidium Bromide

FIG. 37
PVCR Expression in Atlantic Salmon Tissues
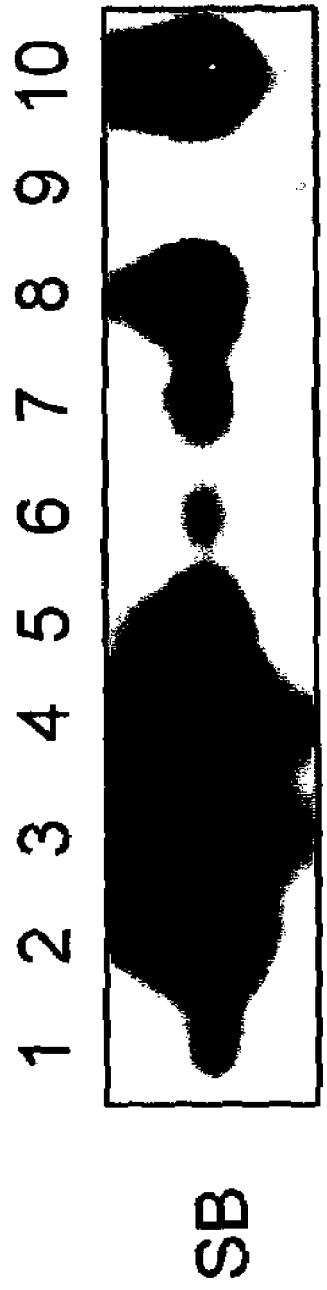

Schematic of PVCR Function

FIG. 40A
PVCR Protein is Expressed Days After Hatching of Atlantic Salmon
Panel A
Developing Nasal Lamellae
In Atlantic Salmon Larvae
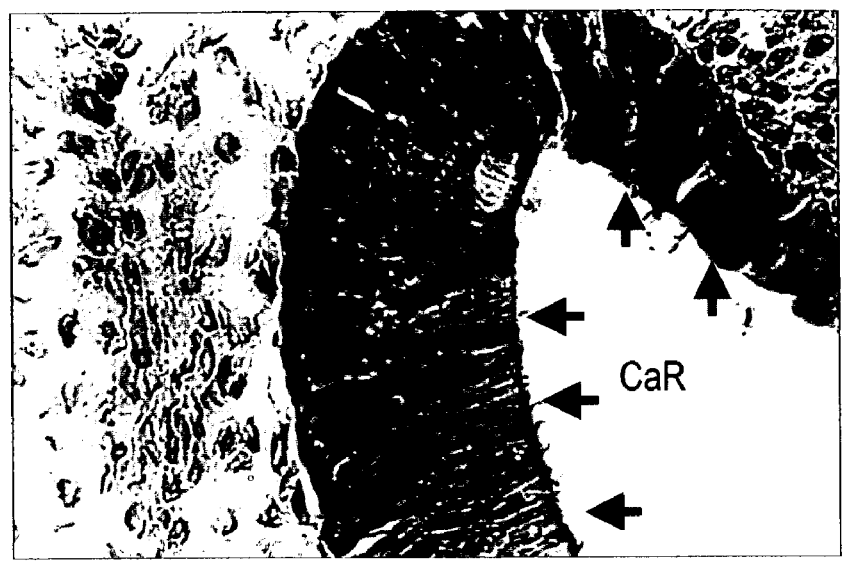
Panel B
Developing Olfactory Bulb and
Skin in Atlantic Salmon Larvae
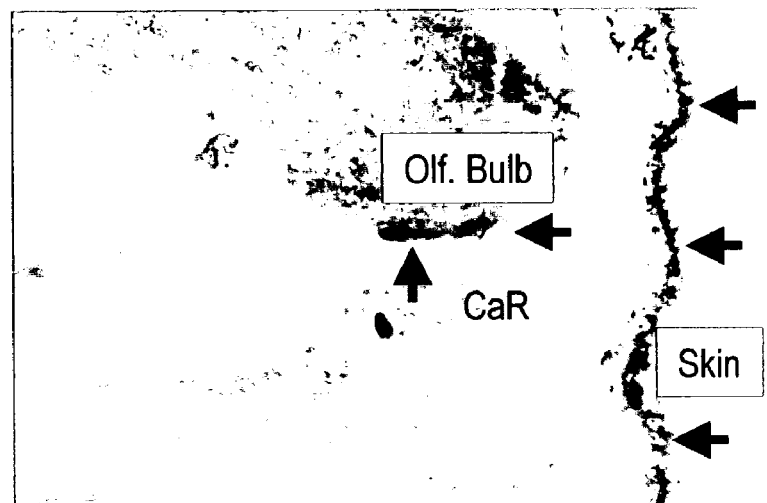

FIG. 40B
Panel A
Panel D
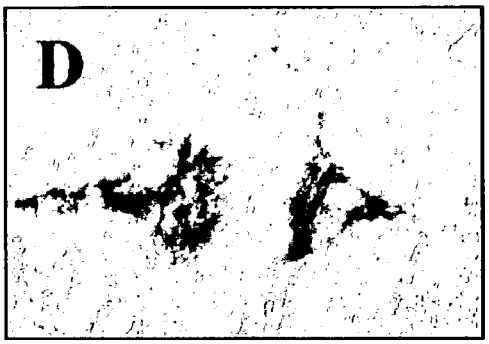
Panel B
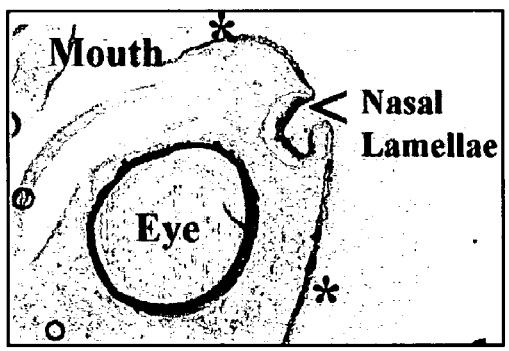
Panel E
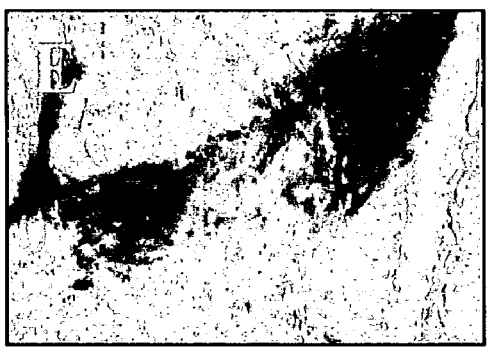
Panel C
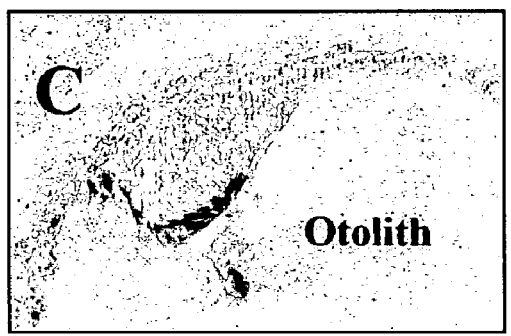
Panel F

FIG. 40C
Panel A
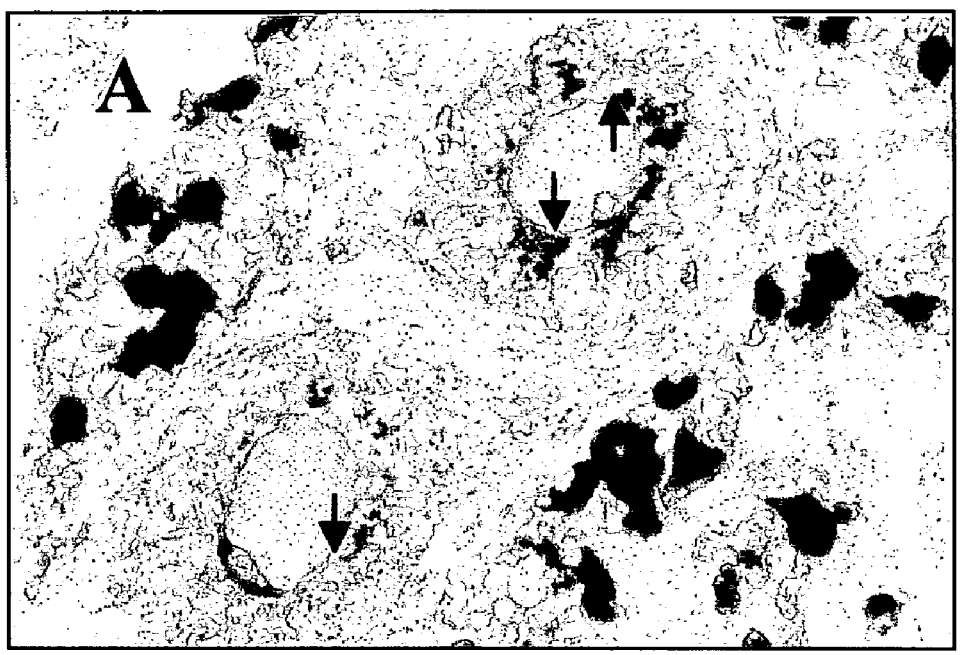
Panel B
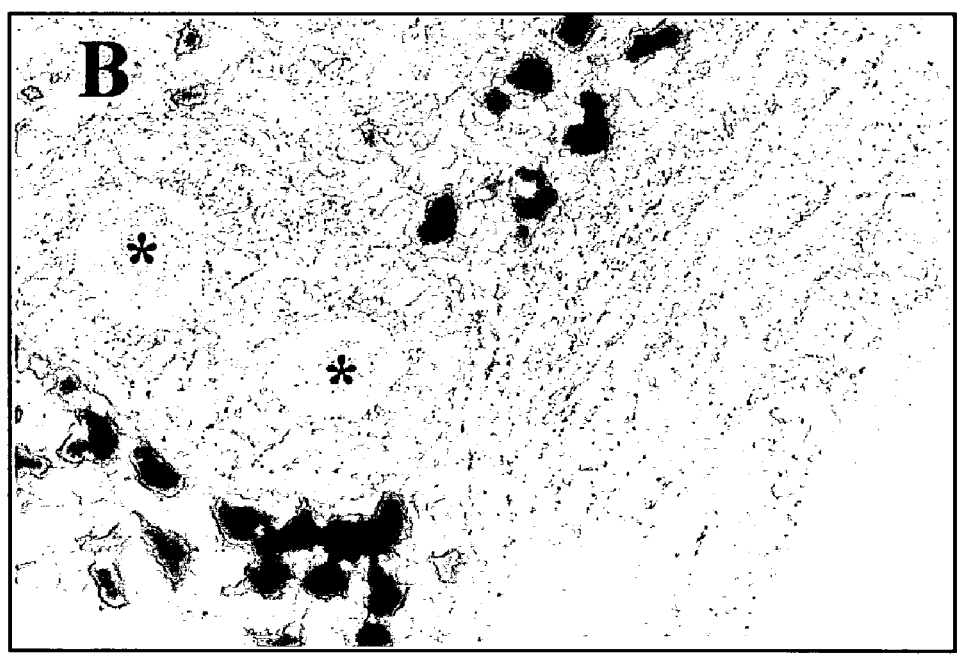

PVCR localization in Nasal Lamellae of Dogfish Shark (Squalus acanthias)

RT-PCR of salmon tissues showing abundant PVCR mRNA in nasal lamellae of freshwater adapted Atlantic salmon.

Atlantic Salmon Tissues

GenBank Acc. No: AB008857

```
   1 taatctcagg agagtttcgt ttccagagga aaccgaactt cttaaacgca ggtaggttgc
  61 aagcgtcata tttcacagtg gaatcaaagg caagaaaacg ggtcattcca agagaaattt
 121 gtcctccttt ctcccagtcg cagcaggaaa aacatgagtc tcctgaaaaa atgcagcagg
 181 cagactgatg ggacaagata agagggaccg tatcacctta aaaaaattat ttttccaaaa
 241 aaatccatta gaaacggcag gatggtgcga ctggtgctgc attatctcat acttctgggg
 301 tccggttatg tcatttcaac atatgggcct aatcagagag cacagatgac tggcgatatt
 361 ctgctggag gactttccc catacacttt ggcattctt ccaaagacga aaacctcgct
 421 gcccgaccgg aatccacaaa gtgtgtcagg taaaactcag cacttcatat gtaactgcat
 481 gtaaatgctt aaatcacgtg tcagcactgt tgagcacttt caaaccttct ttccgcaggt
 541 tcaatttccg tggtttccgc tggctgcagg ccatggtttt cgccatcgag gagatcaaca
 601 acagcagcag cctcctgccc aacatcaccc tcggctacag gatcttcgac acgtgcaaca
 661 cggtttcaaa agccctggag gctacgctga gcttcgtggc ccaaaacaag atcgactccc
 721 tgaattcgga tgaattttgc aactgcacgg atcacatccc ggcaaccatc gcggtggtgg
 781 gagcggcagg gtctgcggtc tctacggcag tcgcaaacct gctgagtctc tttatattc
 841 ctcagtgag tgacggaatt atctttacac tccagttaaa accttaaagt caccgcaatc
 901 ctctatcaca ccagatcagc tatgcgtcct ccagccgctt gctgagcaac aagaatcaat
 961 acaagtcctt catgagaacc atccctacag atgagcacca ggccacagcc atggccgacg
1021 tcatcgagta cttccagtgg aactgggtca ttgccgtggc ctctgatgac gattatgggc
1081 ggcctgggat agaaaagttt gagaaggaga tggaagagcg agacattgc atccatctga
1141 acgaactcat ctctcagtac ttcgaggact gtgaaatcaa agctctcgtg gacagaactg
1201 aaaactccac agccaaagtc atcgttgtgt tgccagcgg ccctgatatc gagcctctga
1261 tcaaagaaat ggtgaggagg aacatcaccg atcggatctg ttagccagt gaagcgtggg
1321 caagctcctc cctcatcgct aaaccagaat atctcgatgt tgtggagggc acaatcggct
1381 ttgttttgaa agcagggaac atacctggtt tcaggagtt cttacagcag gtccagccaa
1441 agagaggcag ccacaacgaa tttgtcaggg agttttggga ggaaaccttc aactgttacc
1501 tggaggacag cccgagactg caagaaagtg agaatggtag cgacagtttc aggccgcttt
1561 gcaccagcga ggaagacatc acgagtgtgg agacccgta cctcgaccac acacacctcc
1621 gtatctccta caatctctat gttgcagttt actccatcgc tcaccccctc caggacatac
1681 tctcctgcac tcctggacat ggactctttg ctaacaactc ttgcgcggat ataagaaaa
1741 tggaagcatg gcaggtaaaa actgctcttt tgcccacaat gttctacttt gtcagcctca
1801 aagggtcaaa tgtgtttgca ggtcctgaag cagctcagac atttgaacta caccaacagc
1861 atgggggaaa aggttcattt tgatgagaac gcagacatgg aagcaaacta caccatcata
1921 aactggcacc ggtctgctga ggacggctca gtgcgttca gggaggtggg ctactaccac
1981 atgcacgcca ggcggggagc caaactgctc attgataaca caaagatgat gtggaatgca
2041 tacagttcag aggtcagtca tcttcagggc aatttcctgt tgtcctgat gtacagtgtc
2101 tctgttcctg acatcattta cgtggcaggg acaccaaatg tggtgtcatg tgagcatcta
2161 agggtttgca tctgttgtcc tttaaggtgc cgttttctaa ctgcagcgag gactgcgaac
2221 ctgggacgag gaagggcatc attgacagca tgcccacgtg ctgctttgaa tgtaccgagt
2281 gctcagacgg cgagtacagc gatcataaag gtagtagcgt ttgtttactg cttcctgtta
2341 ctgtccacga acactcaggt aatcctcaca tgcatgtttc agacgccagc attgcacca
2401 agtgtccaaa caactcctgg tccagtggga accacaccct ctgctttctg aaggaaattg
2461 agttcctggc ctggtcagaa ccctttggga tcgcttggc catctgcgcg gtcctggggg
2521 ttctcctgac ggcatttgtg atgggagtct ttgtcagatt tcgcaacact ccgatcgtga
2581 aggcctcaaa ccgagaactg tcctacgtcc tcttgttgtc actcatctgc tgtttttcca
2641 gctcactcat cttcatcggg gagccccaag actggaccig ccgtttacgc cagcctgcct
2701 tcgggatcag ttttgtcctt tgcatctcct gcatcctcgt gaaaaccaac agggtccttt
2761 tggtgtttga agccaagatc cccaccagca tccatcgtaa atggtggggc ctgaacctgc
2821 agttcctcct ggtgtttctg tgcaccttcg ttcaggtcat gatatgtgtg gtctggcttt
2881 acaacgcccc ccccctccagc tacaggaatc atgacatcga tgagatcatt ttcatcacct
2941 gtaatgaggg atccgtgatg gcgctcgggt ttctcattgg ctacacgtgc ttactagcgg
3001 ccatatgctt cttcttgcg tttaagtcaa ggaaacttcc cgaaaacttc acggaggcca 3051 agttcatcac tttctgcatg ctcatcttct ttattgtctg gatttctttt atccctgcgt
3121 acttcagtac ttacggcaag tttgtttcag cggctagagg cattgccatc tggcatcca
3181 gctacgggat gctagcttgt atttttta ataagtcta catcatcctg ttcaaaccct
3241 gtaggaacac catagaagag gtcaggtgca gcacgccggc ccacgcttc agagtggccg
3301 ccaaagctac attaaaacac agaaccactg tgaggaaaaa gtcgaacagc atcggctcta
3361 ccgcctccac tcatcatca tcaattagcc tgaagaccaa cagcaacgac tgcgactccg
3421 cctcagggag gcataggccg agggtgagct tcggcagcgg aactgtcatg ctgtccttga
3481 gctttgagga gtccaggagg agcctctga tgtgacacac aaaccagttt catccaccg
3541 tcctttcagc ccctaaatcca tctgtccacc cttctaatta ccttgattat taaccotgct
3601 aataaa
```

FIG. 50

GenBank Acc. No: AB008858
```
   1 cttgtggctg gggtcagtag aagaacctag actagcggta catgaaccgt atcaaaagtg
  61 taacggtgaa acattagcac aactgtgtgg gggaggaaat agagtcattg catagtttct
 121 taaaccagtt gtgcagtacc tgagtgacaa actttgtttt gtccatttta tttttgcatt
 181 aaacaaaagc gattttattg gaaattgcct cgatagatgt caataaatct cacatgatgt
 241 tatcagcact tcattacagg tatcataaag atataatagg aacaactgta acttgtattt
 301 gttctaaagg ttataaccct tggggaacag ccagataagg accacgtaat gttttgtctg
 361 actgattaat aataataagc tgacatgagc agaaccaaca cctcagtcta taaaagcatt
 421 tgtgcagaat gctccgagac attttagga tggagatctc tgttatcttc ctttgcttca
 481 tttctctgtt tgatttaaac tcagctggtg acctgaaggc tcctgagaac agtctgaaac
 541 aacaggttgg accgagggag gacacaaccg gtgccgcagc tccgtctgac atatgtcgcc
 601 tccagggttc tgctcgccta cctgctttct caaaggatgg agactttgtc atcgggggg
 661 ttttctccat acaccgctac acagtgacgg tgaaccacaa ctacaccacc atgcctgagc
 721 catttcgctg cagagtgtgc ggagaagaaa atgtttgatt gtttcatttc tggagtatat
 781 atgatgttca cattatgatg cattttttat ttatacctac acttgtgaat gtttgttttc
 841 tgtcatgatg tgcagcatcg accatcatga attgcaactg tctcatgcaa tggtcttcgc
 901 catcgaggag atcaacaaca gcacggagct gcttcctgga atcaaactcg gttaccagat
 961 ccacgactcg tgcgcagccg tgcccatcgc agtaaatgtg gccttccaac tgttaaacac
1021 tctggaccct gtgtttgtca caggtgacaa ctgttcacag tccggtatgg tgatggctgt
1081 cgtcggcgag tctggttcca ctccgtccat cagcatatcc cgcgtcatcg gctccttcga
1141 cattccacta gtgaatattt tcaaccttta ccaaagcaca tgaacacgta atattaacca
1201 tcactgtaat gacacaatgt tcaacttcag gtgagccact ttgccacctg tgcatgcctg
1261 tctgataaac agaagtaccc aagtttcttc agaacgattc ccagtgacca gttccaggcc
1321 gacgctttgg tcaaactcat caaacacttt ggctggactt ggataggtgc tgtgtgctca
1381 gattcagact atggcaataa tggcatggca gcgttcctgc atgcagctca gaaggagggc
1441 atctgtgtgg agtactcgga atcctttat cgcacccacc cgcacagcag gatcaagaga
1501 gtggctgatg tcatccgcag gtgtatagat ctattttgc ttcatgattc atgaaggtat
1561 ttgtgtttgt ttgaaatgac gcatatactt gtgagttttc tgcaggtcaa cagctgtggt
1621 ggttgtagcc tttacagcat ctacagaaat gatgatcctg tcgaggaac tgtctcatga
1681 accctcacca cctcgccagt ggataggcag tgaatcctgg gtaactgacc cagacttgct
1741 gaggttcagc ttctgtgctg gaactattgg atttgccatt cagaggtctg tcatcccagg
1801 cctgagagac ttcctgctgg atctctcccc ctcgaaagtg gcttcatctc ctgtgctcac
1861 tgagttctgg gaggactcat tcaactgccg gttgggaaaa ggtgacagaa gttatacctc
1921 ttcttaattt actgtggata gattttaaat tagtgtccaa atctaataac aaaggctttc
1981 aacagatctc ctgtgttgtc agttgctgtt gcaggtgagc gcatgtgtga tggatctgaa
2041 gacataatga ctctccagag tccgtacact gacacttctg agctccgcat taccaacatg
2101 gtgtacaagg ctgtttatgc aatagctcat gccattcata atgcagtgtg tcaggacaca
2161 aatgctacca ctcggtgtag caaattcacc acgattaacc ccaaaaaggt caaacctaaa
```

FIG. 51A

```
2221 gaattgcctc tgtaactact aacatggttt attacaagtg tttcagctga agtctttcct
2281 ctgactctct gtttcattca attcaggttc tcactcagct gaagacagta aattttccac
2341 aaaatggtta tgctgtatcc tttgatgcca acggggatcc tgtggcatca tatgagctgg
2401 taaactggaa aagagtggg agcgggagca tcgaagttgt gccagtagga tactatgatg
2461 cttcactgcc agaaggccaa gagttccgta tcttcaggga catcacatgg gtggatggca
2521 gaaagcaagt acgacagcca gaataattaa taagacagta attcaggcat gaaaacacaa
2581 catctctgaa ttaaaggctt ttttgttcaa ttgtgactct atgtaaaggc accaacggca
2641 gttctgttaa aatctttttc aactggtggg tgtgtatgtc tcaggtgcca gtgtcagtgt
2701 gcagcgacag ctgtcctcaa ggaactcgta aggtactgca gaaaggaaaa cccatctgct
2761 gttatgactg tgtacaatgt ccagagggag agattagcaa tgttacaggt agttatctag
2821 atttcaaaga cagcagggct aaataaataa tttgtttaaa ccctacatga ttttttgtttc
2881 ctagattctc ctgaatgcat cccttgtctt gatgacttct ggcctaaccc agagagaaat
2941 gcctgttttcc ccaaacctgt ggagtttctt tcctttaacg aggttctagg aatcatccta
3001 gctgtgttct cagtcggtgg tgcctgtctg gctgttatca cagcagctgt attttccat
3061 cacaggacct ctcctattgt cagagccaac aactctgagt tgagcttcct gttgctcttc
3121 tctttgactc tgtgcttctt atgttcactc actttcattg gtgctccctc tcacctgtcc
3181 tgcatgctgc gccacacagc gtttgggatc acctttgtcc tttgcatctc atgtgtttta
3241 gggaaaactg tggtggtgtt gatggccttc agagcgactc tccccgggag taatgtcatg
3301 aagtggttcg gtccacctca gcaaggatg actgttgtga ctttcacgtc tatccaggtt
3361 ttaatatgca ttgtttggtt ggttgtcaat ccccgtttc cagtgagaaa tctgaccacg
3421 tacaaggaga gaatcatcct ggagtgtgcg ttaggctcat ctgttggatt ctggctgta
3481 ctcgggtaca tcggccttct ggcagctgtt tgtttagttc tagccgtcct cgcccgaaaa
3541 ctccccgata atttcaacga agccaaaatg atcaccttca gcatgctgat attctgtgcc
3601 gtctggatca ccttcatccc cgcttacgtc agctctcctg gaaattcac cgtggccgtg
3661 gagatctttg ccatttggc ctccagtttt ggactcatcc tgtgcatttt tgctccaaaa
3721 tgtttttatta ttttatttaa gccagagaaa aatagcaaaa aacacttgat gaacaagaaa
3781 taatcagaat gtctgcaata tgttgggtga gtttaacgac tggaagtatg ggtccgtaca
3841 gcagcaatag cccagtctgt agatgagtga gctgtgggtt tgagggtatc tggttcaagt
3901 tccatttggg aacaaagatt aggaaatgga cctgtagaag gagatgtgca gggacatatt
3961 aagaacccca ctatggtatc attaagcaaa ataccaaacc cccaaatgat aagattgcct
4021 ttatctctct tcatgattgc atgtgcatgt gtttattgta gcttcatgtt taaccgcttg
4081 taacttgtgt gtaacaaagt gtaaacacag acatttcccc tttgtgcttt taatgtatgc
4141 ttttttttctt ctcttgtttt acactgtact gccattcctc caacgttat gtgacaggct
4201 agattaggct gcatgatgta tgagttttag aaaatctcac cctttacaac acaagtccgc
4261 tgatacagtt ttccatctct cctcccttat gtccaccata acctcttttc tattttctat
4321 gtgattgtta acaattaca cttttcattg gaatgttat tgataaatgc aagtaaaact
4381 actgtgatat ctgtgtagat tctcaatcat ccaggtcatg gtcatccaat gcagtttgct
4441 ttgtcaaatg gactgttttt cttctctttg aagttctgga gtgtgatgta ttcaaaacat
4501 cattaaagtt ataagtgggg aacgactgta acagattgt tcaaaaggtt ataacccttg
4561 gggaacagcc agataaagac cacataattg cagaatgctc caagacattt ttaggatgga
4621 gatctgttct cttcctttgc ttcatttctc tgtgtgattt gaactcagct ggtgacctga
4681 aggttcctgg aacagtctg aaacaacagc ttggactgag ggaggacaca accgctgccg
4741 cggctccgtc tgtcatatgt cggctccagg gttttgctcg cctacctgcc ttctcaaaga
4801 atggagactt tgtcatcggg gggggttttc tccatatacc actacaaaat gacagt
```

FIG. 51B

GenBank Acc. No: AB008859

```
   1 gtgtaccgt  ttatgcatt  ataacgaagc  aacaaactca  tatctgcaa  gtttgatgg
  61 acttgctggc  attattaata  cttacaatta  gattagatta  gattagatta  gattagatta
 121 gataaaagaa  attcaggaag  ggaaatgcag  acattatatt  taccaatcct  atgaactatc
 181 caaatcttgc  atagccttaa  attaaacatg  gtctagatga  taaaagtaac  atgtatgaag
 241 tgaacgaatc  tgacgtcatc  ggtcacacct  tgatgggtgg  tgtcatcaga  catggtgaag
 301 acacaactct  gcatataaaa  tatgcagtag  agatgaagag  aacctgaggt  ggaggaagga
 361 ggaagagtga  tggctgacat  cactggcaca  ttgggcctct  tcttcaccct  catccacattg
 421 tttgtctcct  cttccacctc  cttcaatgct  ccgacttgca  agctatggag  gaaatcttcag
 481 cttaatgaga  tgcacgaacc  gggcgatgtg  cttctaggcg  ggcgtttca  agttcattac
 541 agccctgttt  ttcccgagtg  gacgtttaca  tctgaaccac  atcagcctgt  ctgcactagg
 601 taagtttcat  gcacaccaca  aacaatgatt  caagctcaga  ttggtcctgg  aagaaaaatg
 661 tcaattaaat  gtttgtgatg  ggtgaatcca  tccataaagg  gtgtatctgg  agccagttcc
 721 accaggttct  tgttaatggt  tttggtatt  tgcatgtcag  gttgacatt  ctaggcttcc
 781 gtcacgctat  gactatggcc  ttcgctgtcc  aggagataaa  caagaaccct  gacctgcttc
 841 ctaatctgac  tctgggatac  cgtcttcatg  acaactgcgg  agccctgtg  gtggattca
 901 gtggagcgtt  agcactggca  agtggtcagg  aggaggcgtt  tgctcttcag  ggaggctgtg
 961 ctgggagccc  acggtcctg  gggatcgtgg  gtgattcact  ctctacgttc  actactgctt
1021 ctgccagtgt  tttaggcttg  tacaaatac  ccatggtcag  tgattagtgg  cactaaagtt
1081 tgtgtcttgt  atgtgaatta  taaactttca  tcttttgaat  aatattgtaa  aacactggaa
1141 gaaatgtgat  tggttatgta  gagaaatgga  tgtcatctac  tgaagacata  taaataatta
1201 ttacattaat  ttgatcaagt  tcataaatta  accctttttc  aaatgaaaaa  gtattttta
1261 ccaaacaaaa  actgcaaaat  gaacttaaat  cttagttaaa  tttagtgtaa  aagtgatact
1321 cacgcttgg  atcagagtac  agacgcagac  agctaatcct  tggagaaaat  ctaagtgcac
1381 tgagatttaa  aattttgtt  taaacattca  aatgcttctt  tctttctt  tctgtttta
1441 aaaacgttga  tctccttac  acagttaaat  ctgttaaaat  aaaagaataa  ttccatgttc
1501 atgctgagtg  ctccggaaat  ctttaatgct  tgaaaacat  ttaaaaacat  ttgggcttgt
1561 gctgttaat  ttcctattc  taggtaagct  atttctac  atgttcctgt  ctgaccaatc
1621 gtcagcgctt  tccgtcctt  tttagaacca  tcccgagcga  tgattccag  gtaaatatc
1681 cctttcaagc  tgagaatcta  cagagattaa  aaaaactcc  ccacccctcaa  attcaaacaa
1741 atattactta  gtatcagatt  acaaactgtg  ggaactaaaa  cactcaattg  tctggactga
1801 tccccattc  aggtacgtgc  aatgatccag  atcctgaaac  acttggatg  gacttgggtg
1861 ggactgctgg  tcagtgatga  cgattatggg  ctccatgtgg  ccgttcgtt  ccagtctgac
1921 ctggtccagt  cagggcaagg  ttgtctggcc  tacttggagg  tttgcctg  ggacaattat
1981 ctgagtgaaa  acaggaggat  tgtgcacgtg  ataaggaat  caacggctcg  cgtgctgatg
2041 gtgtttgcac  accagtccca  catgattcat  ctcatggagg  aggttgatg  tgcacagaaa
2101 aaactgcagt  gaacacgcta  aagaatgcta  tttctggtat  taataatgat  atgtacaggt
2151 ggtgagacag  aagtgacag  gcttcagtg  gttagcaagt  gaagcttgga  ctggaacgac
2221 cttcctccag  acgccggact  tcatgccgta  cctgaatggc  acgctgggca  tgccatccg
2281 tcgaggtgaa  ataacaggtc  tcagagatcc  ccctacga  atacggcctg  gccagagtag
2341 caacaacact  agttatgata  tggtaattat  ttcttactat  tttaactccc  agaggaactg
2401 ttcatttaaa  aaataaatga  tatatttaa  tctttttca  ggttcaacag  tttgggaat
2461 actcattcca  gtgtaaattt  ggtgcgtcag  gttcagcaga  agcctgcaca  ggagatgaaa
2521 atatccagca  ggtggacgct  gagttttgg  acgtgtctaa  cctcagacca  gagtataaca
2581 tttacaaagc  tgtgtacgct  ttggcgtacg  cgcttgatga  catgctgcag  tgtgagccag
2641 ggaggggggcc  gttcagtgga  ggcagctgcg  cggatattca  caaactggag  ccctggcagg
2701 tgagacctga  cactggaaaa  taacaagcgc  ttcccctttt  agtgtgagcc  tttgaaattt
2761 agattcacca  agtggtccct  cagacctgat  tactgtcaac  ctccatcagc  tgttcaaatt
2821 agagcaacag  ggtccagaat  taggattcga  cctaataagc  ctgaccggt  atgtgcatt
2881 tgcagttcgt  gcattatcta  caacatgtca  attcaccac  aacgtttggc  gatcaagtat
2941 catttgatga  aaatggggac  gtcctaccca  tctatgacat  cctcaactgg  cagtggctcc
3001 ctgatggaag  aactcaggtt  cagaatgtgg  gtgaggtcaa  gaggtcaccg  tccagaggtg
3061 aagaactcca  gatccatgaa  gacaagatct  tctgaactt  tgaatctaat  aaggttattc
3121 ttgtgtgctc  ctgttatctg  ttaaaagaaa  tgcatgaaaa  tcagatgttg  atcctcctc
3181 ctgcagcccc  cacactcagt  gtgcagtgaa  agctgtcctc  ctggaacccg  catgtccagg
3241 aagaaaggac  aacctgtctg  ctgctttgac  tgtcctctt  gttgaggg  gaaaatcagc
3301 aacacaacag  gttggtactt  gattcaaac  actattttgg  gcacattaat  cctaaagctg
3361 cgtccatgtt  ttgcttcaga  ctccatggag  tgcaccagtt  gtcctgagga  cttctggtcc
3421 agccccagc  gggaccactg  cgttcccaag  aaaactgagt  tcctttccta  ccatgaacct
3481 ctgggtatct  gtctgacagc  cgcctccttg  ttgggaacag  tgatcagcgt  ggttgtgttg
3541 ggcatcttca  tccatcatcg  cagtacacct  gtagtacggg  ccaacaattc  cgagcttagc
```

FIG. 52A

```
3601 ttcctgctcc tggtgtccct taagctgtgt ttcctctgtt ctctgctgtt cattggtcgt
3661 cccaggctgt ggacgtgcca gctgagacac gcagcattcg ggatcagctt tgtgctctgt
3721 gtctcgtgca tcctggtgaa aaccatggtg gtcctggctg tcttcagggc ctccaagcca
3781 ggaggggggcg ccactctgaa gtggtttggt gccgtgcagc agagaggaac agttctgggc
3841 cttacttcaa tccaggcagc aatctgcttt gcctggctat tgtcgtcttc accaaagcca
3901 cataaaaaca ttcagtacca caaagacaag atcgtttttg agtgtgtcgt tgggtccaca
3961 gtgggtttcg ctgtattgct cagttacatc ggtttactgg ccatcctcag tttcctgtta
4021 gcatttcttg cacggaatct tcccgacaac ttcaatgagg ccaaactcat cactttcagc
4081 atgctgatct tttgtgctgt gtgggtggcc tttgtcccag cttacatcaa ctcaccgggc
4141 aaatatgcag atgccgtcga ggtctttgct atcctcacct ccagttttgg cctcttggtg
4201 gcgctgtttg gaccaaaatg ttatataatc ctgtttcgtc ctgagaggaa cacaaaaaga
4261 gcaataatgg cccgttgaaa tcagaaccag cacttccaaa tcacaataac aaacactcat
4321 tgaagcatca acagcaaaag tacaaatgca aaaaaatac aattaaaatt aaagcaattc
4381 accccctagt ggttaaagat tgcactgcat tacacgtttt ccccatttcc ccacctttcc
4441 atgtcacatt aacaatgtgc actgctgcat gtattccaac atccacgggg taagataaga
4501 ccatataaga cagaatctca gtcttcattt ttgaatgtca tcaataactg attcttctat
4561 ttctccacac tttctgtttt gcttctcttc ccttctcact gtatttcttg tgctgttatg
4621 ttaaactta ttatgatgat caatgagggc agttgagctg tataatatgc tcactcttgt
4681 tttattgtgg taaataaatt tatatttaaa tctgccacat gcttttggtc agtaaaggtt
4741 tgtgaacgtt ttttttgtcc tgcaatatag aaaaaataat atgtaataaa gatttcaagg
4801 gtcaaacaga aaggtatgac tccatctatc tgtgtggaat agaaaaataa gtaacattta
4861 agcagcaatt aaatacattt ttatcacact tcacatacgc atacaattta aaaaaacaaa
4921 acaaaattcc agcccacgtg gctgaagccc tcacgaggga tgaggaagcc tgagtgactg
4981 a
```

FIG. 52B

```
GenBank Acc. No: AB008860
   1 cagccttcat aaacacaaat aggatatcct atagattggc atagtgaaat ttgaccactt
  61 tcaacttgcc gtctggcatc tggagactag atccagacct gatcagtgcc aaggtcaaac
 121 gctgtaacac agttaaccct tgaatagctg tctttcatgg tgggggaaac tcaaacttca
 181 gtcaaacaga aaaagagaaa gttctaatca gactgatact cccttcatcc ctccactgca
 241 acctggctta gcatccacag gtcaaacctt gtctttatgt tggggagggc acacacattc
 301 catgcacaca gaagtacaat gtgctgattc tacatggaaa aaaattcagg aatctgacag
 361 agattcagat tcagattcag attcagattc agattattga catgatgaaa aggtgataaa
 421 tgttgttgtg ctaaactacc tatctatcat acctgtggcc acaaaacaat cactgcgctc
 481 ttccaaatat catgacttaa agaaaactcc tcaagtatca catttcatt tgaggtctga
 541 catgacatga cagttctgag acattcttct cacacattca actactttca tctttaactt
 601 ccaactaaac tcaatttaga ctatttacaa aacatgaact aataactcag tttgtttgtg
 661 atagcgggt cattcattcc agtgcctgaa agctggctac cagttcatta attggtgacc
 721 ctgaggagac aaattcagtt tatctaacca cttaatccta attaaggttt aaggagactg
 781 aggcaggaaa aaaccctgga caggtcacct gtccaccagt aactgttcac tatcaactag
 841 ggactattaa tcatcactga acctaatatg catgttttta tgctgtggaa gcaacggggg
 901 acagagagaa cgcaaacttc gcgcagaaat gccagagtct ggagccctga atgctcctgc
 961 tctgatattg gtgatcactg caccctcatg cagtctctac aatgacctcc agatgttttc
1021 aggggtttcc aaaaatattt ttttaatcca tctttatttt ctgcgatatt tacaaacaat
1081 gaatcatctc aacaaattct gcagttttt ctcctgtagg atgaaggaaa atcttgctac
1141 ggcccaaagt tgtccctgg gaaatgcagg atgcagagtt cttgatgcaa tagatgcaaa
1201 tctattagta agttgtcgtc atggtgatta tgtaatgaag tagaaaagc aagttaaatg
1261 ttgaagagct gcaccctctg acatcagcaa tgagggcttt cttcttataa aaggatgtta
1321 aacattagga tggcctgcag gagtatataa ttcttctgtt ttcttctgtg agacatttt
1381 gcttacgatt gtgtgtgtca ggttccacca gatgcctgtc tgtgtctgtg taatgcttct
1441 gtttgcgctt ttccacggag cctttggagc cgaggacaat ctaaagtgta agatgttggg
1501 gagaccagag tttccactgt tatctcagga aggagacatc actattgggg gagccttcac
1561 tctccacagc caaatgtcaa aaccttctct ctcctttgaa gagacaccag aagatctcac
1621 atgctccagg taacatttat tttctactgt agtgctattg ttttaccttc agagaaccta
1681 aacctctgtt attttccttt caggattaat ttaagagaat ttcgctttgc ccaaacaatg
1741 attttgcaa tagaggagat caacaacagc agctcgcttt tgccaaatat ttccattggt
1801 tataaagtat ttgacacgtg cggtttgacg ctgccttcta cacgagcagt aatggcctta
1861 atgaatggaa agacaagaac cccagaagga ggctgctcca gtcggacatc tgttcatgca
1921 attattggtg cttcggagtc gtcttcaacc attgtgatgc ttcaaatttc agggatattt
1981 caaataccgg tggtaataat gtgtcatatt tgtgattggt ttgcttttga ttctgtcttt
2041 ggtaaaaaaa atgaccagat tctgattcat gtattgcttt ccctcttgtt ttttcctctc
2101 tttttgttat ctctttttgtt cagataagcc acttgccac ctgtgcatgc ctcagtaaca
2161 ggaaggagta cccctccttc ttcagaacca tcccccagtga cttctatcag agcagagctc
2221 tggctaaact agtgaaacat ttcgggtgga cgtgggtcgg ggctgtgaaa agtgacaatg
2281 attatgggaa caatggcctg gcgacactta ttatgctgc tgagcaggaa ggggtctgtg
2341 ttgagtactc ggagggcttt tcgtggacag accccagcga gcagattgcg agggtggtca
2401 cagtcattaa aagtggcagc gcaagggttt tagtcgcctt ccttgcacag agtgagatgt
2461 ccgctctgct ggaggaggct gtaaagcaga acctgacggg gctgcagtgg gttgggagcg
2521 agtcctggat cacagcaggt cacctggctc ttaagaaata ctcagcaatc ctgacaggt
2581 ccctgggctt caccatcaga aagacaaaga taactggcct tcaggagttt cttttacagg
2641 ttaacccaag tcagaaccct cagaataatc ttctcaaaga attctgggag accacatttg
2701 gttgtagttt ccagtctgat gtgcacgggg ccacccagtg ctctggtgtt gagaagctaa
2761 aggacattca gaatcctttt acagatgtgt cagaacttag gatctccaac aatgtgtata
2821 agctgtgta cgctgtggct catgctatgc atagcatgct aaaatgtggc caaagtggcg
2881 aggcagtgaa tcagtcatgt accactaaaa aggattttga gctaaagcag gtaagatgtt
2941 gtctctaaga attatgtcca gctgaatttc tttacacccc ccattgacct gttctttctg
3001 acaggttgta gagcacctgc aatcagtgaa cttcactctt cagtcaggtg aaagagtgta
3061 ttttgatgac tatggagacc cggcggctac ttatgagctg gtgaactggc agagaagccc
3121 agaaggaaat acagtatttg tggtcgttgg gaactatgac gcttcacaac aaacgggag
3181 gcagtttacc atgaacaaca tcaatataac atgggctgcc aggctgcaga aggtacgacg
3241 catgttaaaa agcattgatt tacacgctga tgtttataca ggcatgggtt aaatggcttc
3301 atctatgtat tttgtatttt cgtcttaaaa cagagaccgc tgtctgtgtg cagtcagagt
3361 tgcattccag gcttccgaca ggctgtgatt aagggaaaac ccatctgctg tttcacctgc
3421 gtcgcctgtg ctgcaggaga gatcagcaac tccagcagta agttcaagtc ttcagagcag
3481 gcaatattta tcctgaaaca atcttttta ctctcttctg cttcaagctt tattcatggc
3541 accttgatt tttagactct gcagagtgtt tgcagtgccc actggagttc tggtcaaacg
```

FIG. 53A

```
3601 aagatcacag ccagtgcgtt ccaaaggtga tcgagttctt atcatttgaa gaaaccatgg
3661 gggcccttct tgccgccgtt tcactgtttg gggctgcgtt aacgtcgctg gtgttttgtg
3721 tctttttcg gttccgtcac acacctcttg tcaaagccag taactccgag ctgagctttc
3781 ttcttctttt ctctctgact ctgtgcttcc tttgttccct cacattcatc gggaggccct
3841 caaggtggtc ctgcgtgctg cgacacacgg cgttcggcat cacctttgct ctctgcatgt
3901 cctgcgtcct ggcaaaaact gtggctgttt tgttcgcatt tacagcaaaa aggccaggaa
3961 acacagtttt ttactgttct gttccacttc agagaacaag tgttttgcc tgcatcactt
4021 tgcaggttat aatttgtgtg ctctggttga cgcttgcccc accacaccct cacaaaaata
4081 ccgctcatgc caaagagcgc attatttag agtgtaattt aggttcccca gtgtggtttt
4141 gggtggtatt ggggtatatc gggctcttgg ctgtgatttg ctttatcctt gctttcttg
4201 ctagaaagct gcctgataat tttaacgaag ctaaattcat caccttcagc atgctgatat
4261 tttgtgcagt ttgggtcact tttatcccag cgtacgtcag ctctcctggg aagttcacag
4321 ttgccgtgga gatctttgct atcctggcct caagttttgg gttactttc tgtatatttg
4381 ccccaaaatg ttatatatta atattgaagc cagaaaaaaa cactaaaaaa cacatgatgg
4441 ggagaaacca tcaaaattag gctgaactga gaattgtatc acttaaataa cagtaatttt
4501 gttctttaat atttaagtcc agaaagtgtt ttattaatac agagcattat gtaagtgcac
4561 atatataaaa tgcacttat gtcagtttga ttttgggatg gaattgactc acatgttaat
4621 gtcatttatc gattaaagct acaataaagt taaactacgt ggacagttgt ttaatagttt
4681 ccctgtcaag tattttaaaa gcaacaattg catgtaaaag caacacagct gtaataggcc
4741 cactcgtctg tcactcacag cagtgaggtg atgccattgg a
```

FIG. 53B

GenBank Acc. No: AB008861

```
   1 gatccaaact tgcgacaggg atttgtgcca gtatatcaac gccagaacgg cgtctggtat
  61 ttgacagtta aggctgtgca gttgtgggag aaagtagatg cttttaact gtttgctcta
 121 gaatttgtgg acactttag tcttaatgga tgtataatca atttcctaat ttctcttgaa
 181 tctggcatat tgcaaacatt tgttgatcac cacaaacaca cacacacaca cacacgcaca
 241 cacacacaca cacacacaca cacacataca cacacactac aaatctacga acttgagctg
 301 cagcagtggg tgcacacgtt tgtattgggc tgtgagtctg ttcacagaat gagttggatg
 361 ggatggattc cctcacaaag aggtgtacaa cttctctgcc ttctgtgctg catgataatt
 421 cctgttgtca ttgccctcct ggatcagagc caacattgca gggtcatccc gggctccatg
 481 tccctgccag tgctggagaa gaggggggac atcattttag gcggtctctt ctctcttcac
 541 gacatggtgg tagagccaaa tctgcccttc acctctacac caccacccac tcagtgcact
 601 aggtaaggta caataatccc ttctacactt ttattcatgt gtaaatttta agttttttgc
 661 tgtaaatata gcagtatgca caattccttg tctcttactg acaagtcagc atcctgtttt
 721 tcatttcttc ttcccagatt cagttttcgg acattccgtt ggatgcaaac catgatcttt
 781 gccgtcgagg agatcaacag aaatgccgaa atccttccca atatcacact gggctacaag
 841 atctacgact cgtgcagcac gccccatcag agtttgaagg ctgccatcga tttaatgggg
 901 agtgagaaag attcccagtt tgagggaaag ttgcagaggg aaggctgcga tgggaacgtg
 961 ccggccgtca tcggagacgg aggatctact cagtctctcg tcgtggcccg tttccttggg
1021 gtctttcatg taccgcaggt atctcgcatt gctgatgctt caaagggaac tcttctctca
1081 tgctagaaat catttgtttg ctaggttca cttaaaagca attatcactt attttggtc
1141 gtgtcaggtc agttattttt ccagctgtgc ctgtctcagc gacaaaacgc agttcccagc
1201 cttttaagg acgatgccca gcgatctctt tcaggtttga ggcagcagcc ttaaaacttt
1261 ttttttaaa tttaaagcta tgagagaacc ttcatctcct tcatttctag gtgggtgccc
1321 ttgtacagct cgtcaagtat ttcggctgga cttgggtcgg agtgattgca ggagacgacg
1381 cttacggccg tggcggagcg gccatattcg ctaatgaggt agtaatgaga acaaatggac
1441 atttcaatgc tttattgagc atcgtgcggg cactgaaaat taggattaat ggcatgtctt
1501 ctatctgggg taggtgagaa ggctcggggc ttgcattgct ctctatgaga tgatccccaa
1561 gacacaatca caggctgcca tttcatctat catttccaac atccgctctc cgggggctcg
1621 tgtagttctg tgtgtttgctg ttgagcaaga cgtggccagg ttgttcgatg aggcagtcag
1681 gtatggcacc tgtgtatccg caaacgtaca aaaacaactc taagctattt agcttctcct
1741 aaatatagac agaagctgac tgggattcag tggttagcca gtgaggcgtg gagcacagct
1801 gccatcctct ccaccctaa aaggtaccac cacatcctgc agggtctat gggatttgct
1861 attcggagag cggacatccc tggactgcaa gacttcctcc ttcgcttgca tccctcgagc
1921 gccgaggctg atgacgatcc tttcctgatc ccattctggg aggaggtgtt tcagtgtagc
1981 ctggatccgc acggccactc tgaggctaaa cgtccctgct ctgggacaga ggagcttagg
2041 agcgtgaaga acatctattc tgatgtatca cagcttagga tttcctacaa tgtctacaag
2101 gcggtttatg ccccttgccta cgccatcaaa gccatgagaa gttgtgaaaa aggaagtggg
2161 ccattttctc aacaagcctg ccctgattta gacaatatcc acccgtggca ggtatgcaat
2221 taacaaaatt ccatgtgcag aatgacttgt gatgttggaa tcgaatcttc cgctctttttt
2281 tcgcagcttc accactacat aaaacaagtg aactacacga acagattcgg cgatgagatt
2341 aaatttgatg aaaacgggga tcccgccgcc atgtatgact tgattaactg gcagctgacg
2401 ccgggcgggg acatggactt cgtcaccgtt gggaaatttg atgacatagc cgggaccgga
2461 aggaagaacc tccacattga ggaagagaag atcgtgtgga atggcaacaa cacccaagta
2521 ggagctgtca ataaatgct tcaacactca cgggtgactc agagatgtat ccttatgtga
2581 ccgtgtgctg tactctagtt tcctcttttg ctcaggttcc cttatcagta tgcagtagca
2641 tctgtccccc ggggacccgc aaggcaatcc gacctaatta ccctatctgc tgccatgact
2701 gtgtggtttg tacagcaggg gagattagca atcaaacagg tgagaagagg aggagaatgg
2761 tcacagtttt actcttccag acctctgtcc ataagccagt gaagtggatt tttgataaaa
2821 tgttccttta cgttttcctc ttttctgcag atgccatag aatgtgcccg ctgcctgccg
2881 gagttctggt ccaatgctga caggacagcc tgtgtcccca acaagtggat gttcctctcc
2941 ttcggtgaca caataggcat tgctctgttg ttgtttccc tgatcggctc cttccttacc
3001 tgcgccgtgg ccctcgtatt cttctatcac aggacctccc catcgtcag agccaacaac
3061 tctgacctga gcttcctgct cctcttctct ctgactctgt gcttcctgtg ctctctgacc
3121 ttcatcagcc caccctccca gtggtcctgc atgctgcgac acacagcctt cgggatcacg
3181 tttgtcctct gcatctcgtg cattgtgggg aaaacaattg tggtcttaat ggcgttcaga
3241 gccacacttc ctggtagtga tgtgatgaaa tggttcggac cagggaagca aaaggcaatt
3301 atcacttca gcacactggt ccaggtaagg gcttctttta agttgtctca aattgttacg
3361 gttgcatgta ttgaatgtaa catttctgat catttcctct tttgttgcag gttgttatt
3421 gcacggtgtg gctggttgtt gctcctccca ccccacgaca gtacatgcca cgtgaaagtg
3481 ctatcatcat tctcttatgt gacgaaggct caaccatagc cttctccctt gttttgggat
3541 acattggcgt tctggcctgt atgtgttttcc tcctagcctt cctggcgaga aaactgccag
3601 acaatttcaa cgaggccaga ctaatcgcct tcagcatgct cattttttgt gcagtctggg
```

FIG. 54A

```
3661 tggcctttgt cccagcttat atcagctctc cagggaaata ctccacgctc acggaaatct
3721 ttgccatctt ggcctccagt tacggactgc tgggctgcat ctttgcaccc aagtgctata
3781 taattctcat gaagtcagaa aagaacacaa ggaaacactt gatgtcaaaa agtgaaagat
3841 tttagagata tattattgct tgcgttgctg tgggttttga aatgaaatgg ggggacaact
3901 ttaaacgtcc gcgtcatgga tgaagtgtct cttttggcca ccagagggaa gtgttgtgct
3961 gctcatgcaa cactggttca ctgcttatac tggaaaaagc acaaaaagaa catgtattgt
4021 ttccacatac tacagtgtgt tcccgataaa acagtaaaat atatggttag cttataaatt
4081 catatagcaa tcatcccatt aatatattga agtgctcatt gtcattaaag tgcaatattc
4141 tcagtgacag tgtgaaggac agcttttttt ttatgacagt gggatttggc agcattttca
4201 gtgctgatat ggcttgaggt ggaatgaggc cctgaggtgt attctgtgga aatcccagct
4261 gttaaattaa atccatacac cccgacggcc ctttcacata aacataaggc cctggctgat
4321 tccctataat aacaaactaa aacgatatat ttcccgccct ccacagctgc tctcaggact
4381 gtatcgaccg ccttccgccg attgatctgt tgtccctccc gaagctgagg agggattgga
4441 aattgaaaga tggggagtca tctctgctgt ccatcaggaa atggcatatg agcacaatct
4501 atttacattc acttcttacc gtcattgttc ttaaatgtcc cactacagcc atctgtgccc
4561 tccccctctc cccatctcaa aagggattat gacaaagtga atttcccttc atagcatgtc
4621 catttcagga gtccttcagt ggctttgctg ttggtttgat tttaattaag gtgaacagga
4681 gagttcacct cagagggttt aatcatcgag tattagaaac acagtcaaag aaaagagtac
4741 aaaagagtca aatggctttc aaataacaat tcacaggaaa catatcagca gaaagtagag
4801 agttaaacaa aggccacgac ttttttagca cattaaaccc aataga
```

FIG. 54B

GenBank Acc. No: AB008862

```
   1 ggacagggt  caacatgggc  accctgactg  gtctgtaact  ggtccccatt  acactgaaat
  61 ctggcatcat  gttgattatt  acgatccagc  tgtaaagcag  ctgacggctc  agaagatgaa
 121 gtctgattgt  tgatgtctga  tgttccttct  tagcccagtt  tagctggtgt  agtggtgaac
 181 agatccctgt  actccagggg  aggggcccca  tgtttctgga  actggaccct  gatcactgtg
 241 actggtgggc  tctattttg   cactaaataa  taaatttaaa  ggctgtatta  cttttattta
 301 ttattaaagt  ttgatcttcc  accatgatca  taaaaaactg  tatcacatga  gatcagtgtg
 361 aatttacaat  gtggtttgaa  aaacaattta  atgaggcatc  ttcataacga  tcccatgatg
 421 aaacaacaat  gtgctgaggg  gggcctggag  gggccggagc  ctgacaggcc  ttctgggata
 481 cgcctggtca  ctgccctcca  ggtgaacgct  gcagtccctc  tttcctctct  ctctctctca
 541 cacatgcaca  cacatgaaca  catgcacaca  aatcactcag  tcatttcatt  attgttttc
 601 ttttgccttt  gagagcggta  atttgatgct  gtgcagttct  gtttactgcc  accctccct
 661 gggctttaca  gcagttataa  atatcagcgc  aggcctgctg  ggcagtcata  tgttcgctcc
 721 gtgtcatgtg  taaggagtga  tgcgttgcag  cgccgtcagg  acatgcctgc  gctccatact
 781 ttgcctctgt  cgtgatctgc  tgtattggtt  tgtttgagca  aatgtaactt  tccatttcca
 841 ggctgttgtc  tggtcattcc  gtcggcgcga  ggtgggctga  acagcatcat  ccatgtctca
 901 gttatcacgg  atcttcacct  tgattgtggg  cttcggtggc  agggagctgg  gactcgggg
 961 ggtcttacag  gtagttcagg  ctctgacttg  ttctcagtgg  tccacaccaa  ctgaacaggg
1021 cctcttccag  gatgggcacg  tggttgtcgg  tgggctcttt  aaccttcatt  acacgcctcc
1081 agacacagcc  aacaacttca  ctcagcaatc  gcattacaaa  gcttgcaccg  ggtacagctg
1141 caatctttca  cgtcatttgt  gtgaactgtt  gtgaccttt   ccctccaaa  tccaatgttt
1201 acacttggat  tctcctcatt  cttggcttca  ggctggaaaa  cctcccttg  cagtacattt
1261 acgccatggt  gtttgcagtg  gaggagatca  atcacagcgc  agcgctgctg  ccaggcgtga
1321 agctcgggta  ccacattcgc  gatagctgcg  ccctccaccc  ctggaccact  caggcggcgc
1381 tggcactggt  cgcaggagac  agtgccagct  gtgaattggc  aaccccagcg  gactactctg
1441 cagagacgag  tgaagaaaaa  ggtactgatt  aagccttgca  atacctgatg  aactcaaact
1501 tgatttaaaa  ttgtaatttt  taaaacaatt  taggtgctgc  ctccgttcct  ttgattattg
1561 gtggcgcttc  ttccaatgca  gcaaaaatac  tcctgggaac  cctgagtcca  ctatctgtac
1621 ctttagtgag  ttttccgtcc  tttcagttta  tataaatcat  atgacatgtt  tttaaagcac
1681 acatgagcct  gcggatgatg  taattggatt  ctatttataa  tataataata  ataatataaaagc
1741 tttaaggatc  tttgtggttg  ttcttccaga  taagctacac  agctagctgc  ccttgcctga
1801 gtgacaggca  ccgatatccc  accttcttca  ggaccatggc  cagtgatatt  taccaggctc
1861 aggctctcgc  ccagcttgtg  ttacgcttca  actggacgtg  gatcggggca  gtggtggcaa
1921 acaatgatta  cggtcatgtg  gcagttaagg  tgaaatattc  tggctaagca  tgcaagacat
1981 tctcctgtgg  ataatcctac  atgcacagct  gcggtgtgtt  tatctgtgta  cgtcaggtgt
2041 ttcaagagca  gactcagggg  aaaggtgtgt  gtctggcgtt  tgtcgagact  ctccagaggg
2101 agacgatcgt  ggcagacgcc  gtgcgtgcgg  cgcgcacaat  tcaggcctcg  actgcgaggg
2161 tgattctggt  ttttagctgg  tacactgacg  tagggcatct  cttccgtcag  ctgcagaaaa
2221 taaacgtgag  aagttctgtg  cagggatctg  agtgtctaat  cagtcagagg  agttctgatc
2281 tttgaacgct  gcctccgctg  caggtgaccg  acagacagtt  tctggccagc  gaggcctgga
2341 gcaccagtga  ggttcttctc  aaagatcctg  acacttctac  agtggcgagt  ggagtcgtcg
2401 gcgtggccat  cgcaagccaa  cacatccctg  ggtttgaccg  tttcctcaga  ggcctgaacc
2461 cgtctcttcg  gcccagcgac  aagttttttac  aagaattctg  ggaggaggaa  tttggctgca
2521 gccgctcgcc  tccttcttca  gagacctctg  tgatttgaa   cgcttcgctg  cctccctgca
2581 gtggtgcaga  gtctctggag  ggagtgcagc  atcccttcac  cgatacctca  cacctgaggg
2641 tgacgtataa  cgtctacctg  gctgtatatg  ctgcggccaa  cgcccttcac  cgccttctct
2701 cttgcccat   tcataacagc  ccttctggaa  cttctcactg  cacctccccg  aagggcatta
2761 aacaacaga   ggtaaagaaa  ataatacaca  gatcaaataa  acgcagtaaa  atcacaaaat
2821 aataataagt  ggcaacaccg  tcgtgtttac  agctgctgca  acacttgagc  aaagtgaatt
2881 tcaccacgcc  gcagggcaaa  cacttgtact  tccgaggtgc  agatattccg  gcaatgtacg
2941 acctcattaa  ctggcagagt  ggcacagacg  gaccctcca   gtcgtcctc  atcggtgccg
3001 tggctggatt  tgacctgcag  ctcaatgagt  cagaaattga  gtggagcgcc  aaatataatc
3061 aggtgattca  gaggaagcat  ctcaatcaca  aaaatctgga  tacatggaaa  cgtatttaat
3121 atgctggggg  tgtgcatgtc  taggtgcctg  tgtcagtgtg  cagtgagagc  tgccccccg
3181 gcaccagaaa  ggccaacagg  aagggagaac  ctctctgctg  cttcgactgt  atcccttgtg
3241 ctgacggcga  gattagcaac  acaagcggtg  agggaaatat  cacagcagct  tctttctgtt
3301 ctgaactttg  ggggtttgaa  cgtctgactg  tcactgttta  ggttctcttc  agtgtgaccg
3361 ttgccctcct  gagttctggt  ccaacgatgg  acggactgct  tgtgttcctc  gacagctgga
3421 ttttctgtcc  tttaatgaaa  ccttgggcgt  tgctctgacc  gccgtggccg  tgtccggcgc
```

FIG. 55A

```
3481 tgtggtgaca acagccgtgt ttgtggtgtt ccttcactat cgtcacacgc ccatggtgag
3541 aactcagagt cacgtcctgg aaaagaaacc actgaatctg tttaatcagt tcatcctaat
3601 ttccattgga aggttcgagc caacaactct gaattgagct tcctgctgct gctgtcactc
3661 aagctgtgtt tcctgtgctc gctggtgttc atcggtcgtc cgtccgtctg gtcctgtcgg
3721 ttccagcagg cggcttttgg gatcagcttc gtgctttgtg tttcctgcct ccaagtcaag
3781 actatagtgg ttctggcagc cttccgctcg gcccggccgg gcgcggggggc cctaatgaag
3841 tggttcggcc cgtcccaaca gagaggaagc gtttgcatct ttacttgtgt acaggcaaga
3901 gttacagatg gattaagaga aaacattgtt tttttaatgt cagtatgatt tatgtgatgt
3961 tatatgagtg tttgttttca cagtgttgag ctgatgttgc acaatgcttt ctttcatcaa
4021 ggttatcatc tgtattgttt ggctgtcact gagcccccca gtgccccaag ctgacttgga
4081 tgtgccgggc ttacaggtca ccctggagtg cgccatggcc tcgtggtgg gcttctctct
4141 ggtcctgggc tacatcggtc tgctggcctg cacctgcctc ctgttggcgt tcctggctcg
4201 gaaactcccc gacaacttca acgaggccaa gctgatcacc ttcagcatgc tgatcttctg
4261 cgccgtctgg gtggccttcg tccccgctta catcagctct cccggaaaat actcagttgc
4321 cgtggaaata tttgccatcc tggcttccag ttatggcctg ctcttctgta tctttgctcc
4381 aaagtgtttc atcatcctgt tgagacccga gaaaacaca aagaaacacc tgatgatgcg
4441 atagcaaaca aaatatgaga tttatattcc tttttagaa atatgcagtc ttaatatctg
4501 ctgctgtgtg ttatttatgc atctgcatca ataaaacgct gaaagaaatt gtaaaacaag
4561 taaaaacatt ctgattctta tttgctttca ttggctattt agaaaaaggt aatgcattat
4621 gggacattta aagcacaggg ttaataaaaa atatactata tcatgtgtct gttgtgtgta
4681 tattctaatg cagtttgatt atttattcat tatggattcc ttatcatgcc acctcaacag
4741 atc
```

FIG. 55B

GenBank Acc. No: AB008863

```
  1 catcatcctc gctggaatct tcctgggcta tatttgtccc ttcaccctca tcgcccgccc
 61 cactgtagct tcctgctacc tccagaggct cctcgtgggg ctctccgctg ccatatgcta
121 ctctgccctt gtcaccaaaa ccaatcgcat cgctcgtatt ctggcaggca gcaaaaagaa
181 gatttgcacc aggaaaccga ggttcatgag cgcctgggct caggtggtca tcgcctttat
241 cctgatcagt ctacagctca gtctggaggt caccctcatc gtcctggagc ctcctgaacc
301 catcaaatcg caccccagca taagagaggt tttcctcatt tgcaacacca gcaacatggg
361 cgtcgtggcg ccgctcggat acaacggcct gcttataatg agctgcacct actacgcctt
421 caagacgcgc aatgtacctg ccaactttaa cgaagccaaa tacatcgcc
```

FIG. 56

GenBank Acc. No: AB008864

```
  1 gcccgcatct tcagcggcgt gaaagatgga gcccagcgac cgcgcttcat cagccccacc
 61 tcccagttag ccatctgcgg cgctcttatc tcctgccagt tgctggtggc gctgatctgg
121 ttaatggtgg aggtgcccgg ggtccgcaag gaagtgagct cggagcggag gaacgtggtc
181 atcctcaagt gcaacagcaa ggacagcagc atgctgatgt cgctgaccta caactgcgtc
241 ctcatcatcc tctgcaccgt ctacgcgttc aagacgcgaa agtgccccga gaacttcaac
301 gaggccaagt tcatcggc
```

FIG. 57

GenBank Acc. No.: AB008865

```
  1 cgtgttgctt acgggcattt tcctcatcta cctcatcacc ttcctcatga tcgccgagcc
 61 aagtgtggct gtgtgtgcct tccgcaggct gtttctgggg ctcggcatgt gcatcagcta
121 ctcggccatg ctcaccaaga ccaaccggat ctaccggatc tttgagcagg gcaaaaagtc
181 agtcacgccc ccgaaattta tcagccccac ctcccagctg attatcacct tcatactcat
241 ctcagtgcag gtatacatgc gcattcacgt gcacgatctg ctgcgaagcc tctgctaacc
301 ctagcccccg tgctccttct cgcagcttct cggggtcttc atctggtttg gcgtgatgcc
361 tccgcacacc atcatcgact acgaagagca gaagcccccg aatccggagt ttgcccgcgg
421 agtcctgaag tgcgacatgt ctgacctctc cctcatctta tgtctgagct acagtctggt 481 gctgatgatc acctgcacgg tgtacgccat caagaacaga agggtccnnn nnnnnttcaa
541 cgaagccaag cccatcggc
```

FIG. 58

GenBank Acc. No: AB008866

```
  1 taccgcatct tcgagcaggg caagaggtcg gtgaccccgc ccaagttcat cagccccact
 61 tcccagctca tcatcacctt cgtgntgatc tctgtgcagg tgagcctggt ggcctgctcc
121 cacttcctgc ccgcctgaag gggcttttt tgaccttcgg ctggtgtttg tgtgcttcag
181 gtcttcggcg tgttcgtgtg gtttgctgtg gtccctcctc acaccatcat cgattacgag
241 gaactgcgtc ctccccagcc caacctggcc cggggcatcc tgaagtgcga catgtccgac
301 ctgtccatca tctgctgcct cagctacagc atcgtgctca tggtaacaca gcgaccttca
361 gccacgtcaa ctcccgctct tgtgaacgat aacaggaaat aagcgtggcg tgtcggtgtg
421 ttgctaggtg acgtgtacgg tgtacgccgt gaagagccgc ggcgttccag agacgtttaa
481 cgaagccaag cccatcggg
```

POLYVALENT CATION-SENSING RECEPTOR IN ATLANTIC SALMON

RELATED APPLICATIONS

This application is a continuation-in-part of U.S. application Ser. No. 10/125,778, filed Apr. 18, 2002 now U.S. Pat. No. 6,979,558; U.S. application Ser. No. 10/125,772, filed Apr. 18, 2002 now U.S. Pat. No. 6,951,739; and U.S. application Ser. No. 10/125,792, all filed Apr. 18, 2002 now U.S. Pat. No. 6,979,559; which are continuation-in-parts of U.S. application Ser. No. 10/121,441, filed Apr. 11, 2002 now abandoned; which is a continuation-in-part and claims priority to International Application No. PCT/US01/31704, which designated the United States and was filed on Oct. 11, 2001, published in English, which claims the benefit of U.S. Provisional Application No. 60/240,392, filed on Oct. 12, 2000, and U.S. Provisional Application No. 60/240,003, filed on Oct. 12, 2000. The entire teachings of the above applications are incorporated herein by reference.

BACKGROUND OF THE INVENTION

In nature, anadromous fish like salmon live most of their adulthood in seawater, but swim upstream to freshwater for the purpose of breeding. As a result, anadromous fish hatch from their eggs and are born in freshwater. As these fish grow, they swim downstream and gradually adapt to the seawater.

Currently, wild Atlantic salmon are classified as endangered species in multiple areas of their native habitats. Among the reasons for their decline has been man made alterations in freshwater conditions in their native streams that have produced multiple problems with their migration, spawning, smoltification and survival. One problem complicating the effective restoration of wild Atlantic salmon is the lack of a fundamental understanding of how these deleterious environmental conditions effect the salmon's ability to home to freshwater streams from the ocean, interchangeably adapt to freshwater and seawater as well as feed and grow in both salinity environments.

Despite the decline of wild populations, the global aquaculture industry has utilized Atlantic salmon as one of chief fish species for large-scale marine farming operations. At the present time, large scale breeding programs of Atlantic salmon provide for high quality fish used in production by selection of specific traits among them rapid growth, seawater adaptability, flesh quality and taste.

However, fish hatcheries have experienced some difficulty in raising salmon because the window of time in which the pre-adult salmon adapts to seawater (e.g., undergoes smoltification) is short-lived, and can be difficult to pinpoint. As a result, these hatcheries can experience significant morbidity and mortality when transferring salmon from freshwater to seawater. Additionally, many of the salmon that do survive the transfer from freshwater to seawater are stressed, and consequently, experience decreased feeding, and increased susceptibility to disease. Therefore, salmon often do not grow well after they are transferred to seawater.

The aquaculture industry loses millions of dollars each year due to problems it encounters in transferring salmon from freshwater to seawater. Therefore, a need exists to gain a better understanding of the biological processes of salmon that are related to smoltification and adaptation to varying salinities, including seawater. In particular, a need exists to identify genes that play an important role in these areas.

SUMMARY OF THE INVENTION

The present invention relates to genes that allow fish to sense and adapt to ion concentrations in the surrounding environment. Modulating one or more of these genes allow anadromous fish like salmon to better adapt to seawater during smoltification, which in turn allows salmon to grow faster and stronger after transfer to seawater. A gene, called a PolyValent Cation-sensing Receptor (PVCR), has been isolated in several species of fish, and in particular, in Atlantic Salmon. In fact, four forms of the PVCR have been isolated in Atlantic Salmon, and have been termed, "SalmoKCaR" genes and individually referred to as "SalmoKCaR#1", "SalmoKCaR#2", "SalmoKCaR#3" and "SalmoKCaR#4". "PVCR" and "SalmoKCaR" are used interchangeably when referring to Atlantic Salmon. These four genes work together to alter the salmon's sensitivity to the surrounding ion concentrations, as further described herein.

The invention embodies nucleic acid molecules (e.g., RNA, genomic DNA and cDNA) having nucleic acid sequences of SalmoKCaR#1 (SEQ ID NO: 7), SalmoKCaR#2 (SEQ ID NO: 9), SalmoKCaR#3 (SEQ ID NO: 11), or SalmoKCaR#4 (SEQ ID NO: 13). The invention also embodies polypeptide molecules having amino acid sequences of SalmoKCaR#1 (SEQ ID NO: 8), SalmoKCaR#2 (SEQ ID NO: 10), SalmoKCaR#3 (SEQ ID NO: 12), or SalmoKCaR#4 (SEQ ID NO: 14). The present invention, in particular, encompasses isolated nucleic acid molecules having nucleic acid sequences of SEQ ID NO: 7, 9, 11, or 13; the complementary strand thereof; the coding region of SEQ ID NO: 7, 9, 11, or 13; or the complementary strand thereof. The present invention also embodies nucleic acid molecules that encode polypeptides having an amino acid sequence of SEQ ID NO: 8, 10, 12, or 14. The present invention, in another embodiment, includes isolated polypeptide molecules having amino acid sequences that comprise SEQ ID NO: 8, 10, 12, or 14; or amino acid sequences encoded by the nucleic acid sequence of SEQ ID NO: 7, 9, 11, or 13.

In one embodiment, the present invention pertains to isolated nucleic acid molecules that have a nucleic acid sequence with at least about 70% (e.g., 75%, 80%, 85%, 90%, or 95%) identity with SEQ ID NO: 7, 9, 11, or 13, or the coding region of SEQ ID NO: 7, 9, 11, or 13. Such a nucleic acid sequence (e.g., SEQ ID NO: 7, 9, 11, or 13) encodes a polypeptide that allows for or assists in one or more of the following functions in Atlantic Salmon: sensing at least one SalmoKCaR modulator in serum or in the surrounding environment; adapting to at least one SalmoKCaR modulator present in the serum or surrounding environment; imprinting with an odorant; altering water intake; altering water absorption; or altering urine output.

The present invention further includes nucleic acid molecules that hybridize, preferably under high stringency conditions, with SalmoKCaR#1, SalmoKCaR#2, SalmoKCaR#3, or SalmoKCaR #4 but not to the Shark Kidney Calcium Receptor related protein (SKCaR) nucleic acid sequence (SEQ ID NO: 1, shown in FIG. 1) and/or the Fugu pheromone receptor (described in Naito, T. et al., *PNAS*, 95:5178–5181 (1998), hereinafter "Naito" and deposited as GenBank Accession Nos: AB008857 (Fugu CaR (01), SEQ ID NO: 31), AB008858 (Fugu Ca02.1, SEQ ID NO: 32), AB008859 (Fugu Ca09, SEQ ID NO: 33), AB008860 (Fugu Ca12, SEQ ID NO: 34), AB008861 (Fugu Ca13, SEQ ID NO: 35), AB008862 (Fugu Ca15.1, SEQ ID NO: 36), AB008863 (Fugu mGluR1, SEQ ID NO: 37), AB008864

(Fugu mGluR2, SEQ ID NO: 38), AB008865 (Fugu mGluR7, SEQ ID NO: 39), and AB008866 (Fugu mGluR8, SEQ ID NO: 40)). The sequences described in the Naito including those deposited under these GenBank Accession Numbers are incorporated by referenced in their entirety, and are referred to herein as the "fugu pheromone receptor" or "fugu receptor." SKCaR is a PVCR isolated from dogfish shark. Specifically, the present invention relates to an isolated nucleic acid molecule that contains a nucleic acid sequence that hybridizes under high stringency conditions to SEQ ID NO: 7, 9, 11, or 13; or the coding region of SEQ ID NO: 7, 9, 11, or 13; but excluding those that hybridize to SEQ ID NO: 1 or the nucleic acid sequence of the fugu pheromone receptor, as described herein, under the same conditions.

The present invention also includes probes, vectors, viruses, plasmids, and host cells that contain the nucleic acid sequences, as described herein. In particular, the present invention includes probes (e.g., nucleic acid probes or DNA probes) having a sequence from or hybridizes to SEQ ID NO: 7, 9, 11, or 13, but not SEQ ID NO: 1 or the nucleic acid sequence of the fugu pheromone receptor, as described herein. The present invention encompasses nucleic acid or peptide molecules purified or obtained from clones deposited with American Type Culture Collection (ATCC), Accession No: PTA-4190, PTA-4191, PTA-4192, or PTA-5131.

In another embodiment, the present invention includes isolated polypeptide molecules having at least about 70% (e.g., 75%, 80%, 85%, 90%, or 95%) identity with SEQ ID NO: 8, 10, 12, or 14; or an amino acid sequence encoded by the nucleic acid sequence of SEQ ID NO: 7, 9, 11, or 13. These polypeptide molecules (e.g., SEQ ID NO: 8, 10, 12, or 14; or those encoded by the nucleic acid sequence of SEQ ID NO: 7, 9, 11, or 13) have one or more of the following functions in Atlantic Salmon: sensing at least one SalmoKCaR modulator in serum or in the surrounding environment; adapting to at least one SalmoKCaR modulator present in the serum or surrounding environment; imprinting with an odorant; altering water intake; altering water absorption; or altering urine output.

Additionally, the present invention relates to antibodies that specifically bind to or are produced in reaction to polypeptide molecules described herein. The invention further includes fusion proteins that contain one of the polypeptide molecules described herein, and a portion of an immunoglobulin.

The present invention also pertains to assays for determining the presence or absence of a SalmoKCaR in a sample by contacting the sample to be tested with an antibody specific to at least a portion of the SalmoKCaR polypeptide sufficiently to allow formation of a complex between SalmoKCaR and the antibody, and detecting the presence or absence of the complex formation. Another assay for determining the presence or absence of a nucleic acid molecule that encodes SalmoKCaR in a sample involves contacting the sample to be tested with a nucleic acid probe that hybridizes under high stringency conditions to a nucleic acid molecule having a sequence of SEQ ID NO: 7, 9, 11, or 13, sufficiently to allow hybridization between the sample and the probe; and detecting the SalmoKCaR nucleic acid molecule in the sample. Such assay methods also include methods for determining whether a compound is a modulator of SalmoKCaR. These methods include contacting a compound to be tested with a cell that contains SalmoKCaR nucleic acid molecules and/or expresses SalmoKCaR proteins, and determining whether compounds are modulators by measuring the expression level or activity (e.g., phosphorylation, dimerization, proteolysis or intracellular signal transduction) of SalmoKCaR proteins. In one embodiment, one can measure changes that occur in one or more intracellular signal transduction systems that are altered by activation of the expressed proteins coded for by a single or combination of nucleic acids. Such methods can also encompass contacting a compound to be tested with a cell that comprises one or more of SalmoKCaR nucleic acid molecules; and determining the level of expression of said nucleic acid molecule. An increase or decrease in the expression level, as compared to a control, indicates that the compound is a modulator.

Lastly, the present invention relates to transgenic fish encoding a SalmoKCaR polypeptide or having one or more nucleic acid molecules that contain the SalmoKCaR nucleic acid sequence, as described herein.

The present invention allows for a number of advantages, including the ability to more efficiently grow Atlantic Salmon, and in particular, transfer them to seawater with increased growth and reduce mortality. The technology of the present invention also allows for assaying or testing these salmon to determine if they are ready for transfer to seawater, so that they can be transferred at the best time. The technology of the present invention provides for the imprinting of salmon with an odorant so that the salmon, once imprinted, can later more easily recognize and/or distinguish the odorant. For example, an attractant that has been used to imprint salmon can be added to feed so that the salmon will consume more feed and grow at a faster rate. A number of additional advantages for the present invention exist and are apparent from the description provided herein.

BRIEF DESCRIPTION OF THE FIGURES

FIGS. 1A–E show the annotated nucleotide sequence (SEQ ID NO: 1) and the deduced amino acids sequence (SEQ ID NO: 2) of SKCaR with the Open Reading Frame (ORF) starting at nucleotide (nt) 439 and ending at 3516.

FIGS. 7A and 7B show an annotated partial nucleotide sequence (SEQ ID NO: 3) and the deduced amino acids sequence (SEQ ID NO: 4) of an Atlantic salmon polyvalent cation-sensing receptor protein.

FIGS. 8A–8C show a second annotated partial nucleotide sequence (SEQ ID NO: 5) and the deduced amino acids sequence (SEQ ID NO: 6) of an Atlantic salmon polyvalent cation-sensing receptor protein.

FIGS. 9A–E show the nucleic acid (SEQ ID NO: 7) and amino acid (SEQ ID NO: 8) sequences of a full length Atlantic Salmon PVCR, SalmoKCaR#1 with the ORF starting at nt 180 and ending at 3005.

FIGS. 10A–E show the nucleic acid (SEQ ID NO: 9) and amino acid (SEQ ID NO: 10) sequences of a full length Atlantic Salmon PVCR, SalmoKCaR#2 with the ORF starting at nt 270 and ending at 3095.

FIGS. 11A–D show the nucleic acid (SEQ ID NO: 11) and amino acid (SEQ ID NO: 12) sequences of a full length Atlantic Salmon PVCR, SalmoKCaR#3 with the ORF starting at nt 181 and ending at 2733.

FIGS. 12A–E show the nucleic acid (SEQ ID NO: 13) and amino acid (SEQ ID NO: 14) sequences of a full length Atlantic Salmon PVCR, SalmoKCaR#4 with the ORF starting at nt 181 and ending at 3006.

FIGS. 13A–L are an alignment showing nucleic acid sequences of two partial Atlantic Salmon Clones (SEQ ID NO: 3 and 5), SalmoKCaR#1 (SEQ ID NO: 7), SalmoKCaR#2 (SEQ ID NO: 9), and SalmoKCaR#3 (SEQ ID NO: 11).

FIGS. 14A–C are an alignment showing amino acid sequences of two partial Atlantic Salmon Clones (SEQ ID NO: 4 and 6), SalmoKCaR#1 (SEQ ID NO: 8), SalmoKCaR#2 (SEQ ID NO: 10), and SalmoKCaR#3 (SEQ ID NO: 12).

Figure 16G:
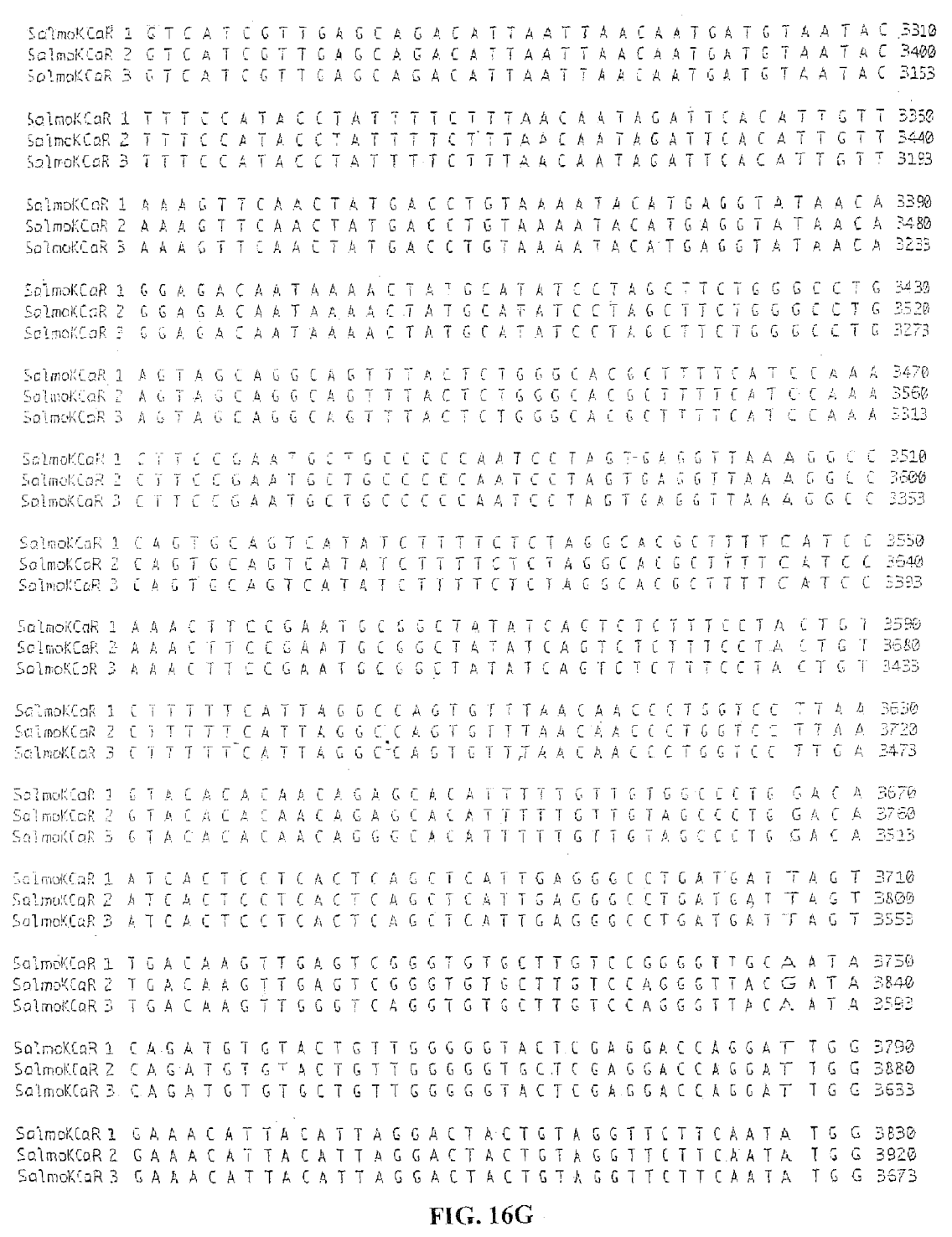

FIGS. 16A–H are an alignment of the full length nucleic acid sequences of SalmoKCaR#1, 2, and 3 (SEQ ID NO: 7, 9, and 11, respectively). Alignment obtained using Clustal method with weighted residue weight table.

FIGS. 17A–L are an alignment showing nucleic acid sequences of SalmoKCaR#1 (SEQ ID NO: 7), SalmoKCaR#2 (SEQ ID NO: 9), SalmoKCaR#3 (SEQ ID NO: 11), and SalmoKCaR#4 (SEQ ID NO: 13). Alignment was obtained using Clustal method with weighted residue weight table.

FIGS. 18A–C are an alignment showing amino acid sequences of SalmoKCaR#1 (SEQ ID NO: 8), SalmoKCaR#2 (SEQ ID NO: 10), SalmoKCaR#3 (SEQ ID NO: 12), and SalmoKCaR#4 (SEQ ID NO: 14).

FIGS. 19A–D are an alignment of the full length amino acid sequences of Human Parathyroid Calcium Receptor (HuPCaR) (SEQ ID NO: 30), SKCaR (SEQ ID NO: 2), SalmoKCaR#1 (SEQ ID NO: 8), SalmoKCaR#2 (SEQ ID NO: 10), and SalmoKCaR#3 (SEQ ID NO: 12), and SalmoKCaR#4 (SEQ ID NO: 14). Alignment obtained using Clustal method with PAM250 residue weight table.

FIGS. 20A–F are graphical representations comparing six photographs of Reverse Transcriptase Polymerase Chain Reaction (RT-PCR) analysis of freshwater (FIGS. 20B, D and F) and seawater (FIGS. 20A, C and E) adapted Atlantic salmon tissues (gill, nasal lamellae, urinary bladder, kidney, stomach, pyloric caeca, proximal intestine, distal intestine, brain, pituitary gland, olfactory bulb, liver and muscle) using either degenerate PVCR (FIGS. 20A–D) or salmon actin PCR primers (FIGS. 20E,F). Wells 1–14 for FIGS. 20A–F, top row, are designated as follows: ladder, gill, nasal lamellae, urinary bladder, kidney, stomach, pyloric caeca, proximal intestine, distal intestine, brain, pituitary gland, olfactory bulb, liver and muscle, respectively. Wells 1, 2, 7, 9, and 12, bottom row, for FIGS. 20A, C, and E are designated as ladder, water, SalmoKCaR #1, SalmoKCaR#2 and SalmoKCaR#3, respectively, and wells 1, 2, 3, 7, 9, and 12, bottom row, for FIGS. 20B,D, and F are designated as ladder, water, ovary, SalmoKCaR #1, SalmoKCaR#2 and SalmoKCaR#3, respectively.

FIG. 21A is photograph of a RT-PCR analysis using degenerate primers of steady state SalmoKCaR mRNA transcripts from kidney tissue of Atlantic Salmon adapted to freshwater, after 9 weeks of Process II treatment or 26 days after transfer to seawater. Process II treatment is defined in the Exemplification.

FIG. 21B is a photograph of a RT-PCR analysis showing increased steady state expression of SalmoKCaR transcripts in pyloric caeca of Process II treated and seawater fish as compared to freshwater Atlantic salmon smolt. Using degenerate (SEQ ID Nos 15 and 16) or actin (SEQ ID No 24 and 25) primers, samples of either freshwater (Panel A Lanes 3 and 6), Process II treated (Panel A Lanes 4 and 7) or seawater adapted (Panel A Lanes 5 and 8) Atlantic salmon smolt were analyzed by RT-PCR. To control for differences in sample loading, these identical samples were subjected to PCR analysis using actin specific primer (Panel A, Lanes 3–5). Note that both ethidium bromide stained gel (Panel A) and its corresponding Southern blot (Panel C) show increased amounts of SalmoKCaR transcripts in pyloric caeca from Process II and seawater adapted fish as compared to freshwater. As a control, Panel B demonstrates that these degenerate primers amplify SalmoKCaR #1 (Lane 1), SalmoKCaR #2 (Lane 2) and SalmoKCaR #3 (Lane 3) transcripts.

FIG. 21C is a photograph of RT-PCR analysis showing expression of SalmoKCaR transcripts in various stages of Atlantic salmon embryo development. Using degenerate (SEQ ID Nos. 15 and 16) or actin (SEQ ID No 24 and 25) primers, RNA obtained from samples of whole Atlantic salmon embryos at various stages of development were analyzed for expression of SalmoKCaRs using RT-PCR. Ethidium bromide staining of samples from dechorionated embryos (Lane 1), 50% hatched (Lane 2), 100% hatched (Lane 3), 2 weeks post hatched (Lane 4) and 4 weeks post hatched (Lane 5) shows that SalmoKCaR transcripts are present in Lanes 1–4). Southern blotting of the same gel (Panel C) confirms expression of SalmoKCaRs in embryos from very early stages up to 2 weeks after hatching. No expression of SalmoKCaR was observed in embryos 4 weeks after hatching. Panel B shows the series of controls where PCR amplification of actin content of each of the 5 samples shows they are approximately equal (lanes 1–5).

FIG. 37 is a photograph of a RT-PCR amplification of a partial SalmoKCaR mRNA transcript from various tissues (gill, nasal lamellae, urinary bladder, kidney, intestine, stomach, liver, and brain (Wells 1–8, respectively)) of Atlantic Salmon. RT-PCR reactions were separated by gel electrophoresis and either stained in ethidium bromide (EtBr) or transferred to a membrane and Southern Blotted (SB) using a 32P-labeled 653 basepair (bp) genomic DNA fragment from the Atlantic salmon SalmoKCaR gene. Wells 9 and 10 are water (blank) and positive control, respectively.

FIG. 40A is a photograph of immunocytochemistry showing the SalmoKCaR protein expression in the developing nasal lamellae (Panel A) and olfactory bulb (Panel B) after hatching of Atlantic salmon using an anti-SalmoKCaR antibody.

FIG. 40B is a photograph of immunocytochemistry of Atlantic salmon or trout larval fish using Sal-I antiserum shows abundant PVCR protein expression by selected cells. Specific binding of Sal-I antiserum denoting the presence of PVCR protein is shown by the dark reaction product. Staining of myosepta between various muscle bundles of larval fish is shown by asterisks (panel A). Panel B shows the head of a trout larvae in cross section where abundant PVCR protein is present in the skin (asterisks) and developing nasal lamellae (open arrowhead). Panel C shows PVCR expression in the developing otolith as well as localized PVCR protein in epithelial cells immediately adjacent to it. Panels D and E show high magnification views of myosepta shown in Panel A. Note the pattern of localized expression of PVCR protein where some cells contain large amounts of PVCR protein while those immediately adjacent to them have little or no expression. Panel F shows a corresponding H+E section where myosepta (open arrowheads) can be clearly distinguished from intervening muscle bundles.

FIG. 40C is a photograph showing localization of Sal ADD antiserum by immunocytochemistry. Panel A shows the pattern of immunostaining of immune anti-Sal ADD serum as compared to lack of reactivity displayed by pre-immune anti-Sal ADD serum when exposed to identical kidney tissue sections (Panel B). Note that anti-Sal ADD reactivity (denoted by arrows) is similar if not identical to that displayed by Sal-I antiserum. Corresponding kidney tubules exposed to preimmune antiserum show no reactivity (denoted by asterisks).

FIG. 50 shows the nucleic acid sequence for a Fugu receptor, Fugu CaR (01), (SEQ ID NO: 31) deposited under GenBank Accession Nos: AB008857.

FIGS. 51A–B show the nucleic acid sequence for a Fugu receptor, Fugu Ca02.1, (SEQ ID NO: 32) deposited under GenBank Accession Nos: AB008858.

FIGS. 52A–B show the nucleic acid sequence for a Fugu receptor, Fugu Ca09, (SEQ ID NO: 33) deposited under GenBank Accession Nos: AB008859.

FIGS. 53A–B show the nucleic acid sequence for a Fugu receptor, Fugu Ca12, (SEQ ID NO: 34) deposited under GenBank Accession Nos: AB008860.

FIGS. 54A–B show the nucleic acid sequence for a Fugu receptor, Fugu Ca13, (SEQ ID NO: 35) deposited under GenBank Accession Nos: AB008861.

FIGS. 55A–B show the nucleic acid sequence for a Fugu receptor, Fugu Ca15.1, (SEQ ID NO: 36) deposited under GenBank Accession Nos: AB008862.

FIG. 56 shows the nucleic acid sequence for a Fugu receptor, Fugu mGluR1, (SEQ ID NO: 37) deposited under GenBank Accession Nos: AB008863.

FIG. 57 shows the nucleic acid sequence for a Fugu receptor, Fugu mGluR2, (SEQ ID NO: 38) deposited under GenBank Accession Nos: AB008864.

FIG. 58 shows the nucleic acid sequence for a Fugu receptor, Fugu mGluR7, (SEQ ID NO: 39) deposited under GenBank Accession Nos: AB008865.

FIG. 59 shows the nucleic acid sequence for a Fugu receptor, Fugu mGluR8, (SEQ ID NO: 40) deposited under GenBank Accession Nos: AB008866.

DETAILED DESCRIPTION OF THE INVENTION

Figure 2:
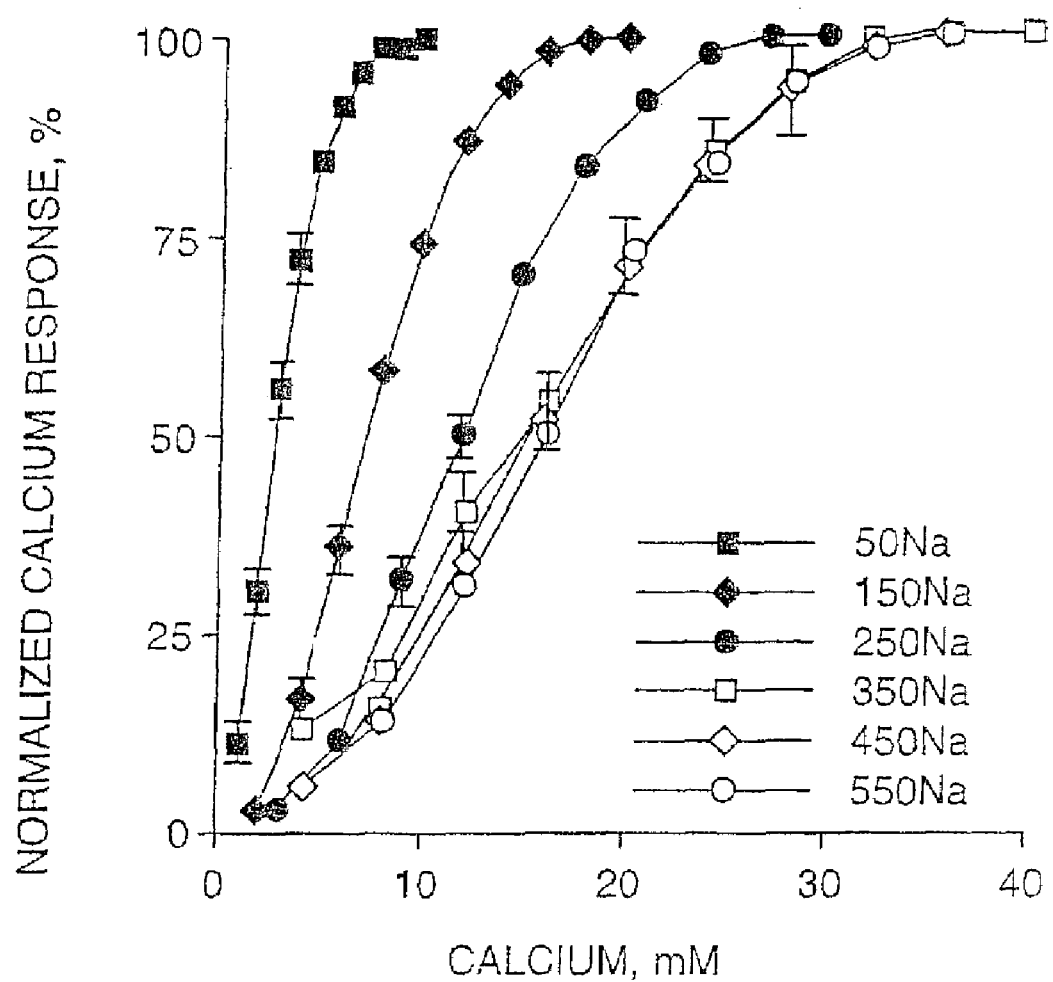
FIG. 2 is a graphical representation showing a normalized calcium response (%) against the amount of Calcium (mM) of the SKCaR-I protein when modulated by alternations in extracellular NaCl concentrations.

The present invention relates to at least four novel isolated sequences from PVCR genes, SalmoKCaR#1, SalmoKCaR#2, SalmoKCaR#3, and SalmoKCaR#4 in Atlantic Salmon. These genes encode four polypeptide sequences that are also the subject of the present invention. These polypeptide sequences allow for or assist in several functions in Atlantic Salmon including sensing at least one SalmoKCaR modulator in serum or in the surrounding environment; adapting to at least one SalmoKCaR modulator present in the serum or surrounding environment; imprinting with an odorant; altering water intake; altering water absorption; or altering urine output.

Uses of the Present Invention

One use of the present invention relates to methods for improving the raising of salmon and/or methods for preparing salmon for transfer from freshwater to seawater. These methods involve adding one or more PVCR (e.g., SalmoKCaR) modulators to the freshwater (e.g., calcium and/or magnesium), and adding a specially made or modified feed to the freshwater for consumption by the fish. The feed contains a sufficient amount of sodium chloride (NaCl) and/or a SalmoKCaR modulator (e.g., an amino acid like tryptophan) to significantly increase levels of the SalmoKCaR modulator in the serum. During this process, the serum level of the SalmoKCaR modulator significantly increases in the salmon, and causes modulated (e.g., increased and/or decreased) SalmoKCaR expression and/or altered SalmoKCaR sensitivity. This process prepares salmon for transfer to seawater, so that they can better adapt to seawater once they are transferred. The details of how to carry out this process is described in the Exemplification Section. In particular, the Exemplification describes two processes. Briefly, Process I involves adding calcium and magnesium to the water, and providing feed containing NaCl; and Process II includes adding calcium and magnesium to the water, and providing feed having both NaCl and tryptophan. Studies performed and described in Example 7 show that Atlantic Salmon maintained in freshwater and subjected to Process I had a survival rate of 91%, and those Atlantic Salmon subjected to Process II had a survival rate of 99%; as compared to control fish having a survival rate of only 67% after transfer to seawater. Similarly, in the same experiment, five days after transfer to seawater, Atlantic Salmon subjected to Process I had a survival rate of 90%, while Atlantic Salmon subjected to Process II had a survival rate of 99%. The control fish had a survival rate of only 50% after being transferred to seawater. Furthermore, experiments described in Example 6 demonstrate that modulated expression of one or more SalmoKCaR genes occurs in various tissues during Process I and Process II. Process I and II, as described herein, modulate the SalmoKCaR genes and allow for increased food consumption, growth and survival; and decreased morbidity and susceptibility to disease.

Process I and II likely have further utility in restoration of wild Atlantic salmon populations. Since a major cause of mortality of wild Atlantic salmon smolt is loss or capture by predators as they are adapting to seawater in river estuaries, treatment of wild Atlantic salmon produced in large numbers, as part of river restocking programs would boost the productivity and survival of fish produced in such programs. Moreover, several studies have shown that salmon smolt are also poisoned by exposure to heavy metals ($Al^{3+}$, $Zn^{2+}$, $Cu^{2+}$) that contaminate their native rivers in both the US and other countries such as Norway. These highly deleterious effects on salmon are manifested principally in rivers with low natural $Ca^{2+}$ concentrations. Thus, treatment of wild strains of Atlantic salmon produced in restocking hatcheries with either Process I or Process II would render these treated smolt less susceptible to the effects of heavy metals since the smoltification process in these treated smolt was much further advanced that in untreated fish. Use of Process I or II to treat Atlantic salmon that would be released into rivers also have commercial utility in large-scale ocean ranching programs where large numbers of salmon smolt are released and captured for human consumption upon their return from 1–3 years in the ocean.

Similarly, since expression of the SalmoKCaR genes changes during Process I and Process II, assaying these genes allows one to determine if the salmon are ready for transfer to seawater. Examples of such assays are ELISAs, radioimmunoassays (RIAs), southern blots and RT-PCR assays, which are described herein in detail. The salmon are subjected to either Process I or Process II for a period of time in freshwater before being transferred to seawater. The SalmoKCaR genes, or polypeptides encoded by these genes, can be assayed for determining the optimal time period for maintaining the salmon in the freshwater, before transfer to seawater. Using methods described herein, salmon can be assayed to determine if modulated levels of the SalmoKCaR genes and/or polypeptides have occurred, as compared to controls. For example, when fish that are maintained in freshwater and subjected to either Process I or Process II and changes in one or more of SalmoKCaR genes and/or polypeptide levels in at least one tissue are modulated such that they mimic changes in the same genes and/or polypeptide levels that would be seen in fish adapted to seawater, then this group of fish are ready to be transferred to seawater. In one experiment, the increased expression of SalmoKCaR genes in the kidney of Atlantic Salmon subjected to Process II was similar to the increased expression in the same tissue for Atlantic Salmon already adapted to seawater, but dissimilar to expression to Atlantic Salmon adapted to freshwater (i.e., no increased expression in the kidney water fish was seen). See Example 6. When levels of SalmoKCaR genes and/or polypeptide encoded by these genes are similar to those levels seen in fish that have been transferred to seawater, then in the experiments described herein, the transfer of these salmon result in several benefits including increased survival and growth. Also, the optimal time periods for subjecting salmon to Process I or Process II are generally between 4–6 weeks, but vary depending on the strain of salmon or process used. Hence, the assays described herein can be used to determine the optimal amount of time for subjecting the salmon to either Process I or Process II before transferring to seawater.

Additionally, comparison of the SalmoKCaR #3 sequence with data generated from site directed mutagenesis studies of mammalian CaRs indicates that the SalmoKCaR #3 protein likely generates a dominant negative effect on the other SalmoKCaR #1, #2 and #4 proteins when they are expressed together in the same cell. This dominant negative effect of SalmoKCaR #3 occurs since it lacks that necessary carboxyl terminal domain to propagate signals generated by the binding of PVCR agonists. Interactions between the fully functional SalmoKCaR #1, #2 or #4 proteins and SalmoKCaR #3 would cause a marked reduction in the sensitivity of the SalmoKCaR #1, #2 or #4 proteins. In one experiment, it was found that increased expression of SalmoKCaR#3 was seen in tissues readily exposed to high concentrations of calcium and magnesium in the surrounding environment (e.g., gill and nasal lamellae) or tissues that excrete high concentrations of calcium and magnesium (e.g., urinary bladder and kidney). Therefore, such assays can be used to determine levels of the individual SalmoKCaR genes, and compare expression levels to one another, and to individual levels of these genes of seawater adapted salmon to determine whether the salmon being tested are ready for transfer to seawater.

Uses of nucleic acids of the present invention include one or more of the following: (1) producing receptor proteins which can be used, for example, for structure determination, to assay a molecule's activity, and to obtain antibodies binding to the receptor; (2) being sequenced to determine a receptor's nucleotide sequence which can be used, for example, as a basis for comparison with other receptors to determine one or more of the following: conserved sequences; unique nucleotide sequences for normal and altered receptors; and nucleotide sequences to be used as target sites for antisense nucleic acids, ribozymes, or PCR amplification primers; (3) as hybridization detection probes to detect the presence of a native receptor and/or a related receptor in a sample, as further described herein to determine the presence or level of SalmoKCaR in a sample for, e.g., assessing whether salmon are ready for transfer to seawater; (4) as PCR primers to generate particular nucleic acid sequence sequences, for example, to generate sequences to be used as hybridization detection probes; and (5) for determining and isolating additional aquatic PVCR homologs in other species.

Another use for nucleic acid sequences of SalmoKCaRs #1, #2, #3, or #4 is as probes for the screening of Atlantic salmon broodstock, eggs, sperm, embryos or larval and juvenile fish as part of breeding programs. Use of SalmoKCaR probes would enable identification of desirable traits such as enhanced salinity responsiveness, homing, growth in seawater or freshwater or improve the feed utilization that were due to or associated with naturally occurring or induced mutations of SalmoKCaR genes. Nucleic acid sequences of SalmoKCaRs #1, #2, #3, or #4 can also be used as probes for screening of wild Atlantic salmon in various regions as a tool to identify specific strains of fish from both sea run and land locked strains. Such strains could then be used to interbreed with existing commercial strains to produce further improvements in fish performance.

The structural-functional data generated via study of recombinant SalmoKCaRs after their expression in cells as functional proteins can be used to identify desirable alternations in the function of SalmoKCaR proteins that could then be screened for as part of genetic selection-broodstock enhancement program.

Cell lines expressing SalmoKCaR proteins, either individually or in various combinations, would have utility and value as a means to assay various compounds, chemicals and water conditions that occur both in the natural and commercial environments. Utilization of transfected cells expressing SalmoKCaR #1–4 proteins either alone or in various combinations can be used in screening methods to identify both naturally occurring and commercially synthesized compounds that would enhance the performance of wild or commercially produced Atlantic salmon including salinity adaption, feeding, growth and maturation, flesh quality, homing to areas of spawning, recognition of specific odorants as part of imprinting, utilization of nutrients with improved efficiency and altered behavior. Such screening assay would be a vast improvement over existing assays where large numbers of fish are required and their end response (e.g., behavior, feeding, growth, survival or appearance is altered) to a given compound produce complicated assays that have many problems with data interpretation. Transfected cells expressing SalmoKCaR #1–4 proteins either alone or in various combinations can also be used in screening methods to screen for specific water conditions including pH, ionic strength and composition of various compounds dissolved in the water to alter the function of SalmoKCaR proteins and thus lead to improved salinity responses in various life stages of Atlantic salmon. Such assays would be designed to determine the interactions and effects of these conditions on SalmoKCaR proteins without having to test the effects of such compounds on either whole living fish or some tissue explants.

Fragments of recombinant SalmoKCaR proteins also provide a utility as modulators of PVCR function that could be added to water, applied to tissue surfaces such as gills or skin or injected into fish via standard techniques. The present invention is also useful in immunization of any one of the various life stages of Atlantic salmon (eggs, embryo, larval or juvenile or adult fish) with either whole or fragments of recombinant SalmoKCaR proteins to create antibody responses that would, in turn, alter SalmoKCaR mediated functions of fish.

The present invention is not limited to the uses described in this section. Based on the data and information described herein, additional uses of the present invention may be readily appreciated by one of skill in the art.

The SalmoKCaR Polypeptides and its Function

The present invention relates to isolated polypeptide molecules that have been isolated in Atlantic Salmon including four full length sequences. The present invention includes polypeptide molecules that contain the sequence of any one of the full length SalmoKCaR amino acid sequence (SEQ ID NO: 8, 10, 12, or 14). See FIGS. 9, 10, 11, and 12. The present invention also pertains polypeptide molecules that are encoded by nucleic acid molecules having the sequence of any one of the isolated full length SalmoKCaR nucleic acid sequences (SEQ ID NO: 7, 9, 11, or 13).

SalmoKCaR polypeptides referred to herein as "isolated" are polypeptides that separated away from other proteins and cellular material of their source of origin. Isolated SalmoKCaR proteins include essentially pure protein, proteins produced by chemical synthesis, by combinations of biological and chemical synthesis and by recombinant methods. The proteins of the present invention have been isolated and characterized as to its physical characteristics using laboratory techniques common to protein purification, for example, salting out, immunoprecipitation, column chromatography, high pressure liquid chromatography or electrophoresis. SalmoKCaR proteins are found in many tissues in fish including gill, nasal lamellae, urinary bladder, kidney, stomach, pyloric caeca, proximal intestine, distal intestine, brain, pituitary gland, olfactory bulb, liver, muscle, skin and brain.

The present invention also encompasses SalmoKCaR proteins and polypeptides having amino acid sequences analogous to the amino acid sequences of SalmoKCaR polypeptides. Such polypeptides are defined herein as SalmoKCaR analogs (e.g., homologues), or mutants or derivatives. "Analogous" or "homolgous" amino acid sequences refer to amino acid sequences with sufficient identity of any one of the SalmoKCaR amino acid sequences so as to possess the biological activity of any one of the native SalmoKCaR polypeptides. For example, an analog polypeptide can be produced with "silent" changes in the amino acid sequence wherein one, or more, amino acid residues differ from the amino acid residues of any one of the SalmoKCaR protein, yet still possesses the function or biological activity of the SalmoKCaR. Examples of such differences include additions, deletions or substitutions of residues of the amino acid sequence of SalmoKCaR. Also encompassed by the present invention are analogous polypeptides that exhibit greater, or lesser, biological activity of any one of the SalmoKCaR proteins of the present invention. Such polypeptides can be made by mutating (e.g., substituting, deleting or adding) one or more amino acid or nucleic acid residues to any of the isolated SalmoKCaR molecules described herein. Such mutations can be performed using methods described herein and those known in the art. In particular, the present invention relates to homologous polypeptide molecules having at least about 70% (e.g., 75%, 80%, 85%, 90% or 95%) identity or similarity with SEQ ID NO: 8, 10, 12, or 14. Percent "identity" refers to the amount of identical nucleotides or amino acids between two nucleotides or amino acid sequences, respectfully. As used herein, "percent similarity" refers to the amount of similar or conservative amino acids between two amino acid sequences. Each of the SalmoKCaR polypeptides are homologous to one another.

The percent identity when comparing one SalmoKCaR amino acid sequence to another are as follows:

| | Percent Identity for Amino Acid Sequences* | | | |
|---|---|---|---|---|
| Query Sequence | SalmoKCaR#1 | SalmoKCaR#2 | SalmoKCaR#3 | SalmoKCaR#4 |
| SalmoKCaR#1 | N/A | 99.9% | 89.6% | 100% |
| SalmoKCaR#2 | 99.9% | N/A | 89.5% | 99.9% |
| SalmoKCaR#3 | 99.2% | 99.1% | N/A | 99.2% |
| SalmoKCaR#4 | 100% | 99.9% | 99.2% | N/A |

*Note that the percentages are based on the number of aa's in the target sequence.

The polypeptides of the present invention, including the full length sequences, the partial sequences, functional fragments and homologues, that allow for or assist in one or more of the following functions (e.g., in Atlantic Salmon): sensing at least one SalmoKCaR modulator in serum or in the surrounding environment; adapting to at least one SalmoKCaR modulator present in the serum or surrounding environment; imprinting with an odorant; altering water intake; altering water absorption; altering urine output. These and additional functions of the polypeptides are further described herein, and illustrated by the Exemplification. The term "sense" or "sensing" refers to the Salmo-KCaR's ability to alter its expression and/or sensitivity in response to a SalmoKCaR modulator.

Homologous polypeptides can be determined using methods known to those of skill in the art. Initial homology searches can be performed at NCBI against the GenBank, EMBL and SwissProt databases using, for example, the BLAST network service. Altschuler, S. F., et al., *J. Mol. Biol.*, 215:403 (1990), Altschuler, S. F., *Nucleic Acids Res.*, 25:3389–3402 (1998). Computer analysis of nucleotide sequences can be performed using the MOTIFS and the FindPatterns subroutines of the Genetics Computing Group (GCG, version 8.0) software. Protein and/or nucleotide comparisons were performed according to Higgins and Sharp (Higgins, D. G. and Sharp, P. M., *Gene,* 73:237–244 (1988) e.g., using default parameters).

The SalmoKCaR proteins of the present invention also encompass biologically active or functional polypeptide fragments of the full length SalmoKCaR proteins. Such fragments can include the partial isolated amino acid sequences (SEQ ID NO: 3 and 5), or part of the full-length amino acid sequence (SEQ ID NO: 8, 10, 12, or 14), yet possess the function or biological activity of the full length sequence. For example, polypeptide fragments comprising deletion mutants of the SalmoKCaR proteins can be designed and expressed by well-known laboratory methods. Fragments, homologues, or analogous polypeptides can be evaluated for biological activity, as described herein.

In one embodiment, the function or biological activity relates to preparing salmon for transfer to seawater. The method for preparing Atlantic Salmon for transfer to seawater includes adding at least one SalmoKCaR modulator (e.g., PVCR modulator) to the freshwater, and adding a specially made or modified feed to the freshwater for consumption by the fish. The feed contains a sufficient amount of sodium chloride (NaCl) (e.g., between about 1% and about 10% by weight, or about 10,000 mg/kg to about 100,000 mg/kg) to significantly increase levels of the SalmoKCaR modulator in the serum. This amount of NaCl in the feed causes or induces the Atlantic Salmon to drink more freshwater. Since the freshwater contains a SalmoKCaR modulator and the salmon ingest increased amounts of it, the serum level of the SalmoKCaR modulator significantly increases in the salmon, and causes modulated (e.g., increased and/or decreased) SalmoKCaR expression and/or altered SalmoKCaR sensitivity. One function or activity of the SalmoKCaR genes is to sense SalmoKCaR modulators in the serum. The SalmoKCaR expression is altered by the SalmoKCaR modulators in the serum, which provides the ability for the salmon to better adapt to seawater, undergo smoltification, survive, grow, consume food and/or to be less susceptible to disease.

A "PVCR modulator" or "SalmoKCaR modulator" refers to a compound which modulates (e.g., increases and/or decreases) expression of SalmoKCaR, or alters the sensitivity or responsiveness of SalmoKCaR genes. Such compounds include, but are not limited to, SalmoKCaR agonists (e.g., inorganic polycations, organic polycations and amino acids), Type II calcimimetics, and compounds that indirectly alter PVCR expression (e.g., 1,25 dihydroxyvitamin D in concentrations of about 3,000–10,000 International Units/kg feed), cytokines such as Interleukin Beta, and Macrophage Chemotatic Peptide-1 (MCP-1)). Examples of Type II calcimimetics, which increase and/or decrease expression, and/or sensitivity of the SalmoKCaR genes, are, for example, NPS-R-467 and NPS-R-568 from NPS Pharmaceutical Inc., (Salt Lake, Utah, U.S. Pat. Nos. 5,962,314; 5,763,569; 5,858,684; 5,981,599; 6,001,884) which can be administered in concentrations of between about 0.1 μM and about 100 μM feed or water. See Nemeth, E. F. et al., *PNAS* 95: 4040–4045 (1998). Examples of inorganic polycations are divalent cations including calcium at a concentration between about 2.0 and about 10.0 mM and magnesium at a concentration between about 0.5 and about 10.0 mM; and trivalent cations including, but not limited to, gadolinium (Gd3+) at a concentration between about 1 and about 500 μM. Organic polycations include, but are not limited to, aminoglycosides such as neomycin or gentamicin in concentrations of between about 1 and about 8 gm/kg feed as well as organic polycations including polyamines (e.g., polyarginine, polylysine, polyhistidine, polyornithine, spermine, spermidine, cadaverine, putrescine, copolymers of poly arginine/histidine, poly lysine/arginine in concentrations of between about 10 μM and 10 mM feed). See Brown, E. M. et al., *Endocrinology* 128: 3047–3054 (1991); Quinn, S. J. et al., *Am. J. Physiol.* 273: C1315–1323 (1997). Additionally, SalmoKCaR agonists include amino acids such as L-Tryptophan L-Tyrosine, L-Phenylalanine, L-Alanine, L-Serine, L-Arginine, L-Histidine, L-Leucine, L-Isoleucine, L-Aspartic acid, L-Glutamic acid, L-Glycine, L-Lysine, L-Methionine, L-Asparagine, L-Proline, L-Glutamine, L-Threonine, L-Valine, and L-Cysteine at concentrations of between about 1 and about 10 gm/kg feed. See Conigrave, A. D., et al., *PNAS* 97: 4814–4819 (2000). Amino acids, in one embodiment, are also defined as those amino acids that can be sensed by at least one SalmoKCaR in the presence of low levels of extracellular calcium (e.g., between about 1 mM and about 10 mM). In the presence of extracellular calcium, the SalmoKCaR in organs or tissues such as the intestine, pyloric caeca, or kidney can better sense amino acids. The molar concentrations refer to free or ionized concentrations of the SalmoKCaR modulator in the freshwater, and do not include amounts of bound SalmoKCaR modulator (e.g., SalmoKCaR modulator bound to negatively charged particles including glass, proteins, or plastic surfaces). Any combination of these modulators can be added to the water or to the feed (in addition to the NaCl, as described herein), so long as the combination modulates expression and/or sensitivity of one or more of the SalmoKCaR genes.

Figure 38:
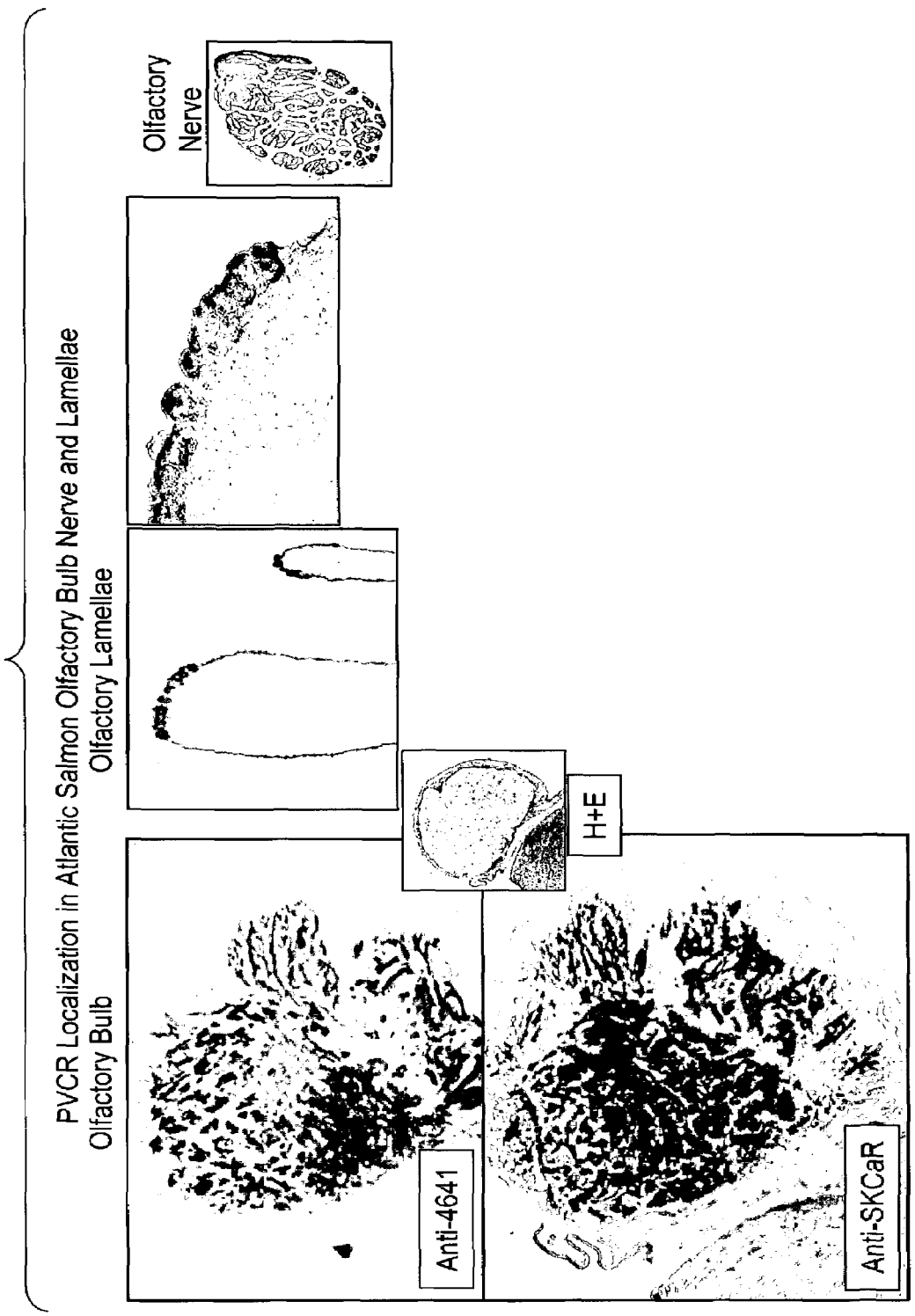
FIG. 38 is a series of photographs of immunocytochemistry showing the SalmoKCaR localization of Atlantic Salmon Olfactory Bulb Nerve and Lamellae using an anti-SalmoKCaR antibody.

Another function of the SalmoKCaR polypeptides involves imprinting Atlantic Salmon with an odorant (e.g., an attractant or repellant). Atlantic Salmon can be imprinted with an odorant so that, when the fish are later exposed to the odorant, they can more easily distinguish the odorant or are sensitized to the odorant. The SalmoKCaR polypeptides can work, for example, with one or more olfactory receptors to modify the generation of the nerve impulse during sensing of an odorant. Generation of this nerve impulse occurs upon binding of the odorant to the olfactory lamellae in the fish. The SalmoKCaR modulator alters the olfactory sensing of the salmon to the odorant. In some cases, the presence of a (e.g., at least one) SalmoKCaR modulator in freshwater reversibly reduces or ablates the fish's ability to sense certain odorants. In other cases it can be heightened or increased. By exposing the salmon in freshwater having a SalmoKCaR modulator to an odorant, the fish have an altered response which depending on the modulator would consist of either a decreased or heightened response to the odorant. Briefly, these imprinting methods involve adding at least one SalmoKCaR modulator (e.g., calcium and magnesium) to the freshwater in an amount sufficient to modulate expression and/or sensitivity of at least one SalmoKCaR gene; and adding feed for fish consumption to the freshwater. The feed contains at least one an attractant (e.g., alanine); an amount of NaCl sufficient to contribute to a significantly increased level of the SalmoKCaR modulator in serum of the Atlantic Salmon; and optionally a SalmoKCaR modulator (e.g., tryptophan). The odorant can also be added to the water, instead of the feed. Salmon that has been imprinted with an attractant consume more feed having this attractant and, as a result, grow faster. The imprinting process occurs during various developmental stages of salmon including the larval stage and the smoltification stage. Localizations of SalmoKCaR proteins and detection of SalmoKCaR expression using RT-PCR in various organs involved in the imprinting process including olfactory lamellae, olfactory bulb and brain is provided for both larval (Example 13) and smolt stages (FIGS. 37 and 38). The process of imprinting the salmon with an odorant refers to creating a lasting effect or impression on the fish so that the fish are sensitized to the odorant or can distinguish the odorant. Being sensitized to the odorant refers to the fish's ability to more easily recognize or recall the odorant. Distinguishing an odorant refers to the fish's ability to differentiate among one or more odorants, or have a preference for one odorant over another.

An odorant is a compound that binds to olfactory receptors and causes fish to sense odorants. Generation of an olfactory nerve impulse occurs upon binding of the odorant to the olfactory lamellae. A fish odorant is either a fish attractant or fish repellant. A fish attractant is a compound to which fish are attracted. The sensitivity of the attractant is modulated, at least in part, by the sensitivity and/or expression of the SalmoKCaR genes in the olfactory apparatus of the fish in response to a SalmoKCaR modulator. Examples of attractants in some fish include amino acids (e.g., L-Tryptophan L-Tyrosine, L-Phenylalanine, L-Alanine, L-Serine, L-Arginine, L-Histidine, L-Leucine, L-Isoleucine, L-Aspartic acid, L-Glutamic acid, L-Glycine, L-Lysine, L-Methionine, L-Asparagine, L-Proline, L-Glutamine, L-Threonine, L-Valine, and L-Cysteine), nucleotides (e.g., inosine monophosphate), organic compounds (e.g., glycine-betaine and trimethylamine oxide), or a combination thereof. Similarly, a fish repellant is a compound that fish are repelled by, and the sensitivity of the fish to the repellant is altered through expression and/or sensitivity of a SalmoKCaR gene in the olfactory apparatus of the fish in the presence of a SalmoKCaR modulator. An example of a repellant is a "finger rinse" which is a mixture of mammalian oils and fatty acids produced by the epidermal cells of the skin, and is left behind after human fingers are rinsed with an aqueous solution. Methods for performing a finger rinse is known in the art and is described in more detailed in the Exemplification Section.

Additionally, the function of SalmoKCaR polypeptides includes its ability to sense or adapt to ion concentrations in the surrounding environment. The SalmoKCaR polypeptides sense various SalmoKCaR modulators including calcium, magnesium and/or sodium. The SalmoKCaR polypeptides are modulated by varying ion concentrations. For instance, any one of the SalmoKCaR polypeptides can be modulated (e.g., increased or decreased) in response to a change in ion concentration (e.g., calcium, magnesium, or sodium). Responses to changes in ion concentrations of Atlantic Salmon containing the SalmoKCaR polypeptides include the ability to adapt to the changing ion concentration. Such responses include the amount the fish drinks, the amount of urine output, and the amount of water absorption. Responses also include changes in biological processes that affect its ability to excrete contaminants.

More specifically, methods are available to regulate salinity tolerance in fish by modulating (e.g., increasing, decreasing or maintaining the expression) the activity of one or more of the SalmoKCaR proteins present in cells involved in ion transport. For example, salinity tolerance of fish adapted (or acclimated) to freshwater can be increased by activating one or more of the SalmoKCaR polypeptides, for example, by increasing the expression of one or more of SalmoKCaR genes, resulting in the secretion of ions and seawater adaption. Alternatively, the salinity tolerance of fish adapted to seawater can be decreased by inhibiting one or more of the SalmoKCaR proteins, resulting in alterations in the absorption of ions and freshwater adaption.

"Salinity" refers to the concentration of various ions in a surrounding aquatic environment. In particular, salinity refers to the ionic concentration of calcium, magnesium and/or sodium (e.g., sodium chloride). "Normal salinity" levels refers to the range of ionic concentrations of typical water environment in which an aquatic species naturally lives. Normal salinity or normal seawater concentrations are about 10 mM Ca, about 40 mM Mg, and about 450 mM NaCl. "Salinity tolerance" refers to the ability of a fish to live or survive in a salinity environment that is different than the salinity of its natural environment. Modulations of the PVCR allows fish to live in about four times and one-fiftieth, preferably, twice and one-tenth the normal salinity.

The ability of anadromous fish (Atlantic salmon, trout and Arctic char) as well as euryhaline fish (flounders, alewives, eels) to traverse from freshwater to seawater environments and back again is of key importance to their lifecycles in the natural environment. Both types of fish have to undergo similar physiological changes including alterations in their urine output, altering water intake and water absorption. Both types of fish utilize environments of either freshwater (Atlantic salmon) or partial salinity (flounders) to spawn and allow for the development of larval fish into juvenile forms that then undergo changes to migrate into full strength seawater. Both types of fish utilize PVCRs to sense when adult fish have arrived in a salinity environment suitable for spawning and to guide their return back to full strength seawater. Similarly, their resulting offspring utilize PVCRs to control various organs allowing for their normal development in fresh or brackish (partial strength seawater) water and subsequently to regulate the physiological changes that permit these fish to migrate into full strength seawater.

The following experiment was done in Summer and Winter Flounder, but is applicable to Atlantic Salmon because both species of fish have PVCRs which respond to ion concentrations in a similar manner. Summer and Winter Flounder were adapted to live in ⅒th seawater (100 mOsm/kg) by reduction in salinity from 450 mM NaCl to 45 mM NaCl over an interval of 8 hrs. Summer and Winter Flounder can be maintained in ⅒ or twice the salinity for over a period of 6 months. After a 10 day interval where the Summer and Winter Flounder were fed a normal diet, the distribution of the PVCR in their urinary bladder epithelial cells was examined using immunocytochemistry. PVCR immunostaining is reduced and localized primarily to the apical membrane of epithelial cells in the urinary bladder. In contrast, the distribution of PVCR in epithelial cells lining the urinary bladders of control flounders continuously exposed to full strength seawater is more abundant and present in both the apical membranes as well as in punctate sequences throughout the cell. These data are consistent with previous Northern data where more PVCR protein is present in the urinary bladders of seawater fish vs fish adapted to brackish water. These data show that PVCR protein is expressed in epithelial cells that line the urinary bladder where the PVCR protein comes into direct contact with the urine that is being formed by the kidney. Due to its location in the cell membrane of these epithelial cells, the PVCR proteins can "sense" changes in the urine's composition on a continuous basis. Depending on the specific ionic concentrations of the urine, the PVCR protein alters the transport of ions across the epithelium of the urinary bladder and, in this way, determines the final composition of the urine. This composition and the amount of water and NaCl absorbed from the urine are critical to salinity regulation in fish.

As urinary magnesium and calcium concentrations increase when fish are present in full strength sea water, activation of apical PVCR protein causes reduction in urinary bladder water transport. The invention provides methods to facilitate euryhaline adaptation of fish to occur, and improve the adaption. More specifically, methods are now available to regulate salinity tolerance in fish by modulating (e.g., alternating, activating and or expressing) the activity of the PVCR protein present in epithelial cells involved in ion transport, as well as in endocrine and nervous tissue. For example, salinity tolerance of fish adapted (or acclimated) to fresh water can be increased by activating the PVCR, for example, by increasing the expression of PVCR in selected epithelial cells, resulting in the secretion of ions and seawater adaption. Specifically, this would involve regulatory events controlling the conversion of epithelial cells of the gill, intestine and kidney. In the kidney, PVCR activation facilitates excretion of divalent metal ions including calcium and magnesium by renal tubules. In the gill, PVCR activation reduces reabsorption of ions by gill cells that occurs in fresh water and promote the net excretion of ions by gill epithelia that occurs in salt water. In the intestine, PVCR activation will permit reabsorption of water and ions across the G.I. tract after their ingestion by fish.

Alternatively, the salinity tolerance of fish adapted to seawater can be deceased by modulating one or more of the SalmoKCaR polypeptides, for example by decreasing the expression of one or more of the SalmoKCaR genes while others may be increased. The net result of these changes would be alterations in the absorption of ions that facilitate the adaption to freshwater conditions.

In another example, Winter and Summer Flounder were maintained in at least twice the normal salinity or 1/10 the normal salinity. See Exemplification. These fish can be maintained in these environments for long periods of time (e.g., over 3 months, over 6 months, or over 1 year). These limits were defined by decreasing or increasing the ionic concentrations of calcium, magnesium, and sodium, keeping a constant ratio between the ions. These salinity limits can be further defined by increasing and/or decreasing an individual ion concentration, thereby changing the ionic concentration ratio among the ions. Increasing and/or decreasing individual ion concentrations can increase and/or decrease salinity tolerance. "Hypersalinity" or "above normal salinity" levels refers to a level of at least one ion concentration that is above the level found in normal salinity. "Hyposalinity" or "below normal salinity" levels refers to a level of at least one ion concentration that is below the level found in normal salinity.

Maintaining fish in a hypersalinity environment also results in fish with a reduced number of parasites or bacteria. Preferably, the parasites and/or bacteria are reduced to a level that is safe for human consumption, raw or cooked. More preferably, the parasites and/or bacteria are reduced to having essentially no parasites and few bacteria. These fish must be maintained in a hypersalinity environment long enough to rid the fish of these parasites or bacteria, (e.g., for at least a few days or at least a few weeks).

The host range of many parasites is limited by exposure to water salinity. For example, Diphyllobothrium species commonly known as fish tapeworms, is encountered in the flesh of fish, primarily fresh water or certain euryhaline species. Foodborne Pathogenic Microorganisms and Natural Toxins Handbook. 1991. US Food and Drug Administration Center for Food Safety and Applied Nutrition, the teachings of which are incorporated herein by reference in their entirety. In contrast, its presence in the flesh of completely marine species is much reduced or absent. Since summer flounder can survive and thrive at salinity extremes as high as 58 ppt (1.8 times normal seawater) for extended periods in recycling water, exposure of summer flounder to hypersalinity conditions might be used as a "biological" remediation process to ensure that no Diphyllobothrium species are present in the GI tract of summer flounder prior to their sale as product.

Data from Cole et al., (*J. Biol. Chem.* 272:12008–12013 (1997)), show that winter flounder elaborate an antimicrobial peptide from their skin to prevent bacterial infections. Their data reveals that in the absence of pleurocidin, *Escherichia coli* are killed by high concentrations of NaCl. In contrast, low concentrations of NaCl (<300 mM NaCl) allow *E. coli* to grow and under these conditions pleurocidin presumably helps to kill them. These data provide evidence of NaCl killing of *E. coli*, as well as highlight possible utility of bacterial elimination in fish.

Similarly, maintaining fish in a hyposalinity environment results in a fish with a reduced amount of contaminants (e.g., hydrocarbons, amines or antibiotics). Preferably, the contaminants are reduced to a level that is safe for human consumption, raw or cooked fish. More preferable, the contaminants are reduced to having essentially very little contaminants left in the fish. These fish must be maintained in a hyposalinity environment long enough to rid the fish of these contaminants, (e.g., for at least a few days or a few weeks).

Organic amines, such as trimethylamine oxide (TMAO) produce a "fishy" taste in seafood. They are excreted via the kidney in flounder. (Krogh, A., Osmotic Regulation in Aquatic Animals, Cambridge University Press, Cambridge, U.K. pgs 1–233 (1939), the teachings of which are incorporated herein by reference in their entirety). TMAO is synthesized by marine organisms consumed by fish that accumulate the TMAO in their tissues. Depending on the species of fish, the muscle content of TMAO and organic amines is either large accounting for the "strong" taste of bluefish and herring or small such as in milder tasting flounder.

The presence of SalmoKCaR in brain reflects both its involvement in basic neurotransmitter release via synaptic vesicles (Brown, E. M. et al., *New England J. of Med.*, 333:234–240 (1995)), as well as its activity to trigger various hormonal and behavioral changes that are necessary for adaptation to either fresh water or marine environments. For example, increases in water ingestion by fish upon exposure to salt water is mediated by SalmoKCaR activation in a manner similar to that described for humans where PVCR activation by hypercalcemia in the subfornical organ of the brain cause an increase in water drinking behavior (Brown, E. M. et al., *New England J. of Med.*, 333:234–240 (1995)). In fish, processes involving both alterations in serum hormonal levels and behavioral changes are mediated by the brain. These include the reproductive and spawning activities of euryhaline fish in fresh water after their migration from salt water as well as detection of salinity of their environment for purposes of feeding, nesting, migration and spawning. The key events for successful reproduction in Atlantic salmon are to migrate to a specific streambed for spawning after 1–3 years of free-swimming existence on the open ocean. Successful achievement of this challenge depends on the combination of adult salmon being able to remember and navigate their way back to this original location as well as successful imprinting of larval and juvenile Atlantic salmon to odors present in freshwater in the freshwater streambed as well as the characteristics of the mouth of the river as the fish exit the river and enter the ocean. Sensing of salinity by PVCR and its modulation of the odorant detection system of salmon for detecting various odorants is critical to the achievement of these processes.

Data obtained recently from mammals now suggest that PVCR activation plays a pivotal role in coordinating these events. For example, alterations in plasma cortisol have been demonstrated to be critical for changes in ion transport necessary for adaptation of salmon smolts from fresh water to salt water (Veillette, P. A., et al., *Gen. and Comp. Physiol.*, 97:250–258 (1995)). As demonstrated recently in humans, plasma Adrenocorticotrophic Hormone (ACTH) levels that regulate plasma cortisol levels are altered by PVCR activation.

Additionally, the function or biological activity of the SalmoKCaR polypeptide or protein is defined, in one aspect, to mean the osmoregulatory activity of SalmoKCaR protein. Assay techniques to evaluate the biological activity of SalmoKCaR proteins and their analogs are described in Brown, et al., *New Eng. J. Med.*, 333:243 (1995); Riccardi, et al, *Proc. Nat. Acad. Sci USA*, 92:131–135 (1995); and Sands, et al., *J. Clinical Investigation* 99:1399–1405 (1997). The biological activity also includes the ability of the SalmoKCaR to modulate signal transduction pathways in specific cells. Thus, depending on the distribution and nature of various signal transduction pathway proteins that are expressed in cells, biologically active SalmoKCaR proteins can modulate cellular functions in either an inhibitory or stimulatory manner.

Biologically active derivatives or analogs of the above described SalmoKCaR polypeptides, referred to herein as peptide mimetics can be designed and produced by techniques known to those of skill in the art. (see e.g., U.S. Pat. Nos. 4,612,132; 5,643,873 and 5,654,276). These mimetics can be based, for example, on a specific SalmoKCaR amino acid sequence and maintain the relative position in space of the corresponding amino acid sequence. These peptide mimetics possess biological activity similar to the biological activity of the corresponding peptide compound, but possess a "biological advantage" over the corresponding SalmoKCaR amino acid sequence with respect to one, or more, of the following properties: solubility, stability and susceptibility to hydrolysis and proteolysis.

Methods for preparing peptide mimetics include modifying the N-terminal amino group, the C-terminal carboxyl group, and/or changing one or more of the amino linkages in the peptide to a non-amino linkage. Two or more such modifications can be coupled in one peptide mimetic molecule. Modifications of peptides to produce peptide mimetics are described in U.S. Pat. Nos. 5,643,873 and 5,654,276. Other forms of the SalmoKCaR polypeptides, encompassed by the present invention, include those which are "functionally equivalent." This term, as used herein, refers to any nucleic acid sequence and its encoded amino acid, which mimics the biological activity of the SalmoKCaR polypeptides and/or functional domains thereof.

SalmoKCaR Nucleic Acid Sequences, Plasmids, Vectors and Host Cells

The present invention, in one embodiment, includes an isolated full length nucleic acid molecule having a sequence of SalmoKCaR#1 (SEQ ID NO: 7), SalmoKCaR#2 (SEQ ID NO: 9), SalmoKCaR#3 (SEQ ID NO: 11), or SalmoKCaR#4 (SEQ ID NO: 13). See FIGS. 9, 10, 11, and 12. The present invention includes sequences to the full length SalmoKCaR nucleic acid sequences, as well as the coding regions thereof. As shown in these figures, the ORF SalmoKCaR#1 begins at nt 180 and ends at nt 3005. For SalmoKCaR#2, it begins at nt 270 and ends at nt 3095, and for SalmoKCaR#3, the ORF begins at nt 181 and ends at nt 2733. SalmoKCaR#4 has an OFR that begins at nt181 and ends at nt 3006.

The present invention also encompasses isolated nucleic acid sequences that encode SalmoKCaR polypeptides, and in particular, those which encode a polypeptide molecule having an amino acid sequence of SEQ ID NO: 8, 10, 12, or 14. The SalmoKCaR full length nucleic acid sequences encode polypeptides that allow or assist in one or more of the following functions in Atlantic Salmon: sensing at least one SalmoKCaR modulator in serum or in the surrounding environment; adapting to at least one SalmoKCaR modulator present in the serum or surrounding environment; imprinting with an odorant; altering water intake; altering water absorption; or altering urine output.

The present invention encompasses the SalmoKCaR full length nucleic acid sequences, SalmoKCaR#1 (SEQ ID NO: 7), SalmoKCaR#2 (SEQ ID NO: 9), SalmoKCaR#3 (SEQ ID NO: 11), and SalmoKCaR #4 (SEQ ID NO: 13), or polypeptides encoded by these sequences, which were deposited under the Budapest Treaty with the ATCC, 10801 University Boulevard, Manassas, Va. 20110-2209, USA, under Accession Numbers PTA-4190 (Mar. 29, 2002), PTA-4191 (Mar. 29, 2002), PTA-4192 (Mar. 29, 2002), and PTA-5131 (Apr. 9, 2003), respectively. These clones are plasmid DNA which can be transformed into *E. coli* and cultured. The viability of the clones can be tested with ampicillin resistance. The sequences of the present invention can be purified from these deposits using techniques known in the art.

As used herein, an "isolated" gene or nucleotide sequence which is not flanked by nucleotide sequences which normally (e.g., in nature) flank the gene or nucleotide sequence (e.g., as in genomic sequences) and/or has been completely or partially purified from other transcribed sequences (e.g., as in a cDNA or RNA library). Thus, an isolated gene or nucleotide sequence can include a gene or nucleotide sequence which is synthesized chemically or by recombinant means. Nucleic acid constructs contained in a vector are included in the definition of "isolated" as used herein. Also, isolated nucleotide sequences include recombinant nucleic acid molecules and heterologous host cells, as well as partially or substantially purified nucleic acid molecules in solution. In vivo and in vitro RNA transcripts of the present invention are also encompassed by "isolated" nucleotide sequences. Such isolated nucleotide sequences are useful for the manufacture of the encoded SalmoKCaR polypeptide, as probes for isolating homologues sequences (e.g., from other mammalian species or other organisms), for gene mapping (e.g., by in situ hybridization), or for detecting the presence (e.g., by Southern blot analysis) or expression (e.g., by Northern blot analysis) of related genes in cells or tissue.

The SalmoKCaR nucleic acid sequences of the present invention include homologues nucleic acid sequences. "Analogous" or "homologous" nucleic acid sequences refer to nucleic acid sequences with sufficient identity of any one of the SalmoKCaR nucleic acid sequences, such that once encoded into polypeptides, they possess the biological activity of any one of the native SalmoKCaR polypeptides. For example, an analogous nucleic acid molecule can be produced with "silent" changes in the sequence wherein one, or more, nt differ from the nt of any one of the SalmoKCaR protein, yet, once encoded into a polypeptide, still possesses the function or biological activity of any one of the native SalmoKCaR. Examples of such differences include additions, deletions or substitutions. Also encompassed by the present invention are nucleic acid sequences that encode analogous polypeptides that exhibit greater, or lesser, biological activity of the SalmoKCaR proteins of the present invention. In particular, the present invention is directed to nucleic acid molecules having at least about 70% (e.g., 75%, 80%, 85%, 90% or 95%) identity with SEQ ID NO: 7, 9, 11, or 13. Each of the SalmoKCaR genes are homologues to one another. The percent identity for the SalmoKCaR nucleic acid sequences are as follows:

be sufficiently similar in sequence to permit hybridization with SalmoKCaR nucleic acid sequence under high stringency conditions. For example, non-complementary bases can be interspersed in a nucleotide sequence, or the sequences can be longer or shorter than the SalmoKCaR nucleic acid sequence, provided that the sequence has a sufficient number of bases complementary to the SalmoKCaR sequence to allow hybridization therewith. Conditions for stringency are described in e.g., Ausubel, F. M., et al., Current Protocols in Molecular Biology, (Current Protocol, 1994), and Brown, et al., *Nature,* 366:575 (1993); and further defined in conjunction with certain assays.

The SalmoKCaR sequence, or a fragment thereof, can be used as a probe to isolate additional homologues. Nucleic acids encoding SalmoKCaR polypeptides were identified by screening a cDNA library with a SalmoKCaR-specific probe under conditions known to those of skill in the art to identify homologous receptor proteins. For example, the full length sequences were isolated by screening Atlantic Salmon intestinal and kidney cDNA libraries with a probe consisting of a 653 nt PCR amplified genomic sequence (SEQ ID NO: 3). Techniques for the preparation and screening of a cDNA library are well-known to those of skill in the art. For example, techniques such as those described in Riccardi, et al., *Proc. Nat. Acad. Sci. USA,* 92:131–135 (1995), can be used. Positive clones can be isolated, subcloned and their sequences determined. Using the sequences of either a full length or several over-lapping partial cDNAs, the complete nucleotide sequence of the SalmoKCaR cDNA were obtained and the encoded amino acid sequence deduced. The sequences of the SalmoKCaRs can be compared to each other and other aquatic PVCRs to determine differences and Percent Identity for Nucleic Acid Sequences

| Query Sequence | SalmoKCaR#1 | SalmoKCaR#2 | SalmoKCaR#3 | SalmoKCaR#4 |
| --- | --- | --- | --- | --- |
| SalmoKCaR#1 | N/A | 99.8% | 95.8% | 99% |
| SalmoKCaR#2 | 97.6% | N/A | 93.6% | 98% |
| SalmoKCaR#3 | 98.7% | 98.7% | N/A | 97% |
| SalmoKCaR#4 | 99% | 98% | 97% | N/A |

The nucleic acid molecules of the present invention, including the full length sequences, the partial sequences, functional fragments and homologues, once encoded into polypeptides, allow for or assist in one or more of the following functions in Atlantic Salmon: sensing at least one SalmoKCaR modulator in serum or in the surrounding environment; adapting to at least one SalmoKCaR modulator present in the serum or surrounding environment; imprinting with an odorant; altering water intake; altering water absorption; or altering urine output. The homologous nucleic acid sequences can be determined using methods known to those of skill in the art, and by methods described herein including those described for determining homologous polypeptide sequences.

Also encompassed by the present invention are nucleic acid sequences, DNA or RNA, which are substantially complementary to the DNA sequences encoding the SalmoKCaR polypeptides and which specifically hybridize with their DNA sequences under conditions of stringency known to those of skill in the art. As defined herein, substantially complementary means that the nucleic acid need not reflect the exact sequence of the SalmoKCaR sequences, but must similarities. Methods for screening and identifying homologues genes as described in e.g., Ausubel, F. M., et al., Current Protocols in Molecular Biology, (Current Protocol, 1994).

SalmoKCaR genes were isolated by Polymerase Chain Reaction (PCR) of genomic DNA with degenerate primers (SEQ ID NOS: 15 and 16) specific to a highly conserved sequence of calcium receptors that does not contain introns. For example, partial Atlantic Salmon clones were obtained by using degenerate primers that permit selective amplification of a sequence (nucleotides 2279–2934 of SKCaR) that is highly conserved in both mammalian and shark kidney calcium receptors. SalmoKCaR #4 was isolated using the full length SalmoKCaR#2, SEQ ID NO.:9 as a probe. See Exemplification. The degenerate primers (SEQ ID NOS: 15 and 16) amplify a sequence of 653 base pairs that is present in the extracellular domain of calcium receptors. This 653 nt sequence refers to SEQ ID NO: 3 with the addition of the sequence of the primers. The resulting amplified 653 bp fragment was ligated into a cloning vector and transformed into bacterial cells for growth, purification and sequencing. Additionally, SalmoKCaR genes can be isolated by Reverse Transcriptase-Polymerase Chain Reaction (RT-PCR) after isolation of poly A+ RNA from aquatic species with the same or similar degenerate primers. Methods of PCR and RT-PCR are well characterized in the art (See generally, *PCR Technology: Principles and Applications for DNA Amplification* (ed. H. A. Erlich, Freeman Press, NY, N.Y., 1992); *PCR Protocols: A Guide to Methods and Applications* (Eds. Innis, et al., Academic Press, San Diego, Calif., 1990); Mattila, et al., *Nucleic Acids Res.,* 19:4967 (1991); Eckert, et al., *PCR Methods and Applications,* 1:17 (1991); PCR (eds. McPherson, et al., IRL Press, Oxford); and U.S. Pat. No. 4,683,202. Poly A+ RNA can be isolated from any tissue which contains one or more of SalmoKCaR polypeptides by standard methods as described. Preferred tissue for polyA+RNA isolation can be determined using an antibody which is specific for the highly conserved sequence of calcium receptors, by standard methods. The partial genomic or cDNA sequences derived from a SalmoKCaR gene are unique and, thus, can be used as a unique probe to isolate the full-length cDNA from other species. Moreover, in one embodiment, this DNA fragment serves as a basis for specific assay kits for detection of SalmoKCaR expression in various tissues of Atlantic Salmon.

Also encompassed by the present invention are nucleic acid sequences, genomic DNA, cDNA, RNA or a combination thereof, which are substantially complementary to the DNA sequences encoding SalmoKCaR nucleic acid molecules and which specifically hybridize with the SalmoKCaR nucleic acid sequences under conditions of sufficient stringency (e.g., high stringency) to identify DNA sequences with substantial nucleic acid identity. In another embodiment, the invention includes nucleic acid sequences that hybridize to the SalmoKCaR sequences, SEQ ID NO: 7, 9, 11, or 13, but not to SEQ ID NO: 1 (SkCaR) or 31–40 (Fugu) under the same conditions.

The present invention embodies nucleic acid molecules (e.g., probes or primers) that hybridize to SEQ ID NO: 7, 9, 11, or 13 under high stringency conditions, as defined herein. In one aspect, the present invention includes molecules that hybridize to at least about 200 contiguous nucleotides or longer in length (e.g., 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, or 4000). Such molecules hybridize to one of the SalmoKCaR nucleic acid sequences (SEQ ID NO: 7, 9, 11, or 13) under high stringency conditions. The present invention includes those molecules that hybridize with SalmoKCaR nucleic acid molecules and encode a polypeptide that has the functions or biological activity described herein.

Typically the nucleic acid probe comprises a nucleic acid sequence (e.g. SEQ ID NO: 7, 9, 11, or 13) and is of sufficient length and complementarity to specifically hybridize to a nucleic acid sequence that encodes a SalmoKCaR polypeptide. For example, a nucleic acid probe can be at least about 5%, 10%, 20%, 30%, 40%, 50%, 60%, 70%, 80% or 90% the length of the SalmoKCaR nucleic acid sequence. The requirements of sufficient length and complementarity can be easily determined by one of skill in the art. Suitable hybridization conditions (e.g., high stringency conditions) are also described herein. Additionally, the present invention encompasses fragments that are biologically active SalmoKCaR polypeptides or nucleic acid sequences that encodes biologically active SalmoKCaR polypeptides, as described further herein.

Such fragments are useful as probes for assays described herein, and as experimental tools, or in the case of nucleic acid fragments, as primers. A preferred embodiment includes primers and probes which selectively hybridize to the nucleic acid constructs encoding any one of the SalmoKCaR proteins. For example, nucleic acid fragments which encode any one of the domains described herein are also implicated by the present invention.

Stringency conditions for hybridization refers to conditions of temperature and buffer composition which permit hybridization of a first nucleic acid sequence to a second nucleic acid sequence, wherein the conditions determine the degree of identity between those sequences which hybridize to each other. Therefore, "high stringency conditions" are those conditions wherein only nucleic acid sequences which are very similar to each other will hybridize. The sequences can be less similar to each other if they hybridize under moderate stringency conditions. Still less similarity is needed for two sequences to hybridize under low stringency conditions. By varying the hybridization conditions from a stringency level at which no hybridization occurs, to a level at which hybridization is first observed, conditions can be determined at which a given sequence will hybridize to those sequences that are most similar to it. The precise conditions determining the stringency of a particular hybridization include not only the ionic strength, temperature, and the concentration of destabilizing agents such as formamide, but also factors such as the length of the nucleic acid sequences, their base composition, the percent of mismatched base pairs between the two sequences, and the frequency of occurrence of subsets of the sequences (e.g., small stretches of repeats) within other non-identical sequences. Washing is the step in which conditions are set so as to determine a minimum level of similarity between the sequences hybridizing with each other. Generally, from the lowest temperature at which only homologous hybridization occurs, a 1% mismatch between two sequences results in a 1° C. decrease in the melting temperature ($T_m$) for any chosen SSC concentration. Generally, a doubling of the concentration of SSC results in an increase in the $T_m$ of about 17° C. Using these guidelines, the washing temperature can be determined empirically, depending on the level of mismatch sought. Hybridization and wash conditions are explained in *Current Protocols in Molecular Biology* (Ausubel, F. M. et al., eds., John Wiley & Sons, Inc., 1995, with supplemental updates) on pages 2.10.1 to 2.10.16, and 6.3.1 to 6.3.6.

High stringency conditions can employ hybridization at either (1) 1×SSC (10×SSC=3 M NaCl, 0.3 M Na$_3$-citrate.2H$_2$O (88 g/liter), pH to 7.0 with 1 M HCl), 1% SDS (sodium dodecyl sulfate), 0.1–2 mg/ml denatured calf thymus DNA at 65° C., (2) 1×SSC, 50% formamide, 1% SDS, 0.1–2 mg/ml denatured calf thymus DNA at 42° C., (3) 1% bovine serum albumin (fraction V), 1 mM Na$_2$.EDTA, 0.5 M NaHPO$_4$ (pH 7.2) (1 M NaHPO$_4$=134 g Na$_2$HPO$_4$.7H$_2$O, 4 ml 85% H$_3$PO$_4$ per liter), 7% SDS, 0.1–2 mg/ml denatured calf thymus DNA at 65° C., (4) 50% formamide, 5×SSC, 0.02 M Tris-HCl (pH 7.6), 1× Denhardt's solution (100×=10 g Ficoll 400, 10 g polyvinylpyrrolidone, 10 g bovine serum albumin (fraction V), water to 500 ml), 10% dextran sulfate, 1% SDS, 0.1–2 mg/ml denatured calf thymus DNA at 42° C., (5) 5×SSC, 5× Denhardt's solution, 1% SDS, 100 µg/ml denatured calf thymus DNA at 65° C., or (6) 5×SSC, 5× Denhardt's solution, 50% formamide, 1% SDS, 100 µg/ml denatured calf thymus DNA at 42° C., with high stringency washes of either (1) 0.3–0.1×SSC, 0.1% SDS at 65° C., or (2) 1 mM Na$_2$EDTA, 40 mM NaHPO$_4$ (pH 7.2), 1% SDS at 65° C. The above conditions are intended to be used for DNA-DNA hybrids of 50 base pairs or longer. Where the hybrid is believed to be less than 18 base pairs in length, the hybridization and wash temperatures should be 5–10° C. below that of the calculated $T_m$ of the hybrid, where $T_m$ in ° C.=(2× the number of A and T bases)+(4× the number of G and C bases). For hybrids believed to be about 18 to about 49 base pairs in length, the $T_m$ in ° C.=(81.5° C.+16.6 ($\log_{10}$M)+0.41(% G+C)−0.61 (% formamide)−500/L), where "M" is the molarity of monovalent cations (e.g., Na$^+$), and "L" is the length of the hybrid in base pairs.

Moderate stringency conditions can employ hybridization at either (1) 4×SSC, (10×SSC=3 M NaCl, 0.3 M Na$_3$-citrate.2H$_2$O (88 g/liter), pH to 7.0 with 1 M HCl), 1% SDS (sodium dodecyl sulfate), 0.1–2 mg/ml denatured calf thymus DNA at 65° C., (2) 4×SSC, 50% formamide, 1% SDS, 0.1–2 mg/ml denatured calf thymus DNA at 42° C., (3) 1% bovine serum albumin (fraction V), 1 mM Na$_2$.EDTA, 0.5 M NaHPO$_4$ (pH 7.2) (1 M NaHPO$_4$=134 g Na$_2$HPO$_4$.7H$_2$O, 4 ml 85% H$_3$PO$_4$ per liter), 7% SDS, 0.1–2 mg/ml denatured calf thymus DNA at 65° C., (4) 50% formamide, 5×SSC, 0.02 M Tris-HCl (pH 7.6), 1× Denhardt's solution (100×=10 g Ficoll 400, 10 g polyvinylpyrrolidone, 10 g bovine serum albumin (fraction V), water to 500 ml), 10% dextran sulfate, 1% SDS, 0.1–2 mg/ml denatured calf thymus DNA at 42° C., (5) 5×SSC, 5× Denhardt's solution, 1% SDS, 100 μg/ml denatured calf thymus DNA at 65° C., or (6) 5×SSC, 5× Denhardt's solution, 50% formamide, 1% SDS, 100 μg/ml denatured calf thymus DNA at 42° C., with moderate stringency washes of 1×SSC, 0.1% SDS at 65° C. The above conditions are intended to be used for DNA-DNA hybrids of 50 base pairs or longer. Where the hybrid is believed to be less than 18 base pairs in length, the hybridization and wash temperatures should be 5–10° C. below that of the calculated $T_m$ of the hybrid, where $T_m$ in ° C.=(2× the number of A and T bases)+(4× the number of G and C bases). For hybrids believed to be about 18 to about 49 base pairs in length, the $T_m$ in ° C.=(81.5° C.+16.6($\log_{10}$M)+0.41(% G+C)−0.61 (% formamide)−500/L), where "M" is the molarity of monovalent cations (e.g., Na$^+$), and "L" is the length of the hybrid in base pairs.

Low stringency conditions can employ hybridization at either (1) 4×SSC, (10×SSC=3 M NaCl, 0.3 M Na$_3$-citrate.2H$_2$O (88 g/liter), pH to 7.0 with 1 M HCl), 1% SDS (sodium dodecyl sulfate), 0.1–2 mg/ml denatured calf thymus DNA at 50° C., (2) 6×SSC, 50% formamide, 1% SDS, 0.1–2 mg/ml denatured calf thymus DNA at 40° C., (3) 1% bovine serum albumin (fraction V), 1 mM Na$_2$.EDTA, 0.5 M NaHPO$_4$ (pH 7.2) (1 M NaHPO$_4$=134 g Na$_2$HPO$_4$.7H$_2$O, 4 ml 85% H$_3$PO$_4$ per liter), 7% SDS, 0.1–2 mg/ml denatured calf thymus DNA at 50° C., (4) 50% formamide, 5×SSC, 0.02 M Tris-HCl (pH 7.6), 1× Denhardt's solution (100×=10 g Ficoll 400, 10 g polyvinylpyrrolidone, 10 g bovine serum albumin (fraction V), water to 500 ml), 10% dextran sulfate, 1% SDS, 0.1–2 mg/ml denatured calf thymus DNA at 40° C., (5) 5×SSC, 5× Denhardt's solution, 1% SDS, 100 μg/ml denatured calf thymus DNA at 50° C., or (6) 5×SSC, 5× Denhardt's solution, 50% formamide, 1% SDS, 100 μg/ml denatured calf thymus DNA at 40° C., with low stringency washes of either 2×SSC, 0.1% SDS at 50° C., or (2) 0.5% bovine serum albumin (fraction V), 1 mM Na$_2$EDTA, 40 mM NaHPO$_4$ (pH 7.2), 5% SDS. The above conditions are intended to be used for DNA-DNA hybrids of 50 base pairs or longer. Where the hybrid is believed to be less than 18 base pairs in length, the hybridization and wash temperatures should be 5–10° C. below that of the calculated $T_m$ of the hybrid, where $T_m$ in ° C.=(2× the number of A and T bases)+(4× the number of G and C bases). For hybrids believed to be about 18 to about 49 base pairs in length, the $T_m$ in ° C.=(81.5° C.+16.6($\log_{10}$M)+0.41(% G+C)−0.61 (% formamide)−500/L), where "M" is the molarity of monovalent cations (e.g., Na$^+$), and "L" is the length of the hybrid in base pairs.

The SalmoKCaR nucleic acid sequence, or a fragment thereof, can also be used to isolate additional aquatic PVCR homologs. For example, a cDNA or genomic DNA library from the appropriate organism can be screened with labeled SalmoKCaR nucleic acid sequence to identify homologous genes as described in e.g., Ausebel, et al., Eds., *Current Protocols In Molecular Biology*, John Wiley & Sons, New York (1997).

In another embodiment, the present invention pertains to a method of isolating a SalmoKCaR nucleic acid comprising contacting an isolated nucleic acid with a SalmoKCaR-specific hybridization probe and identifying an aquatic PVCR. Methods for identifying a nucleic acid by hybridization are routine in the art (see *Current Protocols In Molecular Biology*, Ausubel, F. M. et al., Eds., John Wiley & Sons: New York, N.Y., (1997). The present method can optionally include a labeled SalmoKCaR probe.

The invention also provides vectors, plasmids or viruses containing one or more of the SalmoKCaR nucleic acid molecules. Suitable vectors for use in eukaryotic and prokaryotic cells are known in the art and are commercially available or readily prepared by a skilled artisan. Additional vectors can also be found, for example, in Ausubel, F. M., et al., Current Protocols in Molecular Biology, (Current Protocol, 1994) and Sambrook et al., "Molecular Cloning: A Laboratory Manual," 2nd ED. (1989).

Uses of plasmids, vectors or viruses containing the cloned SalmoKCaR receptors or receptor fragments include one or more of the following; (1) generation of hybridization probes for detection and measuring level of SalmoKCaR in tissue or isolation of SalmoKCaR homologs; (2) generation of SalmoKCaR mRNA or protein in vitro or in vivo; and (3) generation of transgenic non-human animals or recombinant host cells.

In one embodiment, the present invention encompasses host cells transformed with the plasmids, vectors or viruses described above. Nucleic acid molecules can be inserted into a construct which can, optionally, replicate and/or integrate into a recombinant host cell, by known methods. The host cell can be a eukaryote or prokaryote and includes, for example, yeast (such as *Pichia pastorius* or *Saccharomyces cerevisiae*), bacteria (such as *E. coli* or *Bacillus subtilis*), animal cells or tissue, insect Sf9 cells (such as baculoviruses infected SF9 cells) or mammalian cells (somatic or embryonic cells, Human Embryonic Kidney (HEK) cells, Chinese hamster ovary cells, HeLa cells, human 293 cells and monkey COS-7 cells). Host cells suitable in the present invention also include a fish cell, a mammalian cell, a bacterial cell, a yeast cell, an insect cell, and a plant cell.

The nucleic acid molecule can be incorporated or inserted into the host cell by known methods. Examples of suitable methods of transfecting or transforming cells include calcium phosphate precipitation, electroporation, microinjection, infection, lipofection and direct uptake. "Transformation" or "transfection" as used herein refers to the acquisition of new or altered genetic features by incorporation of additional nucleic acids, e.g., DNA. "Expression" of the genetic information of a host cell is a term of art which refers to the directed transcription of DNA to generate RNA which is translated into a polypeptide. Methods for preparing such recombinant host cells and incorporating nucleic acids are described in more detail in Sambrook et al., "Molecular Cloning: A Laboratory Manual," Second Edition (1989) and Ausubel, et al. "Current Protocols in Molecular Biology," (1992), for example.

The host cell is then maintained under suitable conditions for expression and recovery of SalmoKCaR protein. Generally, the cells are maintained in a suitable buffer and/or growth medium or nutrient source for growth of the cells and expression of the gene product(s). The growth media are not critical to the invention, are generally known in the art and include sources of carbon, nitrogen and sulfur. Examples include Luria broth, Superbroth, Dulbecco's Modified Eagles Media (DMEM), RPMI-1640, M199 and Grace's insect media. The growth media can contain a buffer, the selection of which is not critical to the invention. The pH of the buffered Media can be selected and is generally one tolerated by or optimal for growth for the host cell.

The host cell is maintained under a suitable temperature and atmosphere. Alternatively, the host cell is aerobic and the host cell is maintained under atmospheric conditions or other suitable conditions for growth. The temperature should also be selected so that the host cell tolerates the process and can be for example, between about 13–40° C.

Antibodies, Fusion Proteins and Methods of Assessment of the SalmoKCaR Nucleic Acid and Amino Acid Molecules The present invention includes methods of detecting the levels of the SalmoKCaR nucleic acid levels (mRNA levels) and/or polypeptide levels to determine whether fish are ready for transfer from freshwater to seawater. The present invention also includes methods for assaying compounds that modulate SalmoKCaR nucleic acid levels, expression levels or activity of SalmoKCaR polypeptides. Activity of SalmoKCaR polypeptides includes, but is not limited to, phosphorylation of one or more of the SalmoKCaR polypeptides, dimerization of one of the SalmoKCaR polypeptides with a second SalmoKCaR polypeptide, proteolysis of one or more of the SalmoKCaR polypeptides, and/or increase or decrease in the intracellular signal transduction system or pathway of one or more of the SalmoKCaR polypeptides. The present invention also includes assaying activities, as known in the art. Methods that measure SalmoKCaR levels include several suitable assays. Suitable assays encompass immunological methods, such as FACS analysis, radioimmunoassay, flow cytometry, immunocytochemistry, enzyme-linked immunosorbent assays (ELISA) and chemiluminescence assays. Additionally, antibodies, or antibody fragments, can also be used to detect the presence of SalmoKCaR proteins and homologs in other tissues using standard immunohistological methods. For example, immunohistochemical studies were performed using the 1169 antibody which was raised against a portion of the shark kidney calcium receptor demonstrating localized expression in the olfactory organ. Antibodies are absorbed to determine the SalmoKCaR protein levels. Antibodies could be used in a kit to monitor the SalmoKCaR protein level of fish in aquaculture. Any method known now or developed later can be used for measuring SalmoKCaR expression.

Antibodies reactive with any one of the SalmoKCaR or portions thereof can be used. In a preferred embodiment, the antibodies specifically bind with SalmoKCaR polypeptides or a portion thereof. The antibodies can be polyclonal or monoclonal, and the term antibody is intended to encompass polyclonal and monoclonal antibodies, and functional fragments thereof. The terms polyclonal and monoclonal refer to the degree of homogeneity of an antibody preparation, and are not intended to be limited to particular methods of production.

In several of the preferred embodiments, immunological techniques detect SalmoKCaR levels by means of an anti-SalmoKCaR antibody (i.e., one or more antibodies). The term "anti-SalmoKCaR" antibody includes monoclonal and/or polyclonal antibodies, and mixtures thereof.

Anti-SalmoKCaR antibodies can be raised against appropriate immunogens, such as isolated and/or recombinant SalmoKCaR, analogs or portion thereof (including synthetic molecules, such as synthetic peptides). In one embodiment, antibodies are raised against an isolated and/or recombinant SalmoKCaR or portion thereof (e.g., a peptide) or against a host cell which expresses recombinant SalmoKCaR. In addition, cells expressing recombinant SalmoKCaR, such as transfected cells, can be used as immunogens or in a screen for antibody which binds receptor.

Any suitable technique can prepare the immunizing antigen and produce polyclonal or monoclonal antibodies. The art contains a variety of these methods (see e.g., Kohler et al., Nature, 256: 495–497 (1975) and Eur. J. Immunol. 6: 511–519 (1976); Milstein et al., Nature 266: 550–552 (1977); Koprowski et al., U.S. Pat. No. 4,172,124; Harlow, E. and D. Lane, 1988, Antibodies: A Laboratory Manual, (Cold Spring Harbor Laboratory: Cold Spring Harbor, N.Y.); Current Protocols In Molecular Biology, Vol. 2 (Supplement 27, Summer '94), Ausubel, F. M. et al., Eds., (John Wiley & Sons: New York, N.Y.), Chapter 11, (1991)). Generally, fusing a suitable immortal or myeloma cell line, such as SP2/0, with antibody producing cells can produce a hybridoma. Animals immunized with the antigen of interest provide the antibody producing cell, preferably cells from the spleen or lymph nodes. Selective culture conditions isolate antibody producing hybridoma cells while limiting dilution techniques produce them. Researchers can use suitable assays such as ELISA to select antibody producing cells with the desired specificity.

Other suitable methods can produce or isolate antibodies of the requisite specificity. Examples of other methods include selecting recombinant antibody from a library or relying upon immunization of transgenic animals such as mice. Such methods include immunization of various lifestages of Atlantic salmon to produce antibodies to native PVCR proteins and thereby alter their function or specificity.

According to the method, an assay can determine the level of SalmoKCaR in a biological sample. In determining the amounts of SalmoKCaR, an assay includes combining the sample to be tested with an antibody having specificity for the SalmoKCaR, under conditions suitable for formation of a complex between antibody and the SalmoKCaR, and detecting or measuring (directly or indirectly) the formation of a complex. The sample can be obtained directly or indirectly, and can be prepared by a method suitable for the particular sample and assay format selected.

In particular, tissue samples, e.g., gill tissue samples, can be taken from fish after they are anaesthetized with MS-222. The tissue samples are fixed by immersion in 2% paraformaldehyde in appropriate Ringers solution corresponding to the osmolality of the fish, washed in Ringers, then frozen in an embedding compound, e.g., O.C.T.™ (Miles, Inc., Elkahart, Ind., USA) using methylbutane cooled with liquid nitrogen. After cutting 8–10 micron tissue sections with a cryostat, individual sections are subjected to various staining protocols. For example, sections are: 1) blocked with goat serum or serum obtained from the same species of fish, 2) incubated with rabbit anti-CaR or anti-SalmoKCaR antiserum, and 3) washed and incubated with peroxidase-conjugated affinity-purified goat antirabbit antiserum. The locations of the bound peroxidase-conjugated goat antirabbit antiserum are then visualized by development of a rose-colored aminoethylcarbazole reaction product. Individual sections are mounted, viewed and photographed by standard light microscopy techniques. The anti-CaR antiserum used to detect fish SalmoKCaR protein is raised in rabbits using a 23-mer peptide corresponding to amino acids numbers 214–236 localized in the extracellular domain of the RaK-CaR protein. The sequence of the 23-mer peptide is:
ADDDYGRPGIEKFREEAEERDIC (SEQ ID NO.: 26) A small peptide with the sequence DDYGRPGIEKFREE-AEERDICI (SEQ ID NO.: 27) or
ARSRNSADGRSGDDLPC (SEQ ID NO.: 28) can also be used to make antisera containing antibodies to SalmoK-CaRs. Such antibodies can be monoclonal, polyclonal or chimeric.

Suitable labels can be detected directly, such as radioactive, fluorescent or chemiluminescent labels. They can also be indirectly detected using labels such as enzyme labels and other antigenic or specific binding partners like biotin. Examples of such labels include fluorescent labels such as fluorescein, rhodamine, chemiluminescent labels such as luciferase, radioisotope labels such as $^{32}P$, $^{125}I$, $^{131}I$, enzyme labels such as horseradish peroxidase, and alkaline phosphatase, β-galactosidase, biotin, avidin, spin labels, magnetic beads and the like. The detection of antibodies in a complex can also be done immunologically with a second antibody which is then detected (e.g., by means of a label). Conventional methods or other suitable methods can directly or indirectly label an antibody. Labeled primary and secondary antibodies can be obtained commercially or prepared using methods know to one of skill in the art (see Harlow, E. and D. Lane, 1988, *Antibodies: A Laboratory Manual*, (Cold Spring Harbor Laboratory: Cold Spring Harbor, N.Y.).

Figure 22:
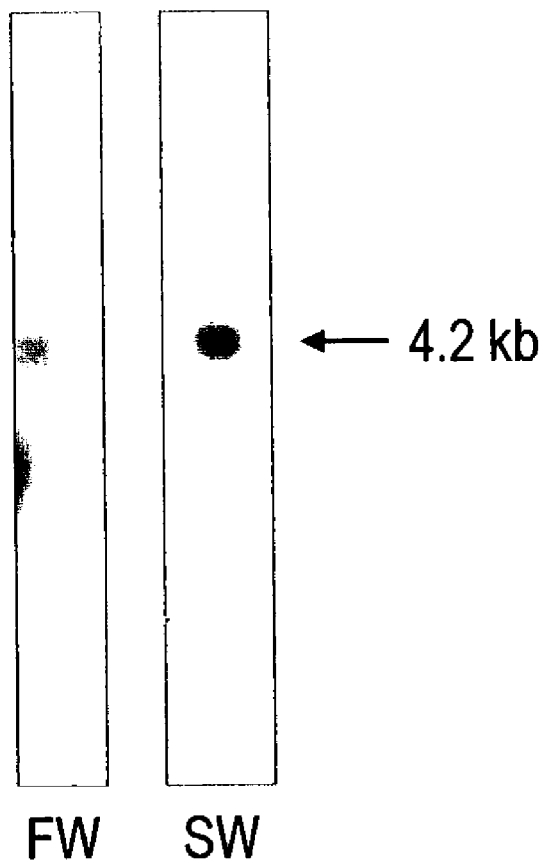
FIG. 22 is a photograph of a RNA blot containing 5 micrograms of poly $A^+$ RNA from kidney tissue dissected from either freshwater adapted (FW) or seawater adapted (SW) Atlantic salmon probed with full length SalmoKCaR #1 clone.
Figure 23A:
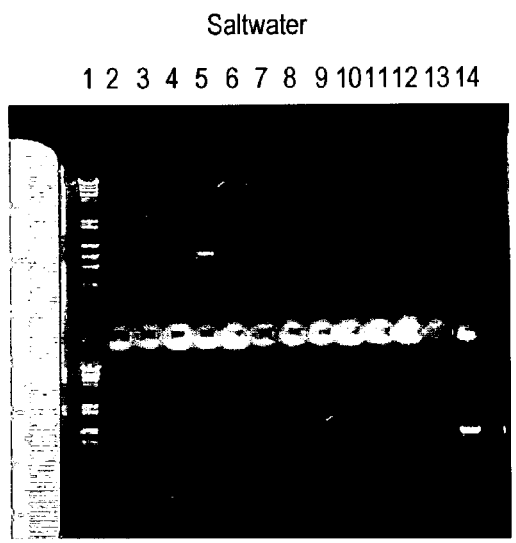
FIGS. 23A–F are graphical representations comparing six photographs showing RT-PCR analysis of freshwater (FIGS. 23B, D and F) and seawater (FIGS. 23A, C and E) adapted Atlantic salmon tissues using either SalmoKCaR #3 specific PCR (FIGS. 23A–D) primers or salmon actin PCR primers (FIGS. 23E,F). Wells 1–14 for FIGS. 23A–F, top row, are designated as follows: ladder, gill, nasal lamellae, urinary bladder, kidney, stomach, pyloric caeca, proximal intestine, distal intestine, brain, pituitary gland, olfactory bulb, liver and muscle, respectively. Wells 1, 2, 8, 11, and 14, bottom row, for FIGS. 23A, C, and E are designated as ladder, water, SalmoKCaR #1, SalmoKCaR#2 and SalmoKCaR#3, respectively, and wells 1, 2, 3, 8, 11, and 14, bottom row, for FIGS. 23B,D, and F are designated as ladder, water, ovary, SalmoKCaR #1, SalmoKCaR#2 and SalmoKCaR#3, respectively.
Figure 23B:
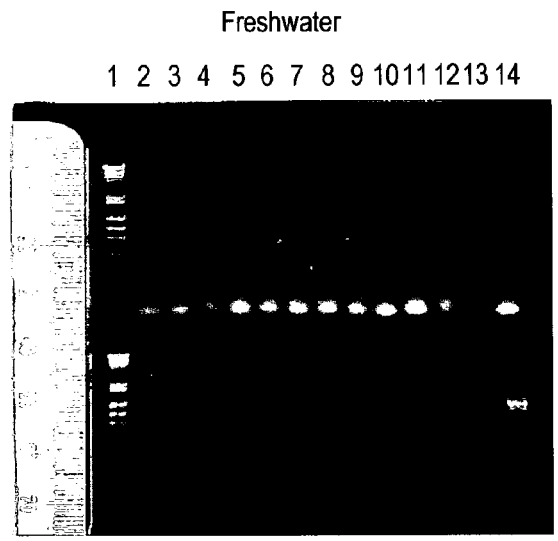
Figure 23C:
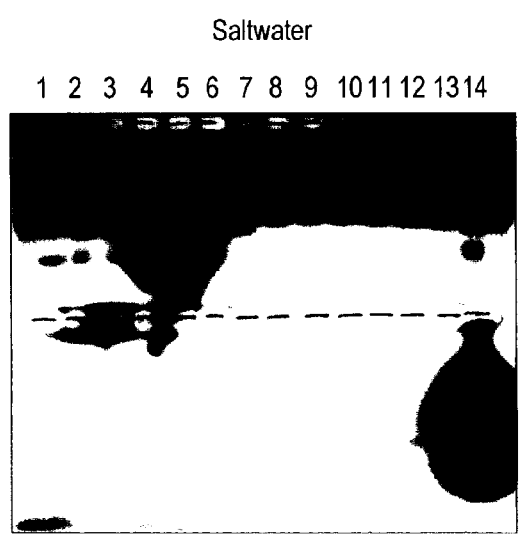
Figure 23D:
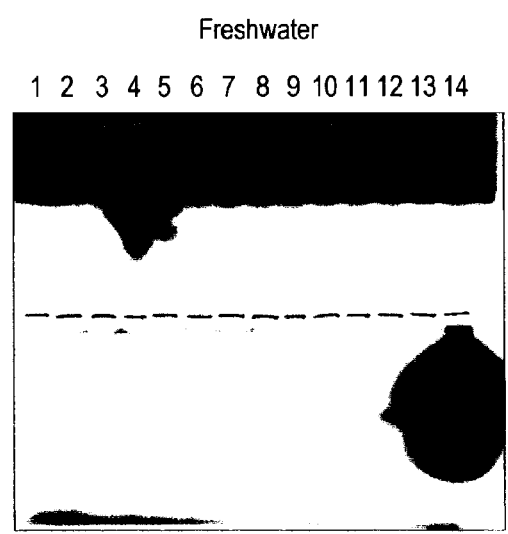
Figure 23E:
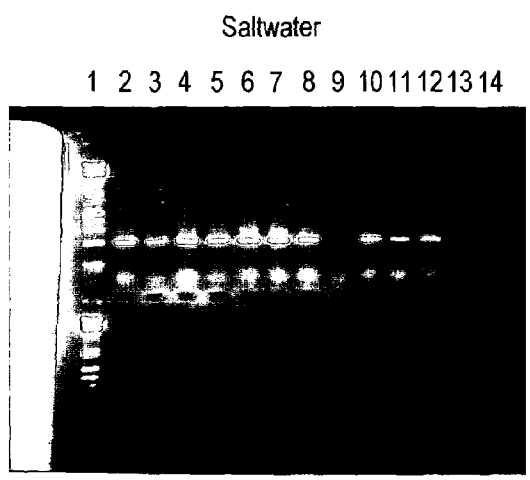
Figure 23F:
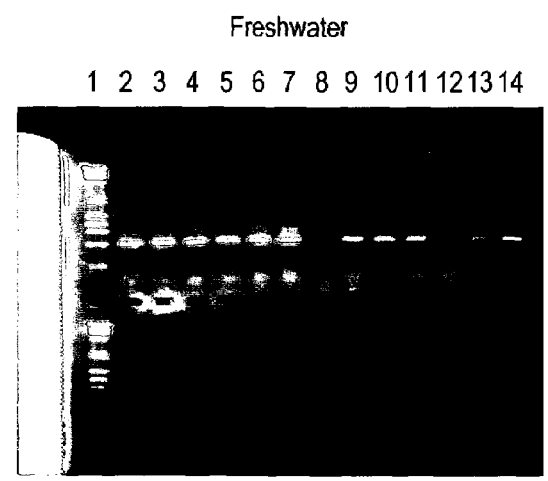
Figure 24A:
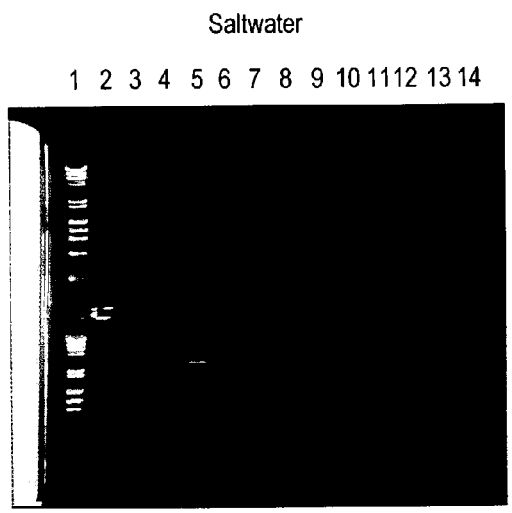
FIGS. 24A–F are graphical representations comparing six photographs showing RT-PCR analysis of freshwater (FIGS. 24B, D and F) and seawater (FIGS. 24A, C and E) adapted Atlantic salmon tissues using either SalmoKCaR #1 specific PCR primers or salmon actin PCR primers. Wells 1–14 for FIGS. 24A–F, top row, are designated as follows: ladder, gill, nasal lamellae, urinary bladder, kidney, stomach, pyloric caeca, proximal intestine, distal intestine, brain, pituitary gland, olfactory bulb, liver and muscle, respectively. Wells 1, 2, 3, 5, 6, and 7. bottom row, for FIGS. 24A, C, and E are designated as ladder, water, Kidney-RT, SalmoKCaR #1, SalmoKCaR#2 and SalmoKCaR#3, respectively, and wells 1, 2, 3, 5, 6, and 7, bottom row, for FIGS. 24B, D, and F are designated as ladder, water, ovary, SalmoKCaR #1, SalmoKCaR#2 and SalmoKCaR#3, respectively.
Figure 24B:
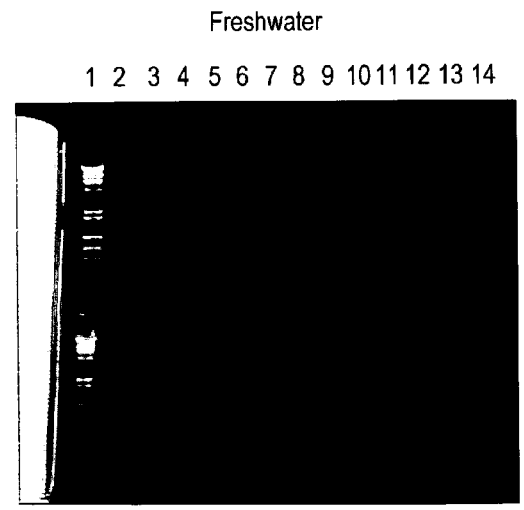
Figure 24C:
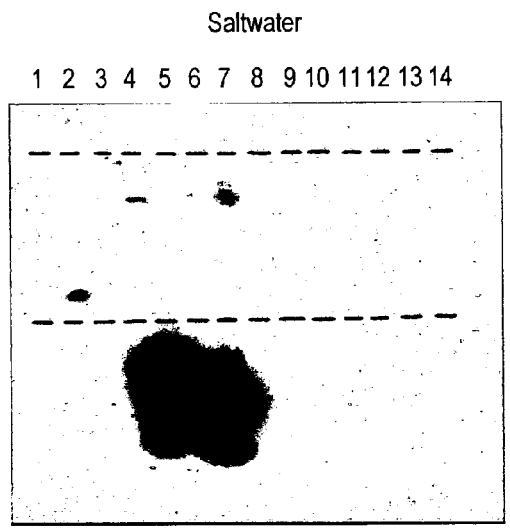
Figure 24D:
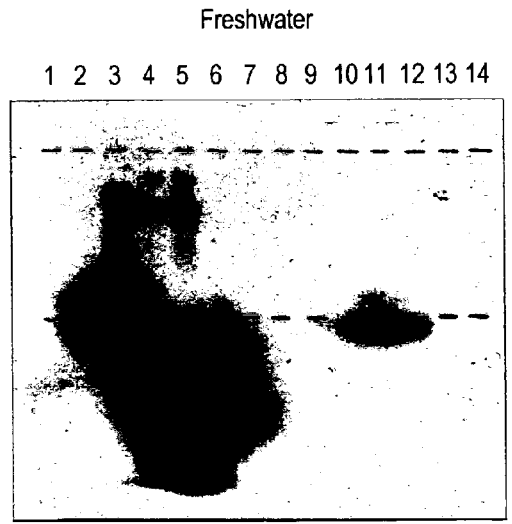
Figure 24E:
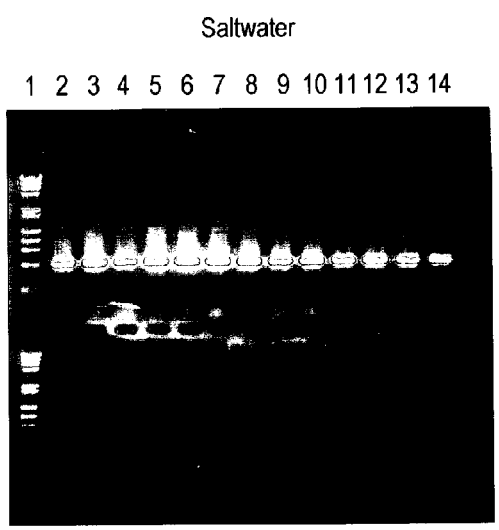
Figure 24F:
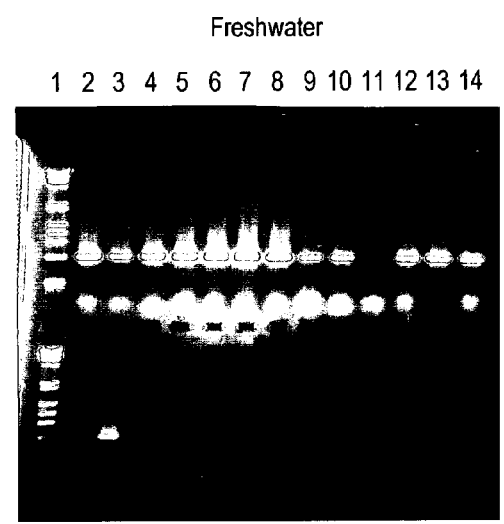
Figure 25A:
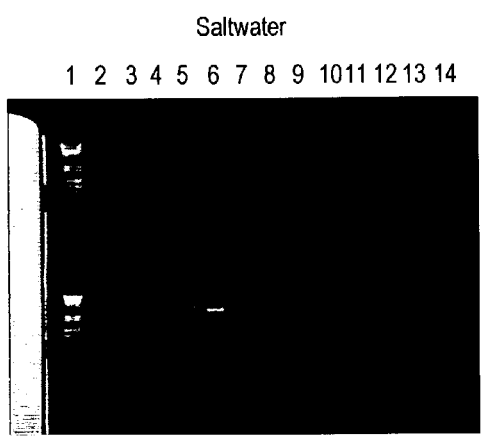
FIGS. 25A–F are graphical representations comparing six photographs showing RT-PCR analysis of freshwater (FIGS. 25B, D and F) and seawater (FIGS. 25A, C and E) adapted Atlantic salmon tissues using either SalmoKCaR #2 specific PCR primers (FIGS. 25A–D) or salmon actin PCR primers (FIGS. 25E,F). Wells 1–14 for FIGS. 25A–F, top row, are designated as follows: ladder, gill, nasal lamellae, urinary bladder, kidney, stomach, pyloric caeca, proximal intestine, distal intestine, brain, pituitary gland, olfactory bulb, liver and muscle, respectively. Wells 1, 2,3, 5, 6, and 7. bottom row, for FIGS. 25A, C, and E are designated as ladder, water, Kidney-RT, SalmoKCaR #1, SalmoKCaR#2 and SalmoKCaR#3, respectively, and wells 1, 2, 3, 5, 6, and 7, bottom row, for FIGS. 25B, D, and F are designated as ladder, water, ovary, SalmoKCaR #1, SalmoKCaR#2 and SalmoKCaR#3, respectively.
Figure 25B:
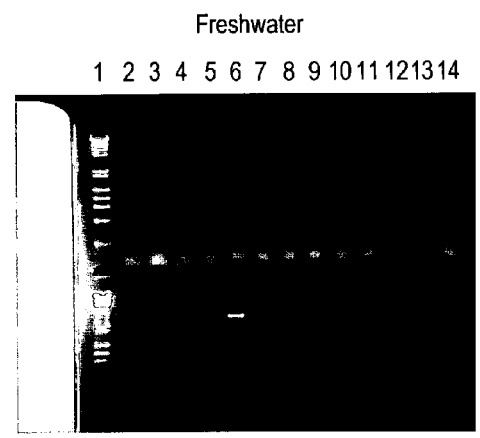
Figure 25C:
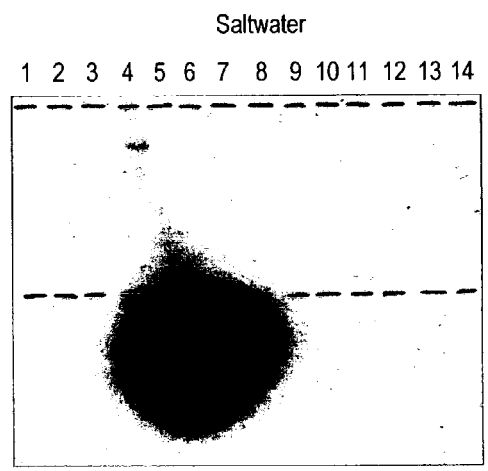
Figure 25D:
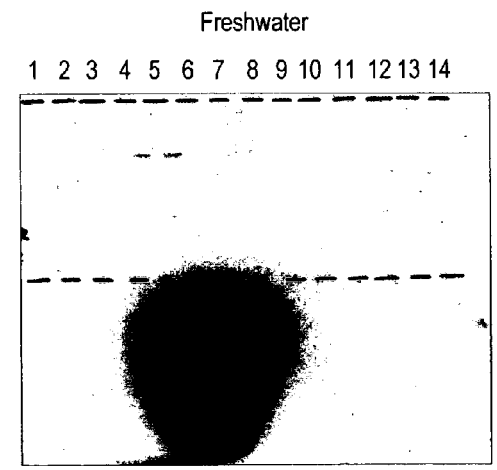
Figure 25E:
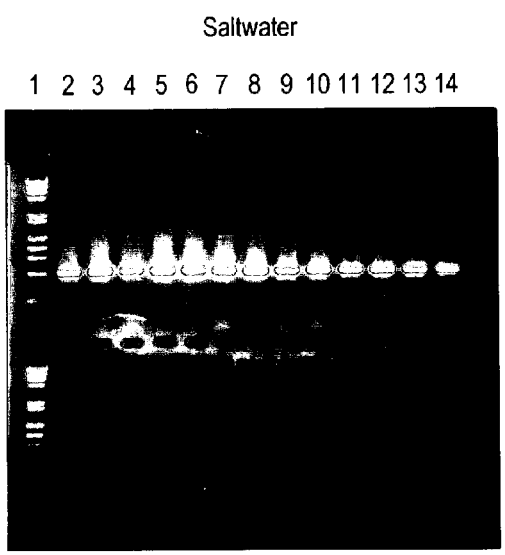
Figure 25F:
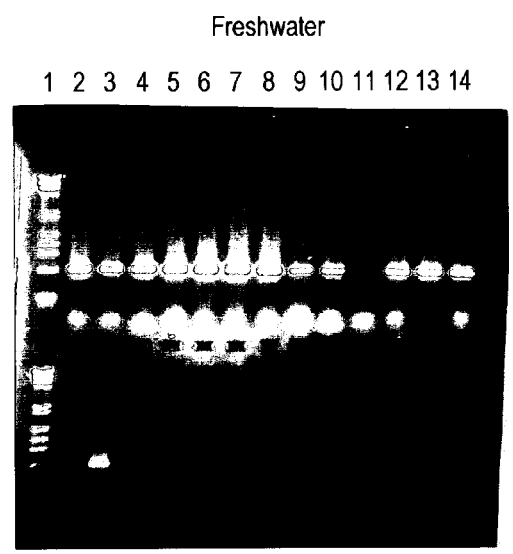

Using the immunocytochemistry method, the levels of SalmoKCaR in various tissues can be detected and examined as to whether they change in comparison to control. Modulated levels or the presence of SalmoKCaR expression in various tissues, as compared to a control, indicate that the fish or the population of fish from which a statistically significant amount of fish were tested, are ready for transfer to freshwater. A control refers to a level of SalmoKCaR, if any, from a fish that is not subjected to the steps of the present invention, e.g., not subjected to freshwater having a SalmoKCaR modulator and/or not fed a NaCl diet. For example, FIGS. 21 and 22 show that fish not subjected to the present invention had no detectable SalmoKCaR level, whereas fish that were subjected to the steps of the invention had SalmoKCaR levels that were easily detected.

In determining whether compounds are modulators, one can measure changes that occur in the expression levels of one or more the SalmoKCaR genes, or those that occur in one or more intracellular signal transduction systems or pathways. A signal transduction pathway is a pathway involved in the sensing and/or processing of stimuli. In particular, such pathways are altered by activation of the expressed proteins coded for by a single or combination of nucleic acids of the present invention.

The SalmoKCaR polypeptides can be in the form of a conjugate or a fusion protein, which can be manufactured by known methods. Fusion proteins can be manufactured according to known methods of recombinant DNA technology. For example, fusion proteins can be expressed from a nucleic acid molecule comprising sequences which code for a biologically active portion of the SalmoKCaR polypeptide and its fusion partner, for example a portion of an immunoglobulin molecule. For example, some embodiments can be produced by the intersection of a nucleic acid encoding immunoglobulin sequences into a suitable expression vector, phage vector, or other commercially available vectors. The resulting construct can be introduced into a suitable host cell for expression. Upon expression, the fusion proteins can be isolated or purified from a cell by means of an affinity matrix. By measurement of the alternations in the functions of transfected cells occurring as a result of expression of recombinant SalmoKCaR proteins, either the cells themselves or SalmoKCaR proteins produced from the cells can be utilized in a variety of screening assays that all have a high degree of utility over screening methods involving tests on the same PVCR proteins in whole fish.

The SalmoKCaRs can also be assayed by Northern blot analysis of mRNA from tissue samples. Northern blot analysis from various shark tissues has revealed that the highest degree of PVCR expression is in gill tissue, followed by the kidney and the rectal gland. There appear to be at least four distinct mRNA species of about 7 kb, 4.2 kb and 2.6 kb.

The SalmoKCaRs can also be assayed by hybridization, e.g., by hybridizing one of the SalmoKCaR sequences provided herein (e.g., SEQ ID NO: 7, 9, 11, or 13) or an oligonucleotide derived from one of the sequences, to a DNA or RNA-containing tissue sample from a fish. Such a hybridization sequence can have a detectable label, e.g., radioactive, fluorescent, etc., attached to allow the detection of hybridization product. Methods for hybridization are well known, and such methods are provided in U.S. Pat. No. 5,837,490, by Jacobs et al., the entire teachings of which are herein incorporated by reference in their entirety. The design of the oligonucleotide probe should preferably follow these parameters: (a) it should be designed to an area of the sequence which has the fewest ambiguous bases ("N's"), if any, and (b) it should be designed to have a $T_m$ of approx. 80° C. (assuming 2° C. for each A or T and 4 degrees for each G or C).

Additionally, the above probes could be used in a kit to identify SalmoKCaR homologs and their expression in various fish tissue. The present invention also encompasses the isolation of SalmoKCaR homologs and their expression in various fish tissues with a kit containing primers specific for conserved sequences of SalmoKCaR nucleic acids and proteins.

The present invention encompasses detection of Salmo-KCaRs with PCR methods using primers disclosed or derived from sequences described herein. For example, SalmoKCaRs can be detected by PCR using SEQ ID Nos: 15 and 16, as described in Example 6. PCR is the selective amplification of a target sequence by repeated rounds of nucleic acid replication utilizing sequence-specific primers and a thermostable polymerase. PCR allows recovery of entire sequences between two ends of known sequence. Methods of PCR are described herein and are known in the art.

In particular, the levels of SalmoKCaR nucleic acid can be determined in various tissues by Reverse Transcriptase-Polymerase Chain Reaction (RT-PCR) after isolation of poly A+ RNA from aquatic species. Methods of PCR and RT-PCR are well characterized in the art (See generally, PCR Technology: Principles and Applications for DNA Amplification (ed. H. A. Erlich, Freeman Press, NY, N.Y., 1992); PCR Protocols: A Guide to Methods and Applications (Eds. Innis, et al., Academic Press, San Diego, Calif., 1990); Mattila et al., Nucleic Acids Res., 19:4967 (1991); Eckert et al., PCR Methods and Applications, 1:17 (1991); PCR (eds.

McPherson et al., IRL Press, Oxford); Ausebel, F. M. et al., Current Protocols in Molecular Biology, Greene Publishing Assoc. and Wiley-Interscience 1987, & Supp. 49, 2000; and U.S. Pat. No. 4,683,202). Briefly, mRNA is extracted from the tissue of interest and reverse transcribed. Subsequently, a PCR reaction is performed with SalmoKCaR-specific primers and the presence of the predicted SalmoKCaR product is determined, for example, by agarose gel electrophoresis. Examples of SalmoKCaR-specific primers are SEQ ID NO: 18–23. The product of the RT-PCR reaction that is performed with SalmoKCaR-specific primers is referred to herein as a RT-PCR product. The RT-PCR product can include nucleic acid molecules having part or all of the SalmoKCaR sequence. The RT-PCR product can optionally be radioactively labeled and the presence or amount of SalmoKCaR product can be determined using autoradiography. Two examples of commercially available fluorescent probes that can be used in such an assay are Molecular Beacons (Stratagene) and Taqman® (Applied Biosystems). Alternative methods of labeling and quantifying the RT-PCR product are well known to one of skill in the art (see Ausebel, F. M. et al., Current Protocols in Molecular Biology, Greene Publishing Assoc. and Wiley-Interscience 1987, & Supp. 49, 2000. Poly A+ RNA can be isolated from any tissue which contains at least one SalmoKCaR by standard methods. Such tissues include, for example, gill, nasal lamellae, urinary bladder, kidney, intestine, stomach, liver and brain.

Hence, the present invention includes kits for the detection of SalmoKCaR or the quantification of SalmoKCaR having either antibodies specific for SalmoKCaR or a portion thereof, or a nucleic acid sequence that can hybridize to the nucleic acid of SalmoKCaR.

Transgenic Fish

Alterations in the expression or sensitivity of SalmoKCaRs could also be accomplished by introduction of a suitable transgene. Suitable transgenes would include either the SalmoKCaR genes itself or modifier genes that would directly or indirectly influence SalmoKCaR gene expression. Methods for successful introduction, selection and expression of the transgene in fish oocytes, embryos and adults are described in Chen, T T et al., Transgenic Fish, *Trends in Biotechnology* 8:209–215 (1990).

The present invention is further and more specifically illustrated by the following Examples, which are not intended to be limiting in any way.

Exemplification

The following examples refer to Process I and Process II throughout. Process I is also referred to herein as "SUPERSMOLT™ I Process" or "APS Process I." A "Process I" fish or smolt refers to a fish or smolt that has undergone the steps of Process I. A Process I smolt is also referred to as a "SUPERSMOLT™ I" or an "APS Process I" smolt. Likewise, Process II is also referred to herein as "SUPERSMOLT™ II Process" or "Process II." A "Process II" fish or smolt refers to a fish or smolt that has undergone the steps of Process II. A Process II smolt is also referred to as a "SUPERSMOLT™ II" or an "APS Process II" smolt.

Process I: Pre-adult anadromous fish (this includes both commercially produced S0, S1 or S2 smolts as well as smaller parr/smolt fish) are exposed to or maintained in freshwater containing either 2.0–10.0 mM Calcium and 0.5–10.0 mM Magnesium ions. This water is prepared by addition of calcium carbonate and/or chloride and magnesium chloride to the freshwater. Fish are fed with feed pellets containing 7% (weight/weight) NaCl. Fish are exposed to or maintained in this regimen of water mixture and feed for a total of 30–45 days, using standard hatchery care techniques. Water temperatures vary between 10–16° C. Fish are exposed to a constant photoperiod for the duration of Process I. A fluorescent light is used for the photoperiod.

Process II: Pre-adult anadromous fish (this includes both commercially produced S0, S1 or S2 smolts as well as smaller parr/smolt fish) are exposed to or maintained in freshwater containing 2.0–10.0 mM Calcium and 0.5–10.0 mM Magnesium ions. This water is prepared by addition of calcium carbonate and/or chloride and magnesium chloride to the freshwater. Fish are fed with feed pellets containing 7% (weight/weight) NaCl and either 2 gm or 4 gm of L-Tryptophan per kg of feed. Fish are exposed to or maintained in this regimen of water mixture and feed for a total of 30–45 days using standard hatchery care techniques. Water temperatures vary between 10–16° C. Fish are exposed to a constant photoperiod for the duration of Process II. A fluorescent light is used for the photoperiod.

EXAMPLE 1

Molecular Cloning of Shark Kidney Calcium Receptor Related Protein (SKCaR)

A shark λZAP cDNA library was manufactured using standard commercially available reagents with cDNA synthesized from poly A+ RNA isolated from shark kidney tissue as described and published in Siner et al. *Am. J. Physiol.* 270:C372–C381, 1996. The shark cDNA library was plated and resulting phage plaques screened using a $^{32}$P-labeled full length rat kidney CaR (RaKCaR) cDNA probe under intermediate stringency conditions (0.5×SSC, 0.1% SDS, 50° C.). Individual positive plaques were identified by autoradiography, isolated and rescued using phagemid infections to transfer cDNA to KS Bluescript vector. The complete nucleotide sequence, FIG. 1, (SEQ ID NO: 1) of the 4.1 kb shark kidney PVCR related protein (SKCaR) clone was obtained using commercially available automated sequencing service that performs nucleotide sequencing using the dideoxy chain termination technique. The deduced amino acid sequence (SEQ ID NO: 2) is shown in FIG. 1. Northern analyses were performed as described in Siner et. al. Am. J. Physiol. 270:C372–C381, 1996. The SKCAR nucleotide sequence was compared to others CaRs using commercially available nucleotide and protein database services including GENBANK and SWISS PIR.

EXAMPLE 2

Expression/Activation Studies of SKCaR in Human Embryonic Kidney (HEK) Cells

PVCRs serve as salinity sensors in fish. These receptors are localized to the apical membranes of various cells within the fish's body (e.g., in the gills, intestine, kidney) that are known to be responsible for osmoregulation. A full-length cation receptor (CaR, also referred to as "PVCR") from the dogfish shark has been expressed in human HEK cells. This receptor was shown to respond to alterations in ionic compositions of NaCl, Ca2+ and Mg2+ in extracellular fluid bathing the HEK cells. The ionic concentrations encompassed the range which includes the transition from freshwater to seawater. Expression of PVCR mRNA is also increased in fish after their transfer from freshwater to seawater, and is modulated by PVCR agonists. Partial genomic clones of PVCRs have also been isolated from other fish species, including winter and summer flounder and lumpfish, by using nucleic acid amplification with degenerate primers.

In particular, the following was shown:
1. SKCaR encodes a functional ion receptor that is sensitive to both Mg2+ and Ca2+ as well as alterations in NaCl.
2. SKCaR's sensitivity to Ca2+, Mg2+ and NaCl occur in the range that is found in marine environments and is consistent with SKCaRs role as a salinity sensor.
3. SKCaR's sensitivity to Mg2+ is further modulated by Ca2+ such that SKCaR is capable to sensing various combinations of divalent and monovalent cations in seawater and freshwater. These data can be used to design novel electrolyte solutions to maintain fish in salinities different from those present in their natural environment.

SKCaR cDNA was ligated into the mammalian expression vector PCDNA II and transfected into HEK cells using standard techniques. The presence of SKCaR protein in transfected cells was verified by western blotting. Activation of SKCaR by extracellular Ca2+, Mg2+ or NaCl was quantified using a well characterized FURA 2 based assay where increases in intracellular Ca2+ produced by SKCaR activation are detected using methodology published previously by Bai, M., S. Quinn, S. Trvedi, O. Kifor, S. H. S. Pearce, M. R. Pollack, K. Krapcho, S. C. Hebert and E. M. Brown. *Expression and characterization of inactivating and activating mutations in the human Ca2+-sensing receptor. J. Biol. Chem.*, 32:19537–19545 (1996); and expressed as % normalized intracellular calcium response to receptor activation.

SKCaR is a functional extracellular Ca2+ sensor where its sensitivity is modulated by alterations in extracellular NaCl concentrations. As shown in FIG. 2, SKCaR is activated by increasing concentrations of extracellular Ca2+ where half maximal activation of SKCaR ranges between 1–15 mM depending on the extracellular concentration of NaCl. These are the exact ranges of Ca2+ (1–10 mM present in marine estuarian areas). Note that increasing concentrations of NaCl reduce the sensitivity of SKCaR to Ca2+. This alteration in SKCaR sensitivity to Ca2+ was not observed after addition of an amount of sucrose sufficient to alter the osmolality of the extracellular medium. This control experiment shows it is not alterations in cell osmolality effecting the changes observed.

Figure 4:
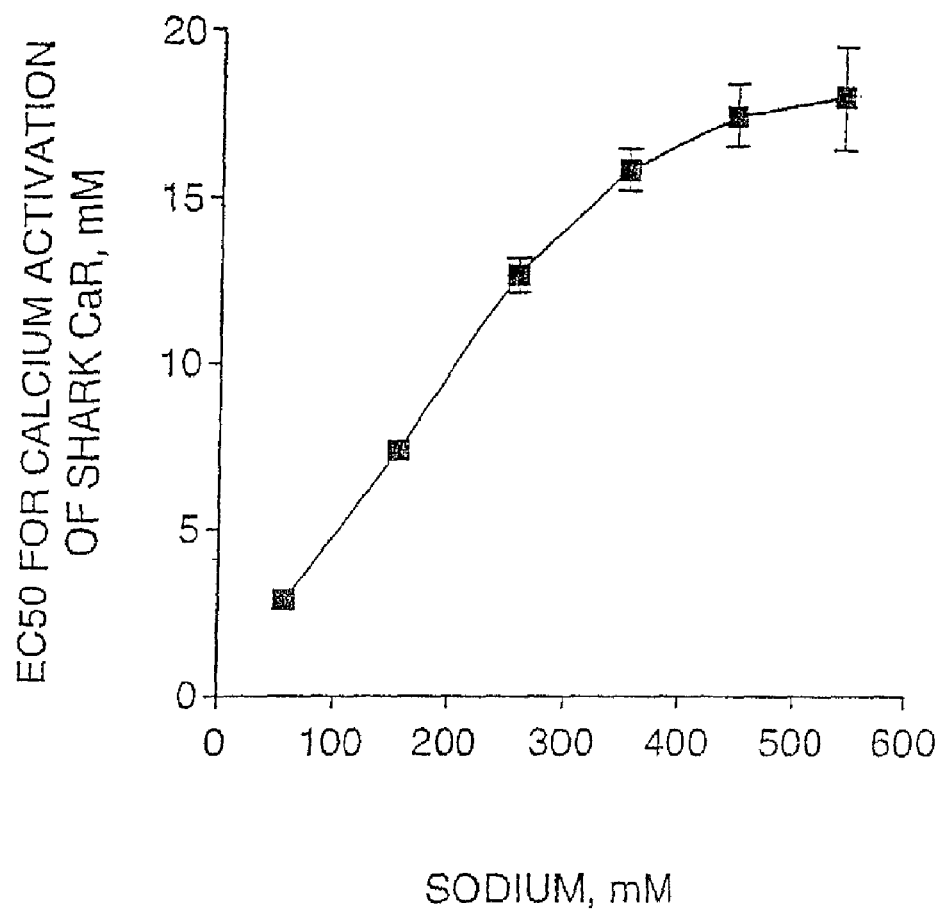
FIG. 4 is a graphical representation showing the EC50 for calcium activation of shark CaR (mM) against the amount of sodium (mM) of the SKCaR-I protein in increasing amounts of extracellular NaCl concentrations.

The half maximal activation ($EC_{50}$) by Ca2+ for SKCaR is reduced in increased concentrations of extracellular NaCl. See FIG. 4. The $EC_{50}$ for data shown on FIG. 4 is displayed as a function of increasing extracellular NaCl concentrations. Note the $EC_{50}$ for Ca2+ increases from less than 5 mM to approximately 18 mM as extracellular NaCl concentrations increase from 50 mM to 550 mM.

Figure 3:
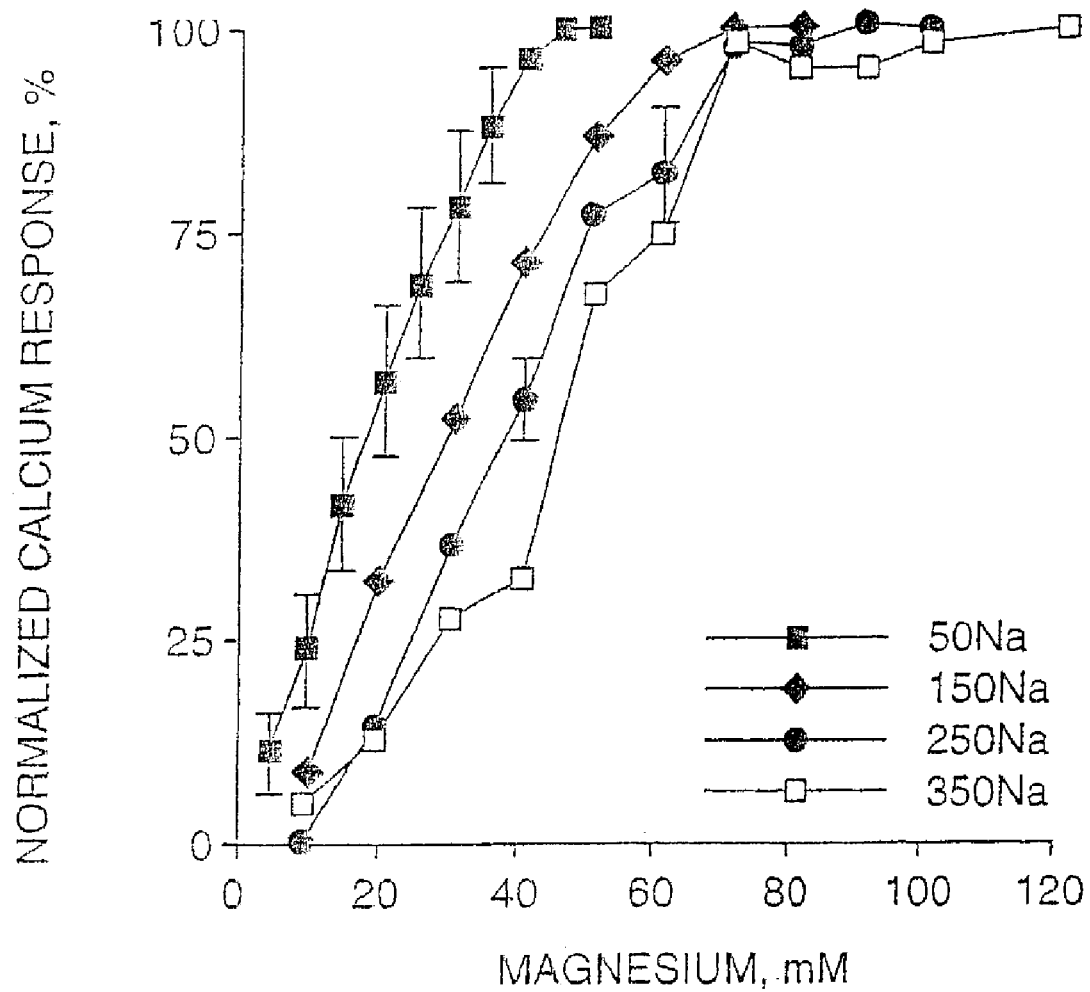
FIG. 3 is a graphical representation showing a normalized calcium response (%) against the amount of magnesium (mM) of the SKCaR protein in increasing amounts of extracellular NaCl concentrations.

SKCaR is a functional extracellular Mg2+ sensor where its sensitivity is modulated by alterations in extracellular NaCl concentrations. As shown in FIG. 3, SKCaR is activated in the range of 5–40 mM extracellular Mg2+ and is modulated in a manner similar to that shown in FIGS. 2 and 4 by increasing concentrations of extracellular NaCl. Similarly, this alteration in SKCaR sensitivity to Ca2+ was not observed after addition of an amount of sucrose sufficient to alter the osmolality of the extracellular medium.

Figure 5:
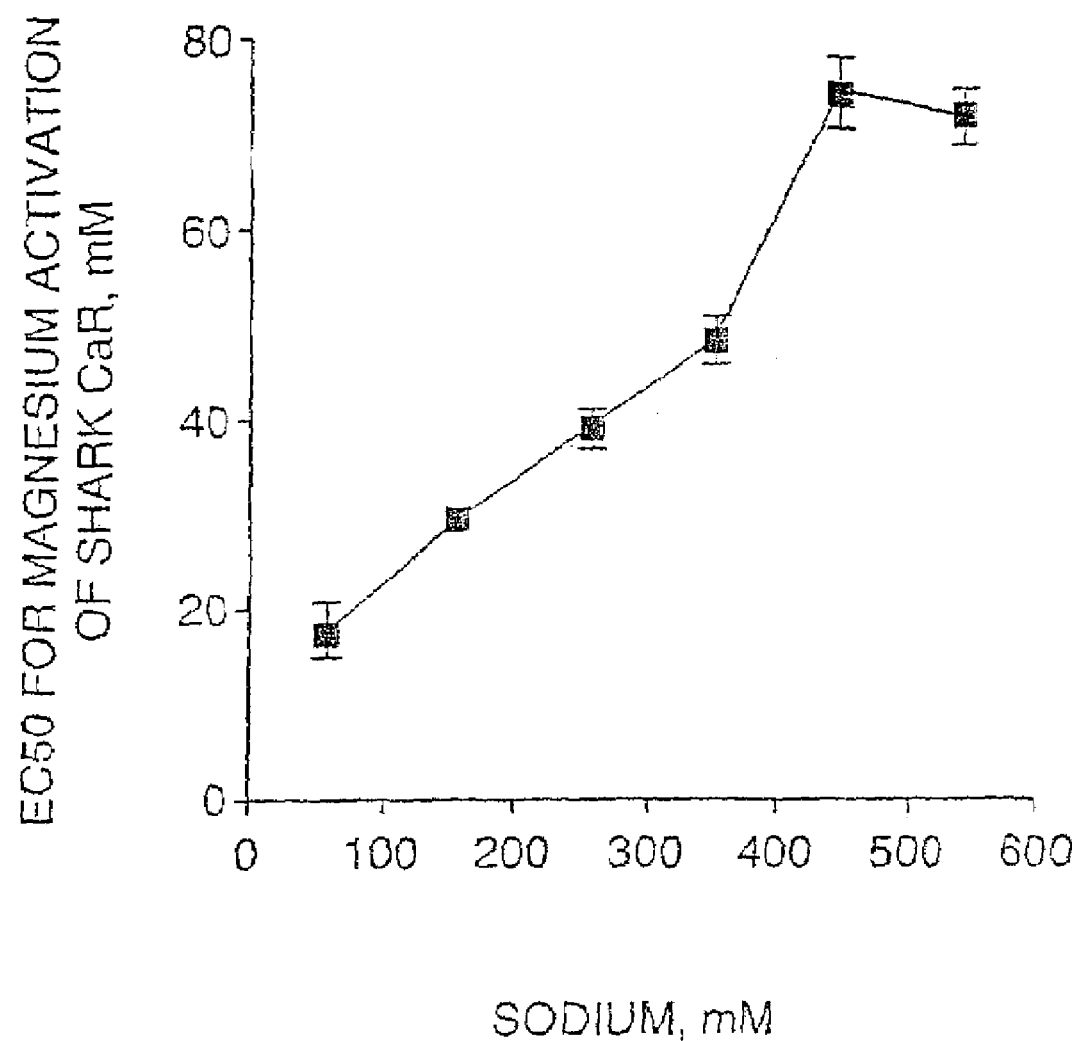
FIG. 5 is a graphical representation showing the EC50 for magnesium activation of shark CaR (mM) against the amount of sodium (mM) of the SKCaR protein in increasing amounts of extracellular NaCl concentrations.

The half maximal activation ($EC_{50}$) by Mg2+ for SKCaR is reduced in increased concentrations of extracellular NaCl. See FIG. 5. The $EC_{50}$ for data shown on FIG. 5 is displayed as a function of increasing extracellular NaCl concentrations. Note the $EC_{50}$ for Mg2+ increases from less than 20 mM to approximately 80 mM as extracellular NaCl concentrations increase from 50 mM to 550 mM.

Figure 6:
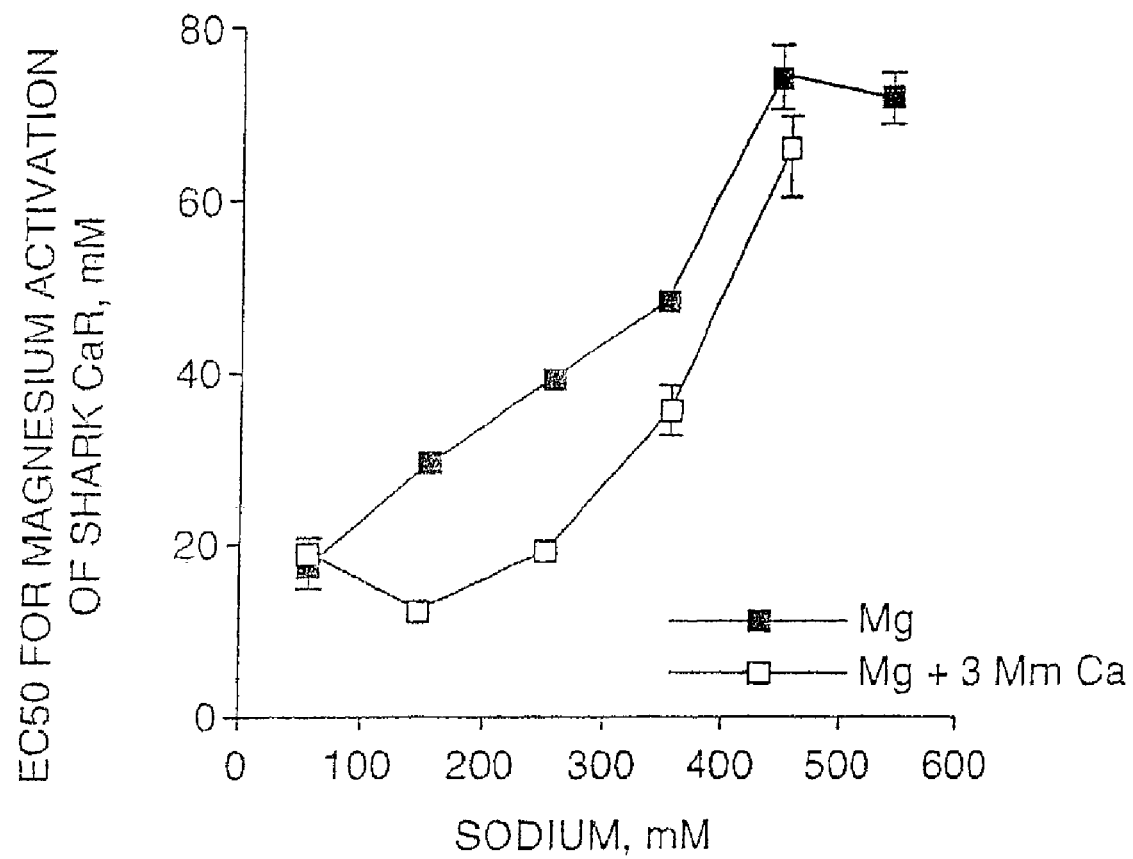
FIG. 6 is a graphical representation showing the EC50 for magnesium activation of shark CaR (mM) against the amount of sodium (mM) of the SKCaR protein in increasing amounts of extracellular NaCl concentrations and added amounts of calcium (3 mM).

Addition of 3 mM Ca2+ alters the sensitivity of SKCaR to Mg2+ and NaCl. See FIG. 6. The $EC_{50}$ for Mg2+ of SKCaR is modulated by increasing concentrations of NaCl as shown both in this FIG. 6 and in FIG. 5. Addition of 3 mM Ca2+ to the extracellular solution alters the sensitivity characteristics of SKCaR as shown. Note the 3 mM Ca2+ increases the sensitivity of SKCaR to Mg2+ as a function of extracellular NaCl concentrations.

This method was also used to isolate partial genomic clones of PVCRs for Atlantic salmon and other species such as Arctic char and rainbow trout, as described herein. FIGS. 19A–D show the amino acid sequences and alignment for the PVCRs from four full length Atlantic salmon clones (SalmoKCaR #1, #2, #3, and #4) relative to the PVCR from the kidney of the dogfish shark (*Squalus acanthias*) (SKCaR) and human parathyroid calcium receptor (HuPCaR).

EXAMPLE 3

Defining Salinity Limits as an Assay to Identify Fish with Enhanced Salinity Responsive and Altered PVCR Function Both anadromous fish (Atlantic salmon, trout and Arctic char) and euryhaline fish (flounders, alewives, eels) traverse from freshwater to seawater environments and back again as part of their lifecycles in the natural environment. To successful accomplish this result; both types of fish have to undergo similar physiological changes including alterations in their urine output, altering water intake and water absorption. In some cases, naturally occurring mutations to PVCR would provide for altered salinity adaptation capabilities that would have significant value for both commercial and environmental restoration uses. For example, identification of selective traits associated with PVCR mediated salinity responses might allow identification of new strains of fish for commercial aquaculture. Similarly, identification of selected environmental parameters from a host of natural and man made variables that are the most important to improve the survival and successful restocking and/or ocean ranching of either wild Atlantic salmon or winter flounder would also be of great utility. To permit the identification of individual fish possessing enhanced salinity responsive characteristics, assays must be designed that enable these fish to survive while others not possessing these characteristics will either die or perform poorly. As described below, such assays would take advantage of the ability of these anadromous and euryhaline fish to withstand a wide range of salinities. Fish that were identified using such assays would then be propagated in breeding-selection programs.

Winter and Summer Flounder can be grown and maintained in recycling water systems. Groups of both winter (*Pleuronectes americanus*) and summer (*Paralichthus dentalus*) flounder were maintained in multiple modular recycling water system units that are composed of a single 1 meter fish tank maintained by a 1 meter biofilter tank located directly above it. The upper tank of each unit contains 168 sq. ft. of biofilter surface area that will support a maximum of 31 lbs of flounder, while maintaining optimal water purity and oxygenation conditions. Each unit is equipped with its own pump and temperature regulator apparatus. Both the temperature and photo-period of each unit can be independently regulated using black plastic curtains that partition each tank off from its neighbor. The inventors have a total of 12 independent modular units that permit 3 experiments each with 4 variables to be performed simultaneously. Using this experimental system, the following data have been obtained.

Salinity survival limits for winter and summer flounder with a constant ratio of divalent and monovalent ions were determined. The survival limit of both winter and summer flounder in waters of salinities greater than normal seawater (10 mM Ca2+, 50 mM Mg2+ and 450 mM NaCl) is water containing twice (20 mM Ca2+, 50 mM Mg2+ and 900 mM NaCl) the normal concentrations of ions present in normal seawater. In contrast, the survival limit of both winter and summer flounder in waters of salinity less than normal seawater is 10% seawater (1 mM Ca2+, 5 mM Mg2+ and 45 mM NaCl).

Use of a fully recycling water system permits growth of flounder at vastly different salinities. Groups of flounder (n=10) were adapted over a 15 day interval and maintained at either low salinity (LS) (e.g., at 10% normal seawater), normal seawater (NS) or hypersalinity (HS) (e.g., 2× seawater) for intervals of 3 months, under otherwise identical conditions. Survival among the 3 groups were comparable (all greater than 80%) and there were no differences in the electrolyte content of their respective sera.

EXAMPLE 4

Isolation of Partial Atlantic Salmon PVCRs

A partial PVCR gene of Atlantic Salmon was isolated as follows: sequences of shark kidney calcium receptor together with the nucleotide sequence of mammalian calcium receptors were used to design degenerate oligonucleotide primers, dSK-F3 (SEQ ID NO: 15) and dSK-R4 (SEQ ID NO: 16), to highly conserved regions in the transmembrane domain of polyvalent cation receptor proteins using standard methodologies (See G M Preston, *Polymerase chain reaction with degenerate oligonucleotide primers to clone gene family members*, Methods in Mol. Biol. Vol. 58 Edited by A. Harwood, Humana Press, pages 303–312, 1993). Using these primers, genomic DNA from the above species was amplified using standard PCR methodology. The PCR product (653 nt) was then purified by agarose gel electrophoresis and ligated into appropriate plasmid vector that was then transformed into a bacterial strain. After growth in liquid media, vectors and inserts are purified using standard techniques, analyzed by restriction enzyme analysis and sequenced. Using this methodology, a total of 8 nucleotide sequences from 8 fish species including Atlantic Salmon were amplified. Each clone is 594 nt (with-out primer sequences) and encodes a 197 amino acid sequence which corresponds to the conserved transmembrane domain of the calcium receptors.

Atlantic salmon partial PVCR nucleic acid sequence (SEQ ID NO: 3) is composed of 594 nucleotides (nt) containing an open reading frame encoding 197 amino acids (SEQ ID NO: 4) (FIG. 7).

EXAMPLE 5

Molecular Cloning of a Second Partial Atlantic Salmon PVCR

A second Atlantic salmon partial PVCR was isolated, as described herein. An Atlantic salmon λZAP cDNA library was manufactured using standard commercially available reagents with cDNA synthesized from poly A+ RNA isolated from Atlantic salmon intestine tissue according to manufacturers instructions (Stratagene, La Jolla, Calif.) and screened using the Atlantic salmon PCR product as a probe. A partial Atlantic salmon PVCR cDNA (SEQ ID NO: 5) is composed of 2021 nucleotides (nt) (FIG. 8A) containing an open reading frame encoding 388 amino acids (SEQ ID NO: 6) (FIG. 8B). The open reading frame encoded by SEQ ID NO: 5 begins at nucleotide position 87.

EXAMPLE 6

Molecular Cloning of 4 Full Length cDNA Clones from Kidney of Atlantic Salmon (*Salmo Salar*) and Determination of their Tissue Specific Expression in Various Salmon Tissues Modulated by Water Salinity In Example 5, a homology based approach was used to screen cDNA libraries under moderate stringency conditions to obtain a full length shark kidney PVCR clone (SKCaR). Using sequence information derived from Examples 4 and 5, both nucleotide (nt) and antibody probes were designed to detect PVCRs in other fish species. Using degenerate primers whose sequence was derived from knowledge of the nt sequence of SKCaR, PCR was utilized to amplify a series of genomic and cDNA (RT-PCR) sequences that contain partial nt and putative protein sequences of PVCRs from multiple fish including Atlantic salmon. See Examples 1, 4, and 5.

The data described in this Example show that the nt and putative protein sequences of 4 PVCR transcripts from Atlantic salmon kidney were isolated and characterized. Additionally, their tissue specific expression and modulation of tissue expression levels by alterations in water salinity were determined. This Example is divided into 2 parts: 1) isolation and sequence of 4 full length PVCR clones from salmon kidney (SalmoKCar#1 (SEQ ID NO: 7), SalmoKCar#2 (SEQ ID NO: 9), SalmoKCaR#3 (SEQ ID NO: 11), and SalmoKCaR#4 (SEQ ID NO: 13)) and 2) use of RT-PCR analysis with degenerate and clone specific SalmoKCaR PCR primers to determine the tissue specific expression of these 4 transcripts in seawater vs. freshwater as well as the SuperSmolt™ process. Taken together, these data provide the framework for achieving a fundamental understanding of both PVCRs in salmonids as well as the their roles in the SuperSmolt™ process.

```
Primer sequences for PCR of PVCR clones:
dSK-F3 5'-TGT CKT GGA CGG AGC CCT TYG GRA TCG C-3'    (SEQ ID NO:15)

dSK-R4 5'-GGC KGG RAT GAA RGA KAT CCA RAC RAT GAA G-3'  (SEQ ID NO:16)

I = deoxyinosine, N = A + C + T + G, R = A = G, Y = C+ T, M = A + C, K
= T + G, S = C + G, W = A + T, H = A + T + C, B = T + C + G, D = A + T + G, V = A + C + G; Product from amplification = 653 nt
```

Part 1. Isolation and Sequence of 4 Full Length PVCR Clones from Salmon Kidney:

Materials and Methods: Total RNA was purified with Stat 60 reagent (Teltest B Friendswood, Tex.) and poly A$^+$ purified with the Micro FastTrack Kit (Invitrogen, Carlsbad, Calif.). cDNA was then synthesized and fractionated whereby selected fractions were ligated and packaged as λZAP libraries (Stratagene, La Jolla, Calif.). For SalmoK-CaR #1, 2, and 3, library phage were then plated and duplicate filter lifts performed that were screened under high stringency (0.1×SSC, 0.1% SDS @ 55° C.) with a $^{32}$P-labeled (RadPrime Kit, Invitrogen, Carlsbad, Calif.) genomic fragment of Atlantic salmon PVCR (653 nt sequence) amplified using protocols and reagents described in Examples 1, 4 and 5. For SalmoKCaR #4, library phage were then plated and duplicate filter lifts performed that were screened under high stringency (0.1×SSC, 0.1% SDS @ 55° C.) with a $^{32}$P-labeled (RadPrime Kit, Invitrogen, Carlsbad, Calif.) full length nucleic acid sequence of SalmoKCaR#2, SEQ ID NO: 9, amplified using protocols and reagents described in Examples 1, 4 and 5. Primary positive plaques were purified, excised and sequenced using commercial sequencing services (U. of Maine, Orono, Me.) and their sequences compared with those of other PVCRs using BLAST. (National Library of Medicine, Bethesda, Md.).

Results:

For Isolation of SalmoKCaR#1, 2, and 3:

A total of seven cDNA clones containing PVCR sequences were identified and purified from Atlantic Salmon kidney and intestine libraries. A total of three of the seven contain full length coding sequences for PVCR proteins together with 5' and 3' regulatory elements. For convenience, these clones are designated *Salmo salar* Kidney PVCRs (SalmoKCaRs) #1, #2 and #3 and their aligned nt and putative protein sequences are shown in FIGS. 9–11, respectively. The remaining 4 positive clones were partial PVCR clones very nearly identical to these 3 full-length SalmoKCaR clones. Comparison of the different nt sequences of these 3 clones reveals the following similarities and differences:

For SalmoKCaR#4:

120,000 additional plaques were screened from the same cDNA library which was used to isolate SalmoKCaRs 1–3. Five positive plaques were picked, plated out and screened on secondary phage plates. Isolated plaques were picked, excised into bacterial plasmids, and transferred into bacterial cells as previously described. Plasmid DNA preparations of all 5 cDNAs showed strong hybridization to SalmoKCaR#3 by Southern blot analysis. Sequence analysis revealed two full length clones and three partials. One of the full length clones was a duplicate of a previously isolated SalmoKCaR, and the other was a new clone, SalmoKCaR4.

This clone was designated as SalmoKCaR#4, commensurate with the naming of the SalmoKCaR#1–3 clones, above. The aligned nt and putative protein sequence for SalmoKCaR #4 is shown in FIG. 12.

Comparison of the Different nt Sequences of these 4 Clones Reveals the Following Similarities and Differences:

The SalmoKCaR #1 nucleic acid sequence (SEQ ID NO: 7) consists of 3941 nts of 5' and 3' regulatory elements together with full-length coding sequence for a 941 AA PVCR protein (SEQ ID NO: 8). See FIGS. 9A–E. The calculated molecular mass of this protein is 106,125 Daltons.

The SalmoKCaR #2 nucleic acid sequence (SEQ ID NO: 9) consists of 4031 nts of 5' and 3' regulatory elements together with full-length coding sequence for a 941 AA PVCR protein (SEQ ID NO: 10). See FIGS. 10A–E. The calculated molecular mass of this protein is 106,180 Daltons.

The SalmoKCaR #3 nucleic acid sequence (SEQ ID NO: 11) consists of 3824 nts of 5' and 3' regulatory elements together with full-length coding sequence for a 850 AA PVCR protein (SEQ ID NO: 12). See FIGS. 11A–D. The calculated molecular mass of this protein is 96,538 Daltons.

The SalmoKCaR#4 nucleic acid sequence (SEQ ID NO: 13) consists of 3988 nt of 5' and 3' regulatory elements together with full-length coding sequence for a 941 AA PVCR protein (SEQ ID NO: 13). See FIGS. 12A–E. The calculated molecular mass of this protein is 106,131 Daltons.

FIGS. 13A–L and 14A–C show an alignment of between the two partial sequences of Atlantic Salmon PVCRs isolated and 3 full length clones, SalmoKCaR #1–3, for both the nucleic acid and amino acid sequences, respectively. One partial nucleic acid sequence of an Atlantic Salmon PVCR, SEQ ID NO: 3, can be found in all three SalmoKCaR nucleic acid sequences between nt 1979 and 2572; nt 2069 and 2662; and nt 1980 and 2573 of SEQ ID NO: 7, 9, and 11, respectively. The second partial Atlantic Salmon clone, SEQ ID NO: 5, can also be found in all three SalmoKCaR nucleic acid sequences: between nt 1753 and 3773; 1843 and 3863, and 1754 and 3616 of SEQ ID NO: 7, 9, and 11, respectively. Similarly, the amino acid sequence of SEQ ID NO: 4 is found between aa 601 and 797 of each of SEQ ID NO: 8, 10, and 12. The amino acid sequence of the second Atlantic Salmon Clone, SEQ ID NO: 6, is found in each of the polypeptides: between aa 554 and 941 of SEQ ID NO: 8; between aa 554 and 941 of SEQ ID NO: 10; and between aa 554 and 850 of SEQ ID NO: 12. Note that the amino acid sequence of SEQ ID NO: 6 extends 91 aa past the end of SEQ ID NO: 12.

FIGS. 17 and 18 show an alignment of between the two partial sequences of Atlantic Salmon PVCRs isolated and all 4 full length clones, SalmoKCaR #1–4, for both the nucleic acid and amino acid sequences, respectively. One partial nucleic acid sequence of an Atlantic Salmon PVCR, SEQ ID NO: 3, can be found from 1980 to 2573 of SalmoKCaR#4, SEQ ID NO: 13. The second partial Atlantic Salmon clone, SEQ ID NO: 5, can also be found in the SalmoKCaR#4 nucleic acid sequence: between nt 1754 and 3774. Similarly, the amino acid sequence of SEQ ID NO: 4 is found between aa 601 and 797 of SEQ ID NO: 14. The amino acid sequence of the second Atlantic Salmon Clone, SEQ ID NO: 6, is found between aa 554 and 941 of SEQ ID NO: 14.

Additional differences between the partial Atlantic salmon PVCR (SEQ ID NO: 5) and full length PVCR (SEQ ID NO: 7, 9, or 11) include: nt 1–112 do not align with any corresponding sequence in SEQ ID NO: 7, 9, or 11. There are also 4 single nt base pair substitutions that are present in SEQ ID NO: 5 that are different than corresponding nt in full length SEQ ID NO: 7, 9, or 11. These include:

nt 1893 change from G to A
nt 1970 change from G to A
nt 1973 change from G to A
nt 2001 change from G to A.

Table 1 compares the overall % identity of nucleotides (nt) between cDNA clones that contain the SalmoKCaRs #1, 2, 3, and 4 vs. shark kidney calcium receptor (SKCaR containing 4079 nts) or human parathyroid CaR (HuPCaR containing 3783 nts). Note that all 4 SalmoKCaR clones possess approximately a 56–57% nt identity to SKCaR and an approximately 50–55% nt identity to HuPCaR. However, in spite of the rather low overall % nt identity between the 4 SalmoKCaR clones and SKCaR, all 4 full length Salmo-KCaR clones hybridize to full length SKCaR clone under high stringency conditions (0.5×SSC, 0.1% SDS @ 65° C.) (See FIG. 15A).

The percentage identities between the aligned nucleotide sequences of the 4 full length SalmoKCaR clones (SEQ ID NO: 7, 9, 11, 13) include:

A total of 99.8% of the nt of SEQ ID NO: 7 are identical to those of corresponding SEQ ID NO: 9. A total of 97.6% of the nt of SEQ ID NO: 9 are identical to those corresponding nt of SEQ ID NO: 7.

A total of 93.6% of the nt of SEQ ID NO: 9 are identical to those corresponding nt of SEQ ID NO: 11. A total of 98.7% of the nt of SEQ ID NO: 11 are identical to the corresponding nt present in SEQ ID NO: 9.

A total of 95.8% of the nt of SEQ ID NO: 7 are identical to the corresponding nt of SEQ ID NO: 11. A total of 98.7% of the nt of SEQ ID NO: 11 are identical to those corresponding in SEQ ID NO: 7.

A total of 99% of the nt of SEQ ID NO: 7 are identical to corresponding nt of SEQ ID NO: 13. A total of 98% of the nt of SEQ ID NO: 9 are identical to corresponding nt of SEQ ID NO: 13. A total of 97% of nt of SEQ ID NO: 13 are identical to corresponding nt of SEQ ID NO: 11.

Table 1: Comparison of the % nucleotide (nt) identity of the complete nt sequence of SalmoKCaR clones #1, #2, #3, and #4 (including 5' and 3' regulatory elements) vs. either the SKCaR clone or the clone HuPCaR clone.

| | % NUCLEOTIDE IDENTITY | | | |
|---|---|---|---|---|
| | SalmoKCaR #1 | SalmoKCaR #2 | SalmoKCaR #3 | SalmoKCaR #4 |
| SKCaR vs. | 56.2 | 56.5 | 57.2 | 56 |
| HuPCaR vs. | 55.0 | 54.9 | 50.9 | 55 |

Table 2 compares both the overall and domain-specific percent amino acid (% AA) identity for each of the Salmo-KCaR clones vs. shark kidney PVCR (SKCaR-upper half) and human parathyroid CaR (HuPCaR-lower half). When compared to SKCaR, all 4 SalmoKCaR proteins possess approximately a 63–68% overall AA identity to SKCaR. However, their domain-specific identities show significant degrees of variation with the carboxyl terminal domain of the SalmoKCaR 3 being the most widely divergent. Not surprisingly, comparisons between the 4 SalmoKCaR proteins vs. HuPCaR reveal that the 7 transmembrane region possesses the highest degree of homology followed by the extracellular domain and finally the intracellular carboxy terminal domain.

The percentage identities between the aligned amino acid sequences of the 4 full length SalmoKCaR clones (SEQ ID NO: 8, 10, 12, or 14) include:

A total of 99.9% of the aa of SEQ ID NO: 8 are identical to those corresponding aas in SEQ ID NO: 10. A total of 99.9% of the aa of SEQ ID NO: 10 are identical to corresponding aa in SEQ ID NO: 8.

A total of 89.5% of the aa of SEQ ID NO: 10 are identical to those corresponding aas in SEQ ID NO: 12. A total of 99.1% of the aa of SEQ ID NO: 12 are identical to those corresponding aa in SEQ ID NO: 10.

A total of 89.6% of the aa of SEQ ID NO: 8 are identical to those corresponding aas in SEQ ID NO: 12. A total of 99.2% of the aa of SEQ ID NO: 12 are identical to those corresponding aa of SEQ ID NO: 8.

A total of 100% of the aa of SEQ ID NO: 8 are identical to those corresponding aa's in SEQ ID NO: 14. A total of 99.9% of the aa of SEQ ID NO: 10 are identical to those corresponding aa's in SEQ ID NO: 14. A total of 99.2% of the aa of SEQ ID NO: 12 are identical to those corresponding aa's in SEQ ID NO: 14.

TABLE 2

Comparison of % amino acid (AA) identities of 4 SalmoKCaR proteins vs. AA sequence of shark kidney CaR (SKCaR-Upper Half) and human parathyroid CaR (HuPCaR-Lower Half).

| | SalmoKCaR #1 | SalmoKCaR #2 | SalmoKCaR #3 | SalmoKCaR #4 |
|---|---|---|---|---|
| % AA Identity to SKCaR | | | | |
| Overall Protein | 68.4 | 68.3 | 63.3 | 68.4 |
| N-terminal Extracellular Ion Binding Domain | 70.0 | 69.8 | 70.0 | 70.0 |
| 7 Transmembrane Region | 87.2 | 87.2 | 86.4 | 87.2 |
| Carboxyl Terminal Intra-Cellular Domain | 31.8 | 31.8 | 0.0 | 31.8 |
| % AA Identity to HuPCaR | | | | |
| Overall Protein | 66.3 | 66.3 | 61.4 | 66.3 |
| N-terminal Extracellular Ion Binding Domain | 71.9 | 71.9 | 72.1 | 71.9 |
| 7 Transmembrane Region | 89.2 | 89.2 | 88.4 | 89.2 |
| Carboxyl Terminal Intra-Cellular Domain | 24.1 | 24.1 | 0 | 24.1 |

Figure 15A:
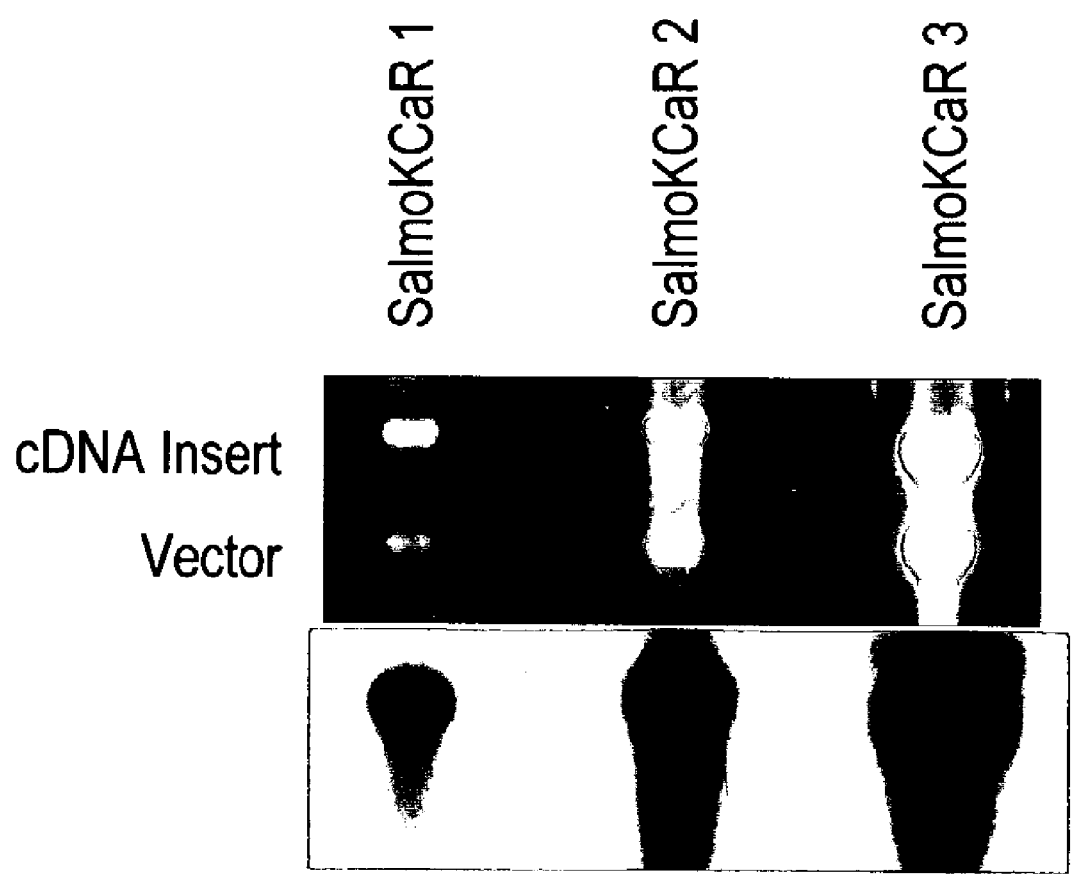
FIG. 15A is photograph showing a Southern blot in which SalmoKCaR#1, 2, and 3 hybridize to nucleic acid derived from SKCaR.

FIG. 15A shows unique SalmoKCaR#1, 2, and 3 clones hybridize to full length shark kidney CaR (SKCaR) under high stringency conditions (0.5×SSC, 0.1% SDS @ 65° C.). Representative autoradiogram of Southern blot was exposed for 30 min. Since the SalmoKCaR nt sequence, SEQ ID NO: 1, is 97–99% identical to SalmoKCaR's #1, 2, and 3, and so it also would be expected to hybridize under these conditions.

Site directed mutagenesis studies of mammalian CaRs, notably HuPCaR, have identified AAs that are particularly important in the various functions of CaRs. Cysteine AAs at AA#101 and AA#236 mediate dimerization of HuPCaR. HuPCaR and native CaRs in rat kidney exist primarily as dimers within the cell membrane where disulfide bond-mediated dimerization is required for normal agonist-mediated CaR activation. SalmoKCaR#1–4 possess Cys at AAs corresponding to HuPCaR AA#101 and AA#236 and presumably functions as dimers in a manner similar to mammalian CaRs.

Nucleotide Sequence Differences in the 5' and 3' Untranslated Regions or UTRs of SalmoKCaRs #1, #2 #3 and #4:

FIG. 16 displays the aligned nucleotide sequences of SalmoKCaR clones #1, #2, and #3, and FIG. 17 displays the aligned nucleotide sequences of SalmoKCaR #1–4. As compared to SalmoKCaR #1 and #3, SalmoKCaR #2 possesses an 89 nt insert in its 5' UTR. SalmoKCaR#4 does not contain the 89 nt insert in the 5' UTR that SalmoKCaR#2 contains. It does not share the 158 nt deletion in the ORF of SalmoKCaR#3. However, it does share a 39 nt insertion in the 3' UTR just prior to the poly A tail with SalmoKCaR#3. This insertion is likely a regulatory element. SalmoKCaR #4 looks as though it would have the same structure and function as SalmoKCaR #1, but would be co-regulated with SalmoKCaR 3. Differences between the 3' UTRs of the 4 SalmoKCaRs include a 36 nt insert just prior to the poly A tail in SalmoKCaR #3 as well as other single nt differences listed below where each difference is compared to the 3 other SalmoKCaR clones:

| | |
|---|---|
| SalmoKCaR #1: | nt 3660 A to G; nt 3739 A to G; nt 3745 A to G |
| SalmoKCaR #2: | nt 1039 A to G; nt 3837 A to G; nt 3862 A to G |
| SalmoKCaR #3: | nt 1462 C to T; nt 3472 A to G; nt 3487 A to G; nt 3564 A to G; nt 3568 G to A; nt 3603 A to G; nt 3786 A to C. |
| SalmoKCaR #4: | nt 3634 A to G; nt 3645 A to G; nt 3661 A to G, nt 3726 G to A, nt 3740 A to G, nt 3746 A to G, nt 3773 A to G |

Although the functional significance of each of these nt differences in the 5' or 3' UTRs is unknown at the present time, each nt difference either individually or in combinations could represent a means for controlling either the stability or processing of the RNA transcript or its translation into each of the 4 SalmoKCaR proteins.

Sequence Differences in the Coding Regions of SalmoKCaRs #1, #2, #3 and #4:

FIG. 19 displays the aligned AA sequences of SalmoKCaRs #1, #2, #3, and #4 as well as the Shark SKCaR protein and HuPCaR proteins. As compared to SalmoKCaR #1 and #4, SalmoKCaR #2 possesses 2 different AA's present at AA#257 and AA#941 of its AA sequence. In contrast to SalmoKCaR #1 and #4 that possesses an Asp in AA#257, SalmoKCaR #2 possesses a Gly. The negative charge in this location may be important since both SKCaR and Fugu PVCR possess Asp at #257 while the mammalian CaRs, HuPCaR and RaKCaR possess a Glu. SalmoKCaR #3 also contains a Asp at AA#257.

At AA #443, SalmoKCaR #1, #2 and #4 both possess a Leu whereas SalmoKCaR #3 contains a Phe. The conserved hydrophobic nature of the AA at this position appears to be important since Fugu PVCR also contains a Leu whereas SKCaR contains an Ile. As compared to SalmoKCaRs #1, 2, or #4 SalmoKCaR #3 possesses a truncated carboxyl terminus as described below.

Sequence Differences in the Coding Regions of SalmoKCaRs #1, #2 #3 and #4 as Compared to Mammalian CaRs.

The putative AA sequences of SalmoKCaR #1, #2, #3 and #4 proteins possess multiple differences in AAs at various positions throughout their extracellular, 7 transmembrane and carboxyl terminal domains when compared to mammalian CaRs such as HuPCaR (see aligned differences with HuPCaR in FIG. 19). While many of the differences between SalmoKCaR species and HuPCaR are conserved substitutions that preserve the overall net charge or hydrophobicity characteristics at that specific position in the PVCR protein, other substitutions may have functional consequences as based on previous structure-functional studies of mammalian CaRs. The actual functional consequences of these AA differences in SalmoKCaR proteins are described herein in the following expression study.

Expression of SalmoKCaR #1 and #3 in Human Embryonic Kidney (HEK) Cells

This express study demonstrates that SalmoKCaR #1 and #3 clones can be expressed in HEK cells to yield corresponding PVCR proteins of predicted molecular mass. It also is a demonstration of creation of HEK cells expressing SalmoKCaRs #1 and #3 as tools for assay systems to measure PVCR interactions and sensitivity to PVCR modulators for another aquatic PVCR, SKCaR. Furthermore, it is a demonstration of the use of SDD and Sal-I antisera, respectively, as reagents to detect either both SalmoKCaRs #1 and #3, or selectively detect SalmoKCaR #1.

Methods for the Transfection and HEK Expression of SalmoKCaRs:

Full length SalmoKCaR 1 and SalmoKCaR 3 cDNAs were directionally cloned into the KpnI and XbaI sites of the mammalian expression vector pcDNA3. 1/Hyg-(Invitrogen) as described for the transfection and transient expression of SKCaR PVCR. DNA was prepared using the Wizard Midiprep Kit (Promega) and 15 μg of sterilized SalmoKCaR 1 or SalmoKCaR 3 DNA was diluted in 1 ml Opti-Mem I reduced serum media (Gibco) and combined with 45 μl Lipofectamine 2000 (Gibco). The DNA/Lipofectamine mixture was diluted with 8 ml Optio-Mem I and added to the flask. Flasks were incubated for 5 hours at 37° C., 5% $CO_2$ to allow transfer of DNA into the cells. 10 ml of Opti-Mem I media supplemented with 20% FBS was added to each flask, for a final concentration of 10% serum. Flasks were incubated overnight at 37° C., 5% $CO_2$. At 24 hours post transfection, the media was replaced with 20 ml full growth media. Flasks were kept at 37° C., 5% $CO_2$ for 24–48 hrs to optimize expression of protein.

Methods for Immunoblotting Analysis of HEK Expression of SalmoKCaR #1 or #2 Using SDD and Sal-1.2 Antisera:

The transfected cells were then rinsed with PBS and treated with trypsin-EDTA (Gibco) for 2 minutes at 37° C., 5% $CO_2$ to detach cells from the surface of the plate. The detached cells were added to 10 ml of full growth media (serum deactivates trypsin) and pelleted at 250×g for 10 minutes. The cells were resuspended in 3 ml homogenization buffer (20 mM Tris, 250 mM sucrose, at pH 7.4 plus protease inhibitors, including 1 μg/ml pepstatin, 0.5 μg/ml leupeptin, and 1 mM PMSF). The cells were homogenized in 14 ml (Falcon) tubes using a polytron motorized homogenizer. The homogenate was centrifuged at 3,000×g for 15 minutes at 4° C. twice, re-suspending pellet in 3 ml of homogenization buffer between spins and pooling supernatant from both spins into high speed centrifuge tubes. Mitochondrial material was then sedimented from pooled supernatant at 22,000×g for 20 minutes at 4° C. The supernatant was subsequently sedimented at 37,000×g for 30 minutes at 4° C. to pellet the plasma membranes, and the resulting pellet was solubilized with 100 μl homogenization buffer. A fresh sample of salmon kidney from a fish 7 weeks post transfer into salt water was prepared using the same homogenization protocol, along with the mock transfected HEK 293 cells and a flask of HEK cells stably transfected with human calcium receptor (5001 HEK) to be used as positive and negative controls on the western blots. Protein was quantified from the plasma membrane preparations using the Bio-Rad Protein Assay (Bio-Rad Laboratories). For the gel shown in FIG. 15B, 20 μg of protein was loaded into each lane except the 5001 HEK of which 15 μg was loaded. Novex 10% Tris-Glycine pre-cast gels (Invitrogen) were used to separate protein bands in each sample by gel electrophoresis. The protein bands were subsequently electro-transferred to a Hybond-P PVDF nitrocellulose membrane (Amersham-Pharmacia). The membranes were blocked overnight at 4° C. in a 5% block solution (Amersham-Pharmacia). The membranes were washed in TBS-T and incubated for 1 hour at room temperature in primary antibodies of SalmoSDD or Sal 1 or the preimmunie serum to those antibodies, at 1:4,000 dilutions. The secondary antibody used was an antirabbit horseradish peroxidase (Amersham-Pharmacia) at 1:50,000 dilution, incubated for 1 hour at room temperature. The protein bands shown in FIG. 15B were detected with an Enhanced Chemiluminescence system (Amersham-Pharmacia) and exposed to high performance chemiluminescence film (Amersham-Pharmacia).

Figure 15B:
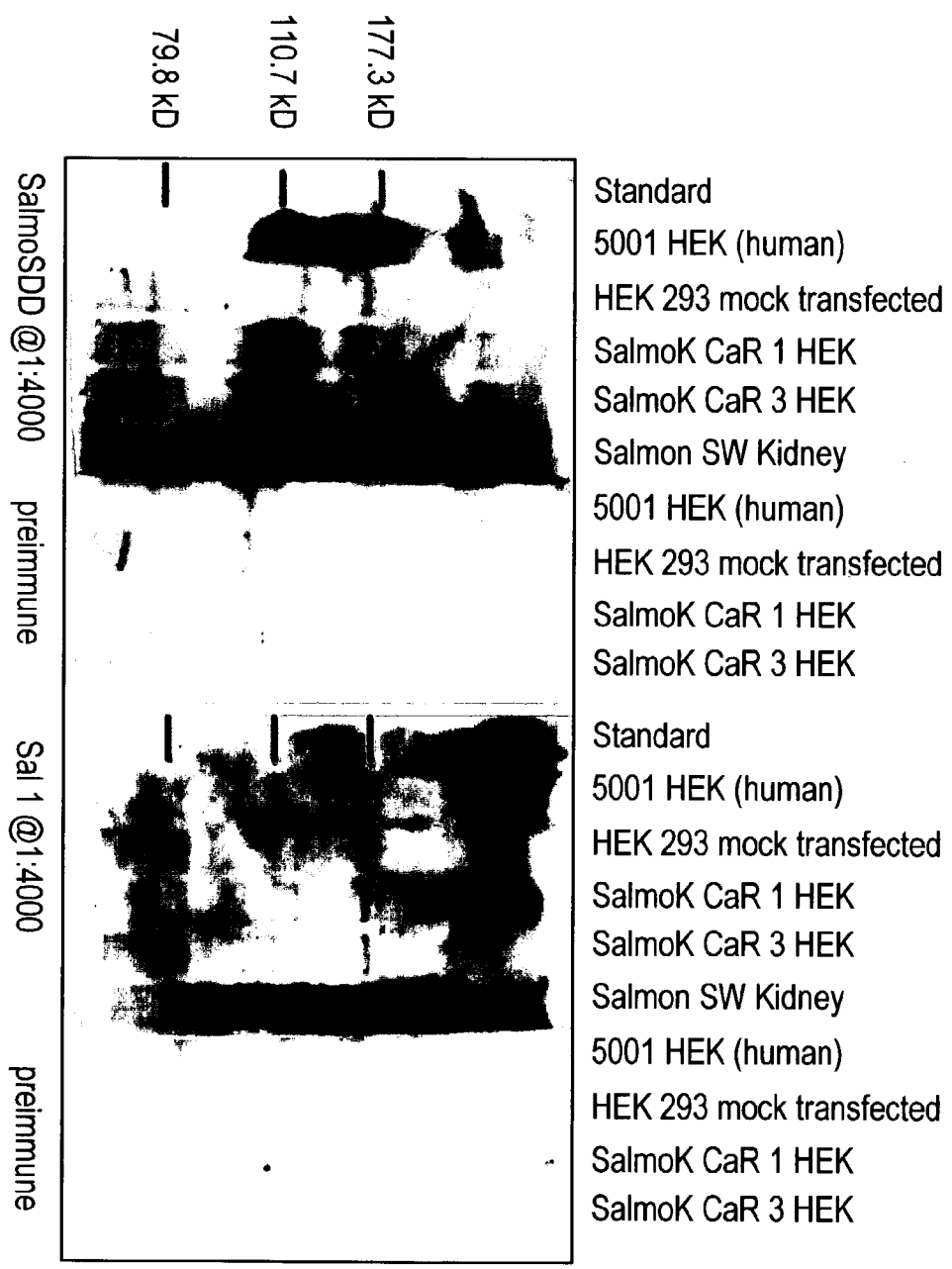
FIG. 15B is a photograph showing a Western blot protein produced by HEK cells transiently transfected with SalmoKCaR#1 and #3 constructs. In particular, the left panel shows an immunoblotting analysis with SDD antiserum while the right panel shows immunoblotting analysis for Sal1 for the following: a standard, 5001 HEK (human) cells, HEK 293 mock transfected cells, SalmoKCaR#1 HEK cells, SalmoKCaR#3 HEK cells, and Salmon SW Kidney.
Figure 20A:
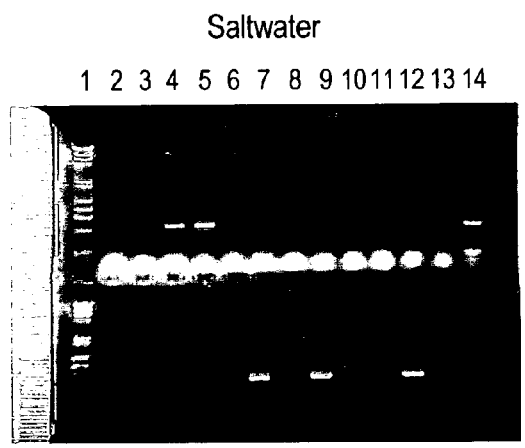
Figure 20B:
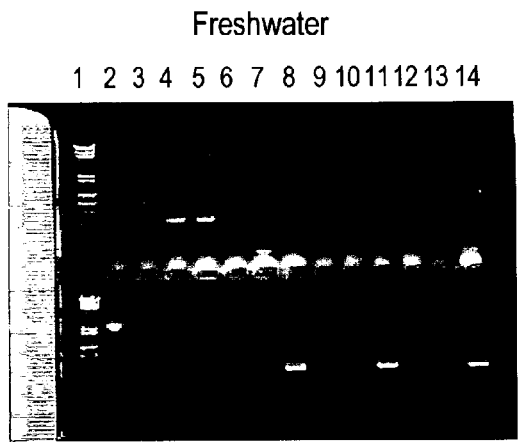
Figure 20C:
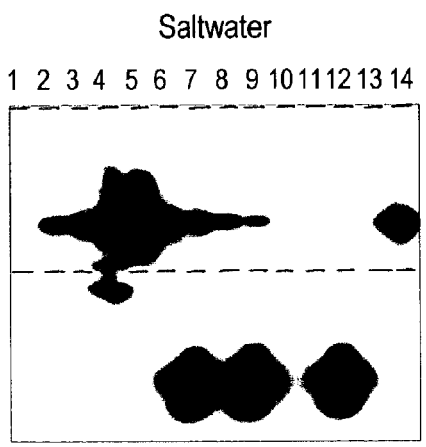
Figure 20D:
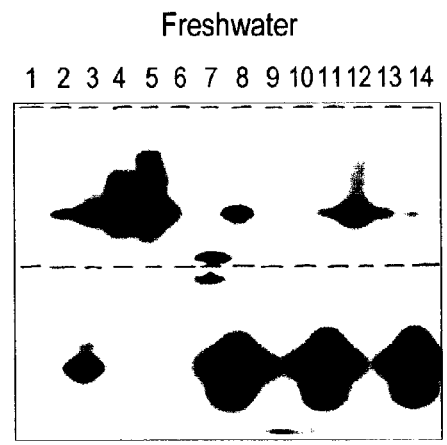

FIG. 15B shows a Western blot analysis of PVCR proteins produced by HEK cells transiently transfected with SalmoKCaR #1 and #3 constructs. Both Right and Left Panels each containing 10 lanes were loaded and electrophoresed with 20 micrograms of protein except for HEK-5001 (HuPCaR control) that contained 15 micrograms. In FIG. 15B, left panel, shows an immunoblotting analysis with SDD antiserum. SDD antiserum recognizes an aa sequence in the extracellular domain of PVCRs that is present in both HUPCaR, SalmoKCaR #1, SalmoKCaR #3 and salmon SW kidney. Thus, HEK cells expressing HuPCaR (Positive Control) display a prominent ~115 kDa band, as well as higher molecular mass bands which represent oligomers of HuPCaR. In contrast, mock transfected HEK cells (Negative Control) show minimal immuoreactivity similar to that present when lanes are exposed to preimmune SDD antiserum. However, SDD antiserum displays intense reactivity to HEK cells transfect with SalmoKCaR #1 (SalmoKCaR #1) or SalmoKCaR #3 (SalmoKCaR #3). Note the immunoreactive band produced by SalmoKCaR #1 is slightly larger (higher molecular mass) when compared to SalmoKCaR #3 as predicted by their nucleotide and amino acid sequence analysis of corresponding clones. Note also the presence of larger immunoreactive bands present in SalmoKCaR #3 lane that corresponds to oligomeric complexes of SalmoKCaR protein. The ability of SalmoKCaR #3 to form oligomeric complexes could result in formation of it exerting a dominant negative effect on the activity of other PVCRs expressed in the same cell. The lane designated Salmon SW kidney is a positive control showing that several bands in both SalmoKCaR #1 and #3 lanes are an identical molecular mass to PVCR proteins present in kidney tissue of Atlantic salmon.

FIG. 15B, right panel, shows immunoblotting analysis with SAL1 antiserum. SAL1 antiserum recognizes an aa sequence in the carboxyl terminal of SalmoKCaR #1 that is not present in either HuPCaR or SalmoKCaR #3. As a result, minimal immunoreactivity is displayed in either immune or preimmune lanes except for SalmoKCaR #1 and Salmon SW Kidney lanes. Note the presence of higher molecular wight immunoreactive SalmoKCaR proteins in both SalmoKCaR #1 and Salmon SW Kidney. The absence of immunoreactivity of SalmoKCaR #3 lane is expected since nucleotide and sequence analyses show that SalmoKCaR #3 is missing the aa sequence that is recognized by Sal-1 antiserum.

Differences between SalmoKCaR proteins vs. mammalian and other fish PVCRs include:

SalmoKCaR #1, #2, #3 and #4 possess a deletion of 15 AA's beginning at AA #369 as compared to either HuPCaR or RaKCaR. Fugu PVCR also exhibits a 19 AA deletion at the same location. In contrast, SKCaR does not exhibit any deletion in this area and thus is more similar to mammalian CaRs as compared to either SalmoKCaR or Fugu in this regard.

Another notable difference between SalmoKCaRs vs. mammalian CaRs and SKCaR is differences in AA #227 where mutagenesis studies have identified the presence of the positively charged Arg as important in CaR sensitivity since its alteration in HuPCaR to a Leu results in over a 2 fold reduction in $EC_{50}$ $Ca^{2+}$ from 4.0 mM to 9.3 mM but not $Gd^{3+}$ sensitivity. In contrast to mammalian CaRs and SKCaR, all 4 SalmoKCaRs possess a negatively charged Glu at AA#227. Fugu PVCR also exhibits the same Glu at AA#227. Interestingly, the AA sequence immediately following AA#227 is Glu-Glu-Ala in the mammalian HuPCaR and elasmobranch SKCaR whereas it is Lys-Glu-Met in all 4 SalmoKCaRs and Fugu.

Lastly, all 4 SalmoKCaR clones as well as Fugu possess an in frame deletion of a single AA at position #757 (between TM4 and 5) as compared to either mammalian CaRs or SKCaR.

SalmoKCaR #3 possesses a truncated carboxyl terminal domain as compared to either SalmoKCaRs #1, #2 or #4. The number of AA that comprise the carboxyl terminal domains of the 4 SalmoKCaRs are different and include: SalmoKCaR #1—96 AA; SalmoKCaR #2—97 AA, SalmoKCaR #3—5 AA, and SalmKCaR #4—96 AA. Reduction in the 91–92AA's in SalmoKCaR #3 vs. SalmoKCaRs #1, #2 or #4 would reduce its estimated molecular mass by 9,600 Daltons.

Studies from multiple site directed mutagenesis studies of HuPCaR reveal that alterations to the structure of the carboxyl terminal domain of PVCRs have profound effects on their function and sensitivity to ligands such as $Ca^{2+}$ and $Mg^{2+}$. Various truncations of the carboxyl terminal domain of HuPCaR have highlighted the importance of HuPCaR AAs #860–910. Truncation of the carboxyl terminal domain of HuPCaR to AAs less than AA#870 produced either an inactive receptor or a modified HuPCaR with a marked decrease in its affinity for extracellular $Ca^{2+}$ as well as a decrease in the apparent cooperativity of $Ca^{2+}$ dependent activation. While the exact functional characteristics of SalmoKCaR #3 remain to be determined using similar HEK transfection studies, these data derived from HuPCaR mutagenesis studies suggest that SalmoKCaR #3 protein is either inactive or exhibits a greatly reduced functional affinity for $Ca^{2+}$. Significant expression of SalmoKCaR #3 together with other SalmoKCaRs #1, #2 or #4 could result in an overall reduction in the response to extracellular Ca2+ due to so called dominant negative effects. These dominant negative effects could occur where SalmoKCaR#3 reduces the overall sensitivity of cells to $Ca^{2+}$ via combinations between SalmoKCaR #3 and SalmoKCaR #1/#2/#4 to reduce the sensitivity of the latter PVCRs via cooperative interactions (dimers and higher oligomers) with them.

Certain mutagenesis studies also highlight the importance of the Threonine AA at AA#888 in mediation of HuPCaR's sensitivity to Ca2+ and normal signal transduction. FIG. 19 shows that AA #888 is a Thr in all wild type CaR and PVCR proteins including HuPCaR, RaKCaR, SKCaR, BoPCaR and SalmoKCaR #1, #2, and #4. SalmoKCaR #3 is missing Thr #888 because of its truncated tail. Of interest is also the presence of consensus sites for receptor kinase phosphorylation (Ser-Ser-Ser) that are present at AA#907–909 in HuPCaR, RaKCaR, SKCaR BoPCaR and SalmoKCaR #1, #2 and #4. In contrast, Fugu PVCR possesses an Asn at AA#908 that would render its site nonrecongizable to protein kinases. A similar protein kinase site also appears in the region of AA#918–921 where HuPCaR, RaKCaR and BoPCaR possess a Ser-Ser-Ser motif. In contrast, SKCaR possesses an inactive site due to its sequence of Ala-Ser-Ser. Fugu PVCR and SalmoKCaR #1, #2 and #4 also have intact Ser-Ser-Ser motifs at position AA #918–920 or #919–921. The exact functional significance of these Ser-Ser-Ser sites possessed by SalmoKCaR #1, #2 and #4 await expression studies.

The Presence of Multiple Differences in the Nucleotide and Putative Protein Sequences of SalmoKCaR Clones #1–#4 Strongly Suggest the Presence of Multiple PVCR Genes within Atlantic Salmon:

Recent studies in rainbow trout provide direct evidence of the existence of multiple genes encoding two different forms of a specific type of protein, each of which are differentially expressed in specific tissues of trout. These proteins are aryl hydrocarbon receptor Type 2 (AhRs). Detailed studies on AhRs have shown the presence of 2 functional genes that produce different closely related AhR proteins, "Two forms of aryl hydrocarbon receptor type 2 in rainbow trout (*Oncorhynchus mykiss*)," by Abnet, C. C., et al., *J. of Biological Chemistry* 274: 15159–15166, (1999). These two proteins are differentially expressed in various tissues where they perform closely related but distinct functions.

The presence of single nucleotide substitutions together with specific large scale alterations in the sequence of SalmoKCaR clones #1–4 including the gapping of large numbers of nucleotides and alterations in reading frame of the resulting SalmoKCaR transcript are not readily explainable on the basis of differential splicing of RNA transcripts derived from a single gene, or perhaps some complex process where different alleles of a single gene are present in salmon. Alternatively, these data suggest that there are multiple PVCR genes present in Atlantic salmon that work in concert to enable Atlantic salmon and likely other salmonids to carry out their lifecycle stages that include hatching as well as development of larval and juvenile phases in freshwater followed by smoltification and migration into seawater with a subsequent return to freshwater for spawning.

Detailed studies in mammals including mice and humans show the presence of a single functional PVCR gene. However, multiple published reports provide support for the possibility that multiple PVCR genes exist in fish, while only a single functional PVCR gene exists in mammals including humans. Support for multiple PVCR genes is provided by detailed studies of well characterized genes that have demonstrated that teleost fish including salmonids possess multiple sets of duplicated genes as compared to mammals. These duplicated genes have arisen as a result of either genomic duplication events occurring early in the evolutionary history of fishes with subsequent gene drop out or via more recent selective duplication of genes or some combination of both. Moreover, it is widely acknowledged that salmonids are polyploid with respect to other teleost fish and have undergone an additional genome duplication. This additional genomic duplication further heightens the possibility that multiple functional PVCR genes exist in salmonids particularly Atlantic salmon.

If the products of a duplicated gene are not important in the development, growth or maintenance of an organism, the nonfunctional gene accumulates natural mutations and is either inactivated becoming a pseudogene or lost from the genome altogether. However, multiple authors have provided evidence that preservation of duplicated genes likely involves changes in the developmental or tissue specific expression pattern of the duplicated vs. original gene or formation of a new functional gene protein product that would interact with the original gene product in novel ways. (See AhR data above). These data provide support for the possible roles of SalmoKCaR transcripts #1–4 as either differentially expressed in various tissues of Atlantic salmon as well as SalmoKCaR #3 exerting a dominant negative effect on the remaining functional SalmoKCaR proteins. As discussed below, such interactions amongst SalmoKCaR transcripts would provide Atlantic salmon and perhaps all salmonids with the ability to exploit a wide variety of freshwater and seawater environments.

Part 2: Use of RT-PCR and Northern Analysis to Determine the Expression of SalmoKCaR Clones #1, #2 and #3 in Various Tissues of Atlantic Salmon:

Background:

SalmoKCaR clones #1, #2 and #3 were originally isolated from a Atlantic salmon kidney cDNA library. To determine the pattern of tissue specific expression of these various SalmoKCaR clones, both degenerate (to amplify all Salmo PVCRs species) and SalmoKCaR primers that will specifically amplify either SalmoKCaR #1 or #2 or #3 were utilized. As shown in "Materials and Methods" Section below, these primers amplify DNA products of different sizes that can be distinguished by agarose gel electrophoresis. PCR on specific cDNA clones confirms that these primer pairs function exclusively on the clones for which they have been designed. Note that both the degenerate and SalmoKCaR #3 specific primers do not span an intron and therefore RNA was treated with DNAse to ensure that there was not amplification of contaminating genomic DNA in the results shown. Primers specific for SalmoKCaR #1 and #2 span introns and therefore DNAase treatment is not required to interpret these results. As a control, the amounts of mRNA added to each RT-PCR reaction was determined by separate amplification of actin using primers designed from the published sequence of Atlantic salmon actin (Genbank Accession #AF012125 Salmo salar beta actin mRNA). SalmoKCaR #4 could be distinguished from SalmoKCaRs #1 or #2 by use of appropriate restriction enzymes that would identify single nt differences between SalmoKCaR's #1, #2 versus #4.

Materials and Methods:

Primers:

Degenerate Primers dSK-F3 and dSK-R4 primers are shown in Example 4.

| SalmoKCaR #1 Specific Primers | | | SalmoKCaR #1 nts |
|---|---|---|---|
| AS1-F17 | 5'- CAA GCA TTA TCA AGA TCA AG -3' | (SEQ ID NO:18) | nt 47–66 |
| AS2-R14 | 5'- CTC AGA GTG GCC TTG GC -3' | (SEQ ID NO:19) | nt 2800–2784 |

Product from amplification=2754 nt. The SalmoKCaR #1 primer pair consists of a forward primer (AS1-F17) spanning the 5' UTR insertion in SalmoKCaR #2, and a reverse primer (AS2-R14) within the 158 bp deleted from SalmoKCaR #3.

| SalmoKCaR #2 Specific Primers | | SalmoKCaR #2 nts |
|---|---|---|
| AS2-F13 5'- CAG TTC TCT CTT TAA TGG AC -3' | (SEQ ID NO:20) | nt 109–128 |
| AS2-R14 5'- CTC AGA GTG GCC TTG GC -3' | (SEQ ID NO:21) | nt 2890–2874 |

Product from amplification=2782 nt. The SalmoKCaR #2 primer pair is a forward primer (AS2-F13) in the 5' UTR insertion in SalmoKCaR #2 clone, and the same reverse primer as SalmoKCaR #1 primer (AS2-R14).

| SalmoKCaR #3 Specific Primers | | SalmoKCaR #3 nts |
|---|---|---|
| AS5-F11 5'- AGT CTA CAT CAT CCA TCA GCC -3' | (SEQ ID NO:22) | nt 2700–2720 |
| AS5-R12 5'- GAT TTT ATT GTC ATT GGA TGC -3' | (SEQ ID NO:23) | nt 3810–3790 |

Product from amplification=1111 nt. The SalmoKCaR #3 primer pair consists of a forward primer (AS5-F11) which spans the 158 bp deletion, and a reverse primer (AS5-R 12) located in the 36 bp insertion at the 3' end of the SalmoKCaR #3 clone.

| Salmon Actin Primers | | |
|---|---|---|
| SA-F1 5'- TGG AAG ATG AAA TCG CCG C -3' | (SEQ ID NO:24) | nt 2-20 |
| SA-R2 5'- GTG GTG GTG AAA CTG TAA CCG C -3' | (SEQ ID NO:25) | nt 608-587 |

Product from amplification=607 nt. This primer set is used to amplify salmon actin mRNA that serves as a control to quantify differences in mRNA content.

RNA Blotting Analysis and RT-PCR of Atlantic Salmon and Elasmobranch Tissues:

Total RNA was purified with Stat 60 reagent (Teltest B Friendswood, Tex.) DNAse (Introgen, Carlsbad, Calif.) treated and used for RT-PCR after cDNA production with cDNA Cycle Kit (Invitrogen, Carlsbad, Calif.). The cDNA was amplified (30 cycles of 1 min @ 94° C., 1 min @ 57° C., 3' @72° C.) using degenerate primers [forward primer dSK-F3 (SKCaR nts 2279–2306) and reverse primer dSK-R4 (SKCaR nts 2904–2934). Aliquots of PCR reactions were subjected to gel electrophoresis and ethidium bromide (EtBr) staining or blotted onto Magnagraph membranes (Osmonics, Westboro, Mass.) and probed with a $^{32}$P-atlantic salmon genomic PCR product (653 bp sequence identical to that shown in SEQ ID NO: 3 with added nt sequences, washed (0.1×SSC, 0.1% SDS @ 55° C.) and autoradiographed. Selected amplified PCR products from Atlantic salmon tissues were sequenced as described above. The following conditions were utilized for each of the SalmoKCaR specific primers and corresponding blots:

SalmoKCaR #1 amplification conditions and primer set: PCR: 1 min @ 94° C., 1 min @ 50° C., 3 min @ 72° C., 35 cycles. Amplification products attached to membrane were probed with full length SalmoKCaR #1 clone and washed (0.1×SSC, 0.1% SDS @ 55° C.) and autoradiographed for 48 hr.

SalmoKCaR #2 amplification conditions and primer set: PCR: 1 min @ 94° C., 1 min @ 50° C., 3 min @ 72° C., 35 cycles. Amplification products attached to membrane were probed with full length SalmoKCaR #2 clone and washed (0.1×SSC, 0.1% SDS @ 55° C.) and autoradiographed for 168 hr.

SalmoKCaR #3 amplification conditions and primer set: PCR: 1 min @ 94° C., 1 min @ 52° C., 3 min @ 72° C., 35 cycles. Amplification products attached to membrane were probed with full length SalmoKCaR #3 clone and washed (0.1×SSC, 0.1% SDS @ 55° C.) and autoradiographed for 72 hr.

Results:

Analysis of Atlantic Salmon Tissues from Freshwater vs. Seawater Adapted Fish Using Degenerate Primers:

FIG. 20 shows data obtained from 14 tissues of freshwater or seawater adapted Atlantic salmon using the degenerate primers described above. Samples were obtained from a single representative seawater adapted salmon (866 gm and 41 cm in length) from a group of 10 fish of average weight of 678 gm. Samples from nasal lamellae, urinary bladder, olfactory bulb and pituitary gland were all pooled samples from all 10 fish. The samples were from a representative single freshwater adapted fish (112 gm and 21.5 cm) selected from a group of 10 fish with an average weight of 142.8 gm. In contrast, samples from nasal lamellae, urinary bladder, olfactory bulb and pituitary gland were all pooled samples from all 10 fish. Note that the amplification products from these degenerate primers do not distinguish between SalmoKCaR #1, #2, #3 or #4 since their nt sequences in the region amplified by the primers are all identical (lanes 7, 9 and 12 Lower gel—Panels A, B, C and D). Moreover, these degenerate primers also possess the capacity to amplify additional PVCRs (if any are present) in salmon tissues that could be distinct from either SalmoKCaR #1–4. Thus, amplified RT-PCR products are referred to as PVCR products since use of these degenerate primers do not distinguish between various PVCR species.

Analysis of panels A–D of FIG. 20 shows that the PVCR degenerate primers yield PCR products in various tissues of both seawater and freshwater adapted fish. These various bands are more visible in Southern blots (Panels C, D) of corresponding ethidium bromide gels (Panels A and B) because detection of PVCR amplified products via hybridization of a $^{32}$P-PVCR probe is more sensitive as compared to ethidium bromide staining. Prominent ethidium bromide stained bands are visible in urinary bladder (lane 4), kidney (lane 5) and muscle (lane 14) in seawater adapted fish (Panel A) while either faint or no bands are seen in other tissues. In contrast, ethidium bromide bands are also visible in nasal lamellae (lane 3), urinary bladder (lane 4) and kidney (lane 5) as well as olfactory bulb (lane 12) in freshwater fish (Panel B). In summary, these data show differential tissue expression of PVCRs.

FIG. 20 shows a RT-PCR analysis of freshwater (Panels B, D and F) and seawater (Panels A, C and E) adapted Atlantic salmon tissues using either degenerate PVCR or salmon actin PCR primers. Total RNA from 13 (seawater adapted) and 14 (freshwater adapted) tissues of Atlantic salmon was first treated with DNAase to remove any genomic DNA contamination then used to synthesize cDNA that was amplified using degenerate primers. (Panels A and B); Ethidium bromide stained agarose gel. DNA markers in lane 1 of both Panels A and B were used to indicate size of amplification products. (Panels C and D) Southern blot of gel in Top Panel using $^{32}$P-labeled Atlantic salmon genomic fragment. (Panels E and F) Ethidium bromide stained gels of RT-PCR amplification products using Atlantic salmon beta actin primers as described above. These reactions serve as controls to ensure that samples contain equal amounts of RNA.

Southern blots (Panels C and D) of the corresponding gels shown in Panels A and B reveal that amplified PVCR products are present in additional tissues not shown by simple ethidium bromide staining as described above. As shown in Panel C, PVCRs are present in tissues of seawater-adapted salmon including gill (lane 2), nasal lamellae (lane 3), urinary bladder (lane 4), kidney (lane 5), stomach (lane 6), pyloric caeca (lane 7), proximal (lane 8) and distal (lane 9) intestine, pituitary gland (11) and muscle (lane 14). Ovary tissue was not tested in seawater-adapted fish. In contrast, freshwater-adapted salmon possess amplified PVCR products in gill (lane 2), nasal lamellae (lane 3), urinary bladder (lane 4), kidney (lane 5), proximal intestine (lane 8), brain (lane 10), pituitary (lane 11), olfactory bulb (lane 12), liver (lane 13), muscle (lane 14) and ovary (lower lane 3). The intensity of individual actin bands shown in Panels E and F performed on identical aliquots of the RT-PCR reactions serve to quantify any differences in pools of cDNA from the individual RT reactions in each sample. Isolation and subcloning of the ethidium bromide stained bands from olfactory lamellae and urinary bladder show that nucleotide sequences of multiple subclones from these bands all are identical to the nucleotide sequence present in SalmoKCaR clones #1–3.

Close examination of the differences in Panel C (seawater adapted) vs. Panel D (freshwater adapted) reveal differences in the apparent abundance of PVCR mRNA in specific tissues. Apparent increases in tissue PVCR mRNA abundance in seawater-adapted salmon vs. freshwater-adapted salmon are present in gill, kidney, stomach, pyloric caeca, distal intestine, and muscle. The increased expression of PVCRs in Atlantic salmon exposed to seawater is consistent with other data that an increase in PVCR expression in at least one tissue occurs upon transfer of Atlantic salmon from freshwater to seawater. In contrast, the abundance of PVCR mRNA species in olfactory bulb tissue of seawater adapted salmon appears to be reduced as compared to olfactory bulbs of freshwater adapted counterparts (Lane 12 in Panels C vs. D). In other tissues such as nasal lamellae (Lane 3 in Panel C vs. D) there is little or no apparent change in the steady state PVCR mRNA content. In summary, these data demonstrate tissue specific changes in the steady state expression of PVCR mRNA species in seawater adapted vs. freshwater adapted Atlantic salmon. Depending on the tissue, steady state PVCR mRNA content is either increased, decreased or remains unchanged when freshwater adapted fish are compared to seawater adapted counterparts. Since these analyses shown in FIG. 20 use PVCR degenerate primers, it is not possible to determine from these experiments whether the alterations in steady state PVCR mRNA content are the result of changes in individual SalmoKCaRs #1–4.

RT-PCR Analysis Using Degenerate Primers Shows that Steady State Content of Kidney PVCRs is Increased by the SuperSmolt™ Process Similar to that Produced by Transfer of Atlantic Salmon to Seawater.

FIG. 21 A shows RT-PCR analysis of a single representative experiment where kidney tissue was harvested from Atlantic salmon that had either been freshwater adapted (lane 1), exposed to 9 weeks of the SuperSmolt™ process in freshwater (lane 2) or transferred to seawater and maintained for 26 days. FIG. 21B shows RT-PCR analysis of a single representative experiment using pyloric caeca from the same fish shown in FIG. 21A. Note the significant increase in amplified PVCR product present in kidney (FIG. 21A) and pyloric caeca (FIG. 21B) for both SuperSmolt™ (lanes 2 and 7, respectively) and seawater adapted (lanes 3 and 8, respectively) fish as compared to freshwater (lanes 1 and 6, respectively). The increased expression of PVCRs in these 2 tissues of Atlantic salmon exposed to the SuperSmolt™ process where this increased PVCR expression mimics that produced after seawater transfer is consistent with earlier data that an increase in PVCR expression in at least one tissue occurs upon either treatment with the SuperSmolt™ process or transfer of Atlantic salmon to seawater.

FIG. 21C shows RT-PCR analysis using the same degenerate primers to detect expression of SalmoKCaR transcripts in various stages of Atlantic salmon embryo development. Using degenerate (SEQ ID Nos 15 and 16) or actin (SEQ ID No 24 and 25) primers, RNA obtained from samples of whole Atlantic salmon embryos at various stages of development were analyzed for expression of SalmoKCaRs using RT-PCR. Ethidium bromide staining of samples from dechorionated embryos (Lane 1), 50% hatched (Lane 2), 100% hatched (Lane 3), 2 weeks post hatched (Lane 4) and 4 weeks post hatched (Lane 5) shows that SalmoKCaR transcripts are present in Lanes 1–4. Southern blotting of the same gel (Panel C) confirms expression of SalmoKCaRs in embryos from very early stages up to 2 weeks after hatching. No expression of SalmoKCaR was observed in embryos 4 weeks after hatching. Panel B shows the series of controls where PCR amplification of actin content of each of the 5 samples shows they are approximately equal.

Northern Blotting of Kidney Poly A$^+$ RNA with SalmoKCaR #1 Reveals an Increase in PVCR Expression in Seawater-Adapted vs. Freshwater-Adapted Atlantic Salmon.

To both confirm the size of SalmoKCaR transcripts and test for changes in SalmoKCaR expression in fish exposed to different salinities, poly A$^+$ RNA from kidney of either freshwater adapted (FW) or seawater adapted (SW) Atlantic salmon were probed with SalmoKCaR #1. As shown in FIG. 22, kidney RNA contains a 4.2 kb band that corresponds to the 3.9–4.0 kb sizes of SalmoKCaR #1–4 as determined by nucleotide sequence analysis. Because of the high degree of nucleotide identities between SalmoKCaR #1–4, the 4.2 kb band is actually derived from the combination of all 4 SalmoKCaR species and any additional PVCR species in salmon kidney due to crosshybridization of SalmoKCaR #1. However, these data show an increase in the intensity of the 4.2 kb SalmoKCaR band in SW adapted fish as compared to their FW adapted counterparts.

FIG. 22 shows a RNA blot containing 5 micrograms of poly A$^+$ RNA from kidney tissue dissected from either freshwater adapted (FW) or seawater adapted (SW) Atlantic salmon probed with full length SalmoKCaR #1 clone. Autoradiogram exposure after 7 days.

Use of RT-PCR with SalmoKCaR #3 Specific Primers Demonstrates that Tissue Specific Alterations in the Steady State Tissue Content of SalmoKCaR #3 mRNA in Freshwater vs. Seawater Adapted Atlantic Salmon.

To determine whether specific SalmoKCaRs #3 are modulated by exposure to different salinities, nucleotide primer sets that allows for the specific amplification of SalmoKCaR transcripts were designed. FIG. 23 shows RT-PCR analysis of freshwater (Panels B, D and F) and seawater (Panels A, C and E) adapted Atlantic salmon tissues using either SalmoKCaR #3 specific PCR primers or salmon actin PCR primers. Total RNA from 13 (seawater adapted) and 14 (freshwater adapted) tissues of Atlantic salmon identical to those shown in FIG. 20 were first treated with DNAase to remove any genomic DNA contamination, then used to synthesize cDNA that was amplified using SalmoKCaR #3 primers. All RNA samples were prepared from a single fish with the exception of olfactory bulb, pituitary, urinary bladder and nasal lamellae that are composed of RNA from pooled samples of fish. Selected reactions were subjected to primer amplification using SalmoKCaR#3 specific primers. DNA markers in lane 1 of both Panels A and B were used to indicate size of amplification products. (Panels C and D) Southern blot of gel in Top Panel using $^{32}$P-labeled Atlantic salmon genomic fragment. (Panels E and F) Ethidium bromide stained gel of RT-PCR amplification products using Atlantic salmon beta actin primers as described above. These reactions serve as controls to ensure that samples contain equal amounts of RNA. The specificity of these SalmoKCaR#3 primers is demonstrated in the bottom half of Panels A and B of FIG. 23. The specific SalmoKCaR #3 primers only amplify product from SalmoKCaR #3 clone (lane 14) and not SalmoKCaR #1 (lane 8) or SalmoKCaR #2 (lane 11) or SalmoKCaR #4. Note that in the tissue sample lanes, ethidium bromide stained bands are present in the kidney of seawater adapted salmon (lane 5 upper gel-Panel A) and only very faintly in urinary bladder of freshwater adapted salmon (lane 4 upper gel-Panel B). The corresponding Southern blots of freshwater adapted tissue samples (Panel D) reveal detectable SalmoKCaR #3 product only in urinary bladder (lane 4) and a small amount in kidney (lane 5). In contrast, in seawater-adapted salmon (Panel C) there are detectable increases in SalmoKCaR #3 product in both urinary bladder (lane 4) and kidney (lane 5) as well as the presence of SalmoKCaR #3 amplified product in gill (lane 2), nasal lamellae (lane 3), pyloric caeca (lane 7) and muscle (lane 14) of seawater adapted fish.

As described above, the increase in tissue expression of SalmoKCaR #3 serves to provide for a possible means to reduce the overall tissue sensitivity to PVCR-mediated sensing via an action where SalmoKCaR #3 would act as a dominant negative effector. In contrast to freshwater where the ambient water concentrations of both $Ca^{2+}$ and $Mg^{2+}$ are low and require a high degree of sensitivity from SalmoKCaRs to sense changes in concentration, the concentrations of $Ca^{2+}$ and $Mg^{2+}$ in seawater are 10 fold and 50 fold higher and thus may require reduction of the high sensitivity of SalmoKCaRs #1, #2 and #4 by SalmoKCaR #3. It is of interest that many of these specific tissues exhibiting significant SalmoKCaR #3 expression are either exposed directly to the high $Ca^{2+}$ and $Mg^{2+}$ content of seawater (gill, nasal lamellae) or experience high $Ca^{2+}$ and $Mg^{2+}$ concentrations as the result of the excretion of these divalent cations (urinary bladder, kidney).

Use of RT-PCR with SalmoKCaR #1 Specific Primers Demonstrates Tissue Specific Alterations in the Steady State Tissue Content of SalmoKCaR #1 mRNA in Freshwater vs. Seawater Adapted Atlantic Salmon.

FIG. 24 shows RT-PCR analysis of freshwater (Panels B, D and F) and seawater (Panels A, C and E) adapted Atlantic salmon tissues using either SalmoKCaR #1 specific PCR primers or salmon actin PCR primers. Total RNA from 13 (seawater adapted) and 14 (freshwater adapted) tissues of Atlantic salmon identical to those shown in FIGS. 20 and 23 were used to synthesize cDNA that was amplified using SalmoKCaR #1 primers. All RNA samples were prepared from a single fish with the exception of olfactory bulb, pituitary, urinary bladder and nasal lamellae that are composed of RNA from pooled samples of fish. As controls to demonstrate primer specificity, selected reactions were subjected to primer amplification of portions of individual SalmoKCaR clones or water alone (Panels A and B): Ethidium bromide stained agarose gel. DNA markers in lane 1 of both Panels A and B were used to indicate size of amplification products. (Panels C and D) Southern blot of gel in Top Panel using $^{32}$P-labeled Atlantic salmon genomic fragment. (Panes E and F) Ethidium bromide stained gel of RT-PCR amplification products using Atlantic salmon beta actin primers as described above. These reactions serve as controls to ensure that samples contain equal amounts of RNA. As shown in lower halves of Panels A and B of FIG. 24, PCR amplification with these primers yields an ethidium bromide staining band (lane 5) when SalmoKCaR #1 clone is used as a template but not either SalmoKCaR #2 (lane 6) or SalmoKCaR #3 (lane 7). Similar analysis could be performed on SalmoKCaR #4. Southern blotting analysis of the gels shown in Panels A and B reveals that the amplification product of the SalmoKCaR #3 is highly positive (lanes 5)—Panels C and D. In the various tissue samples, SalmoKCaR #1 product is amplified in selected tissues including urinary bladder (lane 4) and pyloric caeca (lane 7) in seawater-adapted salmon (Panel C) as compared to urinary bladder (lane 4) and kidney (lane 5) in freshwater-adapted salmon (Panel D). The exact nature of the smaller and larger than expected PCR amplification products present in gill (lane 2—Panels C, D) and nasal lamellae (lane 3—Panel D) are not known at present. These data show tissue specific expression of SalmoKCaR #1 in both freshwater and seawater adapted salmon.

Use of RT-PCR with SalmoKCaR #2 Specific Primers Demonstrates Tissue Specific Alterations in the Steady State Tissue Content of SalmoKCaR #2 mRNA in Freshwater vs. Seawater Adapted Atlantic Salmon.

FIG. 25 shows RT-PCR analysis of freshwater (Panels B, D and F) and seawater (Panels A, C and E) adapted Atlantic salmon tissues using either SalmoKCaR #2 specific PCR primers or salmon actin PCR primers. Total RNA from 13 (seawater adapted) and 14 (freshwater adapted) tissues of Atlantic salmon was used to synthesize cDNA that was amplified using SalmoKCaR #2 primers. All RNA samples were prepared from a single fish with the exception of olfactory bulb, pituitary, urinary bladder and nasal lamellae that are composed of RNA from pooled samples of fish. As controls to demonstrate primer specificity, selected reactions were subjected to primer amplification with samples of portions of individual SalmoKCaR clones or water alone (Panels A and B): Ethidium bromide stained agarose gel. DNA markers in lane 1 Panels A, B, E and F were used to indicate size of amplification products. (Panels C and D) Southern blot of gel in Top Panel using $^{32}$P-labeled Atlantic salmon genomic fragment. (Panes E and F) Ethidium bromide stained gel of RT-PCR amplification products using Atlantic salmon beta actin primers as described above. These reactions serve as controls to ensure that samples contain equal amounts of RNA. FIG. 25 shows data obtained using SalmoKCaR #2 specific primers and the identical tissue RT and plasmid samples as shown in FIGS. 20, 23, and 24. Corresponding Southern blots shown in Panels C and D reveal the presence of SalmoKCaR #2 PCR amplification product in urinary bladder of seawater-adapted salmon (lane 4) as well as urinary bladder (lane 4) and kidney (lane 5) of freshwater-adapted salmon. These data provide evidence of the tissue specific expression of SalmoKCaR #1 in both freshwater and seawater adapted salmon.

EXAMPLE 7

Survival and Growth of Pre-Adult Anadromous Fish by Modulating PVCRS

An important feature of current salmon farming is the placement of smolt from freshwater hatcheries to ocean netpens. Present day methods use smolt that have attained a critical size of approximately 70–110 grams body weight. The methods described herein to modulate one or more PVCRs of the anadromous fish including Atlantic Salmon, can either be utilized both to improve the ocean netpen transfer of standard 70–110 grams smolt as well as permit the successful ocean netpen transfer of smaller smolts weighing, for example, only 15 grams. As shown herein, one utility for the present invention is its use in conjunction with transferring Atlantic Salmon from freshwater to seawater. For standard 70–110 gram smolt, application of the invention eliminates the phenomenon known as "smolt window" and permits fish to be maintained and transferred into ocean water at 15° C. or higher. Use of these methods in 15 gram or larger smolt permits greater utilization of freshwater hatchery capacities followed by successful seawater transfer to ocean netpens. In both cases, fish that undergo the steps described herein feed vigorously within a short interval of time after transfer to ocean netpens and thus exhibit rapid growth rates upon transfer to seawater.

Figure 26:
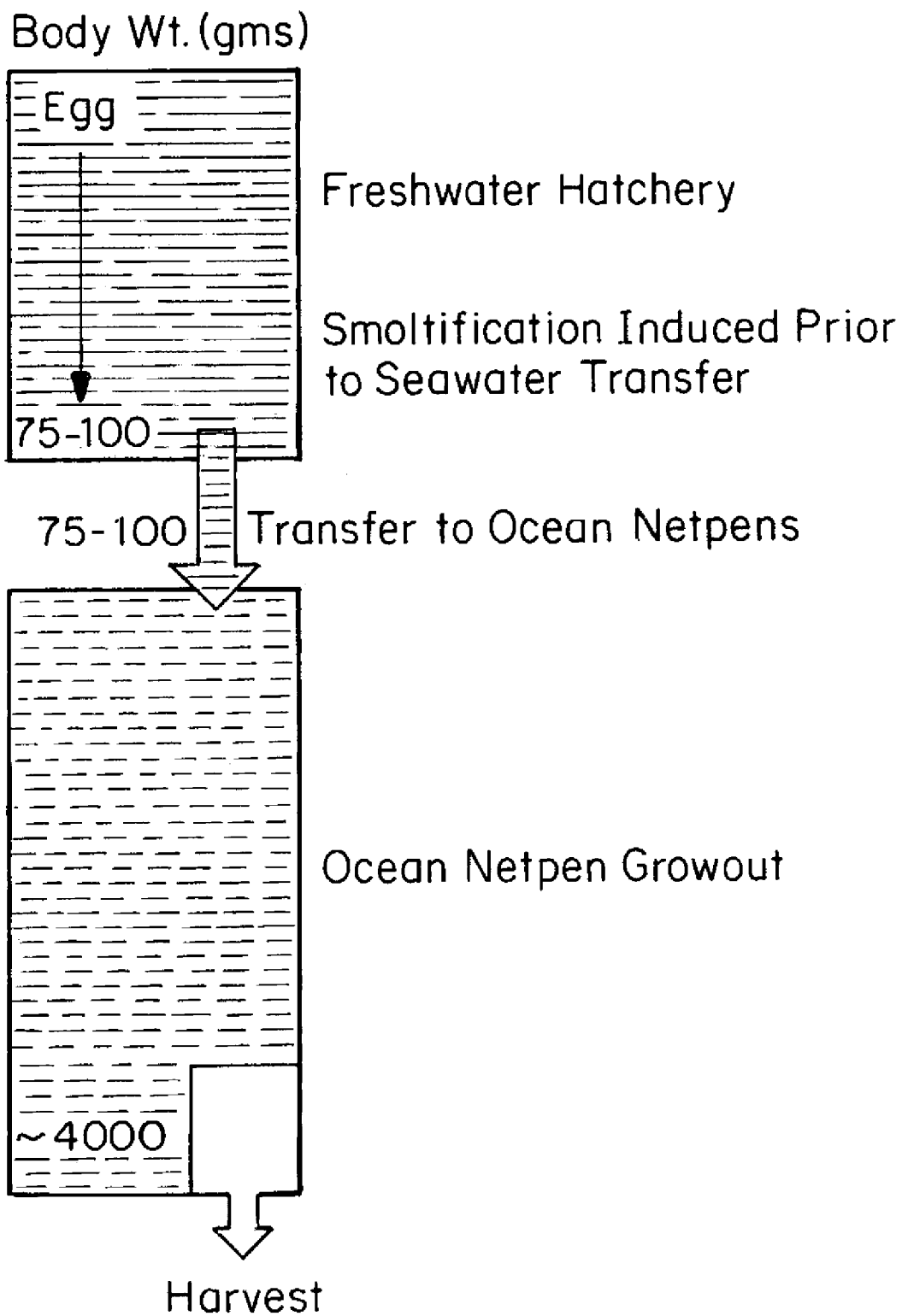
FIG. 26 is a schematic diagram illustrating industry practice for salmon aquaculture production, prior to the discovery of the present invention. The diagram depicts key steps in salmon production for S0 (75 gram) and S1 (100 gram) smolts. The wavy symbol indicates freshwater while the bubbles indicate seawater.

FIG. 26 shows in schematic form the key features of current aquaculture of Atlantic salmon in ocean temperatures present in Europe and Chile. Eggs are hatched in inland freshwater hatcheries and the resulting fry grow into fingerlings and parr. Faster growing parr are able to undergo smoltification and placement in ocean netpens as S0 smolt (70 gram) during year 01. In contrast, slower growing parr are smoltified in year 02 and placed in netpens as S1 smolt (100 gram). In both S0 and S1 transfers to seawater, the presence of cooler ocean and freshwater temperatures are desired to minimize the stress of osmotic shock to newly transferred smolt. This is particularly true for S1 smolt since freshwater hatcheries are often located at significant distances from ocean netpen growout sites and their water temperatures rise rapidly during early summer. Thus, the combination of rising water temperatures and the tendency of smolt to revert or die when held for prolonged intervals in freshwater produces a need to transfer smolt into seawater during the smolt window.

Standard smolts that are newly placed in ocean netpens are not able to grow optimally during their first 40–60 day interval in seawater because of the presence of osmotic stress that delays their feeding. This interval of osmotic adaptation prevents the smolts from taking advantage of the large number of degree days present immediately after either spring or fall placement. The combination of the presence of the smolt window together with delays in achieving optimal smolt growth prolong the growout interval to obtain market size fish. This is particularly problematic for S0's since the timing of their harvest is sometimes complicated by the occurrence of grilsing in maturing fish that are exposed to reductions in ambient photoperiod.

Methods

The smolt were subjected to the steps of Process I and II, as described herein.

Results and Discussion:

Section I: Demonstration of the Benefits of the Process I for Atlantic Salmon

Demonstration of the Benefits of the Process I for Atlantic Salmon:

Process I increases the survival of small Atlantic Salmon S2 like smolt after their transfer to seawater when compared to matched freshwater controls. Optimal survival is achieved by using the complete process consisting of both the magnesium and calcium water mixture as well as NaCl diet. In contrast, administration of calcium and magnesium either via the food only or without NaCl dietary supplementation does not produce results equivalent to Process I.

Table 3 shows data obtained from Atlantic salmon S2 like smolts less than 1 year old weighing approximately 25 gm. This single group of fish was apportioned into 4 specific groups as indicated below and each were maintained under identical laboratory conditions except for the variables tested. All fish were maintained at a water temperature of 9–13° C. and a continuous photoperiod for the duration of the experiment. The control freshwater group that remained in freshwater for the initial 45 day interval experienced a 33% mortality rate under these conditions such that only 67% were able to be transferred to seawater. After transfer to seawater, this group also experienced high mortality where only one half of these smolts survived. Inclusion of calcium (10 mM) and magnesium (5 mM) within the feed offered to smolt (Ca2+/Mg2+diet) reduced survival as compared to controls both in freshwater (51% vs 67%) as well after seawater transfer (1% vs 50%). In contrast, inclusion of 10 mM Ca2+ and 5 mM Mg2+ in the freshwater (Process I Water Only) improved smolt survival in Process I water as well as after transfer of smolt to seawater. However, optimal results were obtained (99% survival in both the Process I water mixture as well as after seawater transfer) when smolt were maintained in Process I water mixture and fed a diet supplemented with 7% sodium chloride.

TABLE 3

Comparison of the Survival of Atlantic Salmon S2 like Smolts After Various Treatments

| Parameter Sampled | Control Freshwater | Ca2+/Mg2+ Diet | Process I Water Only | Process I Water + NaCl Diet |
|---|---|---|---|---|
| Starting # of fish | 66 | 70 | 74 | 130 |
| # of fish | 44 | 36 | 67 | 129 |
| % of fish surviving after 45 days in freshwater or Process I mixture | 67% | 51% | 91% | 99% |
| # of fish | 22 | 2 | 60 | 128 |
| % of fish surviving 5 days after transfer to seawater | 50% | 6% | 90% | 99% |

[1]Survival percentages expressed as rounded whole numbers

Application of the Process I to the Placement of 70–100 gm Smolts in Seawater.

These data show that use of the Process I eliminates the "smolt window" and provides for immediate smolt feeding and significant improvement in smolt growth rates.

Experimental Protocol:

Smolts derived from the St. John strain of Atlantic salmon produced by the Connors Brothers Deblois Hatchery located in Cherryfield, Me., USA were utilized for this large scale test. Smolts were produced using standard practices at this hatchery and were derived from a January 1999 egg hatching. All smolts were transferred with standard commercially available smolt trucks and transfer personnel. S1 smolt were purchased during Maine's year 2000 smolt window and smolt deliveries were taken between the dates of Apr. 29, 2000–May 15, 2000. Smolts were either transferred directly to Polar Circle netpens (24 m diameter) located in Blue Hill Bay Maine (Controls) or delivered to the treatment facility where they were treated with Process I for a total of 45 days.

After receiving the Process I treatment, the smolt were then transported to the identical Blue Hill Bay netpen site and placed in an adjacent rectangular steel cage (15 m×15 m×5 m) for growout. Both groups of fish received an identical mixture of moist (38% moisture) and dry (10% moisture) salmonid feed (Connors Bros). Each of the netpens were fed by hand or feed blower to satiation twice per day using camera visualization of feeding. Mort dives were performed on a regular basis and each netpen received identical standard care practices established on this salmon farm. Sampling of fish for growth analyses was performed at either 42 days (Process I) or 120 days or greater (Control) fish. In both cases, fish were removed from the netpens and multiple analyses performed as described below.

All calculations to obtain feed conversion ratio (FCR) or specific growth rate (SGR) and growth factor (GF3) were performed using standard accepted formulae (Willoughby, S. Manual of Salmonid Farming Blackwell Scientific, Oxford UK 1999) and established measurements of degree days for the Blue Hill Bay site as provided in Table 4 below. A degree day is calculated by multiplying the number of days in a month by the mean daily temperature in degrees Celsius.

TABLE 4

Degree days for Blue Hill Bay Salmon Aquaculture Site

| Month | Degree Days |
|---|---|
| Jan | 60 |
| Feb | 30 |
| Mar | 15 |
| April | 120 |
| May | 210 |
| June | 300 |
| July | 390 |
| Aug | 450 |
| Sept | 420 |
| Oct | 360 |
| Nov | 240 |
| Dec | 180 |

Table 5 displays data obtained after seawater transfer of Control S1 smolt. Smolt ranging from 75–125 gm were placed into 3 independent netpens and subjected to normal farm practices and demonstrated characteristics typical for present day salmon aquaculture in Maine. Significant mortalities (average 3.3%) were experienced after transfer into cool (10° C.) seawater and full feeding was achieved only after a significant interval (~56 days) in ocean netpens. As a result, the average SGR and GF3 values for these 3 netpens were 1.09 and 1.76 respectively for the 105–121 day interval measured.

In contrast to the immediate transfer of Control S1 smolt as described above to ocean netpens (Table 5), a total of 10,600 S1 smolt possessing an average size of 63.6 grams were transported on May 11, 2000 from the Deblois freshwater hatchery to the research facility. While being maintained in standard circular tanks, these fish were held for a total of 45 days at an average water temperature of 11° C. and were subjected to Process I. During this interval, smolt mortality was only 64 fish (0.6%). As a matched control for the Process I fish, a smaller group of control fish (n=220) were held under identical conditions but did not receive the Process I treatment. The mortalities of these control fish were minimized by the holding temperature of 10° C. and were equivalent to treated smolts prior to transfer to seawater.

TABLE 5

Characteristics of St. John S1 smolt subjected to immediate placement in ocean netpens after transport form the freshwater hatchery without Process I or Process II technology (the Control fish)

| | Netpen Number | | |
|---|---|---|---|
| | #17 | #18 | #10 |
| Total Fish | 51,363 | 43,644 | 55,570 |
| Mean Date of Seawater Transfer | May 1, 2000 | May 5, 2000 | May 14, 2000 |
| Average Size at Transfer (grams) | (117.6) 100–125 | 75–100 | 75–100 |
| Mortalities after 30 days (# and % total) | 1,785; 3.5% | 728; 1.7% | 2503; 4.5% |
| Time to achieve full feeding after transfer | 68 days | 48 days | 50 days |
| Interval between netpen placement and analysis Average size at Analysis | 121 | 120 | 105 |
| Weight (gram) | 376.8 ± 74 | 305.80 ± 64 | 298.90 ± 37.40 |
| Length (cm) | 33.4 ± 1.9 | 28.30 ± 9.0 | 30.40 ± 1.17 |
| Condition Factor (k) | 1.02 | 1.34 | 1.06 |
| SGR during initial 120 days | 0.96 | 1.10 | 1.17 |

During the 45 day interval when S1 smolts were receiving Process I, fish grew an average of 10 grams and thus possessed an average weight of 76.6 gm when transferred to an ocean netpen. The actual smolt transfer to seawater occurring on Jun. 26, 2000 was notable for the unusual vigor of the smolt that would have normally been problematic since this time is well past the normal window for ocean placement of smolt. The ocean temperature at the time of Process I smolt netpen placement was 15.1° C. In contrast to the counterpart SI smolts subjected to standard industry practices described above, Process I smolts fed vigorously within 48 hours of ocean placement and continued to increase their consumption of food during the immediate post-transfer period. The mortality of Process I smolts was comparable to that of smolts placed earlier in the summer (6.1%) during initial 50 days after ocean netpen placement and two thirds of those mortalities were directly attributable to scale loss and other physical damage incurred during the transfer process itself.

In contrast, corresponding control fish (held under identical conditions without Process I treatment) did not fare well during transfer to the netpen (17% transfer mortality) and did not feed vigorously at any time during the first 20 days after ocean netpen placement. This smaller number of control fish (176) were held in a smaller (1.5 m×1.5 m×1.5 m) netpen floating within the larger netpen containing Process I smolts. Their mortality post-ocean netpen placement was very high at 63% within the 51 day interval.

Both Process I and control smolts were fed on a daily basis in a manner identical to that experienced by the Industry Standard Fish shown on Table 5. Process I fish were sampled 51 days after their seawater placement and compared to the Industry Standard smolts from Table 5. As shown in Table 6, comparison of their characteristics reveals dramatic differences between Industry Standard smolts vs Process I.

TABLE 6

Comparison of the characteristics of St. John S1 Process I Smolts subjected to Process I treatment and then placed in ocean netpens vs corresponding industry standard smolts.

| | Process I Smolts | Averaged Industry Standard Data from Table 5 in this Example |
|---|---|---|
| Total Fish | 10,600 | 150,577 |
| Mean Date of Seawater Transfer | Jun. 26, 2000 | May 7, 2000 |
| Average Size at Transfer (grams) | 76.6 | 95.8 |
| Mortalities after 30 days (# and %) | 648; 6.1% | 5,016; 3.3% |
| Time to achieve full Feeding after transfer | 2 days | 56 days |
| Interval between netpen placement and analysis Average size at Analysis | 51 | 115 |
| Weight (gram) | 175.48 ± 50 | 327.2 ± 97 |
| Length (cm) | 26.2 ± 32 | 30.7 |
| Condition Factor (k) | 0.95 ± 0.9 | 1.14 |
| SGR | 1.80 | 1.09 |

In summary, notable differences between Process I, Control smolt and Industry Standard smolt include:

1. The mortalities observed after ocean netpen placement were low in Process I (6.1%) vs Control (63%) despite the that fact these fish were transferred to seawater 1.5 months after the smolt window and into a very high (15.1° C.) ocean water temperature. The mortality of Process I was comparable to that of the accepted Industry Standard smolt (3–10%) transferred to cooler (10° C.) seawater during the smolt window. This characteristic of Process I provides for a greater flexibility in freshwater hatchery operations since placement of Process I smolts are not rigidly confined the conventional "smolt window" currently used in industry practice.

2. The Process I fish were in peak condition during and immediately after seawater transfer. Unlike industry standard smolt that required 56 days to reach full feeding, the Process I smolts fed vigorously within 2 days. Moreover, the initial growth rate (SGR 1.8) demonstrated by Process I smolts are significantly greater than published data for standard smolt during their initial 50 days after seawater placement (published values (Stradmeyer, L. Is feeding nonstarters a waste of time. Fish Farmer 3:12–13, 1991; Usher, M L, C Talbot and F B Eddy. Effects of transfer to seawater on growth and feeding in Atlantic salmon smolts (Salmo salar L.) Aquaculture 94:309–326, 1991) for SGR's range between 0.2–0.8). In fact, the growth rates of Process I smolts are significantly larger as compared to Industry standard smolts placed into seawater on the same site despite that industry standard smolt were both larger at the time of seawater placement as well as that their growth was measured 120 days after seawater placement. These data provide evidence that the Process I smolts were not subjected to significant osmoregulatory stress which would prevent them from feeding immediately.

3. The rapid growth of Process I smolts immediately upon ocean netpen placement provides for compounding increases in the size of salmon as seawater growout proceeds. Thus, it is anticipated that if Industry Standard Smolts weighing 112.5 gram (gm) were subjected to Process I treatment, placed in ocean netpens and examined at 120 days after ocean netpen placement their size would be average 782 gram instead of 377 gram as observed. This provides for more than a doubling in size of fish in the early stages of growout. Such fish would reach market size more rapidly as compared to industry standard fish.

Figure 27A:
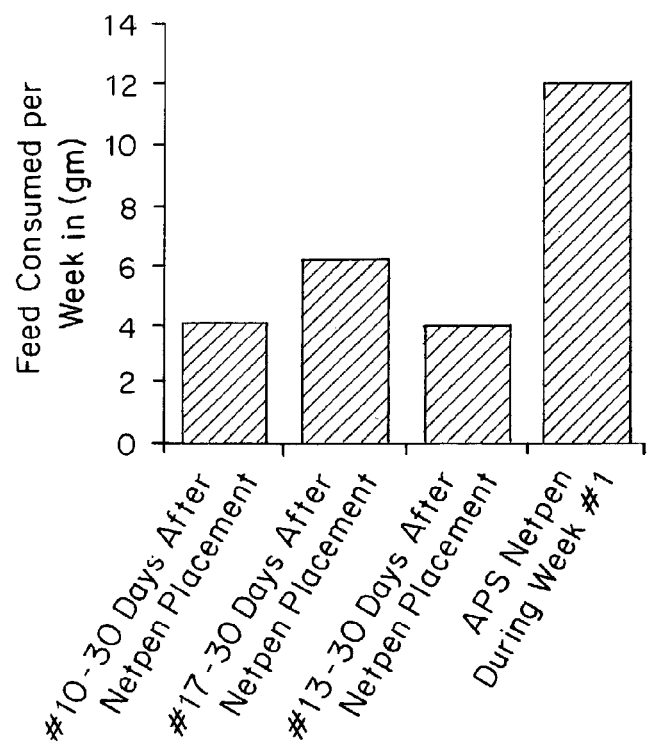
FIG. 27A is a graphical representation comparing the weekly feed consumption on a per fish basis between Process I treated smolts weighing approximately 76.6 gm vs industry standard smolt weighing approximately 95.8 gm. These data are derived from individual netpens of fish containing about 10,000–50,000 fish per pen. As shown, fish treated with Process I consumed approximately twice as much feed per fish during their first week after seawater transfer as compared to the large industry standard smolts weekly food consumption after 30 days. Process I treatment is defined in the Exemplification.

In contrast to the counterpart S1 smolts subjected to standard industry practices, smolt treated with Process I fed vigorously within 48 hours of ocean placement and continued to increase their consumption of food during the immediate post-transfer period. By comparison, the industry standard smolts consumed little or no feed within the first week after transfer. FIG. 27A compares the weekly feed consumption on a per fish basis between Process I treated smolts and industry standard smolts. As shown, Process I treated smolts consumed approximately twice as much feed per fish during their FIRST WEEK as compared to the industry standard smolts after 30 days. Since smolts treated with Process I fed significantly more as compared to Industry standard smolts, the Process I treated smolts grew faster.

Figure 27B:
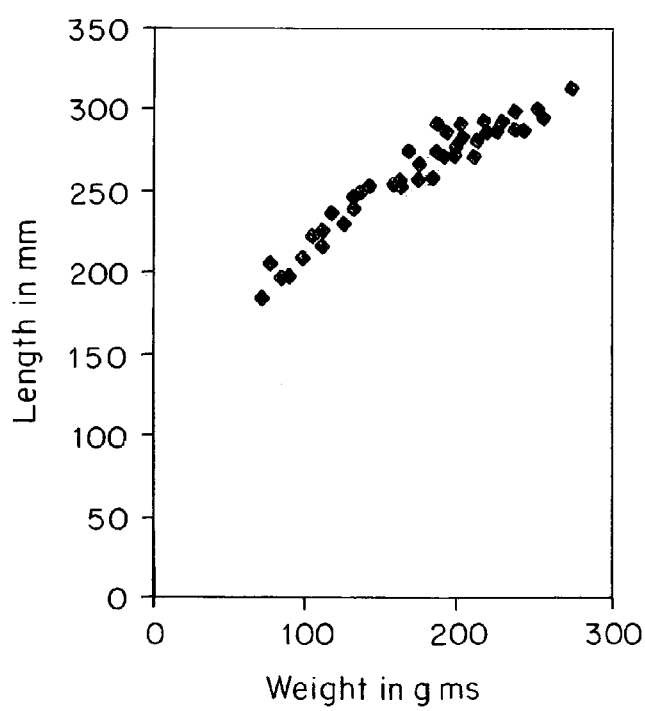
FIG. 27B is a graphical representation illustrating length (cm) and weight (gm) of Process I Smolts 50 days after ocean netpen placement. Process I smolts had an average weight of 76.6 gram when placed in seawater and were sampled after 50 days.

FIG. 27B provides data on the characteristics of Process I smolts after seawater transfer. These experiments were carried out for over 185 days.

Application of the Process I to Atlantic Salmon Pre-Adult Fish that are Smaller than the Industry Standard "Critical Size" Smolt.

A total of 1,400 Landcatch/St John strain fingerlings possessing an average weight of 20.5 gram were purchased from Atlantic Salmon of Maine Inc., Quossic Hatchery, Quossic, Me., USA on Aug. 1, 2000. These fingerlings were derived from an egg hatching in January 2000 and considered rapidly growing fish. They were transported to the treatment facility using standard conventional truck transport. After their arrival, these fingerlings were first placed in typical freshwater growout conditions for 14 days. These fingerlings were then subjected to Process I for a total of 29 days while being exposed to a continuous photoperiod. The Process I were then vaccinated with the Lipogen Forte product (Aquahealth LTD.) and transported to ocean netpens by conventional truck transport and placed into seawater (15.6° C.) in either a research ocean netpen possessing both a predator net as well as net openings small enough (0.25 inch) to prevent loss of these smaller Process I smolts. Alternatively, Process I smolts were placed in circular tanks within the laboratory. Forty eight hours after sea water transfer, Process I smolts were begun on standard moist (38% moisture) smolt feed (Connors Bros.) that had been re-pelletized due to the necessity to provide for smaller size feed for smaller Process I smolts, as compared to normal industry salmon. In a manner identical to that described for 70 gram smolts above, the mortality, feed consumption, growth and overall health of these 30 gram Process I smolts were monitored closely.

Figure 28:
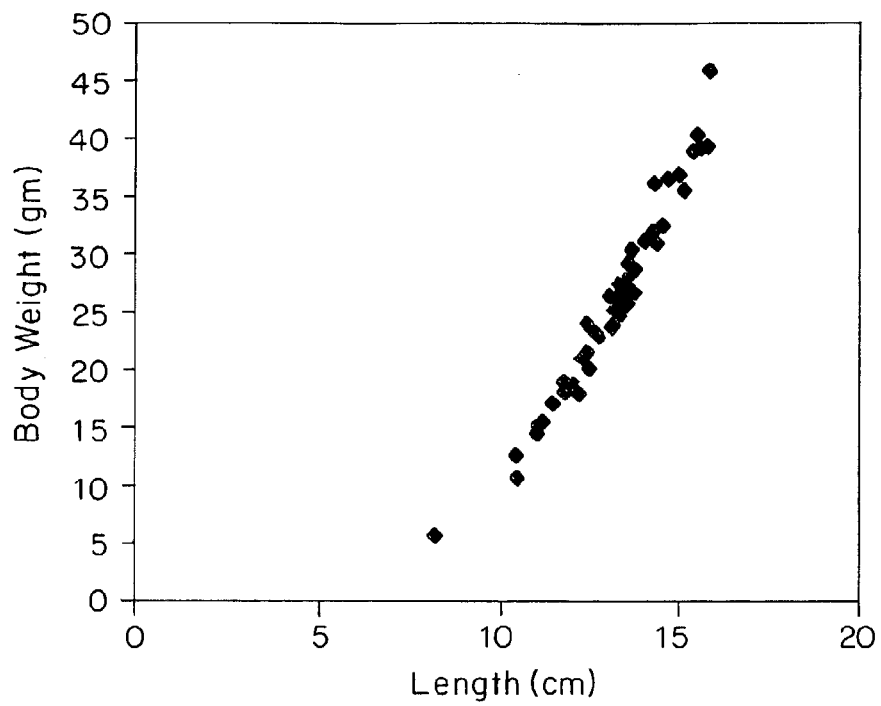
FIG. 28 is a graphical representation illustrating length (cm) and weight (gm) of representative Process I smolts prior to transfer to seawater.

FIG. 28 displays the characteristics of a representative sample of a larger group of 1,209 Process I smolts immediately prior to their transfer to seawater. These parameters included an average weight of 26.6+8.6 gram, length of 13.1+1.54 cm and condition factor of 1.12+0.06. After seawater transfer, Process I smolts exhibited a low initial mortality despite the fact that their average body weight is 26–38% of industry standard 70–100 gram S0–S1 smolts. As shown in Table 7, Process I smolts mortality within the initial 72 hr after seawater placement was 1/140 or 0.07% for the laboratory tank. Ocean netpen mortalities after placement of Process I smolts were 143/1069 or 13.4%. FIG. 28 shows representative Landcatch/St John strain Process I smolts possessing a range of body sizes that were transferred to seawater either in ocean netpens or corresponding laboratory seawater tanks. Process I smolts possess a wide range of sizes (e.g., from about 5.6 grams to about 46.8 grams body weight) with an average body weight of 26.6 gram.

Experiments with these data were carried out for 84 days after the transfer of fish to seawater tanks, and the data from these experiments are described in co-pending application No: 09/975,553.

TABLE 7

Characteristics and survival of Landcatch/St. John Process I fish after their placement into seawater in either a laboratory tank or ocean netpen.

| | Laboratory Tank | Ocean Netpen |
|---|---|---|
| Total Fish | 140 | 1,069 |
| Date of Seawater Transfer | Sep. 5, 2000 (40); Sep. 12, 2000 (100) | Sep. 12, 2000 |
| Average Size at Transfer (gram) | 26.6 | 26.6 |
| Total mortalities after 4 days (# and % total) | 1; 0.7% | 143; 13.4% |
| % mortality of fish weighing 25 gm and above | 0; 0.0% | 4; 0.4% |
| Time to achieve feeding | 48 hrs | 72 hrs |

Figure 29:
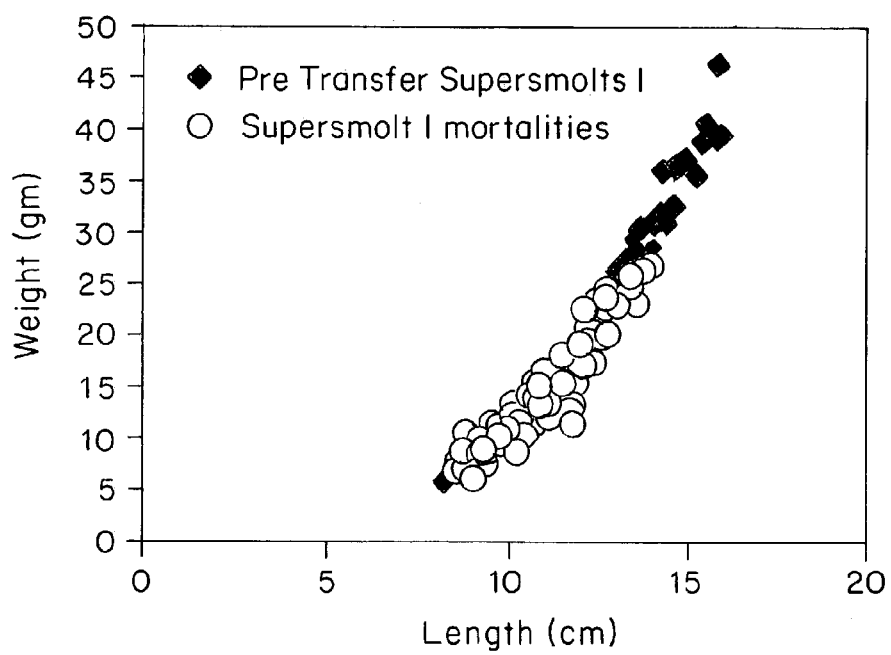
FIG. 29 is a graphical representation illustrating length (cm) and weight (gm) of Process I smolts before transfer, and mortalities after transfer to ocean netpens.

FIG. 29 shows a comparison of the distributions of body characteristics for total group of Landcatch/St John Process I smolts vs. mortalities 72 hr after seawater ocean netpen placement. Length and body weight data obtained from the 143 mortalities occurring after seawater placement of 1,069 Process I smolts were plotted on data obtained from a 100 fish sampling as shown previously in FIG. 28. Note that the mortalities are exclusively distributed among the smaller fish within the larger Process I netpen population.

Length and weight measurements for all mortalities collected from the bottom of the ocean netpen were compared to the distribution of Process I smolt body characteristics obtained from analysis of a representative sample prior shown in FIG. 29. The data show that the mortalities occurred selectively amongst Process I smolts possessing small body sizes such that the mean body weight of mortalities was 54% of the mean body weight of the total transfer population (14.7/27 gram or 54%). Thus, the actual mortality rates of Process I smolts weighing 25–30 gram is 0.4% (4/1069) and those weighing 18–30 gram is 2.9% (31/1069).

Application of Process I to Trout Pre-Adult Fish that are Smaller than the Industry Standard "Critical Size" Smolt.

Table 8 displays data on the use of the Process I on small (3–5 gram) rainbow trout. Juvenile trout are much less tolerant of abrupt transfers from freshwater to seawater as compared to juvenile Atlantic salmon. As a result, many commercial seawater trout producers transfer their fish to brackish water sites located in estuaries or fresh water lenses or construct "drinking water" systems to provide fresh water for trout instead of the full strength seawater present in standard ocean netpens. After a prolonged interval of osmotic adaptation, trout are then transferred to more standard ocean netpen sites to complete their growout cycle. In general, trout are transferred to these ocean sites for growout at body weights of approximately 70–90 or 90–120 gram.

TABLE 8

Comparison of the Survival of Rainbow Trout (3–5 gram) in Seawater After Various Treatments.
Percent Survival of Fish[1]

| Hours Post Seawater Transfer | Control Freshwater | Constant 14 Constant 14 day Photoperiod | Constant 14 day Photoperiod Process I | Constant 23 day Photoperiod + Process I |
|---|---|---|---|---|
| 0 | 100 | 100 | 100 | 100 |
| 24 | 0 | 25 | 80 | 99 |
| 48 |  | 0 | 70 | 81 |
| 72 |  |  | 40 | 68 |
| 96 |  |  | 30 | 58 |
| 120 |  |  | 30 | 46 |
| Number of Fish Per Experiment | 10 | 20 | 30 | 80 |

[1]Survival percentages expressed as rounded whole numbers

A total of 140 trout from a single pool of fish less than 1 year old were divided into groups and maintained at a water temperature of 9–13° C. and pH 7.8–8.3 for the duration of the experiment described below. When control freshwater rainbow trout are transferred directly into seawater, there is 100% mortality within 24 hr (Control Freshwater). Exposure of the trout to a constant photoperiod for 14 days results in a slight improvement in survival after their transfer to seawater. In contrast, exposure of trout to Process I for either 14 days or 23 days results in significant reductions in mortalties after transfer to seawater such that 30% and 46% of the fish respectively have survived after a 5 day interval in seawater. These data demonstrate that application of the Process I increases in the survival of pre-adult trout that are less than 7% of the size of standard "critical size" trout produced by present day industry standard techniques.

Application of the Process I to Arctic Char Pre-Adult Fish that are Smaller than the Industry Standard "Critical Size" Smolt.

Figure 30:
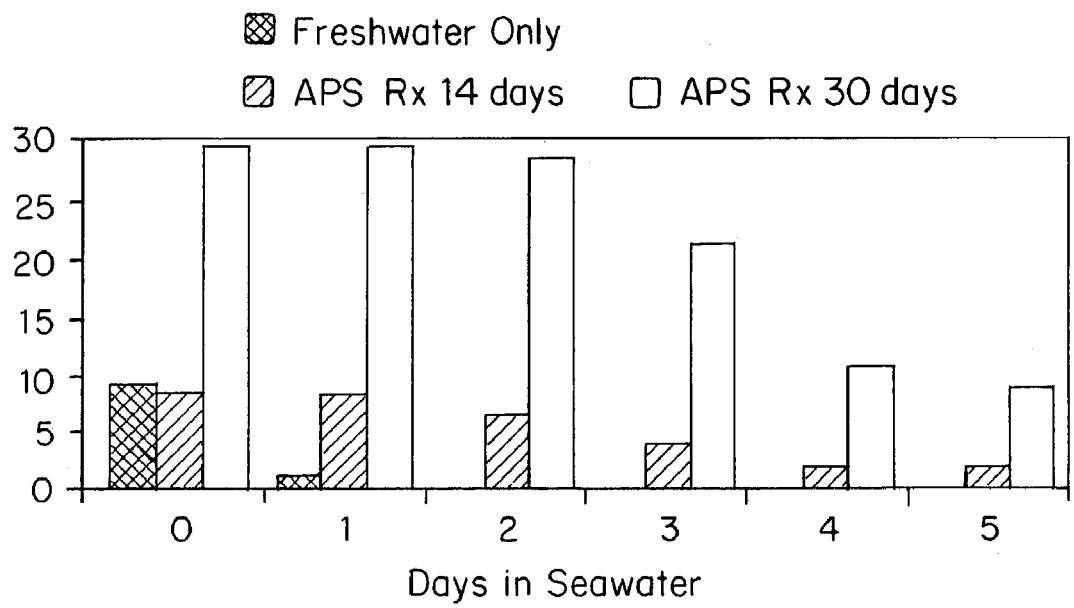
FIG. 30 is a three dimensional graph illustrating the survival over 5 days of Arctic Char in seawater after being maintained in freshwater, Process I for 14 days, and Process I for 30 days.

Although arctic char are salmonids and anadromous fish, their tolerance to seawater transfer is far less as compared to either salmon or trout. FIG. 30 shows the results of exposure of smaller char (3–5 gram) to the Process I for a total of 14 and 30 days. All fish shown in FIG. 30 were exposed to a continuous photoperiod. Transfer of char to seawater directly from freshwater results in the death of all fish within 24 hr. In contrast, treatment of char with the Process I for 14 and 30 days produces an increase in survival such that 33% (3/9) or 73% (22/30) respectively are still alive after a 3 day exposure. These data demonstrate that the enhancement of survival of arctic char that are less than 10% of the critical size as defined by industry standard methods after their exposure to the Process I followed by transfer to seawater.

FIG. 30 shows a comparison of survival of arctic char after various treatments. A single group of arctic char (3–5 gram were obtained from Pierce hatcheries (Buxton, Me.) and either maintained in freshwater or treated with the Process I prior to transfer to seawater.

Section II: The Use of the Process II to Permit Successful Transfer of 10–30 Gram Smolt into Seawater Netpens and Tanks.

The Process II protocol is utilized to treat pre-adult anadromous fish for placement into seawater at an average size of 25–30 gram or less. This method differs from the Process I protocol by the inclusion of L-tryptophan in the diet of pre-adult anadromous fish prior to their transfer to seawater. Process II further improves the osmoregulatory capabilities of pre-adult anadromous fish and provides for still further reductions in the "critical size" for Atlantic salmon smolt transfers. In summary, Process II reduces the "critical size" for successful seawater transfer to less than one fifth the size of the present day industry standard SO smolt.

Application of Process II to Atlantic Salmon Fingerlings:

St John/St John strain pre-adult fingerlings derived from a January 2000 egg hatching and possessing an average weight of 0.8 gram were purchased from Atlantic Salmon of Maine Inc. Kennebec Hatchery, Kennebec Me. on 27 Apr. 2000. These fish were transported to the treatment facility using standard conventional truck transport. After their arrival, these parr were first grown in conventional flow through freshwater growout conditions that included a water temperature of 9.6° C. and a standard freshwater parr diet (Moore-Clark Feeds). On 17 Jul. 2000, fingerlings were begun on Process II for a total of 49 days while being exposed to a continuous photoperiod. Process II smolts were then vaccinated with the Lipogen Forte product (Aquahealth LTD.) on Day 28 (14 Aug. 2000) of Process II treatment. Process II smolts were size graded prior to initiating Process II as well as immediately prior to transfer to seawater. St John/St John Process II smolts were transported to ocean netpens by conventional truck transport and placed into seawater (15.2° C.) in either a single ocean netpen identical to that described for placement of Process I smolts or into laboratory tanks (15.6° C.) within the research facility.

Figure 31:
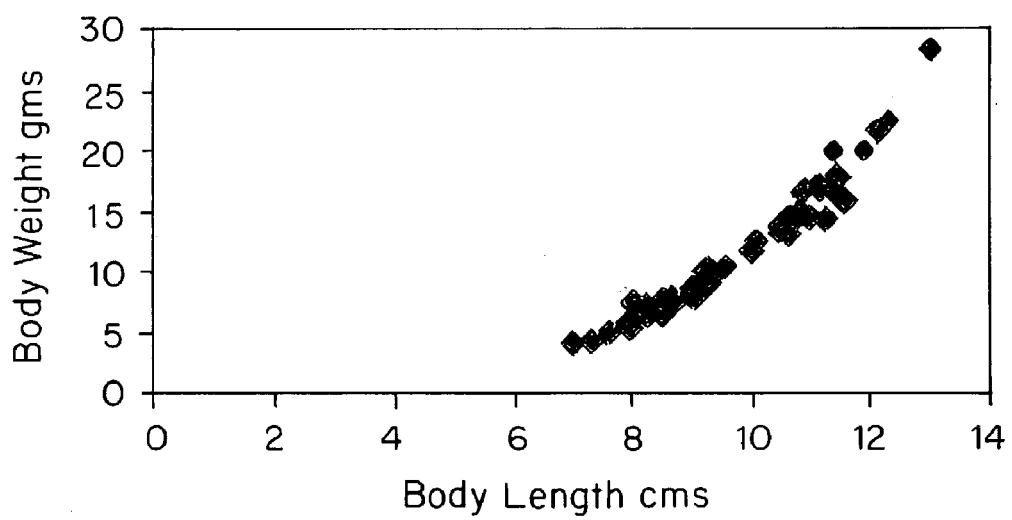
FIG. 31 is a graphical representation illustrating the length (cm) and weight (gm) of St. John/St. John Process II smolts prior to seawater transfer. Process II is defined in the Exemplification Section.

FIG. 31 shows representative St. John/St John strain Process II smolts possessing a range of body sizes were transferred to seawater either in ocean netpens or corresponding laboratory seawater tanks. Note that these Process II smolts possess a wide range of body weights (3.95–28 gram) that comprised an average body weight of 11.5 gram. FIG. 31 shows the characteristics of St. John/St John Process II smolts. The average measurements of these St. John/St. John Process II smolts included a body weight of 11.50+/−5.6 gram, length of 9.6+/−1.5 cm and condition factor of 1.19+/−0.09. The data displayed in Tables 9 and 10 show the outcomes for two groups of Process II smolts derived from a single production pool of fish after their seawater transfer into either laboratory tanks or ocean netpens. Although important variables such as the water temperatures and transportation of fish to the site of seawater transfer were identical, these 2 groups of Process II smolts experienced differential post seawater transfer mortalities after 5 days into laboratory tanks (10% mortality) and ocean netpens (37.7% mortality).

The probable explanation for this discrepancy in mortalities between seawater laboratory tanks (10% mortality) and ocean netpens (37.7% mortality) is exposure of these fish to different photoperiod regimens after seawater placement. Exposure of juvenile Atlantic salmon to a constant photoperiod after seawater placement reduced their post-seawater transfer mortality from approximately 34% to 6%. Fish transferred to ocean netpens experienced natural photoperiod that was not continuous and thus suffered an approximate 4-fold increase in mortality. As shown in Table 9, a separate seawater transfer of St John/St John juvenile Atlantic salmon possessing an average weight of 21 gms exhibited only 0.2% mortality after a six week treatment with Process II and underwater lights. These fish were exposed to a continuous photoperiod by underwater halogen lights for an interval of 30 days.

TABLE 9

Characterization and survival of St. John/St. John Process II fish after their placement into seawater in ocean netpens containing underwater lights.

| | |
|---|---|
| Total Fish | 15,000 |
| Seawater Transfer Date | Aug. 9, 2001 |
| Water Temperature (oC) | 12.6 |
| Size at Transfer (gram) | 21 +/− 4.5 |
| Total Mortalities after 30 days (# and % total) | 250 1.7% |
| % Mortalities weighing 15 grams or greater | 30 0.2% |
| Time to achieve feeding after transfer | 48 hr |

TABLE 10

Characteristics and survival of St. John/St. John Process II fish after their placement into seawater in either a laboratory tank or ocean netpen.

| | Laboratory Tank | Ocean Netpen |
|---|---|---|
| Total Fish | 100 | 1,316 |
| Seawater Transfer Date | Aug. 31, 2000 | Sep. 5, 2000 |
| Water Temperature (° C.) | 15.6 | 15.6 |
| Size at Transfer (gram) | 11.5 | 11.5 |
| Total Mortalities after 5 days (# and % total) | 10; 10% | 496; 37.7% |
| % mortalities weighing 13 grams or greater | 0; 0% | 1; 0.08% |
| Time to achieve feeding after transfer | 48 hrs | 48 hrs |

No apparent problems were observed with the smaller (10–30 gram) Process II smolts negotiating the conditions that exist within the confines of their ocean netpen. This included the lack of apparent problems including the ability to school freely as well as the ability to swim normally against the significant ocean currents that are continuously present in the commercial Blue Hill Bay salmon aquaculture site. While these observations are still ongoing, these data do not suggest that the placement and subsequent growth of Process II smolts in ocean netpens will be comprised because of lack of ability of these pre-adult anadromous fish to swim against existing ocean currents and therefore be unable to feed or develop properly.

Figure 32A:
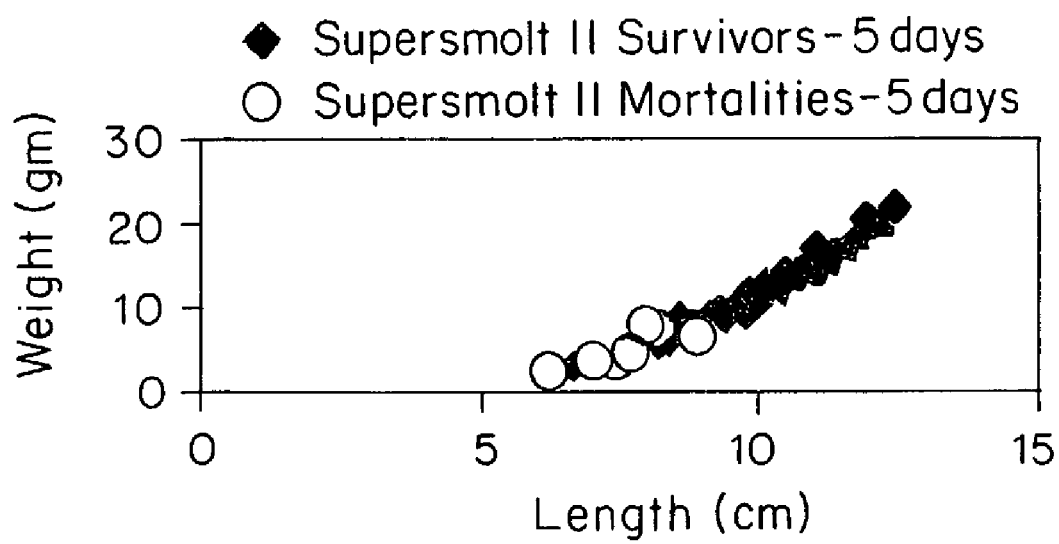
FIGS. 32A and 32B are graphical representations illustrating weight (gm) and length (cm) of Process II smolt survivors and mortalities 5 days after transfer to seawater tanks (A), and 96 hours after transfer to ocean netpens (B).
Figure 32B:
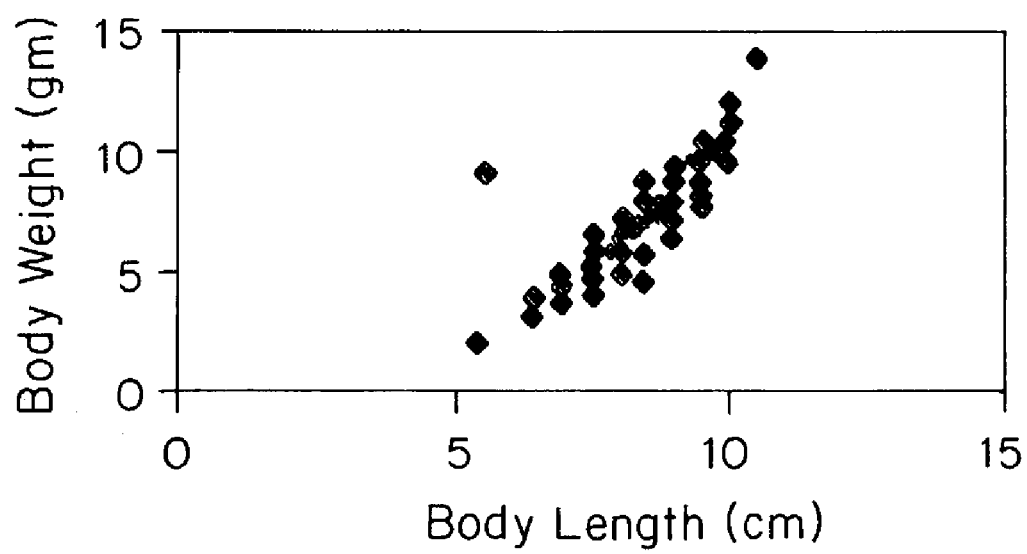

FIG. 32 compares characteristics of survivors and mortalities of Process II smolts after seawater transfer to either laboratory tanks (FIG. 32A) or ocean netpens (FIG. 32B). FIG. 32A data are derived from analyses of 100 Process II smolts transferred to seawater tank where all fish were killed and analyzed on Day 5. In contrast, FIG. 32B displays only mortality data from ocean netpen. In both cases, only smaller Process II smolts experienced mortality. Note differences in Y axis scales of FIGS. 32A–B.

Comparison of the average body size of those Process II smolts that survived seawater transfer vs. those Process II smolts that died shows that unsuccessful Process II smolts possessed significantly smaller body weights as compared to average body size of whole Process II smolt transfer group. Thus, the average weight of mortalities in laboratory tank (5.10±2.2 gram) and ocean netpen (6.46±1.5 gram) are 44% and 56% respectively the value of the average body weight possessed by the entire transfer cohort (11.5 gram). In contrast, the mortalities of Process II smolts with body weights greater than 13 gram is 0/100 in the laboratory tank and 1/1316 or 0.076% for ocean netpens. Together, these data demonstrate that Process II is able to redefine the "critical size" of Atlantic salmon smolts from 70–100 gram to approximately 13 gram.

Quantitation of Feeding and Growth of Process I and II Smolts after Seawater Transfer:

Landcatch/St John Process I smolts were offered food beginning 48 hr after their seawater transfer to either laboratory tanks or ocean netpens. While these Process I smolts that were transferred to laboratory tanks began to feed after 48 hr, those fish transferred to ocean netpens were not observed to feed substantially until 7 days. To validate these observations, the inventors performed direct visual inspection of the gut contents from a representative sample of 49 Process I smolts 4 days after their seawater transfer to laboratory tanks. A total of 21/49 or 42.9% possessed food within their gut contents at that time.

The St John/St John Process II smolts fed vigorously when first offered food 48 hrs after their seawater transfer regardless of whether they were housed in laboratory tanks or ocean netpens. An identical direct analysis of Process II smolts gut contents performed as described above revealed that 61/83 or 73.5% of fish were feeding 4 days after transfer to seawater. The vigorous feeding activity of Process II smolts in an ocean netpen as well as laboratory tanks occurred. Taken together, these data suggest that Process I and II smolts do not suffer from a prolonged (20–40 day) interval of poor feeding after seawater transfer as is notable for the much larger industry standard Atlantic salmon smolts not treated with the process.

The growth rates of identical fish treated with either Process I or II within laboratory seawater tanks has been quantified. As shown in Table 11, both Atlantic salmon treated with Process I or II grow rapidly during the initial interval (21 days) after transfer to seawater. In contrast to industry standard smolt weighing 70–100 grams that eat poorly and thus have little or no growth during their first 20–30 days after transfer to seawater, pre-adult Atlantic salmon receiving Process I or II both exhibited substantial weight gains and growth despite the fact that they are only 27–38% (Process I) and 12–16% (Process II) of the critical size of industry standard smolts. Data that relates to mortalities, SGR, temperature corrected SGR (GF3), FCR, body weights, lengths and condition factors for these same fish were obtained a total of 4 additional intervals during an interval that now extends for 157 days.

TABLE 11

Comparison of Growth Rates of Pre-adult Atlantic Salmon Exposed to either Process I or Process II and Placed in Laboratory Tanks During Initial Interval After Seawater Transfer

| | Process I | Process II |
|---|---|---|
| Number of Fish | 140 | 437 |
| Weight at Placement into Seawater | 26.6 | 11.50 |
| Days in Seawater | 22 | 21 |
| Placement Weight Corrected for Mortalities | 26.6* | 13.15* |
| Weight after Interval in Seawater | 30.3 | 15.2 |
| Weight Gained in Seawater | 3.75 | 2.05 |
| SGR (% body weight/day) | 0.60 | 0.68 |
| FCR | 1.27 | 2.04 |

*Weight gain corrected for selective mortalities amongst smaller fish (4/140 or 2.9% Process I; 103/437 or 23.6% Process II)

EXAMPLE 8

Exposure of Salmon Smolts to Ca2+ and Mg2+ Increased Expression of PVCR in Certain Tissues In smolts that were exposed to 10 mM $Ca^{2+}$ and 5.2 mM $Mg^{2+}$, the expression of PVCR was found to increase in a manner similar to that in smolts that are untreated, but are transferred directly to seawater.

Tissues were taken from either Atlantic salmon or rainbow trout, after anesthesitizing the animal with MS-222. Samples of tissues were then obtained by dissection, fixed by immersion in 3% paraformaldehyde, washing in Ringers then frozen in an embedding compound, e.g., O.C.T.™ (Miles, Inc., Elkahart, Ind., USA) using methylbutane cooled on dry ice. After cutting 8 micron thick tissue sections with a cryostat, individual sections were subjected to various staining protocols. Briefly, sections mounted on glass slides were: 1) blocked with goat serum or serum obtained from the same species of fish, 2) incubated with rabbit anti-CaR antiserum, and 3) washed and incubated with peroxidase-conjugated affinity-purified goat antirabbit antiserum. The locations of the bound peroxidase-conjugated goat anti-rabbit antiserum were visualized by development of a rose-colored aminoethylcarbazole reaction product. Individual sections were mounted, viewed and photographed by standard light microscopy techniques. The methods used to produce anti-PVCR antiserum are described below.

Figure 33A:
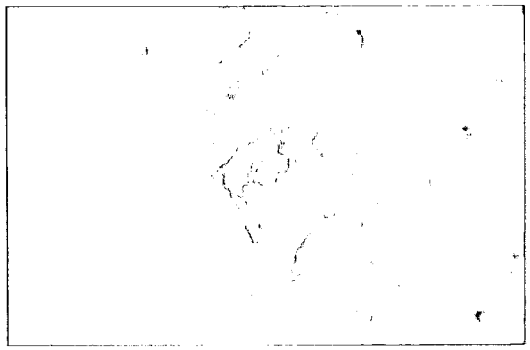
FIGS. 33A–G are photographs of immunocytochemistry of epithelia of the proximal intestine of Atlantic Salmon illustrating SalmoKCaR localization and expression.
Figure 33B:
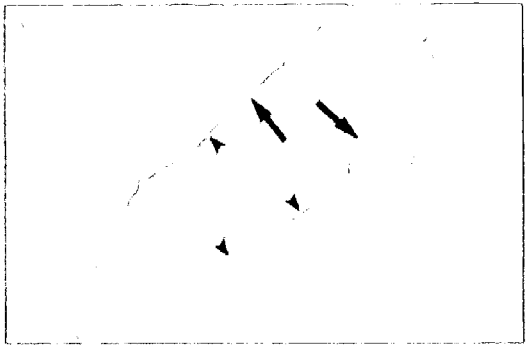
Figure 33C:
Figure 33D:
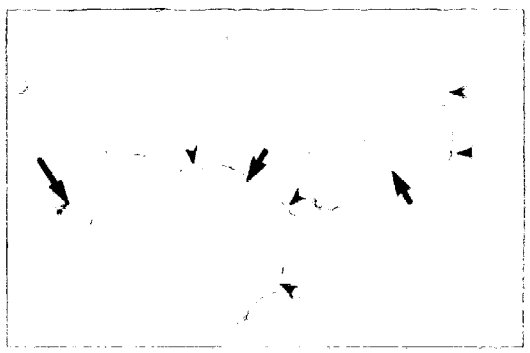
Figure 33E:
Figure 33F:
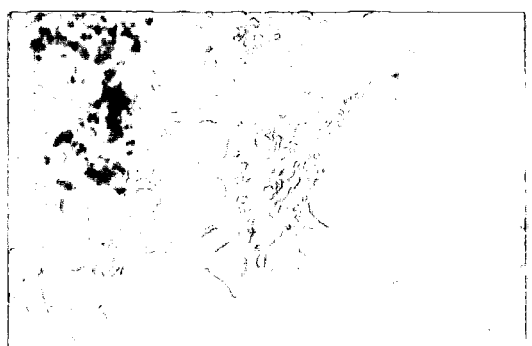
Figure 33G:
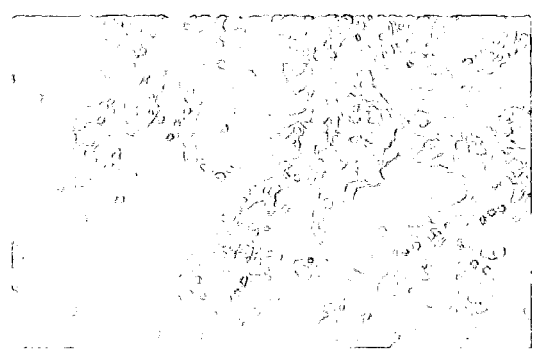
Figure 34:
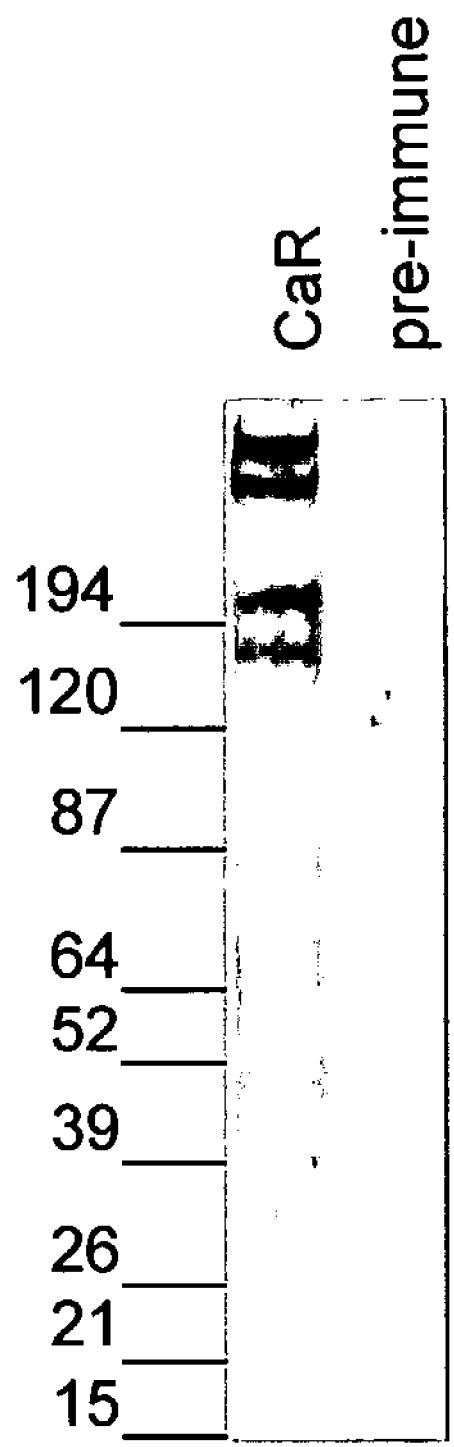
FIG. 34 is a photograph of a Western Blot of intestinal tissue from salmon subjected to Process I for immune (lane marked CaR, e.g., a SalmoKCaR) and preimmune (lane marked preimmune) illustrating SalmoKCaR expression.

The results are shown in FIGS. 33A–33G, which are a set of seven photomicrographs showing immunocytochemistry of epithelia of the proximal intestine of Atlantic salmon smolts using anti-PVCR antiserum, and in FIG. 34, which is a Western blot of intestine of a salmon smolt exposed to Ca2+– and Mg2+– treated freshwater, then transferred to seawater. The antiserum was prepared by immunization of rabbits with a 16-mer peptide containing the protein sequence encoded by the carboxyl terminal domain of the dogfish shark PVCR ("SKCaR") (Nearing, J. et al., 1997, J. Am. Soc. Nephrol. 8:40A). Specific binding of the anti-PVCR antibody is indicated by aminoethylcarbazole (AEC) reaction product.

FIGS. 33A and 33B show stained intestinal epithelia from smolts that were maintained in freshwater then transferred to seawater and held for an interval of 3 days. Abundant PVCR immunostaining is apparent in cells that line the luminal surface of the intestine. The higher magnification (1440×) shown in FIG. 33B displays PVCR protein localized to the apical (luminal-facing) membrane of intestinal epithelial cells. The pattern of PVCR staining is localized to the apical membrane of epithelial cells (small arrowheads) as well as membranes in globular round cells (arrows). FIG. 33C shows stained intestinal epithelia from a representative smolt that was exposed Process I and maintained in freshwater containing 10 mM Ca2+ and 5.2 mM Mg2+ for 50 days. Note that the pattern of PVCR staining resembles the pattern exhibited by epithelial cells displayed in FIGS. 33A and 33B including apical membrane staining (small arrowheads) as well as larger globular round cells (arrows). FIG. 33D shows a 1900× magnification of PVCR-stained intestinal epithelia from another representative fish that was exposed to the Process I and maintained in freshwater containing 10 mM Ca2+ and 5.2 mM Mg2+ for 50 days and fed 1% NaCl in the diet. Again, small arrowhead and arrows denote PVCR staining of the apical membrane and globular cells respectively. In contrast to the prominent PVCR staining shown in FIGS. 33A–D, FIGS. 33E (1440×) and 13F (1900×) show staining of intestinal epithelia from two representative smolt that were maintained in freshwater alone without supplementation of Ca2+ and Mg2+ or dietary NaCl. Both 13E and 13F display a marked lack of significant PVCR staining. FIG. 33G (1440×) shows the lack of any apparent PVCR staining upon the substitution of preimmune serum on a section corresponding to that shown in FIG. 33A where anti-PVCR antiserum identified the PVCR protein. The lack of any PVCR staining with preimmune antiserum is a control to demonstrate the specificity of the anti-PVCR antiserum under these immunocytochemistry conditions.

The relative amount of PVCR protein present in intestinal epithelial cells of freshwater smolts (FIGS. 33E and 33F) was negligible as shown by the faint staining of selected intestinal epithelial cells. In contrast, the PVCR protein content of the corresponding intestinal epithelial cells was significantly increased upon the transfer of these smolts to seawater (FIGS. 33A and 33B). Importantly, the PVCR protein content was also significantly increased in the intestinal epithelial cells of smolts maintained in freshwater supplemented with Ca2+ and Mg2+ (FIGS. 33C and 33D). The AEC staining was specific for the presence of the anti-PVCR antiserum, since substitution of the immune antiserum by the preimmune eliminated all reaction product from intestinal epithelial cell sections (FIG. 33G).

Disclosure of Localization of PVCR Protein(s) in Additional Areas of Osmoregulatory Organs of Atlantic Salmon Using Paraffin Sections. Demonstration that PVCR Proteins are Localized to Both the Apical and Basolateral Membranes of Intestinal Epithelial Cells.

Using the methods described herein, immunolocalization data from paraffin sections of various osmoregulatory organs of seawater-adapted juvenile Atlantic salmon smolt were obtained. PVCR proteins, as determined by the binding of a specific anti-PVCR antibody, were present in the following organs. These organs are important in various osmoregulatory functions. These organs include specific kidney tubules and urinary bladder responsible for processing of urine, and selected cells of the skin, nasal lamellae and gill each of which are bathed by the water surrounding the fish. The PVCR was also seen in various portions of the G.I. tract including stomach, pyloric caeca, proximal intestine and distal intestine that process seawater ingested by fish. These tissues were analyzed after treatment with Processes I and II, and after their transfer from freshwater to seawater. In addition, it is believed that the PVCR protein can also act as a nutrient receptor for various amino acids that are reported to be present in stomach, proximal intestine, pyloric caeca.

In particular, higher magnification views of PVCR immunolocalizations in selected cells of the stomach, proximal intestine and pyloric caeca were obtained. The PVCR protein is not only present on both the apical (luminally facing) and basolateral (blood-facing) membranes of stomach epithelial cells localized at the base of the crypts of the stomach, but also is present in neuroendocrine cells that are located in the submucosal area of the stomach. From its location on neuroendocrine cells of the G.I. tract, the PVCR protein is able to sense the local environment immediately adjacent to intestinal epithelial cells and modulate the secretion and synthesis of important G.I. tract hormones (e.g., 5-hydroxytryptamine (5-HT), serotonin, or cholecystokinin (CCK)). Importantly, it is believed that the constituents of Process II effect G.I. neuroendocrine cells by at least two means. The first way that constituents of Process II remodel the G.I endocrine system is through alterations in the expression and/or sensitivity of PVCRs expressed by these cells. The second way is to supply large quantities of precursor compounds, for example, tryptophan that is converted into 5-HT and serotonin by G.I. metabolic enzymes.

In a similar manner, PVCR protein is localized to both the apical and basolateral membranes of epithelial cells lining the proximal intestine. From their respective locations, PVCR proteins can sense both the luminal and blood contents of divalent cations, NaCl and specific amino acids and thereby integrate the multiple nutrient and ion absorptive-secretory functions of the intestinal epithelial cells. Epithelial cells of pyloric caeca also possess abundant apical PVCR protein.

To further demonstrate the specificity of the anti-CaR antiserum to recognize salmon smolt PVCRs, FIG. 34 shows a Western blot of intestinal protein from salmon smolt maintained in 10 mM Ca2+, 5 mM Mg2+ and fed 1% NaCl in the diet. Portions of the proximal and distal intestine were homogenized and dissolved in SDS-containing buffer, subjected to SDS-PAGE using standard techniques, transferred to nitrocellulose, and equal amounts of homogenate proteins as determined by both protein assay (Pierce Chem. Co, Rocford, Ill.) as well as Coomassie Blue staining were probed for presence of PVCR using standard western blotting techniques. The results are shown in the left lane, labeled "CaR", and shows a broad band of about 140–160 kDa and several higher molecular weight complexes. The pattern of PVCR bands is similar to that previously reported for shark kidney (Nearing, J. et al., 1997, J. Am. Soc. Nephrol. 8:40A) and rat kidney inner medullary collecting duct (Sands, J. M. et al., 1997, J. Clin. Invest. 99:1399–1405). The lane on the right was treated with the preimmune anti-PVCR serum used in FIG. 33G, and shows a complete lack of bands. Taken together with immunocytochemistry data shown in FIG. 33, this immunoblot demonstrates that the antiserum used is specific for detecting the PVCR protein in salmon.

EXAMPLE 9

Immunolocalization of Polyvalent Cation Receptor (PVCR) in Mucous Cells of Epidermis of Salmon The skin surface of salmonids is extremely important as a barrier to prevent water gain or loss depending whether the fish is located in fresh or seawater. Thus, the presence of PVCR proteins in selected cells of the fish's epidermal layer would be able to "sense" the salinity of the surrounding water as it flowed past and provide for the opportunity for continuous remodeling of the salmonid's skin based on the composition of the water where it is located.

Methods: Samples of the skin from juvenile Atlantic Salmon resident in seawater for over 12 days were fixed in 3% paraformaldehyde dissolved in buffer (0.1M NaPO4, 0.15M NaCl, 0.3M sucrose pH 7.4), manually descaled, rinsed in buffer and frozen at −80° C. for cryosectioning. Ten micron sections were either utilized for immunolocalization of PVCR using anti-shark PVCR antiserum or stained directly with 1% Alcian Blue dye to localize cells containing acidic glycoprotein components of mucous.

Figure 35A:
FIGS. 35A–C are photographs of immunolocalization of the SalmoKCaR in the epidermis of salmon illustrating SalmoKCaR localization and expression.
Figure 35B:
Figure 35C:

Results and Discussion: FIG. 35A shows that salmon epidermis contains multiple Alcian Blue staining cells present in the various skin layers. Note that only a portion of some larger cells (that containing acidic mucins) stains with Alcian Blue (denoted by the open arrowheads). For purposes of orientation, note that scales have been removed so asterisks denote surface that was previously bathed in seawater. FIG. 35B shows immunolocalization of salmon skin PVCR protein that is localized to multiple cells (indicated by arrowheads) within the epidermal layers of the skin. Note that anti-PVCR staining shows the whole cell body, which is larger than its corresponding apical portion that stains with Alcian Blue as shown in FIG. 35A. The presence of bound anti-CaR antibody was indicated by the rose color reaction product. Although formal quantitation has not yet been performed on these sections, it appears that the number of PVCR cells is less than the total number of Alcian Blue positive cells. These data indicate that only a subset of Alcian Blue positive cells contain abundant PVCR protein. FIG. 35C shows the Control Preimmune section where the primary anti-PVCR antiserum was omitted from the staining reaction. Note the absence of rose colored reaction product in the absence of primary antibody.

These data demonstrate the presence of PVCR protein in discrete epithelial cells (probably mucocytes) localized in the epidermis of juvenile Atlantic salmon. From this location, the PVCR protein could "sense" the salinity of the surrounding water and modulate mucous production via changes in the secretion of mucous or proliferation of mucous cells within the skin itself. The PVCR agonists (Ca2+, Mg2+) present in the surrounding water activate these epidermal PVCR proteins during the interval when smolts are being exposed to the process of the present invention. This treatment of Atlantic salmon smolts by the process of the present invention is important to increased survival of smolts after their transfer to seawater.

EXAMPLE 10

Figure 36:
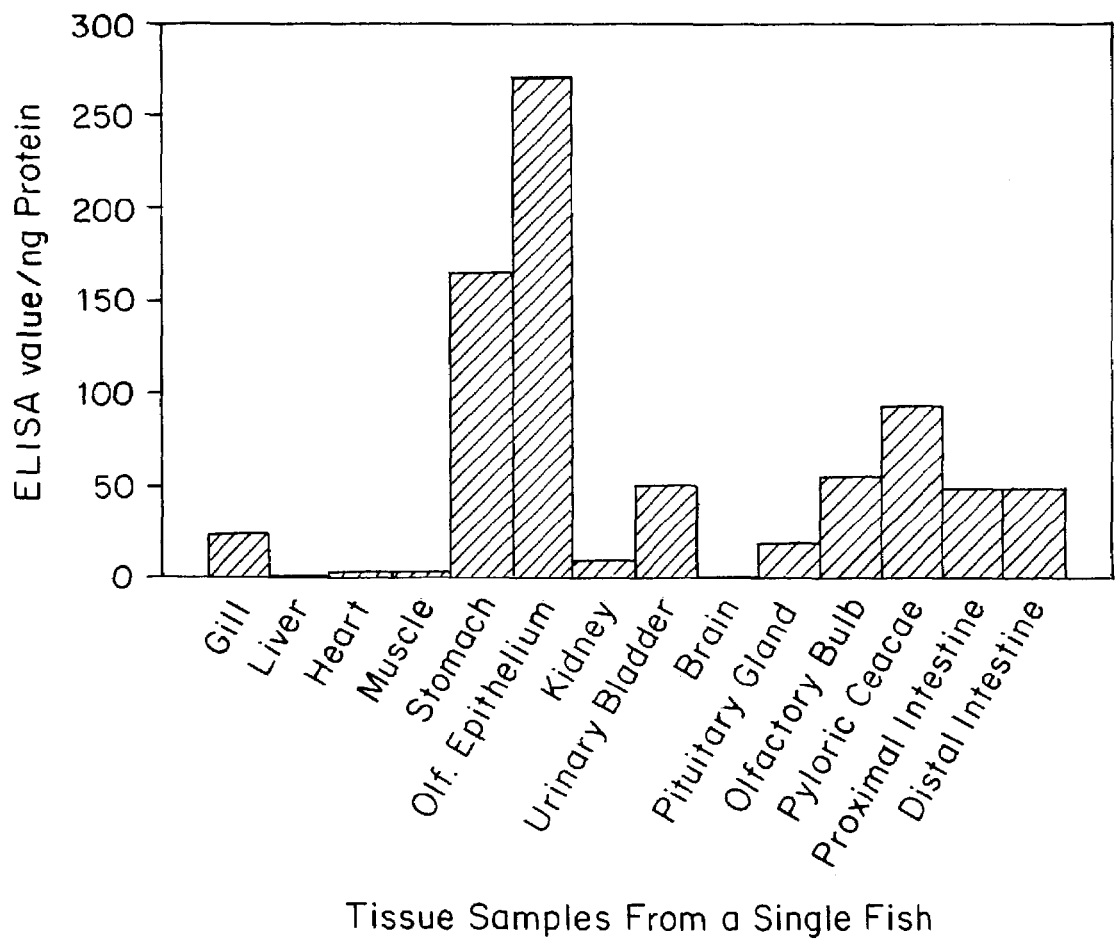
FIG. 36 is a graphical representation quantifying the Enzyme-Linked ImmunoSorbent Assay (ELISA) protein (ng) for various tissue samples (e.g., gill, liver, heart, muscle, stomach, olfactory epithelium, kidney, urinary bladder, brain, pituitary gland, olfactory bulb, pyloric ceacae, proximal intestine, and distal intestine) from a single fish.

Demonstration of the Use of Solid Phase Enzyme-Linked Assay for Detection of PVCRS in Various Tissues of Individual Atlantic Salmon Using Anti-PVCR Polyclonal Antiserum The PVCR content of various tissues of fish can be quantified using an ELISA 96 well plate assay system. The data, described herein, demonstrate the utility of a 96 well ELISA assay to quantify the tissue content of PVCR protein using a rabbit polyclonal anti-PVCR antibody utilized to perform immunocytochemistry and western blotting. These data form the basis for development of commercial assay kits that would monitor the expression levels of PVCR proteins in various tissues of juvenile anadromous fish undergoing the processes of the present invention, as described herein. The sensitivity of this ELISA is demonstrated by measurement of the relative PVCR content of 14 tissues from a single juvenile Atlantic salmon, as shown in FIG. 36.

Description of Experimental Protocol:

Homogenates were prepared by placing various tissues of juvenile Atlantic salmon (St. John/St. John strain average weight 15–20 gm) into a buffer (10 mM HEPES, 1.5 mM MgCl2, 10 mM KCl, 1 mM Phenylmethylsulfonyl fluoride (PMSF), 0.5 dithiothreitol (DTT) and 1 mM benzamidine pH 8.8) and using a standard glass Potter-Elvenhiem homogenizer with a rotary pestle. After centrifugation at 2,550×g for 20 min. at 4° C. to remove larger debris, the supernatant was either used directly or frozen at −80° C. until further use. Homogenate protein concentrations were determined using the BCA assay kit (Pierce Chem. Co.). Aliquots of individual tissue homogenates were diluted into a constant aliquot size of 100 microliters and each was transferred to a 96 well plate (Costar Plastic Plates) and allowed to dry in room air for 15 hr. After blocking of nonspecific binding with a solution of 5% nonfat milk powder +0.5% Tween 20 in TBS (25 mM Tris 137 mM sodium chloride, 2.7 mM KCl pH 8.0), primary antiserum (either rabbit anti-PVCR immune or corresponding rabbit pre-immune antiserum) at a 1:1500 dilution was added. After a 1 hr incubation, individual wells were rinsed 3 times with 500 microliters of TBS, an 1:3000 horseradish peroxidase conjugated goat anti-rabbit (Gibco-BRL) were added and allowed to incubate for 1 hr. Individual wells were then rinsed and bound complex of primary-secondary antibody detected with Sigma A3219 2,2' Azino-bis(3-ethylbenzthiazidine-6-sulfonic acid) color reagent after 15 min of incubation using a Molecular Devices 96 well plate reader (Molecular Devices, VMAX) at 405 nm. Relative amounts of tissue PVCR content were determined after corrections for minimal background and nonspecific antibody binding as measured by binding of preimmune antiserum.

Results and Data Interpretation:

FIG. 36 shows the data obtained from a representative single ELISA determination of PVCR protein content of 14 tissues of a single juvenile Atlantic salmon. Under the conditions specified in the Experimental Protocol as outlined above, nonspecific binding of both primary and secondary antibodies were minimized. While these quantitative values are measured relative to each other and not in absolute amounts, they provide data that parallels extensive immunocytochemistry examination of each of the tissues. Note that the PVCR content of various organs reflects their importance in osmoregulation of Atlantic salmon. Immunocytochemistry data described herein shows that tissues such as intestine (proximal and distal segments), gill, urinary bladder and kidney contained PVCR protein. In each case, epithelial cells that contact fluids that bathe the surfaces of these tissues express PVCR. In contrast, other organs including liver, heart and muscle contain minimal PVCR protein. Note that the highest PVCR content of any tissue tested is the olfactory lamellae where salmon possess the ability to "smell" alterations in calcium concentration in water. The olfactory bulb containing neurons that innervate the olfactory lamellae also possess abundant PVCR. Taken together, these data demonstrate the utility of ELISA kits to measure tissue content of PVCR proteins and form the basis for development of commercial assay kits that would monitor the expression levels of PVCR proteins in various tissues of juvenile anadromous fish undergoing the processes of the present invention. Alterations in PVCR tissue content measured in either relative changes in tissue PVCR content or absolute quantity of PVCR per tissue mass could, in turn, be utilized as correlative assays to determine the readiness of juvenile anadromous fish for sea water transfer or initiation of feeding. These data demonstrate the ability to perform such assays on individual juvenile Atlantic salmon in the range of body sizes that would be utilized to transfer fish from fresh to seawater after treatment with the methods of the present invention.

EXAMPLE 11

Antibodies Made from the Carboxyl Terminal Portion of an Atlantic Salmon PVCR Protein are Effective in Immunocytochemistry and Immunoblotting Assays to Determine the Presence, Absence or Amount of the PVCR Protein Degenerate primers, dSK-F3 (SEQ ID NO: 15) and dSK-R4 (SEQ ID NO: 16), described herein were constructed specifically from the SKCaR DNA sequence. These primers have proved to be useful reagents for amplification of portions of PVCR sequences from both genomic DNA as well as cDNA.

To obtain more cDNA sequence from anadromous fish PVCRs, in particular the putative amino acid sequence of the carboxyl terminal domain of PVCRs that are targets for generation of specific peptides and, as a result, specific anti-Atlantic Salmon PVCR antisera, an unamplified cDNA library from Atlantic salmon intestine was constructed. Phage plaques originating from this cDNA library were screened under high stringency using $^{32}$P-labeled 653 bp genomic Atlantic Salmon PCR product. From this cDNA library screening effort, a 2,021 bp cDNA clone was isolated and contained a single open reading frame for a putative amino acid sequence corresponding to approximately one half of a complete cDNA sequence from an intestinal PVCR protein. This putative amino acid sequence corresponds exactly to the sequence encoded by the corresponding genomic probe as well as the putative amino acid sequence corresponding to the carboxyl terminal domain of the PVCR.

On the basis of the knowledge of this putative amino acid sequence, a peptide, shown below, was synthesized and corresponded to a separate region of the putative carboxyl terminal PVCR amino acid sequence:

The peptide sequence for antibody production is as follows:
Peptide #1: Ac-CTNDNDSPSGQQRIHK-amide (SEQ ID NO.:17) producing rabbit antiserum SAL-1

The peptide was derivatized to carrier proteins and utilized to raise peptide specific antiserum in two rabbits using methods for making a polyclonal antibody.

The resulting peptide specific antiserum was then tested using both immunoblotting and immunocytochemistry techniques to determine whether the antibody bound to protein bands corresponding to PVCR proteins or yielded staining patterns similar to those produced using other anti-PVCR antiserum. A photograph of an immunoblot was taken showing protein bands that were recognized by antisera raised against peptides containing either SAL-1 (SEQ ID NO.: 17) or SKCaR (SEQ ID NO:2). As expected, antiserum raised to the peptide identified protein bands that co-electrophorese with PVCR proteins that are recognized by antisera raised to SKCaR (SEQ ID NO:2). Immunostaining of juvenile Atlantic salmon kidney sections with 3 different anti-PVCR antisera (anti-SalI, anti-4641, and anti-SKCaR) produces similar localizations of PVCR protein within the tubules of salmon kidney. Staining produced by anti-SKCaR antiserum is identical to that produced by anti-4641 antiserum, an anti-peptide antisera corresponding to extracellular domain of mammalian PVCRs that is very similar to SKCaR (SEQ ID NO: 2). These PVCR protein patterns stained identically to that produced by SAL-1 antiserum. Anti-Sal-1 antiserum also exhibits a similar staining pattern for the distribution of intestinal PVCR protein, as compared to anti-SKCaR. Thus, this new antiserum is specific for a PVCR in Atlantic Salmon tissues. This antiserum can be used to determine the presence, absence or amount of PVCR in various tissues of fish, using the methods described herein.

The Sal I antiserum is also useful in localization of SalmoKCaR proteins in larval Atlantic salmon (See FIG. 40B). The Sal I antiserum localizes SalmoKCaR proteins in the developing nasal lamellae of anadromous fish, including Atlantic salmon and trout, skin, myosepta, otolith and sensory epithelium. The myoseptae are collagenous sheets that separate the various muscle bundles in the fish. Myosepta are important in both the development of muscle in larval fish as well as its function for muscle force generation in adult fish. Myosepta are also of significant commercial importance since they are one of the principal determinants of texture of smoked Atlantic salmon fillets.

The otolith is also of considerable importance to Atlantic salmon. It is a calcified structure located in the inner ear of salmon where it is closely associated with epithelial cells responsible for sensing sound and direction. It is likely that the SalmoKCaRs associated with the otolith participate in the calcification of the otolith structure that consists of proteins and calcium precipitate.

A second peptide sequence was used for antibody production:

Peptide #2: CSDDEYGRPGIEKFEKEM (SEQ ID NO: 29).

This peptide was synthesized, derivatized in a manner identical to that described for Peptide #1 and antiserum was raised in rabbits as described above. As expected, this antiserum (Salmo ADD) produced a pattern of immonostaining on sections of juvenile Atlantic salmon that is identical to that exhibited by Sal I. (See FIG. 40C). Since both SalmoKCaR #1, #2 and #4, but not SalmoKCaR #3 possess the carboxyl terminal sequence recognized by the Sal I antibody, the antibody-staining pattern displayed by Sal I show the distribution of SalmoKCaR proteins #1, #2 and #4 but not #3 within the kidney of Atlantic salmon.

In contrast, the Salmo ADD antibody binds to a peptide sequence present in the extracellular domain of all 4 Salmo-KCaR proteins. Thus, any cells that possess no staining of Sal I but staining with Salmo ADD likely express either SalmoKCaR #3 or some similar SalmoKCaR protein.

EXAMPLE 12

Use of Reverse Transcriptase Polymerase Chain Reaction (RT-PCR) to Detect Expression of PVCRS in Various Tissues In Example 4, 2 degenerate primers, dSK-F3 (SEQ ID NO: 15) and dSK-R4 (SEQ ID NO: 16), are disclosed. These two primers were used to amplify genomic DNA and obtain the sequence of a portion of the genomic DNA sequences of PVCRs from various anadromous fish. These same primers can also be used to amplify a portion of corresponding PVCR mRNA transcripts in various tissues. DNA sequence analyses of amplified cDNAs from specific Atlantic salmon tissues (olfactory lamellae, kidney, urinary bladder) verifies these are all identical to certain genomic PVCR sequences described herein. These data show that:

1. PVCR mRNA transcripts are actually expressed in specific tissues of anadromous fish. These data reinforce the data regarding PVCR protein expression as detected by anti-PVCR antisera.
2. RT-PCR methods can be used to detect and quantify the degree of PVCR expression in various tissues, as a means to predict the readiness of anadromous fish for transfer to seawater.
3. cDNA probes can be generated from specific tissues of anadromous fish for use as specific DNA probes to either detect PVCR expression using solution or solid phase DNA-DNA or DNA-RNA nucleic acid hybridization or obtain putative PVCR protein sequences used for generation of specific anti-PVCR antisera.

RT-PCR Method:

Total RNA was purified from selected tissues using Teltest B reagent (Friendswood, Tex.) and accompanying standard protocol. A total of 5 micrograms of total RNA was reverse transcribed with oligo dT primers using Invitrogen's cDNA Cycle Kit (Invitrogen Inc, Madison, Wis.). The resulting cDNA product was denatured and a second round of purification was performed. Two microliters of the resulting reaction mixture was amplified in a PCR reaction (30 cycles of 1 min. @ 94° C., 2 min. @ 57° C., 3 min. @72° C.) using degenerate primers dSK-F3 (SEQ ID NO: 15) and dSK-R 4 (SEQ ID NO: 16). The resulting products were electrophoresed on a 2% (w/v) agarose gel using TAE buffer containing ethidium bromide for detection of amplified cDNA products. Gels were photographed using standard laboratory methods.

DNA Sequencing of RT-PCR Products were Performed as Follows:

A total of 15 microliters of Atlantic Salmon urinary bladder, kidney and nasal lamellae RT-PCR reactions were diluted in 40 microliters of water and purified by size exclusion on Amersham's MicroSpin S-400 HR spin columns (Amersham Inc, Piscataway, N.J.). Purified DNA was sequenced using degenerate PVCR primers (SEQ ID NO.: 15 and 16) as sequencing primers. Automated sequencing was performed using an Applied Biosystems Inc. Model 373A Automated DNA Sequencer (University of Maine, Orono, Me.). The resulting DNA sequences were aligned using MacVector (GCG) and LaserGene (DNA STAR) sequence analysis software.

Detection of Amplified RT-PCR cDNA Products by Southern Blotting:

Alternatively, the presence of amplified PVCR products was detected by Southern blotting analyses of gel fractionated RT-PCR products using a $^{32}$P-labeled 653 bp Atlantic salmon amplified genomic PCR product. A total of 10 microliters of each PCR reaction was electrophoresed on a 2% agarose gel using TAE buffer then blotted onto Magnagraph membrane (Osmonics, Westboro, Mass.). After crosslinking of the DNA, blots were prehybridized and then probed overnight (68° C. in 6×SSC, 5× Denhardt's Reagent, 0.5% SDS, 100 ug/ml calf thymus DNA) with the 653 bp Atlantic salmon PCR product (labeled with RadPrime DNA Labeling System, Gibco Life Sciences). Blots were then washed with 0.1×SSC, 0.1% SDS @ 55° C. and subjected to autoradiography under standard conditions.

FIG. 37 shows the results of RT-PCR amplification of a partial PVCR mRNA transcript from various tissues of juvenile Atlantic salmon. RT-PCR reactions were separated by gel electrophoresis and either stained in ethidium bromide(EtBr) or transferred to a membrane and Southern blotted using a $^{32}$P-labeled 653 bp genomic DNA fragment from the Atlantic salmon PVCR gene. FIG. 37 shows the detection of the PVCR in several tissue types of Atlantic Salmon using the RT-PCR method, as described herein. The types of tissue are gill, nasal lamellae, urinary bladder, kidney, intestine, stomach, liver, and brain.

EXAMPLE 13

Presence and Function of PVCR Protein in Nasal Lamellae and Olfactory Bulb as well as GI Tract of Fish The data described herein described the roles of PVCR proteins in the olfactory organs (nasal lamellae and olfactory bulb) of fish as it relates to the ability of fish to sense or "smell" both alterations in the water salinity and/or ionic composition as well as specific amino acids. These data are particularly applicable to anadromous fish (salmon, trout and char) that are either transferred from freshwater directly to seawater or exposed to Process I or Process II in freshwater and then transferred to seawater.

These data described herein were derived from a combination of sources including immunocytochemistry using anti-PVCR antisera, RT-PCR amplification of PVCRs from nasal lamellae tissue, studies of the function of recombinant aquatic PVCR proteins expressed in cultured cells where these proteins "sense" specific ions or amino acids as well as electrophysiological recordings of nerve cell electrical activity from olfactory nerves or bulb of freshwater salmon.

The combination of immunocytochemistry and RT-PCR data, described herein, reveal the presence of PVCR proteins in both major families of fish (elasmobranch-shark; teleost-salmon) in both larval, juvenile and adult life stages. Immunocytochemistry analyses reveal that one or more PVCR proteins are present both on portions of olfactory receptor cells located in the nasal lamellae of fish (where they are bathed in water from the surrounding environment) as well as on nerve cells that compose olfactory glomeruli present in the olfactory bulb of fish brain (where these cells are exposed to the internal ionic environment of the fish's body). Thus, from these locations fish are able to compare the ionic composition of the surrounding water with reference to their own internal ionic composition. Alterations in the expression and/or sensitivity of PVCR proteins provides the means to enable fish to determine on a continuous basis whether the water composition they encounter is different from that they have been adapted to or exposed to previously. This system is likely to be integral to both the control of the homing of salmon from freshwater to seawater as smolt and their return to freshwater from seawater as adults. Thus, fish have the ability to "smell" changes in water salinity directly via PVCR proteins and respond appropriately to regulate remain in environments that are best for their survival in nature.

One feature of this biological system is alteration in the sensitivity of the PVCR protein for divalent cations such as $Ca^{2+}$ and $Mg^{2+}$ by changes in the NaCl concentration of the water. Thus, PVCRs in fish olfactory organs have different apparent sensitivity to $Ca^{2+}$ in either the presence or absence of NaCl. These data presented here are the first direct evidence for these functions via PVCR proteins present in the olfactory apparatus of fish.

Another feature of PVCR protein function in the olfactory apparatus of fish is to modulate responses of olfactory cells to specific odorants (attractants or repellants). Transduction of cellular signals resulting from the binding of specific odorants to olfactory cells occurs via changes in standing ionic gradients across the plasma membranes of these cells. The binding of specific odorants to olfactory cells results in electrical nerve conduction signals that can be recorded using standardized electrophysiological electrodes and equipment. Using this apparatus, the olfactory apparatus of freshwater adapted salmon:

1. responded to PVCR agonists in a concentration-dependent manner similar to that shown previously for other fish tissues including that shown for winter flounder urinary bladder. These data provide the functional evidence of the presence of a PVCR protein; and
2. that the presence of a PVCR agonist reduces or ablates the signal resulting from odorants including both attractants or repellants. Thus, PVCRs in the olfactory apparatus of salmon possess the capacity of modulating responses to various odorants.

Another feature of PVCR proteins is their ability to "sense" specific amino acids present in surrounding environment. Using the full-length recombinant SKCaR cDNA, functional SKCaR protein was expressed in HEK cells and shown to respond in a concentration-dependent manner to both single and mixtures of L-amino acids. Since PVCR agonists including amino acids as well as polyamines (putrescine, spermine and spermidine) are attractants to marine organisms including fish and crustaceans, these data provide for another means by which PVCR proteins would serve not only as modulators of olfaction in fish but also as sensors of amino acids and polyamines themselves. PVCR proteins in other organs of fish including G.I. tract and endocrine organs of fish also function to sense specific concentrations of amino acids providing for integration of a wide variety of cellular processes in epithelial cells (amino acid transport, growth, ion transport, motility and growth) with digestion and utilization of nutrients in fish.

Description of Experimental Results and Data Interpretation:

PVCR protein and mRNA are localized to the olfactory lamellae, olfactory nerve and olfactory bulb of freshwater adapted larval, juvenile and adult Atlantic salmon as well as the olfactory lamellae of dogfish shark:

FIG. 38 show representative immunocytochemistry photographs of PVCR protein localization in olfactory bulb and nerve as well as olfactory lamellae in juvenile Atlantic salmon. The specificity of staining for PVCR protein is verified by the use of 2 distinct antisera each directed to a different region of the PVCR protein. Thus, antiserum anti-4641 (recognizing an extracellular domain PVCR region) and antiserum anti-SKCaR (recognizing an intracellular domain PVCR region) exhibit similar staining patterns that include various glomeruli on serial sections of olfactory bulb. Using anti-SKCaR antiserum, specific staining of PVCR proteins is observed in discrete regions of the olfactory nerve as well as epithelial cells in the nasal lamellae that are exposed to the external ionic environment.

Figure 39:
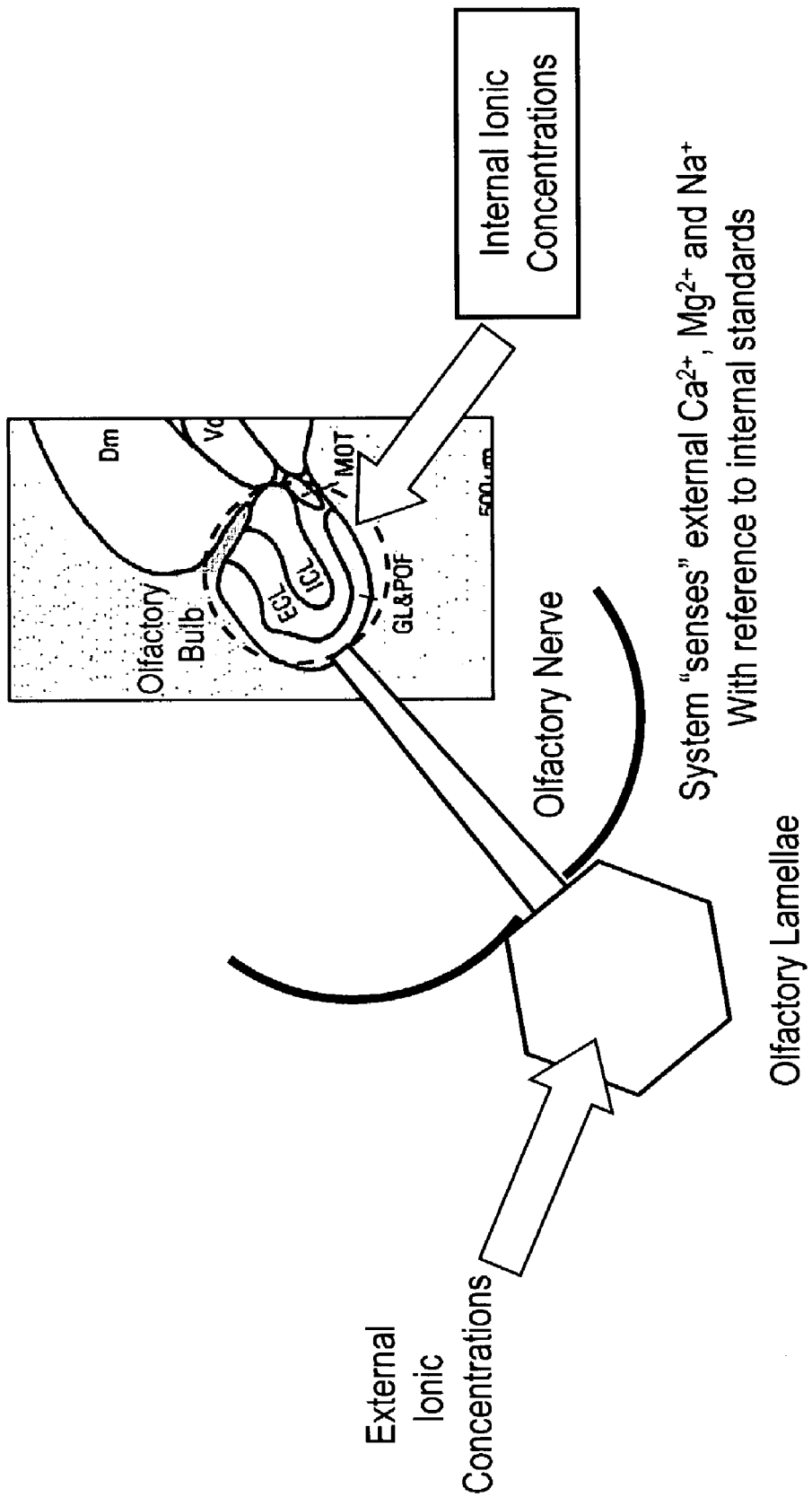
FIG. 39 is a schematic illustrating the effect of external and internal ionic concentrations on the olfactory lamellae in response to SalmoKCaR modulators.

The presence of PVCR protein in both nasal lamellae cells as well as olfactory bulb and nerve shows that these respective PVCR proteins would be able to sense both the internal and external ionic environments of the salmon. For this purpose, cells containing internally-exposed PVCRs are connected to externally-exposed PVCRs via electrical connections within the nervous system. As shown schematically in FIG. 39, these data suggest that externally and internally-exposed PVCRs function together to provide for the ability to sense the ionic concentrations of the surrounding ionic environment using as a reference the ionic concentration of the salmon's body fluids. Changes in the expression and/or sensitivity of the external set of PVCRs vs internal PVCRs would then provide a long term "memory" of the adaptational state of the fish as it travels through ionic environments of different composition. FIG. 40 shows immunocytochemistry using anti-SKCaR antiserum that reveals the presence of PVCR protein in both the developing nasal lamellae cells and olfactory bulb of larval Atlantic salmon only days after hatching (yolk sac stage). As described herein, imprinting of salmon early in development as well as during smoltification have been shown to be key intervals in the successful return of wild salmon to their natal stream. The Sal I antiserum also localizes SalmoKCaR proteins in a variety of tissues in larval Atlantic salmon (FIG. 40B). These tissues include the developing nasal lamellae of salmon and trout, their skin, myosepta, otolith and sensory epithelium. Myosepta are important in both the development of muscle in larval fish since they separate and define the muscle bundles of the salmon. Myosepta are also of significant commercial importance since they are one of the principal determinants of texture for smoked Atlantic salmon fillets. SalmoKCaR proteins are also present in the otolith which is a calcified structure located in the inner ear of the salmon where it is closely associated with epithelial cells responsible for sensing sound and direction. The presence of PVCR proteins at these developmental stages of salmon lifecycle indicate that PVCRs participate in this process.

Figure 41:
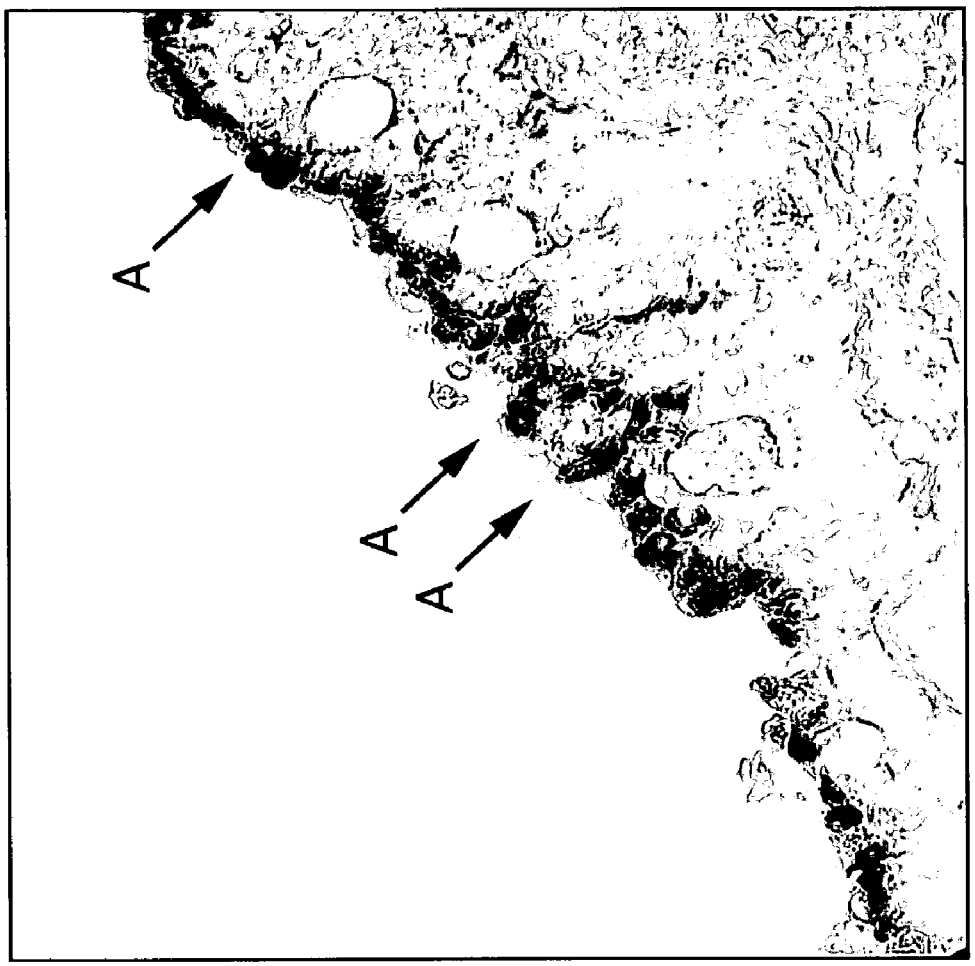
FIG. 41 is a photograph of immunocytochemistry showing the PVCR localization in nasal lamellae of dogfish shark using an anti-PVCR antibody.
Figure 42:
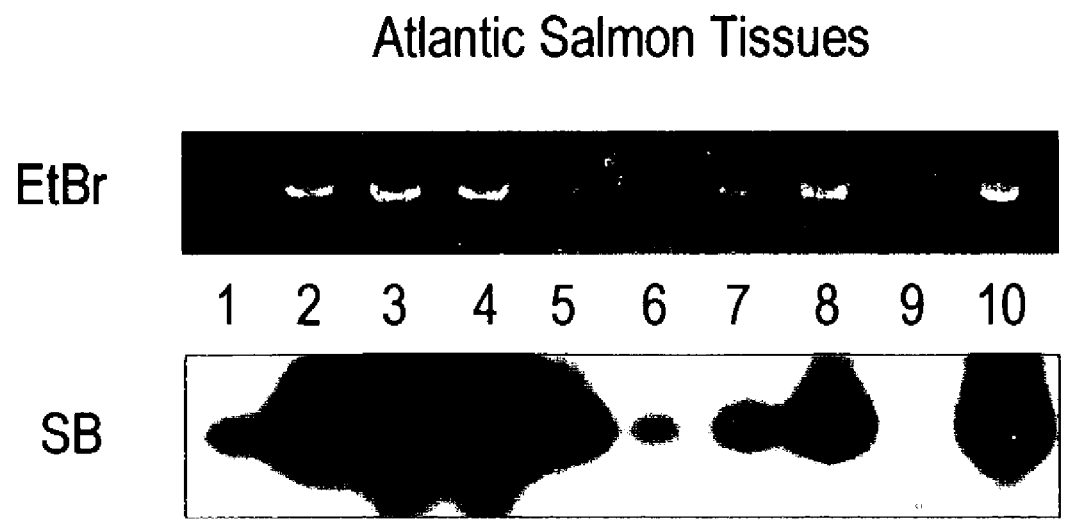
FIG. 42 is a photograph of a Southern blot of RT-PCR analyses of tissues from Atlantic Salmon showing the presence of SalmoKCaR mRNA in nasal lamellae of freshwater adapted fish. Wells 1–10 are designated as follows: gill, nasal lamellae, urinary bladder, kidney, intestine, stomach, liver, brain, water (blank) and positive control, respectively.
Figure 43:
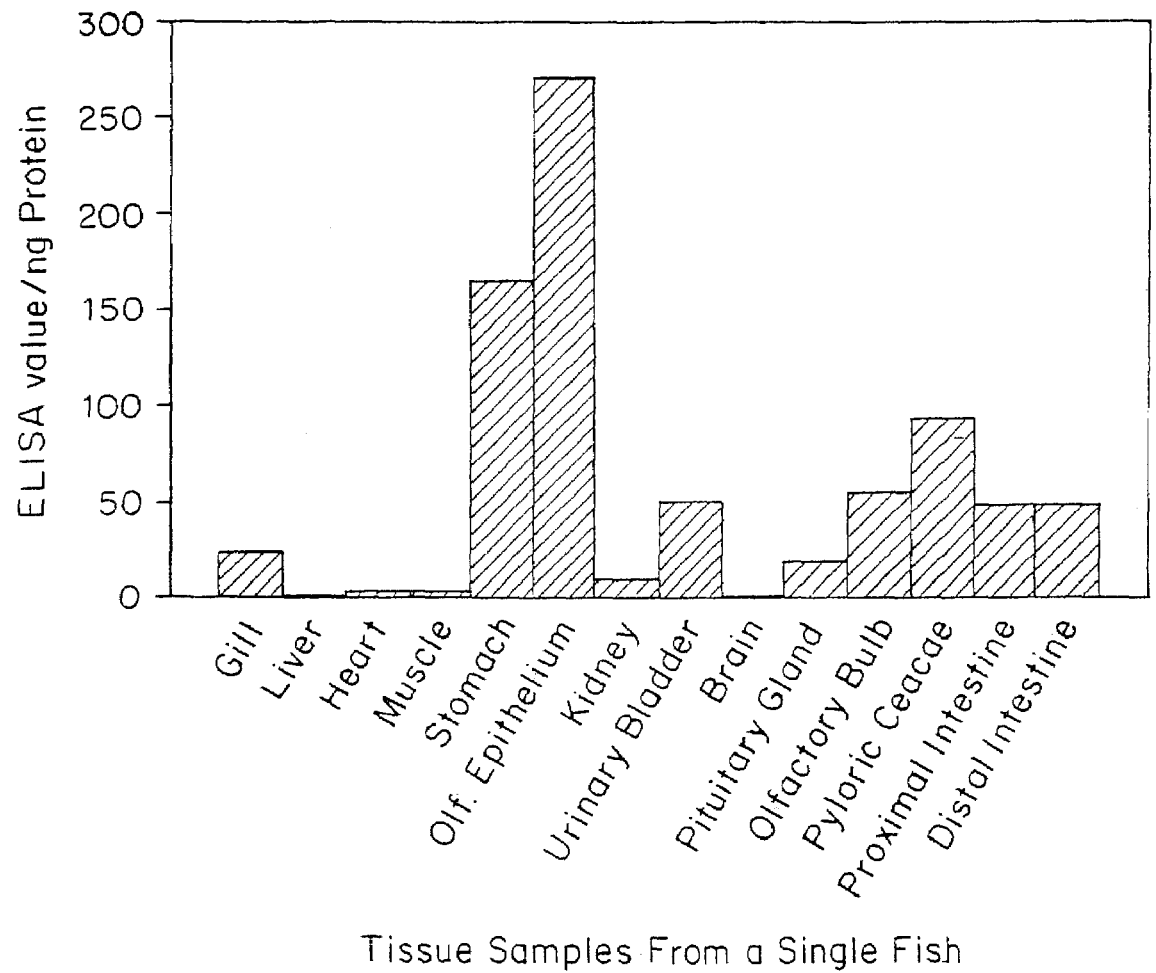
FIG. 43 is a histogram illustrating the amount of Salmo-KCaR protein, as determined by an ELISA (ng) for various tissue samples (gill, liver, heart, muscle, stomach, olfactory epithelium, kidney, urinary bladder, brain, pituitary gland, olfactory bulb, pyloric ceacae, proximal intestine, and distal intestine).

Data obtained from using anti-SKCaR antiserum from other fish species including elasmobranchs display similar staining of PVCR protein in cells (marked A) their nasal lamellae (FIG. 41). Use of other methodology including RT-PCR using specific degenerate primers (FIG. 42) and ELISA methods (FIG. 43) detects the presence of PVCR proteins and mRNA in nasal lamellae of fish. While neither of these 2 techniques provide quantitative measurements as described, both sets of data are consistent and show abundant PVCR protein present in this tissue.

Figure 44:
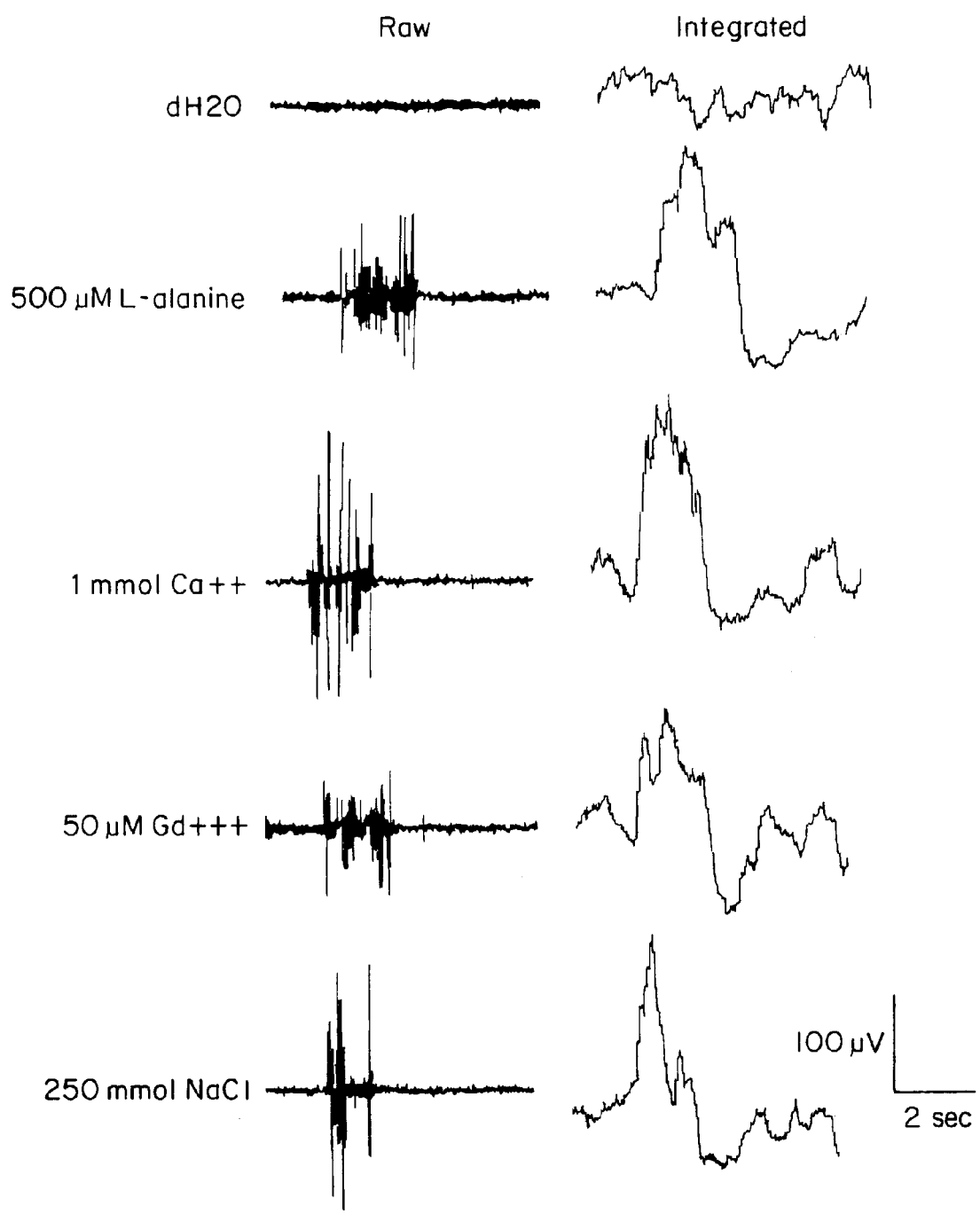
FIG. 44 shows the raw and integrated recordings from high resistance electrodes of freshwater adapted Atlantic Salmon when exposed to 500 µM L-alanine, 1 mmol calcium, 50 µM Gadolinium, and 250 mmol of NaCl. The figures show the existence of an olfactory recording in response to L-alanine, calcium, gadolinium, and NaCl.

Measurement of Extracellular Electrical Potentials (EEG's) from Olfactory Nerve from Freshwater Adapted Atlantic Salmon Reveals the Presence of Functional PVCR Proteins:

FIG. 44 displays representative recordings obtained from 6 freshwater adapted juvenile Atlantic salmon (approximately 300–400 gm) using methods similar to those described in Bodznick, D. J. Calcium ion: an odorant for natural water discriminations and the migratory behavior of sockeye salmon, *Comp. Physiol. A* 127:157–166 (1975), and Hubbard, P C, et al., Olfactory sensitivity to changes in environmental Ca2+ in the marine teleost Sparus Aurata, *J. Exp. Biol.* 203:3821–3829 (2000). After anaesthetizing the fish, it was placed in V-clamp apparatus where its gills were irrigated continuously with aerated seawater and its nasal lamellae bathed continuously by a stream of distilled water via a tube held in position in the inhalant olfactory opening. The olfactory nerves of the fish were exposed by removal of overlying bony structures. Stimuli were delivered as boluses to the olfactory epithelium via a 3 way valve where 1 cc of water containing the stimulus was rapidly injected into the tube containing a continuously stream of distilled water. Extracellular recordings were obtained using high resistance tungsten electrodes where the resultant amplified analog signals (Grass Amplifier Apparatus) were digitized, displayed and analyzed by computer using MacScope software. Using this experimental approach, stable and reproducible recordings could be obtained for up to 6 hr after the initial surgery on the fish.

Figure 45:
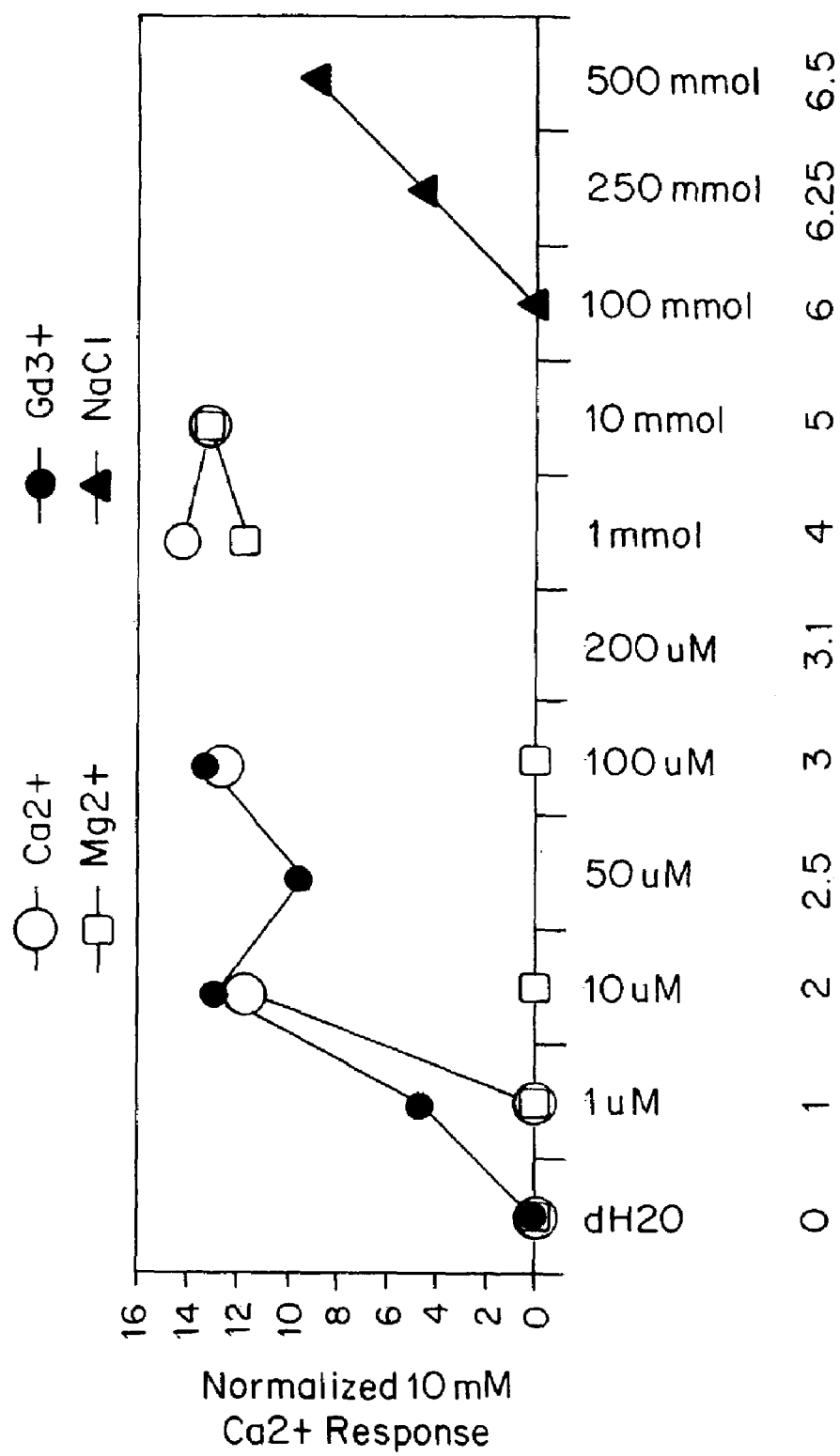
FIG. 45 is a graph showing the response data for freshwater adapted Atlantic salmon nasal lamellae for calcium, magnesium, gadolinium, and sodium chloride normalized to the signal obtained with 10 mM Calcium.

As shown in FIG. 44, irrigation of salmon olfactory epithelium with distilled water produces minimal generation of large signals in olfactory nerve. The data in FIG. 44 are displayed as both raw recordings (left column) and the corresponding integrated signals for each raw recording shown in the right column. Exposure of the olfactory epithelium to 500 micromolar L-alanine (a well known amino acid attractant for fish) produces large increases in both the firing frequency and amplitude in the olfactory nerve lasting approximately 2 seconds in duration. Similarly, application of either 1 mM $Ca^{2+}$ or 250 mM NaCl also produce responses in EEG activity. To test for the presence of functional PVCR protein, the olfactory epithelium was exposed to 50 micromolar gadolinium ($Gd^{3+}$-a PVCR agonist) and also obtained a response. FIG. 45 shows dose response data from multiple fish to various PVCR agonists or modulators where the relative magnitudes of individual olfactory nerve response were normalized relative to the response produced by the exposure of the olfactory epithelium to 10 mM $Ca^{2+}$. As shown in FIG. 45, the olfactory epithelium of freshwater adapted juvenile salmon is very sensitive to $Ca^{2+}$ where the half maximal excitatory response ($EC_{50}$) is approximately 1–10 micromolar. Similarly, exposure of olfactory epithelium to the PVCR agonist $Gd^{3+}$ produces responses of a similar magnitude to those evoked by $Ca^{2+}$ in a concentration range of 1–10 micromolar. In contrast, olfactory epithelium responses to $Mg^{2+}$ do not occur until 10–100 micromolar solutions are applied. These dose response curves ($EC_{50}$ $Gd^{+3} \leq Ca^{2+} < Mg^{2+}$) are similar to those obtained for PVCR modulated responses in other fish epithelium (flounder urinary bladder NaCl-mediated water transport-see SKCaR application).

In contrast, analysis of the olfactory epithelium responses to NaCl exposure shows that it is unresponsive until a concentration of 250 millimolar NaCl is applied. Since NaCl does not directly activate PVCRs in a manner such as $Gd^{3+}Ca^{2+}$ or $Mg^{2+}$ but rather reduces the sensitivity of PVCRs to these agonists, these data are also consistent with the presence of an olfactory epithelium PVCR. The response evoked by exposure of the epithelium to significant concentrations of NaCl likely occurs via other PVCR independent mechanisms.

These data suggest that PVCR proteins present in olfactory epithelium are capable of sensing and generating corresponding olfactory nerve signals in response to PVCR agonists at appropriate concentrations in distilled water.

Figure 46:
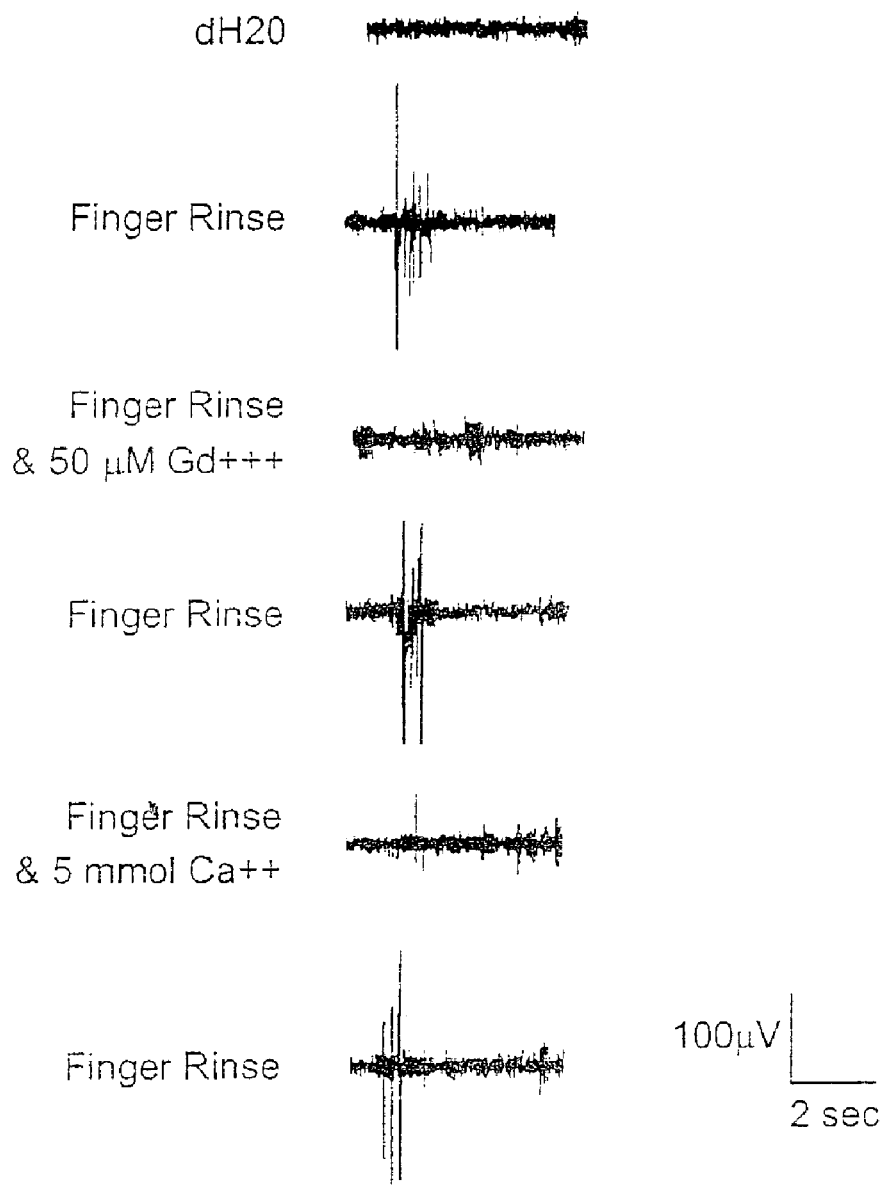
FIG. 46 shows raw recording from high resistance electrodes of olfactory nerve impulse in the presence of a repellant (finger rinse) and in the presence of a SalmoKCaR agonist (gadolinium) and a repellant (finger rinse). The figure shows that the olfactory nerve impulse to the repellant is reversibly altered in the presence of a SalmoKCaR agonist.

Addition of PVCR Agonists Such as Ca2+ or Gd3+ to Distilled Water Containing well known Salmon Repellants Reversibly Ablates the Response of the Olfactory Epithelium to these Stimuli:

FIG. 46 shows representative data obtained from a single continuous recording where the olfactory epithelium was first exposed to a well-known repellant, mammalian finger rinse. Finger rinse is obtained by simply rinsing human fingers of adherent oils and fatty acids using distilled water and has been shown previously to be a powerful repellant stimulus both in EEG recordings as well as behavioral avoidance assays (Royce-Malmgren and W. H Watson *J. Chem. Ecology* 13:533–546(1987)). Note however that inclusion of the PVCR agonists 5 mM $Ca^{2+}$ or 50 micromolar $Gd^{3+}$ reversibly ablated the response by the olfactory epithelium to mammalian finger rinse. These data show that PVCR agonists modulated the response of the olfactory epithelium to an odorant such as mammalian finger rinse. The ablation of responses to both the PVCR agonists as shown in FIG. 45 as well as mammalian finger rinse indicate that there are some complex interactions between PVCR proteins and other odorant receptors. It is also extremely unlikely that inclusion of PVCR agonists removed all the stimulatory components of mammalian finger rinse from solution such that they were not able to stimulate the epithelium.

Figure 47:
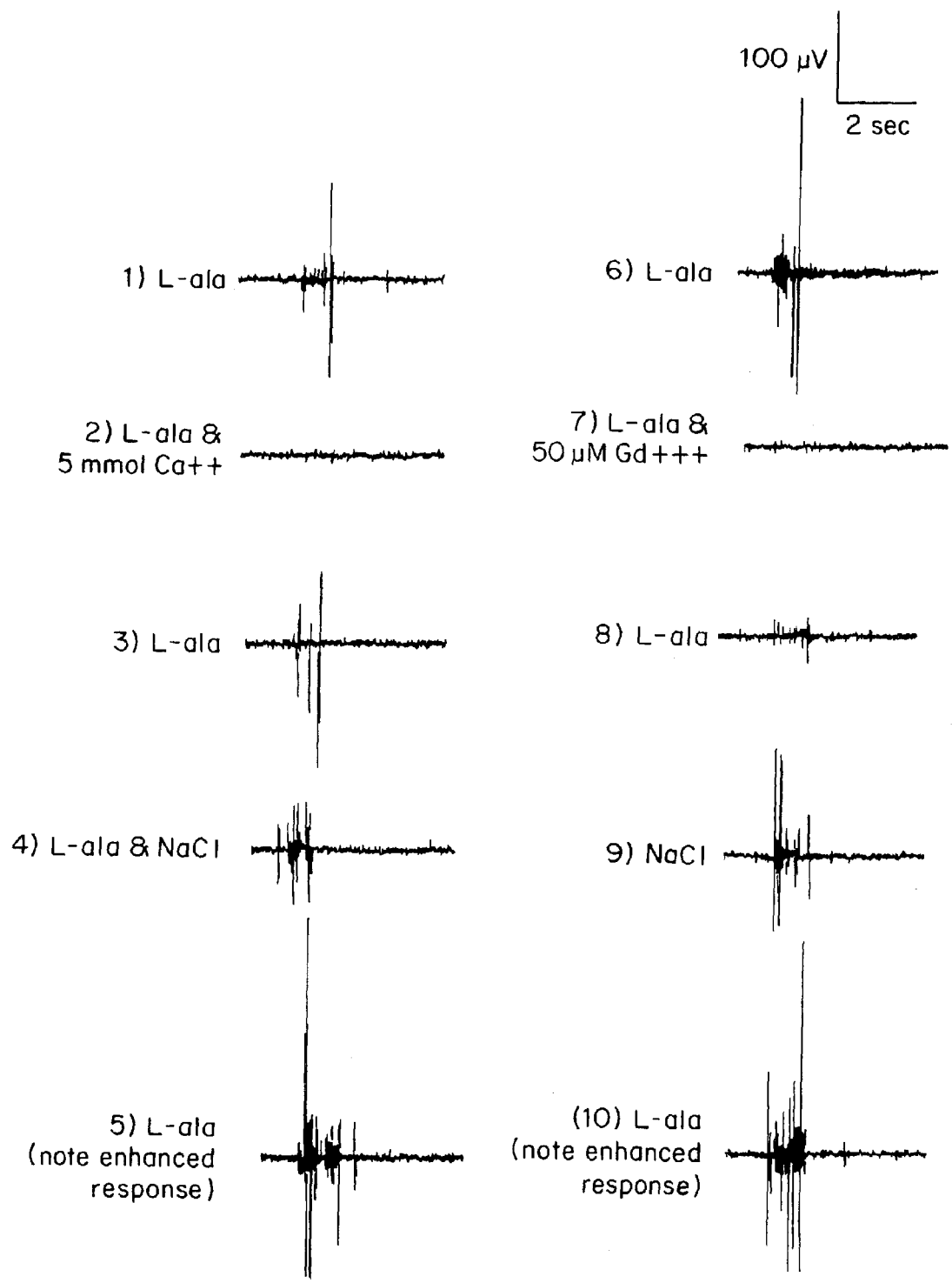
FIG. 47 shows the raw recordings from high resistance electrodes of freshwater adapted Atlantic Salmon in response to a series of repeated stimuli (L-alanine or NaCl) in 2 minute intervals. The figure shows that the olfactory nerve impulse to the attractant is reversibly altered in the presence of a SalmoKCaR agonist.

Addition of PVCR agonists such as Ca2+ or Gd3+ but not NaCl to distilled water containing the well known salmon attractant L-alanine reversibly ablates the response of the olfactory epithelium to these stimuli:

FIG. 47 shows a time series of stimuli (2 min between each stimulus in a single fish) similar to that displayed on FIG. 47 except that 500 micromolar L-Alanine (a salmon attractant) was used to produce a signal in the olfactory nerve. Note that the addition of either 5 mM $Ca^{2+}$ (recording #2) or 50 micromolar $Gd^{3+}$ (recording #7) to 500 micromolar L-alanine resulted in the complete loss of the corresponding response from the olfactory nerve after injection of this mixture. In both cases, this was not due to a permanent alteration of the olfactory epithelium by either of these PVCR agonists because a subsequent identical stimulus without the PVCR agonist (recordings #3 and #8) caused a return of the signal. It is noteworthy that in the case of $Gd^{3+}$ addition, the magnitude of the subsequent L-alanine signal was decreased as compared to control (compare recordings #6 vs #8) indicating that the olfactory epithelium prefers an interval of recovery from its exposure to this potent PVCR agonist. However, the alteration of response to the L-Alanine stimulus is not permanent or nonspecific since combining the same dose of L-Alanine with 250 mM NaCl resulted initially in a similar response (recordings #4 and #9) followed by an enhanced response to L-Alanine alone (recordings #5 and #10).

In summary, the data displayed in FIGS. 46 and 47 show that inclusion of a PVCR agonist in solutions containing either a repellant (finger rinse) or attractant (L-alanine) causes a dramatic reduction in the response of the olfactory epithelium to those odorants. For both repellants and attractants, some form of complex interactions occur within olfactory epithelial cells since mixing of PVCR agonists and odorants renders the epithelia temporary unresponsive to either stimulus. While the nature of such interactions are not known at the present time, such interactions do not occur at the level of the PVCR molecule itself as shown by data from experiments using recombinant PVCR protein SKCaR. As further described herein, inclusion of amino acids in the presence of $Ca^{2+}$ enhances the response of SKCaR to ambient $Ca^{2+}$ concentrations. Regardless of their nature, these negative modulatory effects of PVCR agonists including $Ca^{2+}$ is likely to produce major effects on how freshwater salmon smell objects in their environment after transfer from a low calcium to a high calcium environment. Use of this assay system would permit the identification and analyses of both specific classes of PVCR agonists and antagonists as well as the specific effects of each PVCR modulator on specific odorants including both repellants and attractants.

Recombinant PVCR Protein SKCaR Possesses the Capability to Sense Concentrations of Amino Acids After its Expression in Human Embryonic Kidney (HEK) Cells:

Full length recombinant dogfish (*Squalas acanthias*) shark kidney calcium receptor (SKCaR) was expressed in human embryonic kidney cells using methods described herein. The ability of SKCaR to respond to individual amino acids as well as various mixtures was quantified using FURA-2 ratio imaging fluorescence.

Figure 48:
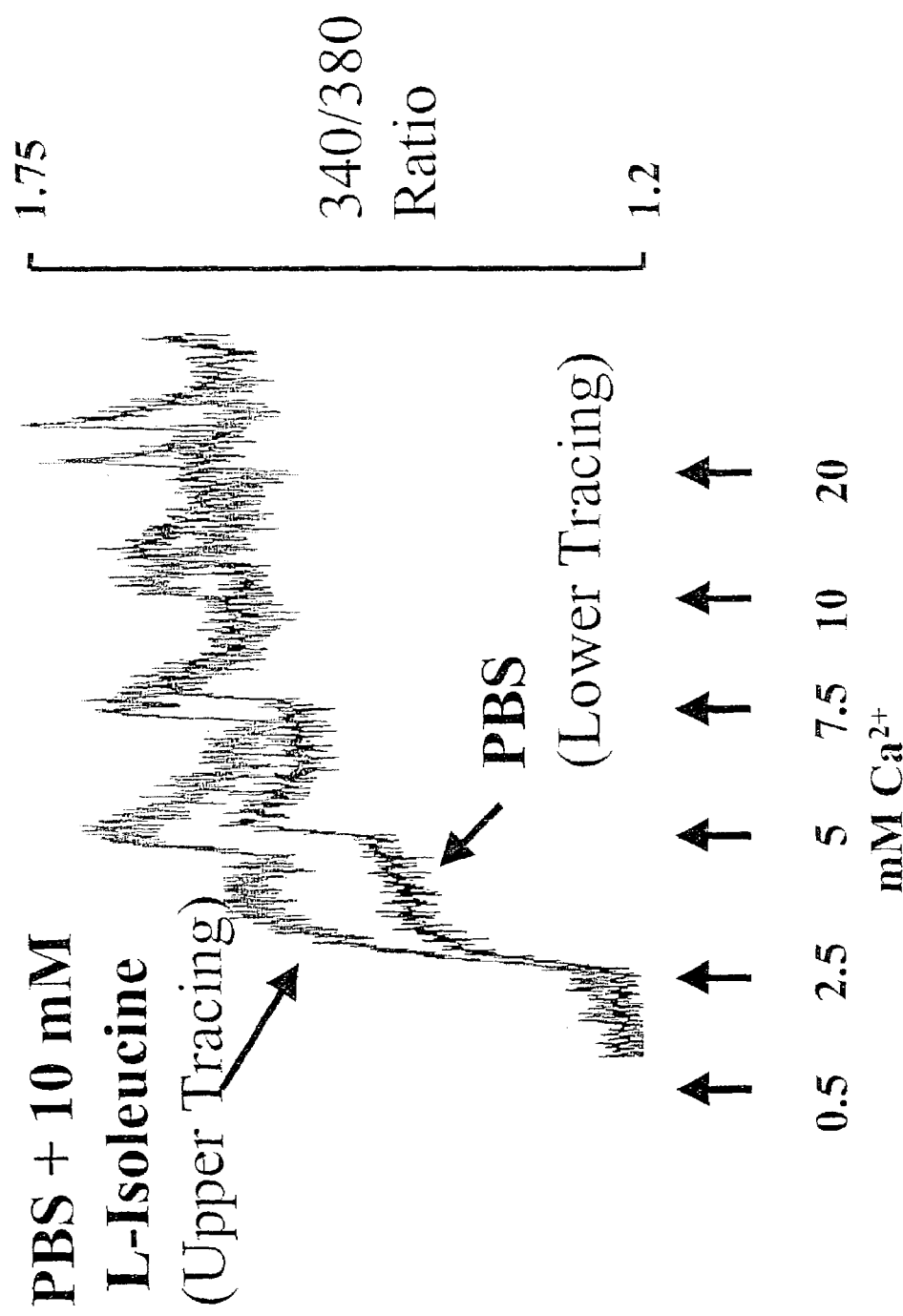
FIG. 48 is a graphical representation of the ratio from FURA-2 cells expressing a PVCR in the presence or absence of 10 mM L-Isoleucine in various concentrations (0.5, 2.5, 5.0, 7.5, 10.0 and 20.0 mM) of extracellular calcium ($Ca^{2+}$).

FIG. 48 shows a comparison of fluorescence tracings of FURA2-loaded cells stably expressing SKCaR that were bathed in physiological saline (125 mM NaCl, 4 mM KCl, 0.5 mM $CaCl_2$, 0.5 mM $MgCl_2$, 20 mM HEPES (NaOH), 0.1% D-glucose pH 7.4) in the presence or absence of 10 mM L-Isoleucine (L-Ile) before being placed into the fluorimeter. Baseline extracellular $Ca^{2+}$ concentration was 0.5 mM. Aliquots of $Ca^{2+}$ were added to produce final extracellular concentrations of 2.5 mM, 5 mM, 7.5 mM, 10 mM and 20 mM $Ca^{2+}$ with changes in the fluorescence recorded. Note that increases in cell fluorescence were greater in the presence of 10 mM Phe for extracellular $Ca^{2+}$ concentrations less than 10 mM.

Figure 49:
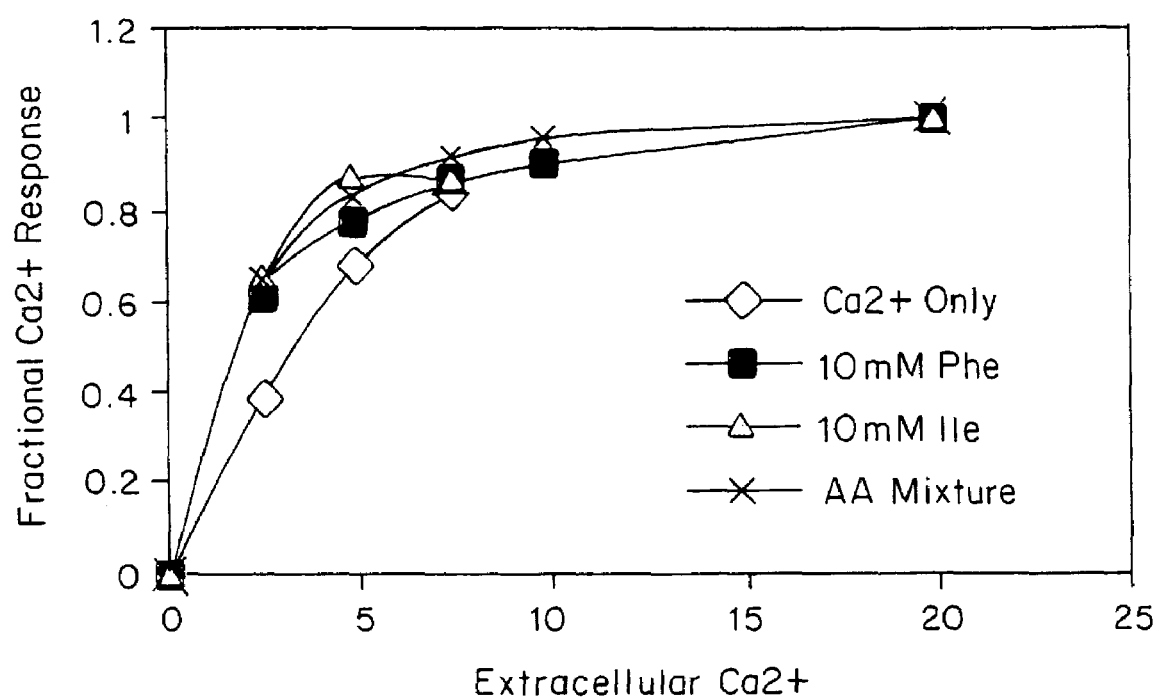
FIG. 49 is a graphical representation of the fractional $Ca^{2+}$ response, as compared to the extracelluar $Ca^{2+}$ (mM) for the PVCR in $Ca^{2+}$ only, Phenylalanine, Isoleucine, or AA Mixture (a variety of L-isomers in various concentrations).

FIG. 49 shows data plotted from multiple experiments as described in FIG. 48 where the effects of 10 mM Phe, 10 mM Ile or an amino acid mixture (AA Mixture) containing all L-isomers in the following concentrations in micromoles/liter: 50 Phe, 50 Trp, 80 His, 60 Tyr, 30 Cys, 300 Ala, 200 Thr, 50 Asn, 600 Gln, 125 Ser, 30 Glu, 250 Gly, 180 Pro, 250 Val, 30 Met, 10 Asp, 200 Lys, 100 Arg, 75 Ile, 150 Leu. Note that both 10 mM Phe and 10 mM Ile as well as the mixture of amino acids increase SKCaR's response to a given $Ca^{2+}$ concentration. Thus, these data show that presence of amino acids either alone or in combination increase the apparent sensitivity to $Ca^{2+}$ permitting SKCaR to "sense" amino acids in the presence of physiological concentrations of $Ca^{2+}$. These data obtained for SKCaR are comparable to those obtained for the human CaR.

The significance of these data for aquatic organisms stand in marked contrast to the roles of human CaRs amino acid sensing capabilities. FIG. 48 shows that SKCaR's maximal capability to sense amino acids is confined to a range of $Ca^{2+}$ that is present both in aquatic external environments as well as the body fluids of various fish. The following physiological processes occur: 1) Sensing of amino acids in the proximal intestine and pyloric caeca of fish: The PVCR present on the apical surface of intestinal epithelial cells is capable of responding to amino acids such as tryptophan as part of the Process II. Inclusion of tryptophan in the feed of fish interacts with the intestinal PVCR to improve the development of juvenile anadromous fish to tolerate seawater transfer. 2) In both adult, juvenile and larval fish, PVCR localized to the apical membrane of stomach and intestinal epithelial cells could "sense" the presence of amino acids produced by the proteolysis of proteins into amino acids. This mechanism could be used to inform both epithelial and neuroendocrine cells of the intestine of the presence of nutrients (proteins) and trigger a multitude of responses including growth and differentiation of intestinal epithelia as well as their accompanying transport proteins, secretion or reabsorption of ions such as gastric acid. The apical PVCR also regulates the secretion of intestinal hormones such as cholecystokin (CCK) and others. 3) PVCR proteins present in cells of the nasal lamellae of fish "smell" both water salinity (via $Ca^{2+}$, $Mg^{2+}$ and NaCl) and amino acids which is an example of an attractant. At the present time, it is unclear whether the amino acid sensing capabilities of PVCRs are utilized by the olfactory epithelium to enable fish to smell various amino acid attractants.

These data show that PVCR sensing of amino acids occurs in a range of extracellular calcium that is present in various concentrations of seawater present in estuaries and fish migration routes as well as various compartments of a fish's body including serum and body cavities including intestine, pyloric caeca and kidney where transepithelial amino acid absorption occurs. These data constitute the first report showing the amino acid sensitivity of a PVCR in fish.

Companion U.S. patent application Ser. No. 10/125,778, filed Apr. 18, 2002; U.S. application Ser. No. 10/125,772, filed Apr. 18, 2002; and U.S. application Ser. No. 10/125,792, filed Apr. 18, 2002; U.S. application Ser. No. 10/121,441, filed Apr. 11, 2002 all entitled "Polyvalent Cation-sensing Receptor in Atlantic Salmon;" U.S. Pat. No. 6,463,882, issued on Oct. 15, 2002, entitled "Growing Marine Fish in Fresh Water;" PCT Application No.: PCT/US01/31625, entitled "Growing Marine Fish in Fresh Water," filed Oct. 11, 2001; U.S. Pat. No. 6,463,883, issued Oct. 15, 20002, entitled "Methods for Raising Pre-adult Anadromous Fish;" U.S. Pat. No. 6,481,379, issued Nov. 19, 2002, entitled "Methods for Raising Pre-adult Anadromous Fish;" U.S. Pat. No. 6,475,792, issued Nov. 5, 2002, entitled "Methods for Raising Pre-Adult Anadromous Fish;" patent application Ser. No. 09/975,553, entitled "Methods for Raising Pre-adult Anadromous Fish," filed on Oct. 11, 2001; International PCT Application No. PCT/US01/31562, entitled, "Methods for Raising Pre-adult Anadromous Fish," filed on Oct. 11, 2001; Provisional Patent Application No. 60/382,464, "Methods for Growing and Imprinting Fish Using an Odorant," filed Oct. 11, 2001; and patent application Ser. No. 10/268,051, "Methods for Growing and Imprinting Fish Using an Odorant," filed Oct. 8, 2002, are all hereby incorporated by reference in their entirety.

Additionally, U.S. Pat. No. 6,334,391, issued on Jan. 8, 2002, International PCT application No. PCT/US97/05031, filed on Mar. 27, 1997, and application Ser. No. 08/622,738 filed Mar. 27, 1996, all entitled, "Polycation Sensing Receptor in Aquatic Species and Methods of Use Thereof" are all hereby incorporated by reference in their entirety. Additionally, EPO application No.: 97937017.8, file Jul. 24, 1997, which describes the SkCaR receptor, is also incorporated herein by reference in its entirety.

All relevant portions of literature articles, references, patent applications, patent publications, and patents cited herein are hereby incorporated by referenced in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. An isolated nucleic acid molecule comprising a nucleic acid sequence that consists essentially of:
    a) SEQ ID NO: 13; or
    b) the complementary strand of a).

2. An isolated nucleic acid molecule that comprises a nucleic acid sequence that has at least about 95% identity with SEQ ID NO: 13, or the coding region of SEQ ID NO: 13; wherein the nucleic acid molecule encodes a polypeptide that allows for or assists in one or more of the following functions in Atlantic Salmon: sensing at least one SalmoKCaR modulator in serum or in the surrounding environment; adapting to at least one SalmoKCaR modulator present in the serum or surrounding environment; imprinting with an odorant; altering water intake; altering water absorption; or altering urine output.

3. An isolated nucleic acid molecule that consists essentially of a nucleic acid sequence comprising the coding region of SEQ ID NO: 13; or the complementary strand of the coding region of SEQ ID NO: 13.

4. An isolated nucleic acid molecule that consists essentially of a nucleic acid sequence that encodes a polypeptide comprising an amino acid sequence of SEQ ID NO: 14.

5. An isolated nucleic acid molecule that consists essentially of a nucleic acid sequence that hybridizes under high stringency conditions to SEQ ID NO: 13; but not to SEQ ID NOs: 1, or 31–40 under said conditions, wherein said conditions are 1×SSC, 1% SDS, and 0.1–2 mg/ml denatured calf thymus DNA at 65° C. and wherein said nucleic acid molecule encodes a polypeptide that allows for or assists in one or more of the following functions: sensing at least one SalmoKCaR modulator in serum or in the surrounding environment; adapting to at least one SalmoKCaR modulator present in the serum or surrounding environment; imprinting Atlantic Salmon with an odorant; or altering water intake, altering water absorption, or altering urine output in Atlantic Salmon.

6. An isolated nucleic acid molecule that consists essentially of a nucleic acid sequence that hybridizes under high stringency conditions to the coding region of SEQ ID NO: 13; but not to the coding region of SEQ ID NO: 1, or 31–40 under said conditions, wherein said conditions are 1×SSC, 1% SDS, and 0.1–2 mg/ml denatured calf thymus DNA at 65° C. and wherein said nucleic acid molecule encodes a polypeptide that allows for or assists in one or more of the following functions: sensing at least one SalmoKCaR modulator in serum or in the surrounding environment; adapting to at least one SalmoKCaR modulator present in the serum or surrounding environment; imprinting Atlantic Salmon with an odorant; or altering water intake, altering water absorption, or altering urine output in Atlantic Salmon.

7. An isolated nucleic acid molecule that consists essentially of a nucleic acid sequence that encodes SEQ ID NO: 14, wherein the nucleic acid molecule is an RNA molecule.

8. A vector or plasmid that comprises a nucleic acid sequence having comprising SEQ ID NO: 13; or the coding region of SEQ ID NO: 13.

9. A vector or plasmid that comprises an isolated nucleic acid sequence that encodes a polypeptide comprising the amino acid sequence of SEQ ID NO: 14.

10. A vector or plasmid that comprises a nucleic acid sequence that hybridizes under high stringency conditions to SEQ ID NO: 13; or to the coding region of SEQ ID NO: 13; but not to SEQ ID NO: 1, or 31–40 or coding region thereof under said conditions, wherein said conditions are 1×SSC, 1% SDS, and 0.1–2 mg/ml denatured calf thymus DNA at 65° C. and wherein said nucleic acid molecule encodes a polypeptide that allows for or assists in one or more of the following functions: sensing at least one SalmoKCaR modulator in serum or in the surrounding environment; adapting to at least one SalmoKCaR modulator present in the serum or surrounding environment; imprinting Atlantic Salmon with an odorant; or altering water intake, altering water absorption, or altering urine output in Atlantic Salmon.

11. An isolated host cell transformed with a nucleic acid molecule that comprises a nucleic acid sequence having comprising SEQ ID NO: 13; or the coding region of SEQ ID NO: 13.

12. An isolated host cell transformed with a nucleic acid molecule that comprises an isolated nucleic acid sequence that encodes a polypeptide comprising an amino acid sequence of SEQ ID NO: 14.

13. An isolated host cell transformed with a nucleic acid molecule that comprises a nucleic acid sequence that hybridizes under high stringency conditions to SEQ ID NO: 13; or to the coding region thereof under said conditions, wherein said conditions are 1×SSC, 1% SDS, and 0.1–2 mg/ml denatured calf thymus DNA at 65° C. and wherein said nucleic acid molecule encodes a polypeptide that allows for or assists in one or more of the following functions: sensing at least one SalmoKCaR modulator in serum or in the surrounding environment; adapting to at least one SalmoKCaR modulator present in the serum or surrounding environment; imprinting Atlantic Salmon with an odorant; or altering water intake, altering water absorption, or altering urine output in Atlantic Salmon.

14. A nucleic acid purified from a clone deposited under ATCC NO: PTA-5131.

15. An isolated nucleic acid molecule that comprises a nucleic acid sequence that encodes a polypeptide comprising at least about 95% identity with SEQ ID NO: 14; and wherein the polypeptide allows for or assists in one or more of the following functions; sensing at least one SalmoKCaR modulator in serum or in the surrounding environment; adapting to at least one SalmoKCaR modulator present in the serum or surrounding environment; imprinting Atlantic Salmon with an odorant; or altering water intake, altering water absorption, or altering urine output in Atlantic Salmon.

* * * * *

UNITED STATES PATENT AND TRADEMARK OFFICE
CERTIFICATE OF CORRECTION

PATENT NO. : 7,101,988 B2
APPLICATION NO. : 10/410885
DATED : September 5, 2006
INVENTOR(S) : H. William Harris, Jr., Jacqueline Nearing and Marlies Betka It is certified that error appears in the above-identified patent and that said Letters Patent is hereby corrected as shown below:

Claim 8, line 55, the word "having" should be deleted.

Signed and Sealed this

Twenty-sixth Day of December, 2006

JON W. DUDAS
*Director of the United States Patent and Trademark Office*

SEQUENCE LISTING

<160> NUMBER OF SEQ ID NOS: 40

<210> SEQ ID NO 1
<211> LENGTH: 4134
<212> TYPE: DNA
<213> ORGANISM: Squalus acanthias

<400> SEQUENCE: 1

```
aattccgttg ctgtcggttc agtccaagtc tcctccagtg caaaatgaga aatggtggtc      60
gccattacag gaacatgcac tacatctgtg ttaatgaaat attgtcagtt atctgaaggt     120
tattaaaatg tttctgcaag gatggcttca cgagaaatca attctgcacg tttccccatt     180
gtcattgtat gaataactga ccaaagggat gtaacaaaat ggaacaaagc tgaggaccac     240 gttcacccet tcttggagca tacgatcaac cctgaaggag atggaagact tgaggaggaa     300
atggggattg atcttccagg agttctgctg taaagcgatc cctcaccatt acaaagataa     360
gcagaaatcc tccaggcatc ctctgtaaac gggctggcgt agtgtggctt ggtcaaggaa     420
cagagacagg gctgcacaat ggctcagctt cactgccaac tcttattctt gggatttaca     480
ctcctacagt cgtacaatgt ctcagggtat ggtccaaacc aaagggccca gaagaaagga     540
gacatcatac tgggaggtct cttcccaata cactttggag tagccgccaa ggatcaggac     600
ttaaaatcga gaccggaggc gacaaaatgt attcggtaca attttcgagg cttccgatgg     660
ctccaggcga tgatattcgc aattgaagag attaacaaca gtatgacttt cctgcccaat     720
atcaccctgg gatatcgcat atttgacacg tgtaacaccg tgtccaaggc gctagaggca     780
acactcagct ttgtggccca gaacaaaatc gactcgctga acttagatga gttctgtaac     840
tgctctgacc atatcccatc cacaatagca gtggtcgggg caaccgggtc aggaatctcc     900
acggctgtgc ccaatctatt gggattattt tacattccac aggtcagcta tgcctcctcg     960
agcaggctgc tcagcaacaa gaatgagtac aaggccttcc tgaggaccat ccccaatgat    1020
gagcaacagg ccacggccat ggccgagatc atcgagcact tccagtggaa ctgggtggga    1080
accctggcag ccgacgatga ctatggccgc ccaggcattg acaagttccg ggaggaggcc    1140
gttaagaggg acatctgtat tgacttcagt gagatgatct ctcagtacta cacccagaag    1200
cagttggagt tcatcgccga cgtcatccag aactcctcgg ccaaggtcat cgtggtcttc    1260
tccaatggcc ccgacctgga gccgctcatc caggagatag ttcggagaaa catcaccgat    1320
cggatctggc tggccagcga ggcttggccc agctcttcgc tcattgccaa gccagagtac    1380
ttccacgtgg tcggcggcac catcggcttc gctctcaggg cggggcgtat cccagggttc    1440
aacaagttcc tgaaggaggt ccaccccagc aggtcctcgg acaatggggt tgtcaaggag    1500
```

-continued

| | |
|---|---|
| ttctgggagg agaccttcaa ctgctacttc accgagaaga ccctgacgca gctgaagaat | 1560 |
| tccaaggtgc cctcgcacgg accggcggct caaggggacg gctccaaggc ggggaactcc | 1620 |
| agacggacag ccctacgcca cccctgcact ggggaggaga acatcaccag cgtggagacc | 1680 |
| ccctacctgg attatacaca cctgaggatc tcctacaatg tatacgtggc cgtctactcc | 1740 |
| attgctcacg ccctgcaaga catccactct tgcaaacccg gcacgggcat ctttgcaaac | 1800 |
| ggatcttgtg cagatattaa aaagttgag gcctggcagg tcctcaacca tctgctgcat | 1860 |
| ctgaagttta ccaacagcat gggtgagcag gttgactttg acgatcaagg tgacctcaag | 1920 |
| gggaactaca ccattatcaa ctggcagctc tccgcagaga tgaatcggt gttgttccat | 1980 |
| gaggtgggca actacaacgc ctacgctaag cccagtgacc gactcaacat caacgaaaag | 2040 |
| aaaatcctct ggagtggctt ctccaaagtg gttcctttct ccaactgcag tcgagactgt | 2100 |
| gtgccgggca ccaggaaggg gatcatcgag ggggagccca cctgctgctt tgaatgcatg | 2160 |
| gcatgtgcag agggagagtt cagtgatgaa acgatgcaa gtgcgtgtac aaagtgcccg | 2220 |
| aatgatttct ggtcgaatga aaccacacg tcgtgcatcg ccaaggagat cgagtacctg | 2280 |
| tcgtggacga gcccttcgg gatcgctctg accatcttcg ccgtactggg catcctgatc | 2340 |
| acctccttcg tgctgggggt cttcatcaag ttcaggaaca ctcccatcgt gaaggccacc | 2400 |
| aaccgggagt tgtcctacct gctgctcttc tccctcatct gctgcttctc cagctcgctc | 2460 |
| atcttcatcg gcgagcccag ggactggacc tgtcggctcc gccaaccggc ctttggcatc | 2520 |
| agcttcgtcc tgtgcatctc ctgcatcctg gtgaagacca accgggtgct gctggtcttc | 2580 |
| gaggccaaga tccccaccag cctccaccgc aagtgggtgg gcctcaacct gcagttcctc | 2640 |
| ctggtcttcc tctgcatcct ggtgcaaatc gtcacctgca tcatctggct ctacaccgcg | 2700 |
| cctccctcca gctacaggaa ccatgagctg gaggacgagg tcatcttcat cacctgcgac | 2760 |
| gagggctcgc tcatggcgct gggcttcctc atcggctaca cctgcctcct cgccgccatc | 2820 |
| tgcttcttct tcgccttcaa gtcccgtaag ctgccggaga acttcaacga ggctaagttc | 2880 |
| atcaccttca gcatgttgat cttcttcatc gtctggatct ccttcatccc cgcctatgtc | 2940 |
| agcacctacg gcaagtttgt gtcggccgtg gaggtgattg ccatcctggc ctccagcttc | 3000 |
| gggctgctgg gctgcattta cttcaacaag tgttacatca tcctgttcaa gccgtgccgt | 3060 |
| aacaccatcg aggaggtgcg ctgcagcacg gcggcccacg ccttcaaggt ggcggcccgg | 3120 |
| gccaccctcc ggcgcagcgc cgcgtctcgc aagcgctcca gcagcctgtg cggctccacc | 3180 |
| atctcctcgc ccgcctcgtc cacctgcggg ccgggcctca ccatggagat gcagcgctgc | 3240 |
| agcacgcaga aggtcagctt cggcagcggc accgtcaccc tgtcgctcag cttcgaggag | 3300 |
| acaggccgat acgccaccct cagccgcacg gcccgcagca ggaactcggc ggatggccgc | 3360 |
| agcggcgacg acctgccatc tagacaccac gaccagggcc cgcctcgaa atgcgagccc | 3420 |
| cagcccgcca acgatgcccg atacaaggcg cgccgaccca agggcaccct agagtcgccg | 3480 |
| ggcggcagca aggagcgccc cacaactatg gaggaaacct aatccaactc ctccatcaac | 3540 |
| cccaagaaca tcctccacgg cagcaccgtc gacaactgac atcaactcct aaccggtggc | 3600 |
| tgcccaacct ctcccctctc cggcactttg cgttttgctg aagattgcag catctgcagt | 3660 |
| tccttttatc cctgattttc tgacttggat atttactagt gtgcgatgga atatcacaac | 3720 |
| ataatgagtt gcacaattag gtgagcagag ttgtgtcaaa gtatctgaac tatctgaagt | 3780 |
| atctgaacta ctttattctc tcgaattgta ttacaaacat ttgaagtatt tttagtgaca | 3840 |
| ttatgttcta acattgtcaa gataatttgt tacaacatat aaggtaccac ctgaagcagt | 3900 |

```
gactgagatt gccactgtga tgacagaact gttttataac atttatcatt gaaacctgga   3960
ttgcaacagg aatataatga ctgtaacaaa aaaattgttg attatcttaa aaatgcaaat   4020
tgtaatcaga tgtgtaaaat tggtaattac ttctgtacat taaatgcata tttcttgata   4080
aaaaaaaaaa aaaaaaaaaa aaaaaaaaaa aaaaaagcgg cccgacagca acgg         4134
```

<210> SEQ ID NO 2
<211> LENGTH: 1027
<212> TYPE: PRT
<213> ORGANISM: Squalus acanthias

<400> SEQUENCE: 2

```
Met Ala Gln Leu His Cys Gln Leu Leu Phe Leu Gly Phe Thr Leu Leu
1               5                   10                  15

Gln Ser Tyr Asn Val Ser Gly Tyr Gly Pro Asn Gln Arg Ala Gln Lys
            20                  25                  30

Lys Gly Asp Ile Ile Leu Gly Gly Leu Phe Pro Ile His Phe Gly Val
        35                  40                  45

Ala Ala Lys Asp Gln Asp Leu Lys Ser Arg Pro Glu Ala Thr Lys Cys
    50                  55                  60

Ile Arg Tyr Asn Phe Arg Gly Phe Arg Trp Leu Gln Ala Met Ile Phe
65                  70                  75                  80

Ala Ile Glu Glu Ile Asn Asn Ser Met Thr Phe Leu Pro Asn Ile Thr
                85                  90                  95

Leu Gly Tyr Arg Ile Phe Asp Thr Cys Asn Thr Val Ser Lys Ala Leu
            100                 105                 110

Glu Ala Thr Leu Ser Phe Val Ala Gln Asn Lys Ile Asp Ser Leu Asn
        115                 120                 125

Leu Asp Glu Phe Cys Asn Cys Ser Asp His Ile Pro Ser Thr Ile Ala
    130                 135                 140

Val Val Gly Ala Thr Gly Ser Gly Ile Ser Thr Ala Val Ala Asn Leu
145                 150                 155                 160

Leu Gly Leu Phe Tyr Ile Pro Gln Val Ser Tyr Ala Ser Ser Ser Arg
                165                 170                 175

Leu Leu Ser Asn Lys Asn Glu Tyr Lys Ala Phe Leu Arg Thr Ile Pro
            180                 185                 190

Asn Asp Glu Gln Gln Ala Thr Ala Met Ala Glu Ile Ile Glu His Phe
        195                 200                 205

Gln Trp Asn Trp Val Gly Thr Leu Ala Ala Asp Asp Tyr Gly Arg
    210                 215                 220

Pro Gly Ile Asp Lys Phe Arg Glu Glu Ala Val Lys Arg Asp Ile Cys
225                 230                 235                 240

Ile Asp Phe Ser Glu Met Ile Ser Gln Tyr Tyr Thr Gln Lys Gln Leu
                245                 250                 255

Glu Phe Ile Ala Asp Val Ile Gln Asn Ser Ser Ala Lys Val Ile Val
            260                 265                 270

Val Phe Ser Asn Gly Pro Asp Leu Glu Pro Leu Ile Gln Glu Ile Val
        275                 280                 285

Arg Arg Asn Ile Thr Asp Arg Ile Trp Leu Ala Ser Glu Ala Trp Ala
    290                 295                 300

Ser Ser Ser Leu Ile Ala Lys Pro Glu Tyr Phe His Val Val Gly Gly
305                 310                 315                 320

Thr Ile Gly Phe Ala Leu Arg Ala Gly Arg Ile Pro Gly Phe Asn Lys
                325                 330                 335
```

```
Phe Leu Lys Glu Val His Pro Ser Arg Ser Ser Asp Asn Gly Phe Val
                340                 345                 350
Lys Glu Phe Trp Glu Thr Phe Asn Cys Tyr Phe Thr Glu Lys Thr
            355                 360                 365
Leu Thr Gln Leu Lys Asn Ser Lys Val Pro Ser His Gly Pro Ala Ala
        370                 375                 380
Gln Gly Asp Gly Ser Lys Ala Gly Asn Ser Arg Arg Thr Ala Leu Arg
385                 390                 395                 400
His Pro Cys Thr Gly Glu Glu Asn Ile Thr Ser Val Glu Thr Pro Tyr
                405                 410                 415
Leu Asp Tyr Thr His Leu Arg Ile Ser Tyr Asn Val Tyr Val Ala Val
                420                 425                 430
Tyr Ser Ile Ala His Ala Leu Gln Asp Ile His Ser Cys Lys Pro Gly
                435                 440                 445
Thr Gly Ile Phe Ala Asn Gly Ser Cys Ala Asp Ile Lys Lys Val Glu
            450                 455                 460
Ala Trp Gln Val Leu Asn His Leu Leu His Leu Lys Phe Thr Asn Ser
465                 470                 475                 480
Met Gly Glu Gln Val Asp Phe Asp Asp Gln Gly Asp Leu Lys Gly Asn
                485                 490                 495
Tyr Thr Ile Ile Asn Trp Gln Leu Ser Ala Glu Asp Ser Val Leu
            500                 505                 510
Phe His Glu Val Gly Asn Tyr Asn Ala Tyr Ala Lys Pro Ser Asp Arg
                515                 520                 525
Leu Asn Ile Asn Glu Lys Lys Ile Leu Trp Ser Gly Phe Ser Lys Val
            530                 535                 540
Val Pro Phe Ser Asn Cys Ser Arg Asp Cys Val Pro Gly Thr Arg Lys
545                 550                 555                 560
Gly Ile Ile Glu Gly Glu Pro Thr Cys Cys Phe Glu Cys Met Ala Cys
                565                 570                 575
Ala Glu Gly Glu Phe Ser Asp Glu Asn Asp Ala Ser Ala Cys Thr Lys
                580                 585                 590
Cys Pro Asn Asp Phe Trp Ser Asn Glu Asn His Thr Ser Cys Ile Ala
            595                 600                 605
Lys Glu Ile Glu Tyr Leu Ser Trp Thr Glu Pro Phe Gly Ile Ala Leu
        610                 615                 620
Thr Ile Phe Ala Val Leu Gly Ile Leu Ile Thr Ser Phe Val Leu Gly
625                 630                 635                 640
Val Phe Ile Lys Phe Arg Asn Thr Pro Ile Val Lys Ala Thr Asn Arg
                645                 650                 655
Glu Leu Ser Tyr Leu Leu Leu Phe Ser Leu Ile Cys Cys Phe Ser Ser
                660                 665                 670
Ser Leu Ile Phe Ile Gly Glu Pro Arg Asp Trp Thr Cys Arg Leu Arg
            675                 680                 685
Gln Pro Ala Phe Gly Ile Ser Phe Val Leu Cys Ile Ser Cys Ile Leu
        690                 695                 700
Val Lys Thr Asn Arg Val Leu Leu Val Phe Glu Ala Lys Ile Pro Thr
705                 710                 715                 720
Ser Leu His Arg Lys Trp Val Gly Leu Asn Leu Gln Phe Leu Leu Val
                725                 730                 735
Phe Leu Cys Ile Leu Val Gln Ile Val Thr Cys Ile Ile Trp Leu Tyr
            740                 745                 750
```

```
Thr Ala Pro Pro Ser Ser Tyr Arg Asn His Glu Leu Glu Asp Glu Val
        755                 760                 765
Ile Phe Ile Thr Cys Asp Glu Gly Ser Leu Met Ala Leu Gly Phe Leu
        770                 775                 780
Ile Gly Tyr Thr Cys Leu Leu Ala Ala Ile Cys Phe Phe Phe Ala Phe
785                 790                 795                 800
Lys Ser Arg Lys Leu Pro Glu Asn Phe Asn Glu Ala Lys Phe Ile Thr
                805                 810                 815
Phe Ser Met Leu Ile Phe Phe Ile Val Trp Ile Ser Phe Ile Pro Ala
            820                 825                 830
Tyr Val Ser Thr Tyr Gly Lys Phe Val Ser Ala Val Glu Val Ile Ala
                835                 840                 845
Ile Leu Ala Ser Ser Phe Gly Leu Leu Gly Cys Ile Tyr Phe Asn Lys
        850                 855                 860
Cys Tyr Ile Ile Leu Phe Lys Pro Cys Arg Asn Thr Ile Glu Glu Val
865                 870                 875                 880
Arg Cys Ser Thr Ala Ala His Ala Phe Lys Val Ala Ala Arg Ala Thr
                885                 890                 895
Leu Arg Arg Ser Ala Ala Ser Arg Lys Arg Ser Ser Leu Cys Gly
            900                 905                 910
Ser Thr Ile Ser Ser Pro Ala Ser Ser Thr Cys Gly Pro Gly Leu Thr
        915                 920                 925
Met Glu Met Gln Arg Cys Ser Thr Gln Lys Val Ser Phe Gly Ser Gly
        930                 935                 940
Thr Val Thr Leu Ser Leu Ser Phe Glu Glu Thr Gly Arg Tyr Ala Thr
945                 950                 955                 960
Leu Ser Arg Thr Ala Arg Ser Arg Asn Ser Ala Asp Gly Arg Ser Gly
                965                 970                 975
Asp Asp Leu Pro Ser Arg His His Asp Gln Gly Pro Pro Gln Lys Cys
            980                 985                 990
Glu Pro Gln Pro Ala Asn Asp Ala Arg Tyr Lys Ala Ala Pro Thr Lys
        995                 1000                1005
Gly Thr Leu Glu Ser Pro Gly Gly Ser Lys Glu Arg Pro Thr Thr
        1010                1015                1020
Met Glu Glu Thr
        1025

<210> SEQ ID NO 3
<211> LENGTH: 594
<212> TYPE: DNA
<213> ORGANISM: Salmo salar

<400> SEQUENCE: 3
cttggcatta tgctctgtgc tgggggtatt cttgacagca ttcgtgatgg gagtgtttat      60
caaatttcgc aacaccccaa ttgttaaggc cacaaacaga gagctatcct acctcctcct     120
gttctcactc atctgctgtt tctccagttc cctcatcttc attggtgaac cccaggactg     180
gacatgccgt ctacgccagc ctgcattcgg gataagtttt gttctctgca tctcctgcat     240
cctggtaaaa actaaccgag tacttctagt gttcgaagcc aagatcccca ccagtctcca     300
tcgtaagtgg tgggggctaa acttgcagtt cctgttagtg ttcctgttca catttgtgca     360
agtgatgata tgtgtggtct ggctttacaa tgctcctccg gcgagctaca ggaaccatga     420
cattgatgag ataattttca ttacatgcaa tgagggctct atgatggcgc ttggcttcct     480
```

-continued

```
aattgggtac acatgcctgc tggcagccat atrcttcttc tttgcattta aatcacgaaa    540
actgccagag aactttactg aggctaagtt catcaccttc agcatgctca tctt          594
```

<210> SEQ ID NO 4
<211> LENGTH: 197
<212> TYPE: PRT
<213> ORGANISM: Salmo salar
<220> FEATURE:
<221> NAME/KEY: misc_feature
<222> LOCATION: (171)..(171)
<223> OTHER INFORMATION: Xaa = Any Amino Acid

<400> SEQUENCE: 4

```
Leu Ala Leu Cys Ser Val Leu Gly Val Phe Leu Thr Ala Phe Val Met
1               5                   10                  15

Gly Val Phe Ile Lys Phe Arg Asn Thr Pro Ile Val Lys Ala Thr Asn
            20                  25                  30

Arg Glu Leu Ser Tyr Leu Leu Leu Phe Ser Leu Ile Cys Cys Phe Ser
        35                  40                  45

Ser Ser Leu Ile Phe Ile Gly Glu Pro Gln Asp Trp Thr Cys Arg Leu
    50                  55                  60

Arg Gln Pro Ala Phe Gly Ile Ser Phe Val Leu Cys Ile Ser Cys Ile
65                  70                  75                  80

Leu Val Lys Thr Asn Arg Val Leu Leu Val Phe Glu Ala Lys Ile Pro
                85                  90                  95

Thr Ser Leu His Arg Lys Trp Trp Gly Leu Asn Leu Gln Phe Leu Leu
            100                 105                 110

Val Phe Leu Phe Thr Phe Val Gln Val Met Ile Cys Val Val Trp Leu
        115                 120                 125

Tyr Asn Ala Pro Pro Ala Ser Tyr Arg Asn His Asp Ile Asp Glu Ile
    130                 135                 140

Ile Phe Ile Thr Cys Asn Glu Gly Ser Met Met Ala Leu Gly Phe Leu
145                 150                 155                 160

Ile Gly Tyr Thr Cys Leu Leu Ala Ala Ile Xaa Phe Phe Ala Phe
                165                 170                 175

Lys Ser Arg Lys Leu Pro Glu Asn Phe Thr Glu Ala Lys Phe Ile Thr
            180                 185                 190

Phe Ser Met Leu Ile
            195
```

<210> SEQ ID NO 5
<211> LENGTH: 2021
<212> TYPE: DNA
<213> ORGANISM: Salmo salar

<400> SEQUENCE: 5

```
gtgatcacaa aggtaagaaa gacagtgaaa aatctgaact accccattat ataatctgtt    60
gctatttcat atgtttctat caataataca aacactactt ctctattcct gcagatgcca   120
gtgtttgtac caagtgtccc aatgactcat ggtctaatga aaccacaca tcttgttccc    180 tgaaggagat agagtttctg tcttggacag agcccttggg gatcgccttg cattatgct    240 ctgtgctggg ggtattcttg acagcattcg tgatgggagt gtttatcaaa tttcgcaaca    300
ccccaattgt taaggccaca aacagagagc tatcctacct cctcctgttc tcactcatct    360
gctgtttctc cagttccctc atcttcattg gtgaacccca ggactggaca tgccgtctac    420
gccagcctgc attcgggata agttttgttc tctgcatctc ctgcatcctg gtaaaaacta    480
```

-continued

```
accgagtact tctagtgttc gaagccaaga tccccaccag tctccatcgt aagtggtggg     540
ggctaaactt gcagttcctg ttagtgttcc tgttcacatt tgtgcaagtg atgatatgtg     600
tggtctggct ttacaatgct cctccggcga gctacaggaa ccatgacatt gatgagataa     660
ttttcattac atgcaatgag ggctctatga tggcgcttgg cttcctaatt gggtacacat     720
gcctgctggc agccatatgc ttcttctttg catttaaatc acgaaaactg ccagagaact     780
ttactgaggc taagttcatc accttcagca tgctcatctt cttcatcgtc tggatctctt     840
tcatccctgc ctacttcagc acttacggaa agtttgtgtc ggctgtggag gtcatcgcca     900
tactagcctc cagctttggc ctgctggcct gtattttctt caataaagtc tacatcatcc     960
tcttcaaacc gtccaggaac actatagagg aggttcgctg tagcactgcg gcccattctt    1020
tcaaagtggc agccaaggcc actctgagac acagctcagc ctccaggaag aggtccagca    1080
gtgtgggggg atcctgtgcc tcaactccct cctcatccat cagcctcaag accaatgaca    1140
atgactcccc atcaggtcag cagagaatcc ataagccaag agtaagcttt ggaagtggaa    1200
cagttactct gtccttgagc tttgaggagt ccagaaagaa ttctatgaag tagggaagtg    1260
tcttttggtg ggccgagagc cttgtcaaaa cctgagttgg tgttgcattc tttgttggct    1320
gggtagttgg agcagaaatt atgatattaa agctttgat gtattcagaa tggtgacaca    1380
gcataggtgg ccaagattcc attatattac aataatctgt gttgttcatt atgaggacat    1440
ttcaaaatgc tgaaaatcat caaatacata atttactgag ttttcttgat aatcttgaga    1500
atagaatagc ctattcaagt catcgttgag cagacattaa ttaacaatga tgtaatactt    1560
tccataccta ttttctttaa caatagattc acattgttaa agttcaacta tgacctgtaa    1620
aatacatgag gtataacagg agacaataaa actatgcata tcctagcttc tgggcctgag    1680
tagcaggcag tttactctgg gcacgctttt catccaaact tccgaatgct gcccccaatc    1740
ctagtgaggt taaaggccca gtgcagtcat atcttttctc taggcacgct tttcatccaa    1800
acttccgaat gcggctatat cagtctcttt cctactgtct ttttcattag gccagtgttt    1860
aacaaccctg gtccttaagt acacacaaca gaacacattt tgttgtagc cctggacaat     1920 cactcctcac tcagctcatt gagggcctga tgattagttg acaagttgaa tcaggtgtgc    1980
ttgtccaggg ttacaataca aatgtgtact gttgggggta c                        2021
```

<210> SEQ ID NO 6
<211> LENGTH: 388
<212> TYPE: PRT
<213> ORGANISM: Salmo salar

<400> SEQUENCE: 6

Tyr Lys His Tyr Phe Ser Ile Pro Ala Asp Ala Ser Val Cys Thr Lys
1               5                   10                  15

Cys Pro Asn Asp Ser Trp Ser Asn Glu Asn His Thr Ser Cys Phe Leu
            20                  25                  30

Lys Glu Ile Glu Phe Leu Ser Trp Thr Glu Pro Phe Gly Ile Ala Leu
        35                  40                  45

Ala Leu Cys Ser Val Leu Gly Val Phe Leu Thr Ala Phe Val Met Gly
    50                  55                  60

Val Phe Ile Lys Phe Arg Asn Thr Pro Ile Val Lys Ala Thr Asn Arg
65                  70                  75                  80

Glu Leu Ser Tyr Leu Leu Leu Phe Ser Leu Ile Cys Cys Phe Ser Ser
                85                  90                  95

-continued

```
Ser Leu Ile Phe Ile Gly Glu Pro Gln Asp Trp Thr Cys Arg Leu Arg
            100                 105                 110

Gln Pro Ala Phe Gly Ile Ser Phe Val Leu Cys Ile Ser Cys Ile Leu
        115                 120                 125

Val Lys Thr Asn Arg Val Leu Leu Val Phe Glu Ala Lys Ile Pro Thr
    130                 135                 140

Ser Leu His Arg Lys Trp Trp Gly Leu Asn Leu Gln Phe Leu Leu Val
145                 150                 155                 160

Phe Leu Phe Thr Phe Val Gln Val Met Ile Cys Val Val Trp Leu Tyr
                165                 170                 175

Asn Ala Pro Pro Ala Ser Tyr Arg Asn His Asp Ile Asp Glu Ile Ile
            180                 185                 190

Phe Ile Thr Cys Asn Glu Gly Ser Met Met Ala Leu Gly Phe Leu Ile
        195                 200                 205

Gly Tyr Thr Cys Leu Leu Ala Ala Ile Cys Phe Phe Ala Phe Lys
    210                 215                 220

Ser Arg Lys Leu Pro Glu Asn Phe Thr Glu Ala Lys Phe Ile Thr Phe
225                 230                 235                 240

Ser Met Leu Ile Phe Phe Ile Val Trp Ile Ser Phe Ile Pro Ala Tyr
                245                 250                 255

Phe Ser Thr Tyr Gly Lys Phe Val Ser Ala Val Glu Val Ile Ala Ile
            260                 265                 270

Leu Ala Ser Ser Phe Gly Leu Leu Ala Cys Ile Phe Phe Asn Lys Val
        275                 280                 285

Tyr Ile Ile Leu Phe Lys Pro Ser Arg Asn Thr Ile Glu Glu Val Arg
    290                 295                 300

Cys Ser Thr Ala Ala His Ser Phe Lys Val Ala Ala Lys Ala Thr Leu
305                 310                 315                 320

Arg His Ser Ser Ala Ser Arg Lys Arg Ser Ser Val Gly Gly Ser
                325                 330                 335

Cys Ala Ser Thr Pro Ser Ser Ile Ser Leu Lys Thr Asn Asp Asn
            340                 345                 350

Asp Ser Pro Ser Gly Gln Gln Arg Ile His Lys Pro Arg Val Ser Phe
        355                 360                 365

Gly Ser Gly Thr Val Thr Leu Ser Leu Ser Phe Glu Glu Ser Arg Lys
    370                 375                 380

Asn Ser Met Lys
385
```

<210> SEQ ID NO 7
<211> LENGTH: 3941
<212> TYPE: DNA
<213> ORGANISM: Salmo salar

<400> SEQUENCE: 7

| | | | | | |
|---|---|---|---|---|---|
| ttccaacagc | atatttttgt | tgtatttgct | ttggtttgtc | tgaaatcaag | cattatcaag | 60 |
| atcaagaaca | gcatgagtca | gaaacaaggc | gacagccaga | gtcactggag | gggacaagac | 120 |
| tgaggttaac | tctgaagtct | aatgtgctga | gaggacaagg | ccctcctgag | agctgaacga | 180 |
| tgagatttta | cctgtattac | ctggtgcttt | tgggcttcag | ttctgtcatc | tccacctatg | 240 |
| ggcctcatca | gagagcacag | aagactgggg | atattctgct | gggcgggctg | tttccaatgc | 300 |
| actttggtgt | tacctccaaa | gaccaagacc | tggcagcgcg | ccagaatcc | acagagtgtg | 360 |
| ttaggtacaa | tttccgggga | ttccgttggc | ttcaggccat | gattttttgca | atagaggaga | 420 |

-continued

```
tcaacaacag cagtactctc ctgcccaaca tcacactggg ctacaggatc tttgacacct      480
gcaacaccgt gtccaaggcc ctggaggcta ccctcagttt cgtagcacag aataagattg      540
actctctgaa cttggatgaa ttctgtaact gcactgatca catcccatcg actatagcag      600 tggtggggc ttctgggtca gcggtctcca ctgctgttgc caatctgttg ggccttttct       660
acatcccaca gatcagctat gcctcttcca gtcgcctact aagcaacaag aaccagttca      720
aatccttcat gaggaccatt cccacagatg agcaccaggc cactgccatg cagatatca      780 tcgactactt ccaatggaat tgggtcattg cagttgcgtc tgatgatgag tatggacgtc      840
cggggattga aaaatttgag aaagagatgg aagaacgaga catttgtatc catctgagtg      900
agctgatctc tcagtacttt gaggagtggc agatccaagg attggttgac cgtattgaga      960
actcctcagc taaagttata gtcgttttcg ccagtgggcc tgacattgag cctcttatta     1020
aagagatggt cagacggaac atcaccgacc gcatctggtt ggccagcgag gcttgggcaa     1080
ccacctccct catcgccaaa ccagagtacc ttgatgttgt agttgggacc attggctttg     1140
ctctcagagc aggcgaaata cctggcttca aggacttctt acaagaggtc acaccaaaga     1200
aatccagcca caatgaattt gtcagggagt tttgggagga acttttaac tgctatctgg      1260 aagacagcca gagactgaga gacagtgaga atgggagcac cagtttcaga ccattgtgta     1320
ctggcgagga ggacattatg ggtgcagaga ccccatatct ggattacact catcttcgta     1380
tttcctataa tgtgtatgtt gcagttcact ccattgcaca ggccctacag gacattctca     1440
cctgcattcc tggacggggt cttttttcca caaactcatg tgcagatata aagaaaatag     1500
aagcatggca ggttctcaag cagctcagac atttaaactt ctcaaacagt atgggagaaa     1560
aggtacattt tgatgagaat gctgatccgt caggaaacta caccattatc aattggcacc     1620
ggtctcctga ggatggttct gttgtgtttg aagaggtcgg tttctacaac atgcgagcta     1680
agagaggagt acaactttc attgataaca caaagattct atggaatgga tataatactg       1740
aggttccatt ctctaactgt agtgaagatt gtgaaccagg caccagaaag gggatcatag      1800
aaagcatgcc aacgtgttgc tttgaatgta cagaatgctc agaaggagag tatagtgatc      1860
acaaagatgc cagtgtttgt accaagtgtc ccaatgactc atggtctaat gagaaccaca     1920
catcttgttt cctgaaggag atagagtttc tgtcttggac agagcccttt gggatcgcct      1980
tggcattatg ctctgtgctg ggggtattct tgacagcatt cgtgatggga gtgtttatca     2040
aatttcgcaa cacccccaatt gttaaggcca caaacagaga gctatcctac ctcctcctgt     2100
tctcactcat ctgctgtttc tccagttccc tcatcttcat tggtgaaccc caggactgga     2160
catgccgtct acgccagcct gcattcggga taagttttgt tctctgcatc tcctgcatcc     2220
tggtaaaaac taaccgagta cttctagtgt tcgaagccaa gatccccacc agtctccatc     2280
gtaagtggtg ggggctaaac ttgcagttcc tgttagtgtt cctgttcaca tttgtgcaag     2340
tgatgatatg tgtggtctgg ctttacaatg ctcctccggc gagctacagg aaccatgaca     2400
ttgatgagat aattttcatt acatgcaatg agggctctat gatggcgctt ggcttcctaa      2460
ttgggtacac atgcctgctg gcagccatat gcttcttctt tgcatttaaa tcacgaaaac      2520
tgccagagaa ctttactgag gctaagttca tcaccttcag catgctcatc ttcttcatcg     2580
tctggatctc tttcatccct gcctacttca gcacttacgg aaagtttgtg tcggctgtgg     2640
aggtcatcgc catactagcc tccagctttg gcctgctggc ctgtatttc ttcaataaag       2700 tctacatcat cctcttcaaa ccgtccagga acactataga ggaggttcgc tgtagcactg     2760
cggcccattc tttcaaagtg gcagccaagg ccactctgag acacagctca gcctccagga     2820
```

-continued

```
agaggtccag cagtgtgggg ggatcctgtg cctcaactcc ctcctcatcc atcagcctca    2880
agaccaatga caatgactcc ccatcaggtc agcagagaat ccataagcca agagtaagct    2940
ttggaagtgg aacagttact ctgtccttga gctttgagga gtccagaaag aattctatga    3000
agtagggaag tgtcttttgg tgggccgaga gccttgtcaa aacctgagtt ggtgttgcat    3060
tctttgttgg ctgggtagtt ggagcagaaa ttatgatatt aaaagctttg atgtattcag    3120
aatggtgaca cagcataggt ggccaagatt ccattatatt acaataatct gtgttgttca    3180
ttatgaggac atttcaaaat gctgaaaatc atcaaataca taatttactg agttttcttg    3240
ataatcttga aatagaata gcctattcaa gtcatcgttg agcagacatt aattaacaat    3300
gatgtaatac tttccatacc tattttcttt aacaatagat tcacattgtt aaagttcaac    3360
tatgacctgt aaaatacatg aggtataaca ggagacaata aaactatgca tatcctagct    3420
tctgggcctg agtagcaggc agtttactct gggcacgctt ttcatccaaa cttccgaatg    3480
ctgcccccaa tcctagtgag gttaaaggcc cagtgcagtc atatcttttc tctaggcacg    3540
cttttcatcc aaacttccga atgcggctat atcagtctct ttcctactgt cttttcatt    3600 aggccagtgt ttaacaaccc tggtccttaa gtacacacaa cagagcacat ttttgttgtg    3660
gccctggaca atcactcctc actcagctca ttgagggcct gatgattagt tgacaagttg    3720
agtcgggtgt gcttgtccgg ggttgcaata cagatgtgta ctgttggggg tactcgagga    3780
ccaggattgg gaaacattac attaggacta ctgtaggttc ttcaatatgg tgtcatacgg    3840
tcatatggtg tcatatggtg tctggttgtt ttctgcatat gtgtatttca ccaagttact    3900
gcacatgtta gacctataca ctggaataaa cattttttt c                        3941
```

<210> SEQ ID NO 8
<211> LENGTH: 941
<212> TYPE: PRT
<213> ORGANISM: Salmo salar

<400> SEQUENCE: 8

```
Met Arg Phe Tyr Leu Tyr Tyr Leu Val Leu Leu Gly Phe Ser Ser Val
  1               5                  10                  15

Ile Ser Thr Tyr Gly Pro His Gln Arg Ala Gln Lys Thr Gly Asp Ile
             20                  25                  30

Leu Leu Gly Gly Leu Phe Pro Met His Phe Gly Val Thr Ser Lys Asp
         35                  40                  45

Gln Asp Leu Ala Ala Arg Pro Glu Ser Thr Glu Cys Val Arg Tyr Asn
     50                  55                  60

Phe Arg Gly Phe Arg Trp Leu Gln Ala Met Ile Phe Ala Ile Glu Glu
 65                  70                  75                  80

Ile Asn Asn Ser Ser Thr Leu Leu Pro Asn Ile Thr Leu Gly Tyr Arg
                 85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Thr Asp His Ile Pro Ser Thr Ile Ala Val Val Gly Ala
    130                 135                 140

Ser Gly Ser Ala Val Ser Thr Ala Val Ala Asn Leu Leu Gly Leu Phe
145                 150                 155                 160

Tyr Ile Pro Gln Ile Ser Tyr Ala Ser Ser Arg Leu Leu Ser Asn
                165                 170                 175
```

-continued

```
Lys Asn Gln Phe Lys Ser Phe Met Arg Thr Ile Pro Thr Asp Glu His
            180                 185                 190

Gln Ala Thr Ala Met Ala Asp Ile Ile Asp Tyr Phe Gln Trp Asn Trp
            195                 200                 205

Val Ile Ala Val Ala Ser Asp Glu Tyr Gly Arg Pro Gly Ile Glu
            210                 215                 220

Lys Phe Glu Lys Glu Met Glu Glu Arg Asp Ile Cys Ile His Leu Ser
225                 230                 235                 240

Glu Leu Ile Ser Gln Tyr Phe Glu Glu Trp Gln Ile Gln Gly Leu Val
            245                 250                 255

Asp Arg Ile Glu Asn Ser Ser Ala Lys Val Ile Val Phe Ala Ser
            260                 265                 270

Gly Pro Asp Ile Glu Pro Leu Ile Lys Glu Met Val Arg Arg Asn Ile
            275                 280                 285

Thr Asp Arg Ile Trp Leu Ala Ser Glu Ala Trp Ala Thr Thr Ser Leu
            290                 295                 300

Ile Ala Lys Pro Glu Tyr Leu Asp Val Val Gly Thr Ile Gly Phe
305                 310                 315                 320

Ala Leu Arg Ala Gly Glu Ile Pro Gly Phe Lys Asp Phe Leu Gln Glu
            325                 330                 335

Val Thr Pro Lys Lys Ser Ser His Asn Glu Phe Val Arg Glu Phe Trp
            340                 345                 350

Glu Glu Thr Phe Asn Cys Tyr Leu Glu Asp Ser Gln Arg Leu Arg Asp
            355                 360                 365

Ser Glu Asn Gly Ser Thr Ser Phe Arg Pro Leu Cys Thr Gly Glu Glu
            370                 375                 380

Asp Ile Met Gly Ala Glu Thr Pro Tyr Leu Asp Tyr Thr His Leu Arg
385                 390                 395                 400

Ile Ser Tyr Asn Val Tyr Val Ala Val His Ser Ile Ala Gln Ala Leu
            405                 410                 415

Gln Asp Ile Leu Thr Cys Ile Pro Gly Arg Gly Leu Phe Ser Asn Asn
            420                 425                 430

Ser Cys Ala Asp Ile Lys Lys Ile Glu Ala Trp Gln Val Leu Lys Gln
            435                 440                 445

Leu Arg His Leu Asn Phe Ser Asn Ser Met Gly Glu Lys Val His Phe
            450                 455                 460

Asp Glu Asn Ala Asp Pro Ser Gly Asn Tyr Thr Ile Ile Asn Trp His
465                 470                 475                 480

Arg Ser Pro Glu Asp Gly Ser Val Val Phe Glu Glu Val Gly Phe Tyr
            485                 490                 495

Asn Met Arg Ala Lys Arg Gly Val Gln Leu Phe Ile Asp Asn Thr Lys
            500                 505                 510

Ile Leu Trp Asn Gly Tyr Asn Thr Glu Val Pro Phe Ser Asn Cys Ser
            515                 520                 525

Glu Asp Cys Glu Pro Gly Thr Arg Lys Gly Ile Ile Glu Ser Met Pro
530                 535                 540

Thr Cys Cys Phe Glu Cys Thr Cys Ser Glu Gly Glu Tyr Ser Asp
545                 550                 555                 560

His Lys Asp Ala Ser Val Cys Thr Lys Cys Pro Asn Asp Ser Trp Ser
            565                 570                 575

Asn Glu Asn His Thr Ser Cys Phe Leu Lys Glu Ile Glu Phe Leu Ser
            580                 585                 590
```

| Trp | Thr | Glu | Pro | Phe | Gly | Ile | Ala | Leu | Ala | Leu | Cys | Ser | Val | Leu | Gly |
| | | 595 | | | | 600 | | | | 605 | | | | | |

Val Phe Leu Thr Ala Phe Val Met Gly Val Phe Ile Lys Phe Arg Asn
          610                 615                 620

Thr Pro Ile Val Lys Ala Thr Asn Arg Glu Leu Ser Tyr Leu Leu Leu
625                 630                 635                 640

Phe Ser Leu Ile Cys Cys Phe Ser Ser Ser Leu Ile Phe Ile Gly Glu
              645                 650                 655

Pro Gln Asp Trp Thr Cys Arg Leu Arg Gln Pro Ala Phe Gly Ile Ser
          660                 665                 670

Phe Val Leu Cys Ile Ser Cys Ile Leu Val Lys Thr Asn Arg Val Leu
          675                 680                 685

Leu Val Phe Glu Ala Lys Ile Pro Thr Ser Leu His Arg Lys Trp Trp
      690                 695                 700

Gly Leu Asn Leu Gln Phe Leu Leu Val Phe Leu Phe Thr Phe Val Gln
705                 710                 715                 720

Val Met Ile Cys Val Val Trp Leu Tyr Asn Ala Pro Pro Ala Ser Tyr
              725                 730                 735

Arg Asn His Asp Ile Asp Glu Ile Ile Phe Ile Thr Cys Asn Glu Gly
          740                 745                 750

Ser Met Met Ala Leu Gly Phe Leu Ile Gly Tyr Thr Cys Leu Leu Ala
      755                 760                 765

Ala Ile Cys Phe Phe Phe Ala Phe Lys Ser Arg Lys Leu Pro Glu Asn
770                 775                 780

Phe Thr Glu Ala Lys Phe Ile Thr Phe Ser Met Leu Ile Phe Phe Ile
785                 790                 795                 800

Val Trp Ile Ser Phe Ile Pro Ala Tyr Phe Ser Thr Tyr Gly Lys Phe
              805                 810                 815

Val Ser Ala Val Glu Val Ile Ala Ile Leu Ala Ser Ser Phe Gly Leu
          820                 825                 830

Leu Ala Cys Ile Phe Phe Asn Lys Val Tyr Ile Ile Leu Phe Lys Pro
      835                 840                 845

Ser Arg Asn Thr Ile Glu Glu Val Arg Cys Ser Thr Ala Ala His Ser
850                 855                 860

Phe Lys Val Ala Ala Lys Ala Thr Leu Arg His Ser Ser Ala Ser Arg
865                 870                 875                 880

Lys Arg Ser Ser Ser Val Gly Gly Ser Cys Ala Ser Thr Pro Ser Ser
              885                 890                 895

Ser Ile Ser Leu Lys Thr Asn Asp Asn Asp Ser Pro Ser Gly Gln Gln
          900                 905                 910

Arg Ile His Lys Pro Arg Val Ser Phe Gly Ser Gly Thr Val Thr Leu
      915                 920                 925

Ser Leu Ser Phe Glu Glu Ser Arg Lys Asn Ser Met Lys
930                 935                 940

<210> SEQ ID NO 9
<211> LENGTH: 4031
<212> TYPE: DNA
<213> ORGANISM: Salmo salar

<400> SEQUENCE: 9
gttccaacag catattttg ttgtatttgc tttggtttgt ctgaaatcaa gcattatcaa     60
ggattgagca agacaactga gttgtcagac taagaatata cacatttcca gttctctctt    120
taatggactt ctcacactga tgttcttcag atcaagaaca gcatgagtca gaaacaaggc    180

```
gacagccaga gtcactggag gggacaagac tgaggttaac tctgaagtct aatgtgctga    240
gaggacaagg ccctcctgag agctgaacga tgagatttta cctgtattac ctggtgcttt    300
tgggcttcag ttctgtcatc tccacctatg ggcctcatca gagagcacag aagactgggg    360
atattctgct gggcgggctg tttccaatgc actttggtgt tacctccaaa gaccaagacc    420
tggcagcgcg gccagaatcc acagagtgtg ttaggtacaa tttccgggga ttccgttggc    480
ttcaggccat gattttttgca atagaggaga tcaacaacag cagtactctc ctgcccaaca    540
tcacactggg ctacaggatc tttgacacct gcaacaccgt gtccaaggcc ctggaggcta    600
ccctcagttt cgtagcacag aataagattg actctctgaa cttggatgaa ttctgtaact    660
gcactgatca catcccatcg actatagcag tggtgggggc ttctgggtca gcggtctcca    720
ctgctgttgc caatctgttg ggccttttct acatcccaca gatcagctat gcctcttcca    780
gtcgcctact aagcaacaag aaccagttca atccttcat gaggaccatt cccacagatg    840
agcaccaggc cactgccatg gcagatatca tcgactactt ccaatggaat tgggtcattg    900
cagttgcgtc tgatgatgag tatggacgtc cggggattga aaaatttgag aaagagatgg    960
aagaacgaga catttgtatc catctgagtg agctgatctc tcagtacttt gaggagtggc   1020
agatccaagg attggttggc cgtattgaga actcctcagc taaagttata gtcgttttcg   1080
ccagtgggcc tgacattgag cctcttatta aagagatggt cagacggaac atcaccgacc   1140
gcatctggtt ggccagcgag gcttgggcaa ccacctccct catcgccaaa ccagagtacc   1200
ttgatgttgt agttgggacc attggctttg ctctcagagc aggcgaaata cctggcttca   1260
aggacttctt acaagaggtc acaccaaaga aatccagcca caatgaattt gtcagggagt   1320
tttgggagga gacttttaac tgctatctgg aagacagcca gagactgaga gacagtgaga   1380
atgggagcac cagtttcaga ccattgtgta ctggcgagga ggacattatg ggtgcagaga   1440
ccccatatct ggattacact catcttcgta tttcctataa tgtgtatgtt gcagttcact   1500
ccattgcaca ggccctacag gacattctca cctgcattcc tggacgggt cttttttcca   1560 acaactcatg tgcagatata aagaaaatag aagcatggca ggttctcaag cagctcagac   1620
atttaaactt ctcaaacagt atgggagaaa aggtacattt tgatgagaat gctgatccgt   1680 caggaaaacta caccattatc aattggcacc ggtctcctga ggatggttct gttgtgtttg   1740
aagaggtcgg tttctacaac atgcgagcta agagaggagt acaactttc attgataaca   1800 caaagattct atggaatgga tataatactg aggttccatt ctctaactgt agtgaagatt   1860
gtgaaccagg caccagaaag gggatcatag aaagcatgcc aacgtgttgc tttgaatgta   1920
cagaatgctc agaaggagag tatagtgatc acaaagatgc cagtgtttgt accaagtgtc   1980
ccaatgactc atggtctaat gagaaccaca catcttgttt cctgaaggag atagagtttc   2040
tgtcttggac agagcccttt gggatcgcct tggcattatg ctctgtgctg ggggtattct   2100
tgacagcatt cgtgatggga gtgtttatca aatttcgcaa cacccccaatt gttaaggcca   2160 caaacagaga gctatcctac ctcctcctgt tctcactcat ctgctgtttc tccagttccc   2220
tcatcttcat tggtgaaccc caggactgga catgccgtct acgccagcct gcattcggga   2280
taagttttgt tctctgcatc tcctgcatcc tggtaaaaac taaccgagta cttctagtgt   2340
tcgaagccaa gatcccacc agtctccatc gtaagtggtg gggctaaac ttgcagttcc   2400 tgttagtgtt cctgttcaca tttgtgcaag tgatgatatg tgtggtctgg ctttacaatg   2460
ctcctccggc gagctacagg aaccatgaca ttgatgagat aattttcatt acatgcaatg   2520
agggctctat gatggcgctt ggcttcctaa ttgggtacac atgcctgctg gcagccatat   2580
```

```
gcttcttctt tgcatttaaa tcacgaaaac tgccagagaa ctttactgag gctaagttca    2640
tcaccttcag catgctcatc ttcttcatcg tctggatctc tttcatccct gcctacttca    2700
gcacttacgg aaagtttgtg tcggctgtgg aggtcatcgc catactagcc tccagctttg    2760
gcctgctggc ctgtattttc ttcaataaag tctacatcat cctcttcaaa ccgtccagga    2820
acactataga ggaggttcgc tgtagcactg cggcccattc tttcaaagtg gcagccaagg    2880
ccactctgag acacagctca gcctccagga agaggtccag cagtgtgggg ggatcctgtg    2940
cctcaactcc ctcctcatcc atcagcctca agaccaatga caatgactcc ccatcaggtc    3000
agcagagaat ccataagcca agagtaagct ttggaagtgg aacagttact ctgtccttga    3060
gctttgagga gtccagaaag aattctatga gtagggaag tgtcttttgg tgggccgaga     3120
gccttgtcaa aacctgagtt ggtgttgcat tctttgttgg ctgggtagtt ggagcagaaa    3180
ttatgatatt aaaagctttg atgtattcag aatggtgaca cagcataggt ggccaagatt    3240
ccattatatt acaataatct gtgttgttca ttatgaggac atttcaaaat gctgaaaatc    3300
atcaaataca taatttactg agttttcttg ataatcttga aatagaata gcctattcaa     3360 gtcatcgttg agcagacatt aattaacaat gatgtaatac tttccatacc tattttcttt    3420
aacaatagat tcacattgtt aaagttcaac tatgacctgt aaaatacatg aggtataaca    3480
ggagacaata aaactatgca tatcctagct tctgggcctg agtagcaggc agtttactct    3540
gggcacgctt ttcatccaaa cttccgaatg ctgcccccaa tcctagtgag gttaaaggcc    3600
cagtgcagtc atatcttttc tctaggcacg cttttcatcc aaacttccga atgcggctat    3660
atcagtctct ttcctactgt cttttttcatt aggccagtgt ttaacaaccc tggtccttaa    3720
gtacacacaa cagagcacat ttttgttgta gccctggaca atcactcctc actcagctca    3780
ttgagggcct gatgattagt tgacaagttg agtcgggtgt gcttgtccag ggttacgata    3840
cagatgtgta ctgttggggg tgctcgagga ccaggattgg gaaacattac attaggacta    3900
ctgtaggttc ttcaatatgg tgtcatacgg tcatatggtg tcatatggtg tctggttgtt    3960
ttctgcatat gtgtatttca ccaagttact gcacatgtta gacctataca ctggaataaa    4020
catttttttt c                                                          4031
```

<210> SEQ ID NO 10
<211> LENGTH: 941
<212> TYPE: PRT
<213> ORGANISM: Salmo salar

<400> SEQUENCE: 10

Met Arg Phe Tyr Leu Tyr Tyr Leu Val Leu Leu Gly Phe Ser Ser Val
1               5                   10                  15

Ile Ser Thr Tyr Gly Pro His Gln Arg Ala Gln Lys Thr Gly Asp Ile
                20                  25                  30

Leu Leu Gly Gly Leu Phe Pro Met His Phe Gly Val Thr Ser Lys Asp
            35                  40                  45

Gln Asp Leu Ala Ala Arg Pro Glu Ser Thr Glu Cys Val Arg Tyr Asn
        50                  55                  60

Phe Arg Gly Phe Arg Trp Leu Gln Ala Met Ile Phe Ala Ile Glu Glu
65                  70                  75                  80

Ile Asn Asn Ser Ser Thr Leu Leu Pro Asn Ile Thr Leu Gly Tyr Arg
                85                  90                  95

Ile Phe Asp Thr Cys Asn Thr Val Ser Lys Ala Leu Glu Ala Thr Leu
                100                 105                 110

-continued

```
Ser Phe Val Ala Gln Asn Lys Ile Asp Ser Leu Asn Leu Asp Glu Phe
            115                 120                 125

Cys Asn Cys Thr Asp His Ile Pro Ser Thr Ile Ala Val Val Gly Ala
            130                 135                 140

Ser Gly Ser Ala Val Ser Thr Ala Val Ala Asn Leu Leu Gly Leu Phe
145                 150                 155                 160

Tyr Ile Pro Gln Ile Ser Tyr Ala Ser Ser Arg Leu Leu Ser Asn
            165                 170                 175

Lys Asn Gln Phe Lys Ser Phe Met Arg Thr Ile Pro Thr Asp Glu His
            180                 185                 190

Gln Ala Thr Ala Met Ala Asp Ile Ile Asp Tyr Phe Gln Trp Asn Trp
            195                 200                 205

Val Ile Ala Val Ala Ser Asp Asp Glu Tyr Gly Arg Pro Gly Ile Glu
210                 215                 220

Lys Phe Glu Lys Glu Met Glu Glu Arg Asp Ile Cys Ile His Leu Ser
225                 230                 235                 240

Glu Leu Ile Ser Gln Tyr Phe Glu Glu Trp Gln Ile Gln Gly Leu Val
            245                 250                 255

Gly Arg Ile Glu Asn Ser Ser Ala Lys Val Ile Val Phe Ala Ser
            260                 265                 270

Gly Pro Asp Ile Glu Pro Leu Ile Lys Glu Met Val Arg Arg Asn Ile
            275                 280                 285

Thr Asp Arg Ile Trp Leu Ala Ser Glu Ala Trp Ala Thr Thr Ser Leu
            290                 295                 300

Ile Ala Lys Pro Glu Tyr Leu Asp Val Val Gly Thr Ile Gly Phe
305                 310                 315                 320

Ala Leu Arg Ala Gly Glu Ile Pro Gly Phe Lys Asp Phe Leu Gln Glu
            325                 330                 335

Val Thr Pro Lys Lys Ser Ser His Asn Glu Phe Val Arg Glu Phe Trp
            340                 345                 350

Glu Glu Thr Phe Asn Cys Tyr Leu Glu Asp Ser Gln Arg Leu Arg Asp
            355                 360                 365

Ser Glu Asn Gly Ser Thr Ser Phe Arg Pro Leu Cys Thr Gly Glu Glu
            370                 375                 380

Asp Ile Met Gly Ala Glu Thr Pro Tyr Leu Asp Tyr Thr His Leu Arg
385                 390                 395                 400

Ile Ser Tyr Asn Val Tyr Val Ala Val His Ser Ile Ala Gln Ala Leu
            405                 410                 415

Gln Asp Ile Leu Thr Cys Ile Pro Gly Arg Gly Leu Phe Ser Asn Asn
            420                 425                 430

Ser Cys Ala Asp Ile Lys Lys Ile Glu Ala Trp Gln Val Leu Lys Gln
            435                 440                 445

Leu Arg His Leu Asn Phe Ser Asn Ser Met Gly Glu Lys Val His Phe
            450                 455                 460

Asp Glu Asn Ala Asp Pro Ser Gly Asn Tyr Thr Ile Ile Asn Trp His
465                 470                 475                 480

Arg Ser Pro Glu Asp Gly Ser Val Phe Glu Glu Val Gly Phe Tyr
            485                 490                 495

Asn Met Arg Ala Lys Arg Gly Val Gln Leu Phe Ile Asp Asn Thr Lys
            500                 505                 510

Ile Leu Trp Asn Gly Tyr Asn Thr Glu Val Pro Phe Ser Asn Cys Ser
            515                 520                 525
```

-continued

```
Glu Asp Cys Glu Pro Gly Thr Arg Lys Gly Ile Ile Glu Ser Met Pro
        530                 535                 540
Thr Cys Cys Phe Glu Cys Thr Glu Cys Ser Glu Gly Glu Tyr Ser Asp
545                 550                 555                 560
His Lys Asp Ala Ser Val Cys Thr Lys Cys Pro Asn Asp Ser Trp Ser
                565                 570                 575
Asn Glu Asn His Thr Ser Cys Phe Leu Lys Glu Ile Glu Phe Leu Ser
            580                 585                 590
Trp Thr Glu Pro Phe Gly Ile Ala Leu Ala Leu Cys Ser Val Leu Gly
        595                 600                 605
Val Phe Leu Thr Ala Phe Val Met Gly Val Phe Ile Lys Phe Arg Asn
610                 615                 620
Thr Pro Ile Val Lys Ala Thr Asn Arg Glu Leu Ser Tyr Leu Leu Leu
625                 630                 635                 640
Phe Ser Leu Ile Cys Cys Phe Ser Ser Leu Ile Phe Ile Gly Glu
                645                 650                 655
Pro Gln Asp Trp Thr Cys Arg Leu Arg Gln Pro Ala Phe Gly Ile Ser
                660                 665                 670
Phe Val Leu Cys Ile Ser Cys Ile Leu Val Lys Thr Asn Arg Val Leu
            675                 680                 685
Leu Val Phe Glu Ala Lys Ile Pro Thr Ser Leu His Arg Lys Trp Trp
        690                 695                 700
Gly Leu Asn Leu Gln Phe Leu Leu Val Phe Leu Phe Thr Phe Val Gln
705                 710                 715                 720
Val Met Ile Cys Val Val Trp Leu Tyr Asn Ala Pro Pro Ala Ser Tyr
                725                 730                 735
Arg Asn His Asp Ile Asp Glu Ile Ile Phe Ile Thr Cys Asn Glu Gly
            740                 745                 750
Ser Met Met Ala Leu Gly Phe Leu Ile Gly Tyr Thr Cys Leu Leu Ala
        755                 760                 765
Ala Ile Cys Phe Phe Phe Ala Phe Lys Ser Arg Lys Leu Pro Glu Asn
770                 775                 780
Phe Thr Glu Ala Lys Phe Ile Thr Phe Ser Met Leu Ile Phe Phe Ile
785                 790                 795                 800
Val Trp Ile Ser Phe Ile Pro Ala Tyr Phe Ser Thr Tyr Gly Lys Phe
                805                 810                 815
Val Ser Ala Val Glu Val Ile Ala Ile Leu Ala Ser Ser Phe Gly Leu
            820                 825                 830
Leu Ala Cys Ile Phe Phe Asn Lys Val Tyr Ile Ile Leu Phe Lys Pro
        835                 840                 845
Ser Arg Asn Thr Ile Glu Glu Val Arg Cys Ser Thr Ala Ala His Ser
850                 855                 860
Phe Lys Val Ala Ala Lys Ala Thr Leu Arg His Ser Ser Ala Ser Arg
865                 870                 875                 880
Lys Arg Ser Ser Ser Val Gly Gly Ser Cys Ala Ser Thr Pro Ser Ser
                885                 890                 895
Ser Ile Ser Leu Lys Thr Asn Asp Asp Ser Pro Ser Gly Gln Gln
            900                 905                 910
Arg Ile His Lys Pro Arg Val Ser Phe Gly Ser Gly Thr Val Thr Leu
        915                 920                 925
Ser Leu Ser Phe Glu Glu Ser Arg Lys Asn Ser Met Lys
930                 935                 940
```

<210> SEQ ID NO 11
<211> LENGTH: 3824
<212> TYPE: DNA
<213> ORGANISM: Salmo salar

<400> SEQUENCE: 11

| | | | | | |
|---|---|---|---|---|---|
| gttccaacag | catatttttg | ttgtatttgc | tttggtttgt | ctgaaatcaa | gcattatcaa | 60 |
| gatcaagaac | agcatgagtc | agaaacaagg | cgacagccag | agtcactgga | ggggacaaga | 120 |
| ctgaggttaa | ctctgaagtc | taatgtgctg | agaggacaag | gccctcctga | gagctgaacg | 180 |
| atgagatttt | acctgtatta | cctggtgctt | tgggcttca | gttctgtcat | ctccacctat | 240 |
| gggcctcatc | agagagcaca | gaagactggg | gatattctgc | tgggcgggct | gtttccaatg | 300 |
| cactttggtg | ttacctccaa | agaccaagac | ctggcagcgc | ggccagaatc | acagagtgt | 360 |
| gttaggtaca | atttccgggg | attccgttgg | cttcaggcca | tgattttgc | aatagaggag | 420 |
| atcaacaaca | gcagtactct | cctgcccaac | atcacactgg | gctacaggat | ctttgacacc | 480 |
| tgcaacaccg | tgtccaaggc | cctggaggct | accctcagtt | tcgtagcaca | gaataagatt | 540 |
| gactctctga | acttggatga | attctgtaac | tgcactgatc | acatcccatc | gactatagca | 600 |
| gtggtgggg | cttctgggtc | agcggtctcc | actgctgttg | ccaatctgtt | gggccttttc | 660 |
| tacatcccac | agatcagcta | tgcctcttcc | agtcgcctac | taagcaacaa | gaaccagttc | 720 |
| aaatccttca | tgaggaccat | tcccacagat | gagcaccagg | ccactgccat | ggcagatatc | 780 |
| atcgactact | ccaatgtgaa | ttgggtcatt | gcagttgcgt | ctgatgatga | gtatggacgt | 840 |
| ccggggattg | aaaaatttga | gaaagagatg | gaagaacgag | acatttgtat | ccatctgagt | 900 |
| gagctgatct | ctcagtactt | tgaggagtgg | cagatccaag | gattggttga | ccgtattgag | 960 |
| aactcctcag | ctaaagttat | agtcgttttc | gccagtgggc | ctgacattga | gcctcttatt | 1020 |
| aaagagatgg | tcagacggaa | catcaccgac | cgcatctggt | tggccagcga | ggcttgggca | 1080 |
| accacctccc | tcatcgccaa | accagagtac | cttgatgttg | tagttgggac | cattggcttt | 1140 |
| gctctcagag | caggcgaaat | acctggcttc | aaggacttct | acaagaggt | cacaccaaag | 1200 |
| aaatccagcc | acaatgaatt | tgtcaggag | ttttgggagg | agacttttaa | ctgctatctg | 1260 |
| gaagacagcc | agagactgag | agacagtgag | aatgggagca | ccagtttcag | accattgtgt | 1320 |
| actggcgagg | aggacattat | gggtgcagag | accccatatc | tggattacac | tcatcttcgt | 1380 |
| atttcctata | atgtgtatgt | tgcagttcac | tccattgcac | aggccctaca | ggacattctc | 1440 |
| acctgcattc | ctggacgggg | tttttttttcc | aacaactcat | gtgcagatat | aaagaaaata | 1500 |
| gaagcatggc | aggttctcaa | gcagctcaga | catttaaact | tctcaaacag | tatgggagaa | 1560 |
| aaggtacatt | ttgatgagaa | tgctgatccg | tcaggaaact | acaccattat | caattggcac | 1620 |
| cggtctcctg | aggatggttc | tgttgtgttt | gaagaggtcg | gtttctacaa | catgcgagct | 1680 |
| aagagaggag | tacaacttt | cattgataac | acaaagattc | tatggaatgg | atataatact | 1740 |
| gaggttccat | tctctaactg | tagtgaagat | tgtgaaccag | gcaccagaaa | ggggatcata | 1800 |
| gaaagcatgc | caacgtgttg | ctttgaatgt | acagaatgct | cagaaggaga | gtatagtgat | 1860 |
| cacaaagatg | ccagtgtttg | taccaagtgt | cccaatgact | catggtctaa | tgagaaccac | 1920 |
| acatcttgtt | tcctgaagga | gatagagttt | ctgtcttgga | cagagccctt | tgggatcgcc | 1980 |
| ttggcattat | gctctgtgct | ggggtattc | ttgacagcat | tcgtgatggg | agtgtttatc | 2040 |
| aaatttcgca | acccccaat | tgttaaggcc | acaaacagag | agctatccta | cctcctcctg | 2100 |
| ttctcactca | tctgctgttt | ctccagttcc | ctcatcttca | ttggtgaacc | ccaggactgg | 2160 |

-continued

```
acatgccgtc tacgccagcc tgcattcggg ataagttttg ttctctgcat ctcctgcatc    2220
ctggtaaaaa ctaaccgagt acttctagtg ttcgaagcca agatccccac cagtctccat    2280
cgtaagtggt gggggctaaa cttgcagttc ctgttagtgt tcctgttcac atttgtgcaa    2340
gtgatgatat gtgtggtctg gctttacaat gctcctccgg cgagctacag gaaccatgac    2400
attgatgaga taattttcat tacatgcaat gagggctcta tgatggcgct tggcttccta    2460
attgggtaca catgcctgct ggcagccata tgcttcttct ttgcatttaa atcacgaaaa    2520
ctgccagaga actttactga ggctaagttc atcaccttca gcatgctcat cttcttcatc    2580
gtctggatct ctttcatccc tgcctacttc agcacttacg gaaagtttgt gtcggctgtg    2640
gaggtcatcg ccatactagc ctccagcttt ggcctgctgg cctgtatttt cttcaataaa    2700
gtctacatca tccatcagcc tcaagaccaa tgacaatgac tccccatcag gtcagcagag    2760
aatccataag ccaagagtaa gctttggaag tggaacagtt actctgtcct tgagctttga    2820
ggagtccaga aagaattcta tgaagtaggg aagtgtcttt tggtgggccg agagccttgt    2880
caaaacctga gttggtgttg cattctttgt tggctgggta gttggagcag aaattatgat    2940
attaaaagct ttgatgtatt cagaatggtg acacagcata ggtggccaag attccattat    3000
attacaataa tctgtgttgt tcattatgag gacatttcaa aatgctgaaa atcatcaaat    3060
acataattta ctgagttttc ttgataatct tgagaataga atagcctatt caagtcatcg    3120
ttgagcagac attaattaac aatgatgtaa tactttccat acctatttt tttaacaata    3180 gattcacatt gttaaagttc aactatgacc tgtaaaatac atgagtata acaggagaca    3240 ataaaactat gcatatccta gcttctgggc ctgagtagca ggcagtttac tctgggcacg    3300
cttttcatcc aaacttccga atgctgcccc caatcctagt gaggttaaag gcccagtgca    3360
gtcatatctt ttctctaggc acgctttca tccaaacttc cgaatgcggc tatatcagtc    3420
tctttcctac tgtctttttc attaggccag tgtttaacaa ccctggtcct tgagtacaca    3480
caacagggca cattttttgtt gtagccctgg acaatcactc ctcactcagc tcattgaggg    3540
cctgatgatt agttgacaag ttgggtcagg tgtgcttgtc cagggttaca atacagatgt    3600
gtgctgttgg gggtactcga ggaccaggat tgggaaacat tacattagga ctactgtagg    3660
ttcttcaata tggtgtcata cggtcatatg gtgtcatatg gtgtctggtt gttttctgca    3720
tatgtgtatt tcaccaagtt actgcacatg ttagacctat acactggaat aaacattttt    3780
tttcacaatg catccaatga caataaaatc accatatgcc aatg                    3824
```

<210> SEQ ID NO 12
<211> LENGTH: 850
<212> TYPE: PRT
<213> ORGANISM: Salmo salar

<400> SEQUENCE: 12

```
Met Arg Phe Tyr Leu Tyr Tyr Leu Val Leu Leu Gly Phe Ser Ser Val
1               5                   10                  15

Ile Ser Thr Tyr Gly Pro His Gln Arg Ala Gln Lys Thr Gly Asp Ile
            20                  25                  30

Leu Leu Gly Gly Leu Phe Pro Met His Phe Gly Val Thr Ser Lys Asp
        35                  40                  45

Gln Asp Leu Ala Ala Arg Pro Glu Ser Thr Glu Cys Val Arg Tyr Asn
    50                  55                  60

Phe Arg Gly Phe Arg Trp Leu Gln Ala Met Ile Phe Ala Ile Glu Glu
65                  70                  75                  80
```

```
Ile Asn Asn Ser Ser Thr Leu Leu Pro Asn Ile Thr Leu Gly Tyr Arg
                85                  90                  95
Ile Phe Asp Thr Cys Asn Thr Val Ser Lys Ala Leu Glu Ala Thr Leu
            100                 105                 110
Ser Phe Val Ala Gln Asn Lys Ile Asp Ser Leu Asn Leu Asp Glu Phe
        115                 120                 125
Cys Asn Cys Thr Asp His Ile Pro Ser Thr Ile Ala Val Val Gly Ala
130                 135                 140
Ser Gly Ser Ala Val Ser Thr Ala Val Ala Asn Leu Leu Gly Leu Phe
145                 150                 155                 160
Tyr Ile Pro Gln Ile Ser Tyr Ala Ser Ser Arg Leu Leu Ser Asn
                165                 170                 175
Lys Asn Gln Phe Lys Ser Phe Met Arg Thr Ile Pro Thr Asp Glu His
            180                 185                 190
Gln Ala Thr Ala Met Ala Asp Ile Ile Asp Tyr Phe Gln Trp Asn Trp
        195                 200                 205
Val Ile Ala Val Ala Ser Asp Asp Glu Tyr Gly Arg Pro Gly Ile Glu
210                 215                 220
Lys Phe Glu Lys Glu Met Glu Glu Arg Asp Ile Cys Ile His Leu Ser
225                 230                 235                 240
Glu Leu Ile Ser Gln Tyr Phe Glu Glu Trp Gln Ile Gln Gly Leu Val
                245                 250                 255
Asp Arg Ile Glu Asn Ser Ser Ala Lys Val Ile Val Val Phe Ala Ser
            260                 265                 270
Gly Pro Asp Ile Glu Pro Leu Ile Lys Glu Met Val Arg Arg Asn Ile
        275                 280                 285
Thr Asp Arg Ile Trp Leu Ala Ser Glu Ala Trp Ala Thr Thr Ser Leu
290                 295                 300
Ile Ala Lys Pro Glu Tyr Leu Asp Val Val Gly Thr Ile Gly Phe
305                 310                 315                 320
Ala Leu Arg Ala Gly Glu Ile Pro Gly Phe Lys Asp Phe Leu Gln Glu
                325                 330                 335
Val Thr Pro Lys Lys Ser Ser His Asn Glu Phe Val Arg Glu Phe Trp
            340                 345                 350
Glu Glu Thr Phe Asn Cys Tyr Leu Glu Asp Ser Gln Arg Leu Arg Asp
        355                 360                 365
Ser Glu Asn Gly Ser Thr Ser Phe Arg Pro Leu Cys Thr Gly Glu Glu
370                 375                 380
Asp Ile Met Gly Ala Glu Thr Pro Tyr Leu Asp Tyr Thr His Leu Arg
385                 390                 395                 400
Ile Ser Tyr Asn Val Tyr Val Ala Val His Ser Ile Ala Gln Ala Leu
                405                 410                 415
Gln Asp Ile Leu Thr Cys Ile Pro Gly Arg Gly Phe Phe Ser Asn Asn
            420                 425                 430
Ser Cys Ala Asp Ile Lys Lys Ile Glu Ala Trp Gln Val Leu Lys Gln
        435                 440                 445
Leu Arg His Leu Asn Phe Ser Asn Ser Met Gly Glu Lys Val His Phe
450                 455                 460
Asp Glu Asn Ala Asp Pro Ser Gly Asn Tyr Thr Ile Asn Trp His
465                 470                 475                 480
Arg Ser Pro Glu Asp Gly Ser Val Val Phe Glu Glu Val Gly Phe Tyr
                485                 490                 495
```

```
Asn Met Arg Ala Lys Arg Gly Val Gln Leu Phe Ile Asp Asn Thr Lys
            500                 505                 510
Ile Leu Trp Asn Gly Tyr Asn Thr Glu Val Pro Phe Ser Asn Cys Ser
        515                 520                 525
Glu Asp Cys Glu Pro Gly Thr Arg Lys Gly Ile Ile Glu Ser Met Pro
530                 535                 540
Thr Cys Cys Phe Glu Cys Thr Glu Cys Ser Glu Gly Glu Tyr Ser Asp
545                 550                 555                 560
His Lys Asp Ala Ser Val Cys Thr Lys Cys Pro Asn Asp Ser Trp Ser
                565                 570                 575
Asn Glu Asn His Thr Ser Cys Phe Leu Lys Glu Ile Glu Phe Leu Ser
            580                 585                 590
Trp Thr Glu Pro Phe Gly Ile Ala Leu Ala Leu Cys Ser Val Leu Gly
        595                 600                 605
Val Phe Leu Thr Ala Phe Val Met Gly Val Phe Ile Lys Phe Arg Asn
    610                 615                 620
Thr Pro Ile Val Lys Ala Thr Asn Arg Glu Leu Ser Tyr Leu Leu Leu
625                 630                 635                 640
Phe Ser Leu Ile Cys Cys Phe Ser Ser Ser Leu Ile Phe Ile Gly Glu
                645                 650                 655
Pro Gln Asp Trp Thr Cys Arg Leu Arg Gln Pro Ala Phe Gly Ile Ser
            660                 665                 670
Phe Val Leu Cys Ile Ser Cys Ile Leu Val Lys Thr Asn Arg Val Leu
        675                 680                 685
Leu Val Phe Glu Ala Lys Ile Pro Thr Ser Leu His Arg Lys Trp Trp
    690                 695                 700
Gly Leu Asn Leu Gln Phe Leu Leu Val Phe Leu Phe Thr Phe Val Gln
705                 710                 715                 720
Val Met Ile Cys Val Val Trp Leu Tyr Asn Ala Pro Pro Ala Ser Tyr
                725                 730                 735
Arg Asn His Asp Ile Asp Glu Ile Ile Phe Ile Thr Cys Asn Glu Gly
            740                 745                 750
Ser Met Met Ala Leu Gly Phe Leu Ile Gly Tyr Thr Cys Leu Leu Ala
        755                 760                 765
Ala Ile Cys Phe Phe Phe Ala Phe Lys Ser Arg Lys Leu Pro Glu Asn
    770                 775                 780
Phe Thr Glu Ala Lys Phe Ile Thr Phe Ser Met Leu Ile Phe Phe Ile
785                 790                 795                 800
Val Trp Ile Ser Phe Ile Pro Ala Tyr Phe Ser Thr Tyr Gly Lys Phe
                805                 810                 815
Val Ser Ala Val Glu Val Ile Ala Ile Leu Ala Ser Ser Phe Gly Leu
            820                 825                 830
Leu Ala Cys Ile Phe Phe Asn Lys Val Tyr Ile Ile His Gln Pro Gln
        835                 840                 845
Asp Gln
    850

<210> SEQ ID NO 13
<211> LENGTH: 3988
<212> TYPE: DNA
<213> ORGANISM: Salmo salar
```

<400> SEQUENCE: 13

```
gttccaacag catattttg ttgtatttgc tttggtttgt ctgaaatcaa gcattatcaa      60
gatcaagaac agcatgagtc agaaacaagg cgacagccag agtcactgga ggggacaaga    120
ctgaggttaa ctctgaagtc taatgtgctg agaggacaag gccctcctga gagctgaacg    180
atgagatttt acctgtatta cctggtgctt ttgggcttca gttctgtcat ctccacctat    240
gggcctcatc agagagcaca gaagactggg gatattctgc tgggcgggct gtttccaatg    300
cactttggtg ttacctccaa agaccaagac ctggcagcgc ggccagaatc cacagagtgt    360
gttaggtaca atttccgggg attccgttgg cttcaggcca tgattttgc aatagaggag     420
atcaacaaca gcagtactct cctgcccaac atcacactgg ctacaggat cttgacacc      480
tgcaacaccg tgtccaaggc cctggaggct accctcagtt tcgtagcaca gaataagatt    540
gactctctga acttggatga attctgtaac tgcactgatc acatcccatc gactatagca    600
gtggtggggg cttctgggtc agcggtctcc actgctgttg ccaatctgtt gggccttttc    660
tacatcccac agatcagcta tgcctcttcc agtcgcctac taagcaacaa gaaccagttc    720
aaatccttca tgaggaccat tcccacagat gagcaccagg ccactgccat ggcagatatc    780
atcgactact ccaatggaa ttgggtcatt gcagttgcgt ctgatgatga gtatggacgt     840
ccggggattg aaaaatttga gaaagagatg gaagaacgag acatttgtat ccatctgagt    900
gagctgatct ctcagtactt tgaggagtgg cagatccaag gattggttga ccgtattgag    960
aactcctcag ctaaagttat agtcgttttc gccagtgggc ctgacattga gcctcttatt   1020
aaagagatgg tcagacggaa catcaccgac cgcatctggt tggccagcga ggcttgggca   1080
accacctccc tcatcgccaa accagagtac cttgatgttg tagttgggac cattggcttt   1140
gctctcagag caggcgaaat acctggcttc aaggacttct acaagaggt cacaccaaag    1200
aaatccagcc acaatgaatt tgtcaggag ttttgggagg agactttaa ctgctatctg     1260
gaagacagcc agagactgag agacagtgag aatgggagca ccagtttcag accattgtgt   1320
actggcgagg aggacattat gggtgcagag acccccatatc tggattacac tcatcttcgt  1380
atttcctata atgtgtatgt tgcagttcac tccattgcac aggccctaca ggacattctc   1440
acctgcattc ctggacgggg tctttttttcc aacaactcat gtgcagatat aaagaaaata  1500
gaagcatggc aggttctcaa gcagctcaga catttaaact tctcaaacag tatgggagaa   1560
aaggtacatt ttgatgagaa tgctgatccg tcaggaaact acaccattat caattggcac   1620
cggtctcctg aggatggttc tgttgtgtt gaagaggtcg gtttctacaa catgcgagct    1680
aagagaggag tacaactttt cattgataac acaaagattc tatggaatgg atataatact   1740
gaggttccat tctctaactg tagtgaagat tgtgaaccag gcaccagaaa ggggatcata   1800
gaaagcatgc caacgtgttg ctttgaatgt acagaatgct cagaaggaga gtatagtgat   1860
cacaaagatg ccagtgtttg taccaagtgt cccaatgact catggtctaa tgagaaccac   1920
acatcttgtt tcctgaagga gatagagttt ctgtcttgga cagagccctt gggatcgcc   1980
ttggcattat gctctgtgct gggggtattc ttgacagcat tcgtgatggg agtgtttatc   2040
aaatttcgca acacccccaat tgttaaggcc acaaacagag agctatccta cctcctcctg   2100
ttctcactca tctgctgttt ctccagttcc ctcatcttca ttggtgaacc ccaggactgg   2160
acatgccgtc tacgccagcc tgcattcggg ataagttttg ttctctgcat ctcctgcatc   2220
ctggtaaaaa ctaaccgagt acttctagtg ttcgaagcca agatccccac cagtctccat   2280
cgtaagtggt gggggctaaa cttgcagttc ctgttagtgt tcctgttcac atttgtgcaa   2340
```

-continued

```
gtgatgatat gtgtggtctg gctttacaat gctcctccgg cgagctacag gaacctatgac    2400 attgatgaga taattttcat tacatgcaat gagggctcta tgatggcgct tggcttccta    2460
attgggtaca catgcctgct ggcagccata tgcttcttct ttgcatttaa atcacgaaaa    2520
ctgccagaga actttactga ggctaagttc atcaccttca gcatgctcat cttcttcatc    2580
gtctggatct ctttcatccc tgcctacttc agcacttacg gaaagtttgt gtcggctgtg    2640
gaggtcatcg ccatactagc ctccagcttt ggcctgctgg cctgtatttt cttcaataaa    2700
gtctacatca tcctcttcaa accgtccagg aacactatag aggaggttcg ctgtagcact    2760
gcggcccatt ctttcaaagt ggcagccaag gccactctga cacagctc agcctccagg    2820 aagaggtcca gcagtgtggg gggatcctgt gcctcaactc cctcctcatc catcagcctc    2880
aagaccaatg acaatgactc cccatcaggt cagcagagaa tccataagcc aagagtaagc    2940
tttggaagtg gaacagttac tctgtccttg agctttgagg agtccagaaa gaattctatg    3000
aagtagggaa gtgtcttttg gtgggccgag agccttgtca aaacctgagt tggtgttgca    3060
ttctttgttg gctgggtagt tggagcagaa attatgatat taaaagcttt gatgtattca    3120
gaatggtgac acagcatagg tggccaagat tccattatat tacaataatc tgtgttgttc    3180
attatgagga catttcaaaa tgctgaaaat catcaaatac ataatttact gagttttctt    3240
gataatcttg agaatagaat agcctattca agtcatcgtt gagcagacat taattaacaa    3300
tgatgtaata ctttccatac ctatttctt taacaataga ttcacattgt taaagttcaa    3360
ctatgacctg taaaatacat gaggtataac aggagacaaa aaaactatgc atatcctagc    3420
ttctgggcct gagtagcagg cagtttactc tgggcacgct tttcatccaa acttccgaat    3480 gctgcccca atcctagtga ggttaaaggc ccagtgcagt catatctttt ctctaggcac    3540
gcttttcatc caaacttccg aatgcggcta tatcagtctc tttcctactg tcttttcat    3600 taggccagtt tttaacaacc ctggtcctta agtgcacaca acagggcaca tttttgttgt    3660
ggccctggac aatcactcct cactcagctc attgagggcc tgatgattag ttgacaagtt    3720
gagtcaggtg tgcttgtccg gggttgcaat acagatgtgt actgttgggg gtgctcgagg    3780
accaggattg ggaaacatta cattaggact actgtaggtt cttcaatatg gtgtcatacg    3840
gtcatatggt gtcatatggt gtctggttgt tttctgcata tgtgtatttc accaagttac    3900
tgcacatgtt agacctatac actggaataa acatttttt tcacaatgca tccaatgaca    3960
ataaaatcac catatgccaa tgaaaaaa                                       3988
```

<210> SEQ ID NO 14
<211> LENGTH: 941
<212> TYPE: PRT
<213> ORGANISM: Salmo salar

<400> SEQUENCE: 14

```
Met Arg Phe Tyr Leu Tyr Tyr Leu Val Leu Leu Gly Phe Ser Ser Val
1               5                   10                  15

Ile Ser Thr Tyr Gly Pro His Gln Arg Ala Gln Lys Thr Gly Asp Ile
            20                  25                  30

Leu Leu Gly Gly Leu Phe Pro Met His Phe Gly Val Thr Ser Lys Asp
        35                  40                  45

Gln Asp Leu Ala Ala Arg Pro Glu Ser Thr Glu Cys Val Arg Tyr Asn
    50                  55                  60

Phe Arg Gly Phe Arg Trp Leu Gln Ala Met Ile Phe Ala Ile Glu Glu
65                  70                  75                  80
```

-continued

```
Ile Asn Asn Ser Ser Thr Leu Leu Pro Asn Ile Thr Leu Gly Tyr Arg
                85                  90                  95
Ile Phe Asp Thr Cys Asn Thr Val Ser Lys Ala Leu Glu Ala Thr Leu
            100                 105                 110
Ser Phe Val Ala Gln Asn Lys Ile Asp Ser Leu Asn Leu Asp Glu Phe
        115                 120                 125
Cys Asn Cys Thr Asp His Ile Pro Ser Thr Ile Ala Val Val Gly Ala
    130                 135                 140
Ser Gly Ser Ala Val Ser Thr Ala Val Ala Asn Leu Leu Gly Leu Phe
145                 150                 155                 160
Tyr Ile Pro Gln Ile Ser Tyr Ala Ser Ser Arg Leu Leu Ser Asn
                165                 170                 175
Lys Asn Gln Phe Lys Ser Phe Met Arg Thr Ile Pro Thr Asp Glu His
            180                 185                 190
Gln Ala Thr Ala Met Ala Asp Ile Ile Asp Tyr Phe Gln Trp Asn Trp
        195                 200                 205
Val Ile Ala Val Ala Ser Asp Asp Glu Tyr Gly Arg Pro Gly Ile Glu
    210                 215                 220
Lys Phe Glu Lys Glu Met Glu Glu Arg Asp Ile Cys Ile His Leu Ser
225                 230                 235                 240
Glu Leu Ile Ser Gln Tyr Phe Glu Glu Trp Gln Ile Gln Gly Leu Val
                245                 250                 255
Asp Arg Ile Glu Asn Ser Ser Ala Lys Val Ile Val Phe Ala Ser
            260                 265                 270
Gly Pro Asp Ile Glu Pro Leu Ile Lys Glu Met Val Arg Arg Asn Ile
        275                 280                 285
Thr Asp Arg Ile Trp Leu Ala Ser Glu Ala Trp Ala Thr Thr Ser Leu
    290                 295                 300
Ile Ala Lys Pro Glu Tyr Leu Asp Val Val Gly Thr Ile Gly Phe
305                 310                 315                 320
Ala Leu Arg Ala Gly Glu Ile Pro Gly Phe Lys Asp Phe Leu Gln Glu
                325                 330                 335
Val Thr Pro Lys Lys Ser Ser His Asn Glu Phe Val Arg Glu Phe Trp
            340                 345                 350
Glu Glu Thr Phe Asn Cys Tyr Leu Glu Asp Ser Gln Arg Leu Arg Asp
        355                 360                 365
Ser Glu Asn Gly Ser Thr Ser Phe Arg Pro Leu Cys Thr Gly Glu Glu
    370                 375                 380
Asp Ile Met Gly Ala Glu Thr Pro Tyr Leu Asp Tyr Thr His Leu Arg
385                 390                 395                 400
Ile Ser Tyr Asn Val Tyr Val Ala Val His Ser Ile Ala Gln Ala Leu
                405                 410                 415
Gln Asp Ile Leu Thr Cys Ile Pro Gly Arg Gly Leu Phe Ser Asn Asn
            420                 425                 430
Ser Cys Ala Asp Ile Lys Lys Ile Glu Ala Trp Gln Val Leu Lys Gln
        435                 440                 445
Leu Arg His Leu Asn Phe Ser Asn Ser Met Gly Glu Lys Val His Phe
    450                 455                 460
Asp Glu Asn Ala Asp Pro Ser Gly Asn Tyr Thr Ile Asn Trp His
465                 470                 475                 480
Arg Ser Pro Glu Asp Gly Ser Val Val Phe Glu Glu Val Gly Phe Tyr
                485                 490                 495
```

```
Asn Met Arg Ala Lys Arg Gly Val Gln Leu Phe Ile Asp Asn Thr Lys
            500                 505                 510
Ile Leu Trp Asn Gly Tyr Asn Thr Glu Val Pro Phe Ser Asn Cys Ser
            515                 520                 525
Glu Asp Cys Glu Pro Gly Thr Arg Lys Gly Ile Ile Glu Ser Met Pro
            530                 535                 540
Thr Cys Cys Phe Glu Cys Thr Glu Cys Ser Glu Gly Glu Tyr Ser Asp
545                 550                 555                 560
His Lys Asp Ala Ser Val Cys Thr Lys Cys Pro Asn Asp Ser Trp Ser
            565                 570                 575
Asn Glu Asn His Thr Ser Cys Phe Leu Lys Glu Ile Glu Phe Leu Ser
            580                 585                 590
Trp Thr Glu Pro Phe Gly Ile Ala Leu Ala Leu Cys Ser Val Leu Gly
            595                 600                 605
Val Phe Leu Thr Ala Phe Val Met Gly Val Phe Ile Lys Phe Arg Asn
            610                 615                 620
Thr Pro Ile Val Lys Ala Thr Asn Arg Glu Leu Ser Tyr Leu Leu Leu
625                 630                 635                 640
Phe Ser Leu Ile Cys Cys Phe Ser Ser Ser Leu Ile Phe Ile Gly Glu
            645                 650                 655
Pro Gln Asp Trp Thr Cys Arg Leu Arg Gln Pro Ala Phe Gly Ile Ser
            660                 665                 670
Phe Val Leu Cys Ile Ser Cys Ile Leu Val Lys Thr Asn Arg Val Leu
            675                 680                 685
Leu Val Phe Glu Ala Lys Ile Pro Thr Ser Leu His Arg Lys Trp Trp
            690                 695                 700
Gly Leu Asn Leu Gln Phe Leu Leu Val Phe Leu Phe Thr Phe Val Gln
705                 710                 715                 720
Val Met Ile Cys Val Val Trp Leu Tyr Asn Ala Pro Pro Ala Ser Tyr
            725                 730                 735
Arg Asn His Asp Ile Asp Glu Ile Ile Phe Ile Thr Cys Asn Glu Gly
            740                 745                 750
Ser Met Met Ala Leu Gly Phe Leu Ile Gly Tyr Thr Cys Leu Leu Ala
            755                 760                 765
Ala Ile Cys Phe Phe Phe Ala Phe Lys Ser Arg Lys Leu Pro Glu Asn
            770                 775                 780
Phe Thr Glu Ala Lys Phe Ile Thr Phe Ser Met Leu Ile Phe Phe Ile
785                 790                 795                 800
Val Trp Ile Ser Phe Ile Pro Ala Tyr Phe Ser Thr Tyr Gly Lys Phe
            805                 810                 815
Val Ser Ala Val Glu Val Ile Ala Ile Leu Ala Ser Ser Phe Gly Leu
            820                 825                 830
Leu Ala Cys Ile Phe Phe Asn Lys Val Tyr Ile Ile Leu Phe Lys Pro
            835                 840                 845
Ser Arg Asn Thr Ile Glu Glu Val Arg Cys Ser Thr Ala Ala His Ser
850                 855                 860
Phe Lys Val Ala Ala Lys Ala Thr Leu Arg His Ser Ser Ala Ser Arg
865                 870                 875                 880
Lys Arg Ser Ser Ser Val Gly Gly Ser Cys Ala Ser Thr Pro Ser Ser
            885                 890                 895
Ser Ile Ser Leu Lys Thr Asn Asp Asn Asp Ser Pro Ser Gly Gln Gln
            900                 905                 910
```

Arg Ile His Lys Pro Arg Val Ser Phe Gly Ser Gly Thr Val Thr Leu
        915                 920                 925

Ser Leu Ser Phe Glu Glu Ser Arg Lys Asn Ser Met Lys
        930                 935                 940

<210> SEQ ID NO 15
<211> LENGTH: 28
<212> TYPE: DNA
<213> ORGANISM: Artificial Sequence
<220> FEATURE:
<223> OTHER INFORMATION: primer

<400> SEQUENCE: 15
tgtcktggac ggagccctty ggratcgc                                       28

<210> SEQ ID NO 16
<211> LENGTH: 31
<212> TYPE: DNA
<213> ORGANISM: Artificial Sequence
<220> FEATURE:
<223> OTHER INFORMATION: primer

<400> SEQUENCE: 16
ggckggratg aargakatcc aracratgaa g                                   31

<210> SEQ ID NO 17
<211> LENGTH: 16
<212> TYPE: PRT
<213> ORGANISM: Artificial Sequence
<220> FEATURE:
<223> OTHER INFORMATION: peptide for Sal-1 antibody production

<400> SEQUENCE: 17

Cys Thr Asn Asp Asn Asp Ser Pro Ser Gly Gln Gln Arg Ile His Lys
1               5                   10                  15

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
caagcattat caagatcaag                                                20

<210> SEQ ID NO 19
<211> LENGTH: 17
<212> TYPE: DNA
<213> ORGANISM: Artificial Sequence
<220> FEATURE:
<223> OTHER INFORMATION: primer

<400> SEQUENCE: 19
ctcagagtgg ccttggc                                                   17

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
cagttctctc tttaatggac                                                20

```
<210> SEQ ID NO 21
<211> LENGTH: 17
<212> TYPE: DNA
<213> ORGANISM: Artificial Sequence
<220> FEATURE:
<223> OTHER INFORMATION: primer

<400> SEQUENCE: 21
ctcagagtgg ccttggc                                                    17

<210> SEQ ID NO 22
<211> LENGTH: 21
<212> TYPE: DNA
<213> ORGANISM: Artificial Sequence
<220> FEATURE:
<223> OTHER INFORMATION: primer

<400> SEQUENCE: 22
agtctacatc atccatcagc c                                               21

<210> SEQ ID NO 23
<211> LENGTH: 21
<212> TYPE: DNA
<213> ORGANISM: Artificial Sequence
<220> FEATURE:
<223> OTHER INFORMATION: primer

<400> SEQUENCE: 23
gattttattg tcattggatg c                                               21

<210> SEQ ID NO 24
<211> LENGTH: 19
<212> TYPE: DNA
<213> ORGANISM: Artificial Sequence
<220> FEATURE:
<223> OTHER INFORMATION: primer

<400> SEQUENCE: 24
tggaagatga aatcgccgc                                                  19

<210> SEQ ID NO 25
<211> LENGTH: 22
<212> TYPE: DNA
<213> ORGANISM: Artificial Sequence
<220> FEATURE:
<223> OTHER INFORMATION: primer

<400> SEQUENCE: 25
gtggtggtga aactgtaacc gc                                              22

<210> SEQ ID NO 26
<211> LENGTH: 23
<212> TYPE: PRT
<213> ORGANISM: Artificial Sequence
<220> FEATURE:
<223> OTHER INFORMATION: peptide for 4641 antibody production

<400> SEQUENCE: 26

Ala Asp Asp Asp Tyr Gly Arg Pro Gly Ile Glu Lys Phe Arg Glu Glu
1               5                   10                  15

Ala Glu Glu Arg Asp Ile Cys
            20
```

```
<210> SEQ ID NO 27
<211> LENGTH: 22
<212> TYPE: PRT
<213> ORGANISM: Artificial Sequence
<220> FEATURE:
<223> OTHER INFORMATION: peptide for 4641 antibody production

<400> SEQUENCE: 27

Asp Asp Tyr Gly Arg Pro Gly Ile Glu Lys Phe Arg Glu Glu Ala Glu
1               5                   10                  15

Glu Arg Asp Ile Cys Ile
            20

<210> SEQ ID NO 28
<211> LENGTH: 17
<212> TYPE: PRT
<213> ORGANISM: Artificial Sequence
<220> FEATURE:
<223> OTHER INFORMATION: peptide for SKCaR antibody production

<400> SEQUENCE: 28

Ala Arg Ser Arg Asn Ser Ala Asp Gly Arg Ser Gly Asp Asp Leu Pro
1               5                   10                  15

Cys

<210> SEQ ID NO 29
<211> LENGTH: 18
<212> TYPE: PRT
<213> ORGANISM: Artificial Sequence
<220> FEATURE:
<223> OTHER INFORMATION: peptide for Sal-ADD antibody production

<400> SEQUENCE: 29

Cys Ser Asp Asp Glu Tyr Gly Arg Pro Gly Ile Glu Lys Phe Glu Lys
1               5                   10                  15

Glu Met

<210> SEQ ID NO 30
<211> LENGTH: 1078
<212> TYPE: PRT
<213> ORGANISM: Homo sapiens

<400> SEQUENCE: 30

Met Ala Phe Tyr Ser Cys Cys Trp Val Leu Leu Ala Leu Thr Trp His
1               5                   10                  15

Thr Ser Ala Tyr Ser Pro Ser Gln Pro Ala Gln Lys Lys Gly Asp Ile
            20                  25                  30

Ile Leu Gly Gly Leu Phe Pro Ile His Phe Gly Val Ala Ala Lys Asp
        35                  40                  45

Gln Asp Leu Lys Ser Arg Pro Glu Ser Val Glu Cys Ile Arg Tyr Asn
    50                  55                  60

Phe Arg Gly Phe Arg Trp Leu Gln Ala Met Ile Phe Ala Ile Glu Glu
65                  70                  75                  80

Ile Asn Ser Ser Pro Ala Leu Leu Pro Asn Leu Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
    130                 135                 140
```

```
Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Ser Arg Leu Leu Ser Asn
                165                 170                 175

Lys Asn Gln Phe Lys Ser Phe Leu Arg Thr Ile Pro Asn Asp Glu His
            180                 185                 190

Cys Ala Thr Ala Met Ala Asp Ile Ile Glu Tyr Phe Arg Trp Asn Trp
        195                 200                 205

Val Gly Thr Ile Ala Ala Asp Asp Tyr Gly Arg Pro Gly Ile Glu
    210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Ile Gln Met Val Val
                245                 250                 255

Glu Val Ile Gln Asn Ser Thr Ala Lys Val Ile Val Phe Ser Ser
                260                 265                 270

Gly Pro Asp Leu Glu Pro Leu Ile Lys Glu Ile Val Pro Arg Asn Ile
    275                 280                 285

Thr Gly Lys Ile Trp Leu Ala Ser Glu Ala Trp Ala Ser Ser Ser Leu
    290                 295                 300

Ile Ala Met Pro Gln Tyr Phe His Val Val Gly Gly Thr Ile Gly Phe
305                 310                 315                 320

Ala Leu Lys Ala Gly Gln Ile Pro Gly Phe Arg Glu Phe Leu Lys Lys
                325                 330                 335

Val His Pro Pro Lys Ser Val Asn Asn Gly Phe Ala Lys Glu Phe Trp
            340                 345                 350

Glu Glu Thr Phe Met Cys His Leu Gln Glu Gly Ala Lys Gly Pro Leu
        355                 360                 365

Pro Val Asp Thr Phe Leu Ala Gly His Glu Glu Ser Gly Asp Arg Phe
    370                 375                 380

Ser Asn Ser Ser Thr Ala Phe Pro Pro Leu Cys Thr Gly Asp Glu Asn
385                 390                 395                 400

Ile Ser Ser Val Glu Thr Pro Tyr Ile Asp Tyr Thr Asn Leu Arg Ile
                405                 410                 415

Ser Tyr Asn Val Tyr Leu Ala Val Tyr Ser Ile Ala Asn Ala Leu Gln
            420                 425                 430

Asp Ile Tyr Thr Cys Leu Pro Gly Arg Gly Leu Phe Thr Asn Gly Ser
        435                 440                 445

Cys Ala Asp Ile Lys Lys Val Glu Ala Trp Gln Val Leu Lys His Leu
450                 455                 460

Arg Asn Leu Asn Phe Thr Asn Asn Met Gly Glu Gln Val Thr Phe Asp
465                 470                 475                 480

Glu Cys Gly Asp Leu Val Gly Asn Tyr Ser Ile Ile Asn Trp His Leu
                485                 490                 495

Ser Pro Glu Asp Gly Ser Ile Val Phe Lys Glu Val Gly Tyr Tyr Asn
            500                 505                 510

Val Tyr Ala Lys Lys Gly Glu Arg Leu Phe Ile Asn Glu Lys Ile
        515                 520                 525

Leu Trp Ser Gly Phe Ser Arg Glu Val Pro Phe Ser Asn Cys Ser Arg
    530                 535                 540

Asp Cys Leu Ala Gly Thr Arg Lys Gly Ile Ile Glu Gly Glu Pro Thr
545                 550                 555                 560
```

```
Cys Cys Phe Glu Cys Val Glu Cys Pro Asp Gly Glu Tyr Ser Asp Glu
            565                 570                 575

Thr Asp Ala Ser Ala Cys Asn Lys Cys Pro Asp Asp Phe Trp Ser Asn
            580                 585                 590

Glu Asn His Thr Ser Cys Ile Ala Lys Glu Ile Glu Phe Leu Ser Trp
            595                 600                 605

Thr Glu Pro Phe Gly Ile Ala Leu Thr Leu Phe Ala Val Leu Gly Ile
            610                 615                 620

Ser Leu Thr Ala Phe Val Leu Gly Val Phe Ile Lys Phe Arg Asn Thr
625                 630                 635                 640

Pro Ile Val Lys Ala Thr Asn Arg Glu Leu Ser Tyr Leu Leu Leu Phe
                645                 650                 655

Ser Leu Leu Cys Cys Phe Ser Ser Ser Leu Phe Phe Ile Gly Glu Pro
                660                 665                 670

Gln Asp Trp Thr Cys Arg Leu Arg Gln Pro Ala Phe Gly Ile Ser Phe
                675                 680                 685

Val Leu Cys Ile Ser Cys Ile Leu Val Lys Thr Asn Arg Val Leu Leu
            690                 695                 700

Val Phe Glu Ala Lys Ile Pro Thr Ser Phe Met Phe Lys Trp Trp Gly
705                 710                 715                 720

Leu Asn Leu Gln Phe Leu Leu Val Phe Leu Cys Thr Phe Asn Gln Ile
                725                 730                 735

Val Ile Cys Val Ile Trp Leu Tyr Thr Ala Pro Pro Ser Ser Tyr Arg
            740                 745                 750

Asn Gln Glu Leu Glu Asp Glu Ile Ile Phe Ile Thr Cys Asn Glu Gly
            755                 760                 765

Ser Leu Met Ala Leu Gly Phe Leu Ile Gly Tyr Thr Cys Leu Leu Ala
770                 775                 780

Ala Ile Cys Phe Phe Phe Ala Phe Lys Ser Arg Lys Leu Pro Glu Asn
785                 790                 795                 800

Phe Asn Glu Ala Lys Phe Ile Thr Phe Ser Met Leu Ile Phe Phe Ile
                805                 810                 815

Val Trp Ile Ser Phe Ile Pro Ala Tyr Ala Ser Thr Tyr Gly Lys Phe
                820                 825                 830

Val Ser Ala Val Glu Val Ile Ala Ile Leu Ala Ala Ser Phe Gly Leu
            835                 840                 845

Leu Ala Cys Ile Phe Phe Asn Lys Ile Tyr Ile Ile Leu Phe Lys Pro
            850                 855                 860

Ser Arg Asn Thr Ile Glu Glu Val Arg Cys Ser Thr Ala Ala Asn Ala
865                 870                 875                 880

Phe Lys Val Ala Ala Arg Ala Thr Leu Arg Arg Ser Asn Val Ser Arg
                885                 890                 895

Lys Arg Ser Ser Ser Leu Gly Gly Ser Thr Gly Ser Thr Pro Ser Ser
                900                 905                 910

Ser Ile Ser Ser Lys Ser Asn Ser Glu Asp Pro Phe Pro Arg Pro Glu
            915                 920                 925

Arg Gln Lys Gln Gln Gln Pro Leu Ala Leu Thr Gln Gln Glu Gln Gln
930                 935                 940

Gln Gln Pro Leu Thr Leu Pro Gln Gln Arg Ser Gln Gln Gln Pro
945                 950                 955                 960

Arg Cys Lys Gln Lys Val Ile Phe Gly Ser Gly Thr Val Thr Phe Ser
                965                 970                 975
```

```
Leu Ser Phe Asp Glu Pro Gln Lys Asn Ala Met Ala Asn Arg Asn Ser
            980                 985                 990

Thr Asn Gln Asn Ser Leu Glu Ala  Gln Lys Ser Ser Asp Thr Leu Thr
            995                 1000                1005

Ala Asn  Gln Pro Leu Leu Pro  Leu Gln Cys Gly Glu  Thr Asp Leu
    1010             1015                 1020

Asp Leu  Thr Val Gln Glu  Thr  Gly Leu Gln Gly Pro  Val Gly Gly
    1025                 1030                1035

Asp Gln  Arg Pro Glu Val Glu  Asp Pro Glu Glu Leu  Ser Pro Ala
    1040                 1045                1050

Leu Val  Val Ser Ser Ser Gln  Ser Phe Val Ile Ser  Gly Gly Gly
    1055                 1060                1065

Ser Thr  Val Thr Glu Asn Val  Val Asn Ser
    1070                 1075

<210> SEQ ID NO 31
<211> LENGTH: 3606
<212> TYPE: DNA
<213> ORGANISM: Fugu rubripes

<400> SEQUENCE: 31
taatctcagg agagtttcgt ttccagagga aaccgaactt cttaaacgca ggtaggttgc      60
aagcgtcata tttcacagtg gaatcaaagg caagaaaacg ggtcatttca agagaaattt    120
gtcctccttt ctcccagtcg cagcaggaaa acatgagtc tcctgaaaaa atgcagcagg     180
cagactgatg ggacaagata gagggaccg tatcaccta aaaaaattat ttttccaaaa      240
aaatccatta gaaagggcag gatggtgcga ctggtgctgc attatctcat acttctgggg    300
tccggttatg tcatttcaac atatgggcct aatcagagag cacagatgac tggcgatatt    360
ctgctgggag acttttccc catacacttt ggcatttctt ccaaagacga aaacctcgct     420
gcccgaccgg aatccacaaa gtgtgtcagg taaaactcag cacttcatat gtaactgcat    480
gtaaatgctt aaatcacgtg tcagcactgt tgagcacttt caaaccttct ttccgcaggt    540
tcaatttccg tggtttccgc tggctgcagg ccatggtttt cgccatcgag agatcaaca    600 acagcagcag cctcctgccc aacatcaccc tcggctacag gatcttcgac acgtgcaaca    660
cggtttcaaa agccctggag gctacgctga gcttcgtggc ccaaaacaag atcgactccc    720
tgaatttgga tgaattttgc aactgcacgg atcacatcc ggcaaccatc gcggtggtgg     780
gagcggcagg gtctgcggtc tctacggcag tcgcaaacct gctgagtctc ttttatattc    840
ctcaggtgag tgacggaatt atctttacac tccagttaaa accttaaagt caccgcaatc    900
ctctatcaca ccagatcagc tatgcgtcct ccagccgctt gctgagcaac aagaatcaat    960
acaagtcctt catgagaacc atccctacag atgagcacca ggccacagcc atggccgacg   1020
tcatcgagta cttccagtgg aactgggtca ttgccgtggc ctctgatgac gattatgggc   1080
ggcctgggat agaaaagttt gagaaggaga tggaagagcg agacatttgc atccatctga   1140
acgaactcat ctctcagtac ttcgaggact gtgaaatcaa agctctcgtg gacagaattg   1200
aaaactccac agccaaagtc atcgttgtgt ttgccagcgg ccctgatatc gagcctctga   1260
tcaaagaaat ggtgaggagg aacatcaccg atcggatctg gttagccagt gaagcgtggg   1320
caagctcctc cctcatcgct aaaccagaat atctcgatgt tgtggagggc acaatcggct   1380
ttgttttgaa agcagggaac atacctggtt caggagagtt cttacagcag gtccagccaa   1440
agagaggcag ccacaacgaa tttgtcaggg agttttggga ggaaaccttc aactgttacc   1500
```

```
tggaggacag cccgagactg caagaaagtg agaatggtag cgacagtttc aggccgcttt    1560
gcaccagcga ggaagacatc acgagtgtgg agacccgta cctcgaccac acacacctcc    1620
gtatctccta caatgtctat gttgcagttt actccatcgc tcacgccctc caggacatac    1680
tctcctgcac tcctggacat ggactctttg ctaacaactc ttgcgcggat ataaagaaaa    1740
tggaagcatg gcaggtaaaa actgctcttt tgcccacaat gttctacttt gtcagcctca    1800
aagggtcaaa tgtgtttgca ggtcctgaag cagctcagac atttgaacta caccaacagc    1860 atggggaaa aggttcattt tgatgagaac gcagacatgg aagcaaacta caccatcata     1920
aactggcacc ggtctgctga ggacggctca gtggcgttca gggaggtggg ctactaccac    1980
atgcacgcca ggcggggagc caaactgctc attgataaca caaagatgat gtggaatgca    2040
tacagttcag aggtcagtca tcttcagggc aatttcctgt tgtcctgat gtacagtgtc      2100 tctgttcctg acatcattta cgtggcaggg acaccaaatg tggtgtcatg tgagcatcta    2160
agggtttgca tctgttgtcc tttaaggtgc cgttttctaa ctgcagcgag gactgcgaac    2220
ctgggacgag gaagggcatc attgacagca tgcccacgtg ctgctttgaa tgtaccgagt    2280
gctcagacgg cgagtacagc gatcataaag gtagtagcgt ttgtttactg cttcctgtta    2340
ctgtccacga acactcaggt aatcctcaca tgcatgtttc agacgccagc atttgcacca    2400
agtgtccaaa caactcctgg tccagtggga accacacctt ctgctttctg aaggaaattg    2460
agttcctggc ctggtcagaa ccctttggga tcgctttggc catctgcgcg gtcctggggg    2520
ttctcctgac ggcatttgtg atgggagtct tgtcagatt tcgcaacact ccgatcgtga    2580
aggcctcaaa ccgagaactg tcctacgtcc tcttgttgtc actcatctgc tgttttttcca    2640 gctcactcat cttcatcggg gagccccaag actggacctg ccgtttacgc cagcctgcct    2700
tcgggatcag ttttgtcctt tgcatctcct gcatcctcgt gaaaaccaac agggttctttt   2760 tggtgtttga agccaagatc cccaccagca tccatcgtaa atggtggggc ctgaacctgc    2820
agttcctcct ggtgtttctg tgcaccttcg ttcaggtcat gatatgtgtg gtctggcttt    2880
acaacgcccc cccctccagc tacaggaatc atgacatcga tgagatcatt tcatcacct    2940 gtaatgaggg atccgtgatg cgctcgggt ttctcattgg ctacacgtgc ttactagcgg     3000
ccatatgctt cttctttgcg tttaagtcaa ggaaacttcc cgaaaacttc acggaggcca    3060
agttcatcac tttctgcatg ctcatcttct ttattgtttg gatttctttt atccctgcgt    3120
acttcagtac ttacggcaag tttgtttcag cggtagaggc cattgccatc ctggcatcca    3180
gctacgggat gctagcttgt attttcttta ataaggtcta catcatcctg ttcaaaccct    3240
gtaggaacac catagaagag gtcaggtgca gcaccgcggc ccacgctttc agagtggccg    3300
ccaaagctac attaaaacac agaaccactg tgaggaaaaa gtcgaacagc atcggctcta    3360
ccgcctccac tccatcatca tcaattagcc tgaagaccaa cagcaacgac tgcgactccg    3420
cctcagggag gcataggccg agggtgagct tcggcagcgg aactgtcatg ctgtccttga    3480
gctttgagga gtccaggagg agctctctga tgtgacacac aaaccagttt catccacccg    3540
tcctttcagc ctctaatcca tctgtccacc cttctaatta ccttgattat taacctgctt    3600
aataaa                                                              3606

<210> SEQ ID NO 32
<211> LENGTH: 4856
<212> TYPE: DNA
<213> ORGANISM: Fugu rubripes
```

-continued

```
<400> SEQUENCE: 32
cttgtggctg gggtcagtag aagaacctag actagcggta catgaaccgt atcaaaagtg      60
taacggtgaa acattagcac aactgtgtgg gggaggaaat agagtcattg catagtttct     120
taaaccagtt gtgcagtacc tgagtgacaa actttgtttt gtccatttta tttttgcatt     180
aaacaaaagc gattttattg gaaattgcct cgatagatgt caataaatct cacatgatgt     240
tatcagcact tcattacagg tatcataaag atataatagg aacaactgta acttgtattt     300
gttctaaagg ttataaccct tggggaacag ccagataagg accacgtaat gttttgtctg     360
actgattaat aataataagc tgacatgagc agaaccaaca cctcagtcta taaaagcatt     420
tgtgcagaat gctccgagac attttaggga tggagatctc tgttatcttc ctttgcttca     480
tttctctgtt tgatttaaac tcagctggtg acctgaaggc tcctgagaac agtctgaaac     540
aacaggttgg accgagggag gacacaaccg gtgccgcagc tccgtctgac atatgtcgcc     600 tccaggggttc tgctcgccta cctgctttct caaaggatgg agactttgtc atcgggggg      660 ttttctccat acaccgctac acagtgacgg tgaaccacaa ctacaccacc atgcctgagc     720
catttcgctg cagagtgtgc ggagaagaaa atgtttgatt gtttcatttc tggagtatat     780
atgatgttca cattatgatg cattttttat ttatacctac acttgtgaat gtttgttttc     840
tgtcatgatg tgcagcatcg accatcatga attgcaactg tctcatgcaa tggtcttcgc     900
catcgaggag atcaacaaca gcacggagct gcttcctgga atcaaactcg gttaccagat     960
ccacgactcg tgcgcagccg tgcccatcgc agtaaatgtg gccttccaac tgttaaacac    1020
tctggaccct gtgtttgtca caggtgacaa ctgttcacag tccggtatgg tgatggctgt    1080
cgtcggcgag tctggttcca ctccgtccat cagcatatcc cgcgtcatcg gctccttcga    1140
cattccacta gtgaatattt tcaacttttta ccaaagcaca tgaacacgta atattaacca    1200
tcactgtaat gacacaatgt tcaacttcag gtgagccact ttgccacctg tgcatgcctg    1260
tctgataaac agaagtaccc aagtttcttc agaacgattc ccagtgacca gttccaggcc    1320
gacgctttgg tcaaactcat caaacacttt ggctggactt ggataggtgc tgtgtgctca    1380
gattcagact atggcaataa tggcatggca gcgttcctgc atgcagctca aaggagggc     1440 atctgtgtgg agtactcgga atcctttttat cgcacccacc cgcacagcag gatcaagaga    1500
gtggctgatg tcatccgcag gtgtatagat ctattttttgc ttcatgattc atgaaggtat    1560 ttgtgttttgt ttgaaatgac gcatatactt gtgagttttc tgcaggtcaa cagctgtggt    1620
ggttgtagcc tttacagcat ctacagaaat gatgatcctg ctcgaggaac tgtctcatga    1680
accctcacca cctcgccagt ggataggcag tgaatcctgg gtaactgacc cagacttgct    1740
gaggttcagc ttctgtgctg gaactattgg atttgccatt cagaggtctg tcatcccagg    1800
cctgagagac ttcctgctgg atctctcccc ctcgaaagtg gcttcatctc ctgtgctcac    1860
tgagttctgg gaggactcat tcaactgccg gttgggaaaa ggtgacagaa gttataacctc   1920 ttccttaattt actgtggata gattttaaat tagtgtccaa atctaataac aaaggctttc    1980
aacagatctc ctgtgttgtc agttgctgtt gcaggtgagc gcatgtgtga tggatctgaa    2040
gacataatga ctctccagag tccgtacact gacacttctg agctccgcat taccaacatg    2100
gtgtacaagg ctgtttatgc aatagctcat gccattcata tgcagtgtg tcaggacaca     2160 aatgctacca ctcggtgtag caaattcacc acgattaacc ccaaaaaggt caaacctaaa    2220
gaattgcctc tgtaactact aacatggttt attacaagtg tttcagctga agtctttcct    2280
ctgactctct gtttcattca attcaggttc tcactcagct gaagacagta aatttttcac    2340
```

-continued

```
aaaatggtta tgctgtatcc tttgatgcca acggggatcc tgtggcatca tatgagctgg    2400
taaactggaa aaagagtggg agcgggagca tcgaagttgt gccagtagga tactatgatg    2460
cttcactgcc agaaggccaa gagttccgta tcttcaggga catcacatgg gtggatggca    2520
gaaagcaagt acgacagcca gaataattaa taagacagta attcaggcat gaaaacacaa    2580
catctctgaa ttaaaggctt ttttgttcaa ttgtgactct atgtaaaggc accaacggca    2640
gttctgttaa atcttttc aactggtggg tgtgtatgtc tcaggtgcca gtgtcagtgt    2700
gcagcgacag ctgtcctcaa ggaactcgta aggtactgca gaaaggaaaa cccatctgct    2760
gttatgactg tgtacaatgt ccagagggag agattagcaa tgttacaggt agttatctag    2820
atttcaaaga cagcagggct aaataaataa tttgtttaaa ccctacatga ttttgtttc    2880 ctagattctc ctgaatgcat cccttgtctt gatgacttct ggcctaaccc agagagaaat    2940
gcctgtttcc ccaaacctgt ggagtttctt tcctttaacg aggttctagg aatcatccta    3000
gctgtgttct cagtcggtgg tgcctgtctg gctgttatca cagcagctgt attttccat    3060 cacaggacct ctcctattgt cagagccaac aactctgagt tgagcttcct gttgctcttc    3120
tctttgactc tgtgcttctt atgttcactc actttcattg gtgctccctc tcacctgtcc    3180
tgcatgctgc gccacacagc gtttgggatc acctttgtcc tttgcatctc atgtgtttta    3240
gggaaaactg tggtggtgtt gatggccttc agagcgactc tccccgggag taatgtcatg    3300
aagtggttcg gtccacctca gcaaaggatg actgttgtga ctttcacgtc tatccaggtt    3360
ttaatatgca ttgtttggtt ggttgtcaat ccccgtttc cagtgagaaa tctgaccacg    3420
tacaaggaga gaatcatcct ggagtgtgcg ttaggctcat ctgttggatt ctggctgta    3480 ctcgggtaca tcggccttct ggcagctgtt tgtttagttc tagccgtcct cgcccgaaaa    3540
ctccccgata atttcaacga agccaaaatg atcaccttca gcatgctgat attctgtgcc    3600
gtctggatca ccttcatccc cgcttacgtc agctctcctg ggaaattcac cgtggccgtg    3660
gagatctttg ccattttggc ctccagtttt ggactcatcc tgtgcatttt tgctccaaaa    3720
tgttttatta ttttatttaa gccagagaaa aatagcaaaa aacacttgat gaacaagaaa    3780
taatcagaat gtctgcaata tgttgggtga gtttaacgac tggaagtatg ggtccgtaca    3840
gcagcaatag cccagtctgt agatgagtga gctgtggtt tgagggtatc tggttcaagt    3900
tccatttggg aacaaagatt aggaaatgga cctgtagaag gagatgtgca gggacatatt    3960
aagaacccca ctatggtatc attaagcaaa ataccaaacc cccaaatgat aagattgcct    4020
ttatctctct tcatgattgc atgtgcatgt gtttattgta gcttcatgtt taaccgcttg    4080
taacttgtgt gtaacaaagt gtaaacacag acatttcccc tttgtgcttt taatgtatgc    4140
ttttttcttt ctcttgtttt acactgtact gccattcctc ccaacgttat gtgacaggct    4200
agattaggct gcatgatgta tgagttttag aaaatctcac cctttacaac acaagtccgc    4260
tgatacagtt ttccatctct cctcccttat gtccaccata acctcttttc tatttctat    4320 gtgattgtta aacaattaca cttttcattg ggaatgttat tgataaatgc aagtaaaact    4380
actgtgatat ctgtgtagat tctcaatcat ccaggtcatg gtcatccaat gcagtttgct    4440
ttgtcaaatg gactgttttt cttctctttg aagttctgga gtgtgatgta ttcaaaacat    4500
cattaaagtt ataagtgggg aacgactgta acagatttgt tcaaaggtt ataaccttg    4560 gggaacagcc agataaagac cacataattg cagaatgctc caagacattt ttaggatgga    4620
gatctgttct cttcctttgc ttcatttctc tgtgtgattt gaactcagct ggtgacctga    4680
aggttcctgg gaacagtctg aaacaacagc ttggactgag ggaggacaca accgctgccg    4740
```

```
cggctccgtc tgtcatatgt cggctccagg gttttgctcg cctacctgcc ttctcaaaga    4800
atggagactt tgtcatcggg gggggttttc tccatatacc actacaaaat gacagt        4856

<210> SEQ ID NO 33
<211> LENGTH: 4981
<212> TYPE: DNA
<213> ORGANISM: Fugu rubripes

<400> SEQUENCE: 33
gtgtatttgt ttatgcattc ataacgaagc aacaaactca tattctgcaa gttttgatgg      60
atttgctggc attattaata cttacaatta gattagatta gattagatta gattagatta     120
gataaaagaa attcaggaag ggaaatgcag acattatatt taccaatcct atgaactatc     180
caaatcttgc atagccttaa attaaacatg gtctagatga taaaagtaac atgtatgaag     240
tgaacgaatc tgacgtcatc ggtcacacct tgatgggtgg tgtcatcaga catggtgaag     300
acacaactct gcatataaaa tatgcagtag agatgaagag aacctgaggt ggaggaagga     360
ggaagagtga tggctgacat cactggcaca ttgggcctct tcttcaccct catcacattg     420
tttgtctcct cttccacctc cttcaatgct ccgacttgca agctatggag gaaatttcag     480
cttaatgaga tgcacgaacc gggcgatgtg cttctaggcg ggctgtttca agttcattac     540
agctctgttt ttcccgagtg gacgtttaca tctgaaccac atcagcctgt ctgcactagg     600
taagtttcat gcacaccaca aacaatgatt caagctcaga ttggtcctgg aagaaaaatg     660
tcaattaaat gttgtgatgg gtgaatcca tccataaagg gtgtatctgg agccagtttc      720
accaggttct tgttaatggt tttggtattt tgcatgtcag gtttgacatt ctaggcttcc     780
gtcacgctat gaccatggcc ttcgctgttc aggagataaa caagaaccct gacctgcttc     840
ctaatctgac tctgggatac cgtctttatg acaactgcgg agcccttgtg gttggattca     900
gtggagcgtt agcactggca agtggtcagg aggaggcgtt tgctcttcag ggaggctgtg     960
ctgggagccc accggtcctg gggatcgtgg gtgattcact ctctacgttc actattgctt    1020
ctgccagtgt tttaggcttg tacaaaatac ccatggtcag tgattagtgg cactaaagtt    1080
tgtgttttgt atgtgaatta taaactttca tcttttgaat aatattgtaa aacactggaa    1140
gaaatgtgat tggttatgta gagaaatgga tgtcatctac tgaagacata taaataatta    1200
ttacattaat ttgatcaagt tcataaatta acccttttc aaatgaaaaa gtattttta      1260 ccaaacaaaa actgcaaaat gaacttaaat cttagttaaa tttagtgtaa aagtgatact    1320
cacgcttcgg atcagagtac agacgcagac agctaatctt tggagaaaat ctaagtgcac    1380
tgagatttaa aatttttgtt taaacattca aatgtctttt tcttttcttt tctgttttta    1440
aaaacgttga tctctcttac acagttaaat ctgttaaaat aaaagaataa tttcatgttc    1500
atgctgagtg ctccggaaat ctttaatgct cgaaaacata tttaaaacat ttgggcttgt    1560
gctgtttaat ttcctatttt taggtaagct attttgctac atgttcctgt ctgaccaatc    1620
gtcagcgctt ccgtcctttt tttagaacca tcccgagcga tgatttccag gtaaatatt     1680 cctttcaagc tgagaatcta cagagattaa aaaaaactcc ccaccctcaa attcaaacaa    1740
atattactta gtatcagatt acaaactgtg ggaactaaaa cactcaattg tctggactga    1800
tcccccattc aggtacgtgc aatgatccag atcctgaaac actttggatg gacttgggtg    1860
ggactgctgg tcagtgatga cgattatggg ctccatgtgg cccgttcgtt ccagtctgac    1920
ctggtccagt cagggcaagg ttgtctggcc tacttggagg ttttgccctg ggacaattat    1980
ctgagtgaaa acaggaggat tgtgcacgtg ataaaggaat caacggctcg cgtgctgatg    2040
```

```
gtgtttgcac accagtccca catgattcat ctcatggagg aggtttgatg tgcacagaaa    2100
aaactgcagt gaacacgcta agaatgcta tttctggtat taataatgat atgtacaggt    2160
ggtgagacag aaggtgacag gccttcagtg gttagcaagt gaagcttgga ctggaacgac    2220
cttcctccag acgccggact tcatgccgta cctgaatggc acgctgggca tcgccatccg    2280
tcgaggtgaa ataacaggtc tcagagattt cctcctacga atacggcctg ccagagtag    2340 caacaacact agttatgata tggtaattat ttcttactat tttaactccc agaggaactg    2400
ttcatttaaa aaataaatga tatattttaa tcttttttca ggttcaacag ttttgggaat    2460
actcattcca gtgtaaattt ggtgcgtcag gttcagcaga agcctgcaca ggagatgaaa    2520
atatccagca ggtggacgct gagttttgg acgtgtctaa cctcagacca gagtataaca    2580
tttacaaagc tgtgtacgct ttggcgtacg cgcttgatga catgctgcag tgtgagccag    2640
ggagggggcc gttcagtgga ggcagctgcg cggatattca caaactggag ccctggcagg    2700
tgagacctga cactggaaaa taacaagcgc ttccccttt agtgtgagcc tttgaaattt    2760
agattcaccc agtggtccct cagacctgat tactgtcaac ctccatcagc tgttcaaatt    2820
agagcaacag ggtccagaat taggattcga cctaataagc ctgatgtggt attgtgcatt    2880
tgcagttcgt gcattatcta caacatgtca atttcaccac aacgtttggc gatcaagtat    2940
catttgatga aaatggggac gtcctaccca tctatgacat cctcaactgg cagtggctcc    3000
ctgatggaag aactcaggtt cagaatgtgg gtgaggtcaa gaggtcaccg tccagaggtg    3060
aagaactcca gatccatgaa gacaagatct tctggaactt tgaatctaat aaggttattc    3120
ttgtgtgctc ctgttatctg ttaaaagaaa tgcatgaaaa tcagatgttg atttttcctc    3180
ctgcagcccc cacactcagt gtgcagtgaa agctgtcctc ctggaacccg catgtccagg    3240
aagaaaggac aacctgtctg ctgctttgac tgtcttcttt gttctgaggg gaaaatcagc    3300
aacacaacag gttggtattt gatttcaaac actattttgg gcacattaat ctcaaagctg    3360
cgtccatgtt ttgcttcaga ctccatggag tgcaccagtt gtcctgagga cttctggtcc    3420 agccccagc gggaccactg cgttcccaag aaaactgagt tcctctccta ccatgaacct    3480
ctgggtatct gtctgacagc cgcctccttg ttgggaacag tgatcagcgt ggttgtgttg    3540
ggcatcttca tccatcatcg cagtacacct gtagtacggg ccaacaattc cgagctcagc    3600
ttcctgctcc tggtgtccct taagctgtgt ttcctctgtt ctctgctgtt cattggtcgt    3660
cccaggctgt ggacgtgcca gctgagacac gcagcattcg ggatcagctt tgtgctctgt    3720
gtctcgtgca tcctggtgaa aaccatggtg gtcctggctg tcttcagggc ctccaagcca    3780 ggaggggcg ccactctgaa gtggtttggt gccgtgcagc agagaggaac agttctgggc    3840
cttacttcaa tccaggcagc aatctgcttt gcctggctat tgtcgtcttc accaaagcca    3900
cataaaaaca ttcagtacca caaagacaag atcgtttttg agtgtgtcgt tgggtccaca    3960
gtgggtttcg ctgtattgct cagttacatc ggttactgg ccatcctcag tttcctgtta    4020
gcatttcttg cacggaatct tcccgacaac ttcaatgagg ccaaactcat cactttcagc    4080
atgctgatct tttgtgctgt gtgggtggcc tttgtcccag cttacatcaa ctcaccgggc    4140
aaatatgcag atgccgtcga ggtctttgct atcctcacct ccagttttgg cctcttggtg    4200
gcgctgtttg gaccaaaatg ttatataatc ctgtttcgtc ctgagaggaa cacaaaaaga    4260
gcaataatgg cccgttgaaa tcagaaccag cacttccaaa tcacaataac aaacactcat    4320
tgaagcatca acagcaaaag tacaaatgca aaaaaaatac aattaaaatt aaagcaattc    4380
accccctagt ggttaaagat tgcactgcat tacacgtttt ccccatttcc ccacctttcc    4440
```

-continued

```
atgtcacatt aacaatgtgc actgctgcat gtattccaac atccacgggg taagataaga    4500
ccatataaga cagaatctca gtcttcattt ttgaatgtca tcaataactg attcttctat    4560
ttctccacac tttctgtttt gcttctcttc ccttctcact gtatttcttg tgctgttatg    4620
ttaaacttta ttatgatgat caatgagggc agttgagctg tataatatgc tcactcttgt    4680
tttattgtgg taaataaatt tatatttaaa tctgccacat gcttttggtc agtaaaggtt    4740
tgtgaacgtt ttttttgtcc tgcaatatag aaaaaataat atgtaataaa gatttcaagg    4800
gtcaaacaga aaggtatgac tccatctatc tgtgtggaat agaaaaataa gtaacattta    4860
agcagcaatt aaatacattt ttatcacact tcacatacgc atacaattta aaaaaacaaa    4920
acaaaattcc agcccacgtg gctgaagccc tcacgaggga tgaggaagcc tgagtgactg    4980
a                                                                    4981

<210> SEQ ID NO 34
<211> LENGTH: 4781
<212> TYPE: DNA
<213> ORGANISM: Fugu rubripes

<400> SEQUENCE: 34
cagccttcat aaacacaaat aggatatcct atagattggc atagtgaaat ttgaccactt      60
tcaacttgcc gtctggcatc tggagactag atccagacct gatcagtgcc aaggtcaaac     120
gctgtaacac agttaaccct tgaatagctg tctttcatgg tgggggaaac tcaaacttca     180
gtcaaacaga aaaagagaaa gttctaatca gactgatact cccttcatcc ctccactgca     240
acctggctta gcatccacag gtcaaacctt gtctttatgt tggggagggc acacacattc     300
catgcacaca gaagtacaat gtgctgattc tacatggaaa aaaattcagg aatctgacag     360
agattcagat tcagattcag attcagattc agattattga catgatgaaa aggtgataaa     420
tgttgttgtg ctaaactacc tatctatcat acctgtggcc acaaaacaat cactgcgctc     480
ttccaaatat catgacttaa agaaaactcc tcaagtatca cattttcatt tgaggtctga     540
catgacatga cagttctgag acattcttct cacacattca actactttca tctttaactt     600
ccaactaaac tcaatttaga ctatttacaa aacatgaact aataactcag tttgtttgtg     660 atagcgggt cattcattcc agtgcctgaa agctggctac cagttcatta attggtgacc     720
ctgaggagac aaattcagtt tatctaacca cttaatccta attaaggttt aaggagactg     780
aggcaggaaa aaaccctgga caggtcacct gtccaccagt aactgttcac tatcaactag     840
ggactattaa tcatcactga acctaatatg catgtttta tgctgtggaa gcaaggggg      900 acagagagaa cgcaaacttc gcgcagaaat gccagagtct ggagccctga atgctcctgc     960
tctgatattg gtgatcactg caccctcatg cagtctctac aatgacctcc agatgttttc    1020 aggggttttcc aaaatatttt ttttaatcca tctttatttt ctgcgatatt tacaaacaat    1080
gaatcatctc aacaaattct gcagtttttc ctcctgtagg atgaaggaaa atcttgctac    1140
ggcccaaagt tgtcccctgg gaaatgcagg atgcagagtt cttgatgcaa tagatgcaaa    1200
tctattagta agttgtcgtc atggtgatta tgtaatgaag tagaaaaagc aagttaaatg    1260
ttgaagagct gcaccctctg acatcagcaa tgagggcttt cttcttataa aaggatgtta    1320
aacattagga tggcctgcag gagtatataa ttcttctgtt ttcttctgtg agacattttt    1380
gcttacgatt gtgtgtgtca ggttccacca gatgcctgtc tgtgtctgtg taatgcttct    1440
gtttgcgctt ttccacggag cctttggagc cgaggacaat ctaaagtgta agatgttggg    1500
gagaccagag tttccactgt tatctcagga aggagacatc actattgggg gagccttcac    1560
```

-continued

```
tctccacagc caaatgtcaa aaccttctct ctcctttgaa gagacaccag aagatctcac    1620
atgctccagg taacatttat ttctactgt agtgctattg ttttaccttc agagaaccta     1680
aacctctgtt attttccttt caggattaat ttaagagaat ttcgctttgc ccaaacaatg    1740 attttgcaa tagaggagat caacaacagc agctcgcttt tgccaaatat ttccattggt     1800
tataaagtat ttgacacgtg cggtttgacg ctgccttcta cacgagcagt aatggcctta    1860
atgaatggaa agacaagaac cccagaagga ggctgctcca gtcggacatc tgttcatgca    1920
attattggtg cttcggagtc gtcttcaacc attgtgatgc ttcaaatttc agggatattt    1980
caaataccgg tggtaataat gtgtcatatt tgtgattggt ttgcttttga ttctgtcttt    2040
ggtaaaaaaa atgaccagat tctgattcat gtattgcttt ccctcttgtt ttttcctctc    2100
tttttgttat cttttttgtt cagataagcc actttgccac ctgtgcatgc ctcagtaaca    2160
ggaaggagta cccctccttc ttcagaacca tccccagtga cttctatcag agcagagctc    2220
tggctaaact agtgaaacat ttcgggtgga cgtgggtcgg ggctgtgaaa agtgacaatg    2280
attatgggaa caatggcctg gcgacattta ttatggctgc tgagcaggaa ggggtctgtg    2340
ttgagtactc ggagggcttt tcgtggacag accccagcga gcagattgcg agggtggtca    2400
cagtcattaa aagtggcagc gcaagggttt tagtcgcctt ccttgcacag agtgagatgt    2460
ccgctctgct ggaggaggct gtaaagcaga acctgacggg gctgcagtgg gttgggagcg    2520
agtcctggat cacagcaggt cacctggctc ttaagaaata ctcagcaatc ctgacagggt    2580
ccctgggctt caccatcaga aagacaaaga taactggcct tcaggagttt cttttacagg    2640
ttaacccaag tcagaaccct cagaataatc ttctcaaaga attctgggag accacatttg    2700
gttgtagttt ccagtctgat gtgcacgggg ccacccagtg ctctggtgtt gagaagctaa    2760
aggacattca gaatcctttt acagatgtgt cagaacttag gatctccaac aatgtgtata    2820
aagctgtgta cgctgtggct catgctatgc atagcatgct aaaatgtggc caaagtggcg    2880
aggcagtgaa tcagtcatgt accactaaaa aggatttga gctaaagcag gtaagatgtt     2940
gtctctaaga attatgtcca gctgaatttc tttacacccc ccattgacct gttctttctg    3000
acaggttgta gagcacctgc aatcagtgaa cttcactctt cagtcaggtg aaagagtgta    3060
ttttgatgac tatggagacc cggcggctac ttatgagctg gtgaactggc agagaagccc    3120
agaaggaaat acagtatttg tggtcgttgg gaactatgac gcttcacaac caaacgggag    3180
gcagtttacc atgaacaaca tcaatataac atgggctgcc aggctgcaga aggtacgacg    3240
catgttaaaa agcattgatt tacacgctga tgtttataca ggcatgggtt aaatggcttc    3300
atctatgtat tttgtatttt cgtcttaaaa cagagaccgc tgtctgtgtg cagtcagagt    3360
tgcattccag gcttccgaca ggctgtgatt aaggggaaac ccatctgctg tttcacctgc    3420
gtcgcctgtg ctgcaggaga gatcagcaac tccagcagta agttcaagtc ttcagagcag    3480
gcaatattta tcctgaaaca atctttttta ctctcttctg cttcaagctt tattcatggc    3540 accttgatt tttagactct gcagagtgtt tgcagtgccc actggagttc tggtcaaacg     3600
aagatcacag ccagtgcgtt ccaaaggtga tcgagttctt atcatttgaa gaaaccatgg    3660
gggcccttct tgccgccgtt tcactgtttg gggctgcgtt aacgtcgctg gtgttttgtg    3720
tcttttttcg gttccgtcac acacctcttg tcaaagccag taactccgag ctgagctttc    3780
ttcttctttt ctctctgact ctgtgcttcc tttgttccct cacattcatc gggaggccct    3840
caaggtggtc ctgcgtgctg cgacacacgg cgttcggcat cacctttgct ctctgcatgt    3900
cctgcgtcct ggcaaaaact gtggctgttt tgttcgcatt tacagcaaaa aggccaggaa    3960
```

-continued

```
acacagtttt ttactgttct gttccacttc agagaacaag tgttttttgcc tgcatcactt    4020 tgcaggttat aatttgtgtg ctctggttga cgcttgcccc accacaccct cacaaaaata    4080
ccgctcatgc caaagagcgc attattttag agtgtaattt aggttcccca gtgtggtttt    4140
gggtggtatt ggggtatatc gggctcttgg ctgtgatttg ctttatcctt gcttttcttg    4200
ctagaaagct gcctgataat tttaacgaag ctaaattcat caccttcagc atgctgatat    4260
tttgtgcagt ttgggtcact tttatcccag cgtacgtcag ctctcctggg aagttcacag    4320
ttgccgtgga gatctttgct atcctggcct caagttttgg gttacttttc tgtatatttg    4380
ccccaaaatg ttatatatta atattgaagc cagaaaaaaa cactaaaaaa cacatgatgg    4440
ggagaaacca tcaaaattag gctgaactga gaattgtatc acttaaataa cagtaatttt    4500
gttctttaat atttaagtcc agaaagtgtt ttattaatac agagcattat gtaagtgcac    4560
atatataaaa tgcaccttat gtcagtttga ttttgggatg gaattgactc acatgttaat    4620
gtcatttatc gattaaagct acaataaagt taaactacgt ggacagttgt ttaatagttt    4680
ccctgtcaag tattttaaaa gcaacaattg catgtaaaag caacacagct gtaataggcc    4740
cactcgtctg tcactcacag cagtgaggtg atgccattgg a                        4781
```

<210> SEQ ID NO 35
<211> LENGTH: 4846
<212> TYPE: DNA
<213> ORGANISM: Fugu rubripes

<400> SEQUENCE: 35

```
gatccaaact tgcgacaggg atttgtgcca gtatatcaac gccagaacgg cgtctggtat      60
ttgacagtta aggctgtgca gttgtgggag aaagtagatg cttttttaact gtttgctcta    120 gaatttgtgg acacttttag tcttaatgga tgtataatca atttcctaat ttctcttgaa    180
tctggcatat tgcaaacatt tgttgatcac cacaaacaca cacacacaca cacacgcaca    240
cacacacaca cacacacaca cacacataca cacacactac aaatctacga acttgagctg    300
cagcagtggg tgcacacgtt tgtattgggc tgtgagtctg ttcacagaat gagttggatg    360
ggatggattc cctcacaaag aggtgtacaa cttctctgcc ttctgtgctg catgataatt    420
cctgttgtca ttgccctcct ggatcagagc caacattgca gggtcatccc gggctccatg    480
tccctgccag tgctggagaa gagggggggac atcatttag gcggtctctt ctctcttcac    540
gacatggtgg tagagccaaa tctgcccttc acctctacac caccacccac tcagtgcact    600
aggtaaggta caataatccc ttctacactt ttattcatgt gtaaattta gttttttgc      660 tgtaaatata gcagtatgca caattccttg tctcttactg acaagtcagc atcctgtttt    720
tcatttcttc ttcccagatt cagttttcgg acattccgtt ggatgcaaac catgatcttt    780
gccgtcgagg agatcaacag aaatgccgaa atccttccca atatcacact gggctacaag    840
atctacgact cgtgcagcac gccccatcag agtttgaagg ctgccatcga tttaatgggg    900
agtgagaaag attcccagtt tgagggaaag ttgcagaggg aaggctgcga tgggaacgtg    960
ccggccgtca tcgagacggg aggatctact cagtctctcg tcgtggcccg tttccttggg   1020
gtctttcatg taccgcaggt atctcgcatt gctgatgctt caagggaac tcttctctca    1080 tgctagaaat catttgtttg ctagggttca cttaaaagca attatcactt attttttggtc   1140 gtgtcaggtc agttattttt ccagctgtgc ctgtctcagc gacaaaacgc agttcccagc   1200 cttttttaagg acgatgccca gcgatctctt tcaggtttga ggcagcagcc ttaaaacttt   1260
tttttttaaa tttaaagcta tgagagaacc ttcatctcct tcatttctag gtgggtgccc   1320
```

```
ttgtacagct cgtcaagtat ttcggctgga cttgggtcgg agtgattgca ggagacgacg    1380
cttacggccg tggcggagcg gccatattcg ctaatgaggt agtaatgaga acaaatggac    1440
atttcaatgc tttattgagc atcgtgcggg cactgaaaat taggattaat ggcatgtctt    1500
ctatctgggg taggtgagaa ggctcgggcc ttgcattgct ctctatgaga tgatccccaa    1560
gacacaatca caggctgcca tttcatctat catttccaac atccgctctt ccggggctcg    1620
tgtagttctg gtgtttgctg ttgagcaaga cgtggccagg ttgttcgatg aggcagtcag    1680
gtatggcacc tgtgtatccg caaacgtaca aaaacaactc taagctattt agcttctcct    1740
aaatatagac agaagctgac tgggattcag tggttagcca gtgaggcgtg gagcacagct    1800
gccatcctct ccacccctaa aagtaccac cacatcctgc aggggtctat gggatttgct    1860
attcggagag cggacatccc tggactgcaa gacttcctcc ttcgcttgca tccctcgagc    1920
gccgaggctg atgacgatcc tttcctgatc ccattctggg aggaggtgtt tcagtgtagc    1980
ctggatccgc acggccactc tgaggctaaa cgtccctgct ctgggacaga ggagcttagg    2040
agcgtgaaga acatctattc tgatgtatca cagcttagga tttcctacaa tgtctacaag    2100
gcggtttatg cccttgccta cgccatcaaa gccatgagaa gttgtgaaaa aggaagtggg    2160 ccatttctc aacaagcctg ccctgattta dacaatatcc acccgtggca ggtatgcaat    2220
taacaaaatt ccatgtgcag aatgacttgt gatgttggaa tcgaatcttc cgctcttttt    2280
tcgcagcttc accactacat aaaacaagtg aactacacga acagattcgg cgatgagatt    2340
aaatttgatg aaaacgggga tcccgccgcc atgtatgact tgattaactg gcagctgacg    2400
ccgggcgggg acatggactt cgtcaccgtt gggaaatttg atgacatagc cgggaccgga    2460
aggaagaacc tccacattga ggaagagaag atcgtgtgga atggcaacaa cacccaagta    2520
ggagctgtca ataaaatgct tcaacactca cgggtgactc agagatgtat ccttatgtga    2580
ccgtgtgctg tactctagtt tcctcttttg ctcaggttcc cttatcagta tgcagtagca    2640
tctgtccccc ggggacccgc aaggcaatcc gacctaatta ccctatctgc tgccatgact    2700
gtgtggtttg tacagcaggg gagattagca atcaaacagg tgagaagagg aggagaatgg    2760
tcacagtttt actcttccag acctctgtcc ataagccagt gaagtggatt tttgataaaa    2820 tgttcccttta cgttttcctc ttttttctgca gatgccatag aatgtgcccg ctgcctgccg    2880
gagttctggt ccaatgctga caggacagcc tgtgtcccca acaagtgga gttcctctcc    2940 ttcggtgaca caataggcat tgctctgttg gttgtttccc tgatcggctc cttccttacc    3000
tgcgccgtgg ccctcgtatt cttctatcac aggacctccc ccatcgtcag agccaacaac    3060
tctgacctga gcttcctgct cctcttctct ctgactctgt gcttcctgtg ctctctgacc    3120
ttcatcagcc caccctccca gtggtcctgc atgctgcgac acacagcctt cgggatcacg    3180
tttgtcctct gcatctcgtg cattctgggg aaaacaattg tggtcttaat ggcgttcaga    3240
gccacacttc ctggtagtga tgtgatgaaa tggttcggac agggaagca aaaggcaatt    3300 atcactttca gcacactggt ccaggtaagg gcttctttta agttgtctca aattgttacg    3360
gttgcatgta ttgaatgtaa catttctgat catttcctct tttgttgcag gttgttattt    3420
gcacggtgtg gctggttgtt gctcctccca ccccacgaca gtacatgcca cgtgaaagtg    3480
ctatcatcat tctcttatgt gacgaaggct caaccatagc cttctccctt gttttgggat    3540
acattggcgt tctggcctgt atgtgtttcc tcctagcctt cctggcgaga aaactgccag    3600
acaatttcaa cgaggccaga ctaatcgcct tcagcatgct catttttttgt gcagtctggg    3660 tggcctttgt cccagcttat atcagctctc cagggaaata ctccacgctc acggaaatct    3720
```

```
ttgccatctt ggcctccagt tacggactgc tgggctgcat ctttgcaccc aagtgctata      3780
taattctcat gaagtcagaa aagaacacaa ggaaacactt gatgtcaaaa agtgaaagat      3840
tttagagata tattattgct tgcgttgctg tgggttttga aatgaaatgg ggggacaact      3900
ttaaacgtcc gcgtcatgga tgaagtgtct cttttggcca ccagagggaa gtgttgtgct      3960
gctcatgcaa cactggttca ctgcttatac tggaaaaagc acaaaaagaa catgtattgt      4020
ttccacatac tacagtgtgt tcccgataaa acagtaaaat atatggttag cttataaatt      4080
catatagcaa tcatcccatt aatatattga agtgctcatt gtcattaaag tgcaatattc      4140
tcagtgacag tgtgaaggac agcttttttt ttatgcagt gggatttggc agcattttca      4200
gtgctgatat ggcttgaggt ggaatgaggc cctgaggtgt attctgtgga atcccagct      4260 gttaaattaa atccatacac cccgacggcc ctttcacata aacataaggc cctggctgat      4320
tccctataat aacaaactaa acgatatat ttcccgccct ccacagctgc tctcaggact      4380
gtatcgaccg ccttccgccg attgatctgt tgtccctccc gaagctgagg agggattgga      4440
aattgaaaga tggggagtca tctctgctgt ccatcaggaa atggcatatg agcacaatct      4500
atttacattc acttcttacc gtcattgttc ttaaatgtcc cactacagcc atctgtgccc      4560 tcccccttctc cccatctcaa aagggattat gacaaagtga atttcccttc atagcatgtc      4620
catttcagga gtccttcagt ggctttgctg ttggtttgat tttaattaag gtgaacagga      4680
gagttcacct cagagggttt aatcatcgag tattagaaac acagtcaaag aaaagagtac      4740
aaaagagtca aatggctttc aaataacaat tcacaggaaa catatcagca gaaagtagag      4800
agttaaacaa aggccacgac tttttttagca cattaaaccc aataga                    4846
```

<210> SEQ ID NO 36
<211> LENGTH: 4743
<212> TYPE: DNA
<213> ORGANISM: Fugu rubripes

<400> SEQUENCE: 36

```
ggacaggggt caacatgggc accctgactg gtctgtaact ggtccccatt acactgaaat        60
ctggcatcat gttgattatt acgatccagc tgtaaagcag ctgacggctc agaagatgaa       120
gtctgattgt tgatgtctga tgttccttct tagcccagtt tagctggtgt agtggtgaac       180
agatccctgt actccagggg aggggcccca tgtttctgga actggaccct gatcactgtg       240
actggtgggc tctattttg cactaaataa taaatttaaa ggctgtatta cttttattta       300
ttattaaagt ttgatcttcc accatgatca taaaaaactg tatcacatga gatcagtgtg       360
aatttacaat gtggtttgaa aaacaattta atgaggcatc ttcataacga tcccatgatg       420
aaacaacaat gtgctgaggg gggcctggag gggccggagc ctgacaggcc ttctgggata       480
cgcctggtca ctgccctcca ggtgaacgct gcagtccctc tttcctctct ctctctctca       540
cacatgcaca cacatgaaca catgcacaca aatcactcag tcatttcatt attgtttttc       600
ttttgccttt gagagcggta atttgatgct gtgcagttct gtttactgcc accctccct       660 gggctttaca gcagttataa atatcagcgc aggcctgctg gcagtcata tgttcgctcc       720 gtgtcatgtg taaggagtga tgcgttgcag cgccgtcagg acatgcctgc gctccatact       780
ttgcctctgt cgtgatctgc tgtattggtt tgtttgagca aatgtaactt tccatttcca       840
ggctgttgtc tggtcattcc gtcggcgcga ggtgggctga acagcatcat ccatgtctca       900
gttatcacgg atcttcacct tgattgtggg cttcggtggc agggagctgg gactcggggg       960
ggtcttacag gtagttcagg ctctgacttg ttctcagtgg tccacaccaa ctgaacaggg      1020
```

```
cctcttccag gatgggcacg tggttgtcgg tgggctcttt aaccttcatt acacgcctcc    1080
agacacagcc aacaacttca ctcagcaatc gcattacaaa gcttgcaccg ggtacagctg    1140
caatctttca cgtcatttgt gtgaactgtt gtgacctttt cccctccaaa tccaatgttt    1200
acacttggat tctcctcatt cttggcttca ggctggaaaa cctcccttttg cagtacattt    1260 acgccatggt gtttgcagtg gaggagatca atcacagcgc agcgctgctg ccaggcgtga    1320
agctcgggta ccacattcgc gatagctgcg ccctccaccc ctggaccact caggcggcgc    1380
tggcactggt cgcaggagac agtgccagct gtgaattggc aaccccagcg gactactctg    1440
cagagacgag tgaagaaaaa ggtactgatt aagccttgca atacctgatg aactcaaact    1500
tgatttaaaa ttgtaatttt taaaacaatt taggtgctgc ctccgttcct ttgattattg    1560
gtggcgcttc ttccaatgca gcaaaaatac tcctgggaac cctgagtcca ctatctgtac    1620
ctttagtgag ttttccgtcc tttcagttta tataaatcat atgacatgtt tttaaagcac    1680
acatgagcct gcggatgatg taattggatt ctatttataa tataataata ataataaagc    1740
tttaaggatc tttgtggttg ttcttccaga taagctacac agctagctgc ccttgcctga    1800
gtgacaggca ccgatatccc accttcttca ggaccatggc cagtgatatt taccaggctc    1860
aggctctcgc ccagcttgtg ttacgcttca actggacgtg gatcggggca gtggtggcaa    1920
acaatgatta cggtcatgtg gcagttaagg tgaaatattc tggctaagca tgcaagacat    1980
tctcctgtgg ataatcctac atgcacagct gcggtgtgtt tatctgtgta cgtcaggtgt    2040
ttcaagagca gactcagggg aaaggtgtgt gtctggcgtt tgtcgagact ctccagaggg    2100
agacgatcgt ggcagacgcc gtgcgtgcgg cgcgcacaat tcaggcctcg actgcgaggg    2160
tgattctggt ttttagctgg tacactgacg tagggcatct cttccgtcag ctgcagaaaa    2220
taaacgtgag aagttctgtg cagggatctg agtgtctaat cagtcagagg agttctgatc    2280
tttgaacgct gcctccgctg caggtgaccg acagacagtt tctggccagc gaggcctgga    2340
gcaccagtga ggttcttctc aaagatcctg acacttctac agtggcgagt ggagtcgtcg    2400
gcgtggccat cgcaagccaa cacatccctg gtttgaccg tttcctcaga ggcctgaacc    2460
cgtctcttcg gcccagcgac aagttttac aagaattctg ggaggaggaa tttggctgca    2520 gccctcgcc tccttcttca gagacctctg gtgatttgaa cgcttcgctg cctccctgca    2580
gtggtgcaga gtctctggag ggagtgcagc atcccttcac cgatacctca cacctgaggg    2640
tgacgtataa cgtctacctg gctgtatatg ctgcggccaa cgcccttcac agccttctct    2700
cttgccccat tcataacagc ccttctggaa cttctcactg cacctcccg aagggcatta    2760 aaacaacaga ggtaaagaaa ataatacaca gatcaaataa acgcagtaaa atcacaaaat    2820
aataataagt ggcaacaccg tcgtgtttac agctgctgca acacttgagc aaagtgaatt    2880
tcaccacgcc gcagggcaaa cacttgtact tccgaggtgc agatattccg gcaatgtacg    2940
acctcattaa ctggcagagt ggcacagacg ggaccctcca gctcgtcctc atcggtgccg    3000
tggctggatt tgacctgcag ctcaatgagt cagaaattga gtggagcgcc aaatataatc    3060
aggtgattca gaggaagcat ctcaatcaca aaaatctgga tacatggaaa cgtatttaat    3120
atgctggggg tgtgcatgtc taggtgcctg tgtcagtgtg cagtgagagc tgcccccccg    3180
gcaccagaaa ggccaacagg aagggagaac ctctctgctg cttcgactgt atcccttgtg    3240
ctgacggcga gattagcaac acaagcggtg agggaaatat cacagcagct tctttctgtt    3300
ctgaactttg ggggtttgaa cgtctgactg tcactgttta ggttctcttc agtgtgaccg    3360
ttgccctcct gagttctggt ccaacgatgg acggactgct tgtgttcctc gacagctgga    3420
```

-continued

```
ttttctgtcc tttaatgaaa ccttgggcgt tgctctgacc gccgtggccg tgtccggcgc    3480
tgtggtgaca acagccgtgt tgtggtgtt ccttcactat cgtcacacgc ccatggtgag    3540
aactcagagt cacgtcctgg aaaagaaacc actgaatctg tttaatcagt tcatcctaat    3600
ttccattgga aggttcgagc caacaactct gaattgagct tcctgctgct gctgtcactc    3660
aagctgtgtt tcctgtgctc gctggtgttc atcggtcgtc cgtccgtctg gtcctgtcgg    3720
ttccagcagg cggcttttgg gatcagcttc gtgctttgtg tttcctgcct ccaagtcaag    3780
actatagtgg ttctggcagc cttccgctcg gcccggccgg gcgcggggc cctaatgaag    3840 tggttcggcc cgtcccaaca gagaggaagc gtttgcatct ttacttgtgt acaggcaaga    3900
gttacagatg gattaagaga aacattgtt ttttaatgt cagtatgatt tatgtgatgt    3960
tatatgagtg tttgttttca cagtgttgag ctgatgttgc acaatgcttt ctttcatcaa    4020
ggttatcatc tgtattgttt ggctgtcact gagcccccca gtgccccaag ctgacttgga    4080
tgtgccgggc ttacaggtca ccctggagtg cgccatggcc tccgtggtgg gcttctctct    4140
ggtcctgggc tacatcggtc tgctggcctg cacctgcctc ctgttggcgt tcctggctcg    4200
gaaactcccc gacaacttca acgaggccaa gctgatcacc ttcagcatgc tgatcttctg    4260
cgccgtctgg gtggccttcg tccccgctta catcagctct cccggaaaat actcagttgc    4320
cgtggaaata tttgccatcc tggcttccag ttatggcctg ctcttctgta tctttgctcc    4380
aaagtgtttc atcatcctgt tgagacccga gaaaaacaca aagaaacacc tgatgatgcg    4440
atagcaaaca aaatatgaga tttatattcc tttttttagaa atatgcagtc ttaatatctg    4500
ctgctgtgtg ttatttatgc atctgcatca ataaaacgct gaaagaaatt gtaaaacaag    4560
taaaaacatt ctgattctta tttgctttca ttggctattt agaaaaaggt aatgcattat    4620
gggacattta aagcacaggg ttaataaaaa atatactata tcatgtgtct gttgtgtgta    4680
tattctaatg cagtttgatt atttattcat tatggattcc ttatcatgcc acctcaacag    4740
atc                                                                  4743
```

<210> SEQ ID NO 37
<211> LENGTH: 469
<212> TYPE: DNA
<213> ORGANISM: Fugu rubripes

<400> SEQUENCE: 37

```
catcatcctc gctggaatct tcctgggcta tatttgtccc ttcaccctca tcgcccgccc      60
cactgtagct tcctgctacc tccagaggct cctcgtgggg ctctccgctg ccatatgcta     120
ctctgccctt gtcaccaaaa ccaatcgcat cgctcgtatt ctggcaggca gcaaaaagaa     180
gatttgcacc aggaaaccga ggttcatgag cgcctgggct caggtggtca tcgccttttat     240 cctgatcagt ctacagctca gtctggaggt caccctcatc gtcctggagc ctcctgaacc     300
catcaaatcg caccccagca taagagaggt tttcctcatt tgcaacacca gcaacatggg     360
cgtcgtggcg ccgctcggat acaacggcct gcttataatg agctgcacct actacgcctt     420
caagacgcgc aatgtacctg ccaactttaa cgaagccaaa tacatcgcc                 469
```

<210> SEQ ID NO 38
<211> LENGTH: 318
<212> TYPE: DNA
<213> ORGANISM: Fugu rubripes

<400> SEQUENCE: 38

```
gcccgcatct tcagcggcgt gaaagatgga gcccagcgac cgcgcttcat cagccccacc     60
tcccagttag ccatctgcgg cgctcttatc tcctgccagt tgctggtggc gctgatctgg    120
ttaatggtgg aggtgcccgg ggtccgcaag gaagtgagct cggagcggag gaacgtggtc    180
atcctcaagt gcaacagcaa ggacagcagc atgctgatgt cgctgaccta caactgcgtc    240
ctcatcatcc tctgcaccgt ctacgcgttc aagacgcgaa agtgccccga gaacttcaac    300
gaggccaagt tcatcggc                                                  318
```

<210> SEQ ID NO 39
<211> LENGTH: 559
<212> TYPE: DNA
<213> ORGANISM: Fugu rubripes
<220> FEATURE:
<221> NAME/KEY: misc_feature
<222> LOCATION: (528)..(535)
<223> OTHER INFORMATION: n is a, c, g, or t

<400> SEQUENCE: 39

```
cgtgttgctt acgggcattt tcctcatcta cctcatcacc ttcctcatga tcgccgagcc     60
aagtgtggct gtgtgtgcct tccgcaggct gtttctgggg ctcggcatgt gcatcagcta    120
ctcggccatg ctcaccaaga ccaaccggat ctaccggatc tttgagcagg caaaaagtc     180
agtcacgccc ccgaaattta tcagccccac ctcccagctg attatcacct tcatactcat    240
ctcagtgcag gtatacatgc gcattcacgt gcacgatctg ctgcgaagcc tctgctaacc    300
ctagccccccg tgctccttct cgcagcttct cggggtcttc atctggtttg gcgtgatgcc    360
tccgcacacc atcatcgact acgaagagca gaagccccccg aatccggagt ttgcccgcgg    420
agtcctgaag tgcgacatgt ctgacctctc cctcatctta tgtctgagct acagtctggt    480
gctgatgatc acctgcacgg tgtacgccat caagaacaga agggtccnnn nnnnnttcaa    540
cgaagccaag cccatcggc                                                 559
```

<210> SEQ ID NO 40
<211> LENGTH: 499
<212> TYPE: DNA
<213> ORGANISM: Fugu rubripes
<220> FEATURE:
<221> NAME/KEY: misc_feature
<222> LOCATION: (85)..(85)
<223> OTHER INFORMATION: n is a, c, g, or t

<400> SEQUENCE: 40

```
taccgcatct tcgagcaggg caagaggtcg gtgaccccgc ccaagttcat cagccccact     60
tcccagctca tcatcacctt cgtgntgatc tctgtgcagg tgagcctggt ggcctgctcc    120
cacttcctgc ccgcctgaag gggcttttttt tgaccttcgg ctggtgtttg tgtgcttcag    180
gtcttcggcg tgttcgtgtg gtttgctgtg gtccctcctc acaccatcat cgattacgag    240
gaactgcgtc ctccccagcc caacctggcc cggggcatcc tgaagtgcga catgtccgac    300
ctgtccatca tctgctgcct cagctacagc atcgtgctca tggtaacaca gcgaccttca    360
gccacgtcaa ctcccgctct tgtgaacgat aacaggaaat aagcgtggcg tgtcggtgtg    420
ttgctaggtg acgtgtacgg tgtacgccgt gaagagccgc ggcgttccag agacgtttaa    480
cgaagccaag cccatcggg                                                 499
```